(12) United States Patent
Feng et al.

(10) Patent No.: US 12,290,519 B2
(45) Date of Patent: May 6, 2025

(54) ANTI-INFLAMMATORY COUPLING COMPOUND DRUG, AND PREPARATION METHOD THEREFOR AND USE THEREOF

(71) Applicant: COVAL BIOPHARMA (SHANGHAI) CO., LTD., Shanghai (CN)

(72) Inventors: Lichun Feng, Shanghai (CN); Weijiang Zhang, Redwood City, CA (US); Guolong Wu, Shanghai (CN); Hao Zhang, Foster City, CA (US); Dafeng Li, Shanghai (CN)

(73) Assignee: COVAL BIOPHARMA (SHANGHAI) CO., LTD., Shanghai (CN)

( * ) Notice: Subject to any disclaimer, the term of this patent is extended or adjusted under 35 U.S.C. 154(b) by 0 days.

(21) Appl. No.: 18/413,842

(22) Filed: Jan. 16, 2024

(65) Prior Publication Data

US 2024/0197741 A1 Jun. 20, 2024

Related U.S. Application Data

(63) Continuation of application No. PCT/CN2022/105503, filed on Jul. 13, 2022.

(30) Foreign Application Priority Data

Jul. 20, 2021 (CN) .......................... 202110834326.4

(51) Int. Cl.
A61K 31/519 (2006.01)
A61P 29/00 (2006.01)

(52) U.S. Cl.
CPC ............ *A61K 31/519* (2013.01); *A61P 29/00* (2018.01)

(58) Field of Classification Search
CPC .............................. A61K 31/519; A61P 29/00
See application file for complete search history.

(56) References Cited

U.S. PATENT DOCUMENTS

| 4,877,620 A | * | 10/1989 | Loew | ...................... | A61P 29/00 424/456 |
| 10,961,267 B2 | * | 3/2021 | Hudson | .................... | C07H 1/00 |

FOREIGN PATENT DOCUMENTS

| CN | 106496233 A | * | 3/2017 | |
| CN | 110256441 A | | 9/2019 | |
| CN | 111588724 A | | 8/2020 | |
| CN | 111763209 A | | 10/2020 | |
| CN | 114907353 A | | 8/2022 | |
| CN | 115867319 A | | 3/2023 | |
| JP | 2015-527987 A | | 9/2015 | |
| WO | WO-2015166434 A1 | * | 11/2015 | .............. A61P 29/00 |
| WO | 2017106957 A1 | | 6/2017 | |
| WO | WO 2020176859 A1 | | 9/2020 | |
| WO | WO 2020191477 A1 | | 10/2020 | |
| WO | WO 2022012492 A1 | | 1/2022 | |
| WO | 2022171140 A1 | | 8/2022 | |

OTHER PUBLICATIONS

Liu et al. Synthesis and Evaluation of Novel 7H-pyrrolo-[2,3-d]pyrimidine derivatives as potential anticancer agents (Future Medicinal Chemistry, 11(9), 959-974). (Year: 2019).*
PCT/CN2022/105503 International Search Report with English translations dated Oct. 10, 2022, 9 pages.
PCT/CN2022/105503 Written Opinion with English translation dated Oct. 10, 2022, 14 pages.
Chinese Patent Application No. 202280035110.4, First Office Action with English translation of Rejection Decision dated Feb. 7, 2024, 23 pages.
Australian Patent Application No. 2022313345 Examination Report dated with English translation dated Dec. 4, 2024, 3 pages.
Russian Patent Application No. 2024104095 Office Action with English translation dated Sep. 26, 2024, 42 pages.
Belikov V.G., "Pharmaceutical Chemistry", Textbook, with English Abstract, 2007, 6 pages.
Russian Patent Application No. 2024104095 Office Action dated Feb. 14, 2025 with English translation, 39 pages.
Japanese Patent Application No. 2024-503816 Office Action dated Feb. 25, 2025 with English translation, 24 pages.

* cited by examiner

*Primary Examiner* — Joseph K McKane
*Assistant Examiner* — Meghan C Heasley
(74) *Attorney, Agent, or Firm* — COZEN O'CONNOR

(57) ABSTRACT

An anti-inflammatory drug compound, and a preparation method therefor and the use thereof. The structural formula of the compound is A-Y—B, wherein A is a group after dehydrogenation of an amine compound having JAK inhibitory activity, Y is a direct connection or —(CH2)-O— or, and B is a group formed by means of dehydroxylation of a carboxy-containing carboxylic acid compound B1, or a group formed by means of dehydrogenation of a hydroxy-containing compound B2. The compound has the special effects of having a strong transdermal property, controlled drug release, high efficacy, etc.

4 Claims, 3 Drawing Sheets

ANTI-INFLAMMATORY COUPLING COMPOUND DRUG, AND PREPARATION METHOD THEREFOR AND USE THEREOF

CROSS-REFERENCE TO RELATED APPLICATIONS

This application is a continuation of International Patent Application No. PCT/CN2022/105503 filed Jul. 13, 2022, which claims priority to Chinese Patent Application No. 202110834326.4 filed Jul. 20, 2021. The entire contents of each of the aforementioned applications is incorporated herein by reference.

TECHNICAL FIELD

The present invention relates to an anti-inflammatory drug suitable for external use, and more particularly, to a compound drug synthesized through coupling and use thereof.

BACKGROUND ART

JAK-STAT signaling pathway is a cytokine-stimulated signal transduction pathway, involved in cell proliferation, differentiation, apoptosis and immune regulation, and other important biological processes. Many cytokines and growth factors signal through the JAK-STAT signaling pathway, including IL (interleukins), GM-CSF (granulocyte/macrophage colony-stimulating factor), GH (growth hormone), EGF (epidermal growth factor), PDGF (platelet-derived factor), and IFN (interferons), among others.

The JAK-STAT signaling pathway consists of three components, a receptor, a tyrosine kinase (JAK), and a transcription factor (STAT). Upon binding of the ligand to the tyrosine kinase-related receptor, the JAK bound thereto is activated. The activated JAK further activates the corresponding STAT protein. The activated STAT protein enters the nucleus to bind to a target gene and regulates the gene transcription.

The JAK family includes JAK1, JAK2, JAK3, and TYK2. These kinases control seven different STATs, namely STAT1, STAT2, STAT3, STAT4, STAT5A, STAT5B, and STAT6. It is precisely by controlling these STATs that cytokines and growth factors can control cell proliferation, differentiation, apoptosis, and immune regulation. Many diseases arise from JAK and STAT mutations. By modulating and selectively inhibiting certain JAK, these diseases can be effectively treated.

Although JAK-STAT is a relatively simple signaling pathway, it is involved in many cellular functions. There are dozens of JAK inhibitors currently on the market and under research. The vast majority of JAK inhibitor programs seek to maximize efficacy and minimize side effects by selectively inhibiting one of the JAK-STAT signaling. However, systemic administration is often unable to circumvent the contradiction between efficacy and side effects. Topical administration of JAK inhibitors may enhance efficacy while reducing systemic side effects. Many of the JAK inhibitor programs under research also have organ selectivity as the ultimate goal to maximize efficacy/risk.

It is also an object of the present invention to maximize the therapeutic effect of dermal administration and minimize systemic toxicity by topical (dermal) administration in combination with optimization of the structure of the compound. Many skin diseases, including psoriasis, vitiligo, alopecia areata, etc. have a clear understanding of their causes and mechanisms of disease treatment. The regulatory and control mechanisms of various JAK-STATs by JAK inhibitors currently on the market and under research have also been very clear. The purpose of selective dermal administration can also be achieved by modifying the chemical structure of the currently known JAK inhibitors to allow them to penetrate more through the protective layer of the dermal. Compared with the development of a skin-selective drug delivery formulation of a completely new compound, the product with a known compound with an optimized structure has a relatively short development cycle, low risk of efficacy failure, low possibility of unknown toxicity and low development cost.

The optimization of a compound structure by increasing compound transdermal penetration can change the physical and chemical properties of the compound by adding non-functional groups to the known compound structure, allowing it to penetrate more through the protective layer of the dermal.

SUMMARY OF THE INVENTION

The present invention is directed to the technical problem that existing JAK inhibitors also require high doses or have side effects, and seeks to optimize the structure of the known JAK compounds so that they can effectively achieve skin-selective administration, thereby increasing the effectiveness for skin diseases and reducing systemic dose and side effects. More specifically, structural optimization and skin-selective administration of known JAK inhibitors are achieved by coupling with other small molecule compounds.

Specifically, the present invention provides the following technical solutions.

1. Depending on the structure of the different JAK inhibitor compounds, specific linkers and coupling small molecules are chosen to allow more final compound (prodrug) to penetrate the protective layer of the dermal.
2. The chemical bond between the linker and the JAK inhibitor is unstable in the human skin, leading to hydrolysis and release of effective ingredients, known as JAK inhibitors.
3. The linkage between the linker and the coupled small molecule is also unstable, leading to the release of the coupled small molecule.
4. The linker is known per se as a simple chemical structure without toxicity.
5. The chemical structure of coupled small molecules is clear, and the pharmacology and toxicology are known.

Specifically, the present invention provides the following technical solutions.

In an aspect, the present invention provides an anti-inflammatory compound, or a stereoisomer, tautomer, nitrogen oxide, metabolite, prodrug, pharmaceutically acceptable salt, or solvate thereof, having a structure shown in general formula (I):

$$A\text{-}Y\text{—}B \tag{I}$$

wherein, A is a group after dehydrogenation of an amine compound having JAK inhibitory activity;
Y is a direct connection or —(CH$_2$)—O— or —(CH$_2$)—;
B is a group formed by means of dehydroxylation of a carboxy-containing carboxylic acid compound B$_1$, or a group formed by means of dehydrogenation of a hydroxy-containing compound B$_2$; and wherein, in the case where the carboxylic acid B$_1$ is dehydroxylated to form a group, the Y group is a direct connection or —(CH$_2$)—O—; in the case where the hydroxy-containing compound B₂ is dehydrogenated to form a group (i.e., B is B₂), the Y group is —(CH₂)—.

In a specific embodiment, the anti-inflammatory compound, or the stereoisomer, tautomer, nitrogen oxide, metabolite, prodrug, pharmaceutically acceptable salt, or solvate thereof described above, having a structure shown in general formulas (II) or (IIa):

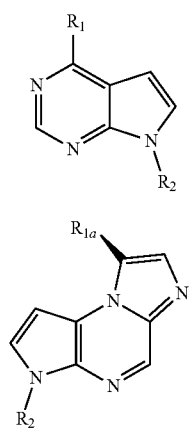

wherein $R_1$ is selected from pyrazolyl or pyrrolyl unsubstituted or substituted with $R_a$; or —N(CH₃)—Cy; $R_{1a}$ represents a pyrrole ring substituted by a halogen-substituted $C_1$-$C_6$ alkylaminoacyl group and/or by a $C_1$-$C_6$ alkyl group;

$C_y$ is a five- or six-membered carbocyclic ring or a five- or six-membered nitrogen-containing heterocyclic ring unsubstituted or substituted by $R_b$; $R_a$ and $R_b$ are each independently groups containing at least one or two groups selected from a group consisting of an acyl group, a sulfonyl group, a cyano group, an amino group or a $C_1$-$C_6$ alkyl-substituted amino group, and a four-, five-, or six-membered nitrogen-containing heterocyclic group, or the nitrogen-containing heterocyclic group substituted with $C_1$-$C_6$ alkyl; preferably $R_a$ and $R_b$ are each independently groups which consist of one group of acyl or sulfonyl and at least one group selected from a group consisting of cyano, amino or $C_1$-$C_6$ alkyl substituted amino, and a four-, five-, or six-membered nitrogen-containing heterocyclyl, or the nitrogen-containing heterocyclyl substituted with $C_1$-$C_6$ alkyl, wherein the $C_1$-$C_6$ alkyl is substitutable by halogen; That is, $R_a$ and $R_b$ herein are each independently preferably a group comprising at least one acyl or sulfonyl-containing group and at least one nitrogen atom-containing group;

$R_2$ in both general formulas (II) and (IIa) is —B, i.e. is a group formed by means of dehydroxylation of a carboxy-containing carboxylic acid compound $B_1$ and is selected from $R_4$—Ar—$R_3$—CO—, wherein $R_3$ is selected from $C_1$-$C_6$ alkylene; —NH—, $R_5$NH—, or $C_1$-$C_6$ alkylene substituted with a $C_1$-$C_6$ alkoxyamide group; or a direct connection, i.e. the Ar group is directly linked to —CO—; $R_3$ is preferably methyl substituted or unsubstituted methylene, —C₂H₄—, or a direct connection; $R_5$ is $C_1$-$C_6$ alkylene; wherein the $C_1$-$C_6$ alkylene is substitutable by halogen (preferably halogen is one or two or more selected from a group consisting of fluorine, chlorine or bromine);

Ar is an aromatic ring group, preferably selected from a benzene ring; a naphthalene ring or an aryl heterocyclic ring; a benzene ring, a naphthalene ring, or an aryl heterocyclic ring or an aryl fused heterocyclic ring (here, the aryl heterocyclic ring being preferably a benzo nitrogen-containing or oxygen-containing benzo heterocyclic ring such as a benzopyrrole ring) substituted with one or more groups selected from halogen, a $C_1$-$C_6$ alkyl group, a $C_1$-$C_6$ alkoxy group, a $C_1$-$C_6$ acyl group, or a $C_1$-$C_6$ alkoxy group; Ar is more preferably an aryl heterocyclic ring containing a nitrogen atom; and $R_4$ is halogen, $C_1$-$C_6$ alkyl, $C_1$-$C_6$ alkoxy, $C_1$-$C_6$ alkyl containing $C_1$-$C_6$ cycloalkanoyl, $C_1$-$C_6$ alkylamido or aryl fused heterocyclic amido, $C_1$-$C_6$ carbonyloxy, halogen substituted benzoyl, $C_1$-$C_6$ alkyl or halogen substituted or unsubstituted phenoxy, $C_1$-$C_6$ alkyl or halogen substituted or unsubstituted phenyl or aryl fused heterocyclic ring, $C_1$-$C_6$ alkyl or halogen substituted or unsubstituted phenylamino, or $R_4$ can also be absent; wherein the $C_1$-$C_6$ alkoxy can also form a bridged ring with Ar.

In a specific embodiment, the anti-inflammatory compound, or the stereoisomer, tautomer, nitrogen oxide, metabolite, prodrug, pharmaceutically acceptable salt, or solvate thereof described above of the present invention, wherein Cy is substituted cyclohexyl or substituted piperidinyl; preferably, the substituted cyclohexyl group is a cyclohexyl group substituted with an amino group and a sulfonyl group, and the substituted piperidinyl group is a piperidinyl group substituted with an acyl group or a sulfonyl group and —CN.

Preferably, the compound, or a stereoisomer, tautomer, nitrogen oxide, metabolite, prodrug, pharmaceutically acceptable salt, or solvate thereof of the present invention is a coupling compound resulting from a condensation reaction of an amine compound A with a carboxylic acid compound $B_1$.

Preferably, the compound, or a stereoisomer, tautomer, nitrogen oxide, metabolite, prodrug, pharmaceutically acceptable salt, or solvate thereof described above of the present invention, wherein A- is a group after dehydrogenation of an amine compound selected from a group consisting of any one of the following groups: tofacitinib, baricitinib, oclacitinib, ruxolitinib, upadacitinib and delgocitinib:

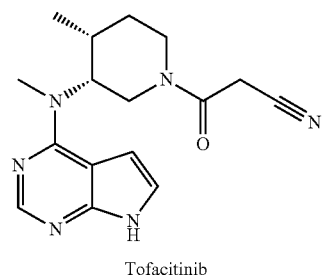
Tofacitinib

-continued

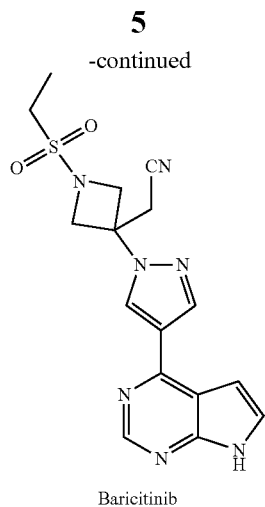

Baricitinib

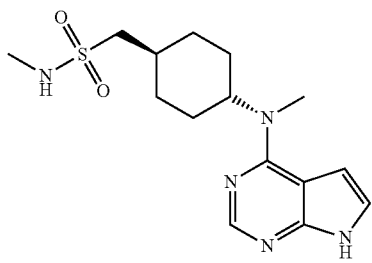

Oclacitinib

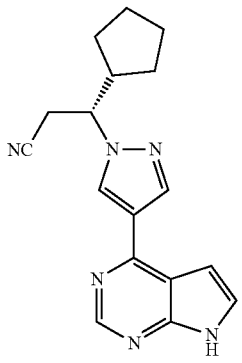

Ruxolitinib

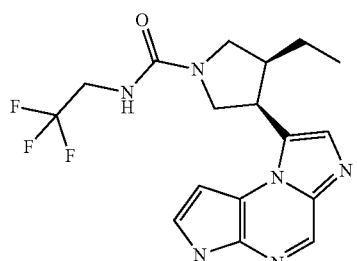

Upadacitinib

-continued

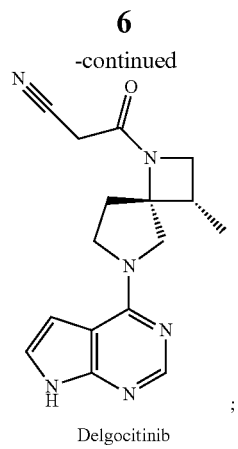

Delgocitinib;

preferably A is a group formed after dehydrogenation of tofacitinib, ruxolitinib, and baricitinib.

Still preferably, the anti-inflammatory compound or a stereoisomer, tautomer, nitrogen oxide, metabolite, prodrug, pharmaceutically acceptable salt, or solvate thereof of the present invention, wherein —$B_1$ is a group after dehydroxylation of a carboxylic acid moiety selected from a group consisting of ibuprofen, (S)-(+)-ibuprofen, naproxen, fenoprofen, flurbiprofen, loxoprofen, ketoprofen, diclofenac, etodolac, actarit, indomethacin, N-Boc-L-phenylglycine, aspirin, indobufen, mefenamic acid and tolfenamic acid:

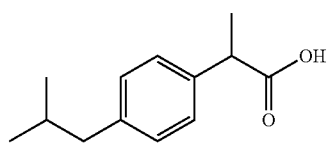

Ibuprofen

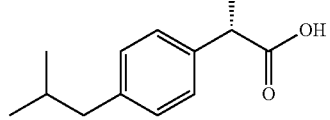

(S)-(+)-ibuprofen

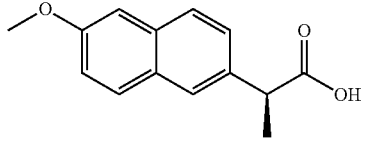

Naproxen

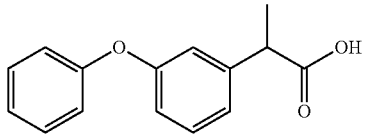

Fenoprofen

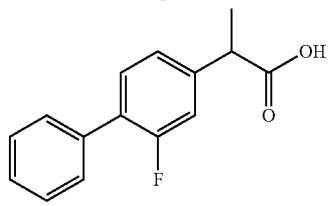

Flurbiprofen

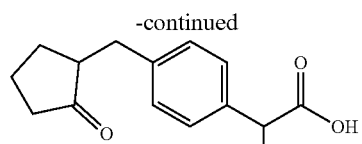

Loxoprofen

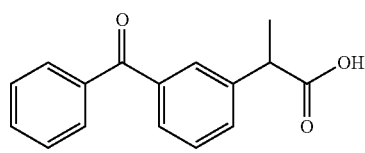

Ketoprofen

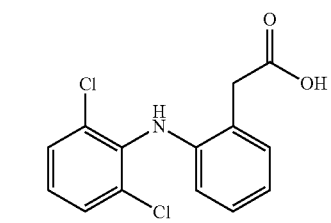

Diclofenac

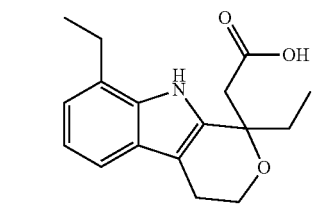

Etodolac

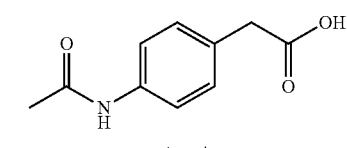

Actarit

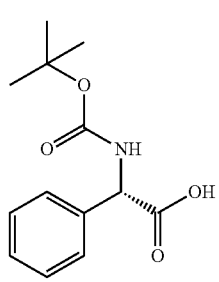

N-Boc-L-phenylglycine

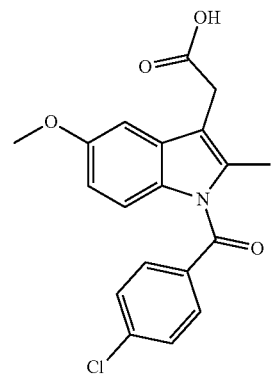

Indomethacin

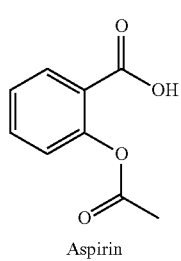

Aspirin

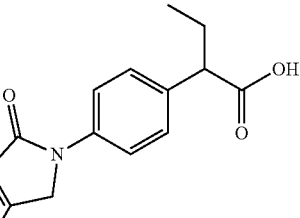

Indobufen

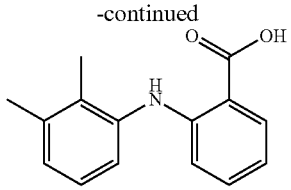

Mefenamic acid

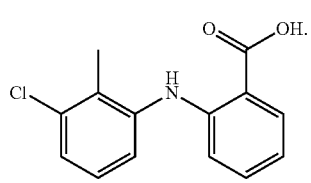

Tolfenamic acid

More preferably, the anti-inflammatory compound, or a stereoisomer, tautomer, N-oxide, metabolite, prodrug, pharmaceutically acceptable salt or solvate thereof of the present invention, wherein the compound is a coupled compound obtained by condensation reaction of an amine compound A selected from the group consisting of tofacitinib, baricitinib, upadacitinib, oclacitinib, and ruxolitinib with a carboxylic acid compound $B_1$ selected from the group consisting of ibuprofen, (S)-(+)-ibuprofen, naproxen, fenoprofen, flurbiprofen, loxoprofen, ketoprofen, etodolac, actarit and indomethacin; preferably, the amine compound is tofacitinib, ruxolitinib and baricitinib. More preferably, the anti-inflammatory compound, or the stereoisomer, tautomer, nitrogen oxide, metabolite, prodrug, pharmaceutically acceptable salt, or solvate thereof of the present invention, wherein the compound is any one of the following specific compounds:

CPD-001

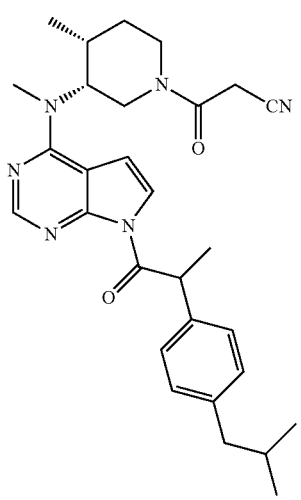

CPD-002
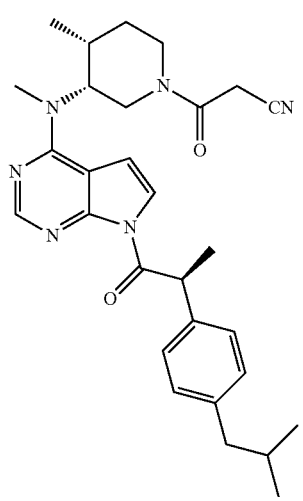
CPD-004
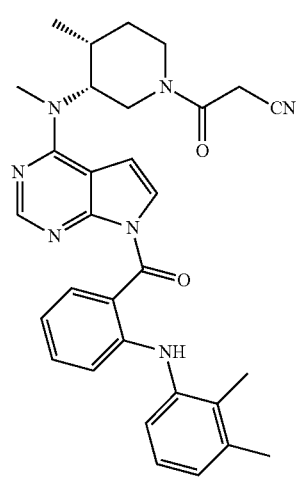
CPD-005
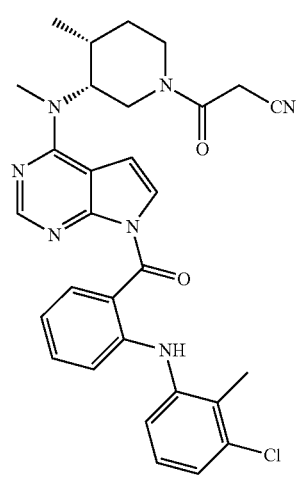
CPD-006
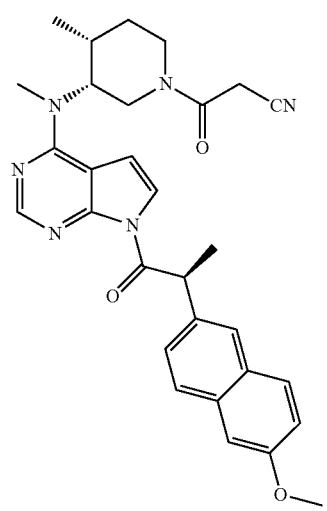
CPD-007
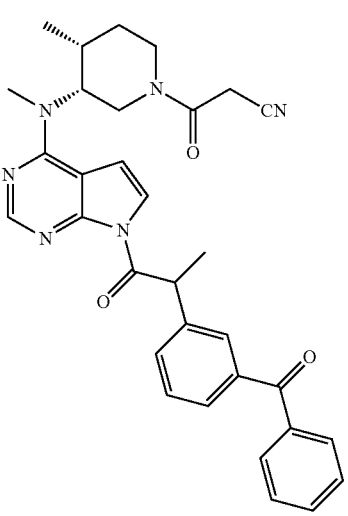
CPD-008
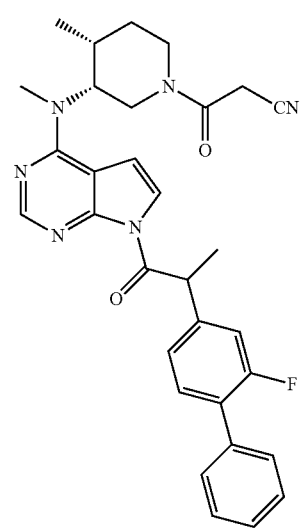

CPD-009
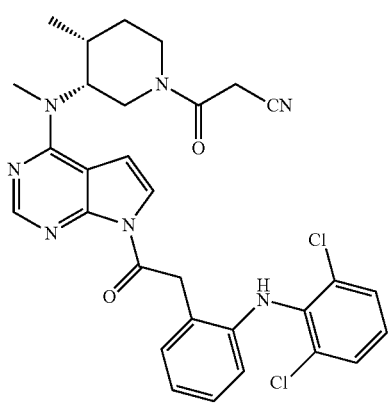
CPD-010
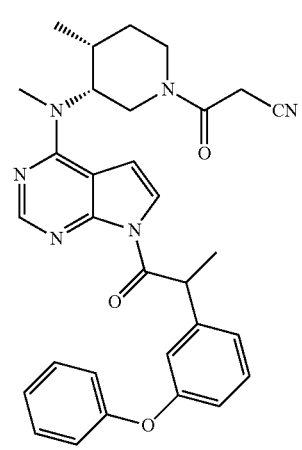
CPD-011
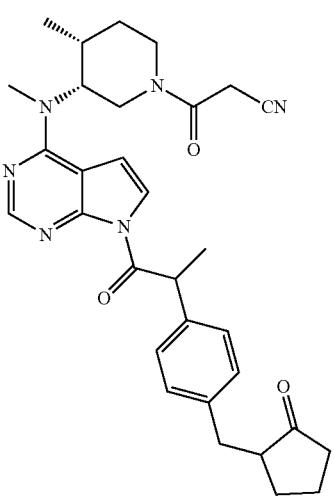
CPD-012
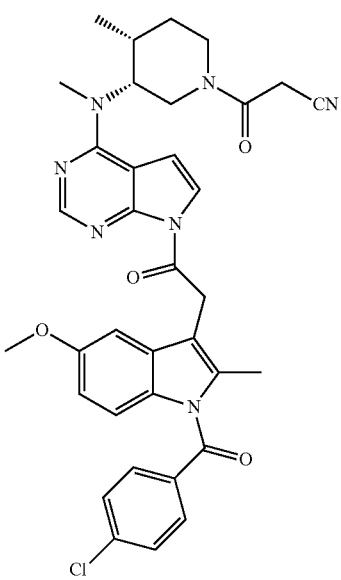
CPD-013
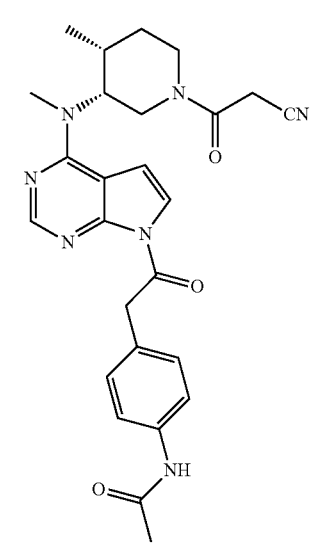
CPD-014
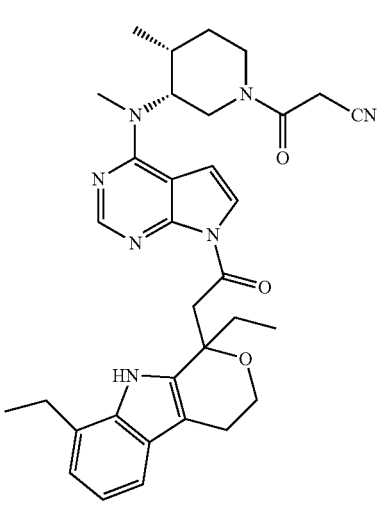

CPD-015
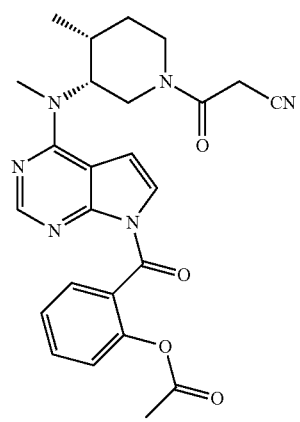
CPD-016
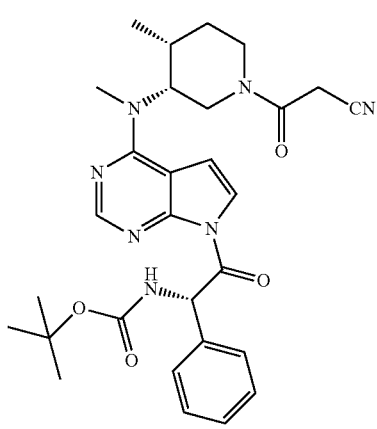
CPD-029
CPD-017
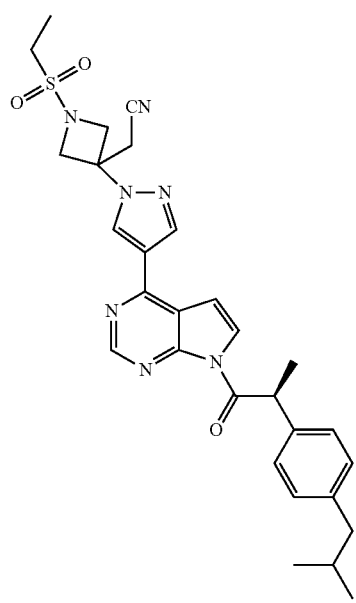
CPD-018
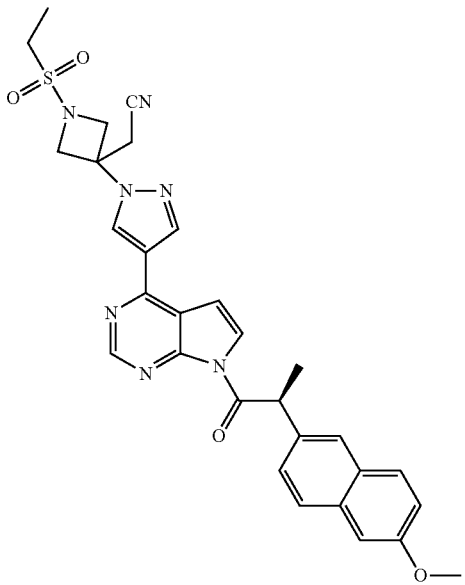

CPD-019
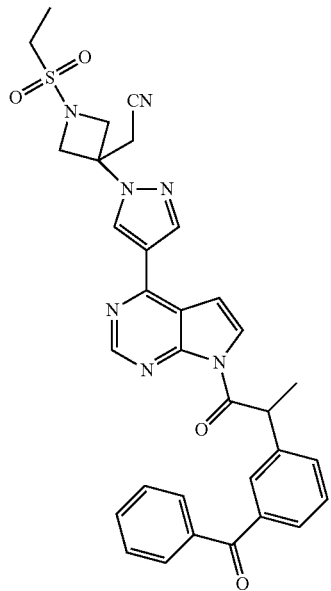
CPD-020
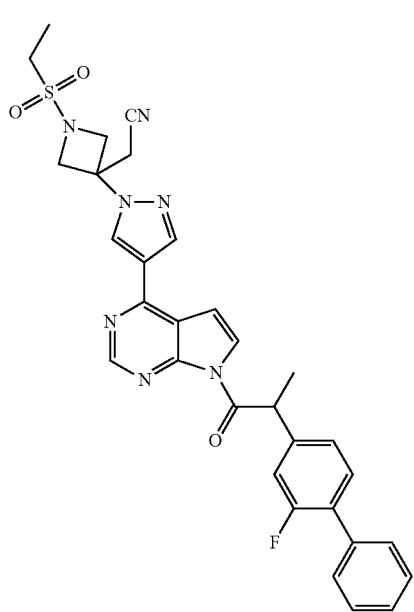
CPD-021
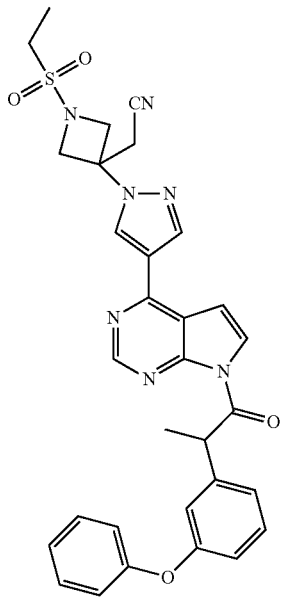
CPD-022
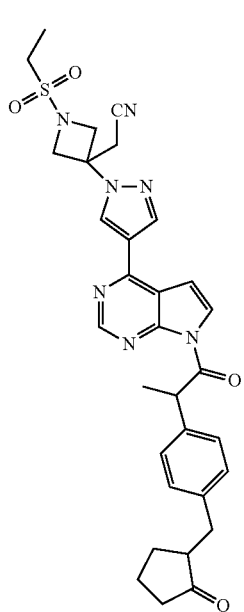

CPD-023
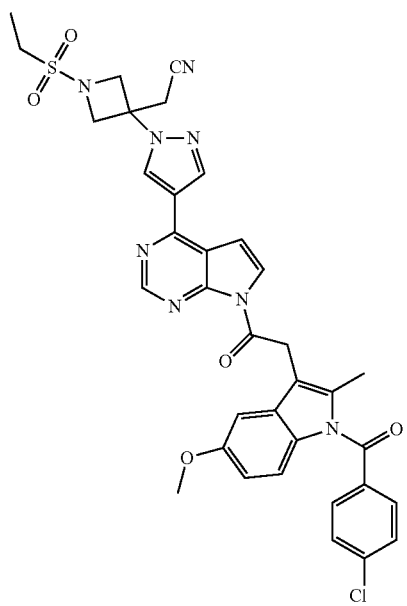
CPD-024
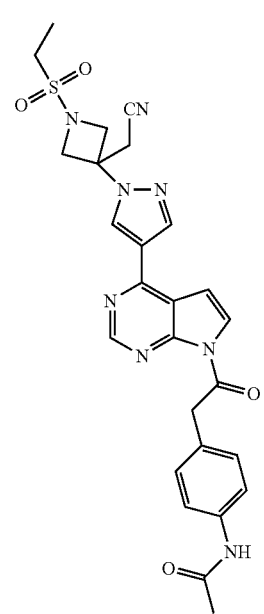
CPD-025
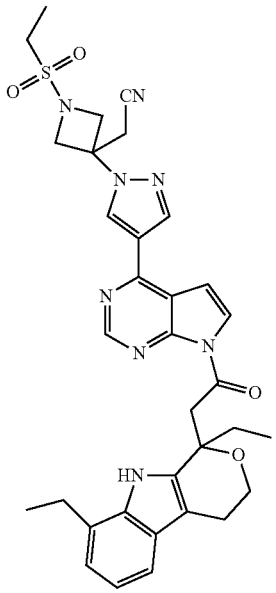
CPD-026
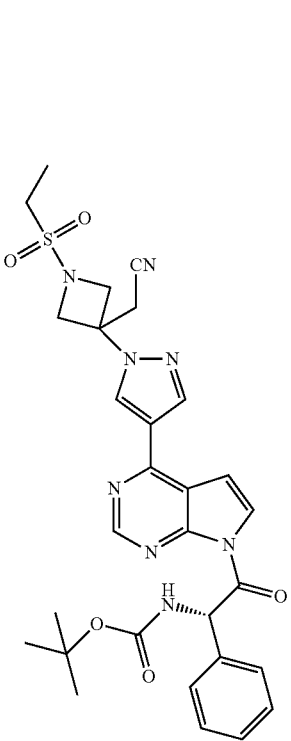

CPD-030
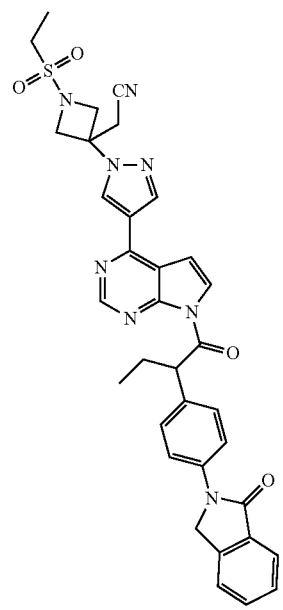
CPD-031
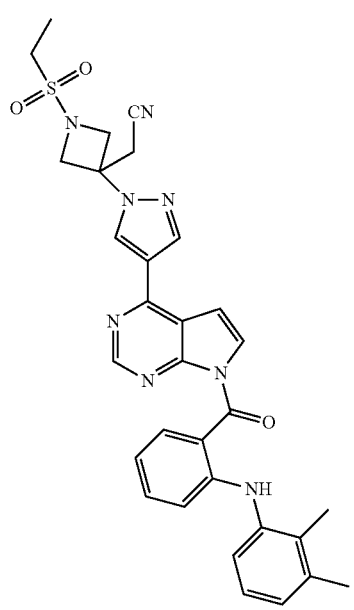
CPD-032
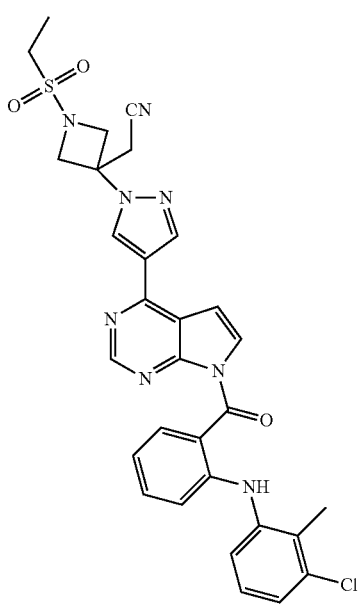
CPD-033
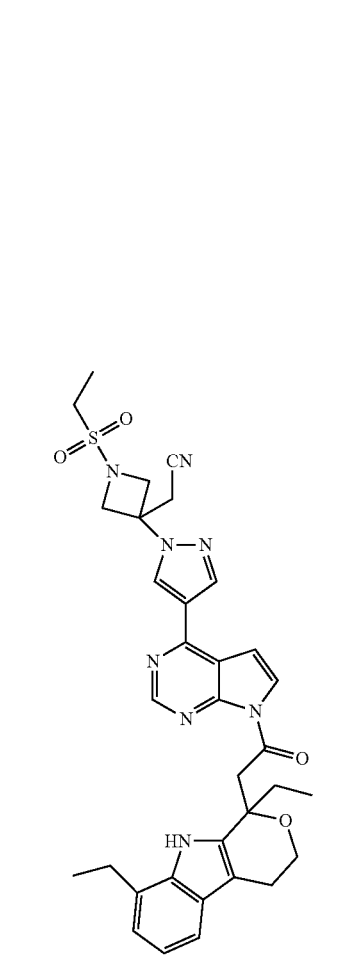

CPD-034
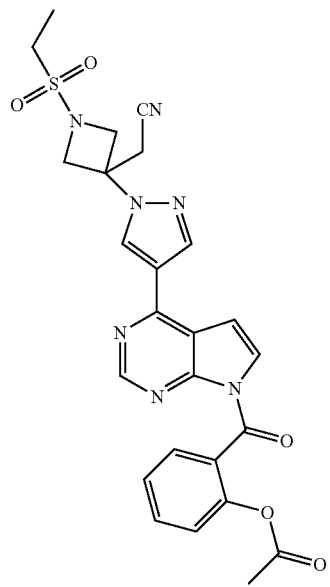
CPD-035
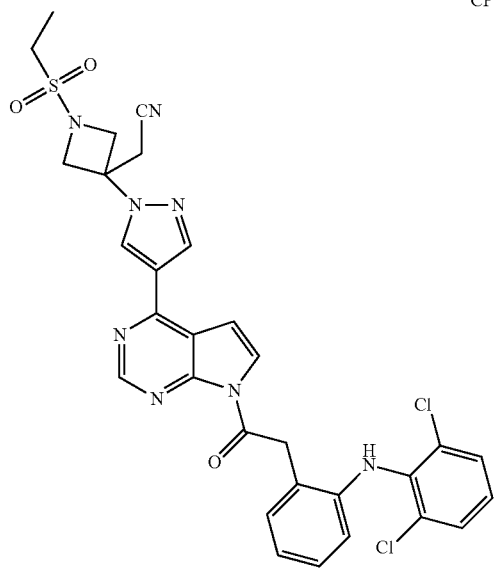
CPD-028
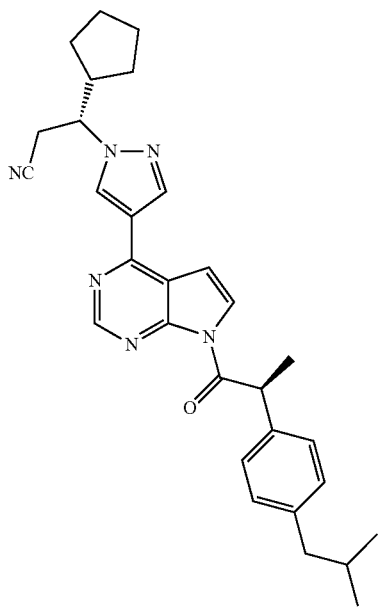
CPD-036
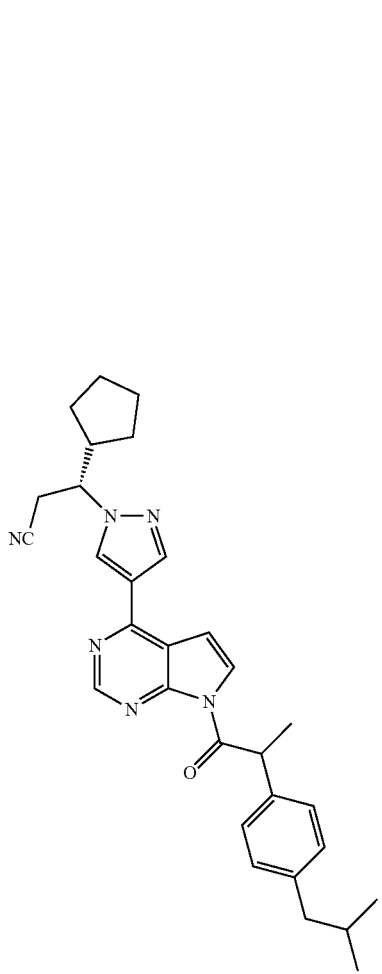

CPD-037
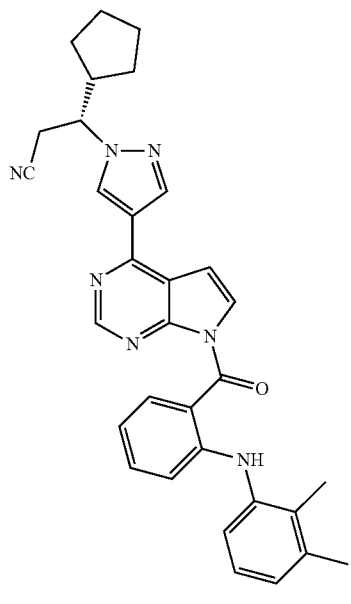
CPD-038
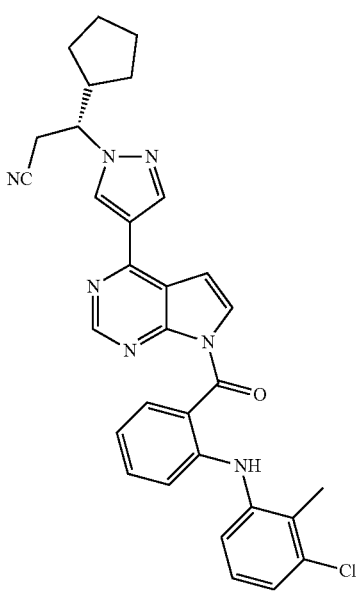
CPD-039
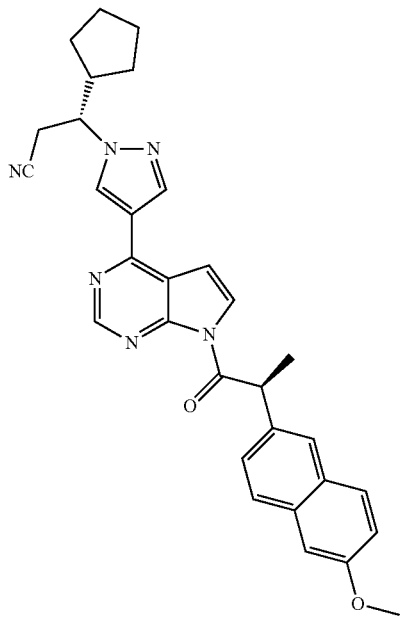
CPD-040
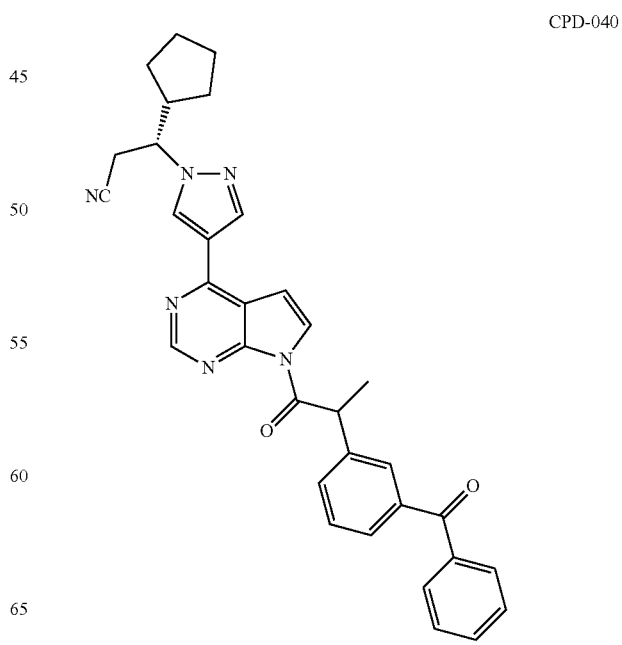

CPD-041
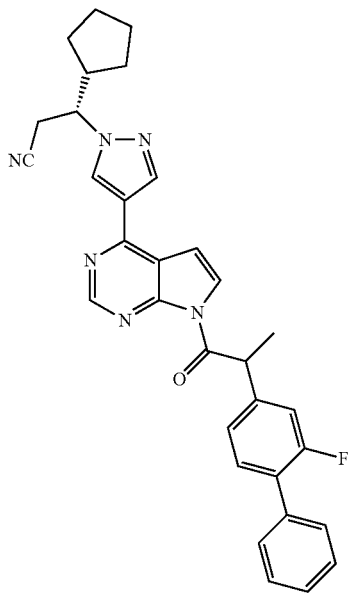
CPD-042
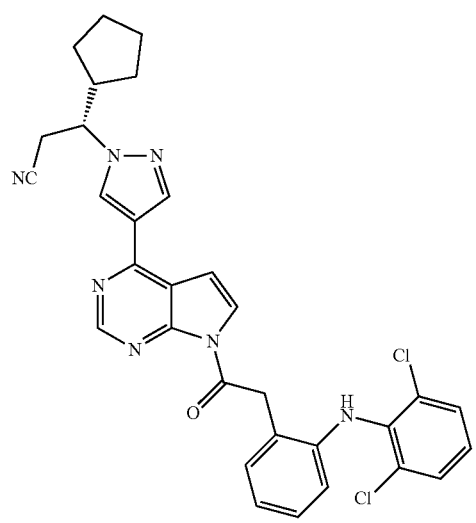
CPD-043
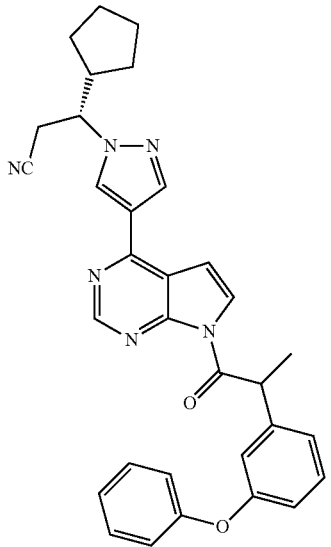
CPD-044
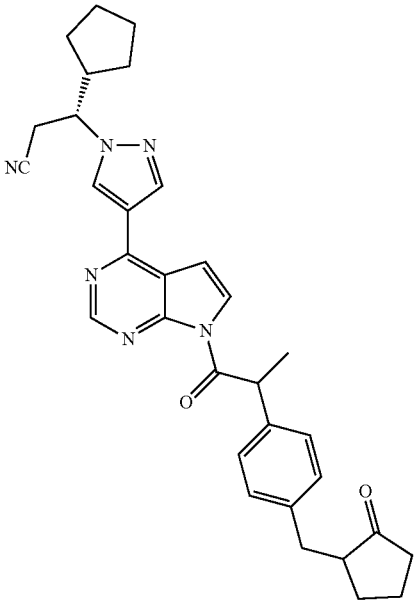
CPD-045
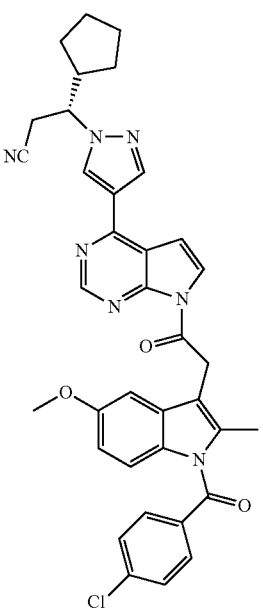

CPD-046
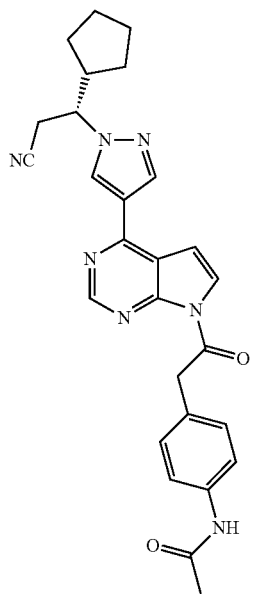
CPD-047
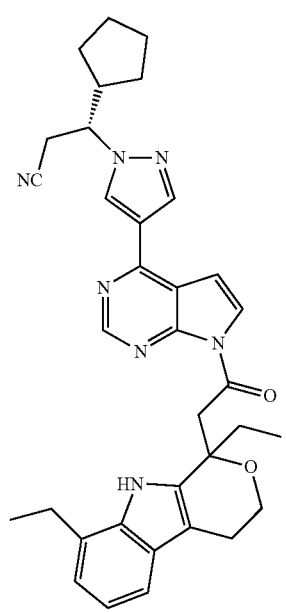
CPD-048
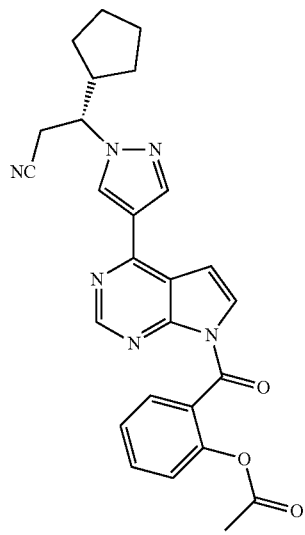
CPD-049
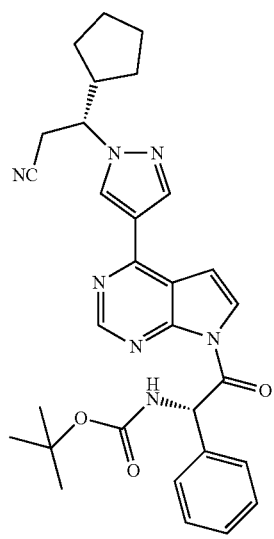
CPD-050
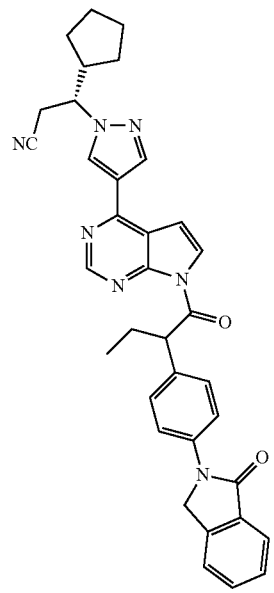

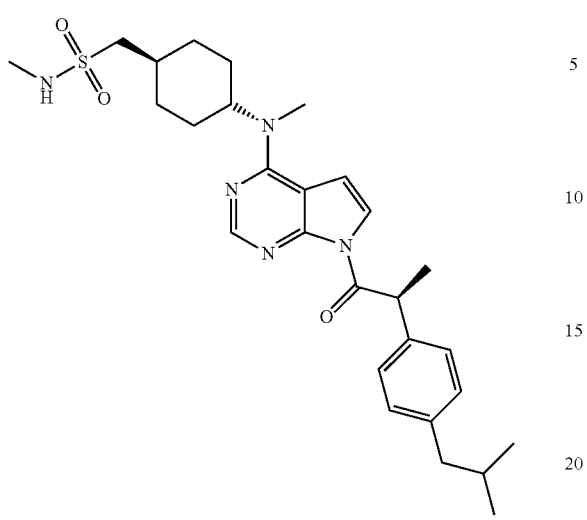
CPD-027
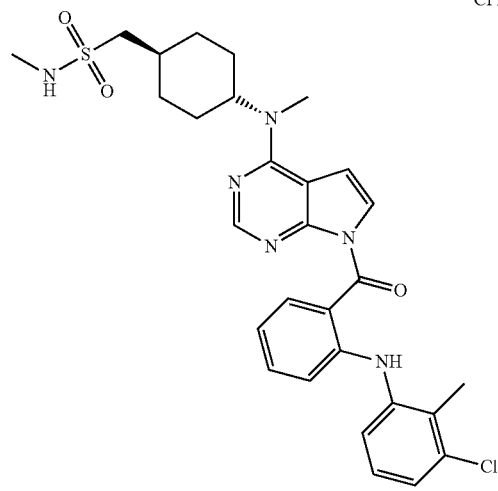
CPD-053
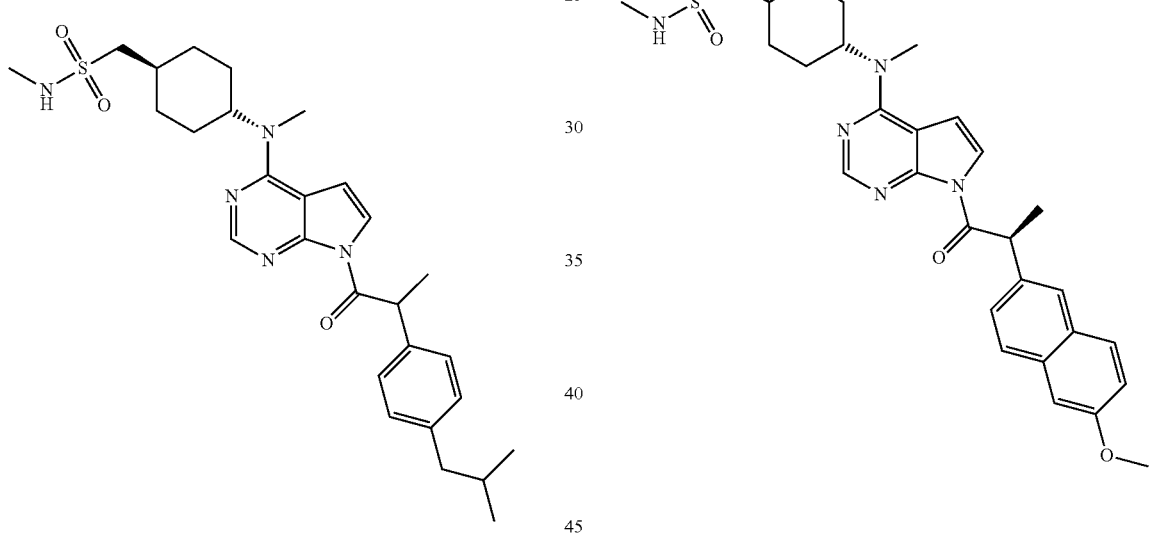
CPD-051
CPD-054
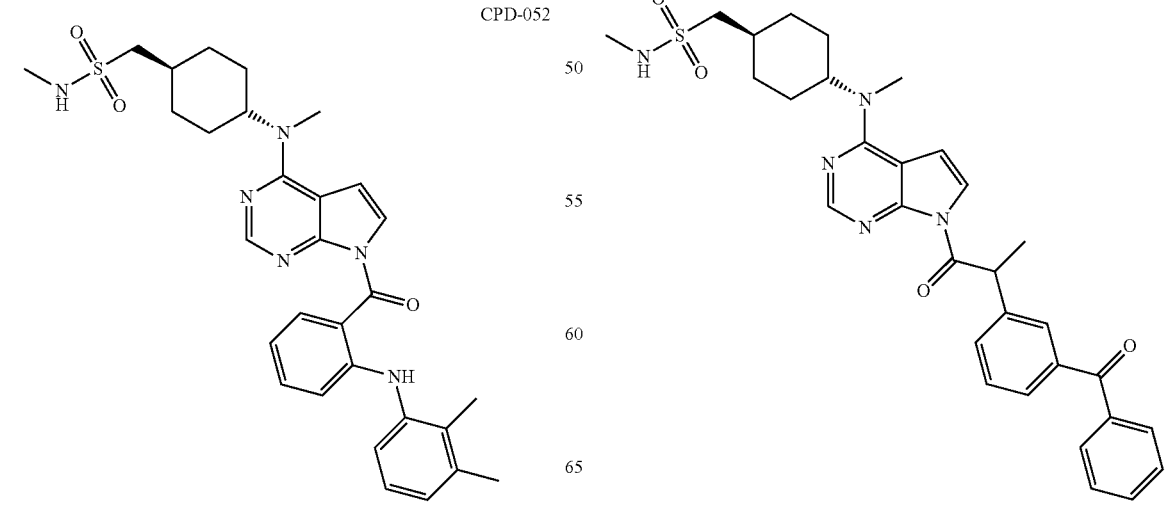
CPD-052
CPD-055

CPD-056
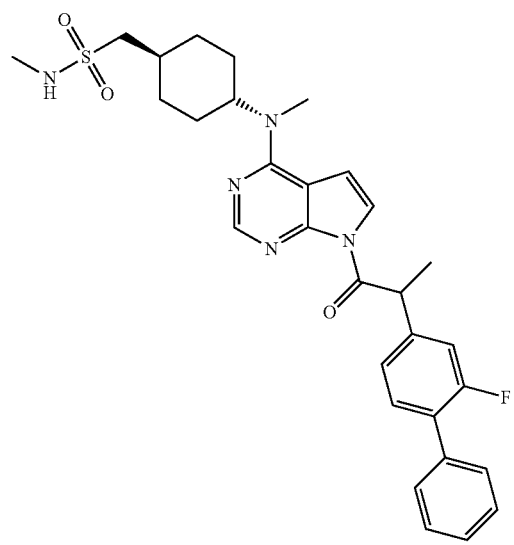
CPD-057
CPD-058
CPD-059
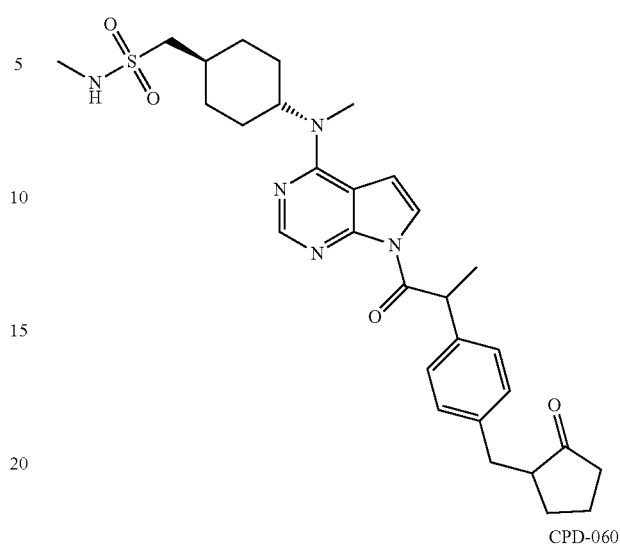
CPD-060
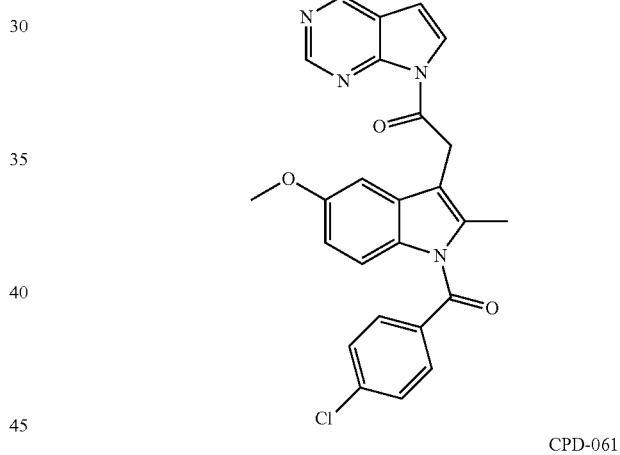
CPD-061
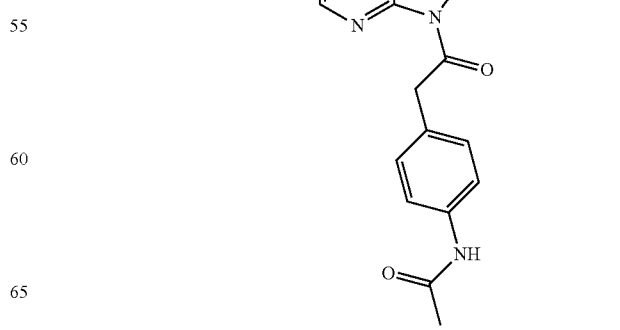

CPD-062
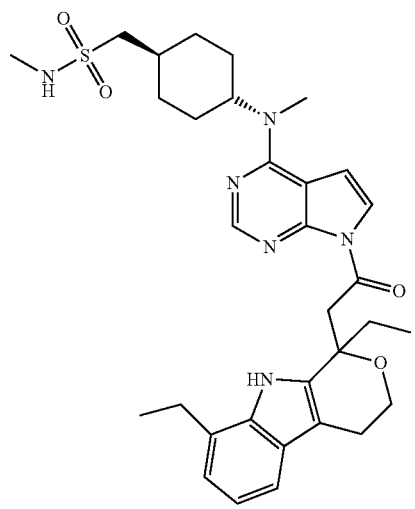
CPD-063
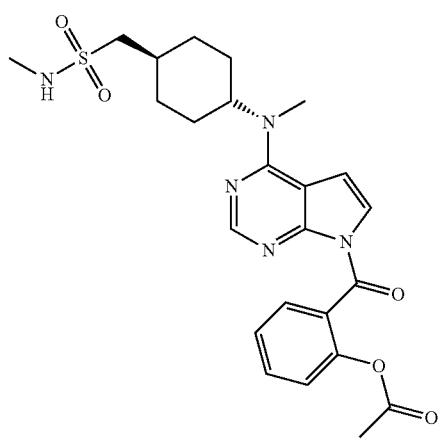
CPD-064
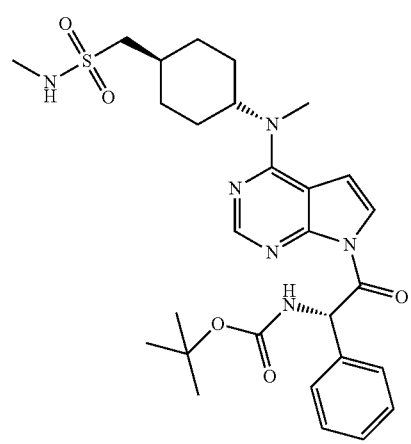
CPD-065
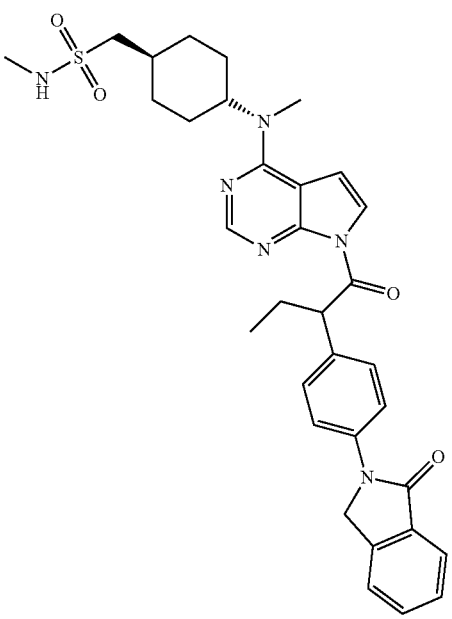
CPD-066
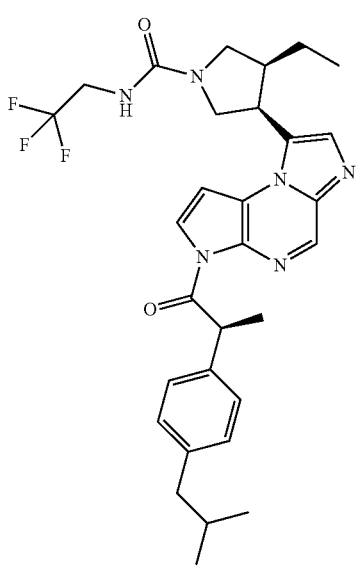

CPD-067
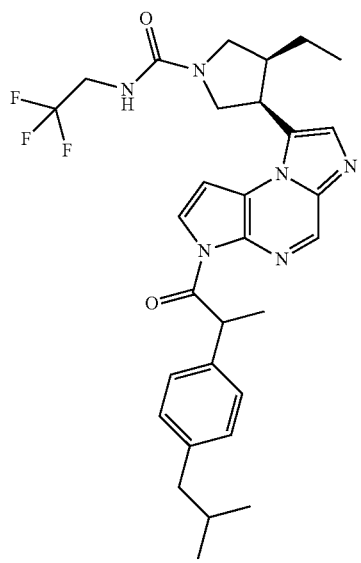
CPD-068
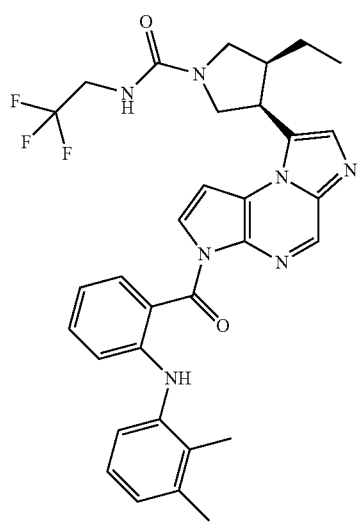
CPD-069
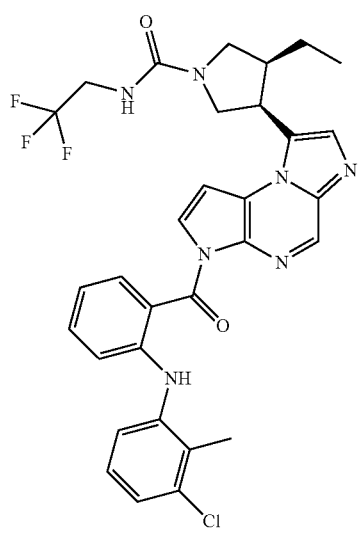
CPD-070
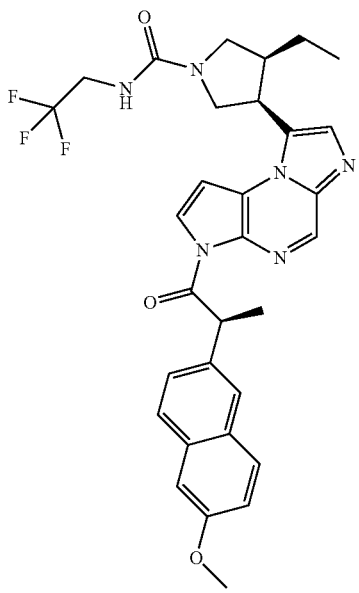
CPD-071
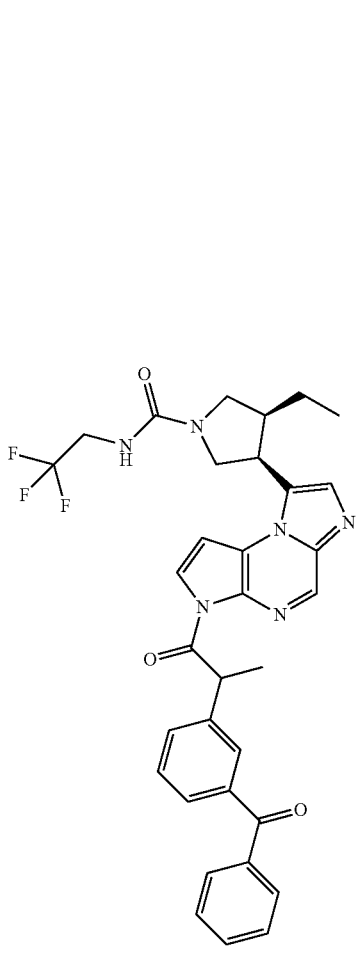

-continued
CPD-072
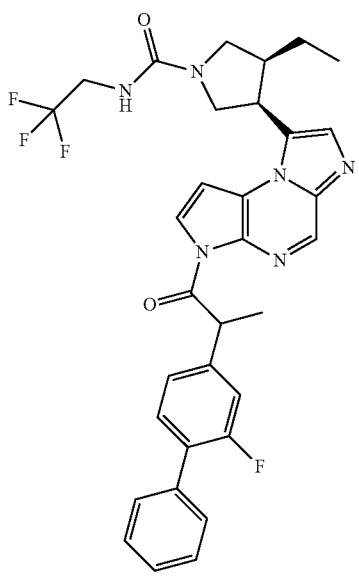
CPD-075
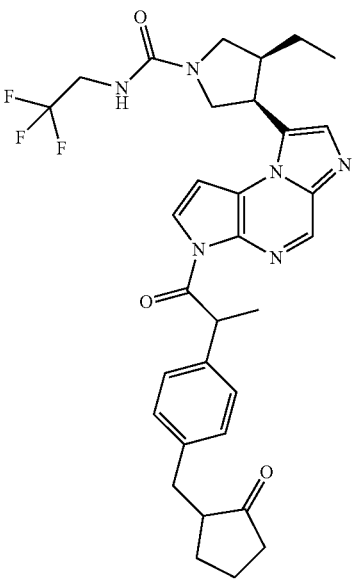
CPD-073
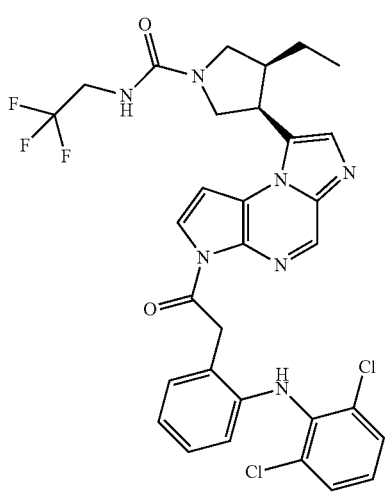
CPD-074
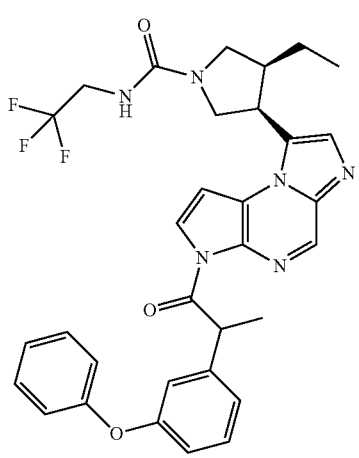
CPD-076
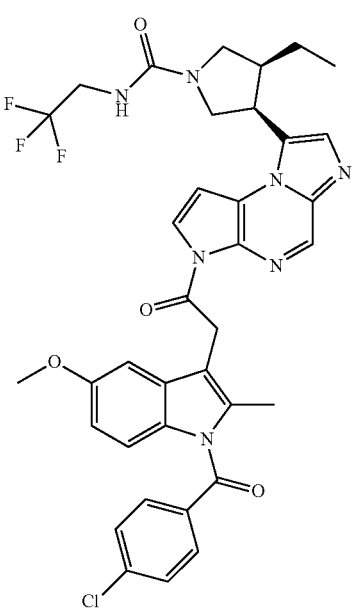

CPD-077
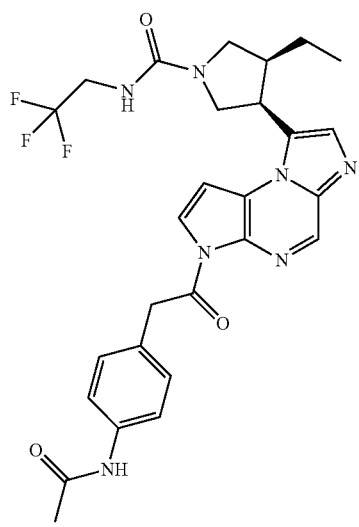
CPD-078
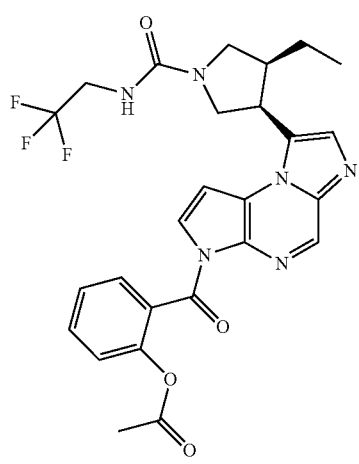
CPD-079
CPD-080
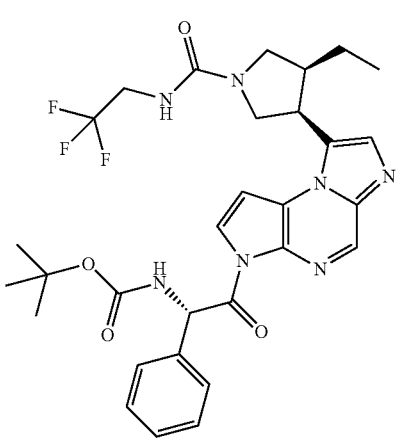
CPD-081
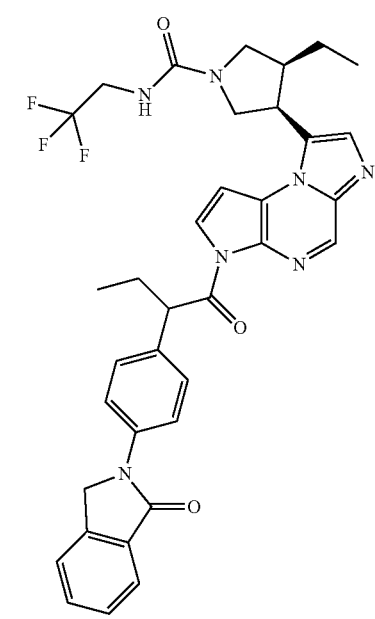
CPD-186
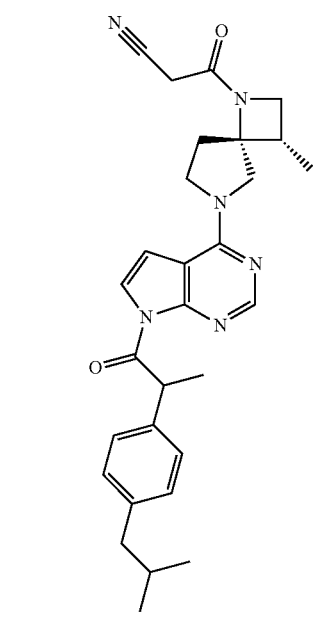

CPD-187
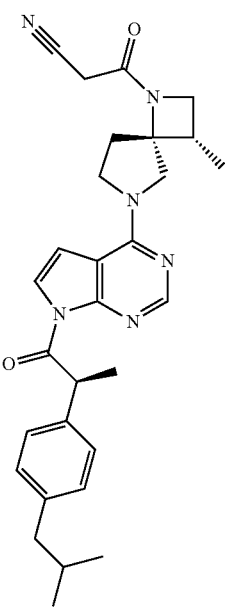
CPD-188
CPD-189
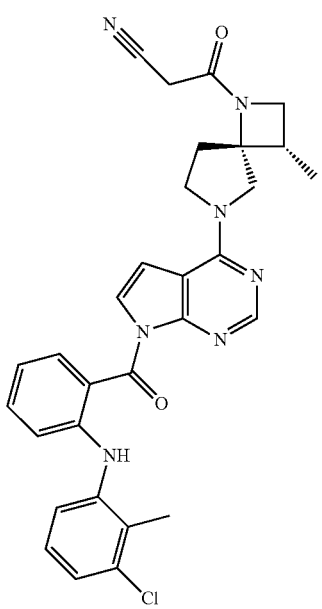
CPD-190
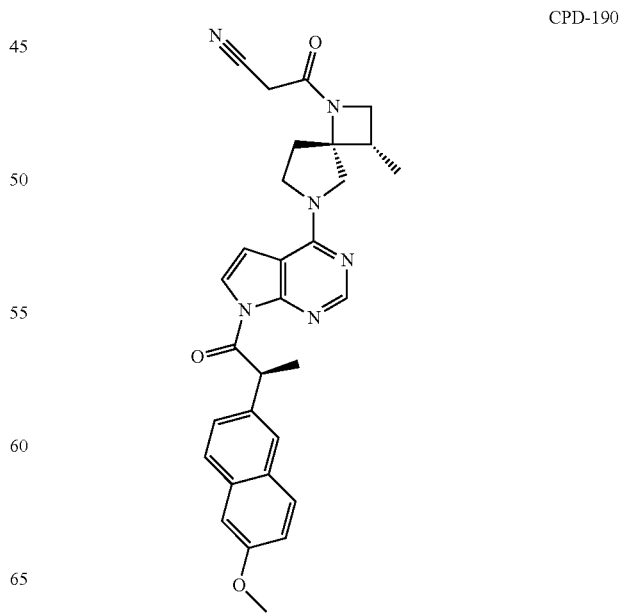

-continued
CPD-191
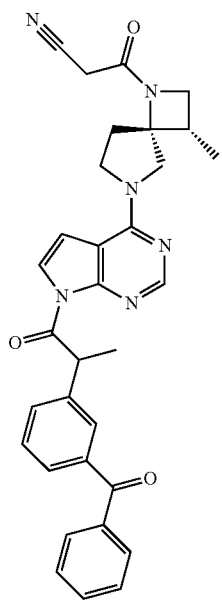
CPD-193
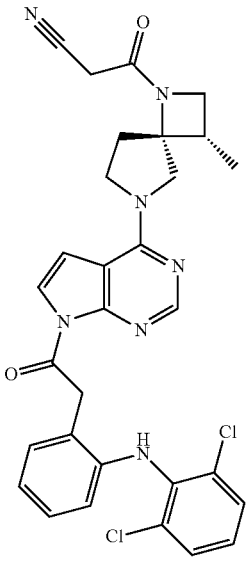
CPD-194
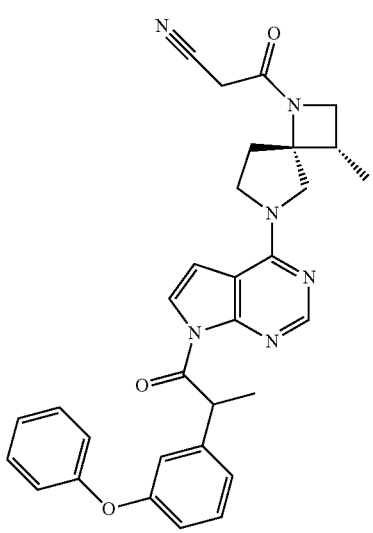
CPD-192
CPD-195
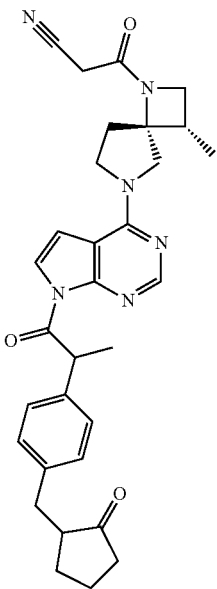

CPD-196
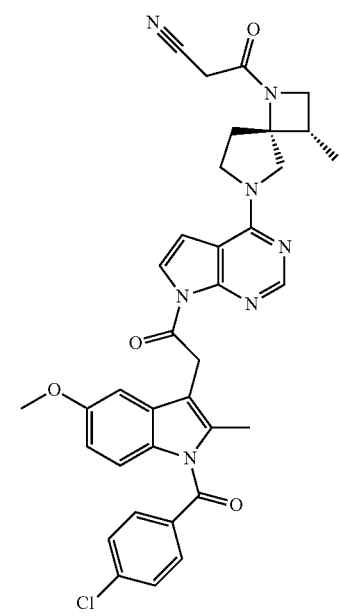
CPD-197
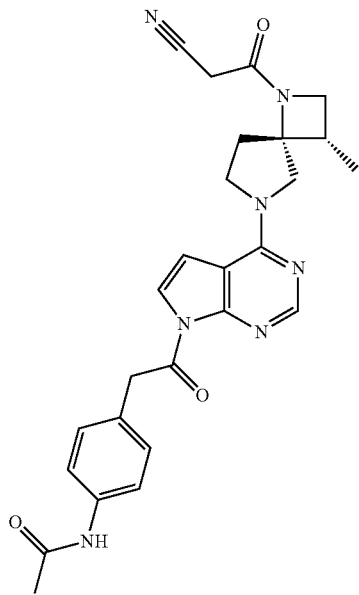
CPD-198
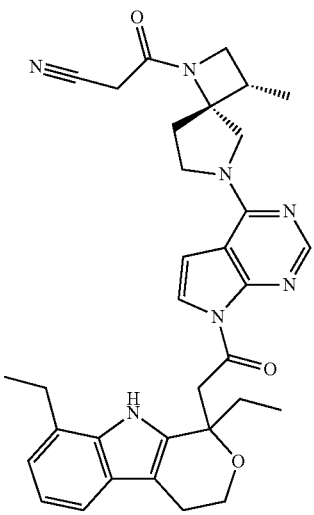
CPD-199
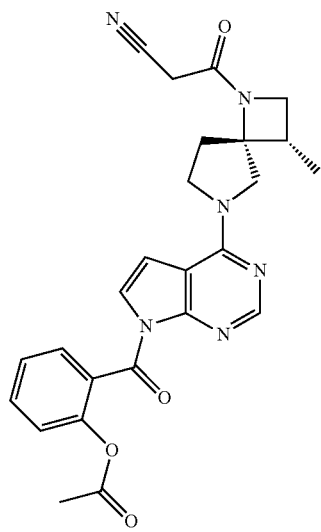
CPD-200
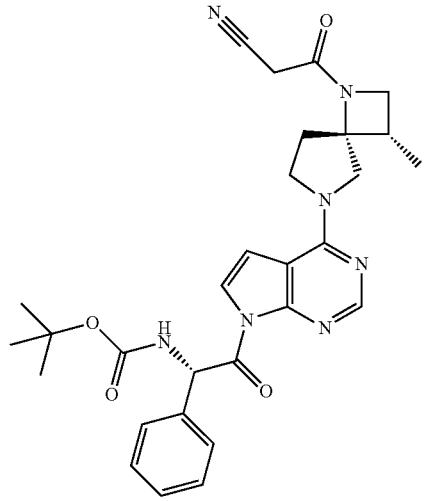

CPD-201
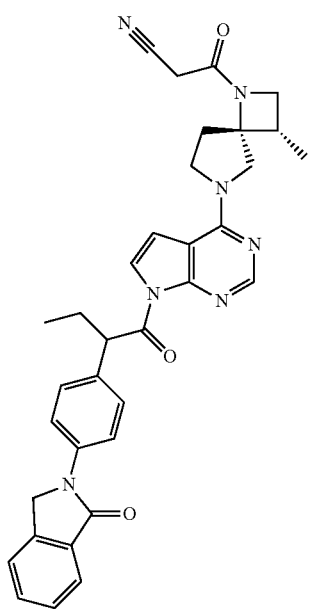
CPD-002
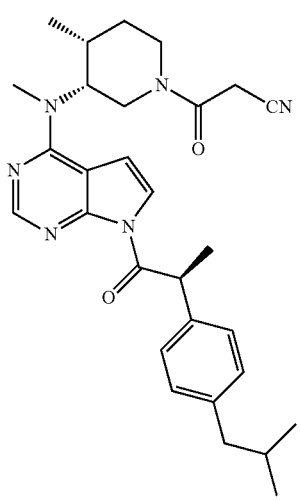
CPD-004
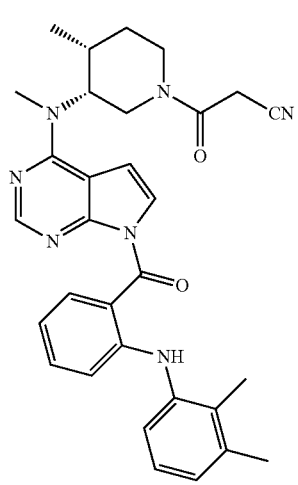
More preferably, the anti-inflammatory compound, or the stereoisomer, tautomer, nitrogen oxide, metabolite, prodrug, pharmaceutically acceptable salt, or solvate thereof of the present invention, wherein the compound is any one of the following specific compounds:
CPD-001
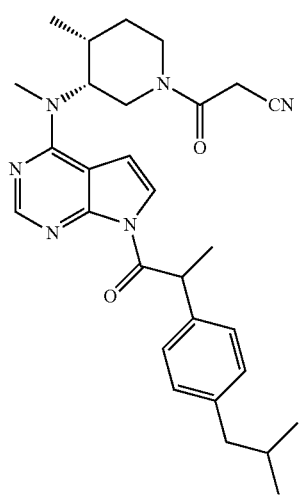
CPD-005
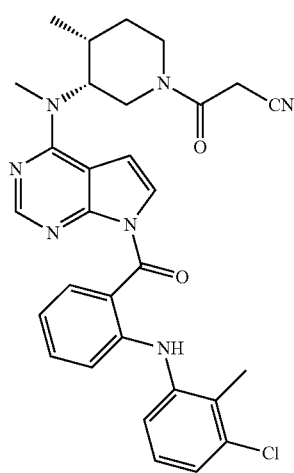

CPD-006
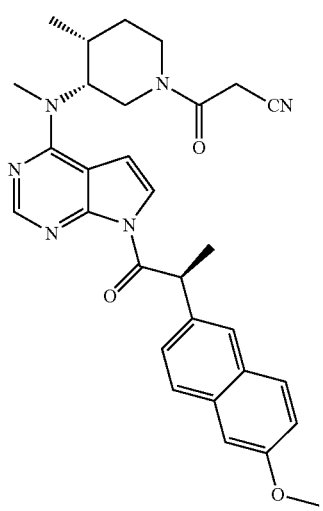
CPD-007
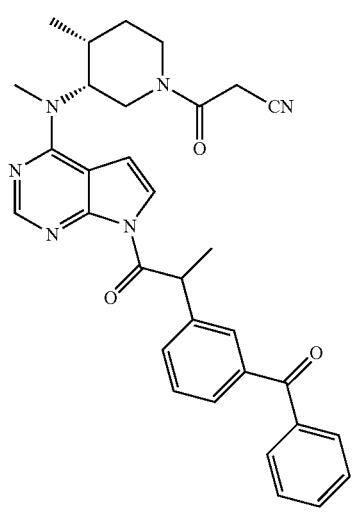
CPD-008
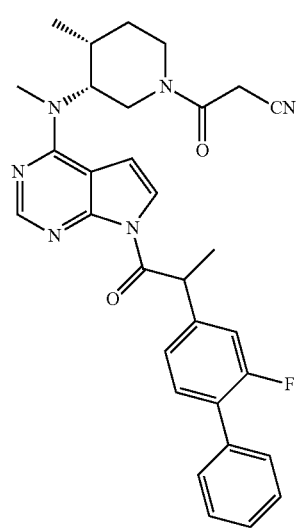
CPD-009
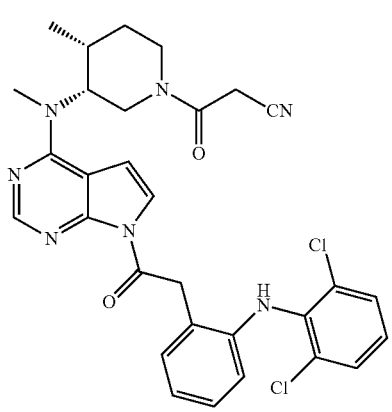
CPD-010
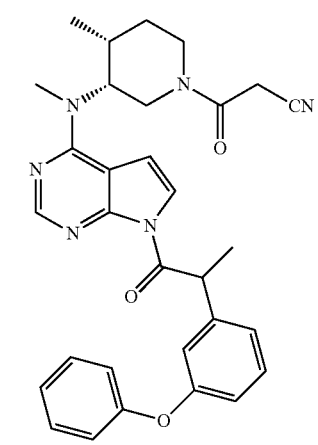
CPD-011
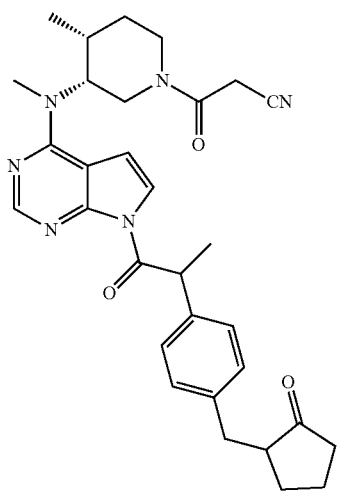

CPD-012
CPD-013
CPD-014
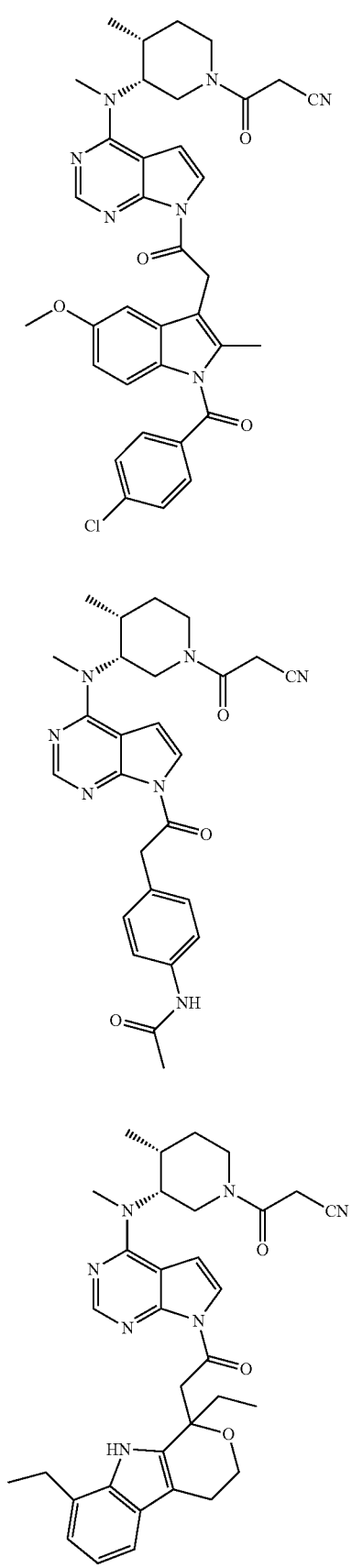
CPD-015
CPD-016
CPD-029
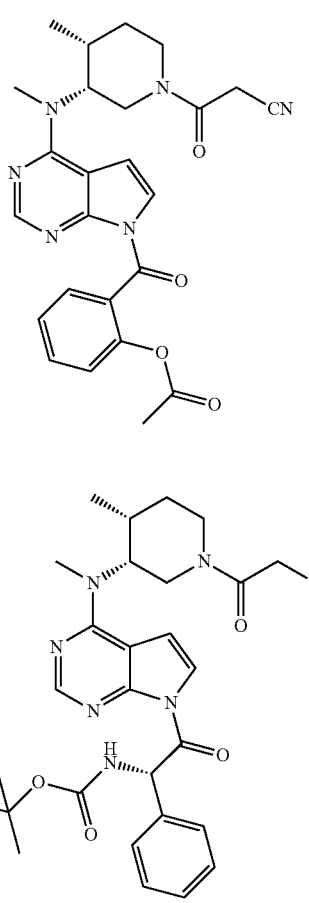
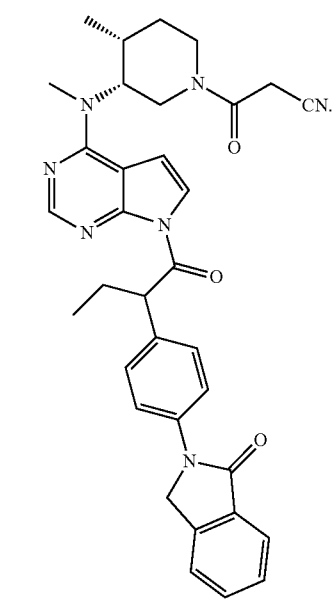
Further preferably, the anti-inflammatory compound, or the stereoisomer, tautomer, nitrogen oxide, metabolite, prodrug, pharmaceutically acceptable salt, or solvate thereof of the present invention, wherein the compound is one of the following specific compounds:

CPD-017
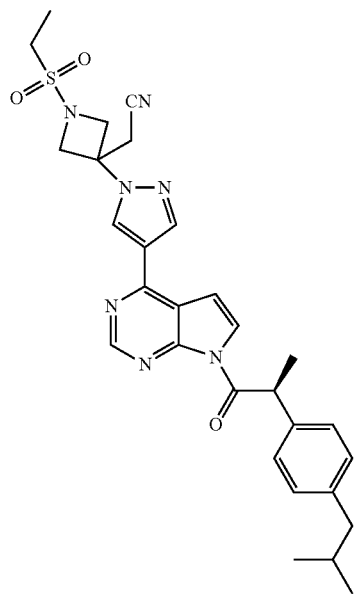
CPD-019
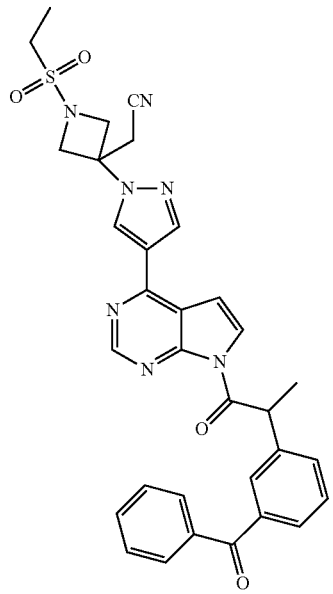
CPD-018
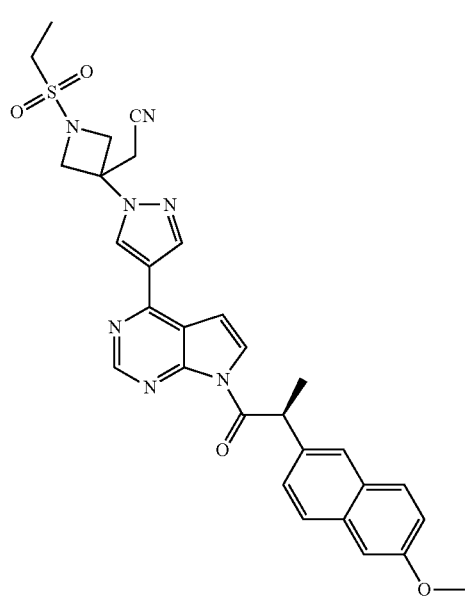
CPD-020
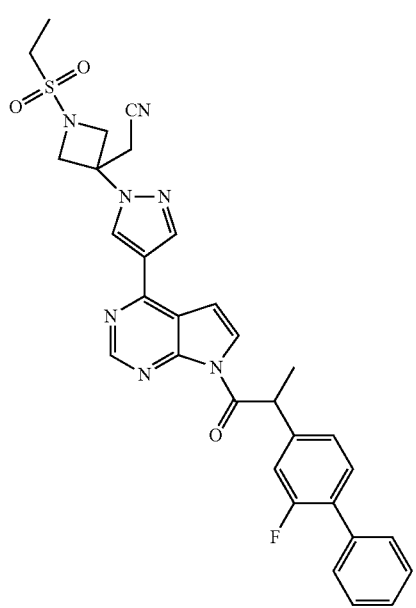

CPD-021
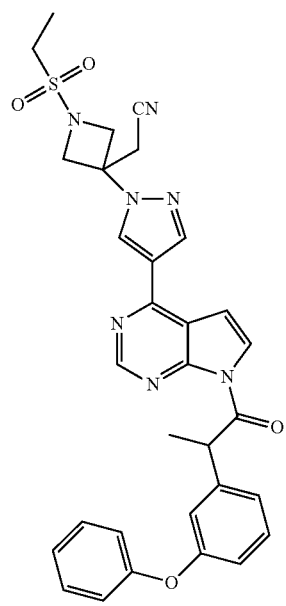
CPD-023
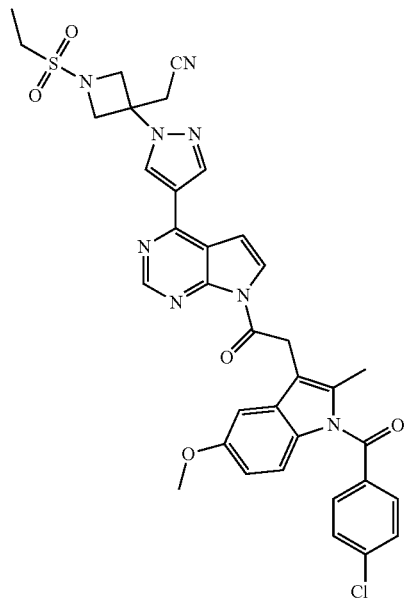
CPD-022
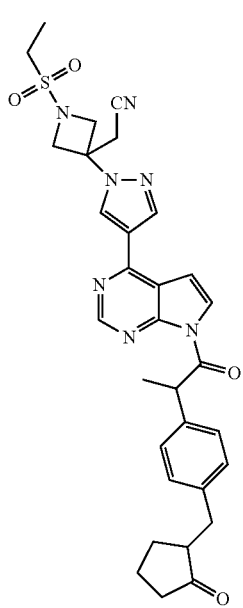
CPD-024
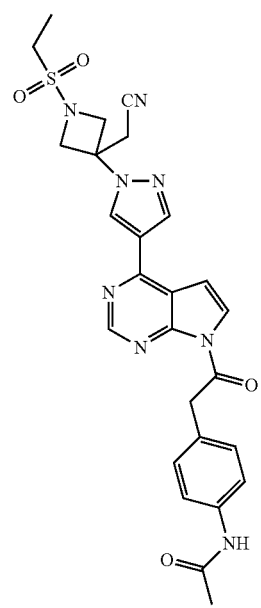

CPD-025
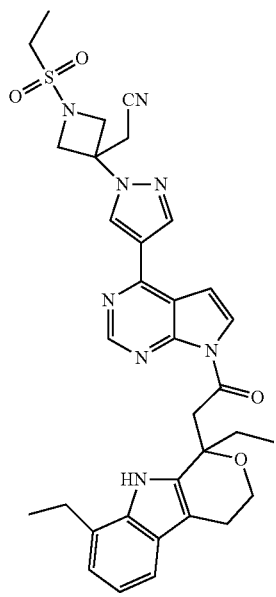
CPD-027
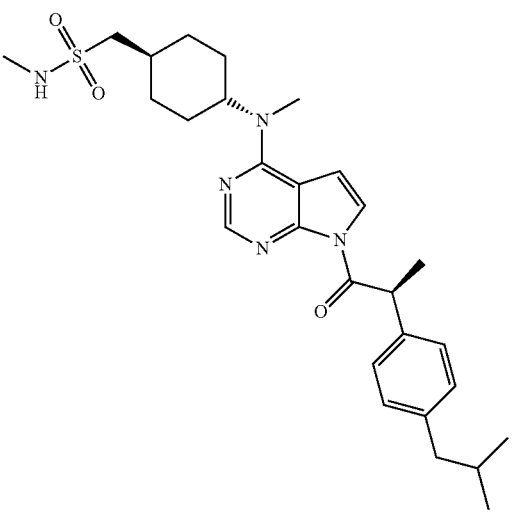
CPD-026
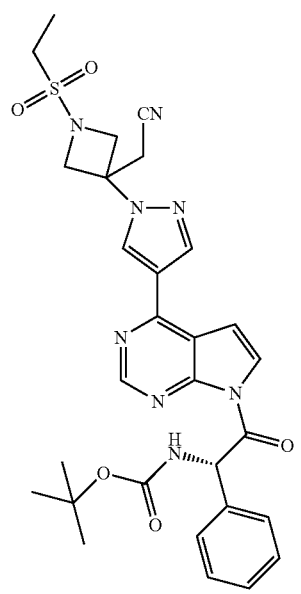
CPD-028
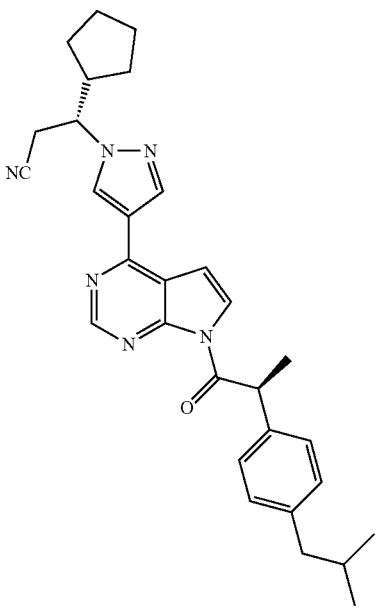

CPD-030
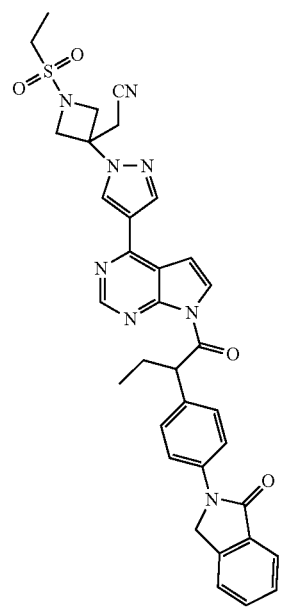
CPD-039
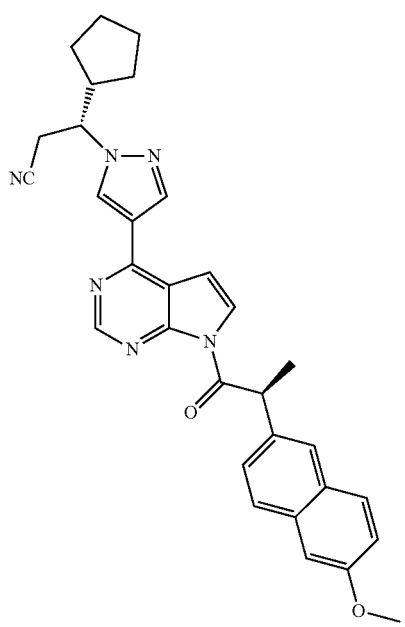
CPD-040
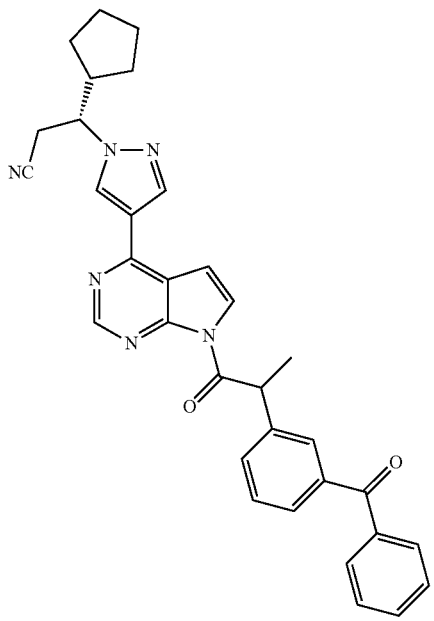
CPD-041
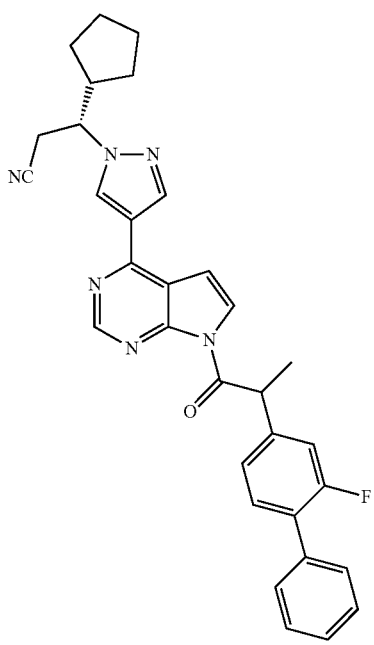

CPD-050
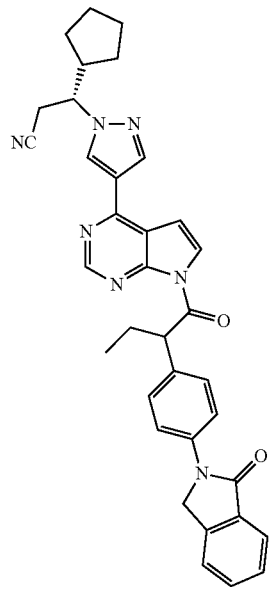
CPD-056
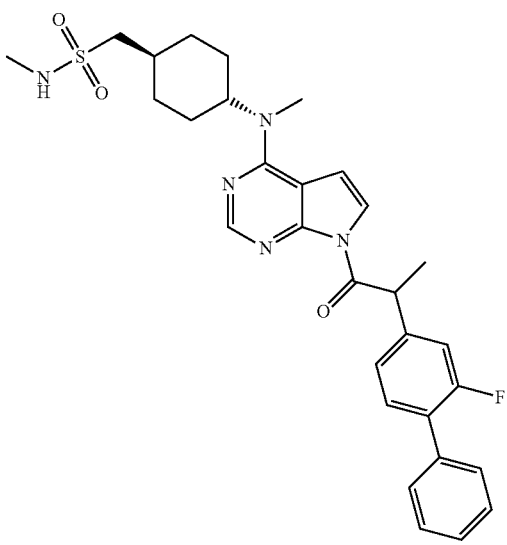
CPD-062
CPD-065
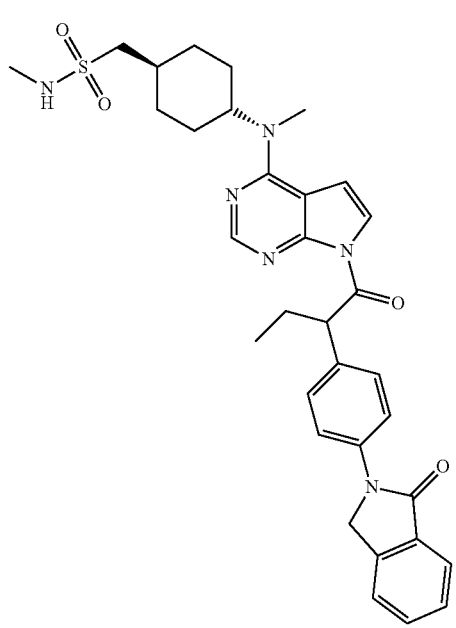
CPD-055
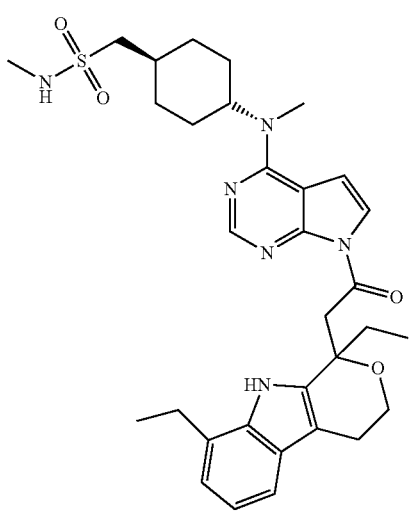

-continued

CPD-054

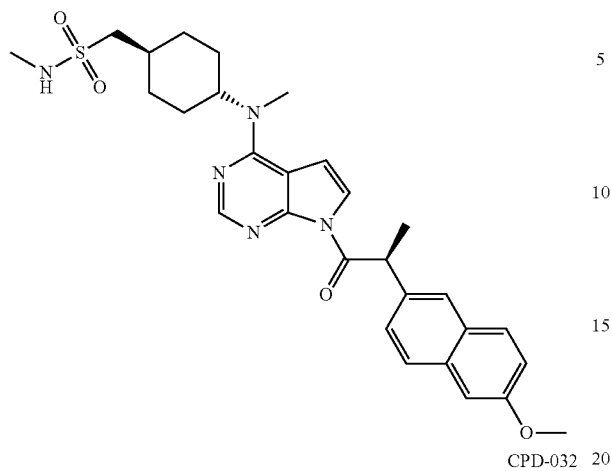

CPD-032

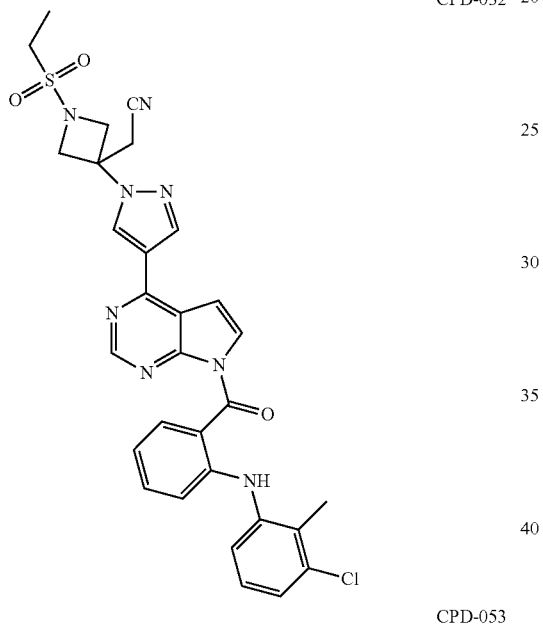

CPD-053

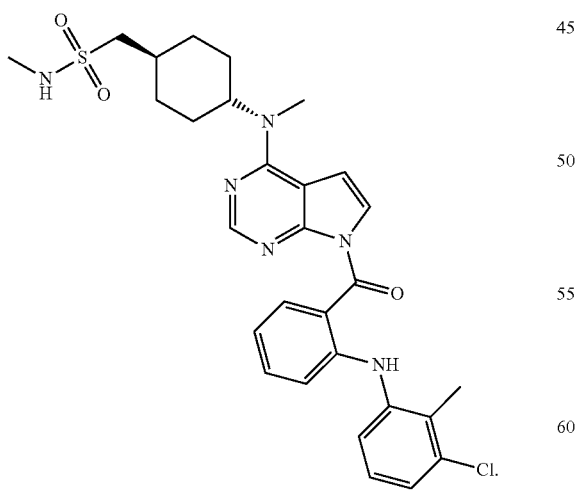

In another scheme of the present invention, the present invention provides an anti-inflammatory compound, or a stereoisomer, tautomer, nitrogen oxide, metabolite, prodrug, pharmaceutically acceptable salt, or solvate thereof, having a structure shown in general formula (III):

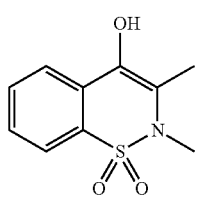
(III)

(IIIa)

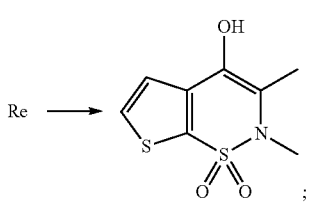

wherein $R_1$ has the same meaning as $R_1$ in general formula (II); $R_{1a}$ has the same meaning as $R_{1a}$ in formula (IIa); $R_2'$ in formula (III) and formula (IIIa) are both Y—B, B is $B_1$ in formula (II) or (IIa), or B is $B_2$; wherein the group —$B_1$ is a group formed by dehydroxylation of a carboxylic acid compound $B_1$ and Y— is (CH$_2$)—O—; the group —$B_2$ is a group formed by dehydrogenation of a hydroxyl-containing compound $B_2$ and Y— is —(CH$_2$)—; the group —$B_1$ has the same meaning as the $R_2$ group in formula (II) or in formula (IIa); the group —$B_2$ is $R_c$—CO—NH—$R_d$, wherein $R_c$ is a 4-hydroxy-benzothiazine dioxide-3-yl represented by the following structural formula (a)(wherein the phenyl ring may be substituted by halogen or $C_1$-$C_6$ alkyl), or a 4-hydroxy-Re substituted thienothiazine dioxide-3-yl represented by the following structural formula (b), wherein —CO—NH—$R_d$ is bonded at the 3-position of the thiazine ring, (a)

(b)

wherein $R_d$ is thiazole, isothiazole, oxazole, isoxazole, or pyridine or the group thereof substituted with $C_1$-$C_6$ alkyl or halogen, preferably a thiazole or isoxazole substituted with methyl; and unsubstituted pyridyl; $R_e$ is $C_1$-$C_6$ alkyl or halogen (preferably halogen is one or two or more selected from a group consisting of fluorine, chlorine, or bromine); a arrow next to $R_e$ in formula (b) indicates that its substitution position on the thiophene ring may be any carbon-linked hydrogen atom capable of undergoing substitution.

More specifically, the anti-inflammatory compound or a stereoisomer, tautomer, nitrogen oxide, metabolite, prodrug, pharmaceutically acceptable salt, or solvate thereof of the present invention, wherein —B$_1$ is a group after dehydroxylation of a carboxylic acid moiety selected from a group consisting of ibuprofen, (S)-(+)-ibuprofen, naproxen, fenoprofen, flurbiprofen, loxoprofen, ketoprofen, diclofenac, etodolac, actarit, indomethacin, N-Boc-L-phenylglycine, aspirin, indobufen, mefenamic acid and tolfenamic acid:

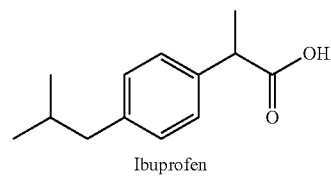
Ibuprofen

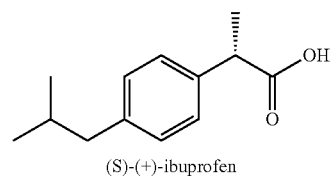
(S)-(+)-ibuprofen

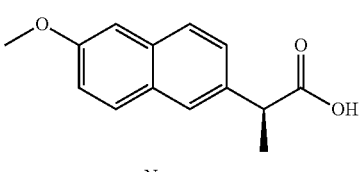
Naproxen

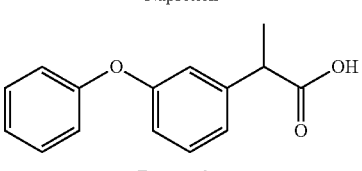
Fenoprofen

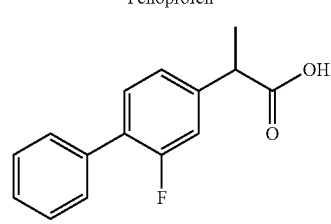
Flurbiprofen

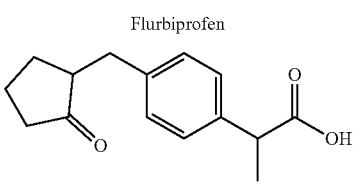
Loxoprofen

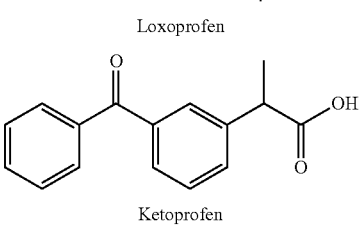
Ketoprofen

-continued

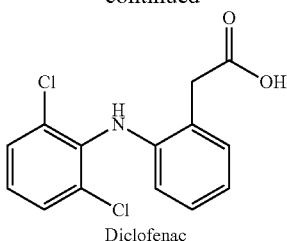
Diclofenac

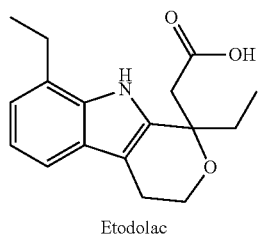
Etodolac

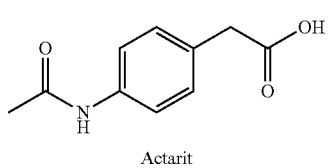
Actarit

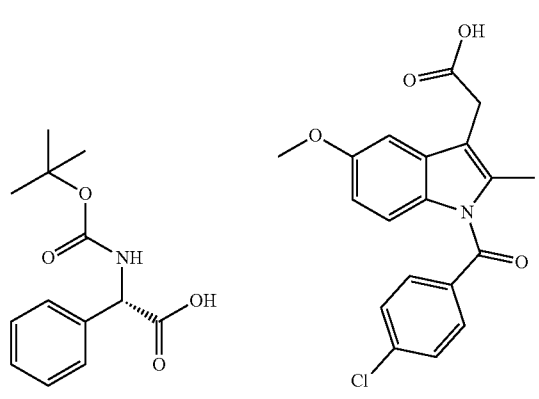
N-Boc-L-phenylglycine          Indomethacin

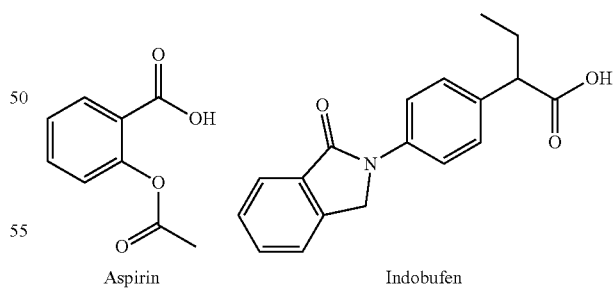
Aspirin          Indobufen

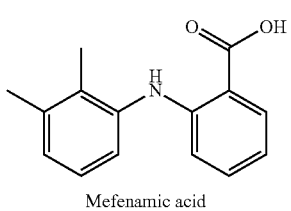
Mefenamic acid

-continued

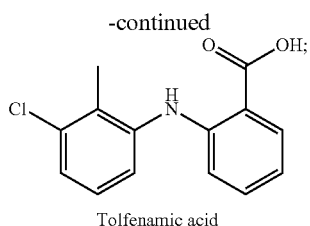

Tolfenamic acid

—B₂ is a group after dehydrogenation of a hydroxyl-containing compound of one of the following specific compounds:

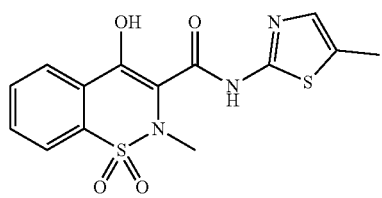

Meloxicam

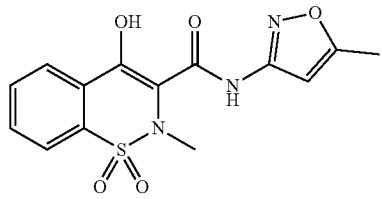

Isoxicam

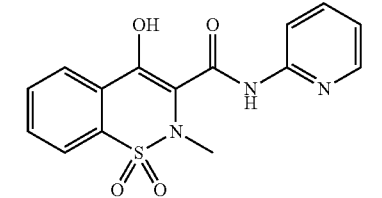

Piroxicam

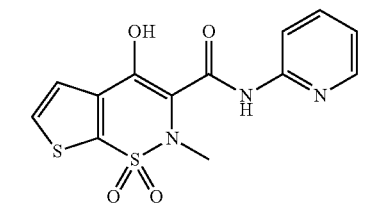

Tenoxicam

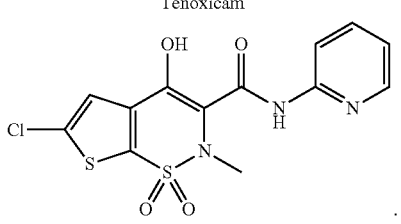

Lornoxicam

Furthermore, more specifically, the anti-inflammatory compound, or the stereoisomer, tautomer, nitrogen oxide, metabolite, prodrug, pharmaceutically acceptable salt, or solvate thereof of the present invention, obtained by a preparation method comprising the steps of:

2) reacting A-CH₂—OH compound with an acyl chloride of B or directly with the B compound;

Wherein the A-CH₂—OH compound is preferably prepared by the following step 1): reacting the amine compound A to form the A-CH₂—OH compound.

More specifically, the anti-inflammatory compound, or a stereoisomer, tautomer, nitrogen oxide, metabolite, prodrug, pharmaceutically acceptable salt, or solvate thereof described above, wherein A- is a group after dehydrogenation of an amine compound selected from a group consisting of any one of the following groups: tofacitinib, baricitinib, oclacitinib, ruxolitinib, upadacitinib and delgocitinib:

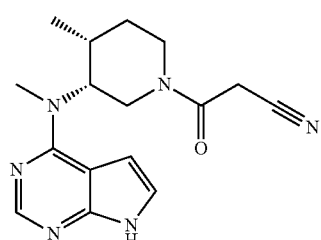

Tofacitinib

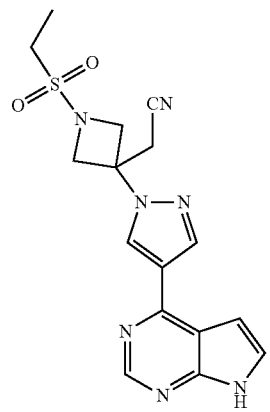

Baricitinib

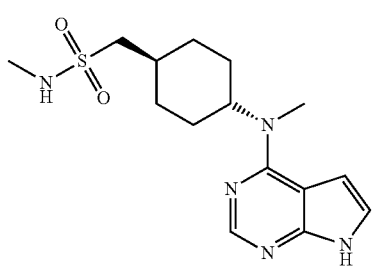

Oclacitinib

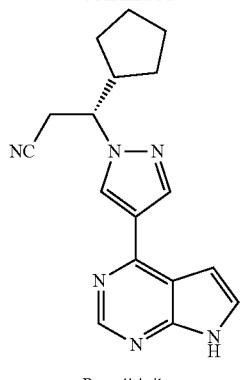

Ruxolitinib

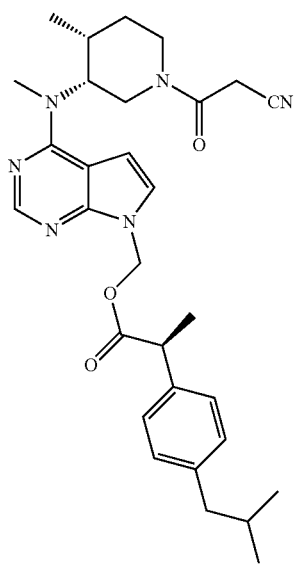

CPD-003

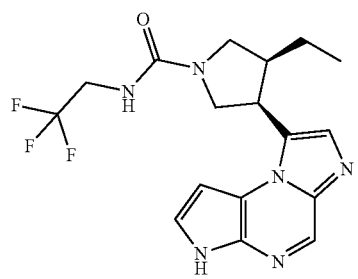

Upadacitinib

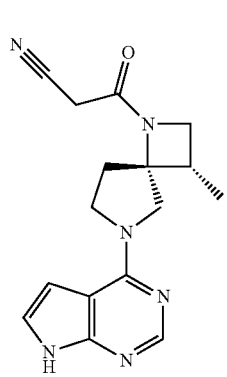

Delgocitinib preferably A is a group formed after dehydrogenation of tofacitinib, ruxolitinib, and baricitinib.

In certain embodiments, A is a group formed by any one of baricitinib, oclacitinib, or upadacitinib.

Further, more specifically, the anti-inflammatory compound, or the stereoisomer, tautomer, nitrogen oxide, metabolite, prodrug, pharmaceutically acceptable salt, or solvate thereof described above, wherein the compound is any one of the following specific compounds:

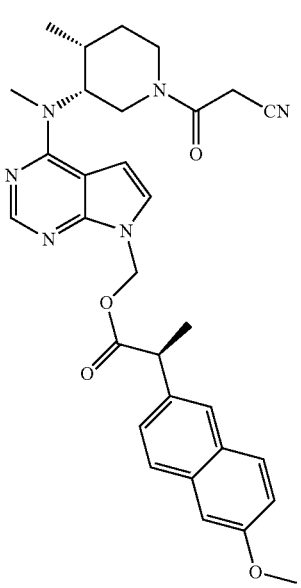

CPD-082

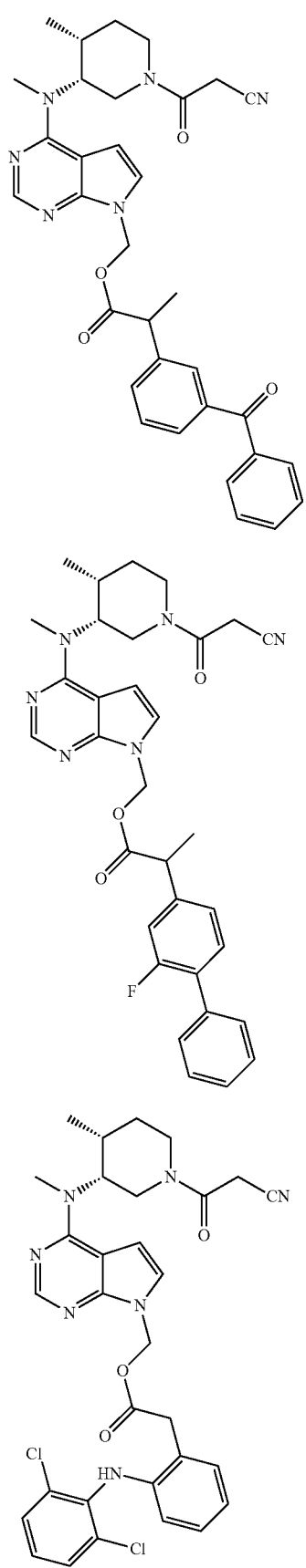
CPD-083
CPD-084
CPD-085
CPD-086
CPD-087

-continued
CPD-088
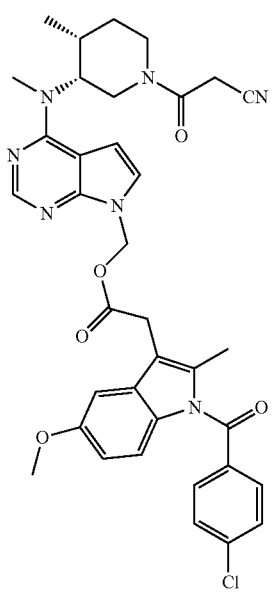
CPD-091
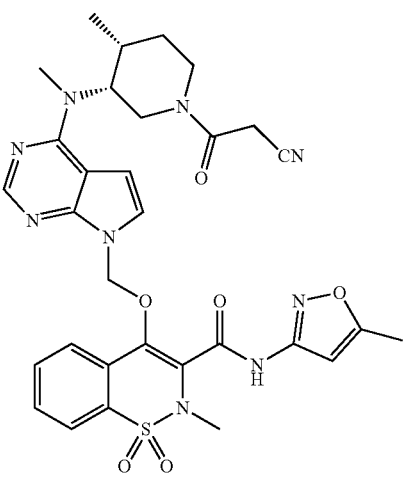
CPD-089
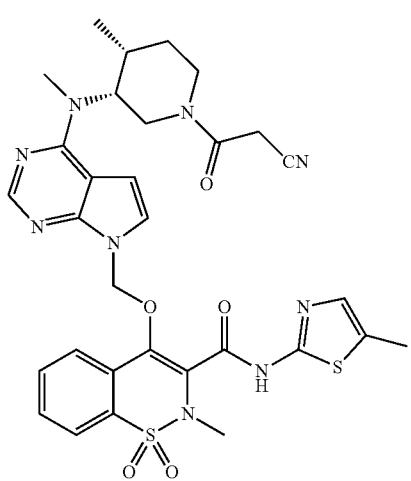
CPD-090
CPD-092
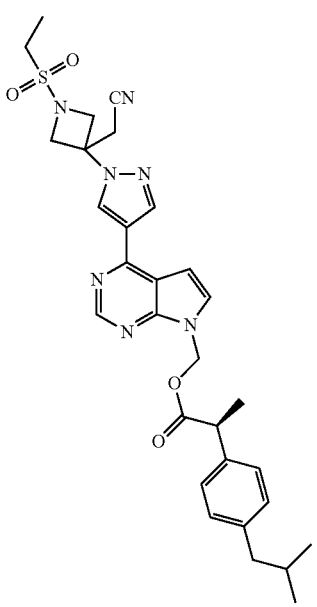

CPD-093
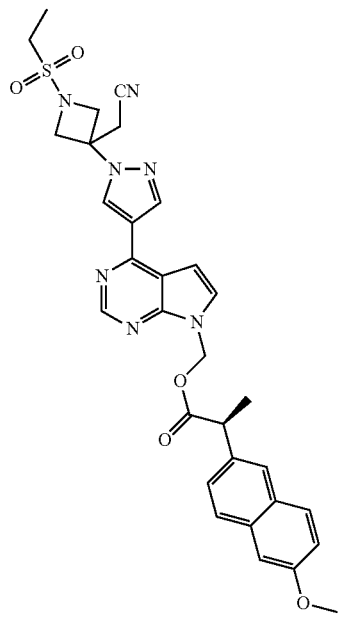
CPD-095
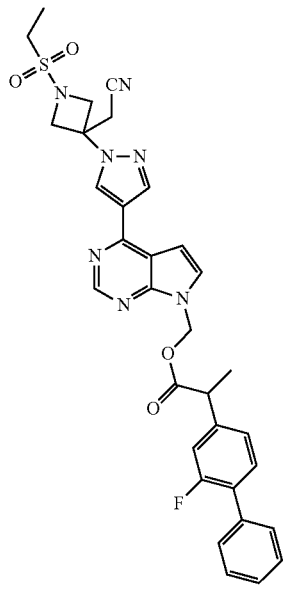
CPD-094
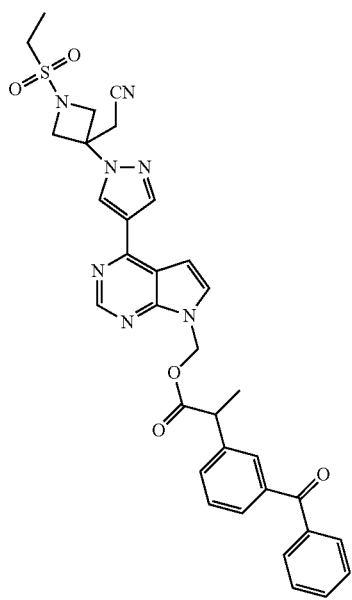
CPD-096
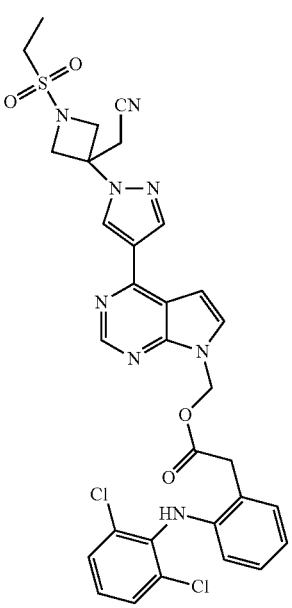

CPD-097
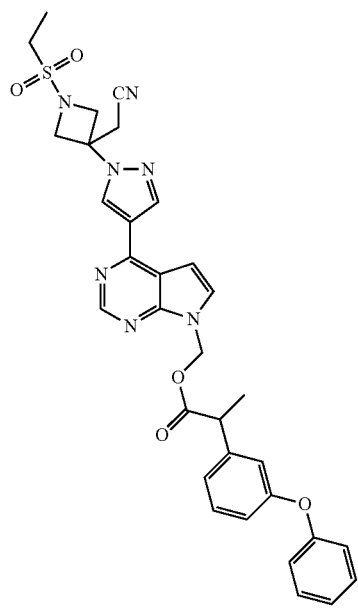
CPD-098
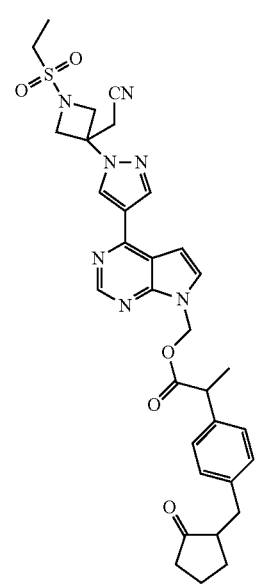
CPD-099
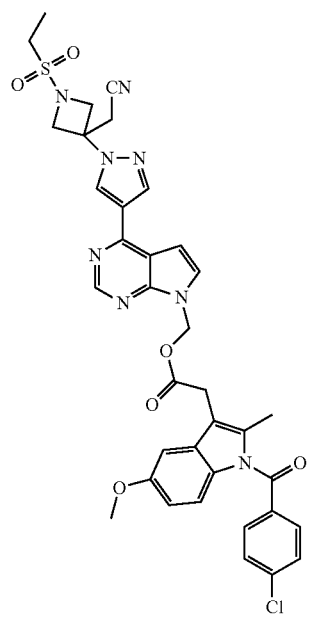
CPD-100
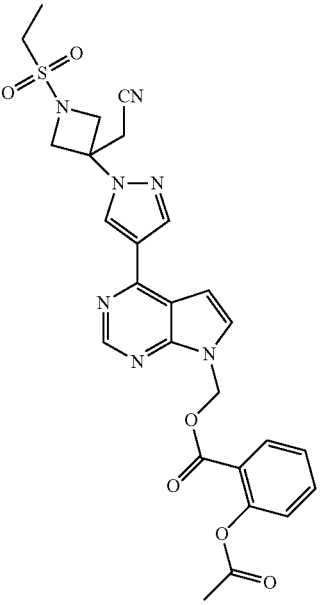

CPD-101
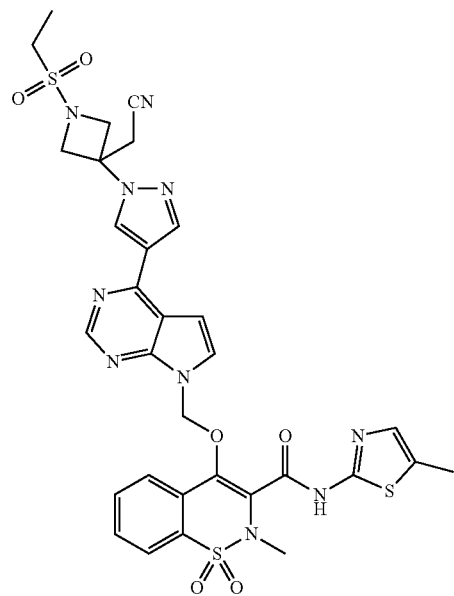
CPD-103
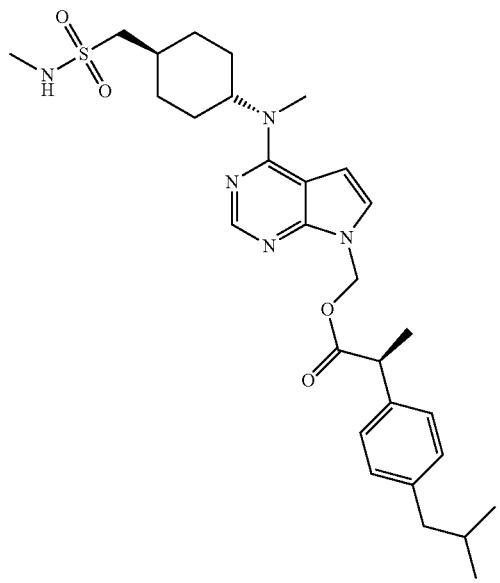
CPD-102
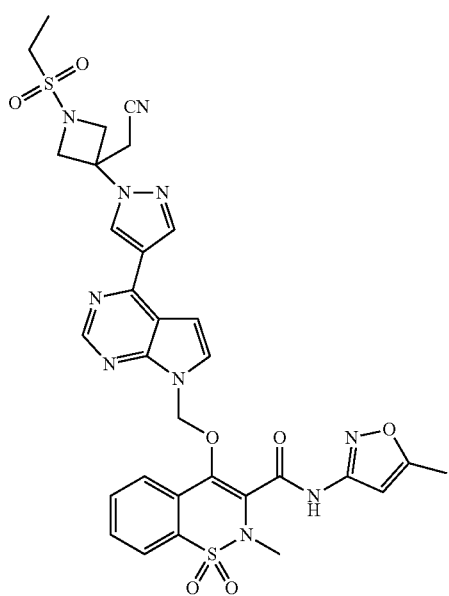
CPD-104
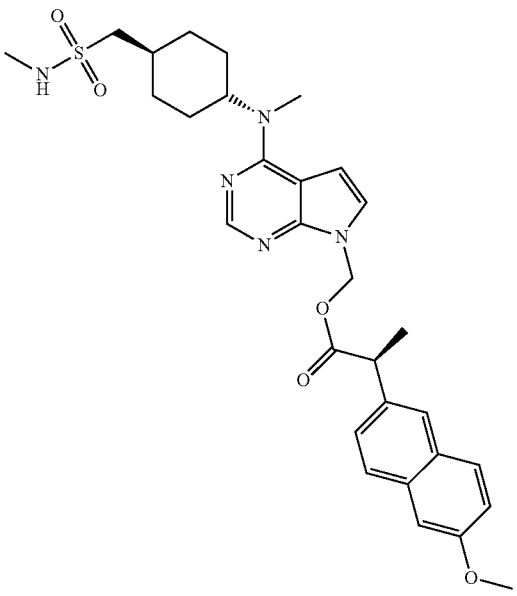

CPD-105
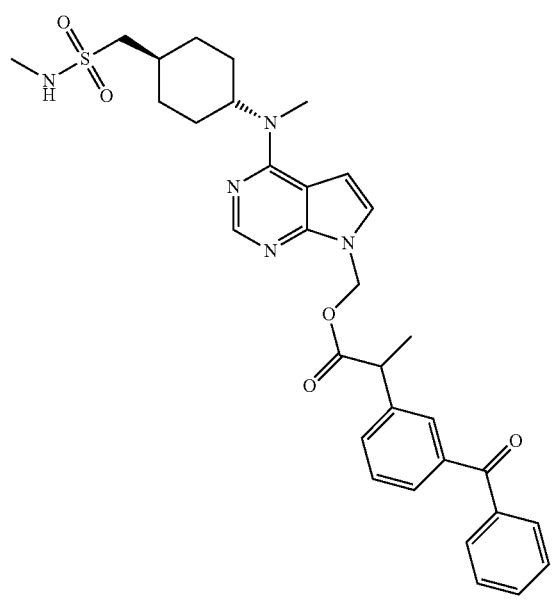
CPD-107
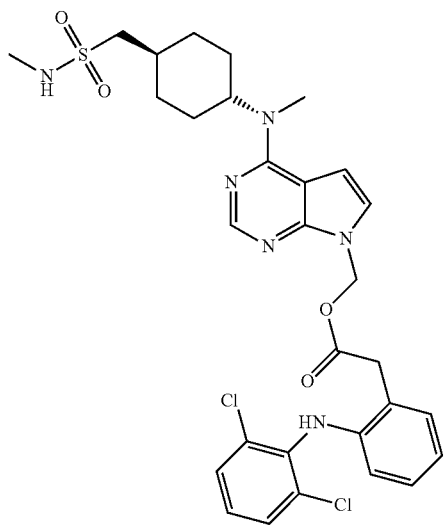
CPD-106
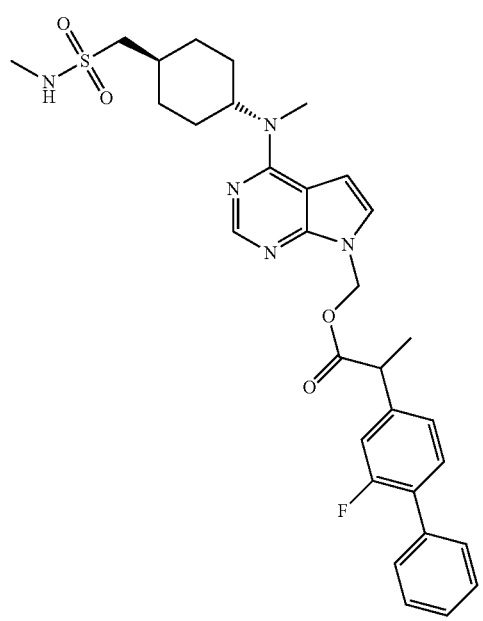
CPD-108
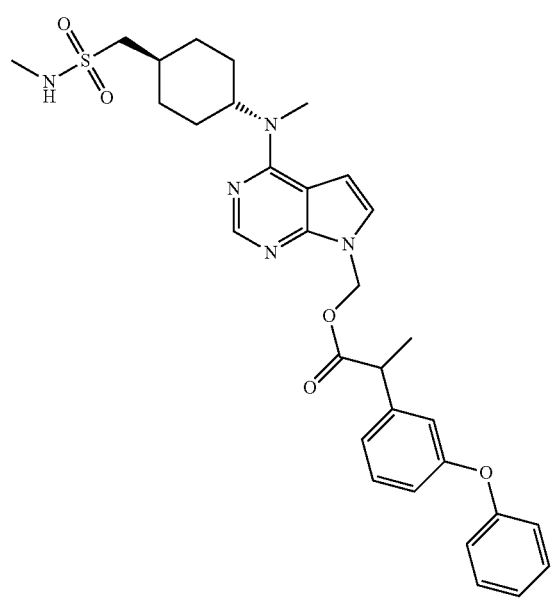

CPD-109
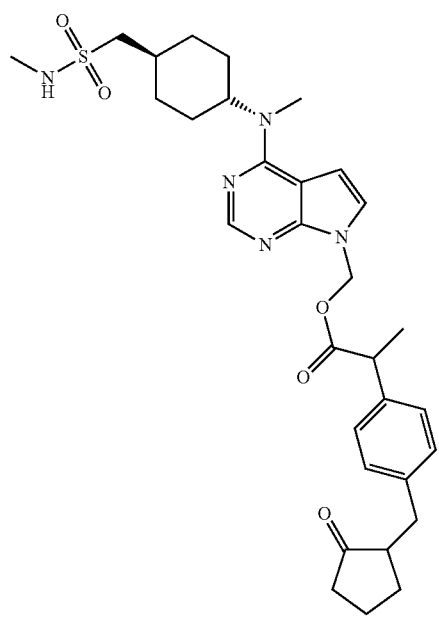
CPD-110
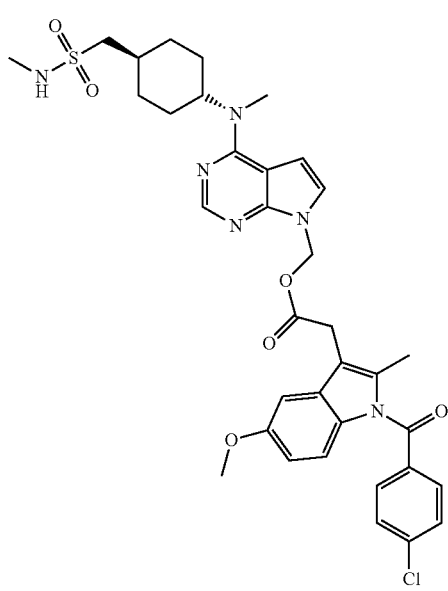
CPD-111
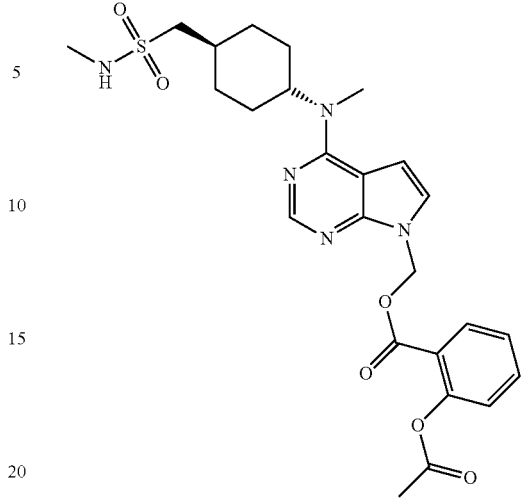
CPD-112
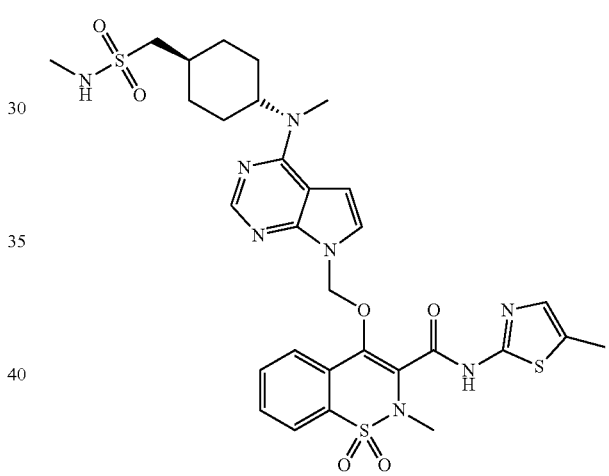
CPD-113
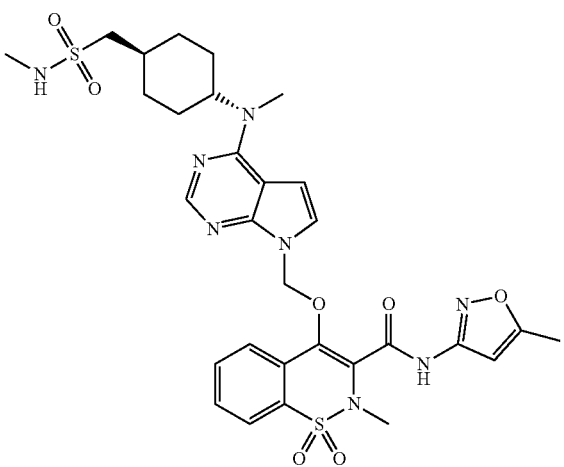

CPD-114
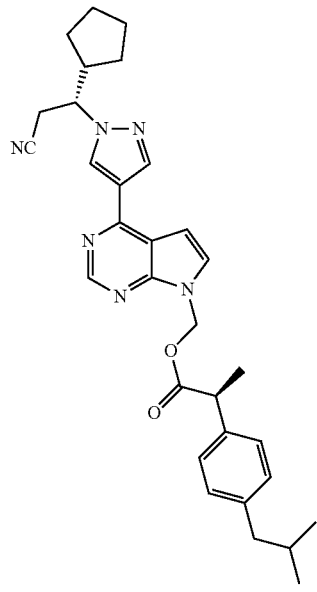
CPD-116
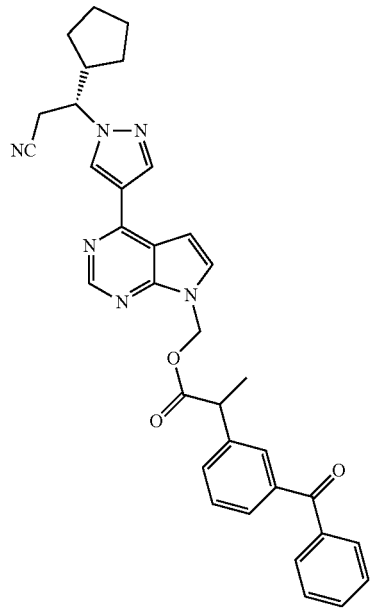
CPD-115
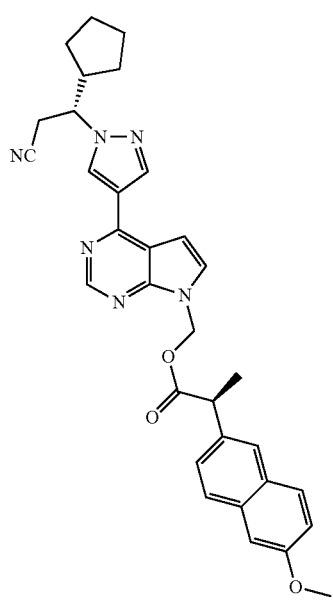
CPD-117
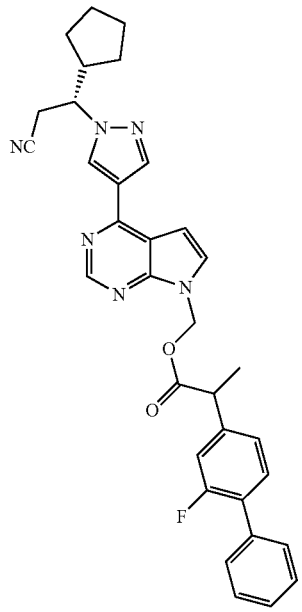

CPD-118
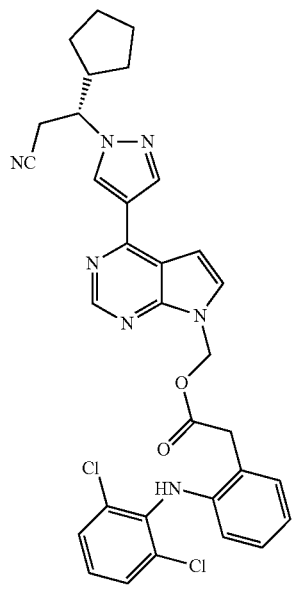
CPD-119
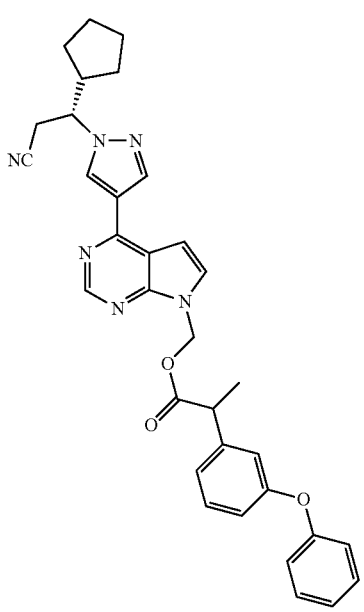
CPD-120
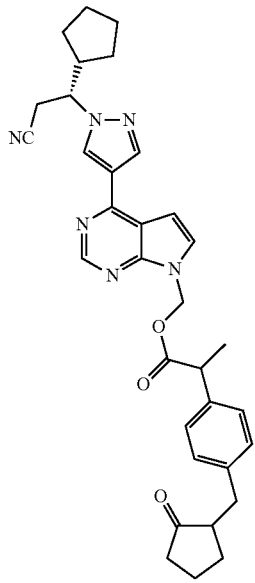
CPD-121
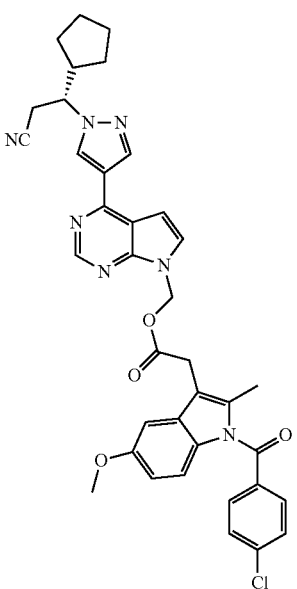

CPD-122
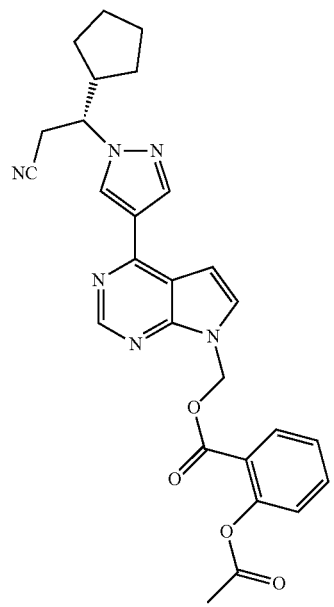
CPD-124
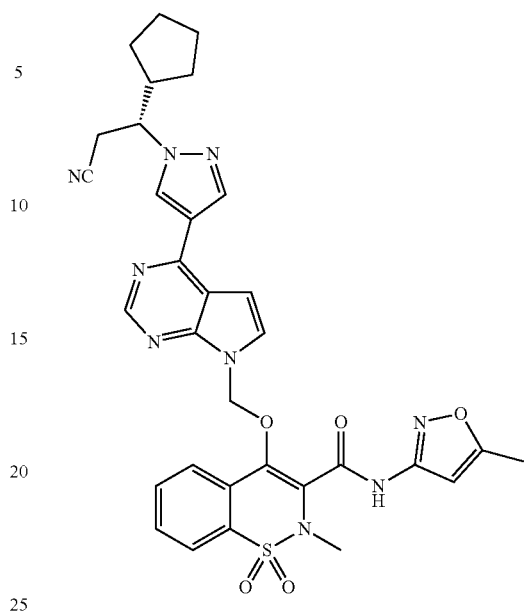
CPD-123
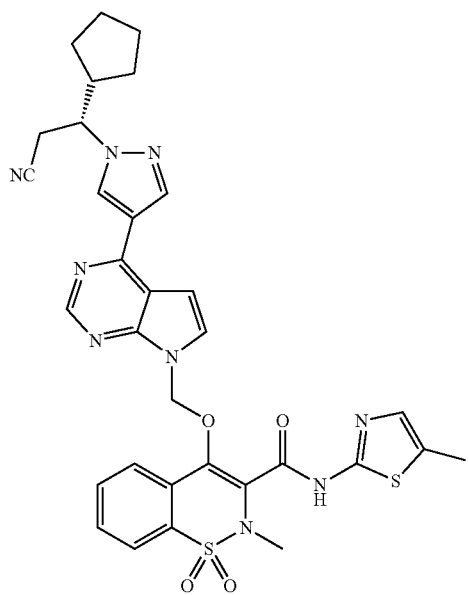
CPD-125
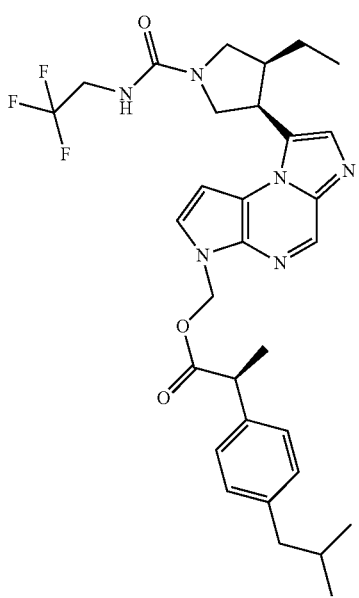

CPD-126
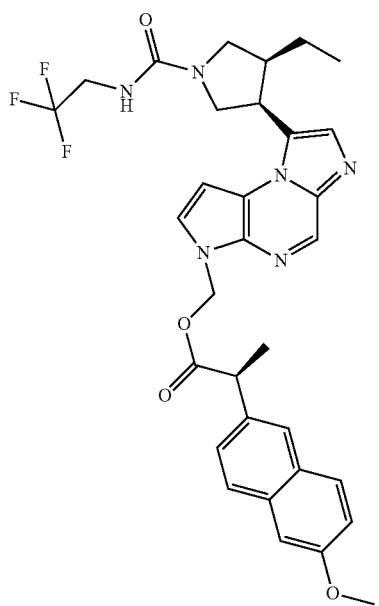
CPD-127
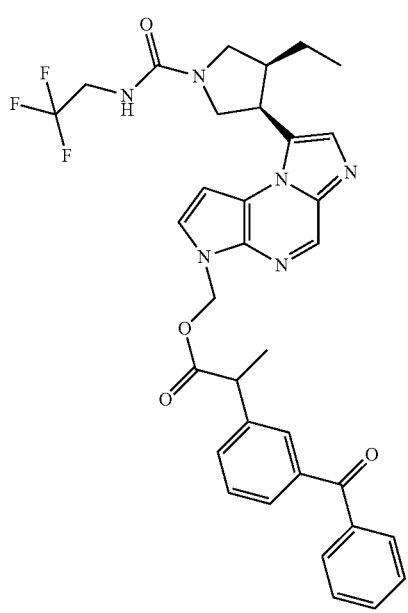
CPD-128
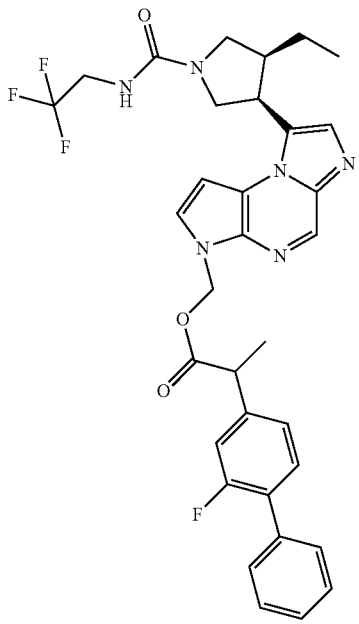
CPD-129
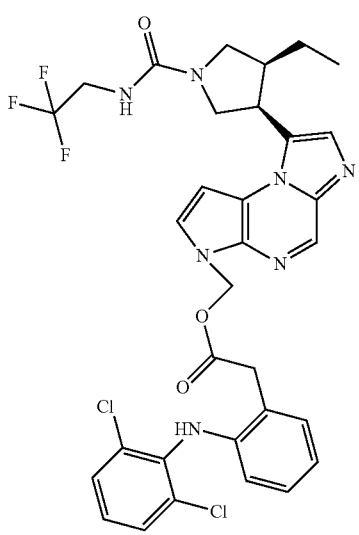

CPD-130
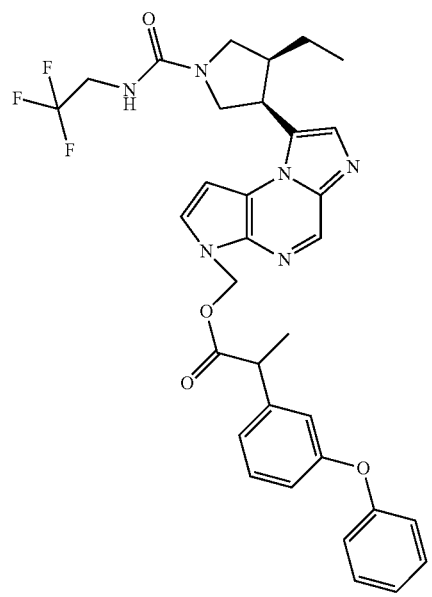
CPD-131
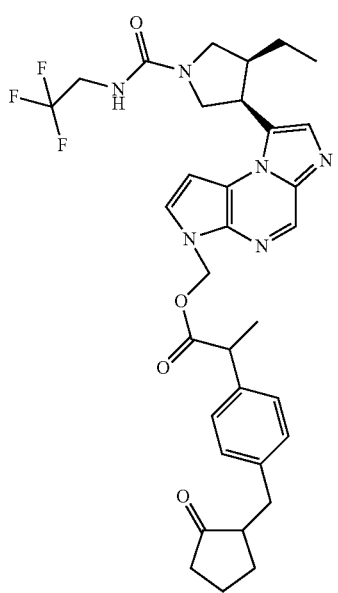
CPD-132
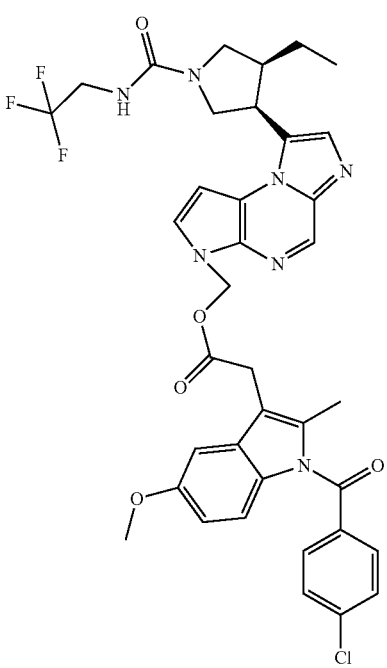
CPD-133
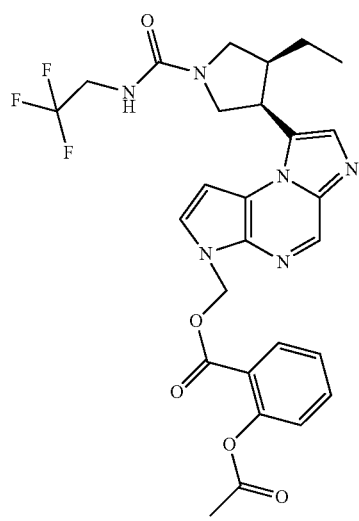
CPD-134
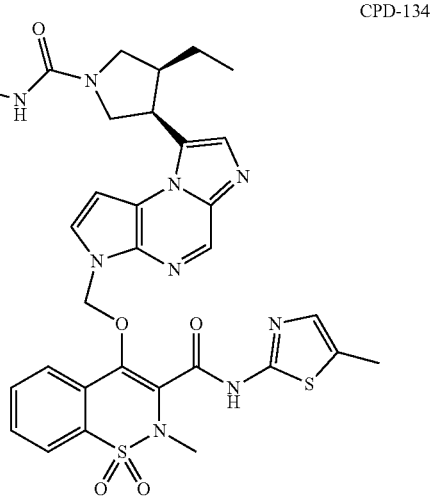

CPD-135
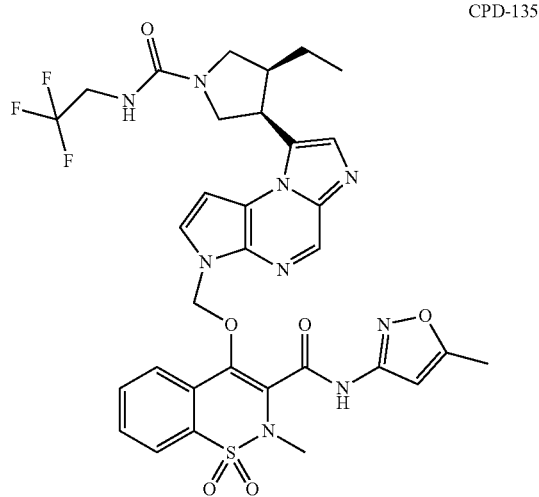
CPD-136
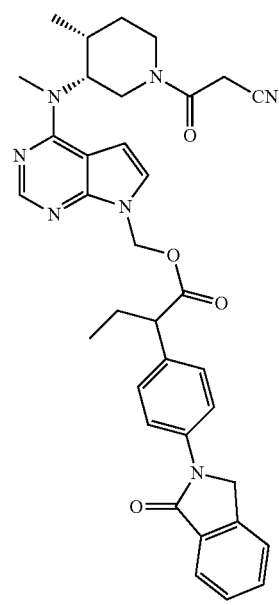
CPD-137
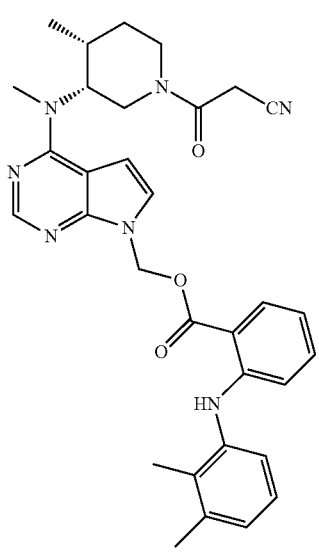
CPD-138
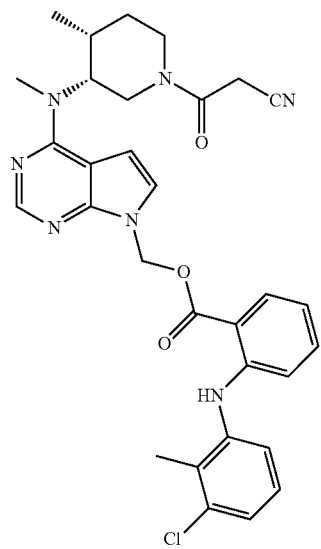
CPD-139
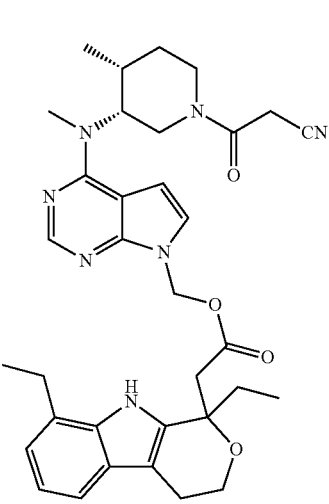
CPD-140
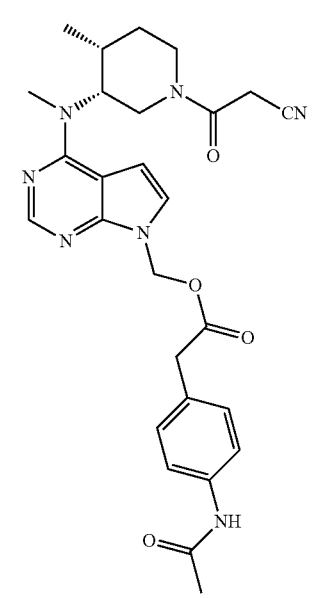

CPD-141
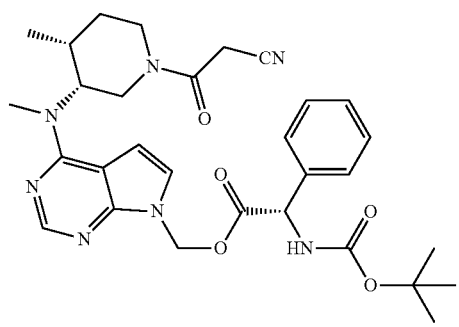
CPD-142
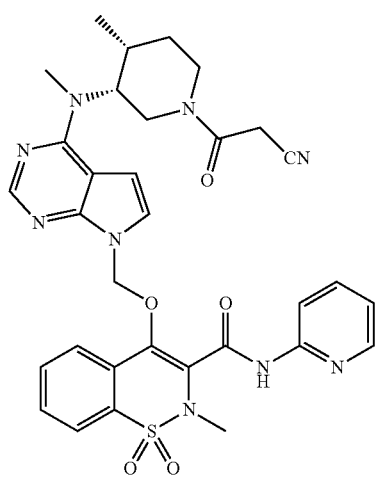
CPD-143
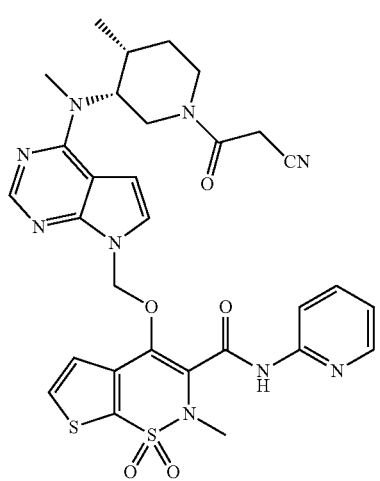
CPD-144
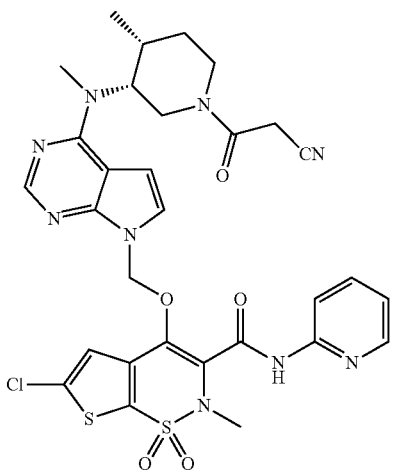
CPD-145
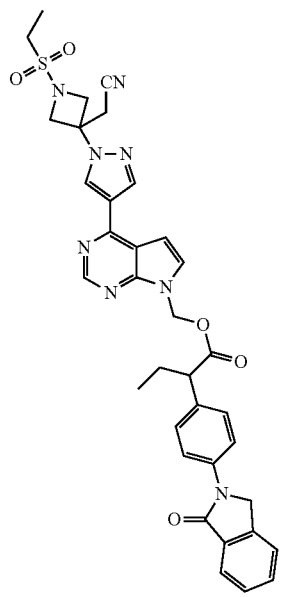
CPD-146
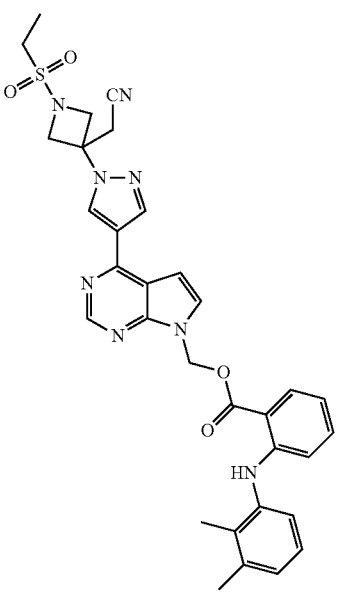

CPD-147
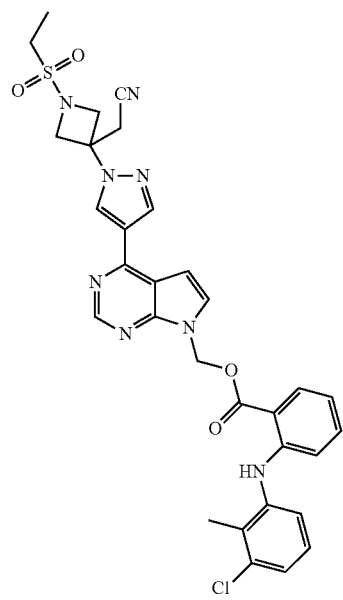
CPD-148
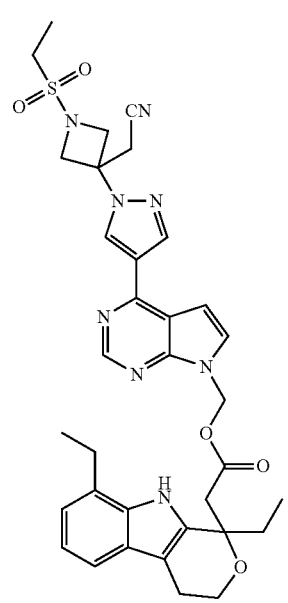
CPD-149
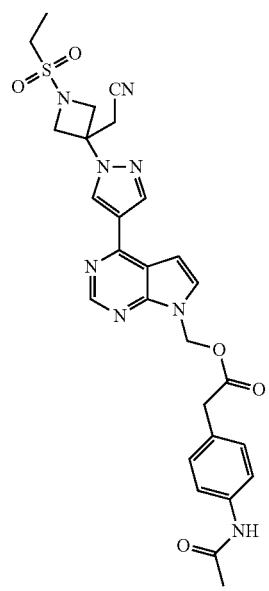
CPD-150
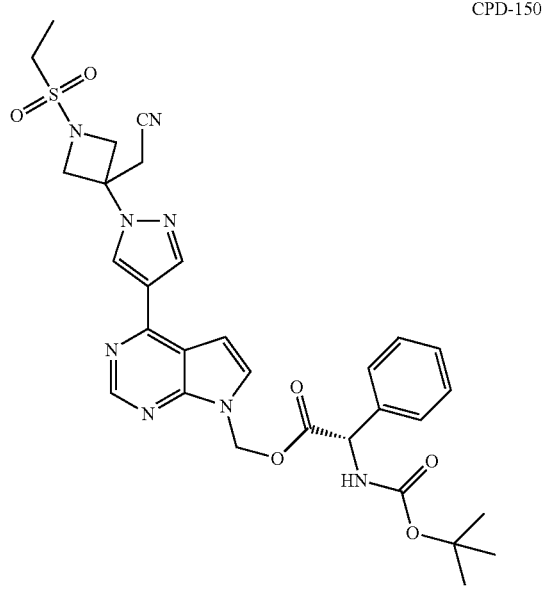

CPD-151
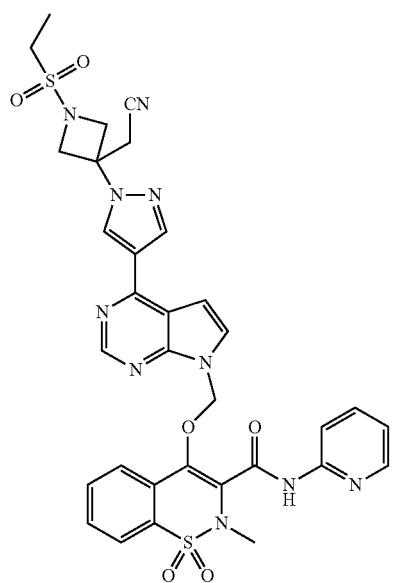
CPD-152
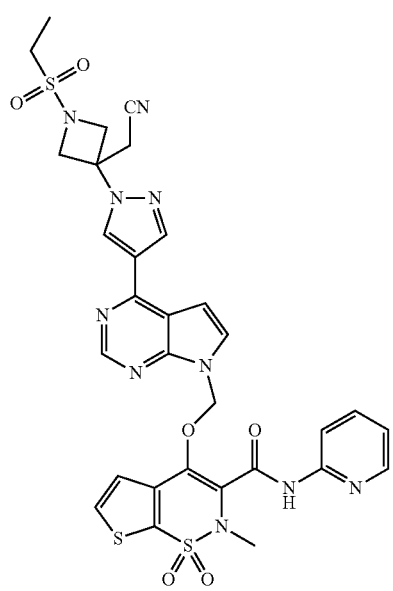
CPD-153
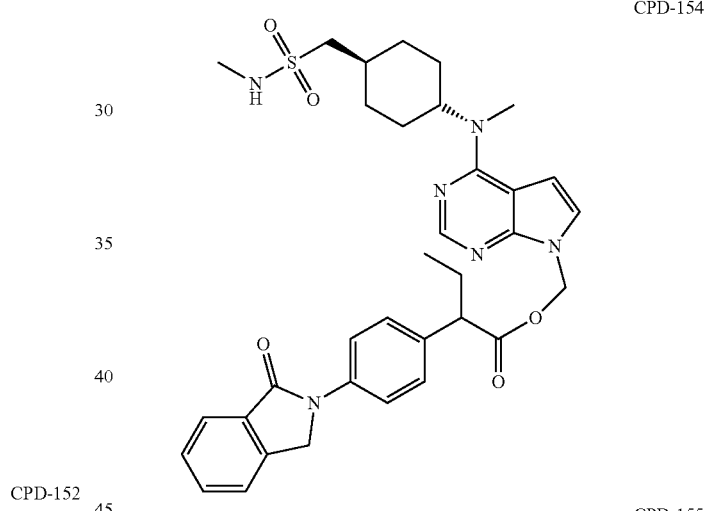
CPD-154
CPD-155
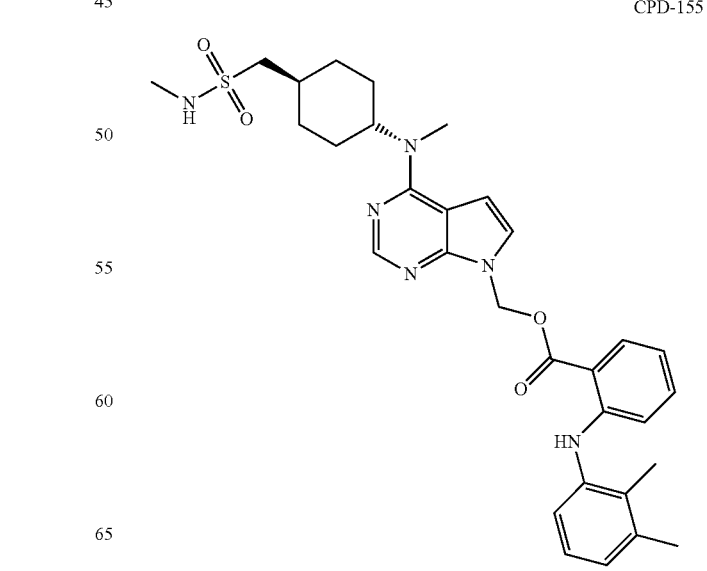

CPD-156
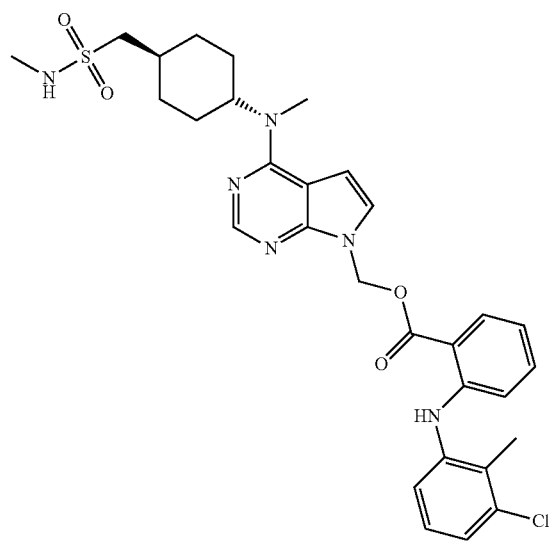
CPD-157
CPD-158
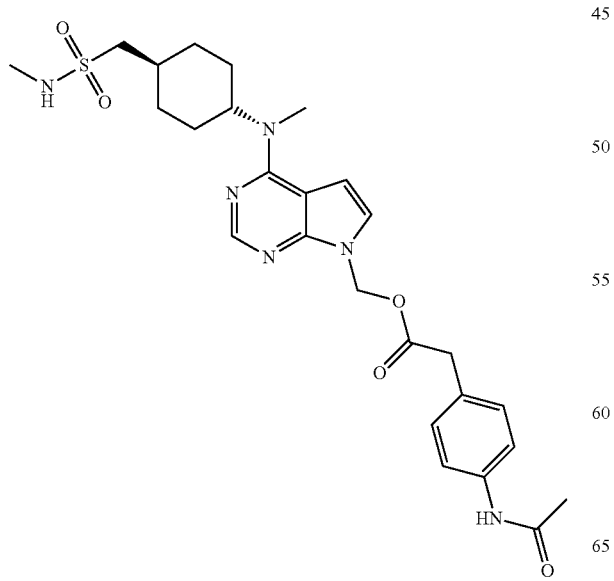
CPD-159
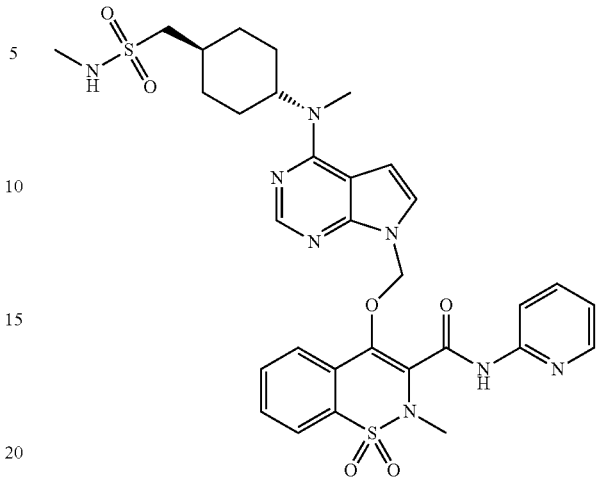
CPD-160
CPD-161
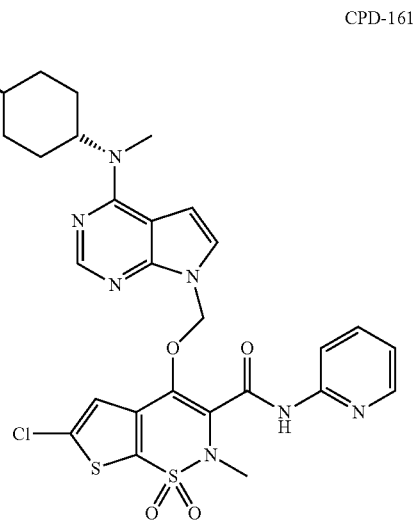

CPD-162
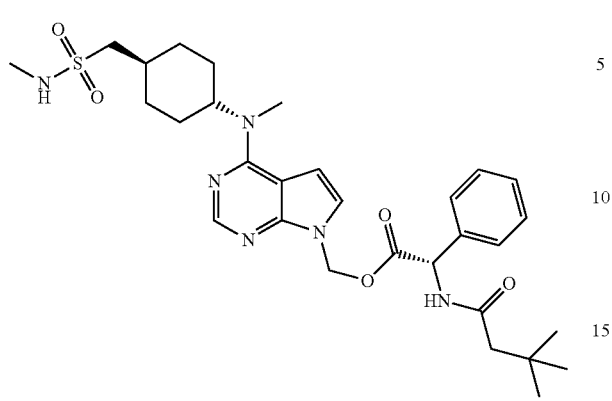
CPD-165
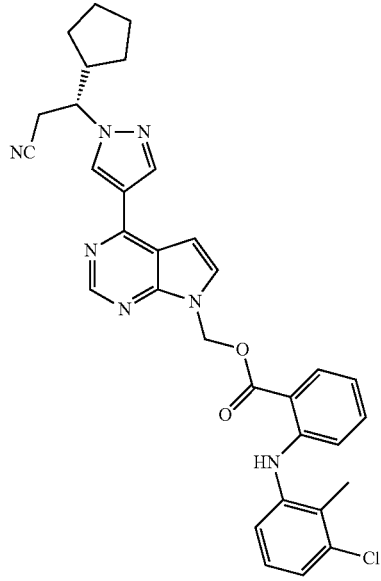
CPD-163
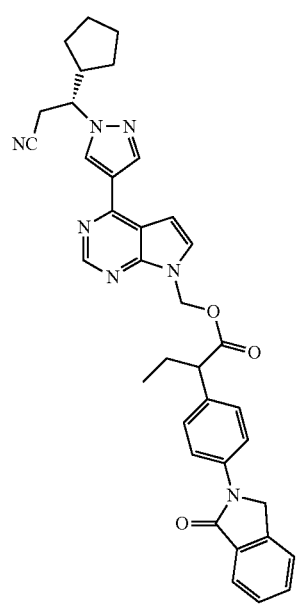
CPD-164
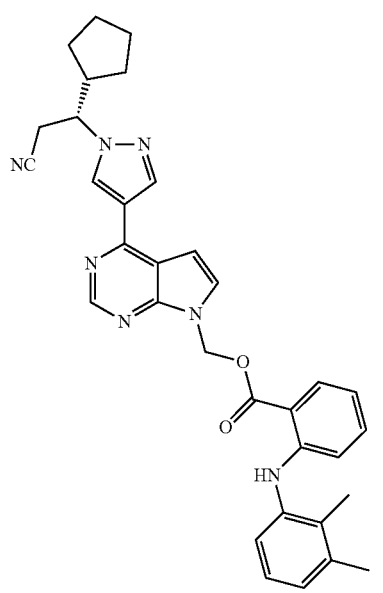
CPD-166
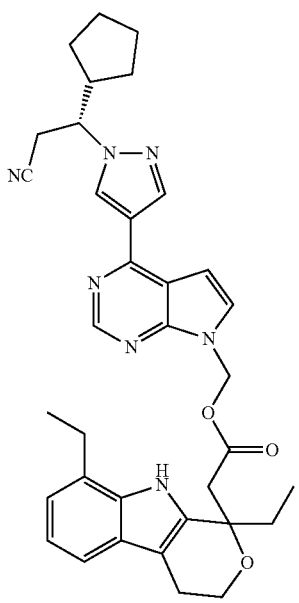

CPD-167
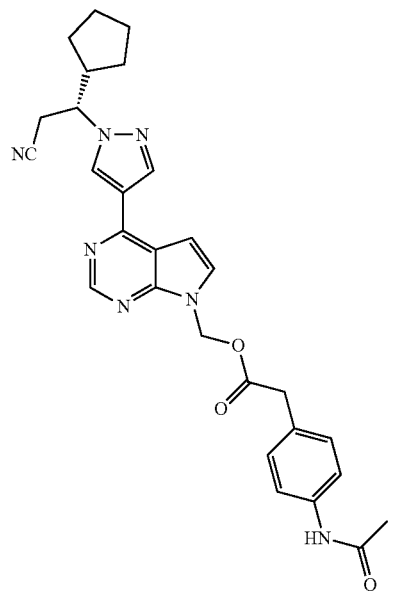
CPD-169
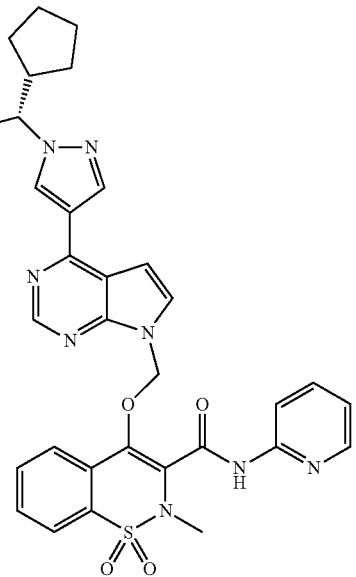
CPD-168
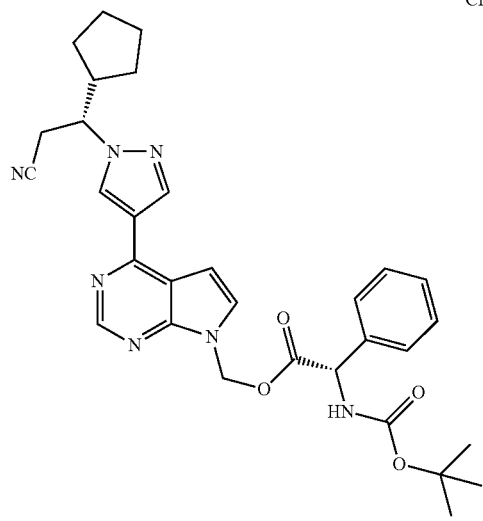
CPD-170
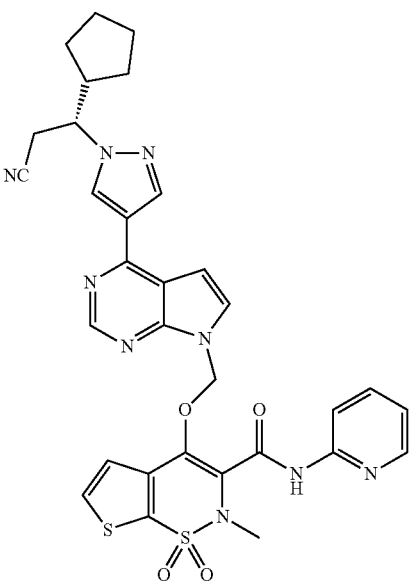

-continued
CPD-171
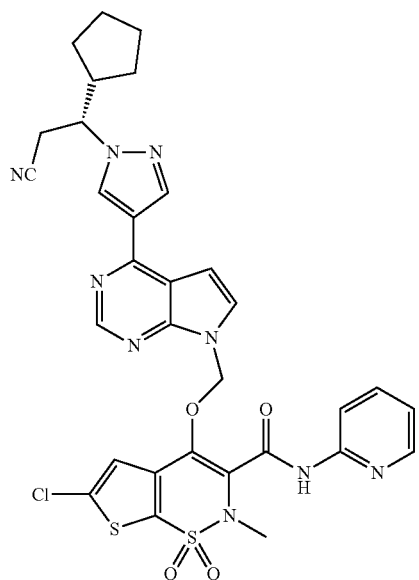
CPD-172
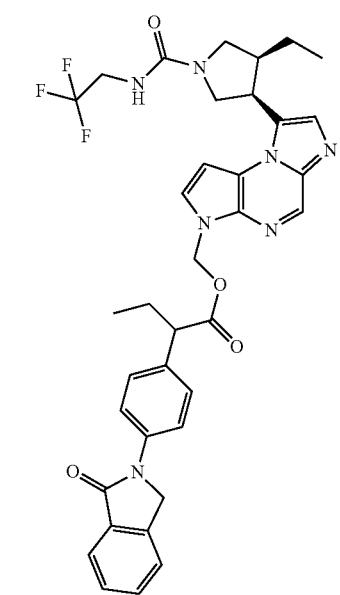
-continued
CPD-173
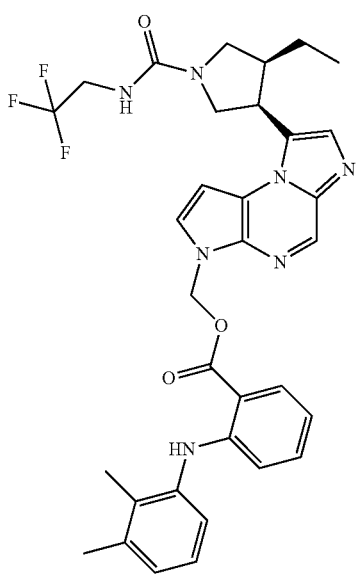
CPD-174
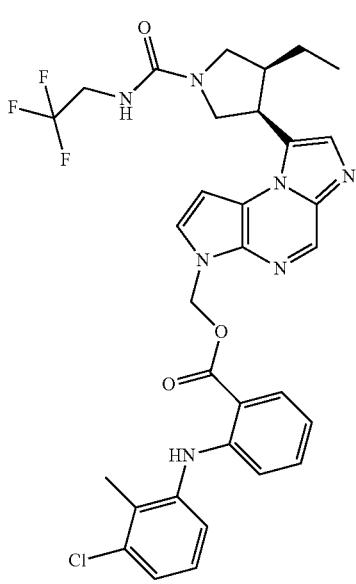
CPD175
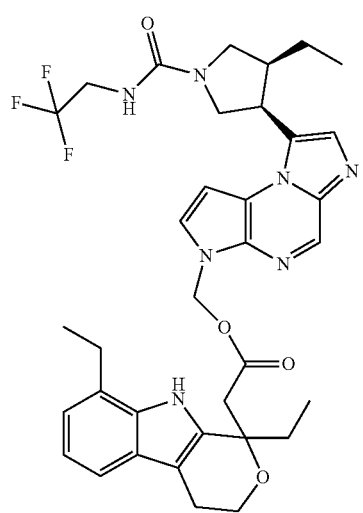

CPD-176
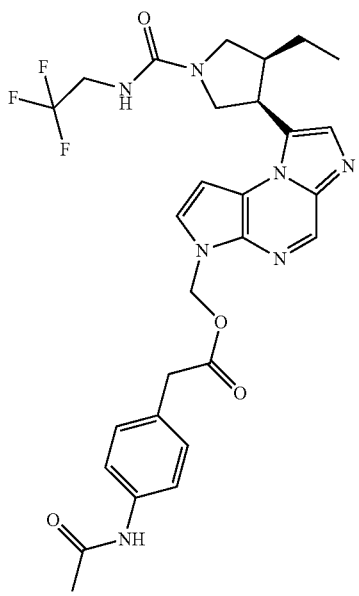
CPD-177
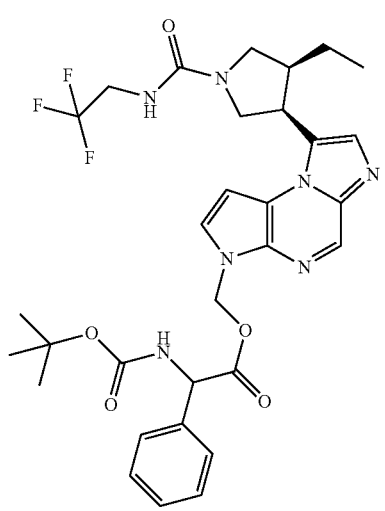
CPD-178
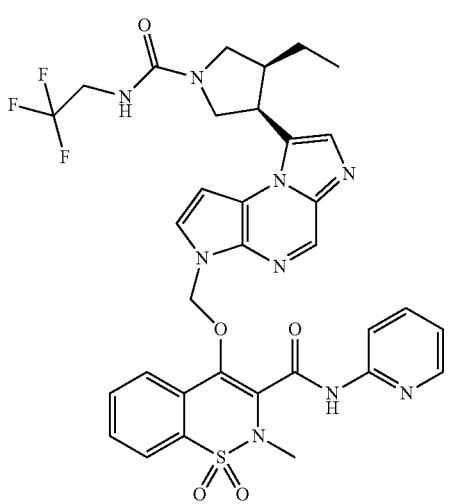
CPD-179
CPD-180
CPD-181
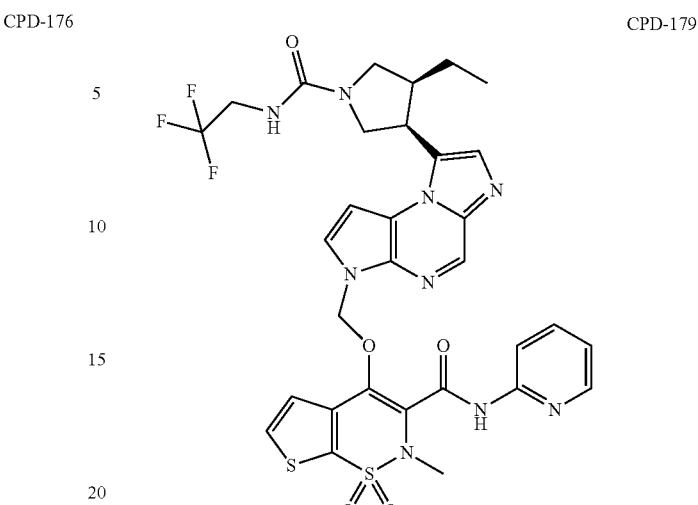

CPD-182
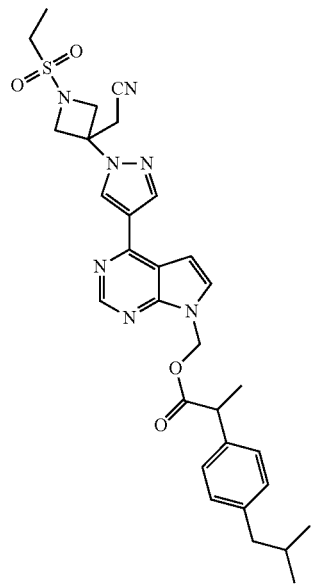
CPD-184
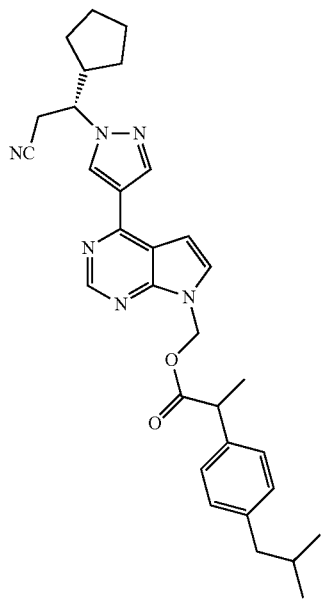
CPD-183
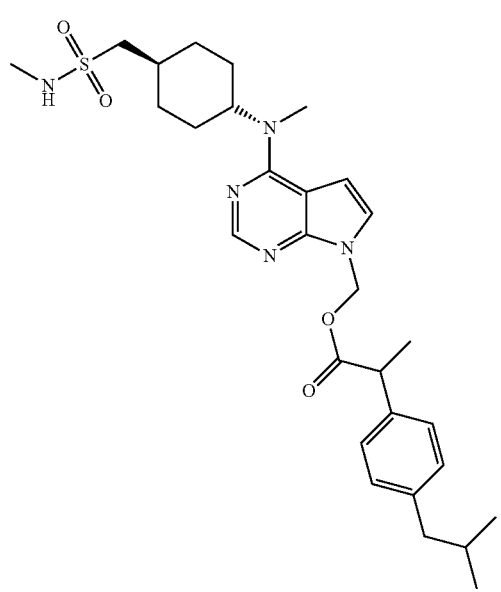
CPD-185
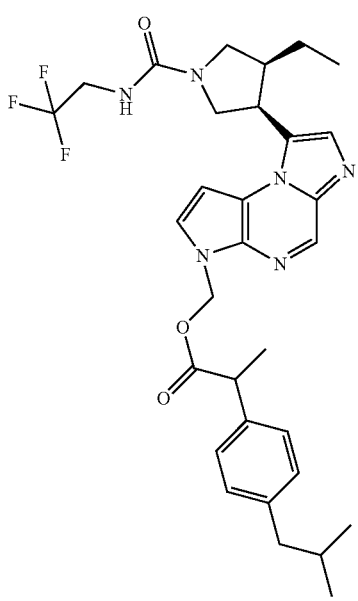

CPD-202

CPD-203

CPD-204

CPD-205

-continued
CPD-206
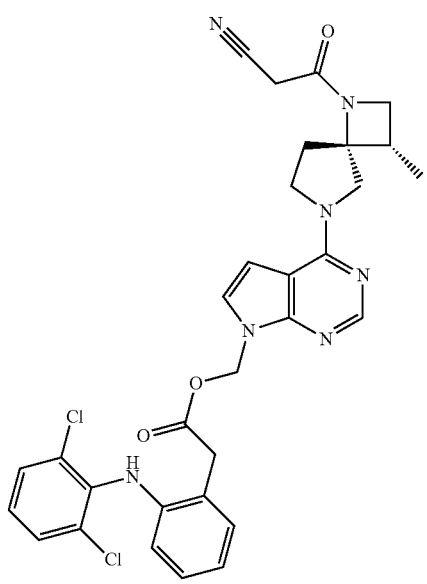
CPD-208
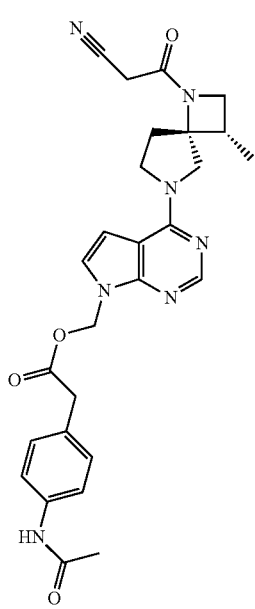
CPD-207
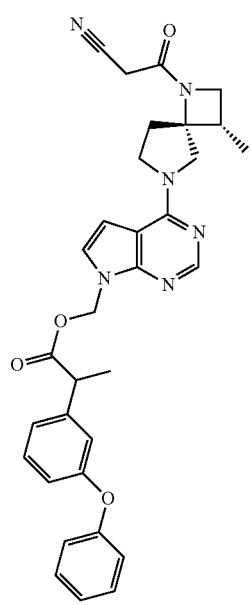
CPD-209
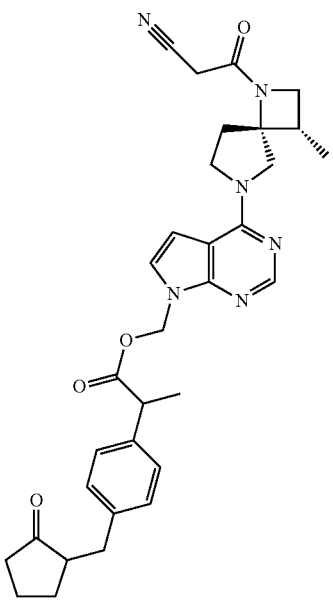

CPD-210
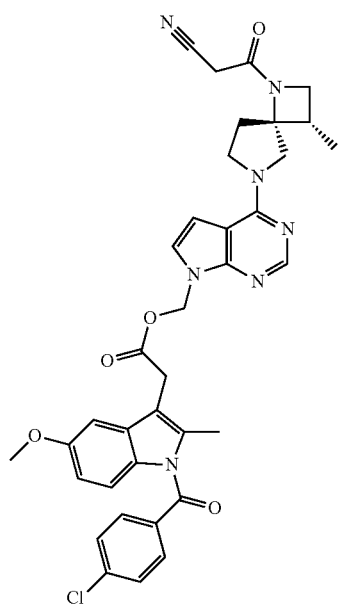
CPD-211
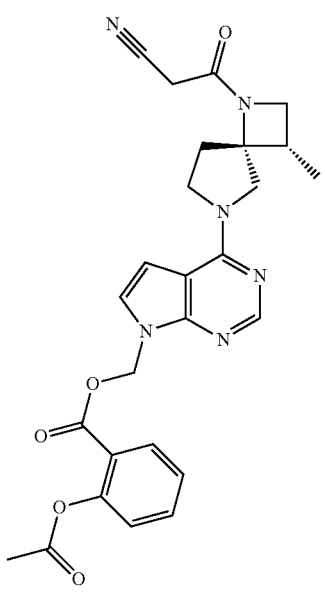
CPD-212
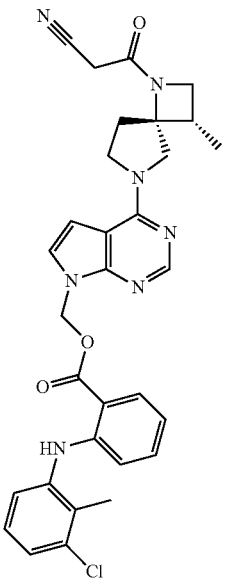
CPD-213
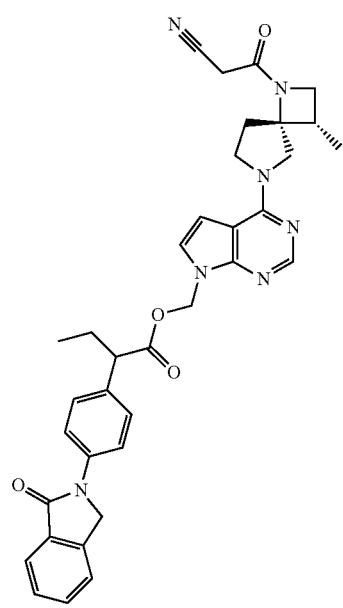

CPD-214
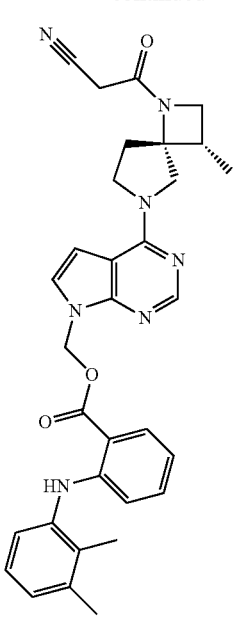
CPD-216
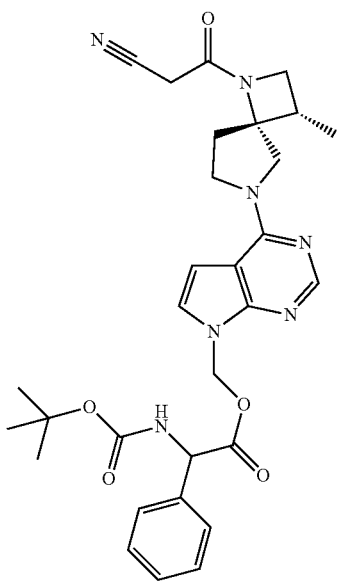
CPD-215
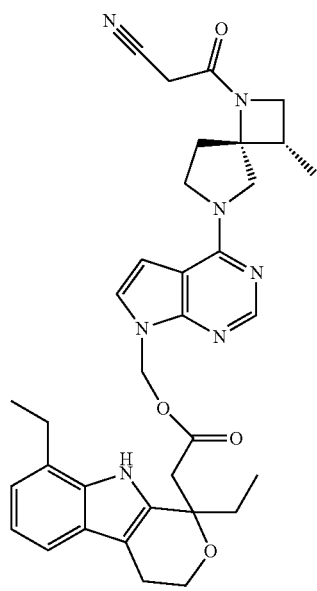
CPD-217
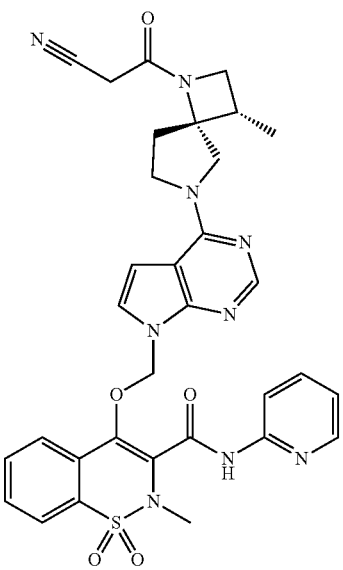

-continued
CPD-218
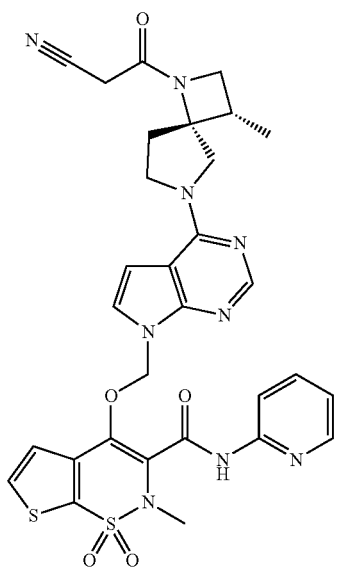
CPD-220
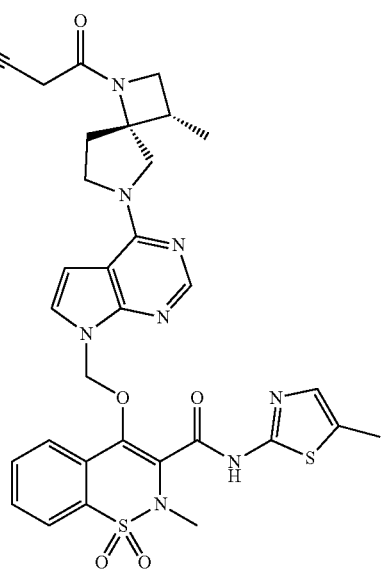
CPD-219
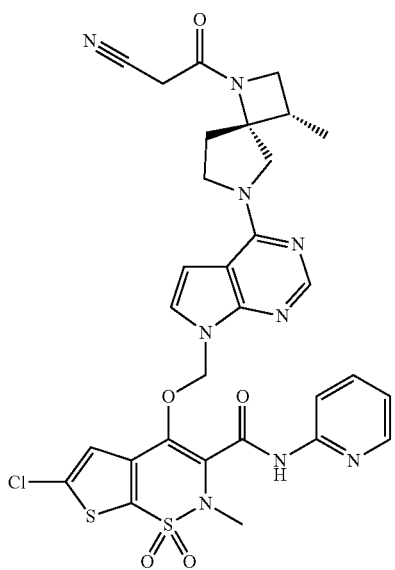
CPD-221
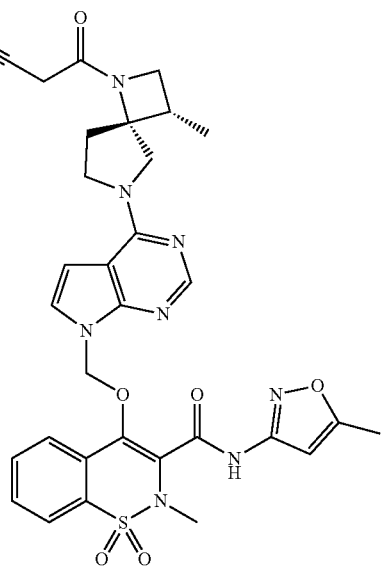

-continued

CPD-222

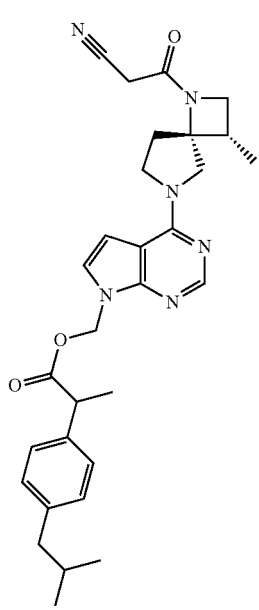

On the other hand, the present invention also provides a method for preparing the anti-inflammatory compound, or the stereoisomer, tautomer, nitrogen oxide, metabolite, prodrug, pharmaceutically acceptable salt, or solvate thereof of the present invention, comprising the steps of:

subjecting A and B to a condensation reaction accompanied by the loss of water in the presence of a catalyst and an organic solvent.

Preferably, for the preparation method of the present invention, the catalyst is one or two or more of EDCI (1-(3-dimethylaminopropyl)-3-ethylcarbodiimide hydrochloride)), DCC (dicyclohexyl carbodiimide), CDI (N, N-carbonyldiimidazole), DMTMM (4-(4, 6-dimethoxytriazine)-4-methylmorpholine hydrochloride), HATU (2-(7-azabenzotriazole)-N, N, N', N'-tetramethyluronium hexafluorophosphate), HCTU (6-chlorobenzotriazole-1, 1, 3, 3-tetramethyluronium hexafluorophosphate), PyBOP (benzotriazol-1-yl-oxytripyrrolidinophosphonium hexafluorophosphate) and NPC; preferably the organic solvent is one or two or more selected from a group consisting of DCM (dichloromethane), DMF (dimethylformamide), petroleum ether, acetone, chloroform, ethyl acetate, acetonitrile and THF (tetrahydrofuran), more preferably dichloromethane and/or dimethylformamide; further preferred, the reaction is carried out in the presence of a basic substance, wherein the basic substance is preferably one or two or more selected from a group consisting of DMAP (dimethylamino pyridine), triethylamine, DIPEA (N, N-diisopropylethyl amine) and hydroxides or salts of sodium, potassium, lithium and ammonium.

Preferably, the method for preparing the anti-inflammatory compound, or the stereoisomer, tautomer, nitrogen oxide, metabolite, prodrug, pharmaceutically acceptable salt, or solvate thereof of the present invention, comprises the steps of subjecting A-CH$_2$OH and B to a condensation reaction on the loss of water.

Preferably, the method for preparing the anti-inflammatory compound, or the stereoisomer, tautomer, nitrogen oxide, metabolite, prodrug, pharmaceutically acceptable salt, or solvate thereof of the present invention, obtained by a preparation method comprising the steps of:

2) reacting A-CH$_2$—OH compound with an acyl chloride of B or directly with the B compound;
wherein the A-CH$_2$—OH compound is preferably prepared by the following step 1):
reacting the amine compound A to generate an A-CH$_2$—OH compound.

More preferably, for the preparation process according to the invention, wherein step 1) comprises: a) adding (2-(chloromethoxy) ethyl) trimethylsilane to A in the presence of a catalyst and a solvent to generate A-CH$_2$O—C$_2$H$_4$—Si(CH$_3$)$_3$; and b) generating A-CH$_2$OH from A-CH$_2$O—C$_2$H$_4$—Si(CH$_3$)$_3$ in the presence of a catalyst and a solvent; step 2) comprises: reacting A-CH$_2$OH with an acid chloride generated from compound B$_1$ or directly with compound B$_2$ to generate A-CH$_2$O—B;

wherein it is preferred that in step b) the reaction is carried out in the presence of TFA (trifluoroacetic acid) as a catalyst and DCM (dichloromethane) as a solvent; or in step 2), A-CH$_2$OH is reacted with the acid chloride generated from the compound B$_1$ in the presence of Et$_3$N (triethylamine) as a catalyst and DCM (dichloromethane) as a solvent or is reacted with compound B$_2$ in the presence of PPh3 (triphenylphosphine) and DIAD (diisopropyl azodicarboxylate) as a catalyst and THF (tetrahydrofuran) as a solvent.

Furthermore, the present invention provides a medicinal use, i.e. provides use of the anti-inflammatory compound, or the stereoisomer, tautomer, nitrogen oxide, metabolite, prodrug, pharmaceutically acceptable salt, or solvate thereof, in the preparation of anti-inflammatory drug preparations or drug compositions (preferably external drug compositions).

Furthermore, the present invention also provides an anti-inflammatory drug preparation or drug composition (preferably external drug compositions) including the anti-inflammatory compound, or the stereoisomer, tautomer, nitrogen oxide, metabolite, prodrug, pharmaceutically acceptable salt, or solvate thereof described above.

It has been found that, by synthesizing the above compounds, the compounds of the present invention have a dissolution rate of 0.04% to 50% per day, thereby increasing the transdermal potential of known JAK inhibitors.

DETAILED DESCRIPTION OF THE INVENTION

Figure 1:
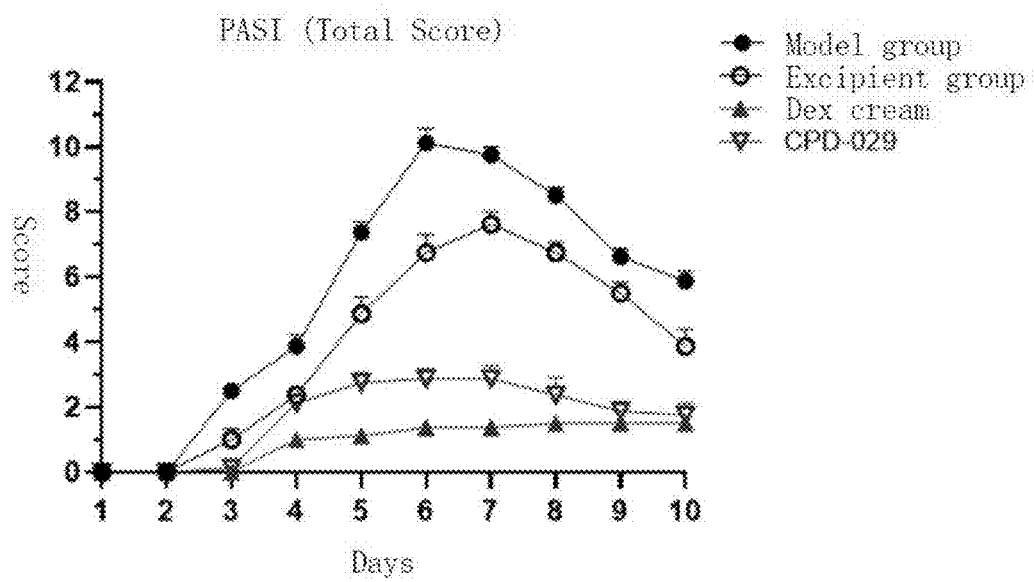
FIG. 1 is a graph of the PASI score of an ointment prepared from CPD-029 of the present invention through skin application to treat psoriasis in a mouse model test.

The present inventors have unexpectedly discovered through intensive studies that the coupling of an anti-inflammatory pharmaceutical compound containing a carboxylic acid or hydroxyl group with a JAK inhibitor compound to form a coupling compound having an acyloxy group and/or methoxy group has a high therapeutic effect and a particular effect of controlled-release pharmaceutical activity.

The anti-inflammatory compound, or a stereoisomer, tautomer, nitrogen oxide, metabolite, prodrug, pharmaceutically acceptable salt, or solvate thereof provided by the present invention, has a structure shown in general formula (I):

$$A-Y-B \quad (1)$$

wherein, A is a group after dehydrogenation of an amine compound having JAK inhibitory activity;

Y is a direct connection or —$(CH_2)$—O—;

B is a group formed by means of dehydroxylation of a carboxylic acid compound $B_1$ with anti-inflammatory effect, or a group formed by means of dehydrogenation of a hydroxy-containing compound $B_2$.

That is to say, the compounds of general formula (I) provided by the present invention actually include two main classes. The first main class refers to the case where A is a direct connection and the structural formula thereof is as shown in (II) or (IIa).

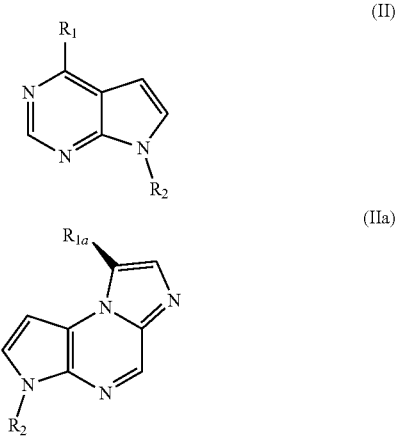

wherein $R_1$ is selected from pyrazolyl or —$N(CH_3)$-Cy unsubstituted or substituted with $R_a$; $R_{1a}$ represents a pyrrole ring substituted a halogen-substituted $C_1$-$C_6$ alkylaminoacyl group and/or a $C_1$-$C_6$ alkyl group;

$C_y$ is a five- or six-membered carbocyclic ring or a five- or six-membered nitrogen-containing heterocyclic ring unsubstituted or substituted by $R_b$; $R_a$ and $R_b$ are each independently at least one or two groups containing an acyl group, a sulfonyl group, a cyano group, an amino group or a $C_1$-$C_6$ alkyl-substituted amino group; preferably $R_a$ and $R_b$ are each independently one of acyl or sulfonyl and at least one group selected from cyano, amino, or $C_1$-$C_6$ alkyl substituted amino, wherein the $C_1$-$C_6$ alkyl is substitutable by halogen;

$R_2$ in both general formulas (II) and (IIa) is —B, i.e. is a group formed by means of dehydroxylation of a carboxy-containing carboxylic acid compound $B_1$ and is selected from $R_4$—Ar—$R_3$—CO—, wherein $R_3$ is selected from $C_1$-$C_4$ alkylene; —NH—, $R_5NH$—, or $C_1$-$C_6$ alkylene substituted with a $C_1$-$C_6$ alkoxyamide group; or a direct connection, i.e. the Ar group is directly linked to —CO—; $R_3$ is preferably methyl substituted or unsubstituted methylene, —$C_2H_4$—, or a direct connection; $R_5$ is $C_1$-$C_6$ alkylene;

wherein the $C_1$-$C_6$ alkylene is substitutable by halogen (preferably halogen is selected from one or two or more of fluorine, chlorine or bromine);

Ar is an aromatic ring group, preferably selected from a benzene ring; a naphthalene ring or an aryl heterocyclic ring; and a benzene ring, a naphthalene ring, or an aryl heterocyclic ring or an aryl fused heterocyclic ring (here, the aryl heterocyclic ring being preferably a benzo nitrogen- or oxygen-containing heterocyclic ring such as a benzopyrrole ring) substituted with a group selected from halogen, a $C_1$-$C_6$ alkyl group, a $C_1$-$C_6$ alkoxy group, a $C_1$-$C_6$ acyl group, or a $C_1$-$C_6$ alkoxy group; Ar is more preferably an aryl heterocyclic ring containing a nitrogen atom; and $R_6$ is halogen, $C_1$-$C_6$ alkyl, $C_1$-$C_6$ alkoxy, or $C_1$-$C_6$ cycloalkanoyl-containing $C_1$-$C_6$ alkyl;

or $R_6$ is $C_1$-$C_6$ alkyl or aromatic ring or aromatic condensed ring or aromatic condensed ring heterocyclic ring containing acyl and/or amino groups, such as $C_1$-$C_6$ alkylamido or aryl fused heterocyclic amido, $C_1$-$C_6$ carbonyloxy, halogen-substituted benzoyl, $C_1$-$C_6$ alkyl or halogen substituted or unsubstituted phenoxy, $C_1$-$C_6$ alkyl or halogen substituted or unsubstituted phenyl or aryl fused heterocyclic ring, $C_1$-$C_6$ alkyl or halogen substituted or unsubstituted phenylamino, or $R_6$ can also be absent; wherein the $C_1$-$C_6$ alkoxy can also form a bridged ring with Ar.

The aforementioned terms in the present invention, as well as all "$C_1$-$C_6$" appearing below, refer to a carbon atom number of 1-6. For example, "$C_1$-$C_6$ alkyl" refers to an alkyl group with a carbon atom number of 1-6. By analogy, the terms "$C_1$-$C_6$ alkoxy" and "$C_1$-$C_6$ acyl" mentioned herein refer to alkoxy groups with a carbon atom number of 1-6 and groups with a carbon atom number of 1-6 containing —C=O, respectively. "$C_1$-$C_6$ alkylamide group" refers to an alkyl group containing amide groups with a carbon atom number of 1-6. "$C_1$-$C_6$ carboacyloxy group" refers to an alkyl group or cycloalkyl group containing acyloxy —CO—O with a carbon atom number of 1-6. "$C_1$-$C_6$ cycloalkanoyl group" refers to a cyclic alkyl group containing —C=O group with a carbon atom number of 1-6. The term "$C_1$-$C_6$ alkyl group containing $C_1$-$C_6$ cycloalkanoyl group" refers to the situation where hydrogen on carbon atoms is substituted by $C_1$-$C_6$ cycloalkanoyl groups in an alkyl group with a carbon atom number of 1-6, i.e., "$C_1$-$C_6$ alkyl group containing $C_1$-$C_6$ cycloalkanoyl group" is equivalent to "$C_1$-$C_6$ alkyl group substituted by $C_1$-$C_6$ cycloalkanoyl group". The "$C_1$-$C_6$" in the present invention may be specifically "$C_1$-$C_6$", "C1-C5", "C1-C4", "C1-C3" or "C1-C2", and may also be C1, i.e. only one carbon atom.

The first general compound described above is a compound A-B (specifically, A-$B_1$) formed by means of dehydrogenation of an amine compound A having JAK inhibitory activity and dehydroxylation of a carboxylic acid compound $B_1$.

The compound of general formula (I) provided by the present invention includes the second main class of compound having a structural formula and structure shown in general formula (III):

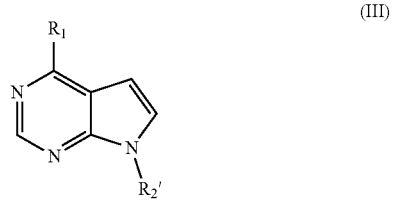

-continued (IIIa)

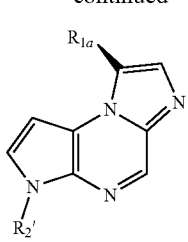

wherein R₁ has the same meaning as R₁ in general formula (II); $R_{1a}$ has the same meaning as $R_{1a}$ in formula (IIa);

The R₂' in general formula (III) and general formula (IIIa) are both —Y—B, where Y is —(CH₂)—O—, and B is —B₁ in general formula (II) or (IIa), i.e. group —B₁ formed by the dehydroxylation of a carboxylic acid compound B₁; or B is —B₂, the group —B₂ is $R_c$—CO—NH—$R_d$, wherein $R_c$ is a 4-hydroxy-benzothiazine dioxide-3-yl represented by the following structural formula (a), wherein the phenyl ring is substitutable by halogen or C₁-C₄ alkyl, or a 4-hydroxy-Re substituted thienothiazine dioxide-3-yl represented by the following structural formula (b), wherein —CO—NH—$R_d$ is attached at the 3-position of the thiazine ring,

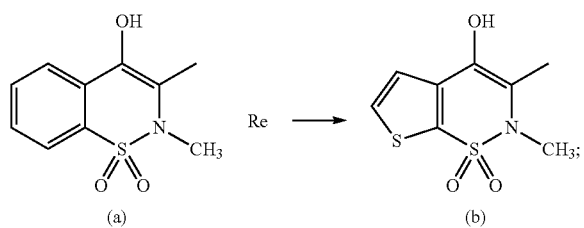

wherein $R_d$ is thiazole, isothiazole, oxazole, isoxazole, or pyridine or a group thereof substituted with C₁-C₆ alkyl or halogen, preferably a thiazole or isoxazole substituted with methyl; and unsubstituted pyridyl; $R_e$ is C₁-C₆ alkyl or halogen (preferably halogen is selected from one or two or more of fluorine, chlorine, or bromine); the arrow next to $R_e$ in formula (b) indicates that its substitution position on the thiophene ring may be any carbon-linked hydrogen atom capable of undergoing substitution.

The second main compound of the present invention is obtained by using A-CH₂OH to undergo a condensation reaction accompanied by loss of water with B.

In particular, the preparation of the second main class of compound comprises the following steps:

2) reacting A-CH₂—OH compound with an acyl chloride of B or directly with the B compound; Wherein the A-CH₂—OH compound is prepared by step 1): reacting A to generate an A-CH₂—OH compound.

The scope of the compound of general formula (I) of the present invention actually also includes the various stereoisomers, tautomers, N-oxides, metabolites, prodrugs, pharmaceutically acceptable salts or solvates thereof, which can be obtained by those skilled in the art according to the common knowledge, that is to say, these compounds, and the various stereoisomers, tautomers, N-oxides, metabolites, prodrugs, pharmaceutically acceptable salts or solvates thereof and the like, which can be modified by those skilled in the art according to common knowledge, can be used in the present invention to achieve the particular effects of the compounds of the present invention, such as strong transdermal performance, controllable drug release, and high efficacy, and therefore all fall within the scope of the present invention.

Examples The following is an example to illustrate how the compound of the present invention is prepared and its performance evaluation.

The NMR Instrument and Mass Spectrometer Instrument Models Used in Examples 1-149 Below are Described Below, Respectively:

Nuclear magnetic resonance spectrometer: Bruker 400M Nuclear Magnetic Resonance Instrument; Liquid Chromatography Mass Spectrometry Instrument: Agilent InfinityLab LC/MSD iQ Table 1 below is a structural formula and a compound name of a target compound prepared in each example.

TABLE 1

Structural formulas and compound names of target compounds prepared in examples

| Examples (Cmpd No.) | Structure | Chinese name |
|---|---|---|
| 1 (CPD-001) | 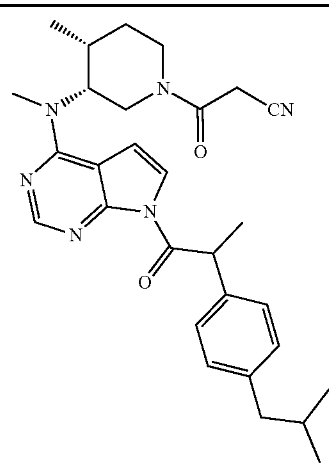 | 3-((3R,4R)-3-((7-(2-(4-isobutylphenyl)propanoyl)-7H-pyrrolo[2,3-d]pyrimidin-4-yl)(methyl)amino)-4-methylpiperidin-1-yl)-3-oxopropanenitrile |

TABLE 1-continued

Structural formulas and compound names of target compounds prepared in examples

| Examples (Cmpd No.) | Structure | Chinese name |
|---|---|---|
| 2 (CPD-002) | 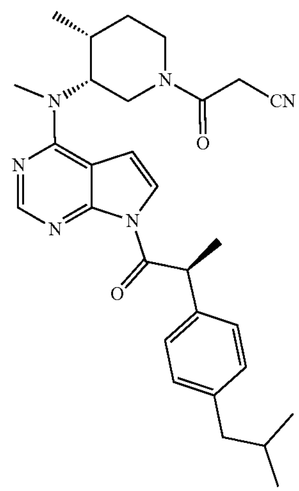 [SMILES: CC(C)Cc1ccc([C@H](C)C(=O)n2ccc3c(N(C)[C@H]4CN(C(=O)CC#N)CC[C@H]4C)ncnc32)cc1] | 3-((3R,4R)-3-((7-((S)-2-(4-isobutylphenyl)propanoyl)-7H-pyrrolo[2,3-d]pyrimidin-4-yl)(methyl)amino)-4-methylpiperidin-1-yl)-3-oxopropanenitrile |
| 3 (CPD-003) | 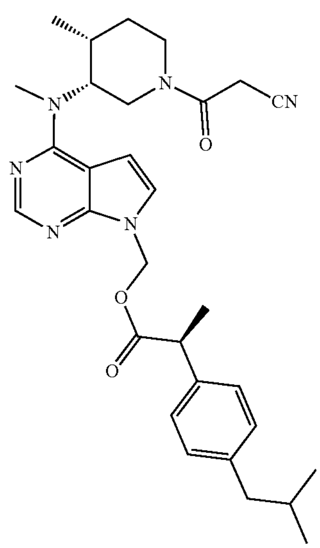 [SMILES: CC(C)Cc1ccc([C@H](C)C(=O)OCn2ccc3c(N(C)[C@H]4CN(C(=O)CC#N)CC[C@H]4C)ncnc32)cc1] | (4-((3R,4R)-1-(2-cyanoacetyl)-4-methylpiperidin-3-yl)(methyl)amino)-7H-pyrrolo[2,3-d]pyrimidin-7-yl)methyl (S)-2-(4-isobutylphenyl)propanoate |
| 4 (CPD-004) | 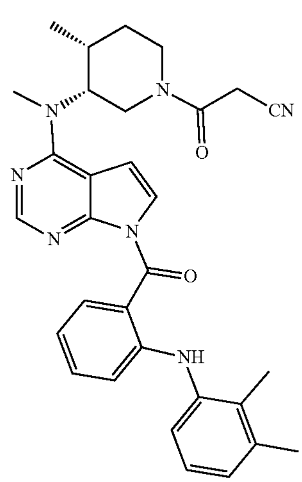 | 3-((3R,4R)-3-((7-(2-((2,3-dimethylphenyl)amino)benzoyl)-7H-pyrrolo[2,3-d]pyrimidin-4-yl)(methyl)amino)-4-methylpiperidin-1-yl)-3-oxopropanenitrile |

TABLE 1-continued

Structural formulas and compound names of target compounds prepared in examples

| Examples (Cmpd No.) | Structure | Chinese name |
|---|---|---|
| 5 (CPD-005) | 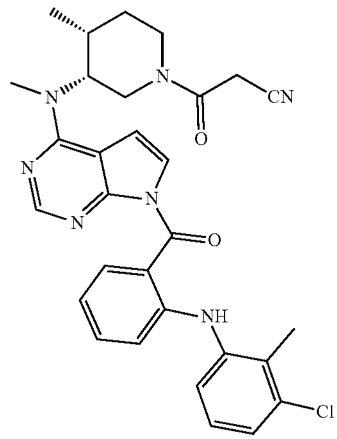 [SMILES: Cc1c(Cl)cccc1Nc1ccccc1C(=O)n1ccc2c(N(C)[C@H]3CN(C(=O)CC#N)CC[C@H]3C)ncnc21] | 3-((3R, 4R)-3-((7-(2-((3-chloro-2-methylphenyl) amino)benzoyl)-7H-pyrrolo[2,3-d] pyrimidin-4-yl)(methyl) amino)-4-methylpiperidin-1-yl)-3-oxopropanenitrile |
| 6 (CPD-006) | 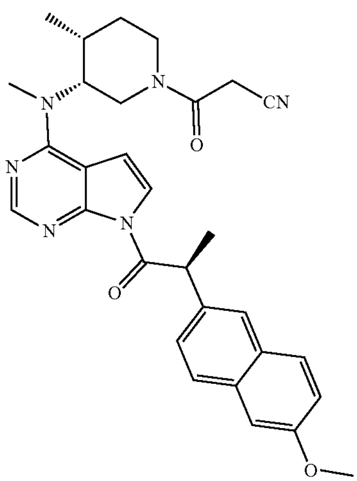 | 3-((3R, 4R)-3-((7-((S)-2-(6-methoxynaphthalen-2-yl) propanoyl)-7H-pyrrolo[2,3-d]pyrimidin-4-yl) (methyl) amino)-4-methylpiperidin-1-yl)-3-oxopropanenitrile |
| 7 (CPD-007) | 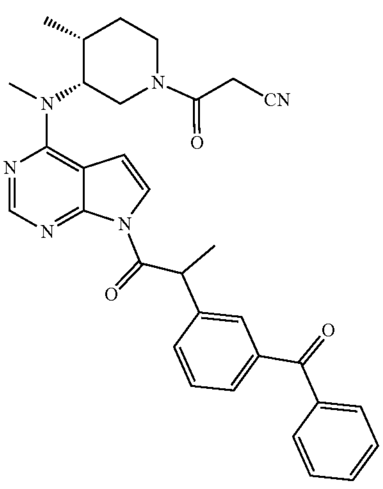 [SMILES: CC(C(=O)n1ccc2c(N(C)[C@H]3CN(C(=O)CC#N)CC[C@H]3C)ncnc21)c1cccc(C(=O)c2ccccc2)c1] | 3-((3R,4R)-3-((7-(2-(3-benzoylphenyl) propanoyl)-7H-pyrrolo[2,3-d]pyrimidin-4-yl) (methyl) amino)-4-methylpiperidin-1-yl)-3-oxopropanenitrile |

TABLE 1-continued

Structural formulas and compound names of target compounds prepared in examples

| Examples (Cmpd No.) | Structure | Chinese name |
|---|---|---|
| 8 (CPD-008) | 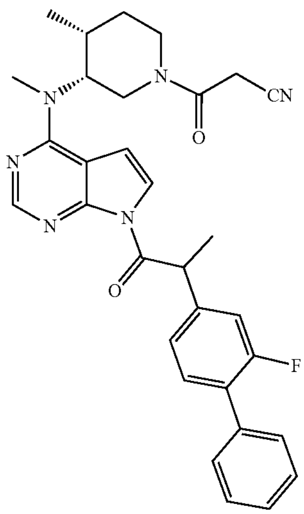 [SMILES: CC(C(=O)n1ccc2c(N(C)[C@H]3CN(C(=O)CC#N)CC[C@H]3C)ncnc21)c1ccc(-c2ccccc2)c(F)c1] | 3-((3R, 4R)-3-((7-(2-(2-fluoro-[1, 1'-biphenyl]-4-yl)propanoyl)-7H-pyrrolo[2, 3-d]pyrimidin-4-yl)(methyl) amino)-4-methylpiperidin-1-yl)-3-oxopropanenitrile |
| 9 (CPD-009) | 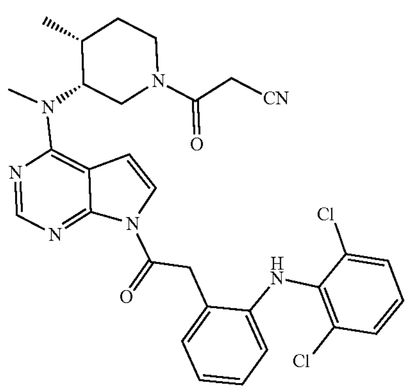 [SMILES: C[C@@H]1CCN(C(=O)CC#N)C[C@@H]1N(C)c1ncnc2c1ccn2C(=O)Cc1ccccc1Nc1c(Cl)cccc1Cl] | 3-((3R,4R)-3-((7-(2-(2-(2-(2-(2, 6-dichlorophenyl)amino)phenyl) acetyl)-7H-pyrrolo[2,3-d]pyrimidin-4-yl) (methyl) amino)-4-methylpiperidin-1-yl)-3-oxopropanenitrile |
| 10 (CPD-010) | 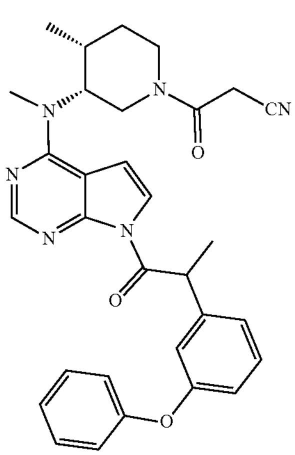 [SMILES: CC(C(=O)n1ccc2c(N(C)[C@H]3CN(C(=O)CC#N)CC[C@H]3C)ncnc21)c1cccc(Oc2ccccc2)c1] | 3-((3R,4R)-4-methyl-3-(methyl (7-(2-(3-phenoxyphenyl) propanoyl)-7H-pyrrolo [2,3-d]pyrimidin-4-yl) amino)piperidin-1-yl)-3-oxopropanenitrile |

TABLE 1-continued

Structural formulas and compound names of target compounds prepared in examples

| Examples (Cmpd No.) | Structure | Chinese name |
|---|---|---|
| 11 (CPD-011) | 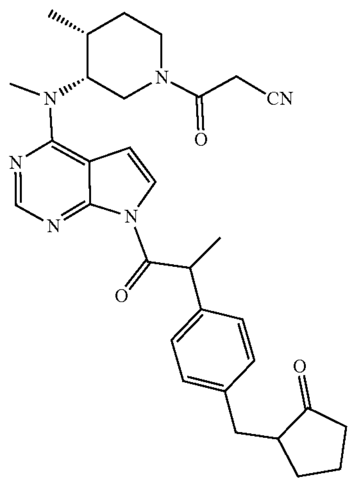 [SMILES: CC(C(=O)n1ccc2c(N(C)[C@H]3CN(C(=O)CC#N)CC[C@H]3C)ncnc21)c1ccc(CC2CCCC2=O)cc1] | 3-((3R,4R)-4-methyl-3-(methyl (7-(2-(4-((2-oxocyclopentyl)methyl)phenyl) propanoyl)-7H-pyrrolo[2,3-d]pyrimidin-4-yl) amino)piperidin-1-yl)-3-oxopropanenitrile |
| 12 (CPD-012) | 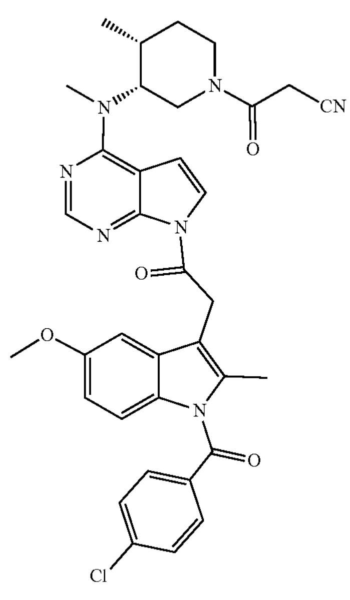 [SMILES: COc1ccc2c(c1)c(CC(=O)n1ccc3c(N(C)[C@H]4CN(C(=O)CC#N)CC[C@H]4C)ncnc31)c(C)n2C(=O)c1ccc(Cl)cc1] | 3-((3R, 4R)-3-((7-(2-(1-(4-chlorobenzoyl)-5-methoxy-2-methyl-1H-indol-3-yl)acetyl)-7H-pyrrolo[2, 3-d]pyrimidin-4-yl)(methyl) amino)-4-methylpiperidin-1-yl)-3-oxopropanenitrile |

TABLE 1-continued

Structural formulas and compound names of target compounds prepared in examples

| Examples (Cmpd No.) | Structure | Chinese name |
|---|---|---|
| 13 (CPD-013) | 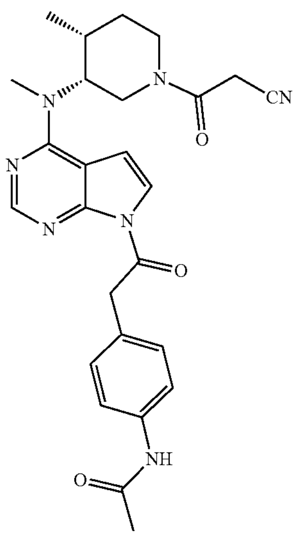 [SMILES: CC(=O)Nc1ccc(CC(=O)n2ccc3c(N(C)[C@H]4CN(C(=O)CC#N)CC[C@H]4C)ncnc32)cc1] | N-(4-(2-(4-(((3R, 4R)-1-(2-cyanoacetyl)-4-methylpiperidin-3-yl) (methyl)amino)-7H-pyrrolo[2,3-d] pyrimidin-7-yl)-2-oxoethyl)phenyl)acetamide |
| 14 (CPD-014) | 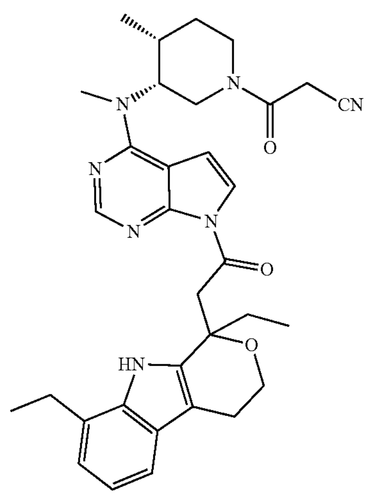 [SMILES: CCc1cccc2c3c([nH]c12)C(CC)(CC(=O)n1ccc2c(N(C)[C@H]4CN(C(=O)CC#N)CC[C@H]4C)ncnc21)OCC3] | 3-((3R,4R)-3-((7-(2-(1,8-diethyl-1,3,4, 9-tetrahydropyrano[3,4-b]indol-1-yl) acetyl)-7H-pyrrolo[2,3-d]pyrimidin-4-yl) (methyl) amino)-4-methylpiperidin-1-yl)-3-oxopropanenitrile |
| 15 (CPD-015) | 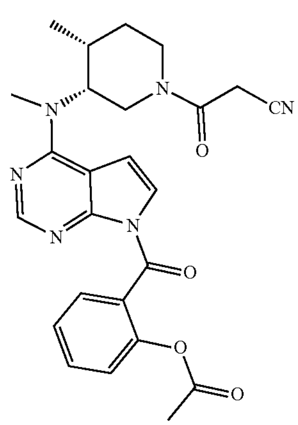 [SMILES: CC(=O)Oc1ccccc1C(=O)n1ccc2c(N(C)[C@H]3CN(C(=O)CC#N)CC[C@H]3C)ncnc21] | 2-(4-((3R, 4R)-1-(2-cyanoacetyl)-4-methylpiperidin-3-yl) (methyl)amino)-7H-pyrrolo[2,3-d] pyrimidine-7-carbonyl)phenyl acetate |

TABLE 1-continued

Structural formulas and compound names of target compounds prepared in examples

| Examples (Cmpd No.) | Structure | Chinese name |
|---|---|---|
| 16 (CPD-016) | 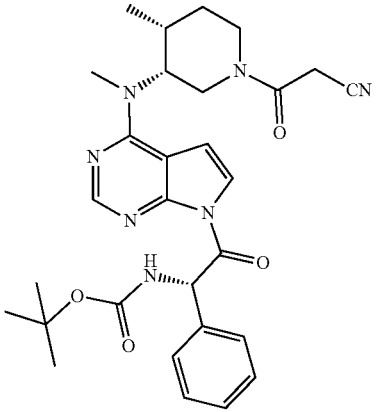 [SMILES: C[C@@H]1CCN(C(=O)CC#N)C[C@@H]1N(C)c1ncnc2c1ccn2C(=O)[C@@H](NC(=O)OC(C)(C)C)c1ccccc1] | Tert-butyl ((S)-2-(4-(((3R, 4R)-1-(2-cyanoacetyl)-4-methylpiperidin-3-yl) (methyl)amino)-7H-pyrrolo[2,3-d]pyrimidin-7-yl)-2-oxo-1-phenylethyl)carbamate |
| 17 (CPD-017) | 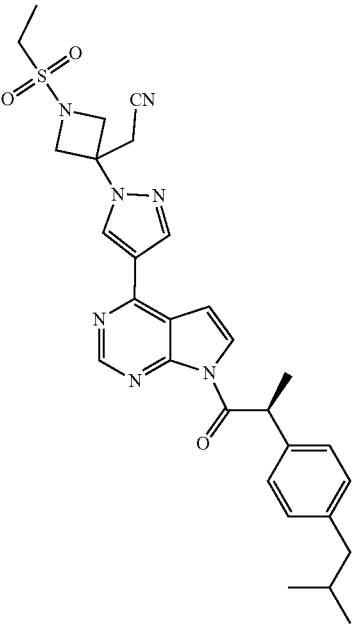 [SMILES: CCS(=O)(=O)N1CC(CC#N)(n2cc(-c3ncnc4c3ccn4C(=O)[C@@H](C)c3ccc(CC(C)C)cc3)cn2)C1] | (S)-2-(1-(ethylsulfonyl)-3-(4-(7-(2-(4-isobutyl-phenyl)propanoyl)-7H-pyrrolo[2,3-d]pyrimidin-4-yl)-1H-pyrazol-1-yl)azetidin-3-yl)acetonitrile |

TABLE 1-continued

Structural formulas and compound names of target compounds prepared in examples

| Examples (Cmpd No.) | Structure | Chinese name |
|---|---|---|
| 18 (CPD-018) | 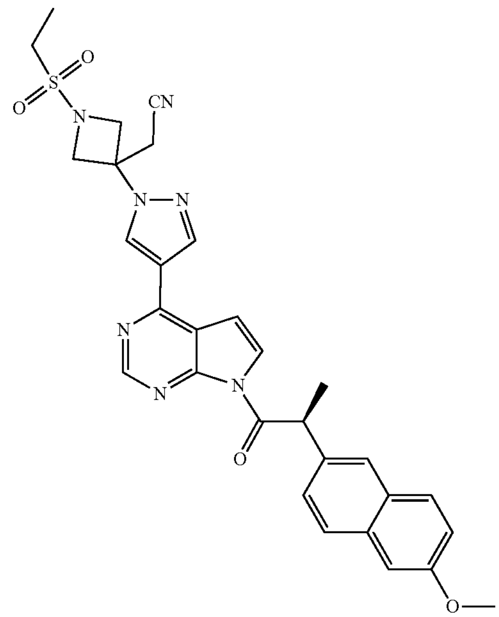 [SMILES: CCS(=O)(=O)N1CC(CC#N)(n2cc(-c3ncnc4c3ccn4C(=O)[C@@H](C)c3ccc4cc(OC)ccc4c3)cn2)C1] | (S)-2-(1-(ethylsulfonyl)-3-(4-(7-(2-(6-methoxy naphthalen-2-yl)propanoyl)-7H-pyrrolo[2,3-d]pyrimidin-4-yl)-1H-pyrazol-1-yl) azetidin-3-yl)acetonitrile |
| 19 (CPD-019) | 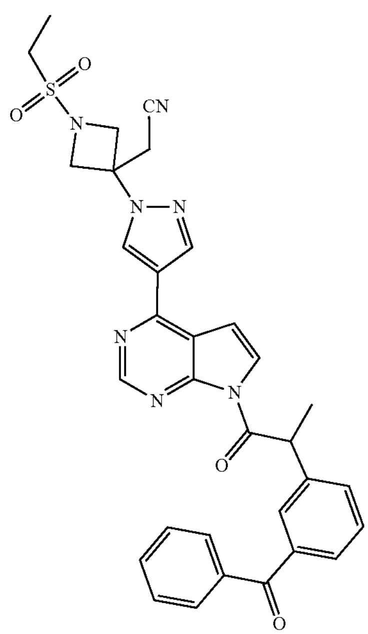 [SMILES: CCS(=O)(=O)N1CC(CC#N)(n2cc(-c3ncnc4c3ccn4C(=O)C(C)c3cccc(C(=O)c4ccccc4)c3)cn2)C1] | 2-(3-(4-(7-(2-(3-benzoylphenyl) propanoyl)-7H-pyrrolo[2,3-d] pyrimidin-4-yl)-1H-pyrazol-1-yl)-1-(ethylsulfonyl)azetidin-3-yl)acetonitrile |

TABLE 1-continued

Structural formulas and compound names of target compounds prepared in examples

| Examples (Cmpd No.) | Structure | Chinese name |
|---|---|---|
| 20 (CPD-020) | 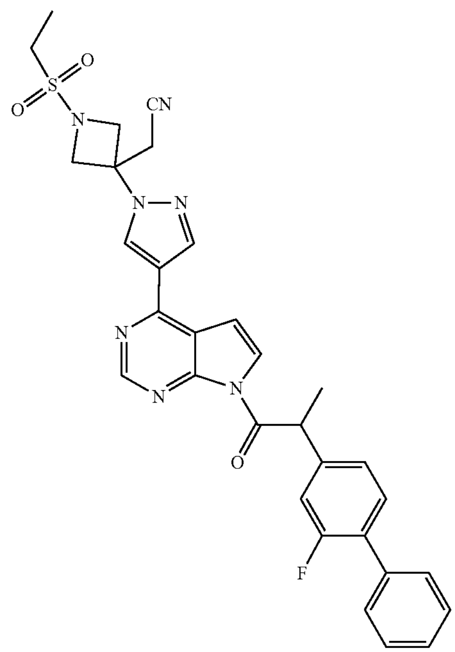 [SMILES: CCS(=O)(=O)N1CC(CC#N)(n2cc(-c3ncnc4c3ccn4C(=O)C(C)c3ccc(-c4ccccc4)c(F)c3)cn2)C1] | 2-(1-(ethylsulfonyl)-3-(4-(7-(2-(2-fluoro-[1,1'-biphenyl]-4-yl)propanoyl)-7H-pyrrolo[2,3-d]pyrimidin-4-yl)-1H-pyrazol-1-yl)azetidin-3-yl)acetonitrile |
| 21 (CPD-021) | 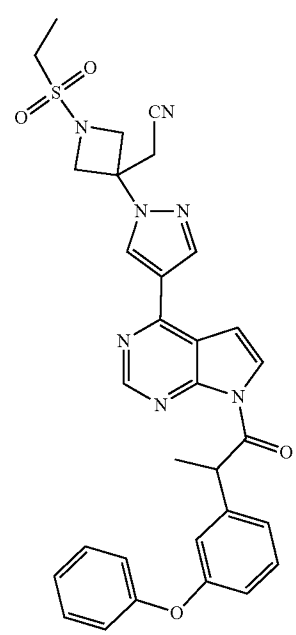 [SMILES: CCS(=O)(=O)N1CC(CC#N)(n2cc(-c3ncnc4c3ccn4C(=O)C(C)c3cccc(Oc4ccccc4)c3)cn2)C1] | 2-(1-(ethylsulfonyl)-3-(4-(7-(2-(3-phenoxyphenyl)propanoyl)-7H-pyrrolo[2,3-d]pyrimidin-4-yl)-1H-pyrazol-1-yl)azetidin-3-yl)acetonitrile |

TABLE 1-continued

Structural formulas and compound names of target compounds prepared in examples

| Examples (Cmpd No.) | Structure | Chinese name |
|---|---|---|
| 22 (CPD-022) | 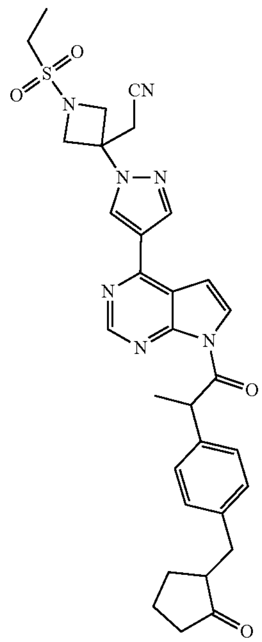 [SMILES: CCS(=O)(=O)N1CC(CC#N)(n2cc(-c3ncnc4c3ccn4C(=O)C(C)c3ccc(CC4CCCC4=O)cc3)cn2)C1] | 2-(1-(ethylsulfonyl)-3-(4-(7-(2-(4-(2-oxocyclopentyl)methyl)phenyl)propanoyl)-7H-pyrrolo[2,3-d]pyrimidin-4-yl)-1H-pyrazol-1-yl)azetidin-3-yl)acetonitrile |
| 23 (CPD-023) | 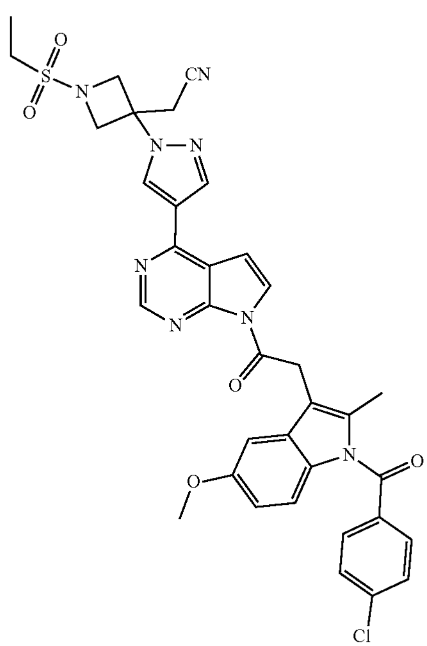 [SMILES: CCS(=O)(=O)N1CC(CC#N)(n2cc(-c3ncnc4c3ccn4C(=O)Cc3c(C)n(C(=O)c4ccc(Cl)cc4)c4ccc(OC)cc34)cn2)C1] | 2-(3-(4-(7-(2-(1-(4-chlorobenzoyl)-5-methoxy-2-methyl-1H-indol-3-yl)acetyl)-7H-pyrrolo[2,3-d]pyrimidin-4-yl)-1H-pyrazol-1-yl)-1-(ethylsulfonyl)azetidin-3-yl)acetonitrile |

TABLE 1-continued

Structural formulas and compound names of target compounds prepared in examples

| Examples (Cmpd No.) | Structure | Chinese name |
|---|---|---|
| 24 (CPD-024) | 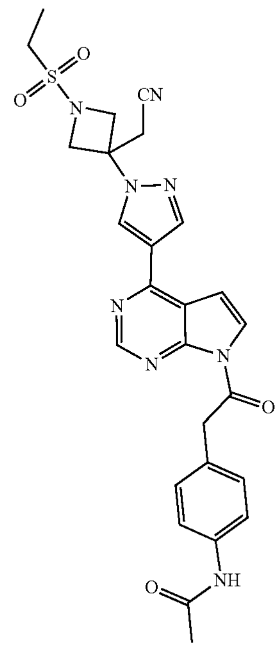 [SMILES: CCS(=O)(=O)N1CC(CC#N)(n2cc(-c3ncnc4c3ccn4C(=O)Cc3ccc(NC(C)=O)cc3)cn2)C1] | N-(4-(2-(4-(1-(3-(cyanomethyl)-1-(ethylsulfonyl)azetidin-3-yl)-1H-pyrazol-4-yl)-7H-pyrrolo[2,3-d]pyrimidin-7-yl)-2-oxoethyl)phenyl)acetamide |
| 25 (CPD-025) | 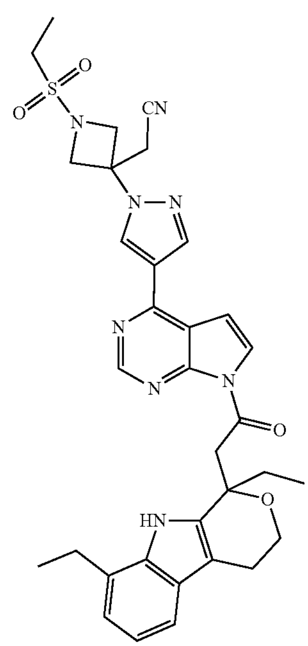 [SMILES: CCc1cccc2c3c([nH]c12)C(CC)(CC(=O)n1ccc2c(-c4cnn(C5(CC#N)CN(S(=O)(=O)CC)C5)c4)ncnc21)OCC3] | 2-(3-(4-(7-(2-(1,8-diethyl-1,3,4,9-tetrahydropyrano[3,4-b]indol-1-yl)acetyl)-7H-pyrrolo[2,3-d]pyrimidin-4-yl)-1H-pyrazol-1-yl)-1-(ethylsulfonyl)azetidin-3-yl)acetonitrile |

TABLE 1-continued

Structural formulas and compound names of target compounds prepared in examples

| Examples (Cmpd No.) | Structure | Chinese name |
|---|---|---|
| 26 (CPD-026) | 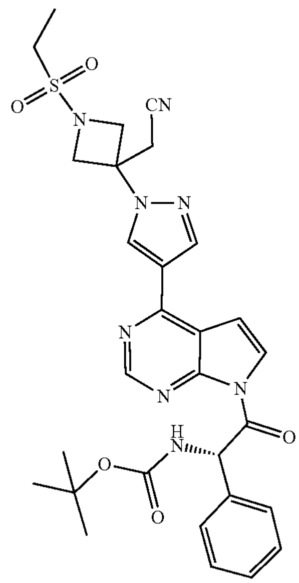 [SMILES: CCS(=O)(=O)N1CC(CC#N)(n2cc(-c3ncnc4c3ccn4C(=O)[C@@H](NC(=O)OC(C)(C)C)c3ccccc3)cn2)C1] | Tert-butyl (S)-(2-(4-(1-(3-(cyanomethyl)-1-(ethylsulfonyl)azetidin-3-yl)-1H-pyrazol-4-yl)-7H-pyrrolo[2,3-d]pyrimidin-7-yl)-2-oxo-1-phenylethyl)carbamate |
| 27 (CPD-027) | 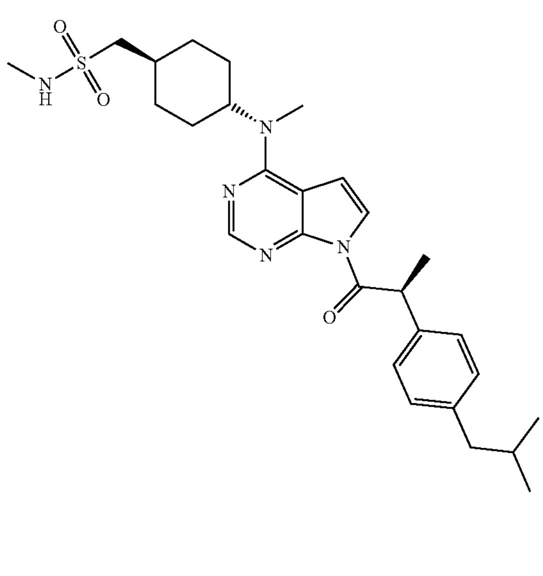 | 1-((Trans-)-4-((7-((S)-2-(4-isobutylphenyl)propanoyl)-7H-pyrrolo[2,3-d]pyrimidin-4-yl)(methyl)amino)cyclohexyl)-N-methyl methanesulfonamide |

TABLE 1-continued

Structural formulas and compound names of target compounds prepared in examples

| Examples (Cmpd No.) | Structure | Chinese name |
|---|---|---|
| 28 (CPD-028) | 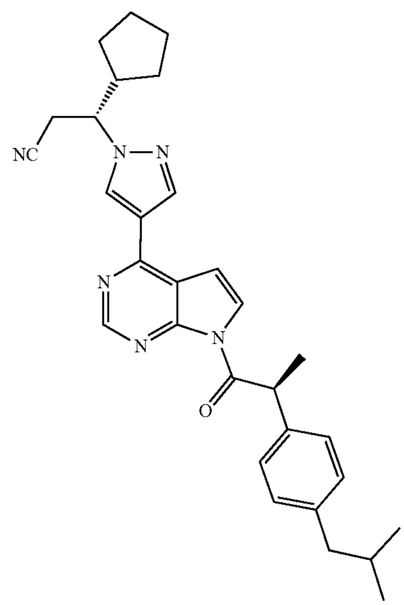 [SMILES: CC(C)Cc1ccc([C@H](C)C(=O)n2ccc3c(-c4cnn([C@H](CC#N)C5CCCC5)c4)ncnc32)cc1] | (R)-3-cyclopentyl-3-(4-(7-(S)-2-(4-isobutylphenyl)propanoyl)-7H-pyrrolo[2,3-d]pyrimidin-4-yl)-1H-pyrazol-1-yl)propanenitrile |
| 29 (CPD-029) | 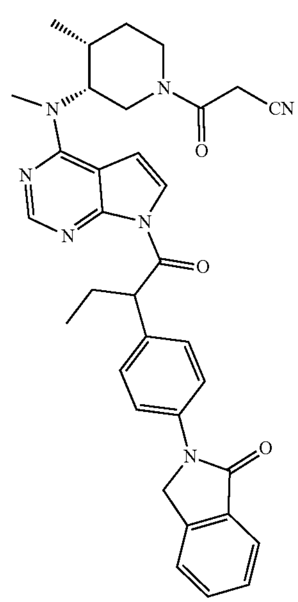 [SMILES: CCC(C(=O)n1ccc2c(N(C)[C@H]3CN(C(=O)CC#N)CC[C@H]3C)ncnc21)c1ccc(N2Cc3ccccc3C2=O)cc1] | 3-((3R,4R)-4-methyl-3-(methyl(7-(2-(4-(1-oxoisoindolin-2-yl)phenyl)butanoyl)-7H-pyrrolo[2,3-d]pyrimidin-4-yl)amino)piperidin-1-yl)-3-oxopropanenitrile |

TABLE 1-continued

Structural formulas and compound names of target compounds prepared in examples

| Examples (Cmpd No.) | Structure | Chinese name |
|---|---|---|
| 30 (CPD-030) | 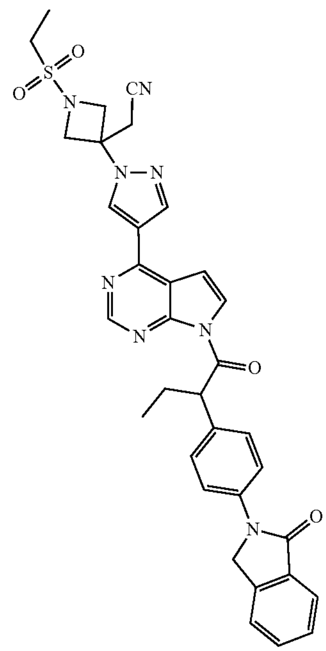 [SMILES: CCC(C(=O)n1ccc2c(-c3cnn(C4(CC#N)CN(S(=O)(=O)CC)C4)c3)ncnc21)c1ccc(N2Cc3ccccc3C2=O)cc1] | 2-2-(1-(Ethylsulfonyl)-3-(4-(7-(2-(4-(1-oxoiso-indolin-2-yl)phenyl)butanoyl)-7H-pyrrolo[2,3-d]pyrimidin-4-yl)-1H-pyrazol-1-yl)azetidin-3-yl)acetonitrile |
| 31 (CPD-039) | 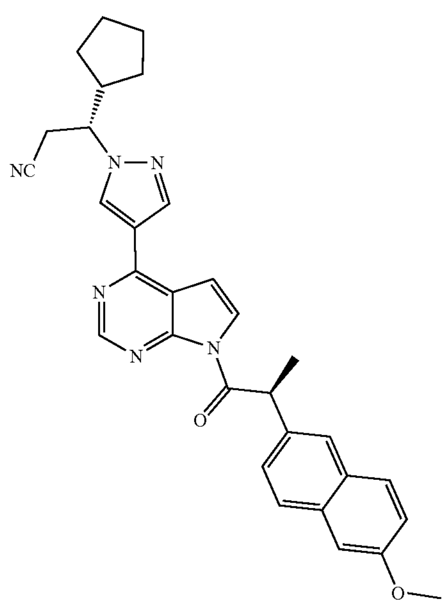 [SMILES: COc1ccc2cc([C@H](C)C(=O)n3ccc4c(-c5cnn([C@H](CC#N)C6CCCC6)c5)ncnc43)ccc2c1] | (R)-3-cyclopentyl-3-(4-(7-((S)-2-(6-methoxy-naphthalen-2-yl)propanoyl)-7H-pyrrolo[2,3-d]pyrimidin-4-yl))-1H-pyrazol-1-yl)propanenitrile |

TABLE 1-continued

Structural formulas and compound names of target compounds prepared in examples

| Examples (Cmpd No.) | Structure | Chinese name |
|---|---|---|
| 32 (CPD-040) | 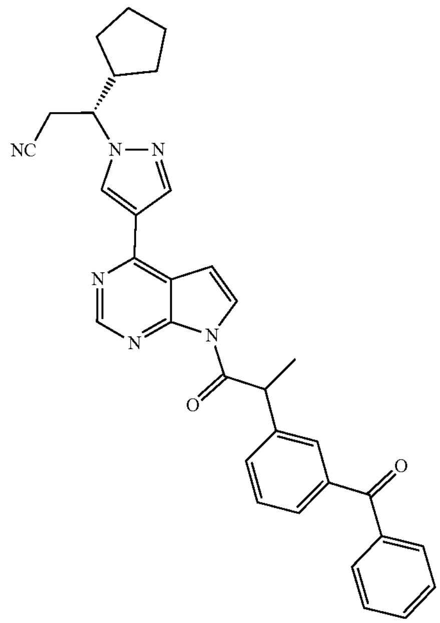 [SMILES: CC(C(=O)n1ccc2c(-c3cnn([C@H](CC#N)C4CCCC4)c3)ncnc21)c1cccc(C(=O)c2ccccc2)c1] | (3R)-3-(4-(7-(2-(3-benzoylphenyl)propanoyl)-7H-pyrrolo[2,3-d]pyrimidin-4-yl)-1H-pyrazol-1-yl)-3-cyclopentylpropanenitrile |
| 33 (CPD-041) | 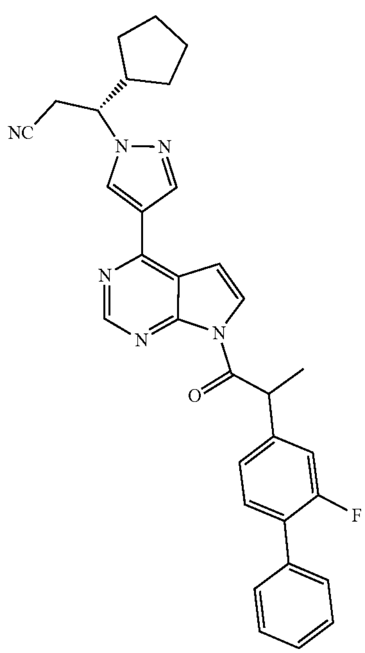 [SMILES: CC(C(=O)n1ccc2c(-c3cnn([C@H](CC#N)C4CCCC4)c3)ncnc21)c1ccc(-c2ccccc2)c(F)c1] | (3R)-3-cyclopentyl-3-(4-(7-(2-(2-fluoro-[1,1'-biphenyl]-4-yl)propanoyl)-7H-pyrrolo[2,3-d]pyrimidin-4-yl)-1H-pyrazol-1-yl)propanenitrile |

TABLE 1-continued

Structural formulas and compound names of target compounds prepared in examples

| Examples (Cmpd No.) | Structure | Chinese name |
|---|---|---|
| 34 (CPD-050) | 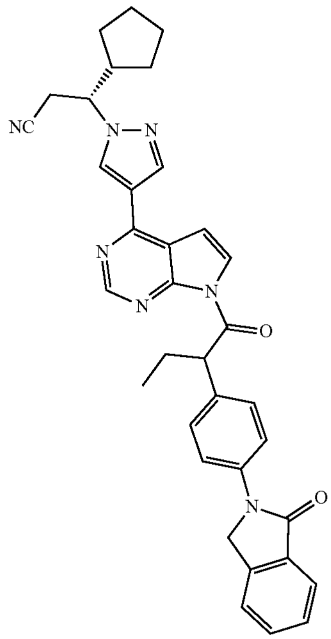 [SMILES: CCC(C(=O)n1ccc2c(-c3cnn([C@H](CC#N)C4CCCC4)c3)ncnc21)c1ccc(N2Cc3ccccc3C2=O)cc1] | (3R)-3-cyclopentyl-3-(4-(7-(2-(4-(1-oxoisoindolin-2-yl)phenyl)butanoyl)-7H-pyrrolo[2,3-d]pyrimidin-4-yl)-1H-pyrazol-1-yl)propanenitrile |
| 35 (CPD-065) | 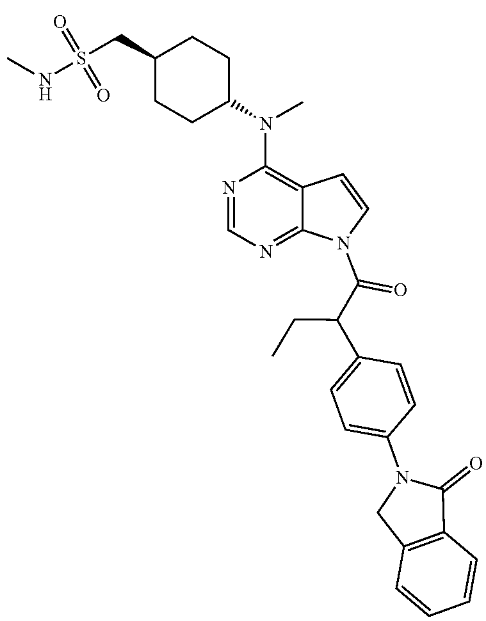 | N-methyl-1-((trans)-4-(methyl(7-(2-(4-(1-oxoisoindolin-2-yl)phenyl)butanoyl)-7H-pyrrolo[2,3-d]pyrimidin-4-yl)amino)cyclohexyl)methanesulfonamide |

TABLE 1-continued

Structural formulas and compound names of target compounds prepared in examples

| Examples (Cmpd No.) | Structure | Chinese name |
|---|---|---|
| 36 (CPD-056) | 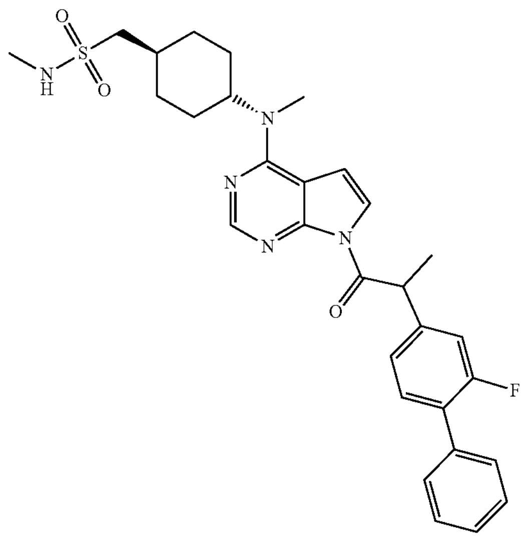 | 1-((Trans)-4-((7-(2-(2-fluoro-[1,1'-biphenyl]-4-yl)propanoyl)-7H-pyrrolo[2,3-d]pyrimidin-4-yl)(methyl)amino)cyclohexyl)-N-methyl methanesulfonamide |
| 37 (CPD-062) | 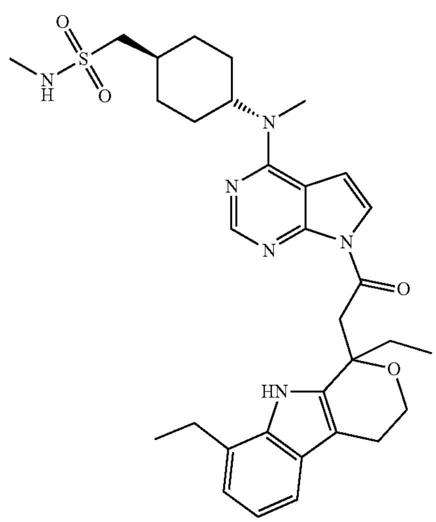 | 1-((Trans)-4-((7-(2-(1,8-diethyl-1,3,4,9-tetrahydropyrano[3,4-b]indol-1-yl)acetyl)-7H-pyrrolo[2,3-d]pyrimidin-4-yl)(methyl)amino)cyclohexyl)-N-methyl methanesulfonamide |
| 38 (CPD-055) | 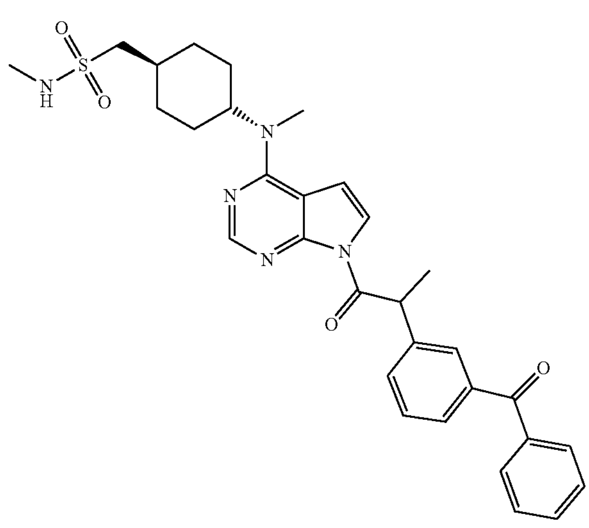 | 1-((Trans)-4-((7-(2-(3-benzoylphenyl)propanoyl)-7H-pyrrolo[2,3-d]pyrimidin-4-yl)(methyl)amino)cyclohexyl)-N-methyl methanesulfonamide |

TABLE 1-continued

Structural formulas and compound names of target compounds prepared in examples

| Examples (Cmpd No.) | Structure | Chinese name |
|---|---|---|
| 39 (CPD-054) | 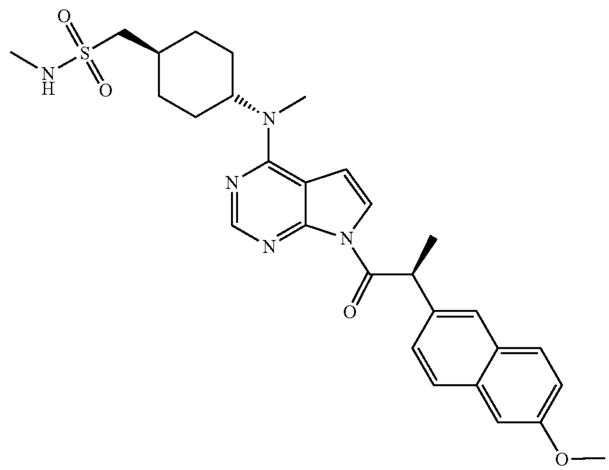 | 1-((Trans)-4-((7-((S)-2-(6-methoxynaphthalen-2-yl)propanoyl)-7H-pyrrolo[2,3-d]pyrimidin-4-yl)(methyl)amino)cyclohexyl)-N-methyl methanesulfonamide |
| 40 (CPD-032) | 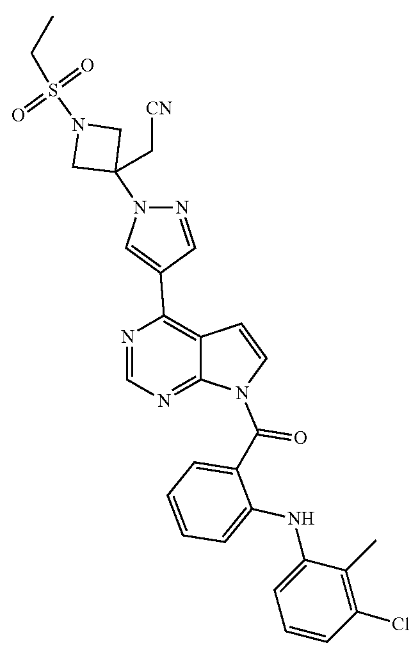 [SMILES: CCS(=O)(=O)N1CC(CC#N)(n2cc(-c3ncnc4c3ccn4C(=O)c3ccccc3Nc3cccc(Cl)c3C)cn2)C1] | 2-(3-(4-(7-(2-((3-Chloro-2-methylphenyl)amino)benzoyl)-7H-pyrrolo[2,3-d]pyrimidin-4-yl)-1H-pyrazol-1-yl)-1-(ethylsulfonyl)azetidin-3-yl)acetonitrile |

TABLE 1-continued

Structural formulas and compound names of target compounds prepared in examples

| Examples (Cmpd No.) | Structure | Chinese name |
|---|---|---|
| 41 (CPD-053) | 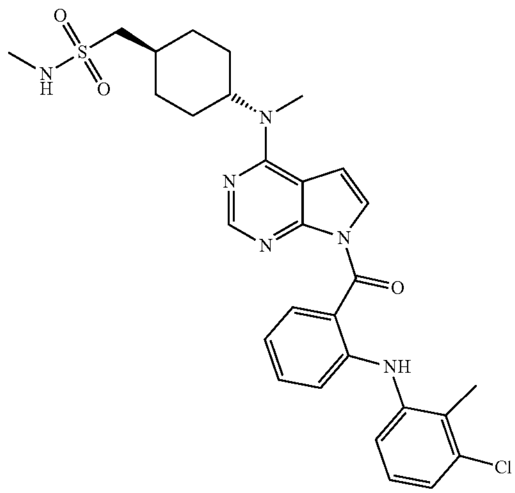 | 1-((Trans)-4-((7-(2-((3-chloro-2-methylphenyl)amino)benzoyl)-7H-pyrrolo[2,3-d]pyrimidin-4-yl)(methyl)amino)cyclohexyl)-N-methyl methanesulfonamide |
| 42 (CPD-060) | 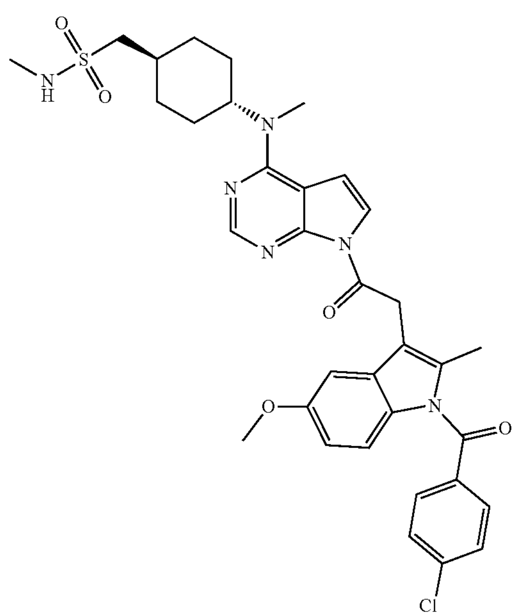 [SMILES: CNS(=O)(=O)C[C@H]1CC[C@H](N(C)c2ncnc3c2ccn3C(=O)Cc2c(C)n(C(=O)c3ccc(Cl)cc3)c3ccc(OC)cc23)CC1] | 1-((Trans)-4-((7-(2-(1-(4-chlorobenzoyl)-5-methoxy-2-methyl-1H-indol-3-yl)acetyl)-7H-pyrrolo[2,3-d]pyrimidin-4-yl)(methyl)amino)cyclohexyl)-N-methylmethanesulfonamide |

TABLE 1-continued

Structural formulas and compound names of target compounds prepared in examples

| Examples (Cmpd No.) | Structure | Chinese name |
|---|---|---|
| 43 (CPD-052) | 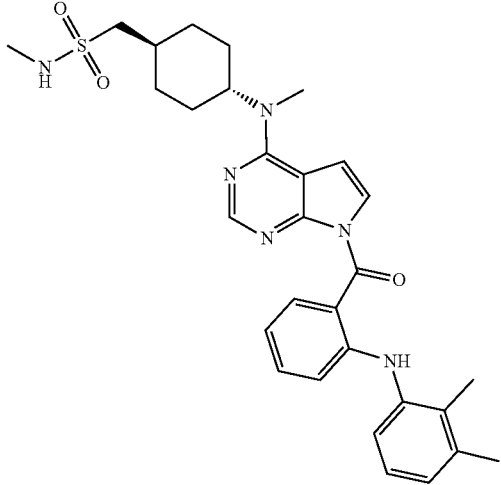 | 1-((Trans)-4-((7-(2-((2,3-dimethylphenyl)amino)benzoyl)-7H-pyrrolo[2,3-d]pyrimidin-4-yl)(methyl)amino)cyclohexyl)-N-methyl methanesulfonamide |
| 44 (CPD-059) | 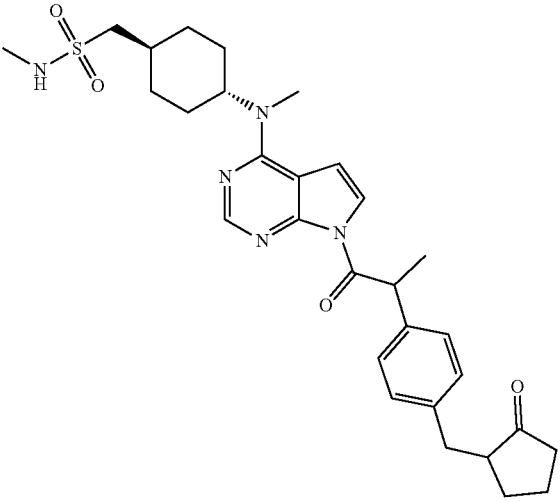 [SMILES: CNS(=O)(=O)C[C@H]1CC[C@H](N(C)c2ncnc3c2ccn3C(=O)C(C)c2ccc(CC3CCCC3=O)cc2)CC1] | N-methyl-1-((trans)-4-(methyl(7-(2-(4-((2-oxocyclopentyl)methyl)phenyl)propanoyl)-7H-pyrrolo[2,3-d]pyrimidin-4-yl)amino)cyclohexyl)methanesulfonamide |

TABLE 1-continued

Structural formulas and compound names of target compounds prepared in examples

| Examples (Cmpd No.) | Structure | Chinese name |
|---|---|---|
| 45 (CPD-047) | 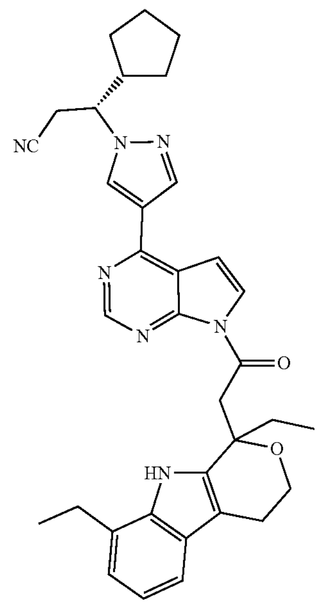 [SMILES: CCc1cccc2c3c([nH]c12)C(CC)(CC(=O)n1ccc2c(-c4cnn([C@H](CC#N)C5CCCC5)c4)ncnc21)OCC3] | (3R)-3-cyclopentyl-3-(4-(7-(2-(1,8-diethyl-1,3,4,9-tetrahydropyran[3,4-b]indol-1-yl)acetyl)-7H-pyrrolo[2,3-d]pyrimidin-4-yl)-1H-pyrazol-1-yl)propanenitrile |
| 46 (CPD-064) | 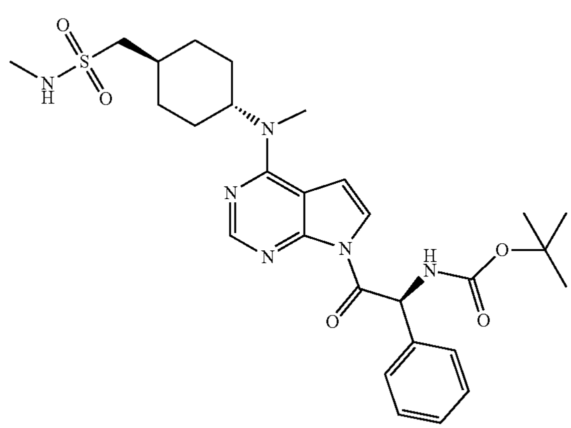 [SMILES: CNS(=O)(=O)C[C@H]1CC[C@H](N(C)c2ncnc3c2ccn3C(=O)[C@@H](NC(=O)OC(C)(C)C)c2ccccc2)CC1] | Tert-butyl ((S)-2-(4-(methyl((trans)-4-((N-methylsulfamoyl)methyl)cyclohexyl)amino)-7H-pyrrolo[2,3-d]pyrimidin-7-yl)-2-oxo-1-phenylethyl)carbamate |

TABLE 1-continued

Structural formulas and compound names of target compounds prepared in examples

| Examples (Cmpd No.) | Structure | Chinese name |
|---|---|---|
| 47 (CPD-031) | 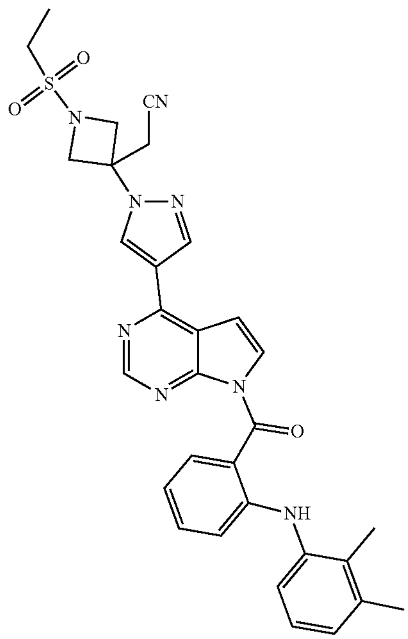 [SMILES: CCS(=O)(=O)N1CC(CC#N)(n2cc(-c3ncnc4c3ccn4C(=O)c3ccccc3Nc3cccc(C)c3C)cn2)C1] | 2-(3-(4-(7-(2-((2,3-Dimethylphenyl)amino) benzoyl)-7H-pyrrolo[2,3-d]pyrimidin-4-yl)-1H-pyrazol-1-yl)-1-(ethylsulfonyl) azetidin-3-yl)acetonitrile |
| 48 (CPD-082) | 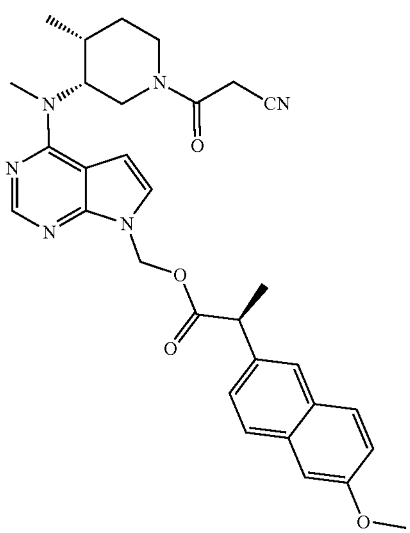 | 4-(((3R, 4R)-1-(2-cyanoacetyl)-4-methylpiperidin-3-yl) (methyl)amino)-7H-pyrrolo[2,3-d]pyrimidin-7-yl)methyl (S)-2-(6-methoxynaphthalen-2-yl)propanoate |

TABLE 1-continued

Structural formulas and compound names of target compounds prepared in examples

| Examples (Cmpd No.) | Structure | Chinese name |
|---|---|---|
| 49 (CPD-083) | 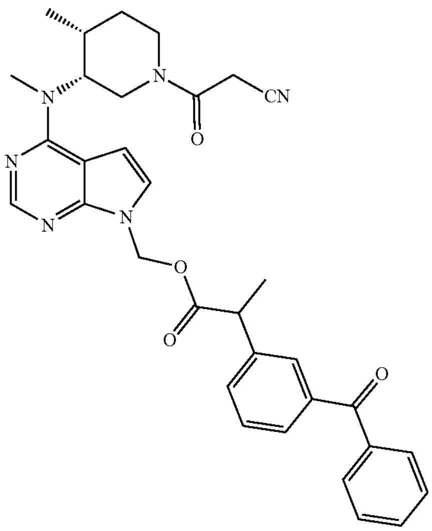 [SMILES: CC(C(=O)OCn1ccc2c(N(C)[C@H]3CN(C(=O)CC#N)CC[C@H]3C)ncnc21)c1cccc(C(=O)c2ccccc2)c1] | (4-(((3R, 4R)-1-(2-cyanoacetyl)-4-methylpiperidin-3-yl) (methyl)amino)-7H-pyrrolo[2,3-d]pyrimidin-7-yl)methyl 2-(3-benzoylphenyl)propanoate |
| 50 (CPD-084) | 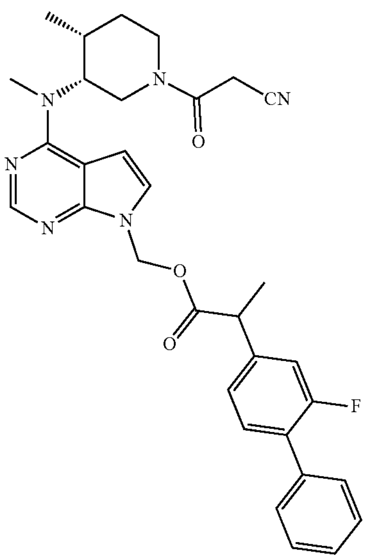 [SMILES: CC(C(=O)OCn1ccc2c(N(C)[C@H]3CN(C(=O)CC#N)CC[C@H]3C)ncnc21)c1ccc(-c2ccccc2)c(F)c1] | (4-(((3R, 4R)-1-(2-cyanoacetyl)-4-methylpiperidin-3-yl) (methyl)amino)-7H-pyrrolo[2,3-d]pyrimidin-7-yl)methyl 2-(2-fluoro-[1,1'-biphenyl]-4-yl) propanoate |
| 51 (CPD-085) | 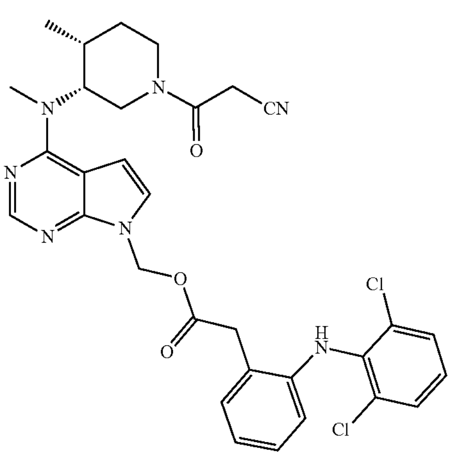 [SMILES: C[C@@H]1CCN(C(=O)CC#N)C[C@@H]1N(C)c1ncnc2c1ccn2COC(=O)Cc1ccccc1Nc1c(Cl)cccc1Cl] | (4-(((3R, 4R)-1-(2-cyanoacetyl)-4-methylpiperidin-3-yl) (methyl)amino)-7H-pyrrolo[2,3-d]pyrimidin-7-yl)methyl 2-(2-((2,6-dichlorophenyl) amino)phenyl)acetate |

TABLE 1-continued

Structural formulas and compound names of target compounds prepared in examples

| Examples (Cmpd No.) | Structure | Chinese name |
|---|---|---|
| 52 (CPD-086) | 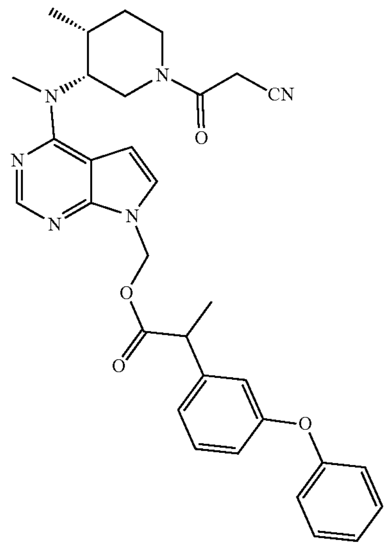 [SMILES: CC(C(=O)OCn1ccc2c(N(C)[C@H]3CN(C(=O)CC#N)CC[C@H]3C)ncnc21)c1cccc(Oc2ccccc2)c1] | (4-(((3R, 4R)-1-(2-cyanoacetyl)-4-methylpiperidin-3-yl)(methyl)amino)-7H-pyrrolo[2,3-d]pyrimidin-7-yl)methyl 2-(3-phenoxyphenyl)propanoate |
| 53 (CPD-087) | 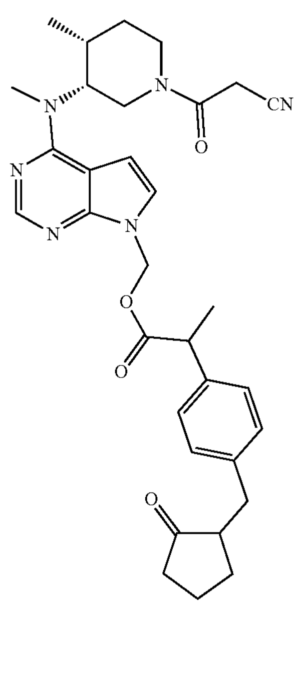 [SMILES: CC(C(=O)OCn1ccc2c(N(C)[C@H]3CN(C(=O)CC#N)CC[C@H]3C)ncnc21)c1ccc(CC2CCCC2=O)cc1] | (4-(((3R,4R)-1-(2-cyanoacetyl)-4-methylpiperidin-3-yl)(methyl)amino)-7H-pyrrolo[2,3-d]pyrimidin-7-yl)methyl 2-(4-((2-oxocyclopentyl)methyl)phenyl)propanoate |

TABLE 1-continued

Structural formulas and compound names of target compounds prepared in examples

| Examples (Cmpd No.) | Structure | Chinese name |
|---|---|---|
| 54 (CPD-043) | 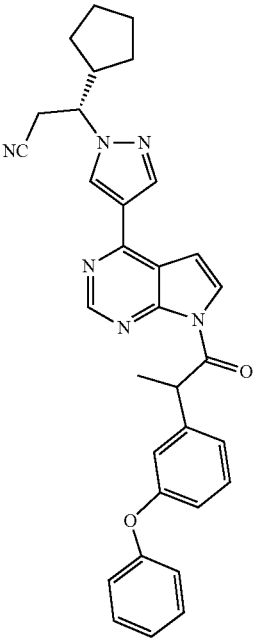 [SMILES: CC(C(=O)n1ccc2c(-c3cnn([C@H](CC#N)C4CCCC4)c3)ncnc21)c1cccc(Oc2ccccc2)c1] | (3R)-3-cyclopentyl-3-(4-(7-(2-(3-phenoxyphenyl)propanoyl)-7H-pyrrolo[2,3-d]pyrimidin-4-yl)-1H-pyrazol-1-yl)propanenitrile |
| 55 (CPD-088) | 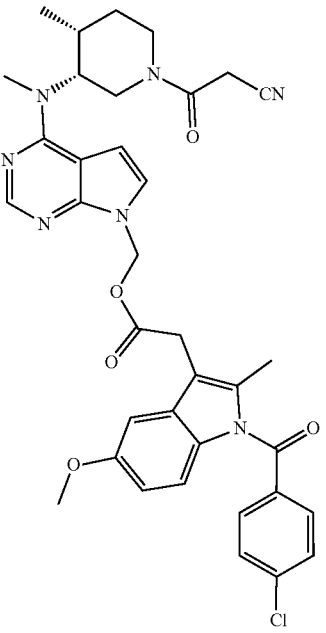 [SMILES: COc1ccc2c(c1)c(CC(=O)OCn1ccc3c(N(C)[C@H]4CN(C(=O)CC#N)CC[C@H]4C)ncnc31)c(C)n2C(=O)c1ccc(Cl)cc1] | (4-(((3R,4R)-1-(2-cyanoacetyl)-4-methylpiperidin-3-yl)(methyl)amino)-7H-pyrrolo[2,3-d]pyrimidin-7-yl)methyl 2-(1-(4-chlorobenzoyl)-5-methoxy-2-methyl-1H-indol-3-yl)acetate |

TABLE 1-continued

Structural formulas and compound names of target compounds prepared in examples

| Examples (Cmpd No.) | Structure | Chinese name |
|---|---|---|
| 56 (CPD-089) | 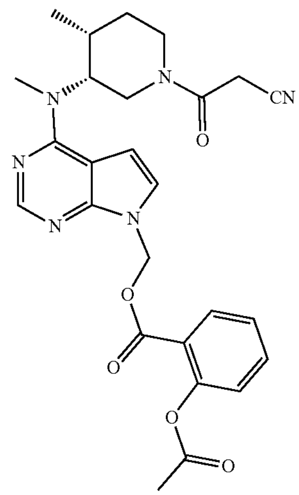 [SMILES: CC(=O)Oc1ccccc1C(=O)OCn1ccc2c(N(C)[C@H]3CN(C(=O)CC#N)CC[C@H]3C)ncnc21] | (4-(((3R, 4R)-1-(2-cyanoacetyl)-4-methylpiperidin-3-yl)(methyl)amino)-7H-pyrrolo[2,3-d]pyrimidin-7-yl)methyl 2-acetoxybenzoate |
| 57 (CPD-038) | 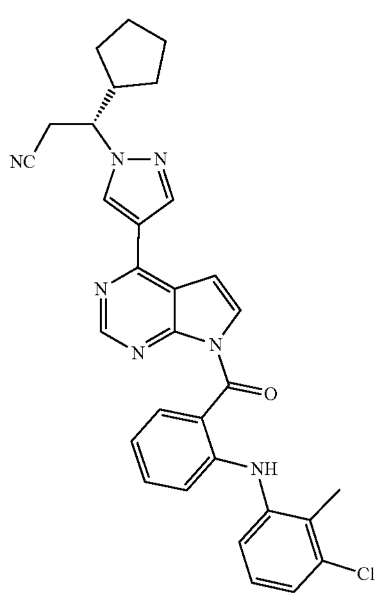 [SMILES: Cc1c(Cl)cccc1Nc1ccccc1C(=O)n1ccc2c(-c3cnn([C@H](CC#N)C4CCCC4)c3)ncnc21] | (R)-3-(4-(7-(2-((3-chloro-2-methylphenyl)amino)benzoyl)-7H-pyrrolo[2,3-d]pyrimidin-4-yl)-1H-pyrazol-1-yl)-3-cyclopentylpropanenitrile |

TABLE 1-continued

Structural formulas and compound names of target compounds prepared in examples

| Examples (Cmpd No.) | Structure | Chinese name |
|---|---|---|
| 58 (CPD-061) | 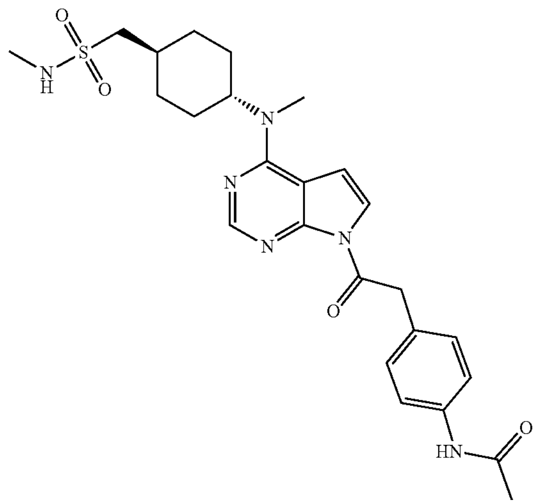 [SMILES: CNS(=O)(=O)C[C@H]1CC[C@H](N(C)c2ncnc3c2ccn3C(=O)Cc2ccc(NC(C)=O)cc2)CC1] | N-(4-(2-(4-(methyl ((trans)-4-((N-methylsulfamoyl)methyl) cyclohexyl)amino)-7H-pyrrolo[2,3-d] pyrimidin-7-yl)-2-oxoethyl)phenyl)acetamide |
| 59 (CPD-140) | 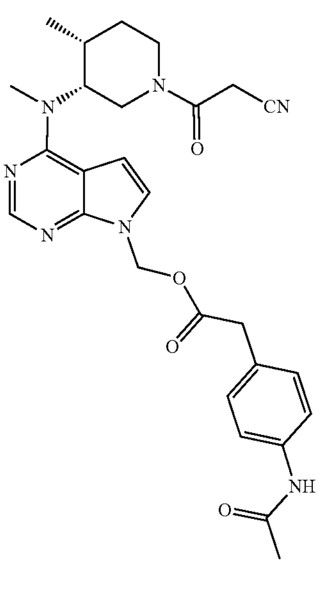 [SMILES: CC(=O)Nc1ccc(CC(=O)OCn2ccc3c(N(C)[C@H]4CN(C(=O)CC#N)CC[C@H]4C)ncnc32)cc1] | (4-(((3R, 4R)-1-(2-cyanoacetyl)- 4-methylpiperidin-3-yl) (methyl)amino)-7H-pyrrolo[2,3-d]pyrimidin- 7-yl)methyl 2-(4-acetamidophenyl)acetate |

TABLE 1-continued

Structural formulas and compound names of target compounds prepared in examples

| Examples (Cmpd No.) | Structure | Chinese name |
|---|---|---|
| 60 (CPD-092) | 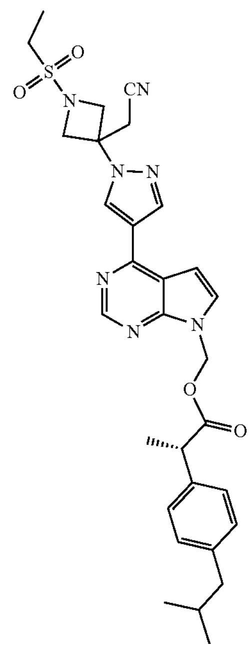 [SMILES: CCS(=O)(=O)N1CC(CC#N)(n2cc(-c3ncnc4c3ccn4COC(=O)[C@@H](C)c3ccc(CC(C)C)cc3)cn2)C1] | Methyl (4-(1-(3-(cyanomethyl)-1-(ethylsulfonyl) azetidin-3-yl)-1H-pyrazol-4-yl)-7H-pyrrolo[2,3-d]pyrimidin-7-yl) (S)-2-(4-isobutylphenyl) propanoate |
| 61 (CPD-093) | 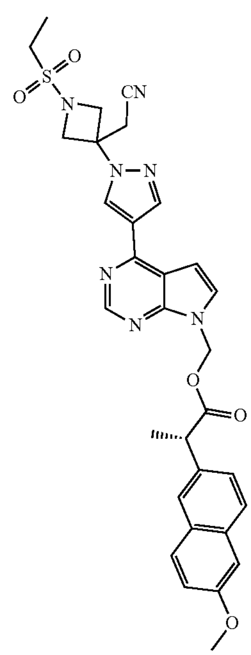 [SMILES: CCS(=O)(=O)N1CC(CC#N)(n2cc(-c3ncnc4c3ccn4COC(=O)[C@@H](C)c3ccc4cc(OC)ccc4c3)cn2)C1] | Methyl (4-(1-(3-(cyanomethyl)-1-(ethylsulfonyl) azetidin-3-yl)-1H-pyrazol-4-yl)-7H-pyrrolo[2,3-d]pyrimidin-7-yl) (S)-2-(6-methoxynaphthalen-2-yl)propanoate |

TABLE 1-continued

Structural formulas and compound names of target compounds prepared in examples

| Examples (Cmpd No.) | Structure | Chinese name |
|---|---|---|
| 62 (CPD-094) | 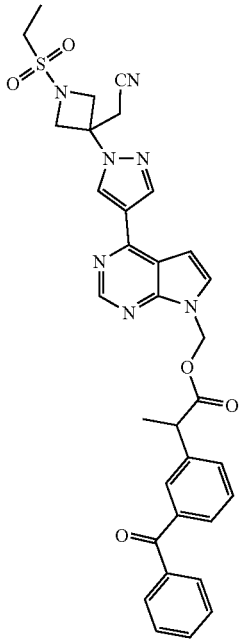 [SMILES: CCS(=O)(=O)N1CC(CC#N)(n2cc(-c3ncnc4c3ccn4COC(=O)C(C)c3cccc(C(=O)c4ccccc4)c3)cn2)C1] | 4-(1-(3-(cyanomethyl)-1-(ethylsulfonyl) azetidin-3-yl)-1H-pyrazol-4-yl)-7H-pyrrolo[2,3-d]pyrimidin-7-yl)methyl 2-(3-benzoylphenyl)propanoate |
| 63 (CPD-139) | 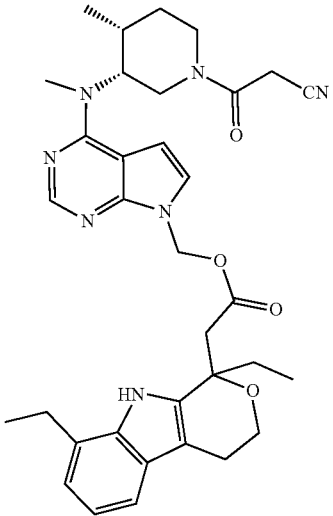 [SMILES: CCc1cccc2c3c([nH]c12)C(CC)(CC(=O)OCn1ccc2c(N(C)[C@H]4CN(C(=O)CC#N)CC[C@H]4C)ncnc21)OCC3] | (4-(((3R,4R)-1-(2-cyanoacetyl)-4-methylpiperidin-3-yl)(methyl)amino)-7H-pyrrolo[2,3-d]pyrimidin-7-yl)methyl 2-(1,8-diethyl-1,3,4,9-tetrahydropyrano[3,4-b]indol-1-yl)acetate |

TABLE 1-continued

Structural formulas and compound names of target compounds prepared in examples

| Examples (Cmpd No.) | Structure | Chinese name |
|---|---|---|
| 64 (CPD-141) | 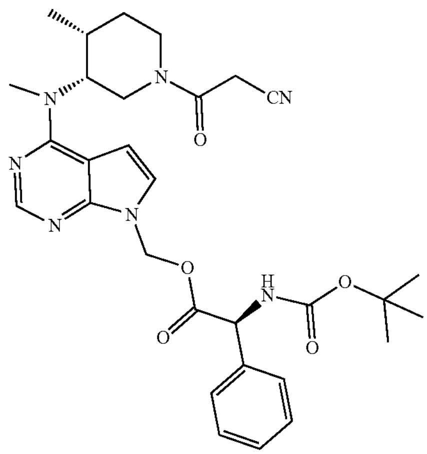 [SMILES: C[C@@H]1CCN(C(=O)CC#N)C[C@@H]1N(C)c1ncnc2c1ccn2COC(=O)[C@@H](NC(=O)OC(C)(C)C)c1ccccc1] | (4-(((3R, 4R)-1-(2-cyanoacetyl)-4-methylpiperidin-3-yl) (methyl)amino)-7H-pyrrolo[2,3-d]pyrimidin-7-yl)methyl (S)-2-((tert-butoxycarbonyl) amino)-2-phenylacetate |
| 65 (CPD-136) | 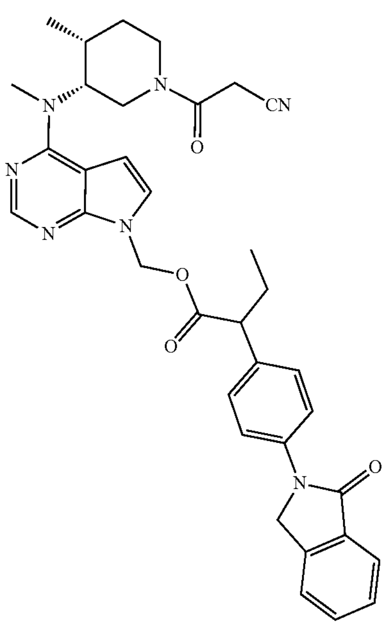 [SMILES: CCC(C(=O)OCn1ccc2c(N(C)[C@H]3CN(C(=O)CC#N)CC[C@H]3C)ncnc21)c1ccc(N2Cc3ccccc3C2=O)cc1] | (4-(((3R, 4R)-1-(2-cyanoacetyl)-4-methylpiperidin-3-yl) (methyl)amino)-7H-pyrrolo[2,3-d]pyrimidin-7-yl)methyl 2-(4-(1-oxoisoindol-2-yl)) phenyl)butanoate |

TABLE 1-continued

Structural formulas and compound names of target compounds prepared in examples

| Examples (Cmpd No.) | Structure | Chinese name |
|---|---|---|
| 66 (CPD-138) | 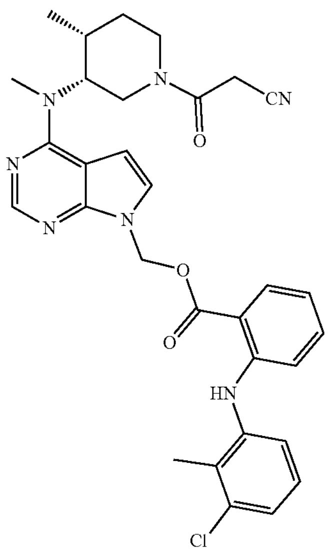 [SMILES: Cc1c(Cl)cccc1Nc1ccccc1C(=O)OCn1ccc2c(N(C)[C@H]3CN(C(=O)CC#N)CC[C@H]3C)ncnc21] | (4-(((3R, 4R)-1-(2-cyanoacetyl)-4-methylpiperidin-3-yl)(methyl)amino)-7H-pyrrolo[2,3-d]pyrimidin-7-yl)methyl 2-((3-chloro-2-methylphenyl)amino)benzoate |
| 67 (CPD-137) | 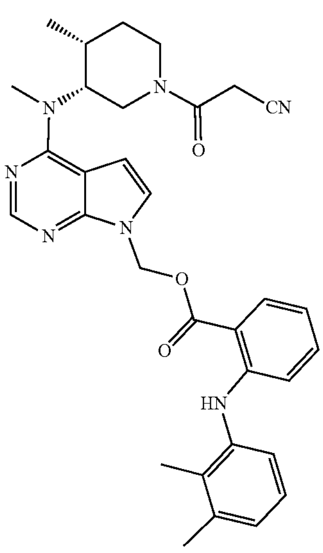 [SMILES: Cc1cccc(Nc2ccccc2C(=O)OCn2ccc3c(N(C)[C@H]4CN(C(=O)CC#N)CC[C@H]4C)ncnc32)c1C] | (4-(((3R, 4R)-1-(2-cyanoacetyl)-4-methylpiperidin-3-yl)(methyl)amino)-7H-pyrrolo[2,3-d]pyrimidin-7-yl)methyl 2-((2,3-dimethylphenyl)amino)benzoate |

TABLE 1-continued

Structural formulas and compound names of target compounds prepared in examples

| Examples (Cmpd No.) | Structure | Chinese name |
|---|---|---|
| 68 (CPD-058) | 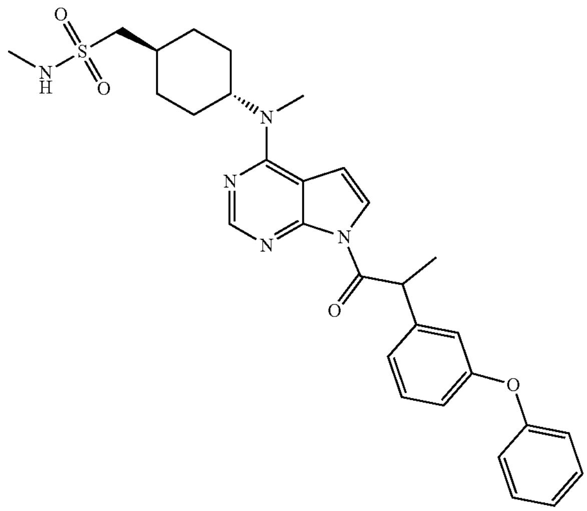 [SMILES: CNS(=O)(=O)C[C@H]1CC[C@H](N(C)c2ncnc3c2ccn3C(=O)C(C)c2cccc(Oc3ccccc3)c2)CC1] | N-methyl-1-((trans)-4-(methyl (7-(2-(3-phenoxyphenyl) propanoyl)-7H-pyrrolo[2,3-d]pyrimidin-4-yl) amino)cyclohexyl)methanesulfonamide |
| 69 (CPD-095) | 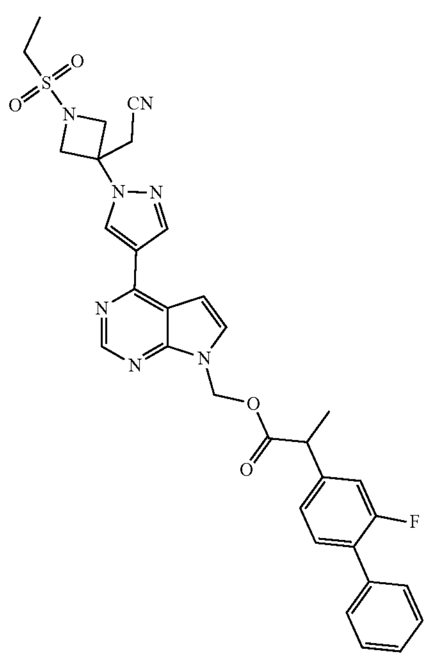 [SMILES: CCS(=O)(=O)N1CC(CC#N)(n2cc(-c3ncnc4c3ccn4COC(=O)C(C)c3ccc(-c4ccccc4)c(F)c3)cn2)C1] | Methyl (4-(1-(3-(cyanomethyl)-1-(ethylsulfonyl) azetidin-3-yl)-1H-pyrazol-4-yl)-7H-pyrrolo[2, 3-d]pyrimidin-7-yl) 2-(2-fluoro-[1, 1'-biphenyl]-4-yl)propanoate |

TABLE 1-continued

Structural formulas and compound names of target compounds prepared in examples

| Examples (Cmpd No.) | Structure | Chinese name |
|---|---|---|
| 70 (CPD-096) | 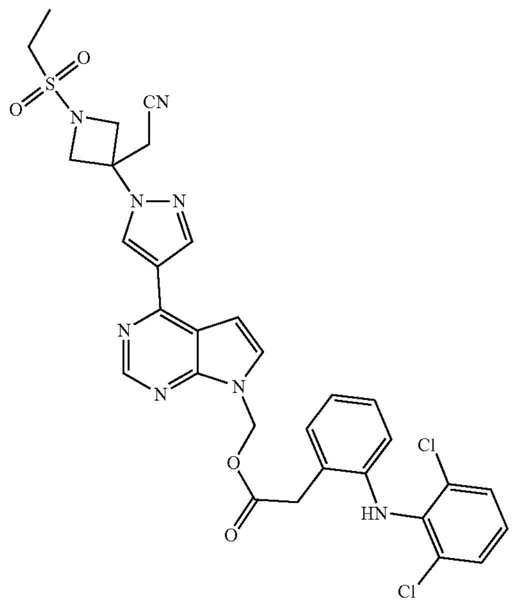 [SMILES: CCS(=O)(=O)N1CC(CC#N)(n2cc(-c3ncnc4c3ccn4COC(=O)Cc3ccccc3Nc3c(Cl)cccc3Cl)cn2)C1] | Methyl (4-(1-(3-(cyanomethyl)-1-(ethylsulfonyl) azetidin-3-yl)-1H-pyrazol-4-yl)-7H-pyrrolo[2, 3-d]pyrimidin-7-yl) 2-(2-((2, 6-dichlorophenyl)amino)phenyl)acetate |
| 71 (CPD-097) | 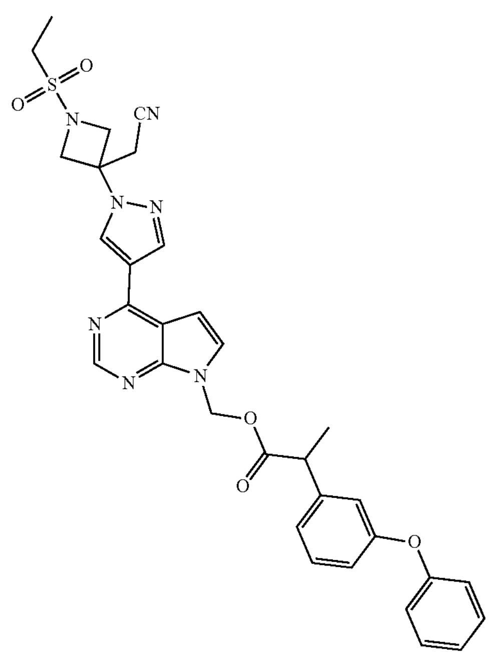 [SMILES: CCS(=O)(=O)N1CC(CC#N)(n2cc(-c3ncnc4c3ccn4COC(=O)C(C)c3cccc(Oc4ccccc4)c3)cn2)C1] | Methyl (4-(1-(3-(cyanomethyl)-1-(ethylsulfonyl) azetidin-3-yl)-1H-pyrazol-4-yl)-7H-pyrrolo[2, 3-d]pyrimidin-7-yl) 2-(3-phenoxyphenyl) propanoate |

TABLE 1-continued

Structural formulas and compound names of target compounds prepared in examples

| Examples (Cmpd No.) | Structure | Chinese name |
|---|---|---|
| 72 (CPD-098) | 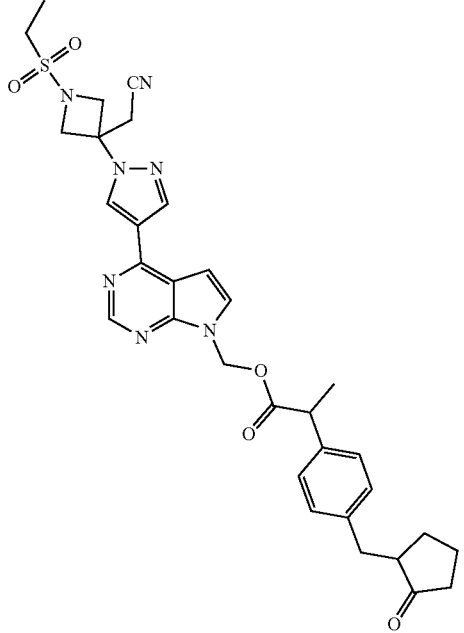 [SMILES: CCS(=O)(=O)N1CC(CC#N)(n2cc(-c3ncnc4c3ccn4COC(=O)C(C)c3ccc(CC4CCCC4=O)cc3)cn2)C1] | Methyl (4-(1-(3-(cyanomethyl)-1-(ethylsulfonyl) azetidin-3-yl)-1H-pyrazol-4-yl)-7H-pyrrolo[2, 3-d]pyrimidin-7-yl) 2-(4-((2-oxocyclopentyl) methyl)phenyl)propanoate |
| 73 (CPD-099) | 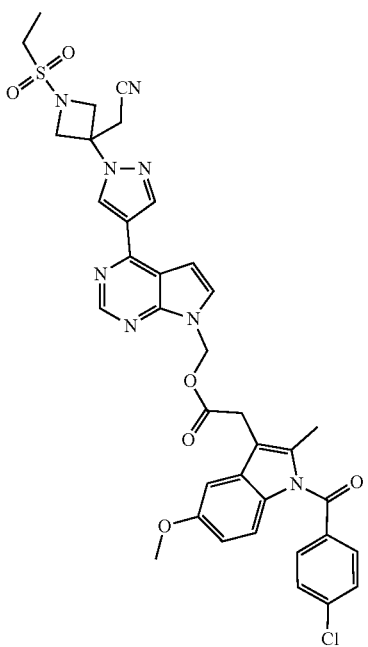 [SMILES: CCS(=O)(=O)N1CC(CC#N)(n2cc(-c3ncnc4c3ccn4COC(=O)Cc3c(C)n(C(=O)c4ccc(Cl)cc4)c4ccc(OC)cc34)cn2)C1] | Methyl (4-(1-(3-(cyanomethyl)-1-(ethylsulfonyl) azetidin-3-yl)-1H-pyrazol-4-yl)-7H-pyrrolo[2, 3-d]pyrimidin-7-yl) 2-(1-(4-chlorobenzoyl)-5-methoxy-2-methyl-1H-indol-3-yl)acetate |

TABLE 1-continued

Structural formulas and compound names of target compounds prepared in examples

| Examples (Cmpd No.) | Structure | Chinese name |
|---|---|---|
| 74 (CPD-150) | 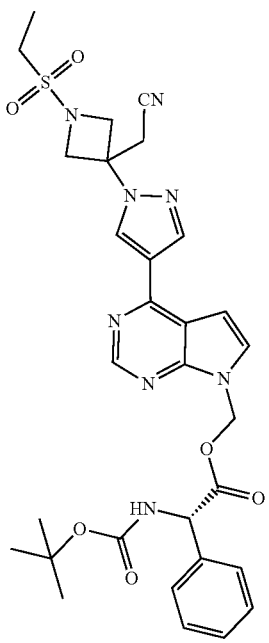 | Methyl (4-(1-(3-(cyanomethyl)-1-(ethylsulfonyl) azetidin-3-yl)-1H-pyrazol-4-yl)-7H-pyrrolo [2,3-d]pyrimidin-7-yl) (S)-2-((tert-butoxycarbonyl) amino)-2-phenylacetate |
| 75 (CPD-042) | 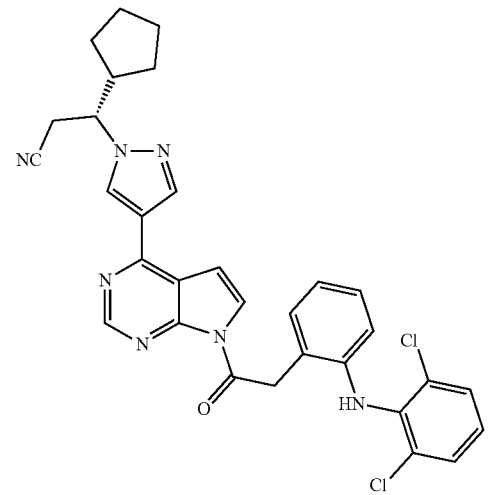 [SMILES: N#CC[C@H](C1CCCC1)n1cc(-c2ncnc3c2ccn3C(=O)Cc2ccccc2Nc2c(Cl)cccc2Cl)cn1] | (R)-3-cyclopentyl-3-(4-(7-(2-(2-((2, 6-dichlorophenyl)amino)phenyl) acetyl)-7H-pyrrolo[2,3-d]pyrimidin-4-yl)-1H-pyrazol-1-yl)propanenitrile |

TABLE 1-continued

Structural formulas and compound names of target compounds prepared in examples

| Examples (Cmpd No.) | Structure | Chinese name |
|---|---|---|
| 76 (CPD-145) | 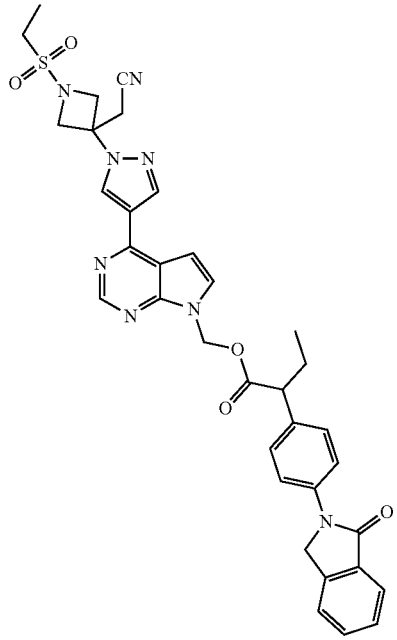 [SMILES: CCC(C(=O)OCn1ccc2c(-c3cnn(C4(CC#N)CN(S(=O)(=O)CC)C4)c3)ncnc21)c1ccc(N2Cc3ccccc3C2=O)cc1] | Methyl (4-(1-(3-(cyanomethyl)-1-(ethylsulfonyl) azetidin-3-yl)-1H-pyrazol-4-yl)-7H-pyrrolo [2,3-d]pyrimidin-7-yl) 2-(4-(1-oxoisoindolin-2-yl)phenyl)butanoate |
| 77 (CPD-044) | 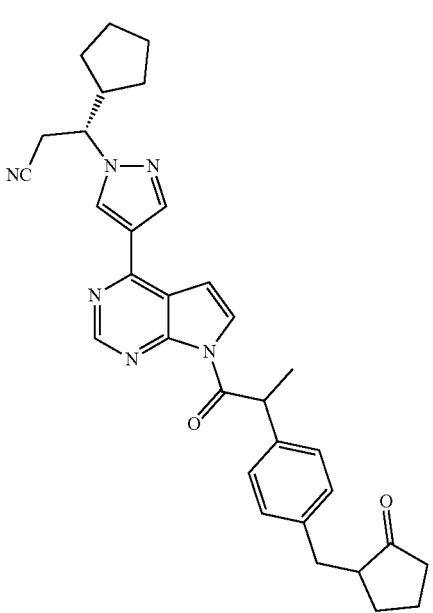 [SMILES: CC(C(=O)n1ccc2c(-c3cnn([C@H](CC#N)C4CCCC4)c3)ncnc21)c1ccc(CC2CCCC2=O)cc1] | (3R)-3-cyclopentyl-3- (4-(7-(2-(4-((2-oxocyclo- pentyl)methyl)phenyl)propanoyl)-7H-pyrrolo [2,3-d]pyrimidin-4-yl)-1H-pyrazol-1-yl) propanenitrile |

TABLE 1-continued

Structural formulas and compound names of target compounds prepared in examples

| Examples (Cmpd No.) | Structure | Chinese name |
|---|---|---|
| 78 (CPD-046) | 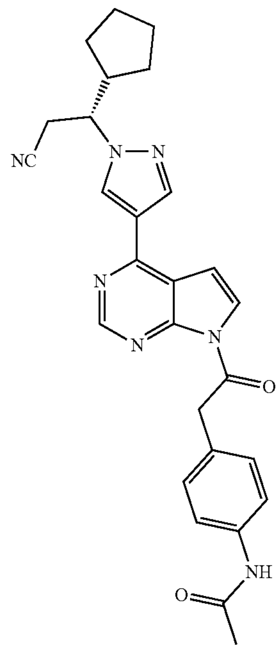 [SMILES: CC(=O)Nc1ccc(CC(=O)n2ccc3c(-c4cnn([C@H](CC#N)C5CCCC5)c4)ncnc32)cc1] | (R)-N-(4-(2-(4-(1-(2-cyano-1-cyclopentylethyl)-1H-pyrazol-4-yl)-7H-pyrrolo[2,3-d]pyrimidin-7-yl)-2-oxoethyl)phenyl)acetamide |
| 79 (CPD-045) | 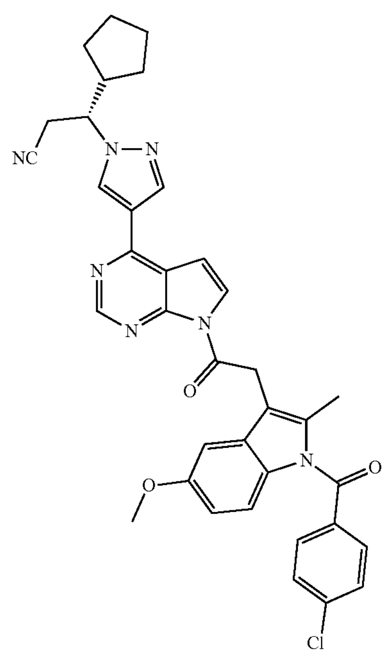 [SMILES: COc1ccc2c(c1)c(CC(=O)n1ccc3c(-c4cnn([C@H](CC#N)C5CCCC5)c4)ncnc31)c(C)n2C(=O)c1ccc(Cl)cc1] | (R)-3-(4-(7-(2-(1-(4-chlorobenzoyl)-5-methoxy-2-methyl-1H-indol-3-yl)acetyl)-7H-pyrrolo[2,3-d]pyrimidin-4-yl)-1H-pyrazol-1-yl)-3-cyclopentylpropanenitrile |

TABLE 1-continued

Structural formulas and compound names of target compounds prepared in examples

| Examples (Cmpd No.) | Structure | Chinese name |
|---|---|---|
| 80 (CPD-049) | 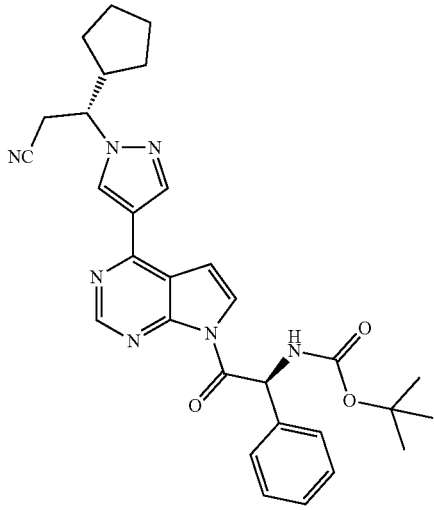 [SMILES: CC(C)(C)OC(=O)N[C@H](C(=O)n1ccc2c(-c3cnn([C@H](CC#N)C4CCCC4)c3)ncnc21)c1ccccc1] | Tert-butyl ((S)-2-(4-(1-((R)-2-cyano-1-cyclopentylethyl)-1H-pyrazol-4-yl)-7H-pyrrolo[2,3-d]pyrimidin-7-yl)-2-oxo-1-phenylethyl)carbamate |
| 81 (CPD-147) | 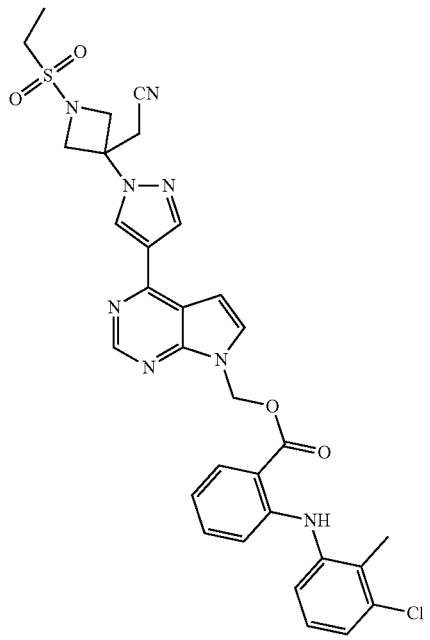 [SMILES: CCS(=O)(=O)N1CC(CC#N)(n2cc(-c3ncnc4c3ccn4COC(=O)c3ccccc3Nc3cccc(Cl)c3C)cn2)C1] | Methyl (4-(1-(3-(cyanomethyl)-1-(ethylsulfonyl) azetidin-3-yl)-1H-pyrazol-4-yl)-7H-pyrrolo[2,3-d]pyrimidin-7-yl) 2-((3-chloro-2-methylphenyl)amino)benzoate |

TABLE 1-continued

Structural formulas and compound names of target compounds prepared in examples

| Examples (Cmpd No.) | Structure | Chinese name |
|---|---|---|
| 82 (CPD-037) | 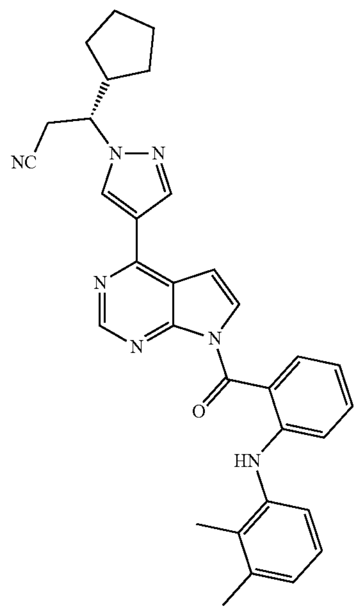 [SMILES: Cc1cccc(Nc2ccccc2C(=O)n2ccc3c(-c4cnn([C@H](CC#N)C5CCCC5)c4)ncnc32)c1C] | (R)-3-cyclopentyl-3-(4-(7-(2-((2,3-dimethylphenyl)amino)benzoyl)-7H-pyrrolo[2,3-d]pyrimidin-4-yl)-1H-pyrazol-1-yl)propanenitrile |
| 83 (CPD-146) | 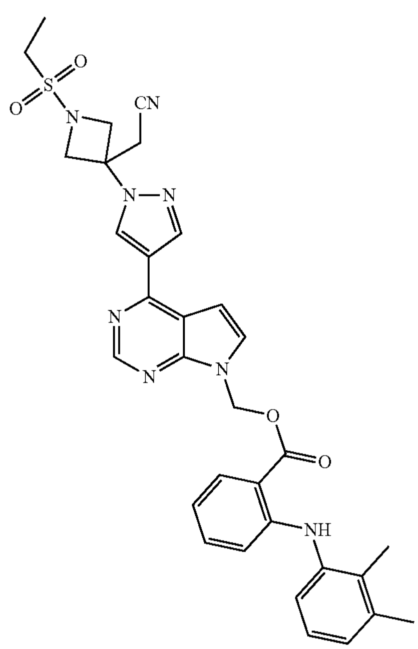 [SMILES: CCS(=O)(=O)N1CC(CC#N)(n2cc(-c3ncnc4c3ccn4COC(=O)c3ccccc3Nc3cccc(C)c3C)cn2)C1] | Methyl (4-(1-(3-(cyanomethyl)-1-(ethylsulfonyl)azetidin-3-yl)-1H-pyrazol-4-yl)-7H-pyrrolo[2,3-d]pyrimidin-7-yl) 2-((2,3-dimethylphenyl)amino)benzoate |

TABLE 1-continued

Structural formulas and compound names of target compounds prepared in examples

| Examples (Cmpd No.) | Structure | Chinese name |
|---|---|---|
| 84 (CPD-149) | 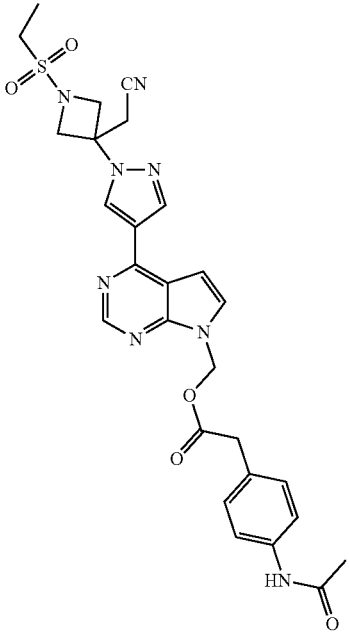 [SMILES: CCS(=O)(=O)N1CC(CC#N)(n2cc(-c3ncnc4c3ccn4COC(=O)Cc3ccc(NC(C)=O)cc3)cn2)C1] | Methyl (4-(1-(3-(cyanomethyl)-1-(ethylsulfonyl) azetidin-3-yl)-1H-pyrazol-4-yl)-7H-pyrrolo[2, 3-d]pyrimidin-7-yl) 2-(4-acetamidophenyl) acetate |
| 85 (CPD-148) | 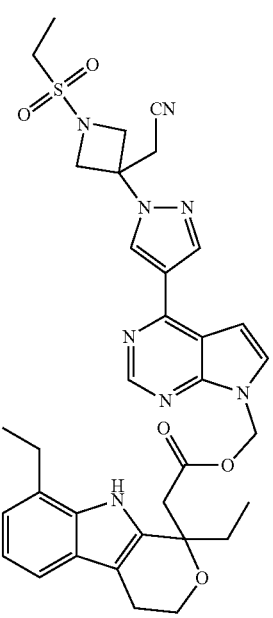 [SMILES: CCc1cccc2c3c([nH]c12)C(CC)(CC(=O)OCn1ccc2c(-c4cnn(C5(CC#N)CN(S(=O)(=O)CC)C5)c4)ncnc21)OCC3] | Methyl (4-(1-(3-(cyanomethyl)-1-(ethylsulfonyl) azetidin-3-yl)-1H-pyrazol-4-yl)-7H-pyrrolo[2, 3-d]pyrimidin-7-yl) 2-(1,8-diethyl-1,3,4, 9-tetrahydropyrano[3,4-b]indol-1-yl)acetate |

TABLE 1-continued

Structural formulas and compound names of target compounds prepared in examples

| Examples (Cmpd No.) | Structure | Chinese name |
|---|---|---|
| 86 (CPD-114) | 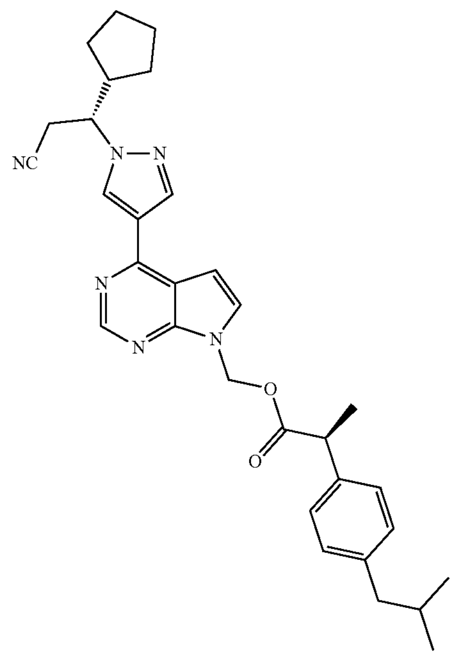 [SMILES: CC(C)Cc1ccc([C@H](C)C(=O)OCn2ccc3c(-c4cnn([C@H](CC#N)C5CCCC5)c4)ncnc32)cc1] | (4-(1-((R)-2-cyano-1-cyclopentylethyl)-1H-pyrazol-4-yl)-7H-pyrrolo[2,3-d]pyrimidin-7-yl) methyl (S)-2-(4-isobutylphenyl)propanoate |
| 87 (CPD-115) | 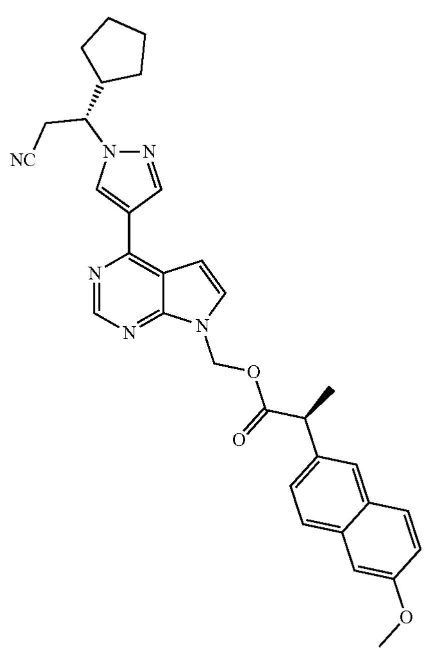 [SMILES: COc1ccc2cc([C@H](C)C(=O)OCn3ccc4c(-c5cnn([C@H](CC#N)C6CCCC6)c5)ncnc43)ccc2c1] | (4-(1-((R)-2-cyano-1-cyclopentylethyl)-1H-pyrazol-4-yl)-7H-pyrrolo[2,3-d]pyrimidin-7-yl) methyl (S)-2-(6-methoxynaphthalen-2-yl)propanoate |

TABLE 1-continued

Structural formulas and compound names of target compounds prepared in examples

| Examples (Cmpd No.) | Structure | Chinese name |
|---|---|---|
| 88 (CPD-103) | 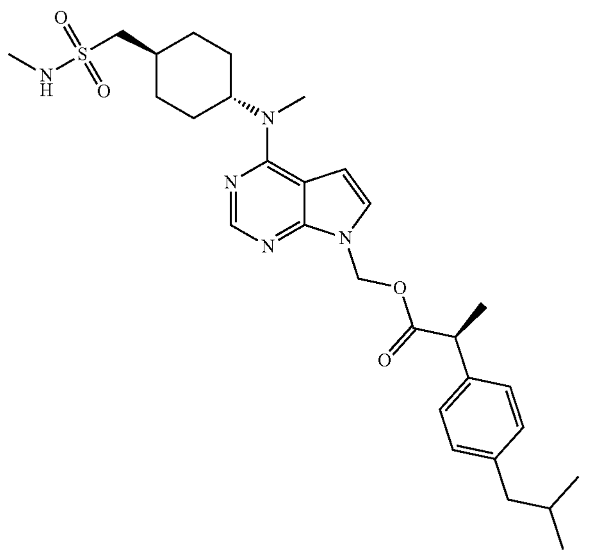 [SMILES: CNS(=O)(=O)C[C@H]1CC[C@H](N(C)c2ncnc3c2ccn3COC(=O)[C@@H](C)c2ccc(CC(C)C)cc2)CC1] | (4-(Methyl((trans)-4-((N-methylsulfamoyl) methyl)cyclohexyl)amino)-7H-pyrrolo[2, 3-d]pyrimidin-7-yl)methyl (S)-2-(4-isobutylphenyl)propanoate |
| 89 (CPD-104) | 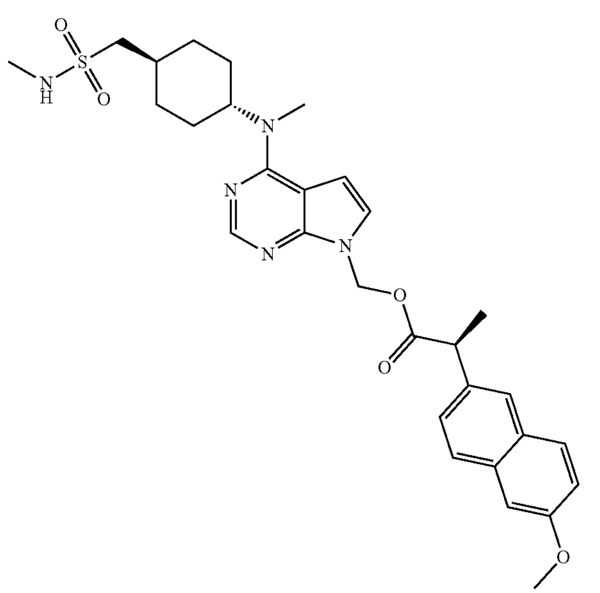 [SMILES: CNS(=O)(=O)C[C@H]1CC[C@H](N(C)c2ncnc3c2ccn3COC(=O)[C@@H](C)c2ccc3cc(OC)ccc3c2)CC1] | (4-(Methyl((trans)-4-((N-methylsulfamoyl) methyl)cyclohexyl)amino)-7H-pyrrolo[2, 3-d]pyrimidin-7-yl)methyl (S)-2-(6-methoxynaphthalen-2-yl)propanoate |

TABLE 1-continued

Structural formulas and compound names of target compounds prepared in examples

| Examples (Cmpd No.) | Structure | Chinese name |
|---|---|---|
| 90 (CPD-105) | 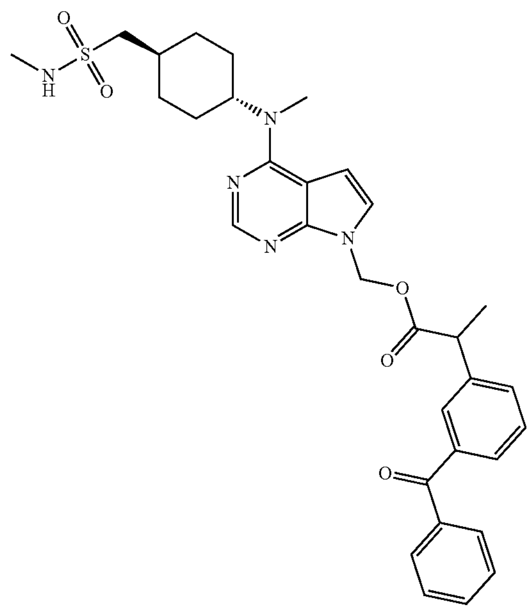 [SMILES: CNS(=O)(=O)C[C@H]1CC[C@H](N(C)c2ncnc3c2ccn3COC(=O)C(C)c2cccc(C(=O)c3ccccc3)c2)CC1] | (4-(Methyl((trans)-4-((N-methylsulfamoyl)methyl)cyclohexyl)amino)-7H-pyrrolo[2,3-d]pyrimidin-7-yl)methyl 2-(3-benzoylphenyl)propanoate |
| 91 (CPD-162) | 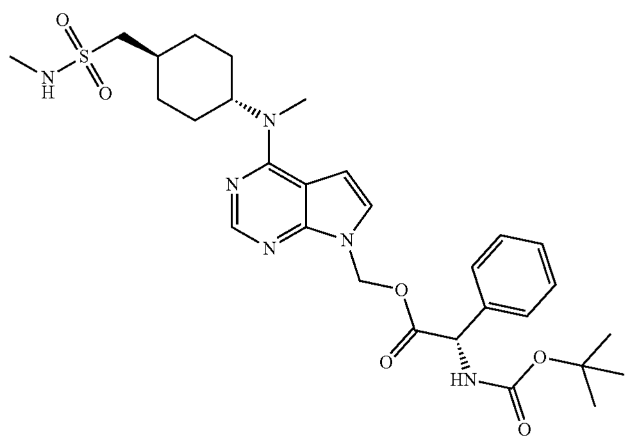 [SMILES: CNS(=O)(=O)C[C@H]1CC[C@H](N(C)c2ncnc3c2ccn3COC(=O)[C@@H](NC(=O)OC(C)(C)C)c2ccccc2)CC1] | (4-(Methyl((trans)-4-((N-methylsulfamoyl)methyl)cyclohexyl)amino)-7H-pyrrolo[2,3-d]pyrimidin-7-yl)methyl (S)-2-((tert-butoxycarbonyl)amino)-2-phenylacetate |
| 92 (CPD-107) | 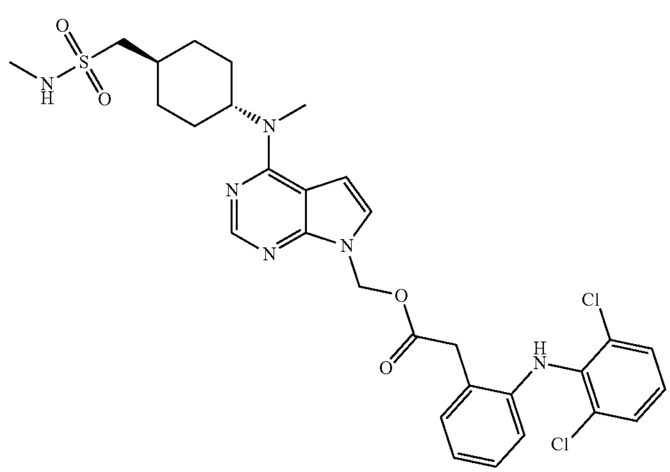 [SMILES: CNS(=O)(=O)C[C@H]1CC[C@H](N(C)c2ncnc3c2ccn3COC(=O)Cc2ccccc2Nc2c(Cl)cccc2Cl)CC1] | (4-(Methyl((trans)-4-((N-methylsulfamoyl)methyl)cyclohexyl)amino)-7H-pyrrolo[2,3-d]pyrimidin-7-yl)methyl 2-(2-((2,6-dichlorophenyl)amino)phenyl)acetate |

TABLE 1-continued

Structural formulas and compound names of target compounds prepared in examples

| Examples (Cmpd No.) | Structure | Chinese name |
|---|---|---|
| 93 (CPD-158) | 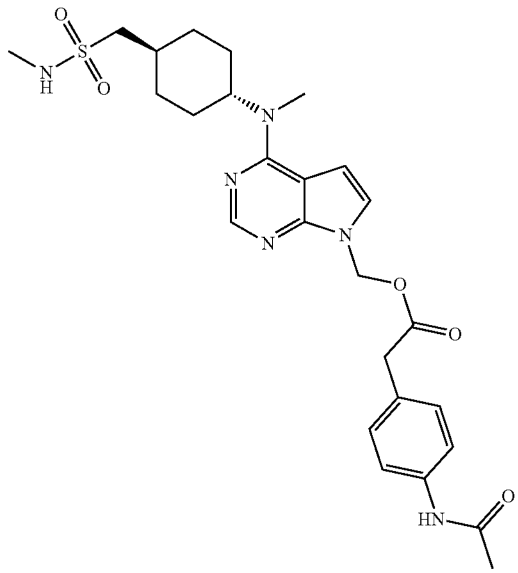 [SMILES: CNS(=O)(=O)C[C@H]1CC[C@H](N(C)c2ncnc3c2ccn3COC(=O)Cc2ccc(NC(C)=O)cc2)CC1] | (4-(Methyl((trans)-4-((N-methylsulfamoyl) methyl)cyclohexyl)amino)-7H-pyrrolo[2, 3-d]pyrimidin-7-yl)methyl 2-(4-acetamidophenyl)acetate |
| 94 (CPD-157) | 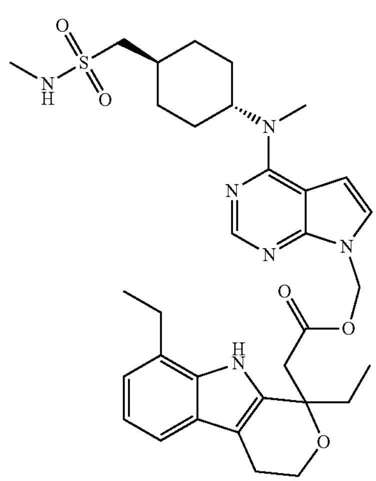 [SMILES: CCc1cccc2c3c([nH]c12)C(CC)(CC(=O)OCn1ccc2c(N(C)[C@H]4CC[C@H](CS(=O)(=O)NC)CC4)ncnc21)OCC3] | (4-(Methyl((trans)-4-((N-methylsulfamoyl) methyl)cyclohexyl)amino)-7H-pyrrolo[2, 3-d]pyrimidin-7-yl)methyl 2-(1,8-diethyl-1, 3,4,9-tetrahydropyran[3,4-b]indol-1-yl) acetate |

TABLE 1-continued

Structural formulas and compound names of target compounds prepared in examples

| Examples (Cmpd No.) | Structure | Chinese name |
|---|---|---|
| 95 (CPD-033) | 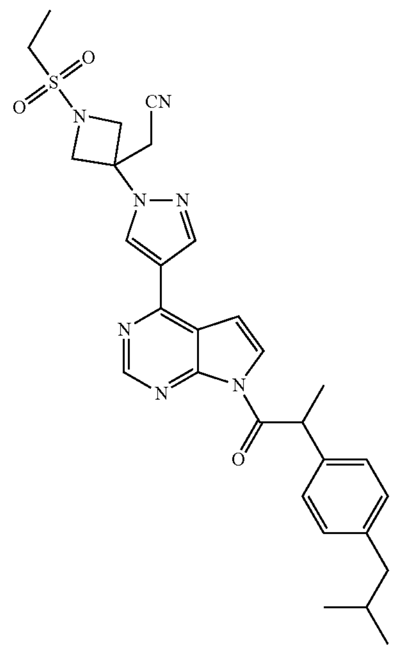 [SMILES: CCS(=O)(=O)N1CC(CC#N)(n2cc(-c3ncnc4c3ccn4C(=O)C(C)c3ccc(CC(C)C)cc3)cn2)C1] | 2-(1-(Ethylsulfonyl)-3-(4-(7-(2-(4-isobutylphenyl)propanoyl)-7H-pyrrolo[2,3-d]pyrimidin-4-yl)-1H-pyrazol-1-yl)azetidin-3-yl)acetonitrile |
| 96 (CPD-051) | 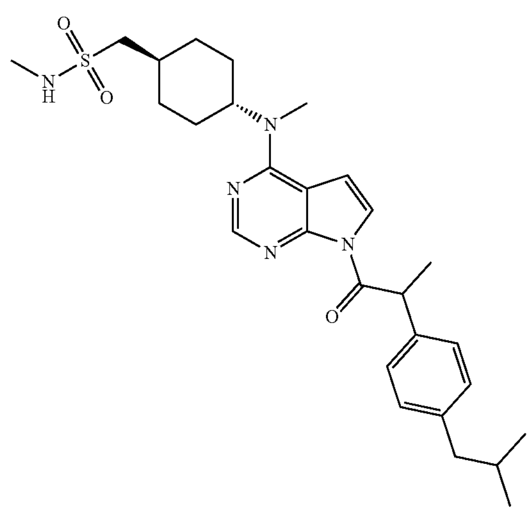 [SMILES: CNS(=O)(=O)C[C@H]1CC[C@H](N(C)c2ncnc3c2ccn3C(=O)C(C)c2ccc(CC(C)C)cc2)CC1] | 1-((Trans)-4-((7-(2-(4-isobutylphenyl)propanoyl)-7H-pyrrolo[2,3-d]pyrimidin-4-yl)(methyl)amino)cyclohexyl)-N-methyl methanesulfonamide |

TABLE 1-continued

Structural formulas and compound names of target compounds prepared in examples

| Examples (Cmpd No.) | Structure | Chinese name |
|---|---|---|
| 97 (CPD-142) | 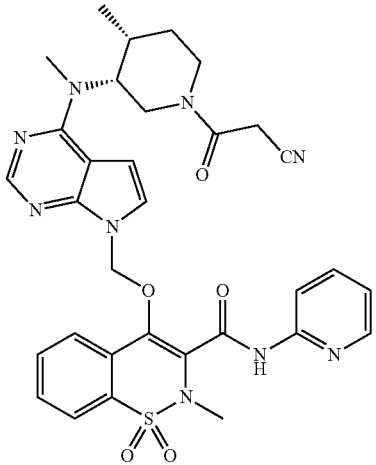 [SMILES: C[C@@H]1CCN(C(=O)CC#N)C[C@@H]1N(C)c1ncnc2c1ccn2COC1=C(C(=O)Nc2ccccn2)N(C)S(=O)(=O)c2ccccc21] | 4-((4-(((3R, 4R)-1-(2-cyanoacetyl)-4-methylpiperidin-3-yl) (methyl)amino)-7H-pyrrolo[2,3-d]pyrimidin-7-yl) methoxy)-2-methyl-N-(pyridin-2-yl)-2H-benzo [e][1,2]thiazine-3-carboxamide 1,1-dioxide |
| 98 (CPD-036) | 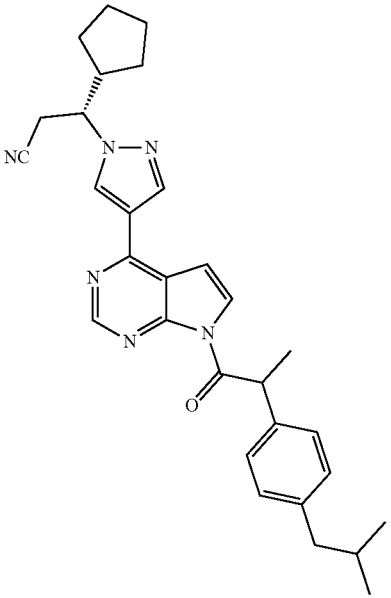 [SMILES: CC(C)Cc1ccc(C(C)C(=O)n2ccc3c(-c4cnn([C@H](CC#N)C5CCCC5)c4)ncnc32)cc1] | (R)-3-cyclopentyl-3-(4-(7-2-(4-isobutylphenyl) propanoyl)-7H-pyrrolo[2,3-d]pyrimidin-4-yl)-1H-pyrazol-1-yl)propanenitrile |

TABLE 1-continued

Structural formulas and compound names of target compounds prepared in examples

| Examples (Cmpd No.) | Structure | Chinese name |
|---|---|---|
| 99 (CPD-116) | 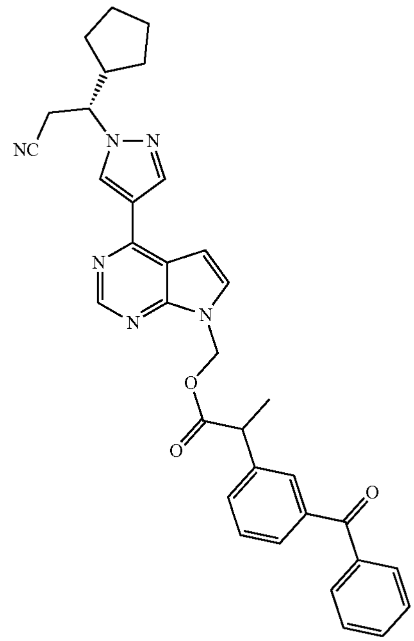 [SMILES: CC(C(=O)OCn1ccc2c(-c3cnn([C@H](CC#N)C4CCCC4)c3)ncnc21)c1cccc(C(=O)c2ccccc2)c1] | (4-(1-((R)-2-cyano-1-cyclopentylethyl)-1H-pyrazol-4-yl)-7H-pyrrolo[2,3-d]pyrimidin-7-yl) methyl 2-(3-benzoylphenyl)propanoate |
| 100 (CPD-117) | 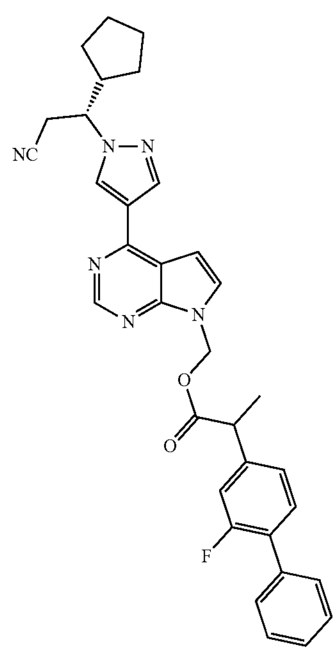 [SMILES: CC(C(=O)OCn1ccc2c(-c3cnn([C@H](CC#N)C4CCCC4)c3)ncnc21)c1ccc(-c2ccccc2)c(F)c1] | (4-(1-((R)-2-cyano-1-cyclopentylethyl)-1H-pyrazol-4-yl)-7H-pyrrolo[2,3-d]pyrimidin-7-yl) methyl 2-(2-fluoro-[1,1'-biphenyl]-4-yl)propanoate |

TABLE 1-continued
Structural formulas and compound names of target compounds prepared in examples
| Examples (Cmpd No.) | Structure | Chinese name |
|---|---|---|
| 101 (CPD-118) | 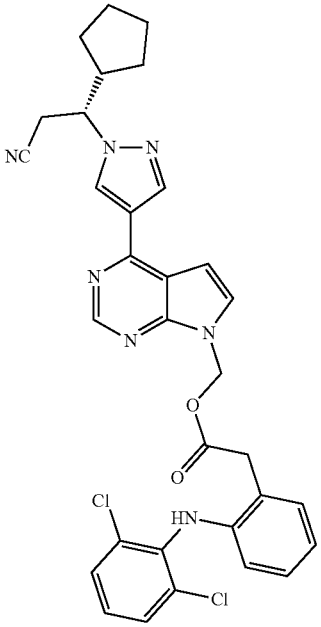 [SMILES: N#CC[C@H](C1CCCC1)n1cc(-c2ncnc3c2ccn3COC(=O)Cc2ccccc2Nc2c(Cl)cccc2Cl)cn1] | (R)-(4-(1-(2-cyano-1-cyclopentylethyl)-1H-pyrazol-4-yl)-7H-pyrrolo[2,3-d]pyrimidin-7-yl) methyl 2-(2-((2,6-dichlorophenyl)amino)phenyl)acetate |
| 102 (CPD-119) | 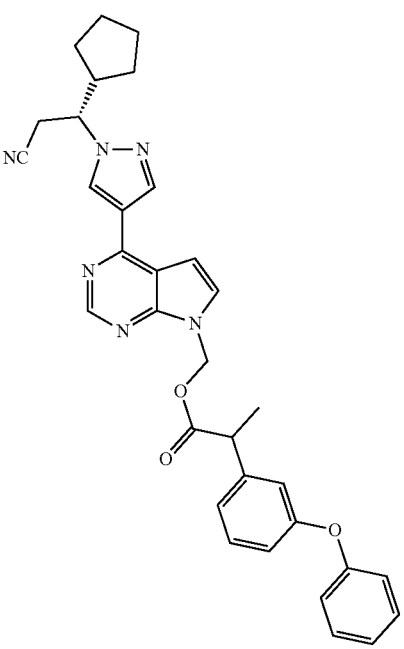 [SMILES: CC(C(=O)OCn1ccc2c(-c3cnn([C@H](CC#N)C4CCCC4)c3)ncnc21)c1cccc(Oc2ccccc2)c1] | (4-(1-((R)-2-cyano-1-cyclopentylethyl)-1H-pyrazol-4-yl)-7H-pyrrolo[2,3-d]pyrimidin-7-yl) methyl 2-(3-phenoxyphenyl)propanoate |

TABLE 1-continued

Structural formulas and compound names of target compounds prepared in examples

| Examples (Cmpd No.) | Structure | Chinese name |
|---|---|---|
| 103 (CPD-120) | 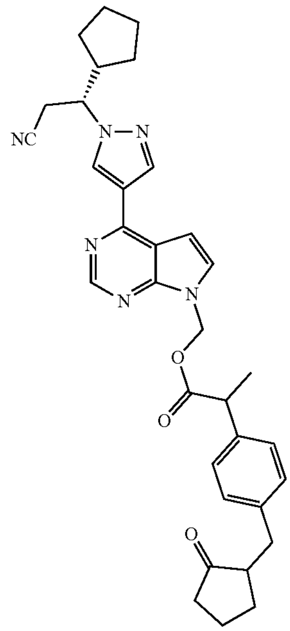 [SMILES: CC(C(=O)OCn1ccc2c(-c3cnn([C@H](CC#N)C4CCCC4)c3)ncnc21)c1ccc(CC2CCCC2=O)cc1] | (4-(1-((R)-2-cyano-1-cyclopentylethyl)-1H-pyrazol-4-yl)-7H-pyrrolo[2,3-d]pyrimidin-7-yl) methyl 2-(4-((2-oxocyclopentyl)methyl)phenyl)propanoate |
| 104 (CPD-121) | 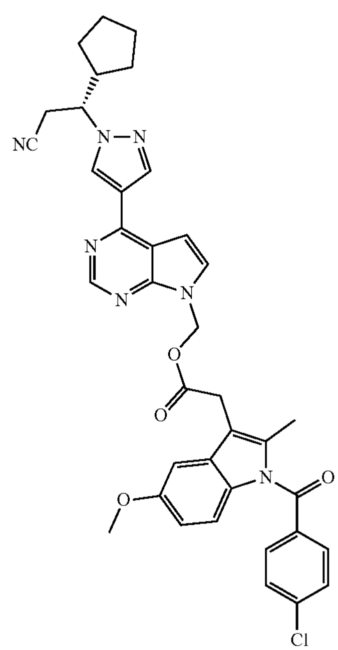 [SMILES: COc1ccc2c(c1)c(CC(=O)OCn1ccc3c(-c4cnn([C@H](CC#N)C5CCCC5)c4)ncnc31)c(C)n2C(=O)c1ccc(Cl)cc1] | (R)(4-(1-(2-cyano-1-cyclopentylethyl)-1H-pyrazol-4-yl)-7H-pyrrolo[2,3-d]pyrimidin-7-yl) methyl 2-(1-(4-chlorobenzoyl)-5-methoxy-2-methyl-1H-indol-3-yl)acetate |

TABLE 1-continued

Structural formulas and compound names of target compounds prepared in examples

| Examples (Cmpd No.) | Structure | Chinese name |
|---|---|---|
| 105 (CPD-163) | 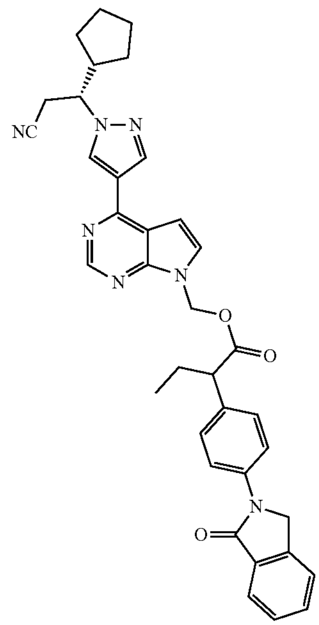 [SMILES: CCC(C(=O)OCn1ccc2c(-c3cnn([C@H](CC#N)C4CCCC4)c3)ncnc21)c1ccc(N2Cc3ccccc3C2=O)cc1] | (4-(1-((R)-2-cyano-1-cyclopentylethyl)-1H-pyrazol-4-yl)-7H-pyrrolo[2,3-d]pyrimidin-7-yl) methyl 2-(4-(1-oxoisoindolin-2-yl)phenyl) butanoate |
| 106 (CPD-164) | 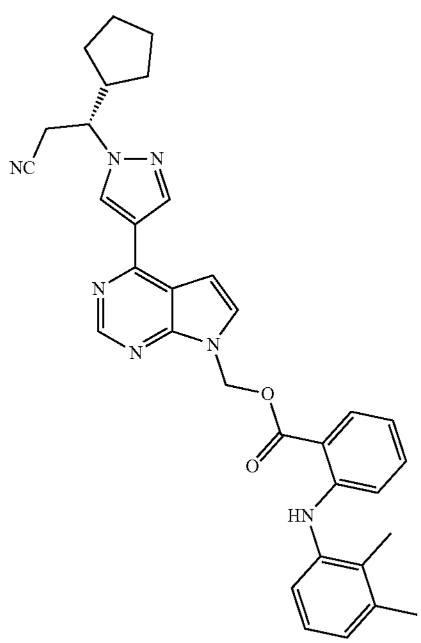 [SMILES: Cc1cccc(Nc2ccccc2C(=O)OCn2ccc3c(-c4cnn([C@H](CC#N)C5CCCC5)c4)ncnc32)c1C] | (R)-(4-(1-(2-cyano-1-cyclopentylethyl)-1H-pyrazol-4-yl)-7H-pyrrolo[2,3-d]pyrimidin-7-yl) methyl 2-((2,3-dimethylphenyl)amino) benzoate |

TABLE 1-continued

Structural formulas and compound names of target compounds prepared in examples

| Examples (Cmpd No.) | Structure | Chinese name |
|---|---|---|
| 107 (CPD-165) | 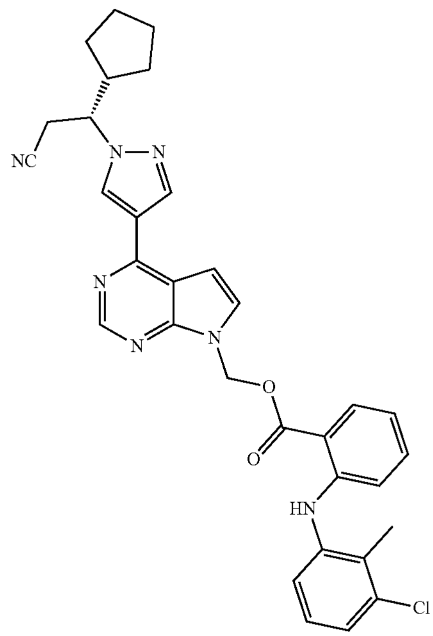 [SMILES: Cc1c(Cl)cccc1Nc1ccccc1C(=O)OCn1ccc2c(-c3cnn([C@H](CC#N)C4CCCC4)c3)ncnc21] | (R)-(4-(1-(2-cyano-1-cyclopentylethyl)-1H-pyrazol-4-yl)-7H-pyrrolo[2,3-d]pyrimidin-7-yl) methyl 2-((3-chloro-2-methylphenyl)amino)benzoate |
| 108 (CPD-184) | 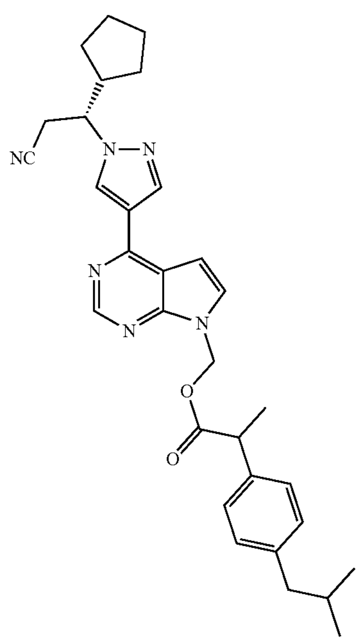 [SMILES: CC(C)Cc1ccc(C(C)C(=O)OCn2ccc3c(-c4cnn([C@H](CC#N)C5CCCC5)c4)ncnc32)cc1] | (4-(1-((R)-2-cyano-1-cyclopentylethyl)-1H-pyrazol-4-yl)-7H-pyrrolo[2,3-d]pyrimidin-7-yl) methyl 2-(4-isobutylphenyl)propanoate |

| Examples (Cmpd No.) | Structure | Chinese name |
|---|---|---|
| 109 (CPD-166) | 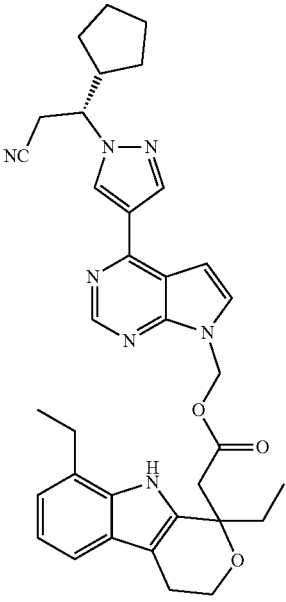 [SMILES: CCc1cccc2c3c([nH]c12)C(CC)(CC(=O)OCn1ccc2c(-c4cnn([C@H](CC#N)C5CCCC5)c4)ncnc21)OCC3] | (4-(1-((R)-2-cyano-1-cyclopentylethyl)-1H-pyrazol-4-yl)-7H-pyrrolo[2,3-d]pyrimidin-7-yl) methyl 2-(1,8-diethyl-1,3,4,9-tetrahydropyran[3,4-b]indol-1-yl)acetate |
| 110 (CPD-167) | 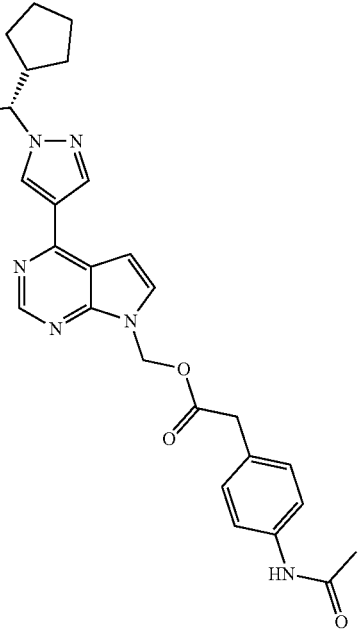 | (R)-(4-(1-(2-cyano-1-cyclopentylethyl)-1H-pyrazol-4-yl)-7H-pyrrolo[2,3-d]pyrimidin-7-yl) methyl 2-(4-acetamidophenyl)acetate |

TABLE 1-continued

Structural formulas and compound names of target compounds prepared in examples

| Examples (Cmpd No.) | Structure | Chinese name |
|---|---|---|
| 111 (CPD-168) | 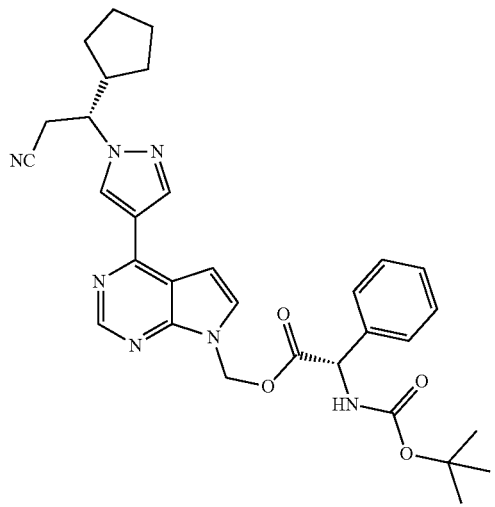 [SMILES: CC(C)(C)OC(=O)N[C@H](C(=O)OCn1ccc2c(-c3cnn([C@H](CC#N)C4CCCC4)c3)ncnc21)c1ccccc1] | (4-(1-((R)-2-cyano-1-cyclopentylethyl)-1H-pyrazol-4-yl)-7H-pyrrolo[2,3-d]pyrimidin-7-yl) methyl (S)-2-((tert-butoxycarbonyl)amino)-2-phenylacetate |
| 112 (CPD-182) | 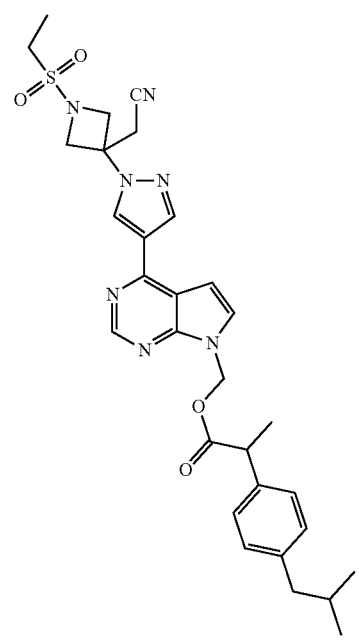 [SMILES: CCS(=O)(=O)N1CC(CC#N)(n2cc(-c3ncnc4c3ccn4COC(=O)C(C)c3ccc(CC(C)C)cc3)cn2)C1] | Methyl (4-(1-(3-(cyanomethyl)-1-(ethylsulfonyl)azetidin-3-yl)-1H-pyrazol-4-yl)-7H-pyrrolo[2,3-d]pyrimidin-7-yl) 2-(4-isobutylphenyl)propanoate |

TABLE 1-continued

Structural formulas and compound names of target compounds prepared in examples

| Examples (Cmpd No.) | Structure | Chinese name |
|---|---|---|
| 113 (CPD-106) | 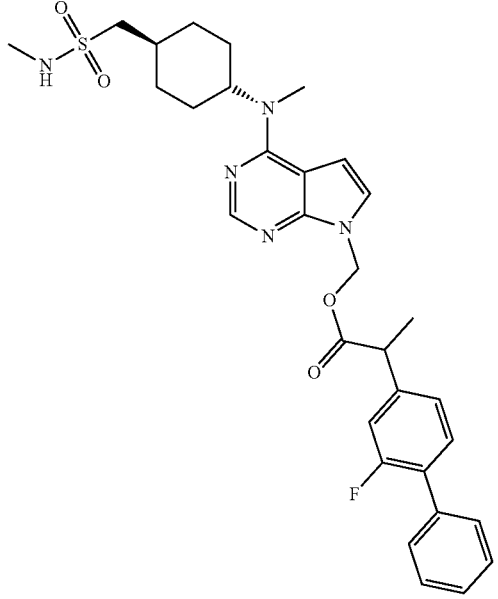 | (4-(Methyl((trans)-4-((N-methylsulfamoyl) methyl)cyclohexyl)amino)-7H-pyrrolo[2, 3-d]pyrimidin-7-yl)methyl 2-(2-fluoro-[1, 1'-biphenyl]-4-yl) propanoate |
| 114 (CPD-108) | 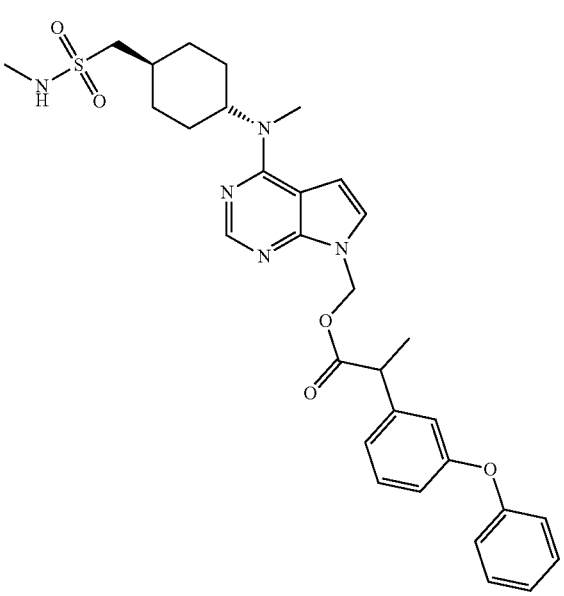 | (4-(Methyl((trans)-4-((N-methylsulfamoyl) methyl)cyclohexyl)amino)-7H-pyrrolo[2, 3-d]pyrimidin-7-yl)methyl 2-(3-phenoxyphenyl)propanoate |

TABLE 1-continued

Structural formulas and compound names of target compounds prepared in examples

| Examples (Cmpd No.) | Structure | Chinese name |
|---|---|---|
| 115 (CPD-109) | 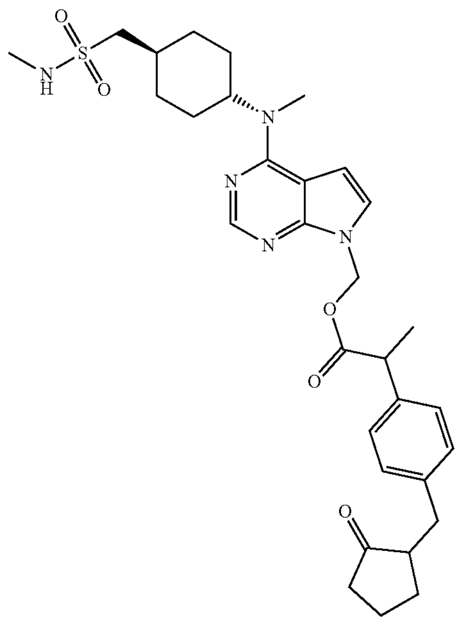 | (4-(Methyl((trans)-4-((N-methylsulfamoyl) methyl)cyclohexyl)amino)-7H-pyrrolo[2, 3-d]pyrimidin-7-yl)methyl 2-(4-((2-oxocyclopentyl)methyl)phenyl) propanoate |
| 116 (CPD-110) | 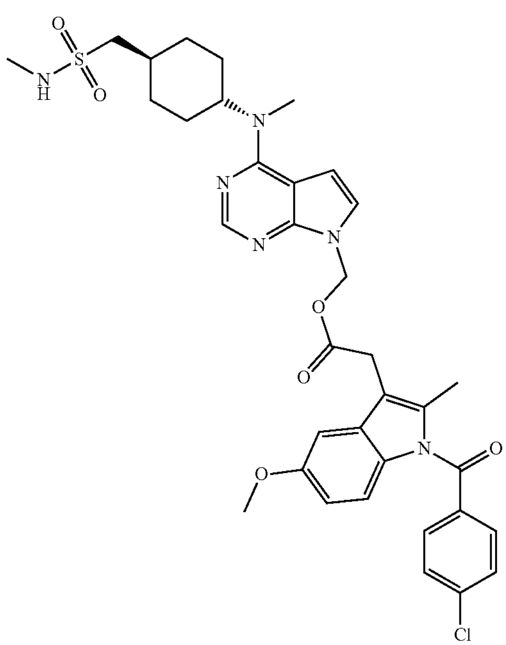 | (4-(Methyl((trans)-4-((N-methylsulfamoyl) methyl)cyclohexyl)amino)-7H-pyrrolo[2, 3-d]pyrimidin-7-yl)methyl 2-(1-(4-chlorobenzoyl)-5-methoxy-2-methyl-1H-indol-3-yl)acetate |

TABLE 1-continued

Structural formulas and compound names of target compounds prepared in examples

| Examples (Cmpd No.) | Structure | Chinese name |
|---|---|---|
| 117 (CPD-154) | 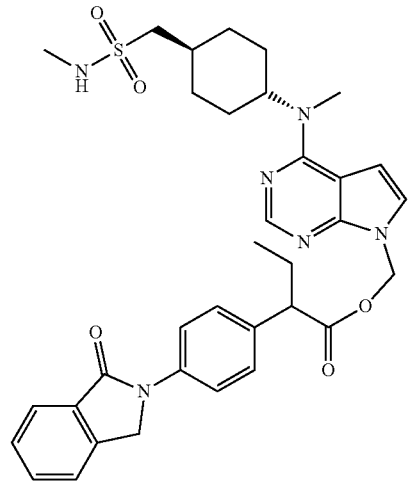 | (4-(Methyl((trans)-4-((N-methylsulfamoyl)methyl)cyclohexyl)amino)-7H-pyrrolo[2,3-d]pyrimidin-7-yl)methyl 2-(4-(1-oxoisoindolin-2-yl)phenyl)butanoate |
| 118 (CPD-155) | 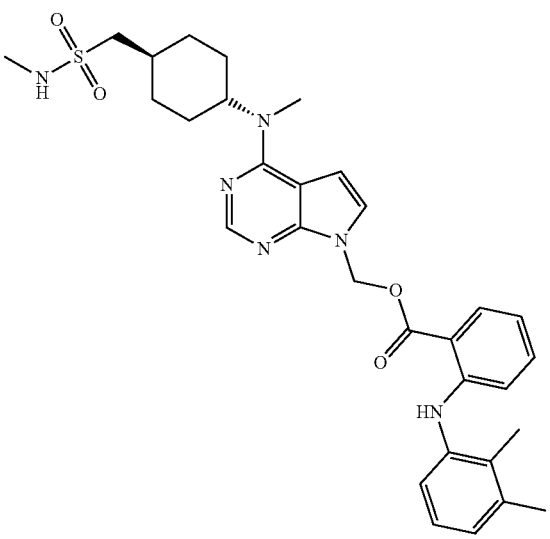 | (4-(Methyl((trans)-4-((N-methylsulfamoyl)methyl)cyclohexyl)amino)-7H-pyrrolo[2,3-d]pyrimidin-7-yl)methyl 2-((2,3-dimethylphenyl)amino)benzoate |

TABLE 1-continued

Structural formulas and compound names of target compounds prepared in examples

| Examples (Cmpd No.) | Structure | Chinese name |
|---|---|---|
| 119 (CPD-183) | 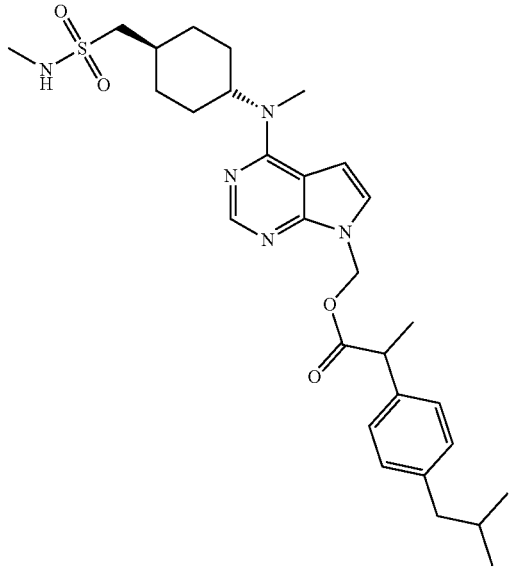 | (4-(Methyl((trans)-4-((N-methylsulfamoyl)methyl)cyclohexyl)amino)-7H-pyrrolo[2,3-d]pyrimidin-7-yl)methyl 2-(4-isobutylphenyl)propanoate |
| 120 (CPD-156) | 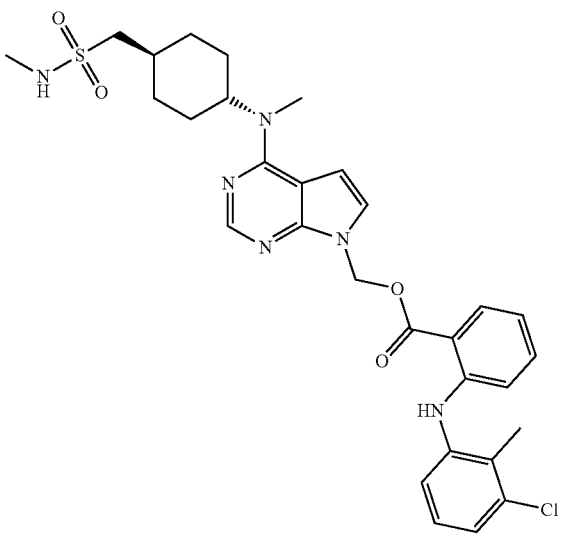 | (4-(Methyl((trans)-4-((N-methylsulfamoyl)methyl)cyclohexyl)amino)-7H-pyrrolo[2,3-d]pyrimidin-7-yl)methyl 2-((3-chloro-2-methylphenyl)amino)benzoate |

TABLE 1-continued

Structural formulas and compound names of target compounds prepared in examples

| Examples (Cmpd No.) | Structure | Chinese name |
|---|---|---|
| 121 (CPD-151) | 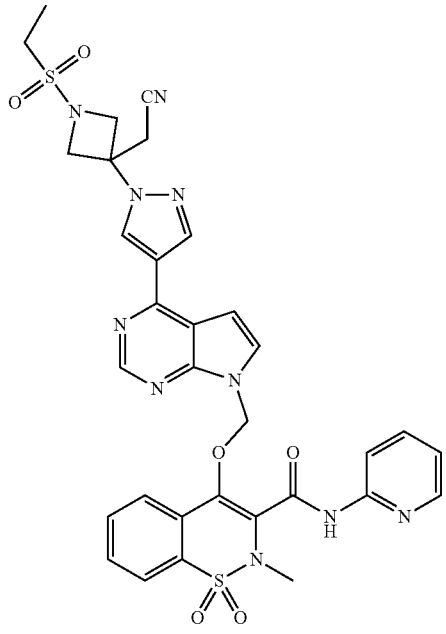 [SMILES: CCS(=O)(=O)N1CC(CC#N)(n2cc(-c3ncnc4c3ccn4COC3=C(C(=O)Nc4ccccn4)N(C)S(=O)(=O)c4ccccc43)cn2)C1] | 4-((4-(1-(3-(Cyanomethyl)-1-(ethylsulfonyl) azetidin-3-yl)-1H-pyrazol-4-yl)-7H-pyrrolo [2,3-d]pyrimidin-7-yl) methoxy)-2-methyl-N-(pyridin-2-yl)-2H-benzo [e][1,2]thiazine-3-carboxamide 1,1-dioxide |
| 122 (CPD-101) | 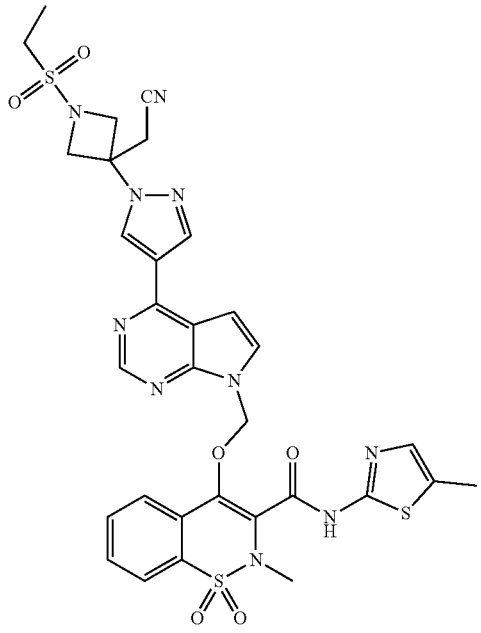 [SMILES: CCS(=O)(=O)N1CC(CC#N)(n2cc(-c3ncnc4c3ccn4COC3=C(C(=O)Nc4ncc(C)s4)N(C)S(=O)(=O)c4ccccc43)cn2)C1] | 4-((4-(1-(3-(Cyanomethyl)-1-(ethylsulfonyl) azetidin-3-yl)-1H-pyrazol-4-yl)-7H-pyrrolo [2,3-d]pyrimidin-7-yl) methoxy)-2-methyl-N-(5-methylthiazol-2-yl)-2H-benzo[e][1,2]thiazine-3-carboxamide 1,1-dioxide |

TABLE 1-continued

Structural formulas and compound names of target compounds prepared in examples

| Examples (Cmpd No.) | Structure | Chinese name |
|---|---|---|
| 123 (CPD-066) | 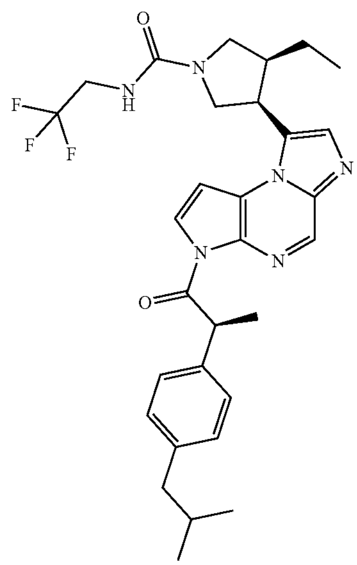 [SMILES: CC[C@@H]1CN(C(=O)NCC(F)(F)F)C[C@@H]1c1cnc2cnc3c(ccn3C(=O)[C@@H](C)c3ccc(CC(C)C)cc3)n12] | (3S,4R)-3-ethyl-4-(3-((S)-2-(4-isobutylphenyl)propanoyl)-3H-imidazo[1,2-a]pyrrolo[2,3-e]pyrazin-8-yl)-N-(2,2,2-trifluoroethyl)pyrrolidine-1-carboxamide |
| 124 (CPD-067) | 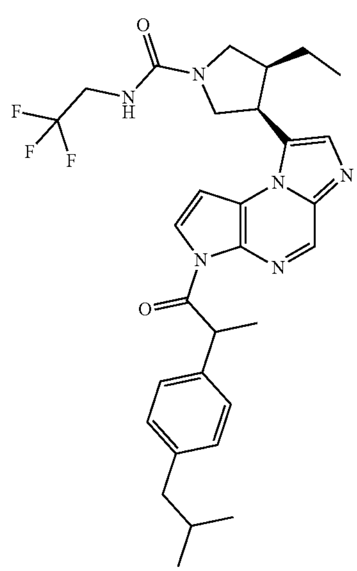 [SMILES: CC[C@@H]1CN(C(=O)NCC(F)(F)F)C[C@@H]1c1cnc2cnc3c(ccn3C(=O)C(C)c3ccc(CC(C)C)cc3)n12] | (3S,4R)-3-ethyl-4-(3-((R)-2-(4-isobutylphenyl)propanoyl)-3H-imidazo[1,2-a]pyrrolo[2,3-e]pyrazin-8-yl)-N-(2,2,2-trifluoroethyl)pyrrolidine-1-carboxamide |

TABLE 1-continued

Structural formulas and compound names of target compounds prepared in examples

| Examples (Cmpd No.) | Structure | Chinese name |
|---|---|---|
| 125 (CPD-072) | 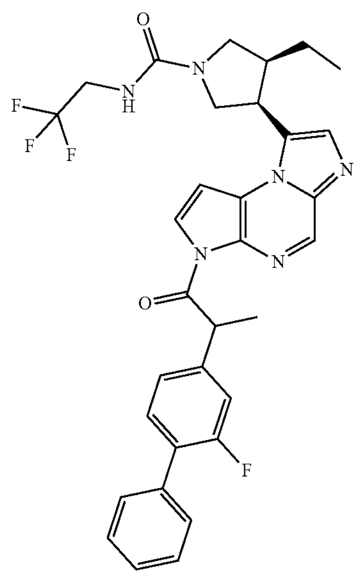 [SMILES: CC[C@@H]1CN(C(=O)NCC(F)(F)F)C[C@@H]1c1cnc2cnc3c(ccn3C(=O)C(C)c3ccc(-c4ccccc4)c(F)c3)n12] | (3S,4R)-3-ethyl-4-(3-(2-(2-fluoro-[1,1'-biphenyl]-4-yl)propanoyl)-3H-imidazo[1,2-a]pyrrolo[2,3-e]pyrazin-8-yl)-N-(2,2,2-trifluoroethyl)pyrrolidine-1-carboxamide |
| 126 (CPD-071) | 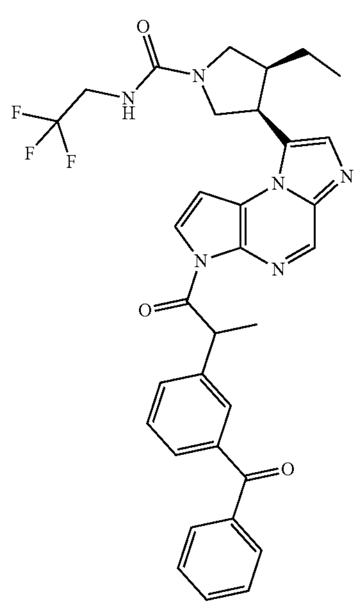 [SMILES: CC[C@@H]1CN(C(=O)NCC(F)(F)F)C[C@@H]1c1cnc2cnc3c(ccn3C(=O)C(C)c3cccc(C(=O)c4ccccc4)c3)n12] | (3R,4S)-3-(3-(2-(3-benzoylphenyl)propanoyl)-3H-imidazo[1,2-a]pyrrolo[2,3-e]pyrazin-8-yl)-4-ethyl-N-(2,2,2-trifluoroethyl)pyrrolidine-1-carboxamide |

TABLE 1-continued

Structural formulas and compound names of target compounds prepared in examples

| Examples (Cmpd No.) | Structure | Chinese name |
|---|---|---|
| 127 (CPD-073) | 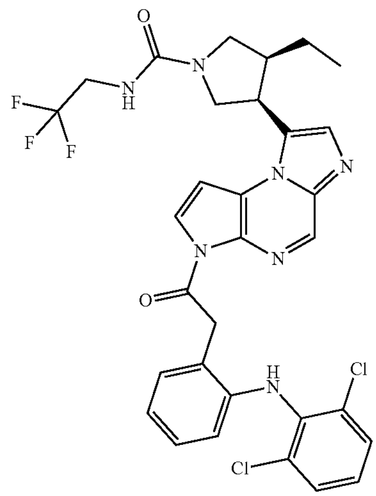 [SMILES: CC[C@@H]1CN(C(=O)NCC(F)(F)F)C[C@@H]1c1cnc2cnc3c(ccn3C(=O)Cc3ccccc3Nc3c(Cl)cccc3Cl)n12] | (3R,4S)-3-(3-(2-(2-((2,6-dichlorophenyl)amino)phenyl)acetyl)-3H-imidazo[1,2-a]pyrrolo[2,3-e]pyrazin-8-yl)-4-ethyl-N-(2,2,2-trifluoroethyl)pyrrolidine-1-carboxamide |
| 128 (CPD-074) | 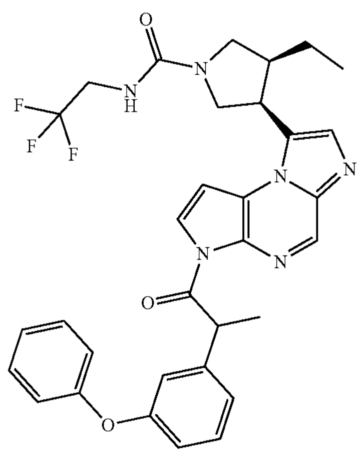 [SMILES: CC[C@@H]1CN(C(=O)NCC(F)(F)F)C[C@@H]1c1cnc2cnc3c(ccn3C(=O)C(C)c3cccc(Oc4ccccc4)c3)n12] | (3S,4R)-3-ethyl-4-(3-(2-(3-phenoxyphenyl)propanoyl)-3H-imidazo[1,2-a]pyrrolo[2,3-e]pyrazin-8-yl)-N-(2,2,2-trifluoroethyl)pyrrolidine-1-carboxamide |
| 129 (CPD-068) | 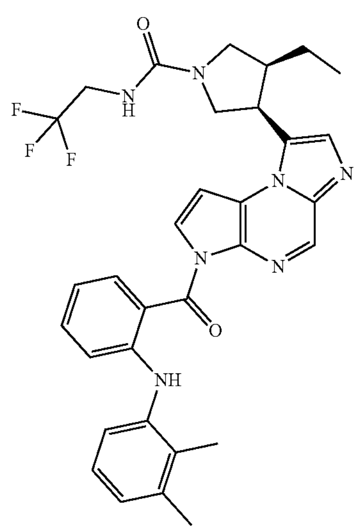 [SMILES: CC[C@@H]1CN(C(=O)NCC(F)(F)F)C[C@@H]1c1cnc2cnc3c(ccn3C(=O)c3ccccc3Nc3cccc(C)c3C)n12] | (3R,4S)-3-(3-(2-((2,3-dimethylphenyl)amino)benzoyl)-3H-imidazo[1,2-a]pyrrolo[2,3-e]pyrazin-8-yl)-4-ethyl-N-(2,2,2-trifluoroethyl)pyrrolidine-1-carboxamide |

TABLE 1-continued

Structural formulas and compound names of target compounds prepared in examples

| Examples (Cmpd No.) | Structure | Chinese name |
|---|---|---|
| 130 (CPD-069) | 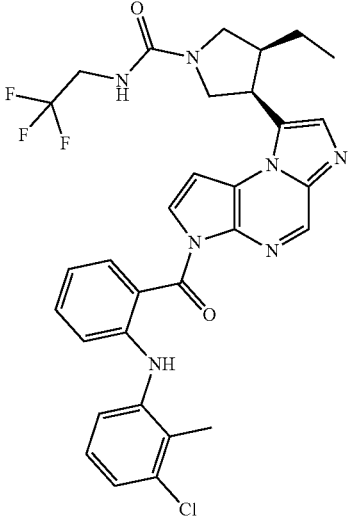 [SMILES: CC[C@@H]1CN(C(=O)NCC(F)(F)F)C[C@@H]1c1cnc2cnc3c(ccn3C(=O)c3ccccc3Nc3cccc(Cl)c3C)n12] | (3R,4S)-3-(3-(2-((3-chloro-2-methylphenyl)amino)benzoyl)-3H-imidazo[1,2-a]pyrrolo[2,3-e]pyrazin-8-yl)-4-ethyl-N-(2,2,2-trifluoroethyl)pyrrolidine-1-carboxamide |
| 131 (CPD-070) | 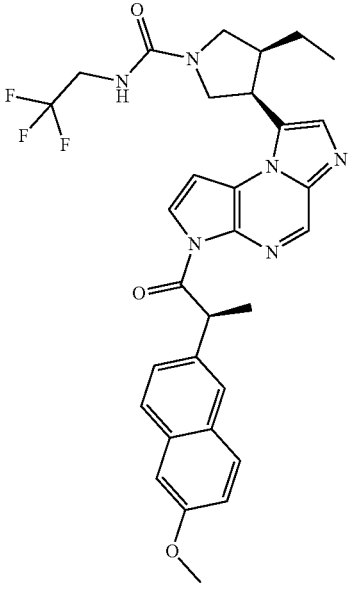 [SMILES: CC[C@@H]1CN(C(=O)NCC(F)(F)F)C[C@@H]1c1cnc2cnc3c(ccn3C(=O)[C@@H](C)c3ccc4cc(OC)ccc4c3)n12] | (3S,4R)-3-ethyl-4-(3-((S)-2-(6-)methoxynaphthalen-2-yl)propanoyl)-3H-imidazo[1,2-a]pyrrolo[2,3-e]pyrazin-8-yl)-N-(2,2,2-trifluoroethyl)pyrrolidine-1-carboxamide |

TABLE 1-continued

Structural formulas and compound names of target compounds prepared in examples

| Examples (Cmpd No.) | Structure | Chinese name |
|---|---|---|
| 132 (CPD-075) | 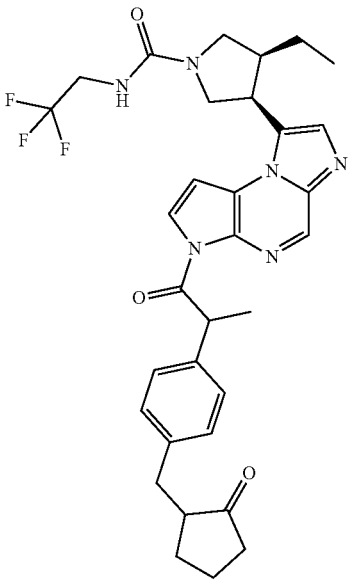 [SMILES: CC[C@@H]1CN(C(=O)NCC(F)(F)F)C[C@@H]1c1cnc2cnc3c(ccn3C(=O)C(C)c3ccc(CC4CCCC4=O)cc3)n12] | (3S, 4R)-3-ethyl-4-(3-(2-(4-((2-oxocyclopentyl)methyl)phenyl)propanoyl)-3H-imidazo[1,2-a]pyrrolo[2,3-e]pyrazin-8-yl)-N-(2,2,2-trifluoroethyl)pyrrolidine-1-carboxamide |
| 133 (CPD-076) | 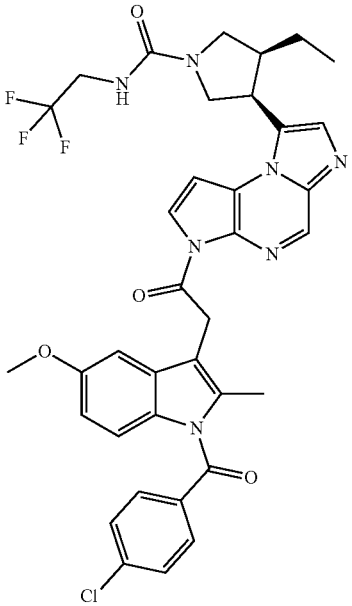 [SMILES: CC[C@@H]1CN(C(=O)NCC(F)(F)F)C[C@@H]1c1cnc2cnc3c(ccn3C(=O)Cc3c(C)n(C(=O)c4ccc(Cl)cc4)c4ccc(OC)cc34)n12] | (3R,4S)-3-(3-(2-(1-(4-Chlorobenzoyl)-5-methoxy-2-methyl-1H-indol-3-yl)acetyl)-3H-imidazo[1,2-a]pyrrolo[2,3-e]pyrazin-8-yl)-4-ethyl-N-(2,2,2-trifluoroethyl)pyrrolidine-1-carboxamide |

TABLE 1-continued

Structural formulas and compound names of target compounds prepared in examples

| Examples (Cmpd No.) | Structure | Chinese name |
|---|---|---|
| 134 (CPD-077) | 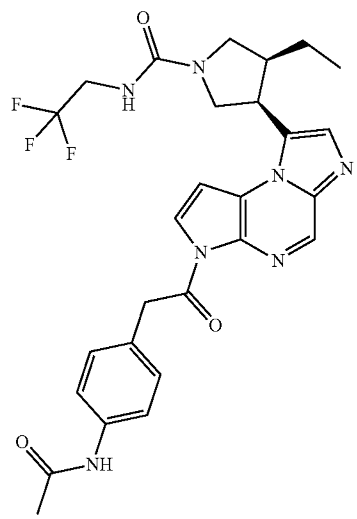 [SMILES: CC[C@@H]1CN(C(=O)NCC(F)(F)F)C[C@@H]1c1cnc2cnc3c(ccn3C(=O)Cc3ccc(NC(C)=O)cc3)n12] | (3R,4S)-3-(3-(2-(4-acetamidophenyl)acetyl)-3H-imidazo[1,2-a]pyrrolo[2,3-e]pyrazin-8-yl)-4-ethyl-N-(2,2,2-trifluoroethyl)pyrrolidine-1-carboxamide |
| 135 (CPD-078) | 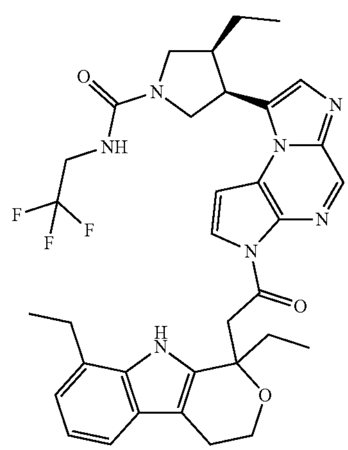 [SMILES: CCc1cccc2c3c([nH]c12)C(CC)(CC(=O)n1ccc2c1ncc1ncc([C@H]4CN(C(=O)NCC(F)(F)F)C[C@H]4CC)n12)OCC3] | (3R,4S)-3-(3-(2-(1,8-diethyl-1,3,4,9-tetrahydropyrano[3,4-b]indol-1-yl)acetyl)-3H-imidazo[1,2-a]pyrrolo[2,3-e]pyrazin-8-yl)-4-ethyl-N-(2,2,2-trifluoroethyl)pyrrolidine-1-carboxamide |
| 136 (CPD-079) | 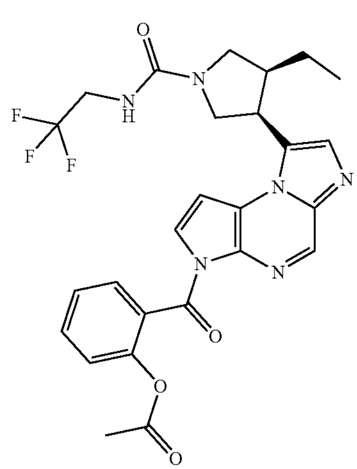 [SMILES: CC[C@@H]1CN(C(=O)NCC(F)(F)F)C[C@@H]1c1cnc2cnc3c(ccn3C(=O)c3ccccc3OC(C)=O)n12] | 2-(8-((3R,4S)-4-ethyl-1-((2,2,2-trifluoroethyl)carbamoyl)pyrrolidin-3-yl)-3H-imidazo[1,2-a]pyrrolo[2,3-e]pyrazine-3-carbonyl)phenylacetate |

257
258

TABLE 1-continued

Structural formulas and compound names of target compounds prepared in examples

| Examples (Cmpd No.) | Structure | Chinese name |
|---|---|---|
| 137 (CPD-080) | 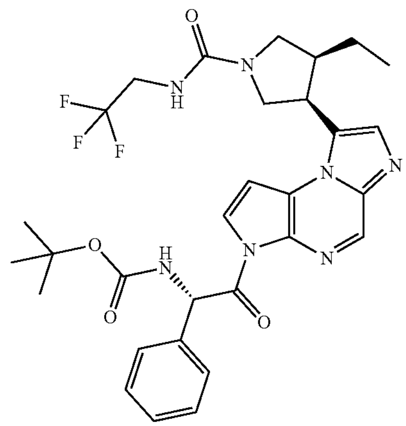 [SMILES: CC[C@@H]1CN(C(=O)NCC(F)(F)F)C[C@@H]1c1cnc2cnc3c(ccn3C(=O)[C@@H](NC(=O)OC(C)(C)C)c3ccccc3)n12] | Tert-butyl ((S)-2-(8-((3R,4S)-4-ethyl-1-((2,2,2-trifluoroethyl)carbamoyl)pyrrolidin-3-yl)-3H-imidazo[1,2-a]pyrrolo[2,3-e]pyrazin-3-yl)-2-oxo-1-phenethyl)carbamate |
| 138 (CPD-081) | 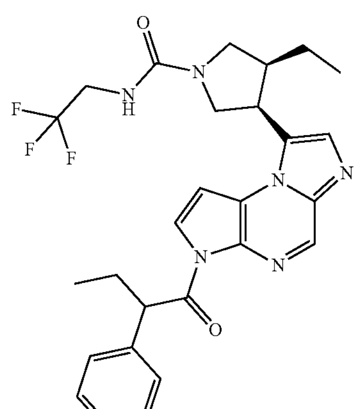 | (3S,4R)-3-ethyl-4-(3-(2-(4-(1-)oxoisoindolin-2-yl)phenyl)butanoyl)-3H-imidazo[1,2-a]pyrrolo[2,3-e]pyrazin-8-yl)-N-(2,2,2-trifluoroethyl)pyrrolidine-1-carboxamide |

TABLE 1-continued
Structural formulas and compound names of target compounds prepared in examples
| Examples (Cmpd No.) | Structure | Chinese name |
|---|---|---|
| 139 (CPD-186) | 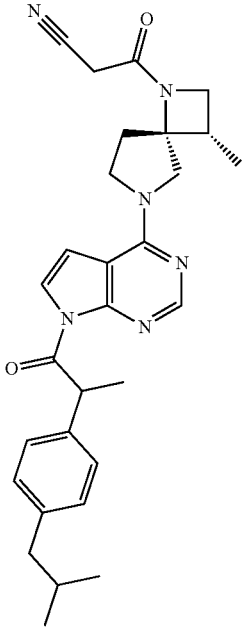 [SMILES: CC(C)Cc1ccc(C(C)C(=O)n2ccc3c(N4CC[C@]5(C4)[C@@H](C)CN5C(=O)CC#N)ncnc32)cc1] | 3-((3S,4R)-6-(7-(2-(4-isobutylphenyl)propanoyl)-7H-pyrrolo[2,3-d]pyrimidin-4-yl)-3-methyl-1,6-diazaspiro[3.4]oct-1-yl)-3-oxopropanenitrile |
| 140 (CPD-187) | 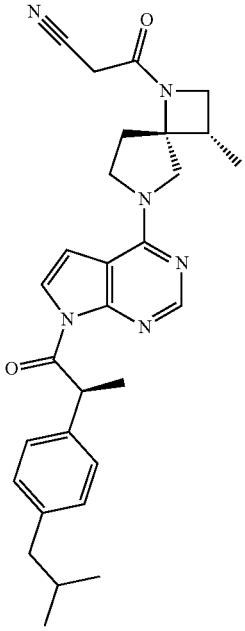 [SMILES: CC(C)Cc1ccc([C@H](C)C(=O)n2ccc3c(N4CC[C@]5(C4)[C@@H](C)CN5C(=O)CC#N)ncnc32)cc1] | 3-((3S,4R)-6-(7-((S)-2-(4-isobutylphenyl)propanoyl)-7H-pyrrolo[2,3-d]pyrimidin-4-yl)-3-methyl-1,6-diazaspiro[3.4]oct-1-yl)-3-oxopropanenitrile |

TABLE 1-continued

Structural formulas and compound names of target compounds prepared in examples

| Examples (Cmpd No.) | Structure | Chinese name |
|---|---|---|
| 141 (CPD-190) | 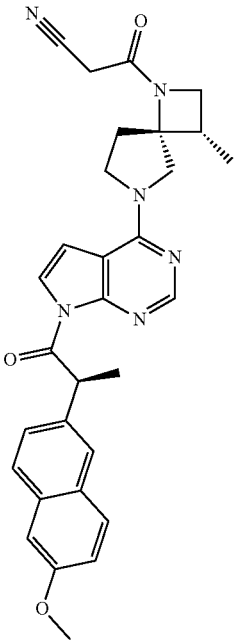 [SMILES: COc1ccc2cc([C@H](C)C(=O)n3ccc4c(N5CC[C@]6(C5)[C@@H](C)CN6C(=O)CC#N)ncnc43)ccc2c1] | 3-((3S,4R)-6-(7-((S)-2-(6-methoxynaphthalen-2-yl)propanoyl)-7H-pyrrolo[2,3-d]pyrimidin-4-yl)-3-methyl-1,6-diazaspiro[3.4]octan-1-yl)-3-oxopropanenitrile |
| 142 (CPD-090) | 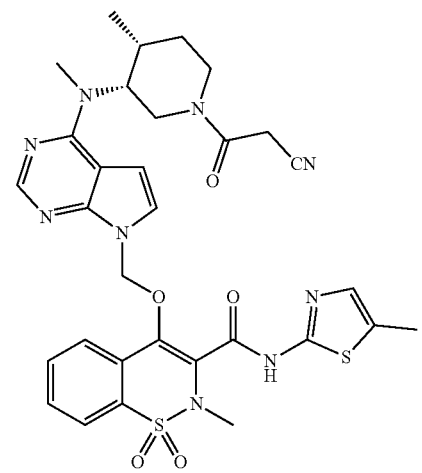 [SMILES: Cc1cnc(NC(=O)C2=C(OCn3ccc4c(N(C)[C@H]5CN(C(=O)CC#N)CC[C@H]5C)ncnc43)c3ccccc3S(=O)(=O)N2C)s1] | 4-((4-(((3R,4R)-1-(2-cyanoacetyl)-4-methylpiperidin-3-yl)(methyl)amino)-7H-pyrrolo[2,3-d]pyrimidin-7-yl)methoxy)-2-methyl-N-(5-methylthiazol-2-yl)-2H-benzo[e][1,2]thiazine-3-carboxamide 1,1-dioxide |

TABLE 1-continued

Structural formulas and compound names of target compounds prepared in examples

| Examples (Cmpd No.) | Structure | Chinese name |
|---|---|---|
| 143 (CPD-201) | 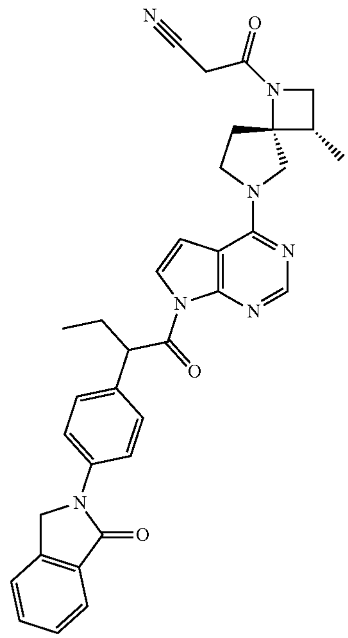 [SMILES: CCC(C(=O)n1ccc2c(N3CC[C@]4(C3)[C@@H](C)CN4C(=O)CC#N)ncnc21)c1ccc(N2Cc3ccccc3C2=O)cc1] | 3-((3S,4R)-3-methyl-6-(7-(2-(4-(1-oxoisoindolin-2-yl)phenyl)butanoyl)-7H-pyrrolo[2,3-d]pyrimidin-4-yl)-1,6-diazaspiro[3.4]octan-1-yl)-3-oxopropanenitrile |
| 144 (CPD-202) | 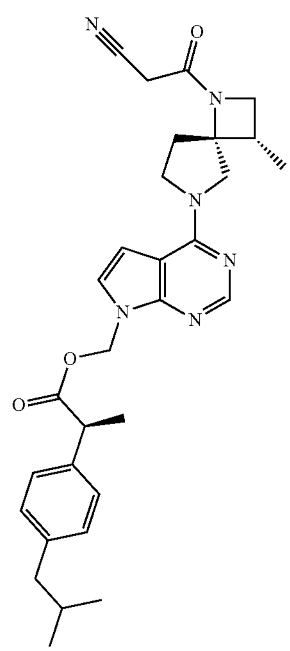 [SMILES: CC(C)Cc1ccc([C@H](C)C(=O)OCn2ccc3c(N4CC[C@]5(C4)[C@@H](C)CN5C(=O)CC#N)ncnc32)cc1] | (4-((3S,4R)-1-(2-cyanoacetyl)-3-methyl-1,6-diazaspiro[3.4]octan-6-yl)-7H-pyrrolo[2,3-d]pyrimidin-7-yl)methyl (S)-2-(4-isobutylphenyl)propanoate |

TABLE 1-continued

Structural formulas and compound names of target compounds prepared in examples

| Examples (Cmpd No.) | Structure | Chinese name |
|---|---|---|
| 145 (CPD-191) | 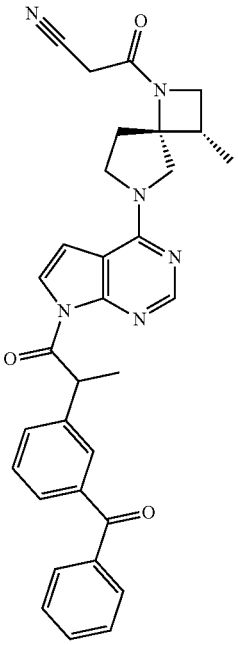 [SMILES: CC(C(=O)n1ccc2c(N3CC[C@]4(C3)[C@@H](C)CN4C(=O)CC#N)ncnc21)c1cccc(C(=O)c2ccccc2)c1] | 3-((3S,4R)-6-(7-(2-(3-benzoylphenyl)propanoyl)-7H-pyrrolo[2,3-d]pyrimidin-4-yl)-3-methyl-1,6-diazaspiro[3.4]oct-1-yl)-3-oxopropanenitrile |
| 146 (CPD-143) | 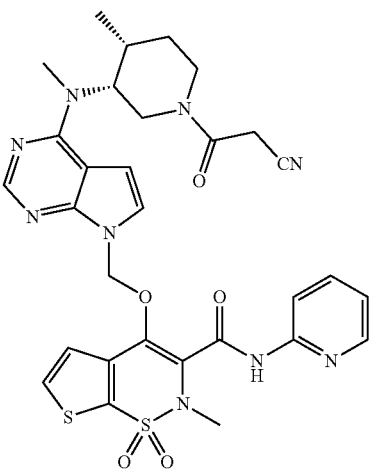 [SMILES: C[C@@H]1CCN(C(=O)CC#N)C[C@@H]1N(C)c1ncnc2c1ccn2COC1=C(C(=O)Nc2ccccn2)N(C)S(=O)(=O)c2sccc21] | 4-((4-(((3R,4R)-1-(2-cyanoacetyl)-4-methylpiperidin-3-yl)(methyl)amino)-7H-pyrrolo[2,3-d]pyrimidin-7-yl)methoxy)-2-methyl-N-(pyridin-2-yl)-2H-thieno[3,2-e][1,2]thiazine-3-carboxamide 1,1-dioxide |

TABLE 1-continued

Structural formulas and compound names of target compounds prepared in examples

| Examples (Cmpd No.) | Structure | Chinese name |
|---|---|---|
| 147 (CPD-159) | 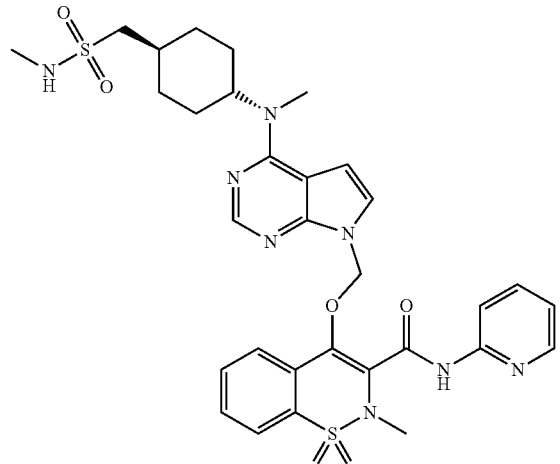 | 2-Methyl-4-((4-(methyl ((trans)-4-((N-methylsulfamoyl)methyl) cyclohexyl)amino)-7H-pyrrolo[2,3-d] pyrimidin-7-yl) methoxy)-N-(pyridin-2-yl)-2H-benzo[e][1,2] thiazine-3-carboxamide 1,1-dioxide |
| 148 (CPD-152) | 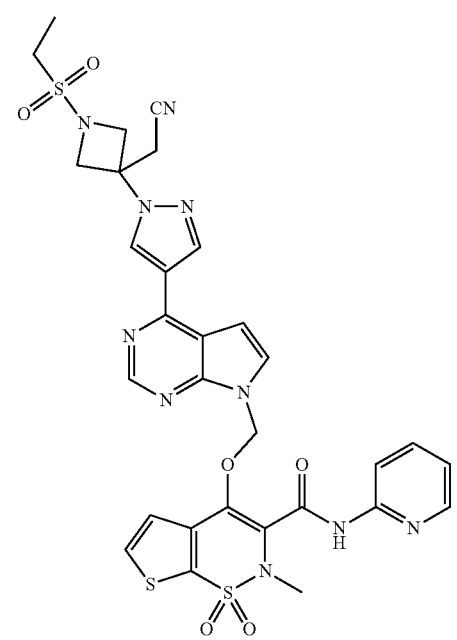 [SMILES: CCS(=O)(=O)N1CC(CC#N)(n2cc(-c3ncnc4c3ccn4COC3=C(C(=O)Nc4ccccn4)N(C)S(=O)(=O)c4sccc43)cn2)C1] | 4-((4-(1-(3-(Cyanomethyl)-1-(ethylsulfonyl) azetidin-3-yl)-1H-pyrazol-4-yl)-7H-pyrrolo [2,3-d]pyrimidin-7-yl) methoxy)-2-methyl-N- (pyridin-2-yl)-2H-thieno [3,2-e][1,2]thiazine-3-carboxamide 1,1-dioxide |

TABLE 1-continued

Structural formulas and compound names of target compounds prepared in examples

| Examples (Cmpd No.) | Structure | Chinese name |
|---|---|---|
| 149 (CPD-160) | 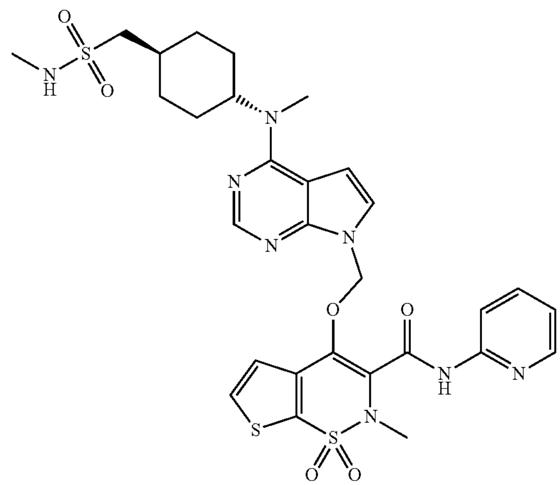 | 2-Methyl-4-((4-(methyl ((trans)-4-((N-methylsulfamoyl)methyl) cyclohexyl)amino)-7H-pyrrolo[2,3-d] pyrimidin-7-yl) methoxy)-N-(pyridin-2-yl)-2H-thieno[3,2-e] [1,2]thiazine-3-carboxamide 1,1-dioxide |

Example 1

3-((3R, 4R)-3-((7-(2-(4-isobutylphenyl) propanoyl)-7H-pyrrolo [2, 3-d] pyrimidin-4-yl) (methyl) amino)-4-methylpiperidin-1-yl)-3-oxopropanenitrile

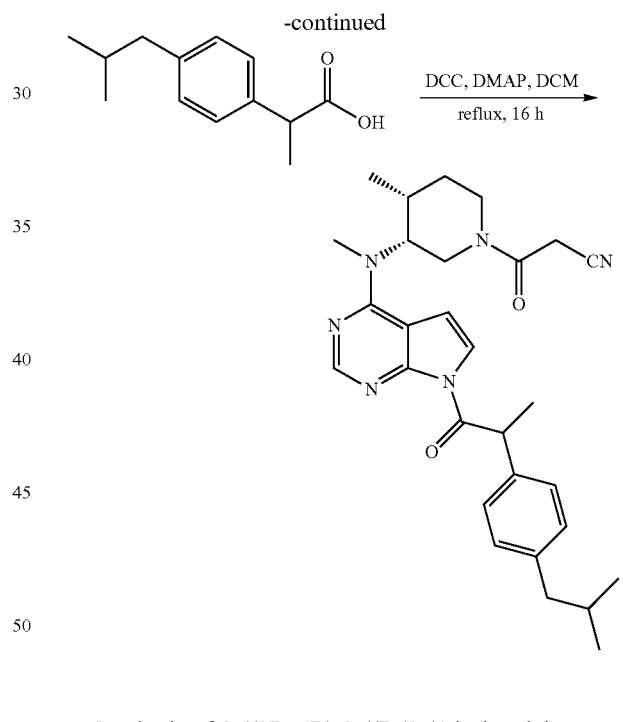

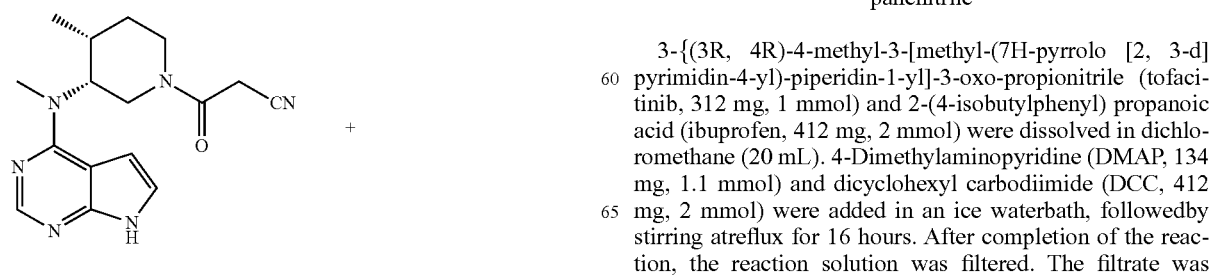

Synthesis of 3-((3R, 4R)-3-((7-(2-(4-isobutylphenyl) propanoyl)-7H-pyrrolo [2, 3-d] pyrimidin-4-yl) (methyl) amino)-4-methylpiperidin-1-yl)-3-oxopropanenitrile 3-{(3R, 4R)-4-methyl-3-[methyl-(7H-pyrrolo [2, 3-d] pyrimidin-4-yl)-piperidin-1-yl]-3-oxo-propionitrile (tofacitinib, 312 mg, 1 mmol) and 2-(4-isobutylphenyl) propanoic acid (ibuprofen, 412 mg, 2 mmol) were dissolved in dichloromethane (20 mL). 4-Dimethylaminopyridine (DMAP, 134 mg, 1.1 mmol) and dicyclohexyl carbodiimide (DCC, 412 mg, 2 mmol) were added in an ice waterbath, followed by stirring at reflux for 16 hours. After completion of the reaction, the reaction solution was filtered. The filtrate was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=5:1 to 2:1) to give the title compound as a white solid, 0.292 g, 58% yield. MS (m/z): [M+H]⁺ calcd for $C_{29}H_{36}N_6O_2$, 501.65; found, 501.2. $^1$H NMR (400 MHz, Chloroform-d) δ 8.39 (d, J=7.3 Hz, 1H), 7.68 (dd, J=15.2, 4.2 Hz, 1H), 7.44-7.33 (m, 2H), 7.08-7.03 (m, 2H), 6.61 (t, J=4.2 Hz, 1H), 6.13 (tt, J=7.3, 3.5 Hz, 1H), 5.09 (s, 1H), 4.09-3.70 (m, 2H), 3.66-3.44 (m, 4H), 3.33 (d, J=16.4 Hz, 3H), 2.39 (d, J=7.2 Hz, 3H), 1.88-1.70 (m, 2H), 1.67-1.60 (m, 4H), 1.15-1.03 (m, 3H), 0.86 (d, J=6.6 Hz, 6H).

Example 2

3-((3R, 4R)-3-((7-((S)-2-(4-isobutylphenyl) propanoyl)-7H-pyrrolo [2, 3-d] pyrimidin-4-yl)(methyl) amino)-4-methylpiperidin-1-yl)-3-oxopropanenitrile

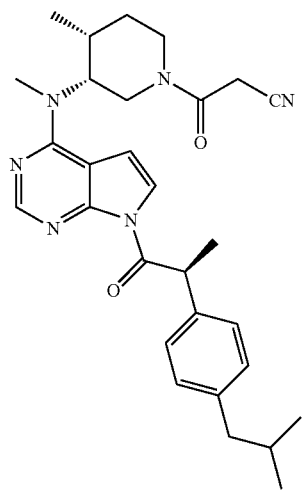

+

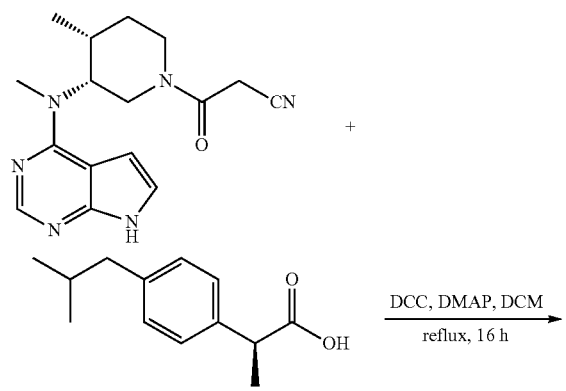

DCC, DMAP, DCM
reflux, 16 h

-continued

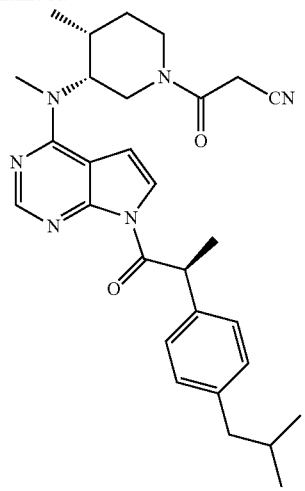

Synthesis of 3-((3R, 4R)-3-((7-((S)-2-(4-isobutylphenyl) propanoyl)-7H-pyrrolo [2, 3-d] pyrimidin-4-yl) (methyl) amino)-4-methylpiperidin-1-yl)-3-oxopropanenitrile 3-{(3R, 4R)-4-methyl-3-[methyl-(7H-pyrrolo [2, 3-d] pyrimidin-4-yl)-piperidin-1-yl]-3-oxo-propionitrile (tofacitinib, 312 mg, 1 mmol) and S)-(+)-2-(4-isobutylphenyl) propanoic acid ((S)-(+)-ibuprofen, 309 mg, 1.5 mmol) were dissolved in dichloromethane (20 mL). 4-Dimethylaminopyridine (DMAP, 134 mg, 1.1 mmol) and dicyclohexyl carbodiimide (DCC, 412 mg, 2 mmol) were added in an ice water bath, followed by stirring at reflux for 16 hours. After completion of the reaction, the reaction solution was filtered. The filtrate was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=5:1 to 2:1) to give the title compound as a white solid, 0.24 g, 48% yield. MS (m/z): [M+H]⁺ calcd for $C_{29}H_{36}N_6O_2$, 501.65; found, 501.2. $^1$H NMR (400 MHz, DMSO-d6) δ 8.38 (d, J=4.6 Hz, 1H), 7.68 (dd, J=4.3, 2.8 Hz, 1H), 7.29 (dd, J=8.2, 2.6 Hz, 2H), 7.06 (d, J=7.9 Hz, 2H), 6.88 (d, J=4.2 Hz, 1H), 6.09 (qd, J=6.7, 3.0 Hz, 1H), 4.85 (s, 1H), 4.18-3.59 (m, 5H), 3.41 (q, J=5.3, 4.9 Hz, 1H), 3.24 (d, J=2.4 Hz, 3H), 2.36 (d, J=7.2 Hz, 3H), 1.87-1.65 (m, 2H), 1.63-1.48 (m, 4H), 1.00 (dd, J=7.2, 2.6 Hz, 3H), 0.81 (d, J=6.6 Hz, 6H).

Example 3

(4-((3R, 4R)-1-(2-cyanoacetyl)-4-methylpiperidin-3-yl) (methyl) amino)-7H-pyrrolo [2, 3-d] pyrimidin-7-yl) methyl (S)-2-(4-isobutylphenyl) propanoate

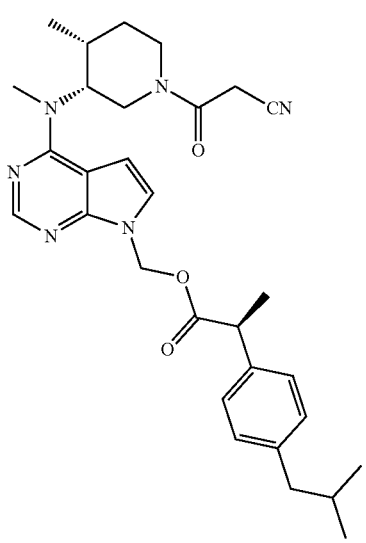 [SMILES: CC(C)Cc1ccc([C@H](C)C(=O)OCn2ccc3c(N(C)[C@H]4CN(C(=O)CC#N)CC[C@H]4C)ncnc32)cc1]

First Step: Synthesis of 3-((3R, 4R)-4-methyl-3-(methyl (7-(2-(trimethylsilyl) ethoxy) methyl)-7H-pyrrolo [2, 3-d] pyrimidin-4-yl) amino) piperidin-1-yl)-3-oxopropanenitrile

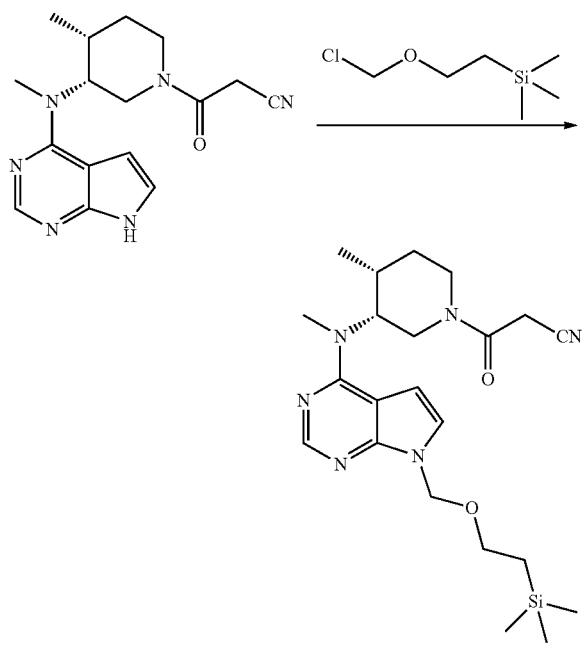

3-{(3R, 4R)-4-methyl-3-[methyl-(7H-pyrrolo [2, 3-d] pyrimidin-4-yl)-piperidin-1-yl]-3-oxo-propionitrile (tofacitinib, 9 g, 28.81 mmol) was dissolved in dichloromethane (180 mL) and diethyl acetate (3.745 g, 28.81 mol) under nitrogen protection. After stirring at room temperature for half an hour, (2-(chloromethoxy) ethyl) trimethylsilane (4.8 g, 28.81 mmol) was added and the stirring was continued at room temperature overnight. The solvent was evaporated under reduced pressure to give the crude product. The crude product was further isolated by silica gel column chromatography to give the title compound as a white solid, 9 g, 71% yield. MS (m/z): [M+H]$^+$ calcd for $C_{22}H_{34}N_6O_2Si$, 443.25; found, 443.2.

Second Step: Synthesis of 3-((3R, 4R)-3-((7-(hydroxymethyl)-7H-pyrrolo [2, 3-d] pyrimidin-4-yl) (methyl) amino)-4-methylpiperidin-1-yl)-3-oxopropanenitrile

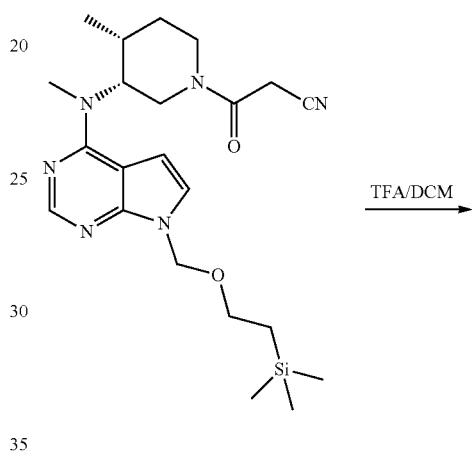

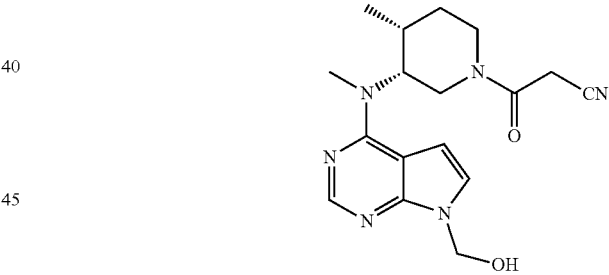

Trifluoroacetic acid (6.44 g, 56.5 mmol) was slowly added dropwise to a solution of 3-((3R, 4R)-4-methyl-3-(methyl (7-(2-(trimethylsilyl) ethoxy) methyl)-7H-pyrrolo [2, 3-d] pyrimidin-4-yl) amino) piperidin-1-yl)-3-oxopropanenitrile (5 g, 11.3 mmol) in dichloromethane (100 mL) under nitrogen protection in an ice-water bath. After half an hour, the ice-water bath was removed and the temperature was raised to room temperature and stirring was continued for 24 hours. Saturated sodium bicarbonate solution was added to the above reaction solution at 0° C. to adjust the pH to 8. Then, the mixture was poured into a separation funnel and separated. The organic layer was washed with a saturated salt water solution, and dried over anhydrous sodium sulfate. After filtration, the solvent was evaporated under reduced pressure to give the title product 3.5 g, 90% yield. MS (m/z): [M+H]$^+$ calcd for $C_{17}H_{22}N_6O_2$, 343.18; found, 343.1.

275

Third Step: Synthesis of (4-((3R, 4R)-1-(2-cyano-acetyl)-4-methylpiperidin-3-yl) (methyl) amino)-7H-pyrrolo [2, 3-d] pyrimidin-7-yl) methyl (S)-2-(4-isobutylphenyl) propanoate

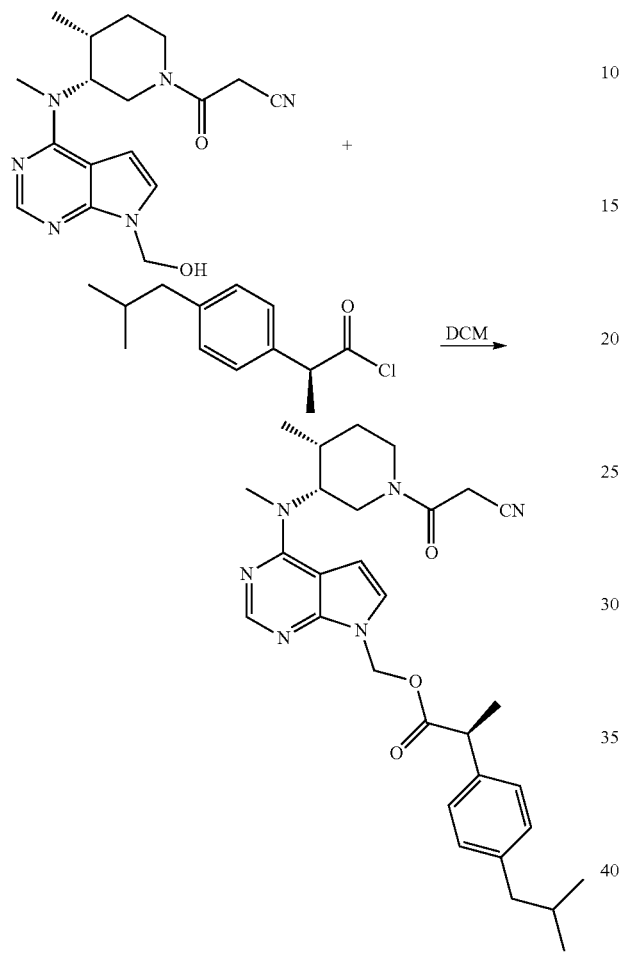

3-((3R, 4R)-3-((7-(hydroxymethyl)-7H-pyrrolo [2, 3-d] pyrimidin-4-yl) (methyl) amino)-4-methylpiperidin-1-yl)-3-oxopropanenitrile (6.63 g, 19.4 mmol), (S)-2-(4-isobutylphenyl) propanoyl chloride (8.72 g, 38.8 mmol) and triethylamine (3.93 g, 38.8 mmol) were dissolved in dichloromethane (100 mL). After stirring at room temperature for 24 hours, the reaction mixture was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=2:1 to 1:1) to give the title compound, 4.05 g, 39.4% yield. MS (m/z): [M+H]$^+$ calcd for $C_{30}H_{38}N_6O_3$, 531.67; found, 531.2. $^1$H NMR (400 MHz, CDCl$_3$) δ 8.32 (d, J=7.4 Hz, 1H), 7.11 (dd, J=12.7, 5.5 Hz, 3H), 7.03 (d, J=7.6 Hz, 2H), 6.51 (s, 1H), 6.18 (dd, J=10.4, 4.0 Hz, 1H), 6.14-6.06 (m, 1H), 5.13 (s, 1H), 4.06 (dd, J=13.2, 3.8 Hz, 1H), 3.81 (dd, J=18.3, 10.5 Hz, 1H), 3.69 (q, J=7.1 Hz, 1H), 3.61 (t, J=11.8 Hz, 1H), 3.55-3.47 (m, 2H), 3.37 (d, J=17.9 Hz, 3H), 2.58-2.46 (m, 1H), 2.42 (d, J=7.1 Hz, 2H), 2.05-1.91 (m, 1H), 1.83 (td, J=13.0, 6.2 Hz, 2H), 1.45 (d, J=7.1 Hz, 3H), 1.28 (s, 1H), 1.09 (dd, J=12.9, 7.1 Hz, 3H), 0.88 (d, J=6.6 Hz, 6H).

276

Example 4

3-((3R, 4R)-3-((7-(2-((2, 3-dimethylphenyl) amino) benzoyl)-7H-pyrrolo [2, 3-d] pyrimidin-4-yl) (methyl) amino)-4-methylpiperidin-1-yl)-3-oxopropanenitrile

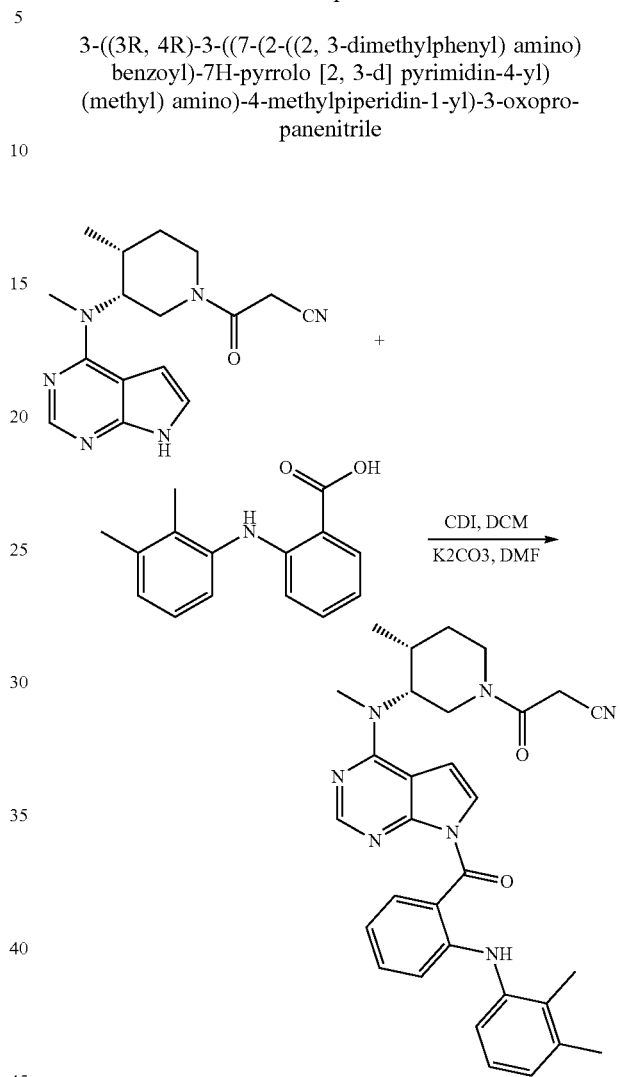

3-{(3R, 4R)-4-methyl-3-[methyl-(7H-pyrrolo [2, 3-d] pyrimidin-4-yl)-piperidin-1-yl]-3-oxo-propionitrile (tofacitinib, 312 mg, 1 mmol), 4-dimethylamino pyridine (DMAP, 12 mg, 0.1 mmol), 2-((2, 3-dimethylphenyl) amino) benzoic acid (mefenamic acid, 314 mg, 1.3 mmol) and 1-(3-dimethylaminopropyl)-3-ethylcarbodiimide hydrochloride (EDCI, 288 mg, 1.5 mmol) were dissolved in dichloromethane (10 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further purified by silica gel column chromatography (petroleum ether/ethyl acetate=2:1 to 1:1) to give the title compound as a yellow solid, 0.1 g, yield 18.6%. MS (m/z): [M+H]$^+$ calcd for $C_{31}H_{33}N_7O_2$, 536.65; found, 536.2. $^1$H NMR (400 MHz, DMSO) δ 8.60 (d, J=16.4 Hz, 1H), 8.14 (d, J=7.5 Hz, 1H), 7.55-7.43 (m, 1H), 7.35 (dt, J=17.9, 8.5 Hz, 2H), 7.06 (d, J=6.2 Hz, 2H), 6.98 (s, 1H), 6.87 (t, J=12.4 Hz, 1H), 6.80 (d, J=8.4 Hz, 1H), 6.73 (t, J=7.4

Hz, 1H), 4.86 (s, 1H), 4.20-3.90 (m, 3H), 3.87-3.64 (m, 2H), 3.42 (s, 1H), 3.30 (s, 3H), 2.39 (d, J=5.3 Hz, 1H), 2.26 (s, 3H), 2.10-1.96 (m, 3H), 1.90-1.67 (m, 1H), 1.66-1.53 (m, 1H), 1.03 (d, J=6.9 Hz, 3H).

Example 5

3-((3R, 4R)-3-((7-(2-((3-chloro-2-methylphenyl) amino) benzoyl)-7H-pyrrolo [2, 3-d] pyrimidin-4-yl) (methyl) amino)-4-methylpiperidin-1-yl)-3-oxo-propanenitrile

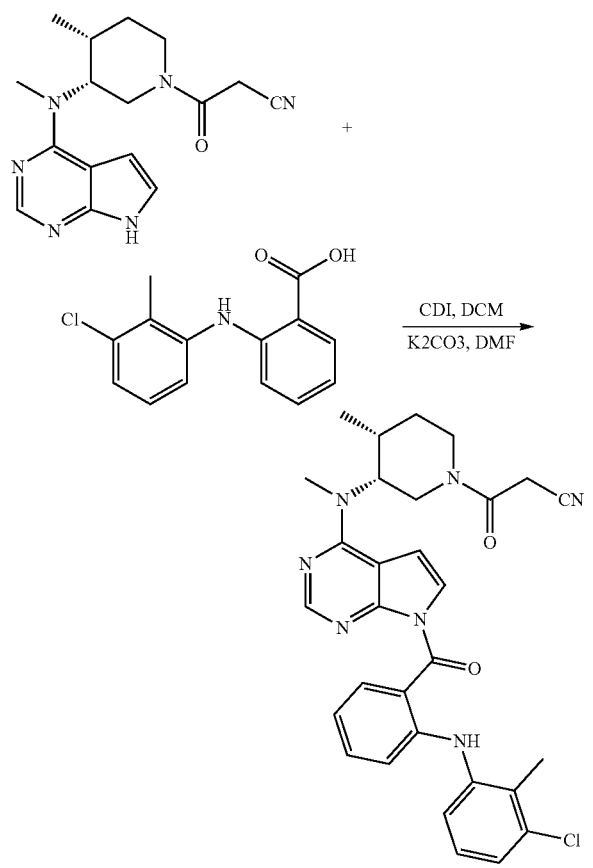

3-{(3R, 4R)-4-methyl-3-[methyl-(7H-pyrrolo [2, 3-d] pyrimidin-4-yl)-piperidin-1-yl]-3-oxo-propionitrile (tofacitinib, 187 mg, 0.6 mmol), 4-dimethylamino pyridine (DMAP, 7 mg, 0.6 mmol), 2-((3-chloro-2-methylphenyl) amino) benzoic acid (tofenamic acid, 204 mg, 0.78 mmol) and 1-(3-dimethylaminopropyl)-3-ethylcarbodiimide hydrochloride (EDCI, 173 mg, 0.9 mmol) was dissolved in dichloromethane (10 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further purified by silica gel column chromatography (petroleum ether/ethyl acetate=2:1 to 1:1) to give the title compound as a yellow solid, 0.12 g, 35.9% yield. MS (m/z): [M+H]+ calcd for $C_{30}H_{30}Cl_1N_7O_2$, 557.07; found, 557.2. $^1$H NMR (400 MHz, DMSO-d6) δ 8.23 (d, J=17.2 Hz, 1H), 8.10 (d, J=8.3 Hz, 1H), 7.46 (ddd, J=8.6, 7.1, 1.6 Hz, 1H), 7.43-7.34 (m, 2H), 7.07 (tq, J=7.0, 4.8, 3.6 Hz, 3H), 6.96 (d, J=8.3 Hz, 1H), 6.90 (t, J=7.5 Hz, 1H), 6.84 (d, J=4.1 Hz, 1H), 4.84 (s, 1H), 4.19-3.90 (m, 3H), 3.74 (dtd, J=34.8, 14.2, 13.1, 7.4 Hz, 2H), 3.50-3.39 (m, 1H), 3.29-3.21 (m, 3H), 2.46-2.32 (m, 1H), 2.06 (d, J=8.5 Hz, 3H), 1.92-1.66 (m, 1H), 1.64-1.51 (m, 1H), 1.03 (d, J=7.1 Hz, 3H).

Example 6

3-((3R, 4R)-3-((7-((S)-2-(6-methoxynaphthalen-2-yl) propanoyl)-7H-pyrrolo [2, 3-d] pyrimidin-4-yl) (methyl) amino)-4-methylpiperidin-1-yl)-3-oxopropanenitrile

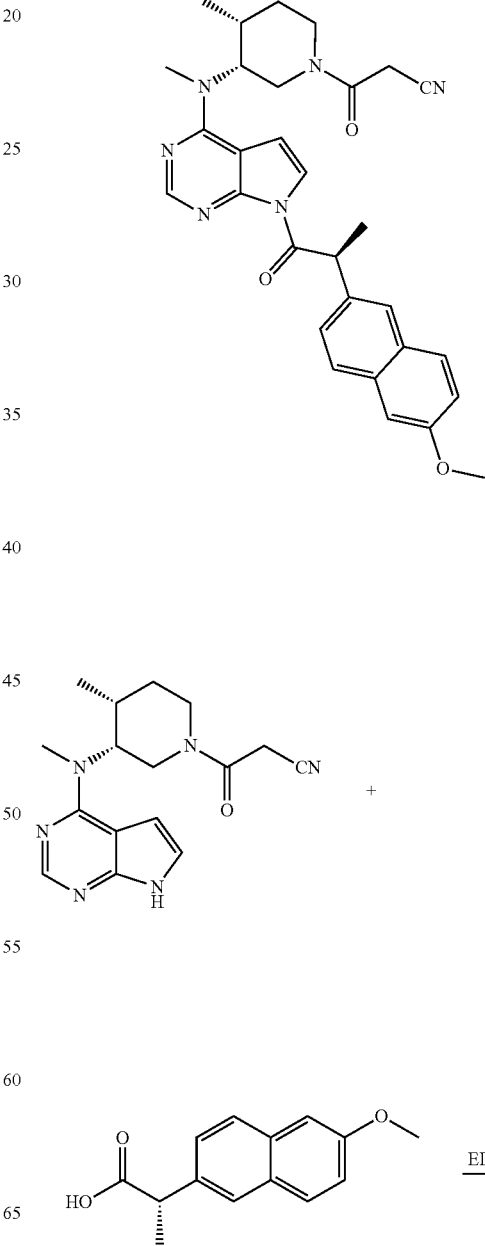

279

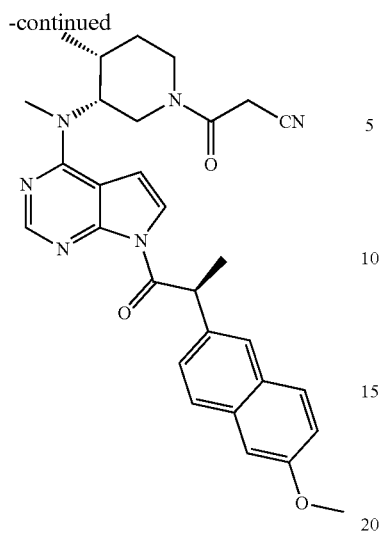

Synthesis of 3-((3R, 4R)-3-((7-((S)-2-(6-methoxynaphthalen-2-yl) propanoyl)-7H-pyrrolo [2, 3-d] pyrimidin-4-yl) (methyl) amino)-4-methylpiperidin-1-yl)-3-oxopropanenitrile 3-{(3R, 4R)-4-methyl-3-[methyl-(7H-pyrrolo [2, 3-d] pyrimidin-4-yl)-piperidin-1-yl]-3-oxo-propionitrile (tofacitinib, 624 mg, 2 mmol), (S)-(+)-2-(6-methoxy-2-naphthyl) propanoic acid (naproxen, 506 mg, 2.2 mmol) and 1-(3-dimethylaminopropyl)-3-ethylcarbodiimide hydrochloride (EDCI, 863 mg, 4.5 mmol) were dissolved in dichloromethane (40 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=1:1 to 1:2) to give the title compound as a white solid, 0.7 g, 66.8% yield. MS (m/z): [M+H]$^+$ calcd for C$_{30}$H$_{32}$N$_6$O$_3$, 525.63; found, 525.3. $^1$H NMR (400 MHz, DMSO) δ 8.41 (s, 1H), 7.81-7.69 (m, 4H), 7.50 (dd, J=7.0, 5.3 Hz, 1H), 7.24 (s, 1H), 7.12 (dd, J=8.9, 2.3 Hz, 1H), 6.88 (d, J=3.7 Hz, 1H), 6.25-6.16 (m, 1H), 4.83 (s, 1H), 4.17-3.87 (m, 3H), 3.84 (s, 3H), 3.72-3.59 (m, 2H), 3.41-3.39 (m, 1H), 3.23 (s, 3H), 2.32 (d, J=13.3 Hz, 1H), 1.83-1.49 (m, 5H), 0.99 (d, J=7.1 Hz, 3H)

280

Example 7

3-((3R, 4R)-3-((7-(2-(3-benzoylphenyl) propanoyl)-7H-pyrrolo [2, 3-d] pyrimidin-4-yl) (methyl) amino)-4-methylpiperidin-1-yl)-3-oxopropanenitrile

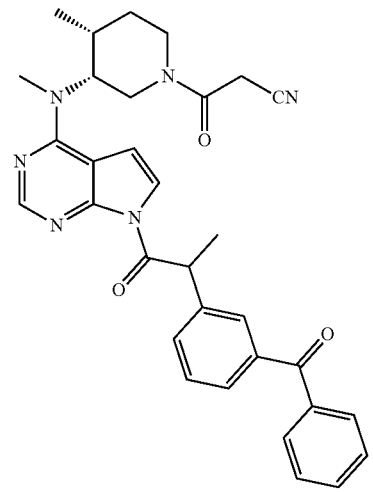

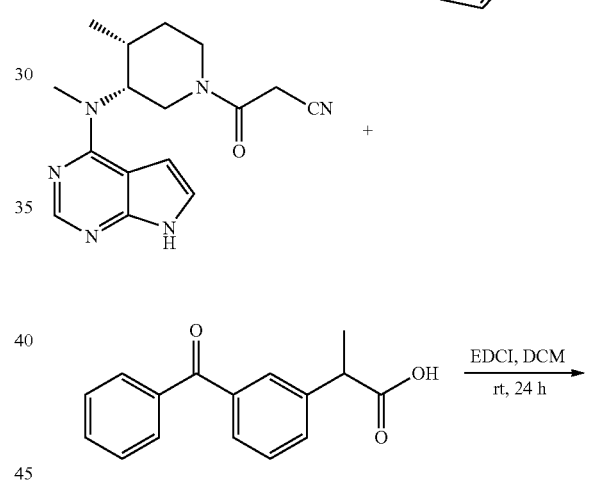

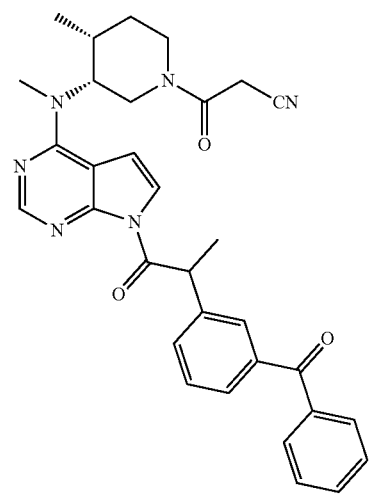

281

Synthesis of 3-((3R, 4R)-3-((7-(2-(3-benzoylphenyl) propanoyl)-7H-pyrrolo [2, 3-d] pyrimidin-4-yl) (methyl) amino)-4-methylpiperidin-1-yl)-3-oxopropanenitrile 3-{(3R, 4R)-4-methyl-3-[methyl-(7H-pyrrolo [2, 3-d] pyrimidin-4-yl)-piperidin-1-yl]-3-oxo-propionitrile (tofacitinib, 624 mg, 2 mmol), 2-(3-benzoylphenyl) propanoic acid (ketoprofen, 559 mg, 2.2 mmol) and 1-(3-dimethylaminopropyl)-3-ethylcarbodiimide hydrochloride (EDCI, 576 mg, 3 mmol) were dissolved in dichloromethane (20 mL) and stirred at room temperature for 24 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=2:1 to 1:2) to give the title compound as a white solid, 0.73 g, 66.6% yield. MS (m/z): [M+H]$^+$ calcd for $C_{32}H_{32}N_6O_3$, 549.65; found, 549.3. $^1$H NMR (400 MHz, DMSO) δ 8.33 (d, J=7.4 Hz, 1H), 7.79 (d, J=1.6 Hz, 1H), 7.76-7.63 (m, 5H), 7.61 (d, J=7.8 Hz, 1H), 7.57 (d, J=8.5 Hz, 1H), 7.54 (s, 1H), 7.51 (d, J=7.7 Hz, 1H), 6.94 (d, J=3.8 Hz, 1H), 6.16 (q, J=6.8 Hz, 1H), 4.85 (s, 1H), 4.14-3.90 (m, 3H), 3.83-3.60 (m, 2H), 3.46-3.39 (m, 1H), 3.26 (s, 3H), 2.44-2.29 (m, 1H), 1.90-1.68 (m, 1H), 1.67-1.51 (m, 4H), 1.02 (t, J=9.4 Hz, 3H).

Example 8

3-((3R, 4R)-3-((7-(2-(2-fluoro-[1, 1'-biphenyl]-4-yl) propanoyl)-7H-pyrrolo [2, 3-d] pyrimidin-4-yl) (methyl) amino)-4-methylpiperidin-1-yl)-3-oxopropanenitrile

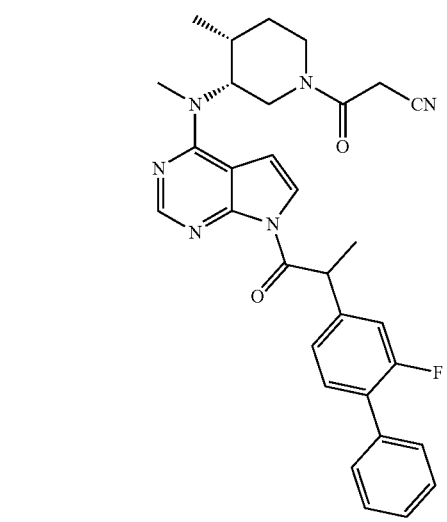

+

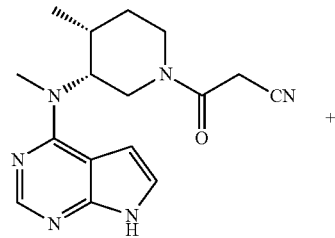

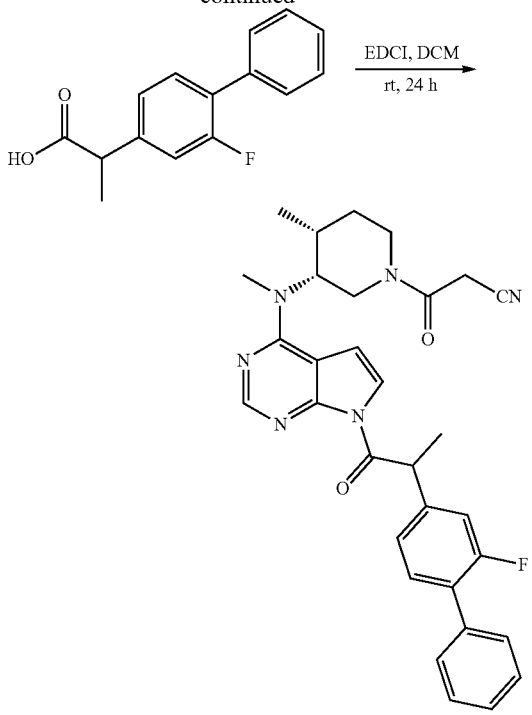

Synthesis of 3-((3R, 4R)-3-((7-(2-(2-fluoro-[1, 1'-biphenyl]-4-yl) propanoyl)-7H-pyrrolo [2, 3-d] pyrimidin-4-yl) (methyl) amino)-4-methylpiperidin-1-yl)-3-oxopropanenitrile 3-{(3R, 4R)-4-methyl-3-[methyl-(7H-pyrrolo [2, 3-d] pyrimidin-4-yl)-piperidin-1-yl]-3-oxo-propionitrile (tofacitinib, 624 mg, 2 mmol), 2-(2-fluoro-4-biphenyl) propanoic acid (flurbiprofen, 537 mg, 2.2 mmol) and 1-(3-dimethylaminopropyl)-3-ethylcarbodiimide hydrochloride (EDCI, 576 mg, 3 mmol) were dissolved in dichloromethane (20 mL) and stirred at room temperature for 24 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=1:1 to 1:2) to give the title compound as a white solid, 0.73 g, 67.8% yield. MS (m/z): [M+H]$^+$ calcd for $C_{31}H_{31}FN_6O_2$, 539.63; found, 539.2. $^1$H NMR (400 MHz, DMSO) δ 8.41 (dd, J=5.7, 1.3 Hz, 1H), 7.72 (d, J=4.2 Hz, 1H), 7.54-7.43 (m, 5H), 7.41-7.27 (m, 3H), 6.93 (s, 1H), 6.16 (q, J=6.7 Hz, 1H), 4.84 (s, 1H), 4.16-3.99 (m, 2H), 3.98-3.87 (m, 1H), 3.75-3.59 (m, 2H), 3.45-3.39 (m, 1H), 3.23 (s, 3H), 2.43-2.27 (m, 1H), 1.88-1.66 (m, 1H), 1.65-1.52 (m, 4H), 1.04-0.93 (m, 3H).

Example 9

3-((3R, 4R)-3-((7-(2-(2-(2-(2-(2-(2, 6-dichlorophenyl) amino) phenyl) acetyl)-7H-pyrrolo [2, 3-d] pyrimidin-4-yl) (methyl) amino)-4-methylpiperidin-1-yl)-3-oxopropanenitrile

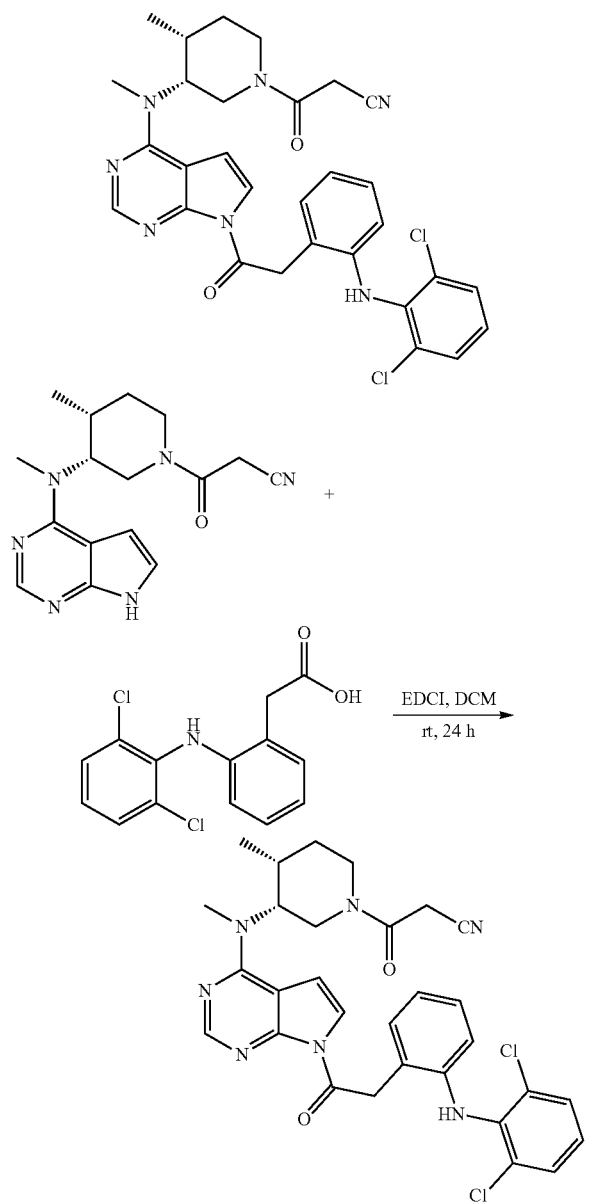

Synthesis of 3-((3R, 4R)-3-((7-(2-(2-(2-(2-(2, 6-dichlorophenyl) amino) phenyl) acetyl)-7H-pyrrolo [2, 3-d]pyrimidin-4-yl) (methyl) amino)-4-methylpiperidin-1-yl)-3-oxopropanenitrile 3-{(3R, 4R)-4-methyl-3-[methyl-(7H-pyrrolo [2, 3-d] pyrimidin-4-yl)-piperidin-1-yl]-3-oxo-propionitrile (tofacitinib, 624 mg, 2 mmol), 2-(2, 6-dichlorophenylamino) phenylacetic acid (diclofenac, 651 mg, 2.2 mmol) and 1-(3-dimethylaminopropyl)-3-ethylcarbodiimide hydrochloride (EDCI, 576 mg, 3 mmol) were dissolved in dichloromethane (6 mL) and stirred at room temperature for 24 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=5:1 to 1:2) to give the title compound as a white solid, 0.25 g, 21.2% yield. MS (m/z): [M+H]$^+$ calcd for $C_{30}H_{29}Cl_2N_7O_2$, 590.51; found, 590.2. $^1$H NMR (400 MHz, DMSO) δ 8.41 (d, J=5.9 Hz, 1H), 7.75 (d, J=4.1 Hz, 1H), 7.51 (d, J=8.1 Hz, 2H), 7.35 (d, J=12.7 Hz, 1H), 7.28 (d, J=7.0 Hz, 1H), 7.20 (t, J=8.1 Hz, 1H), 7.07 (t, J=7.7 Hz, 1H), 6.96 (d, J=3.8 Hz, 1H), 6.83 (t, J=7.4 Hz, 1H), 6.22 (d, J=8.0 Hz, 1H), 4.99-4.83 (m, 3H), 4.16-3.99 (m, 3H), 3.88-3.61 (m, 2H), 3.40 (d, J=14.4 Hz, 1H), 3.29 (s, 3H), 2.45-2.29 (m, 1H), 1.89-1.67 (m, 1H), 1.65-1.52 (m, 1H), 1.01 (d, J=7.1 Hz, 3H).

Example 10

3-((3R, 4R)-4-methyl-3-(methyl (7-(2-(3-phenoxyphenyl) propanoyl)-7H-pyrrolo [2, 3-d] pyrimidin-4-yl) amino) piperidin-1-yl)-3-oxopropanenitrile

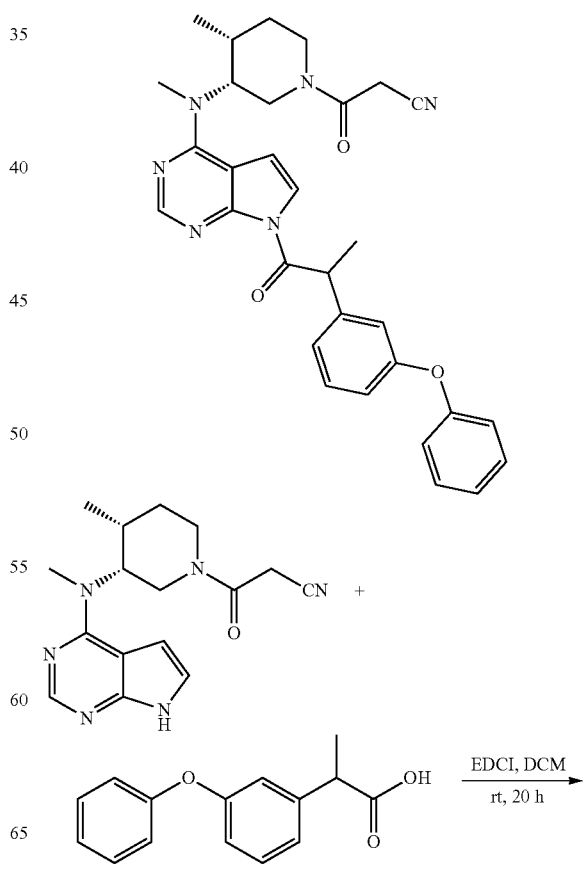

285

-continued

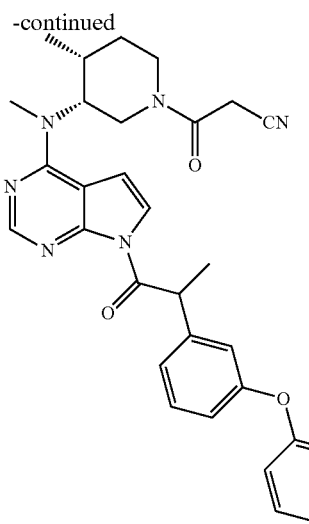

Synthesis of 3-((3R, 4R)-4-methyl-3-(methyl (7-(2-(3-phenoxyphenyl) propanoyl)-7H-pyrrolo [2, 3-d] pyrimidin-4-yl) amino) piperidin-1-yl)-3-oxopropanenitrile 3-{(3R, 4R)-4-methyl-3-[methyl-(7H-pyrrolo [2, 3-d] pyrimidin-4-yl)-piperidin-1-yl]-3-oxo-propionitrile (tofacitinib, 781 mg, 2.5 mmol), 2-(3-phenoxyphenyl) propanoic acid (fenoprofen, 787.4 mg, 3.25 mmol) and 1-(3-dimethylaminopropyl)-3-ethylcarbodiimide hydrochloride (EDCI, 720.5 mg, 3.75 mmol) were dissolved in dichloromethane (20 mL) and stirred at room temperature for 20 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=5:1 to 1:2) to give the title compound as a white solid, 1.1 g, 82% yield. MS (m/z): [M+H]$^+$ calcd for C$_{31}$H$_{32}$N$_6$O$_3$ 537.64; found, 537.3. $^1$H NMR (400 MHz, Chloroform-d) δ 8.30 (dd, J=10.4, 4.8 Hz, 1H), 7.77-7.61 (m, 1H), 7.36-7.16 (m, 5H), 7.10 (t, J=7.4 Hz, 1H), 6.98-6.92 (m, 2H), 6.83 (dt, J=7.7, 2.0 Hz, 1H), 6.62 (t, J=4.2 Hz, 1H), 6.10 (qd, J=7.0, 4.5 Hz, 1H), 5.09 (ddq, J=14.2, 9.9, 4.8 Hz, 1H), 4.12-3.67 (m, 2H), 3.63-3.41 (m, 4H), 3.33 (d, J=15.6 Hz, 3H), 2.48 (ddt, J=17.9, 12.9, 5.9 Hz, 1H), 1.93 (dddd, J=17.4, 12.6, 7.5, 3.9 Hz, 1H), 1.81-1.68 (m, 1H), 1.66-1.58 (m, 3H), 1.08 (dd, J=12.6, 7.1 Hz, 3H).

286

Example 11

3-((3R, 4R)-4-methyl-3-(methyl (7-(2-(4-((2-oxocyclopentyl) methyl) phenyl) propanoyl)-7H-pyrrolo [2, 3-d]pyrimidin-4-yl) amino) piperidin-1-yl)-3-oxopropanenitrile

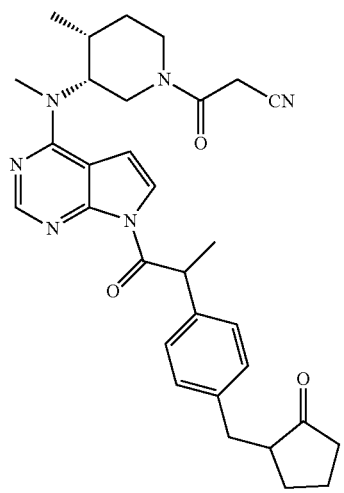

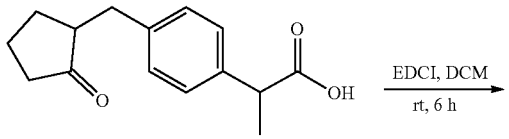

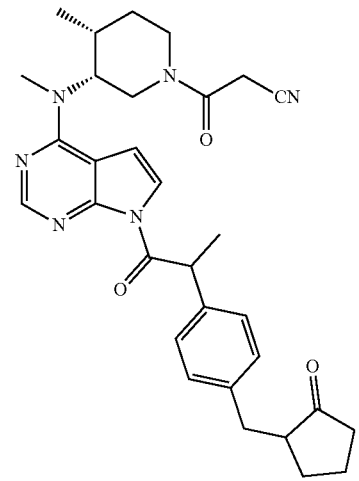

Synthesis of 3-((3R, 4R)-4-methyl-3-(methyl (7-(2-(4-((2-oxocyclopentyl) methyl) phenyl) propanoyl)-7H-pyrrolo [2, 3-d] pyrimidin-4-yl) amino) piperidin-1-yl)-3-oxopropanenitrile 3-{(3R, 4R)-4-methyl-3-[methyl-(7H-pyrrolo [2, 3-d] pyrimidin-4-yl)-piperidin-1-yl]-3-oxo-propionitrile (tofacitinib, 624 mg, 2 mmol), 2-[4-(2-oxocyclopentan-1-ylmethyl) phenyl] propanoic acid (loxoprofen, 541 mg, 2.2 mmol) and 1-(3-dimethylaminopropyl)-3-ethylcarbodiimide hydrochloride (EDCI, 576 mg, 3 mmol) were dissolved in dichloromethane (20 mL) and stirred at room temperature for 6 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=5:1 to 1:2) to give the title compound as a white solid, 0.48 g, 44.4% yield. MS (m/z): [M+H]$^+$ calcd for $C_{31}H_{36}N_6O_3$, 541.67; found, 541.3. $^1$H NMR (400 MHz, DMSO) δ 8.38 (dd, J=6.2, 1.5 Hz, 1H), 7.80-7.60 (m, 1H), 7.32 (dd, J=17.9, 16.2 Hz, 2H), 7.10 (d, J=7.9 Hz, 2H), 6.89 (d, J=4.3 Hz, 1H), 6.19-5.98 (m, 1H), 4.84 (s, 1H), 4.17-3.98 (m, 2H), 3.96-3.57 (m, 3H), 3.40 (t, J=5.9 Hz, 1H), 3.21 (s, 3H), 2.94-2.83 (m, 1H), 2.41-2.25 (m, 3H), 2.25-2.14 (m, 1H), 2.09-2.02 (m, 1H), 1.90-1.80 (m, 3H), 1.72-1.48 (m, 5H), 1.48-1.37 (m, 1H), 1.07-0.93 (m, 3H).

Example 12

3-((3R, 4R)-3-((7-(2-(1-(4-chlorobenzoyl)-5-methoxy-2-methyl-1H-indol-3-yl) acetyl)-7H-pyrrolo [2, 3-d]pyrimidin-4-yl) (methyl) amino)-4-methylpiperidin-1-yl)-3-oxopropanenitrile

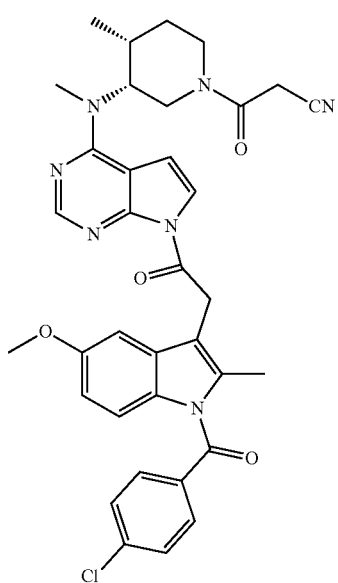

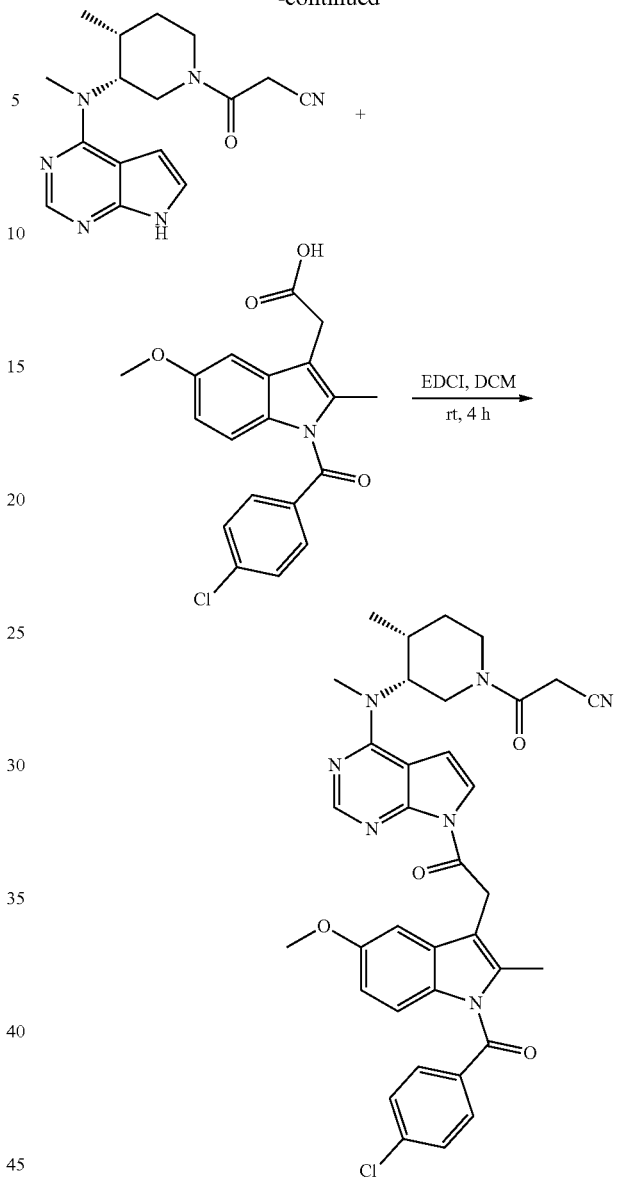

Synthesis of 3-((3R, 4R)-3-((7-(2-(1-(4-chlorobenzoyl)-5-methoxy-2-methyl-1H-indol-3-yl) acetyl)-7H-pyrrolo [2, 3-d] pyrimidin-4-yl) (methyl) amino)-4-methylpiperidin-1-yl)-3-oxopropanenitrile 3-{(3R, 4R)-4-methyl-3-[methyl-(7H-pyrrolo [2, 3-d] pyrimidin-4-yl)-piperidin-1-yl]-3-oxo-propionitrile (tofacitinib, 156 mg, 0.5 mmol), 1-(4-chlorobenzoyl)-5-methoxy-2-methyl-1H-indole-3-acetic acid (indomethacin, 233 mg, 0.65 mmol) and 1-(3-dimethylaminopropyl)-3-ethylcarbodiimide hydrochloride (EDCI, 144 mg, 0.75 mmol) were dissolved in dichloromethane (10 mL) and stirred at room temperature for 4 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=2:1 to 2:3) to give the title compound as a white solid, 0.16 g, 49.1% yield. MS (m/z): [M+H]$^+$ calcd for $C_{35}H_{34}Cl_1N_7O_4$, 653.15; found, 653.3. ¹H NMR (400 MHz, DMSO-d₆) δ 8.45 (d, J=6.4 Hz, 1H), 7.77-7.61 (m, 5H), 7.11 (t, J=2.8 Hz, 1H), 6.97 (t, J=6.7 Hz, 2H), 6.71 (dd, J=9.1, 2.5 Hz, 1H), 5.05-4.86 (m, 3H), 4.21-3.89 (m, 3H), 3.86-3.64 (m, 5H), 3.46-3.40 (m, 1H), 3.31 (s, 3H), 2.44-2.38 (m, 1H), 1.88-1.52 (m, 2H), 1.32-1.21 (m, 3H), 1.02 (d, J=7.1 Hz, 3H).

Example 13

N-(4-(2-(4-(((3R, 4R)-1-(2-cyanoacetyl)-4-methylpiperidin-3-yl) (methyl) amino)-7H-pyrrolo [2, 3-d] pyrimidin-7-yl)-2-oxoethyl) phenyl) acetamide

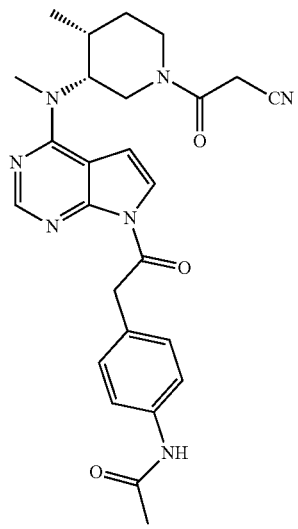

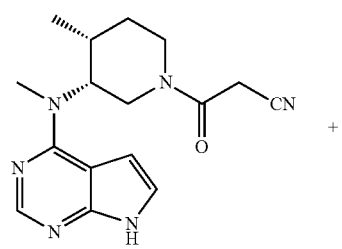
+
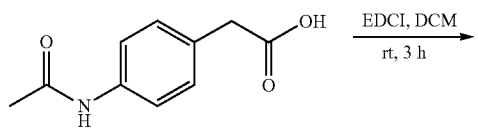

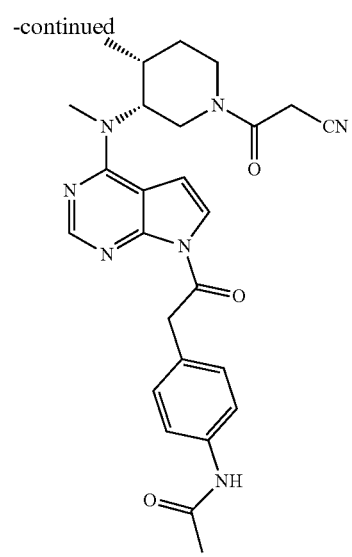

Synthesis of N-(4-(2-(4-(((3R, 4R)-1-(2-cyanoacetyl)-4-methylpiperidin-3-yl) (methyl) amino)-7H-pyrrolo [2, 3-d] pyrimidin-7-yl)-2-oxoethyl) phenyl) acetamide 3-{(3R, 4R)-4-methyl-3-[methyl-(7H-pyrrolo [2, 3-d] pyrimidin-4-yl)-piperidin-1-yl]-3-oxo-propionitrile (tofacitinib, 156 mg, 0.5 mmol), 2-(4-acetamidophenyl) acetic acid (actarit, 126 mg, 0.65 mmol) and 1-(3-dimethylaminopropyl)-3-ethylcarbodiimide hydrochloride (EDCI, 144 mg, 0.75 mmol) were dissolved in dichloromethane (8 mL) and stirred at room temperature for 3 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=1:1 to 1:6) to give the title compound as a white solid, 0.118 g, 48.6% yield. MS (m/z): [M+H]⁺ calcd for C₂₆H₂₉N₇O₃, 488.56; found, 488.2. ¹H NMR (400 MHz, DMSO-d₆) δ 9.90 (s, 1H), 8.39 (d, J=5.8 Hz, 1H), 7.70 (d, J=4.1 Hz, 1H), 7.51 (d, J=8.1 Hz, 2H), 7.26 (d, J=8.1 Hz, 2H), 6.94 (d, J=4.4 Hz, 1H), 4.97-4.71 (m, 3H), 4.24-3.89 (m, 3H), 3.85-3.59 (m, 1H), 3.49-3.40 (m, 1H), 3.28 (s, 3H), 2.39 (q, J=6.2 Hz, 1H), 2.03 (s, 3H), 1.88-1.46 (m, 2H), 1.02 (d, J=7.0 Hz, 3H).

Example 14

3-((3R, 4R)-3-((7-(2-(1, 8-diethyl-1, 3, 4, 9-tetrahydropyrano [3, 4-b] indol-1-yl) acetyl)-7H-pyrrolo [2, 3-d]pyrimidin-4-yl) (methyl) amino)-4-methylpiperidin-1-yl)-3-oxopropanenitrile

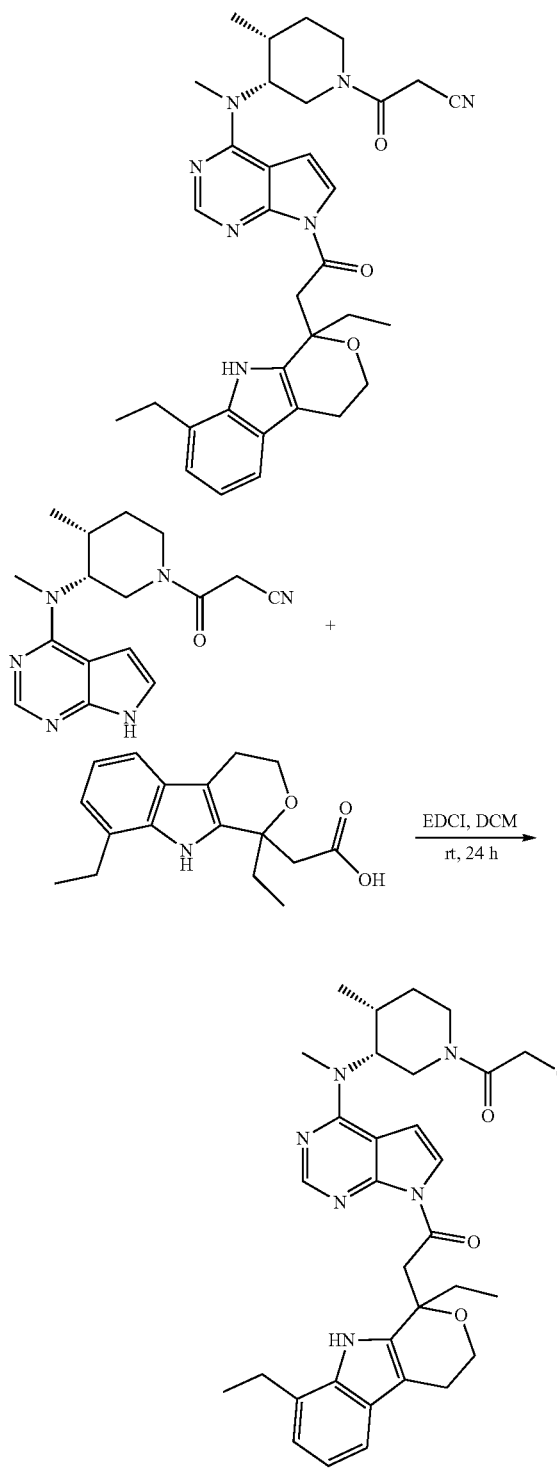

Synthesis of 3-((3R, 4R)-3-((7-(2-(1, 8-diethyl-1, 3, 4, 9-tetrahydropyrano [3, 4-b] indol-1-yl) acetyl)-7H-pyrrolo [2, 3-d] pyrimidin-4-yl) (methyl) amino)-4-methylpiperidin-1-yl)-3-oxopropanenitrile 3-{(3R, 4R)-4-methyl-3-[methyl-(7H-pyrrolo [2, 3-d] pyrimidin-4-yl)-piperidin-1-yl]-3-oxo-propionitrile (tofacitinib, 156 mg, 0.5 mmol), 1, 8-diethyl-1, 3, 4, 9-tetrahydropyran [3, 4-b] indole-1-acetic acid (etodolac, 158 mg, 0.55 mmol) and 1-(3-dimethylaminopropyl)-3-ethylcarbodiimide hydrochloride (EDCI, 144 mg, 0.75 mmol) were dissolved in dichloromethane (10 mL) and stirred at room temperature for 24 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=1:1 to 1:2) to give the title compound as a white solid, 0.11 g, 37.8% yield. MS (m/z): [M+H]$^+$ calcd for $C_{33}H_{39}N_7O_3$, 582.72; found, 582.3.1H NMR (400 MHz, DMSO-d$_6$) δ 10.50 (s, 1H), 8.29 (s, 1H), 7.67 (td, J=4.5, 2.2 Hz, 1H), 7.23 (dd, J=7.5, 2.0 Hz, 1H), 6.98-6.81 (m, 3H), 4.84 (s, 1H), 4.67 (ddd, J=14.7, 8.6, 6.3 Hz, 1H), 4.20-3.98 (m, 3H), 3.98-3.82 (m, 2H), 3.81-3.61 (m, 3H), 3.47-3.38 (m, 1H), 3.27 (s, 3H), 2.84 (q, J=7.5 Hz, 2H), 2.60 (dt, J=9.4, 4.7 Hz, 2H), 2.45-2.30 (m, 1H), 2.16 (qq, J=6.9, 4.5, 3.9 Hz, 2H), 1.83 (s, 2H), 1.26 (td, J=7.6, 3.1 Hz, 3H), 1.01 (dt, J=7.2, 2.8 Hz, 3H), 0.69 (td, J=7.1, 3.4 Hz, 3H).

Example 15

2-(4-((3R, 4R)-1-(2-cyanoacetyl)-4-methylpiperidin-3-yl) (methyl) amino)-7H-pyrrolo [2, 3-d] pyrimidine-7-carbonyl) phenyl acetate

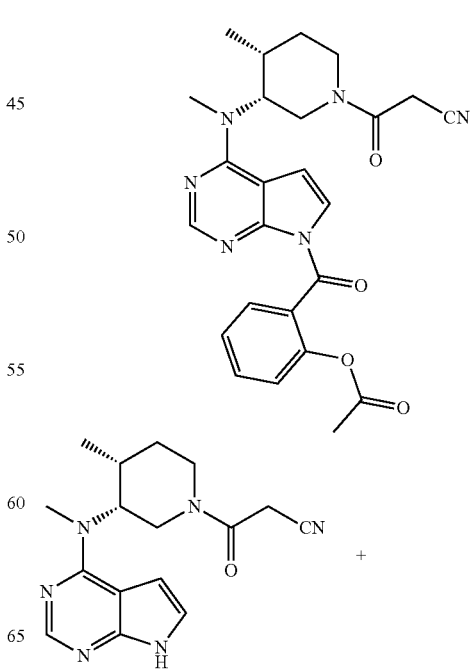

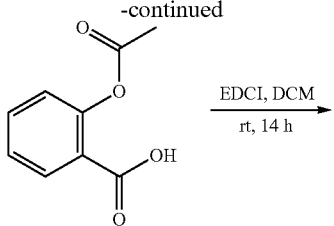

Synthesis of 2-(4-((3R, 4R)-1-(2-cyanoacetyl)-4-methylpiperidin-3-yl) (methyl) amino)-7H-pyrrolo [2, 3-d]pyrimidine-7-carbonyl) phenyl acetate 3-{(3R, 4R)-4-methyl-3-[methyl-(7H-pyrrolo [2, 3-d]pyrimidin-4-yl)-piperidin-1-yl]-3-oxo-propionitrile (tofacitinib, 312 mg, 1 mmol), 2-acetoxybenzoic acid (aspirin, 216 mg, 1.2 mmol) and 1-(3-dimethylaminopropyl)-3-ethylcarbodiimide hydrochloride (EDCI, 288 mg, 1.5 mmol) were dissolved in dichloromethane (10 mL) and stirred at room temperature for 14 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=1:1 to 1:2) to give the title compound as a white solid, 0.06 g, 12.6% yield. MS (m/z): [M+H]$^+$ calcd for $C_{25}H_{26}N_6O_4$, 475.52; found, 475.2. $^1$H NMR (400 MHz, DMSO-d$_6$) δ 8.02 (d, J=6.8 Hz, 1H), 7.69-7.57 (m, 2H), 7.58 (d, J=4.1 Hz, 1H), 7.43-7.36 (m, 1H), 7.29 (d, J=8.1 Hz, 1H), 6.98 (t, J=5.0 Hz, 1H), 4.84 (s, 1H), 4.19-3.87 (m, 3H), 3.84-3.62 (m, 2H), 3.44-3.29 (m, 1H), 3.28 (s, 3H), 2.37 (dq, J=12.0, 6.7, 5.6 Hz, 1H), 1.92 (d, J=1.7 Hz, 3H), 1.88-1.66 (m, 1H), 1.58 (p, J=8.0, 7.0 Hz, 1H), 1.01 (d, J=7.1 Hz, 3H).

Example 16 tert-butyl ((S)-2-(4-(((3R, 4R)-1-(2-cyanoacetyl)-4-methylpiperidin-3-yl) (methyl) amino)-7H-pyrrolo [2, 3-d]pyrimidin-7-yl)-2-oxo-1-phenylethyl) carbamate

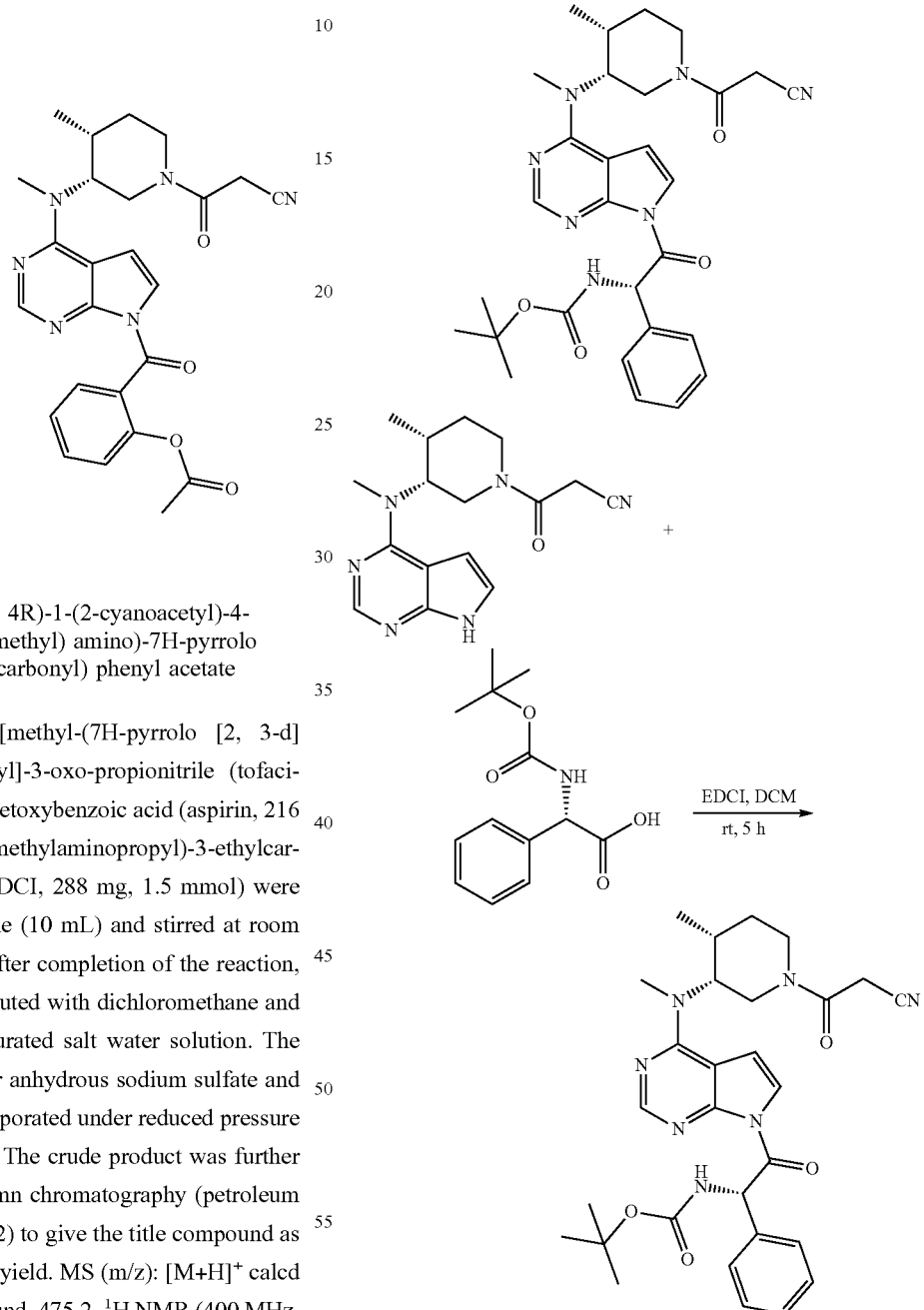

Synthesis of tert-butyl ((S)-2-(4-(((3R, 4R)-1-(2-cyanoacetyl)-4-methylpiperidin-3-yl) (methyl) amino)-7H-pyrrolo [2, 3-d] pyrimidin-7-yl)-2-oxo-1-phenylethyl) carbamate 3-{(3R, 4R)-4-methyl-3-[methyl-(7H-pyrrolo [2, 3-d] pyrimidin-4-yl)-piperidin-1-yl]-3-oxo-propionitrile (tofacitinib, 312 mg, 1 mmol), N-Boc-L-phenylglycine (326 mg, 1.3 mmol) and 1-(3-dimethylaminopropyl)-3-ethylcarbodiimide hydrochloride (EDCI, 288 mg, 1.5 mmol) were dissolved in dichloromethane (10 mL) and stirred at room temperature for 5 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=1:1 to 1:2) to give the title compound as a white solid, 0.3 g, yield 55%. MS (m/z): [M+H]$^+$ calcd for $C_{29}H_{35}N_7O_4$, 546.64; found, 546.3. 1H NMR (400 MHz, DMSO-d6) δ 8.38 (d, J=4.7 Hz, 1H), 7.85 (d, J=7.3 Hz, 1H), 7.70 (d, J=4.1 Hz, 1H), 7.48 (t, J=7.4 Hz, 3H), 7.35-7.21 (m, 3H), 7.02-6.83 (m, 1H), 4.86 (s, 1H), 4.08-3.97 (m, 3H), 3.82-3.54 (m, 2H), 3.42-3.39 (m, 1H), 3.24 (s, 3H), 2.35 (s, 1H), 1.81-1.56 (m, 2H), 1.39 (s, 9H), 1.06-0.90 (m, 3H).

Example 17

(S)-2-(1-(ethylsulfonyl)-3-(4-(7-(2-(4-isobutylphenyl) propanoyl)-7H-pyrrolo [2, 3-d] pyrimidin-4-yl)-1H-pyrazol-1-yl) azetidin-3-yl) acetonitrile

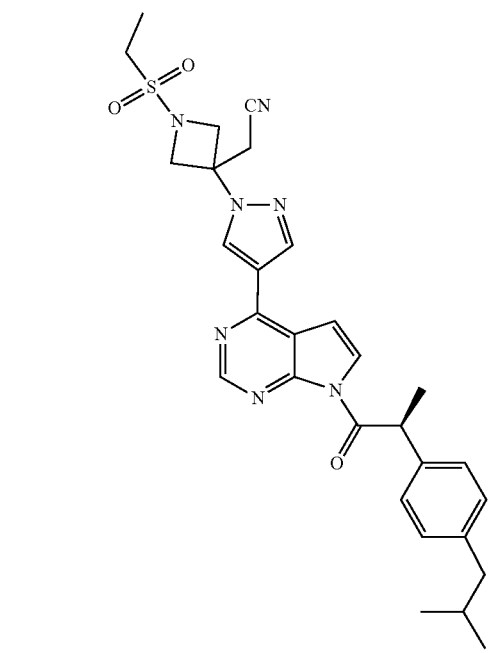

+

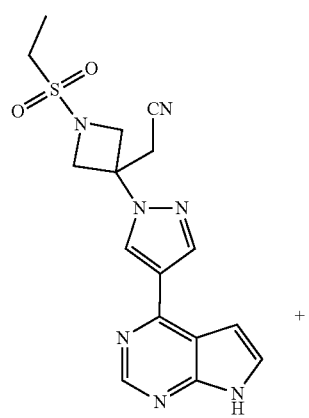

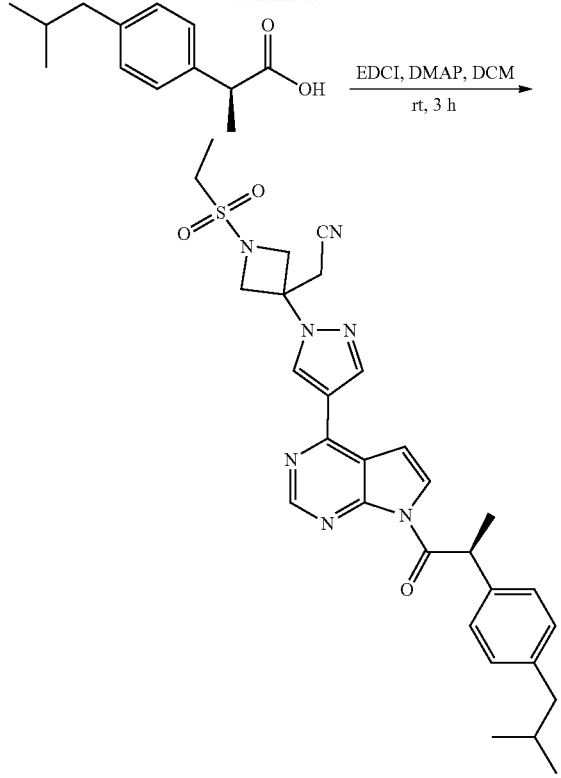

Synthesis of (S)-2-(1-(ethylsulfonyl)-3-(4-(7-(2-(4-isobutylphenyl) propanoyl)-7H-pyrrolo [2, 3-d] pyrimidin-4-yl)-1H-pyrazol-1-yl) azetidin-3-yl) acetonitrile 1-(Ethylsulfonyl)-3-[4-(7H-pyrrolo [2, 3-d] pyrimidin-4-yl)-1H-pyrazol-1-yl]-3-azetidine acetonitrile (baricitinib, 742 mg, 2 mmol), 4-dimethylamino pyridine (DMAP, 488 mg, 4 mmol), (S)-(+)-2-(4-isobutylphenyl) propanoic acid ((S)-(+)-ibuprofen, 453 mg, 2.2 mmol) and 1-(3-dimethylaminopropyl)-3-ethylcarbodiimide hydrochloride (EDCI, 576 mg, 3 mmol) was dissolved in dichloromethane (20 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=2:1 to 1:2) to give the title compound as a white solid, 0.5 g, 44.7% yield. MS (m/z): [M+H]$^+$ calcd for $C_{29}H_{33}N_7O_3S$, 560.69; found, 560.2. $^1$H NMR (400 MHz, Chloroform-d) δ 8.96 (s, 1H), 8.41 (s, 1H), 8.26 (s, 1H), 8.03 (d, J=4.2 Hz, 1H), 7.47-7.34 (m, 2H), 7.06 (d, J=7.9 Hz, 2H), 6.81 (d, J=4.1 Hz, 1H), 6.06 (q, J=6.9 Hz, 1H), 4.62 (d, J=9.2 Hz, 2H), 4.34-4.16 (m, 2H), 3.40 (s, 2H), 3.08 (q, J=7.4 Hz, 2H), 2.39 (d, J=7.2 Hz, 2H), 1.80 (dp, J=13.5, 6.8 Hz, 1H), 1.68 (d, J=6.9 Hz, 3H), 1.41 (t, J=7.4 Hz, 3H), 0.95-0.82 (m, 6H).

Example 18

(S)-2-(1-(ethylsulfonyl)-3-(4-(7-(2-(6-methoxynaphthalen-2-yl) propanoyl)-7H-pyrrolo [2, 3-d] pyrimidin-4-yl)-1H-pyrazol-1-yl) azetidin-3-yl) acetonitrile

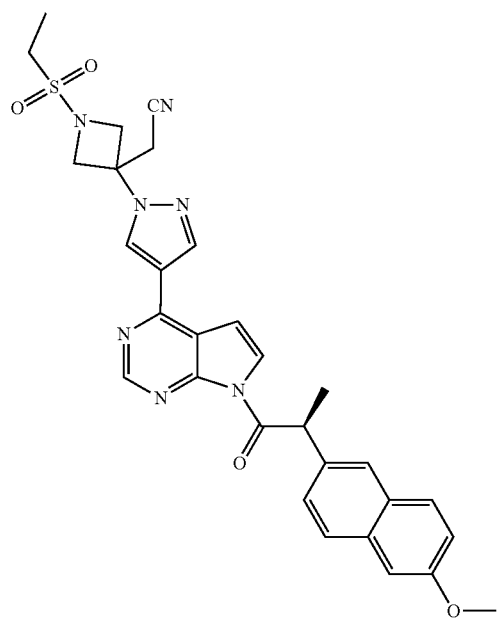

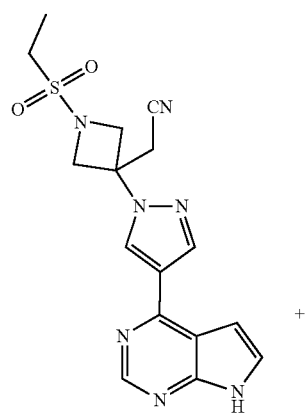

+

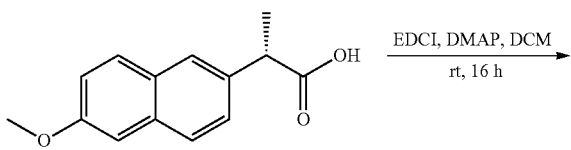

EDCI, DMAP, DCM
rt, 16 h

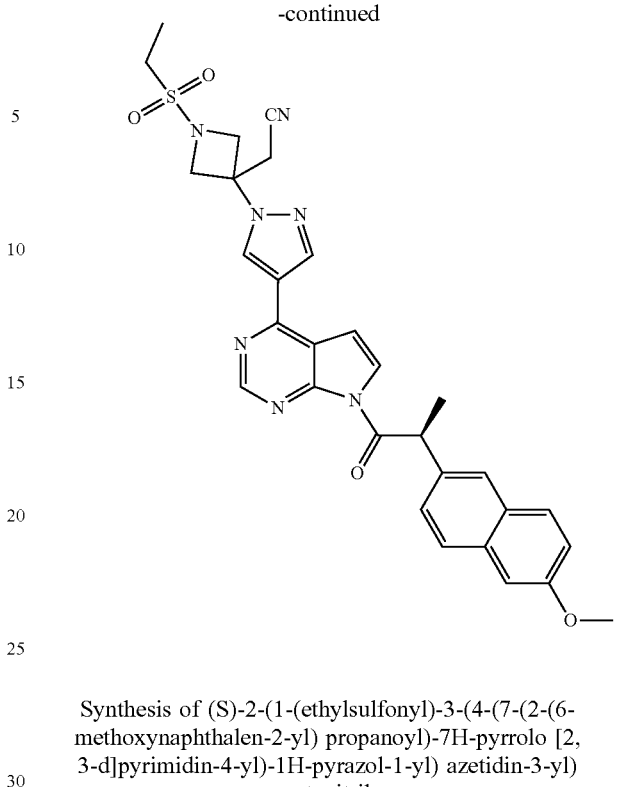

Synthesis of (S)-2-(1-(ethylsulfonyl)-3-(4-(7-(2-(6-methoxynaphthalen-2-yl) propanoyl)-7H-pyrrolo [2, 3-d]pyrimidin-4-yl)-1H-pyrazol-1-yl) azetidin-3-yl) acetonitrile 1-(Ethylsulfonyl)-3-[4-(7H-pyrrolo [2, 3-d] pyrimidin-4-yl)-1H-pyrazol-1-yl]-3-azetidine acetonitrile (baricitinib, 371 mg, 1 mmol), 4-dimethylamino pyridine (DMAP, 305 mg, 2.5 mmol), (S)-(+)-2-(6-methoxy-2-naphthyl) propanoic acid (Naproxen, 230 mg, 1.1 mmol) and 1-(3-dimethylaminopropyl)-3-ethylcarbodiimide hydrochloride (EDCI, 288 mg, 1.5 mmol) were dissolved in dichloromethane (10 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=1:1 to 1:2) to give the title compound as a white solid, 0.25 g, 42.9% yield. MS (m/z): [M+H]$^+$ calcd for $C_{30}H_{29}N_7O_4S$, 584.67; found, 584.2. $^1$H NMR (400 MHz, DMSO) δ 9.03 (s, 1H), 8.98 (s, 1H), 8.49 (s, 1H), 8.18 (d, J=4.2 Hz, 1H), 7.85 (s, 1H), 7.80-7.74 (m, 2H), 7.58-7.54 (m, 1H), 7.40 (d, J=4.2 Hz, 1H), 7.25 (d, J=2.2 Hz, 1H), 7.12 (dd, J=9.0, 2.4 Hz, 1H), 6.12 (q, J=6.8 Hz, 1H), 4.58 (d, J=9.2 Hz, 2H), 4.23 (d, J=9.2 Hz, 2H), 3.83 (s, 3H), 3.68 (s, 2H), 3.23 (q, J=7.3 Hz, 2H), 1.68 (d, J=6.9 Hz, 3H), 1.24 (t, J=7.3 Hz, 3H).

Example 19

2-(3-(4-(7-(2-(3-benzoylphenyl) propanoyl)-7H-pyrrolo [2, 3-d]pyrimidin-4-yl)-1H-pyrazol-1-yl)-1-(ethylsulfonyl) azetidin-3-yl) acetonitrile

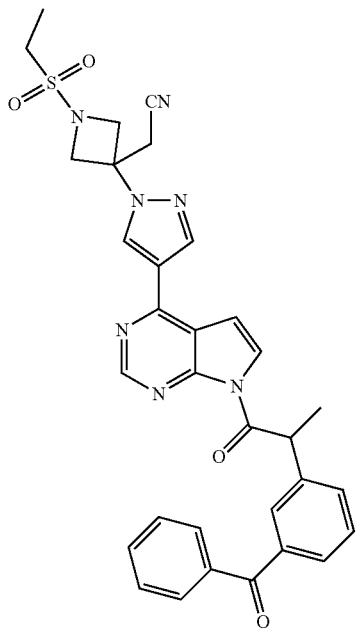

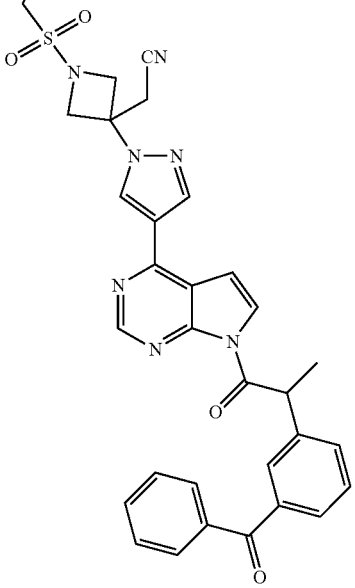

Synthesis of 2-(3-(4-(7-(2-(3-benzoylphenyl) propanoyl)-7H-pyrrolo [2, 3-d] pyrimidin-4-yl)-1H-pyrazol-1-yl)-1-(ethylsulfonyl) azetidin-3-yl) acetonitrile 1-(Ethylsulfonyl)-3-[4-(7H-pyrrolo [2, 3-d] pyrimidin-4-yl)-1H-pyrazol-1-yl]-3-azetidine acetonitrile (baricitinib, 371 mg, 1 mmol), 4-dimethylamino pyridine (DMAP, 244 mg, 2 mmol), 2-(3-benzoylphenyl) propanoic acid (ketoprofen, 280 mg, 1.1 mmol) and 1-(3-dimethylaminopropyl)-3-ethylcarbodiimide hydrochloride (EDCI, 288 mg, 1.5 mmol) were dissolved in dichloromethane (15 mL) and stirred at room temperature for 3 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=2:1 to 1:2) to give the title compound as a white solid, 0.2 g, 32.9% yield. MS (m/z): [M+H]$^+$ calcd for $C_{32}H_{129}N_7O_4S$, 608.69; found, 608.3. $^1$H NMR (400 MHz, DMSO) δ 9.00 (s, 1H), 8.93 (s, 1H), 8.51 (s, 1H), 8.17 (d, J=4.2 Hz, 1H), 7.81 (s, 1H), 7.76 (d, J=7.7 Hz, 1H), 7.70-7.58 (m, 4H), 7.52 (t, J=7.6 Hz, 3H), 7.43 (d, J=4.2 Hz, 1H), 6.06 (q, J=6.8 Hz, 1H), 4.59 (d, J=9.1 Hz, 2H), 4.24 (d, J=9.1 Hz, 2H), 3.68 (s, 2H), 3.23 (q, J=7.3 Hz, 2H), 1.63 (d, J=6.9 Hz, 3H), 1.24 (t, J=7.3 Hz, 3H).

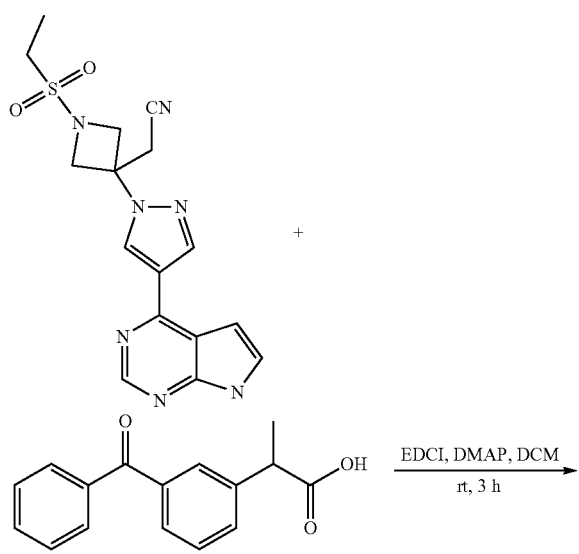

Example 20

2-(1-(ethylsulfonyl)-3-(4-(7-(2-(2-fluoro-[1, 1'-biphenyl]-4-yl) propanoyl)-7H-pyrrolo [2, 3-d] pyrimidin-4-yl)-1H-pyrazol-1-yl) azetidin-3-yl) acetonitrile

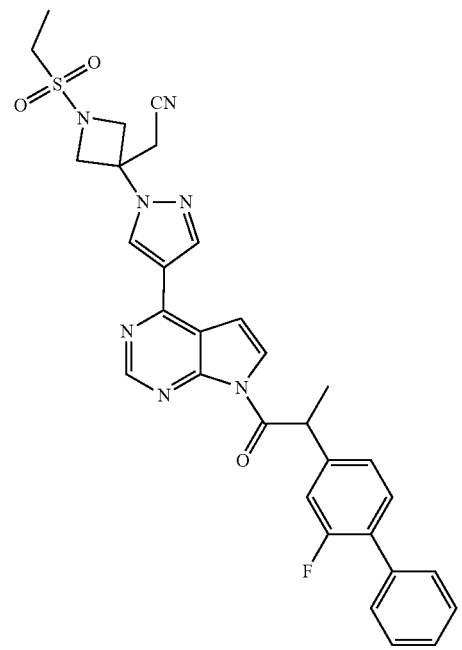

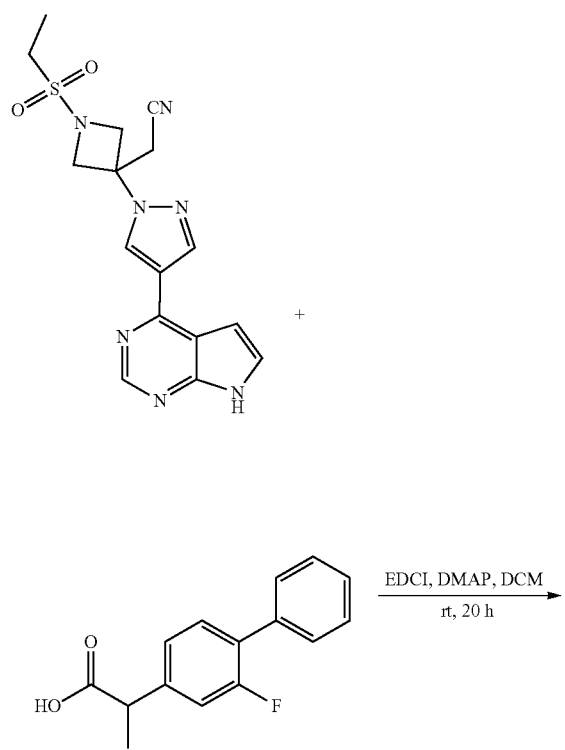

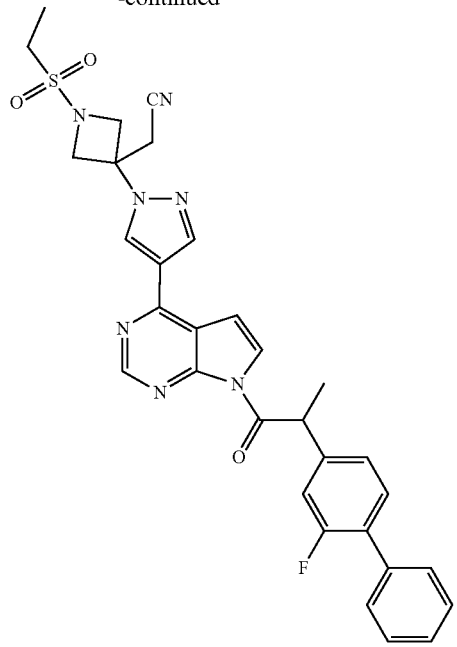

Synthesis of 2-(1-(ethylsulfonyl)-3-(4-(7-(2-(2-fluoro-[1, 1'-biphenyl]-4-yl) propanoyl)-7H-pyrrolo [2, 3-d]pyrimidin-4-yl)-1H-pyrazol-1-yl) azetidin-3-yl) acetonitrile 1-(Ethylsulfonyl)-3-[4-(7H-pyrrolo [2, 3-d] pyrimidin-4-yl)-1H-pyrazol-1-yl]-3-azetidine acetonitrile (baricitinib, 742 mg, 2 mmol), 4-dimethylamino pyridine (DMAP, 610 mg, 5 mmol), 2-(2-fluoro-4-biphenyl) propanoic acid (flurbiprofen, 537 mg, 2.2 mmol) and 1-(3-dimethylaminopropyl)-3-ethylcarbodiimide hydrochloride (EDCI, 576 mg, 3 mmol) were dissolved in dichloromethane (20 mL) and stirred at room temperature for 20 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=1:1 to 1:2) to give the title compound as a white solid, 0.3 g, 25.1% yield. MS (m/z): [M+H]$^+$ calcd for $C_{31}H_{28}FN_7O_3S$, 598.67; found, 598.2. $^1$H NMR (400 MHz, DMSO) δ 9.05 (s, 1H), 9.02 (s, 1H), 8.53 (s, 1H), 8.20 (d, J=4.2 Hz, 1H), 7.54-7.35 (m, 9H), 6.08 (q, J=7.0 Hz, 1H), 4.61 (d, J=9.2 Hz, 2H), 4.25 (d, J=9.2 Hz, 2H), 3.70 (s, 2H), 3.24 (q, J=7.4 Hz, 2H), 1.66 (d, J=7.0 Hz, 3H), 1.25 (t, J=7.3 Hz, 3H).

Example 21

2-(1-(Ethylsulfonyl)-3-(4-(7-(2-(3-phenoxyphenyl)propanoyl)-7H-pyrrolo [2, 3-d] pyrimidin-4-yl)-1H-pyrazol-1-yl) azetidin-3-yl) acetonitrile

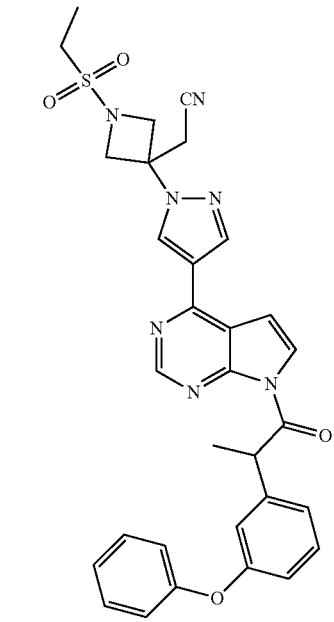

+

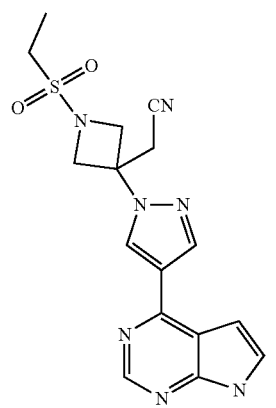

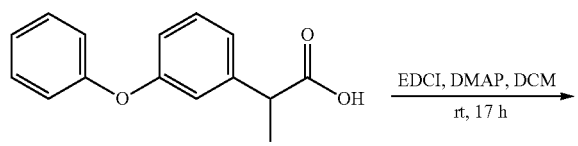

EDCI, DMAP, DCM
rt, 17 h

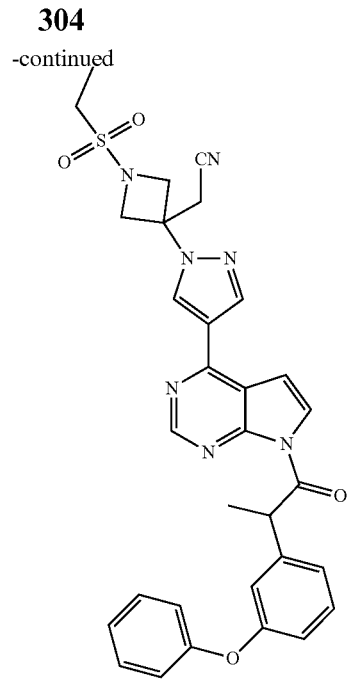

Synthesis of 2-(1-(ethylsulfonyl)-3-(4-(7-(2-(3-phenoxyphenyl) propanoyl)-7H-pyrrolo [2, 3-d] pyrimidin-4-yl)-1H-pyrazol-1-yl) azetidin-3-yl) acetonitrile 1-(Ethylsulfonyl)-3-[4-(7H-pyrrolo [2, 3-d] pyrimidin-4-yl)-1H-pyrazol-1-yl]-3-azetidine acetonitrile (baricitinib, 186 mg, 0.5 mmol), 4-dimethylamino pyridine (DMAP, 61 mg, 0.5 mmol), 2-(3-phenoxyphenyl) propanoic acid (fenoprofen, 133 mg, 0.55 mmol) and 1-(3-dimethylaminopropyl)-3-ethylcarbodiimide hydrochloride (EDCI, 144 mg, 0.75 mmol) were dissolved in dichloromethane (10 mL) and stirred at room temperature for 17 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=5:1 to 1:2) to give the title compound as a white solid, 0.11 g, 74.5% yield. MS (m/z): [M+H]$^+$ calcd for $C_{31}H_{29}N_7O_4S$, 596.68; found, 596.2. $^1$H NMR (400 MHz, DMSO-d$_6$) δ 8.99 (s, 1H), 8.86 (s, 1H), 8.50 (s, 1H), 8.12 (d, J=4.2 Hz, 1H), 7.40 (d, J=4.2 Hz, 1H), 7.37-7.25 (m, 3H), 7.21-7.10 (m, 2H), 7.07 (t, J=2.1 Hz, 1H), 6.95-6.89 (m, 2H), 6.86-6.78 (m, 1H), 5.94 (d, J=6.9 Hz, 1H), 4.60 (d, J=9.1 Hz, 2H), 4.24 (d, J=9.1 Hz, 2H), 3.68 (s, 2H), 3.23 (q, J=7.3 Hz, 2H), 1.57 (d, J=6.9 Hz, 3H), 1.24 (t, J=7.4 Hz, 3H).

Example 22

2-(1-(ethylsulfonyl)-3-(4-(7-(2-(4-(2-oxocyclopentyl) methyl) phenyl) propanoyl)-7H-pyrrolo [2, 3-d] pyrimidin-4-yl)-1H-pyrazol-1-yl) azetidin-3-yl) acetonitrile

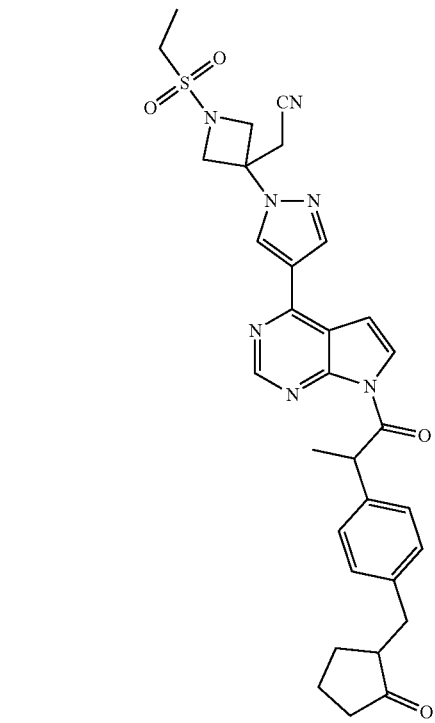

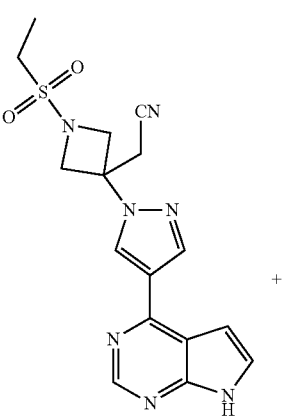

+

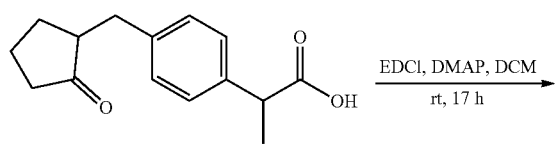

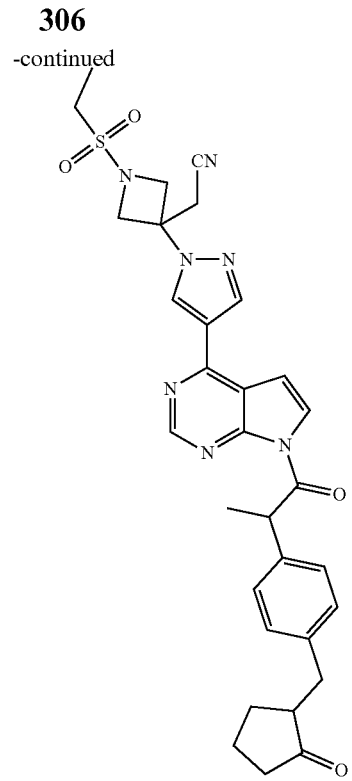

Synthesis of 2-(1-(ethylsulfonyl)-3-(4-(7-(2-(4-(2-oxocyclopentyl) methyl) phenyl) propanoyl)-7H-pyrrolo [2, 3-d] pyrimidin-4-yl)-1H-pyrazol-1-yl) azetidin-3-yl) acetonitrile 1-(Ethylsulfonyl)-3-[4-(7H-pyrrolo [2, 3-d] pyrimidin-4-yl)-1H-pyrazol-1-yl]-3-azetidine acetonitrile (baricitinib, 186 mg, 0.5 mmol), 4-dimethylamino pyridine (DMAP, 61 mg, 0.5 mmol), 2-[4-(2-oxocyclopentan-1-ylmethyl) phenyl] propanoic acid (loxoprofen, 136 mg, 0.55 mmol) and 1-(3-dimethylaminopropyl)-3-ethylcarbodiimide hydrochloride (EDCI, 144 mg, 0.75 mmol) was dissolved in dichloromethane (10 mL) and stirred at room temperature for 17 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=2:1 to 3:4) to give the title compound as a white solid, 0.13 g, 43.4% yield. MS (m/z): [M+H]$^+$ calcd for $C_{31}H_{33}N_7O_4S$, 600.71; found, 600.3. $^1$H NMR (400 MHz, DMSO-d$_6$) δ 8.99 (d, J=3.4 Hz, 2H), 8.50 (s, 1H), 8.14 (d, J=4.2 Hz, 1H), 7.40 (d, J=4.2 Hz, 1H), 7.34 (d, J=7.9 Hz, 2H), 7.12 (d, J=7.9 Hz, 2H), 5.98 (q, J=6.9 Hz, 1H), 4.59 (d, J=9.1 Hz, 2H), 4.24 (d, J=9.1 Hz, 2H), 3.69 (s, 2H), 3.33-3.19 (m, 2H), 2.96-2.83 (m, 1H), 2.44-2.27 (m, 2H), 2.20 (dd, J=18.5, 8.5 Hz, 1H), 2.03 (ddd, J=18.6, 10.1, 8.6 Hz, 1H), 1.95-1.74 (m, 2H), 1.70-1.61 (m, 1H), 1.58 (d, J=6.9 Hz, 3H), 1.42 (dd, J=10.6, 6.9 Hz, 1H), 1.24 (dd, J=8.7, 6.1 Hz, 3H).

Example 23

2-(3-(4-(7-(2-(1-(4-chlorobenzoyl)-5-methoxy-2-methyl-1H-indol-3-yl) acetyl)-7H-pyrrolo [2, 3-d] pyrimidin-4-yl)-1H-pyrazol-1-yl)-1-(ethylsulfonyl) azetidin-3-yl) acetonitrile

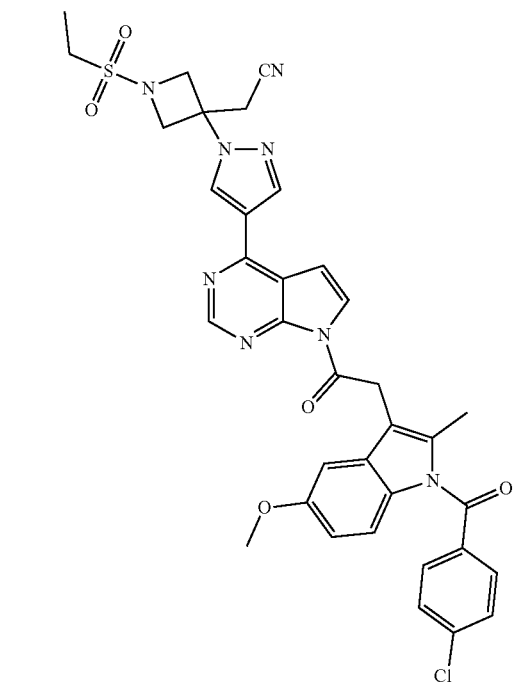

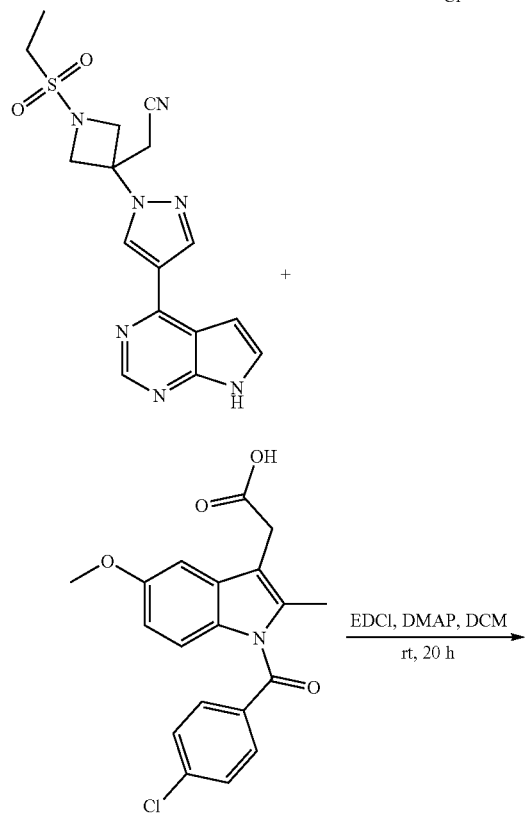

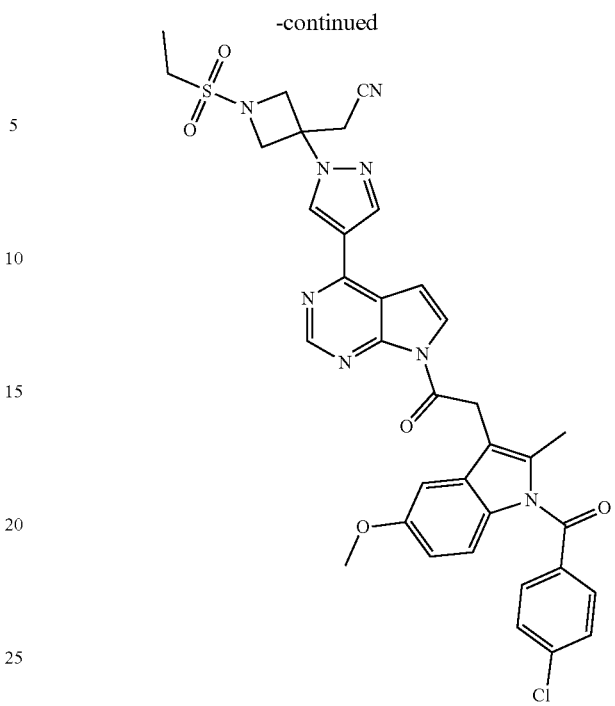

Synthesis of 2-(3-(4-(7-(2-(1-(4-chlorobenzoyl)-5-methoxy-2-methyl-1H-indol-3-yl) acetyl)-7H-pyrrolo [2, 3-d] pyrimidin-4-yl)-1H-pyrazol-1-yl)-1-(ethylsulfonyl) azetidin-3-yl) acetonitrile 1-(Ethylsulfonyl)-3-[4-(7H-pyrrolo [2, 3-d] pyrimidin-4-yl)-1H-pyrazol-1-yl]-3-azetidine acetonitrile (baricitinib, 186 mg, 0.5 mmol), 4-dimethylamino pyridine (DMAP, 61 mg, 0.5 mmol), 1-(4-chlorobenzoyl)-5-methoxy-2-methyl-1H-indole-3-acetic acid (indomethacin, 197 mg, 0.55 mmol) and 1-(3-dimethylaminopropyl)-3-ethylcarbodiimide hydrochloride (EDCI, 144 mg, 0.75 mmol) were dissolved in dichloromethane (10 mL) and stirred at room temperature for 20 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=1:1 to 1:5) to give the title compound as a white solid, 0.18 g, 50.6% yield. MS (m/z): [M+H]$^+$ calcd for $C_{35}H_{31}C_1N_8O_5S$, 712.19; found, 711.2. $^1$H NMR (400 MHz, DMSO-d$_6$) δ 9.05 (d, J=2.4 Hz, 2H), 8.56 (s, 1H), 8.17 (d, J=4.2 Hz, 1H), 7.77-7.61 (m, 4H), 7.47 (d, J=4.2 Hz, 1H), 7.18 (d, J=2.6 Hz, 1H), 6.99 (d, J=9.0 Hz, 1H), 6.72 (dd, J=9.0, 2.6 Hz, 1H), 5.04 (s, 2H), 4.64 (d, J=9.1 Hz, 2H), 4.28 (d, J=9.1 Hz, 2H), 3.71 (d, J=6.8 Hz, 5H), 3.25 (q, J=7.3 Hz, 2H), 2.27 (s, 3H), 1.26 (t, J=7.3 Hz, 3H).

Example 24

N-(4-(2-(4-(1-(3-(cyanomethyl)-1-(ethylsulfonyl) azetidin-3-yl)-1H-pyrazol-4-yl)-7H-pyrrolo [2, 3-d] pyrimidin-7-yl)-2-oxoethyl) phenyl) acetamide

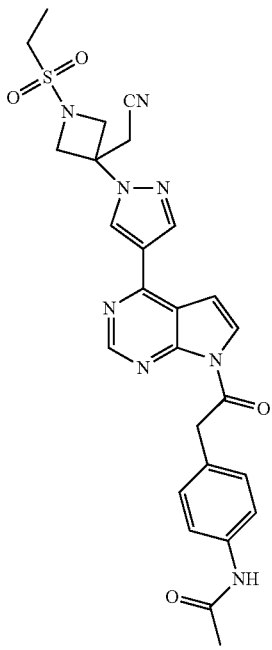 [SMILES: CCS(=O)(=O)N1CC(CC#N)(n2cc(-c3ncnc4c3ccn4C(=O)Cc3ccc(NC(C)=O)cc3)cn2)C1]

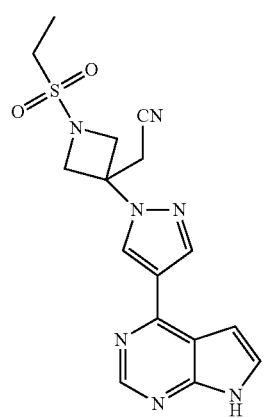

+

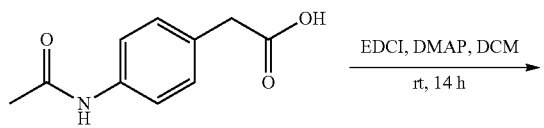

EDCI, DMAP, DCM
rt, 14 h
→

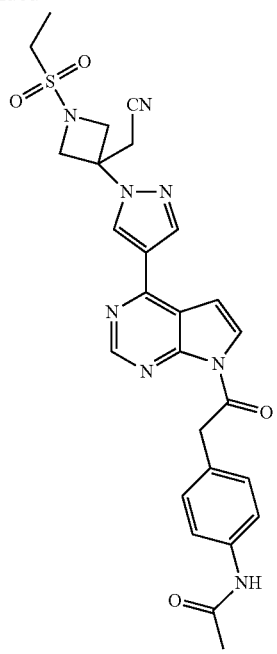

Synthesis of N-(4-(2-(4-(1-(3-(cyanomethyl)-1-(ethylsulfonyl) azetidin-3-yl)-1H-pyrazol-4-yl)-7H-pyrrolo [2, 3-d] pyrimidin-7-yl)-2-oxoethyl) phenyl) acetamide 1-(Ethylsulfonyl)-3-[4-(7H-pyrrolo [2, 3-d] pyrimidin-4-yl)-1H-pyrazol-1-yl]-3-azetidine acetonitrile (baricitinib, 186 mg, 0.5 mmol), 4-dimethylamino pyridine (DMAP, 61 mg, 0.5 mmol), 2-(4-acetamidophenyl) acetic acid (actarit, 106 mg, 0.55 mmol) and 1-(3-dimethylaminopropyl)-3-ethylcarbodiimide hydrochloride (EDCI, 144 mg, 0.75 mmol) was dissolved in a mixed solvent of dichloromethane (10 mL) and DMF (2 mL) and stirred at room temperature for 14 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=2:1 to 1:2) to give the title compound as a white solid, 0.03 g, 10% yield. MS (m/z): [M+H]$^+$ calcd for $C_{26}H_{26}N_8O_4S$, 547.61; found, 547.3. $^1$H NMR (400 MHz, DMSO-$d_6$) δ 9.93 (s, 1H), 9.01 (d, J=10.0 Hz, 2H), 8.53 (s, 1H), 8.14 (d, J=4.2 Hz, 1H), 7.54 (d, J=8.1 Hz, 2H), 7.44 (d, J=4.2 Hz, 1H), 7.30 (d, J=8.0 Hz, 2H), 4.87 (s, 2H), 4.62 (d, J=9.0 Hz, 2H), 4.26 (d, J=9.1 Hz, 2H), 3.71 (s, 2H), 3.25 (q, J=7.3 Hz, 2H), 2.04 (s, 3H), 1.26 (t, J=7.4 Hz, 3H).

Example 25

2-(3-(4-(7-(2-(1, 8-diethyl-1, 3, 4, 9-tetrahydropyrano [3, 4-b] indol-1-yl) acetyl)-7H-pyrrolo [2, 3-d] pyrimidin-4-yl)-1H-pyrazol-1-yl)-1-(ethylsulfonyl) azetidin-3-yl) acetonitrile

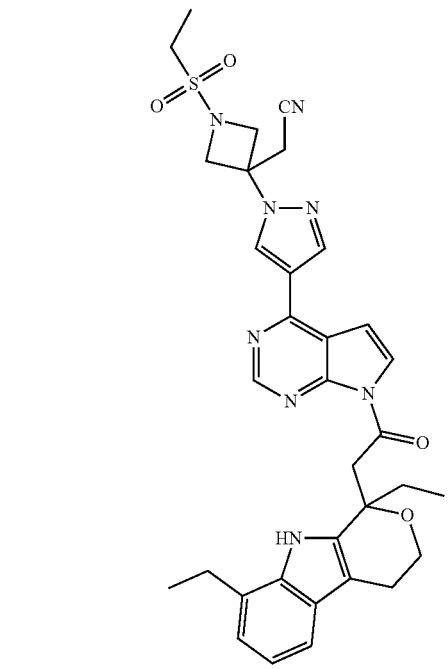

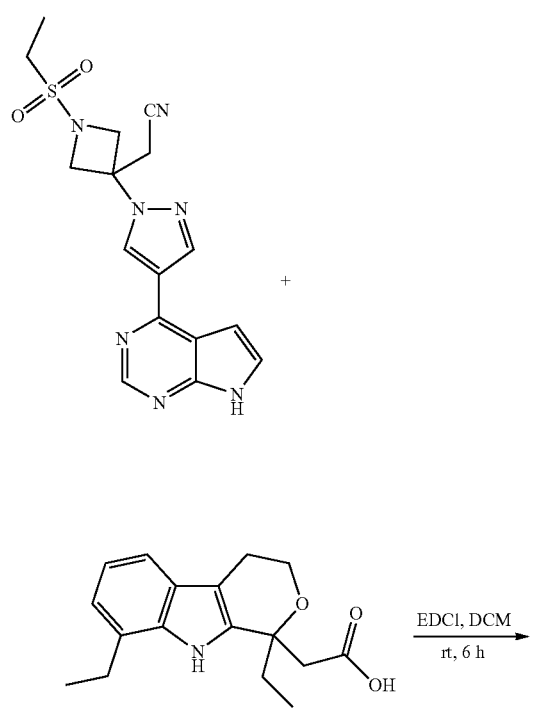

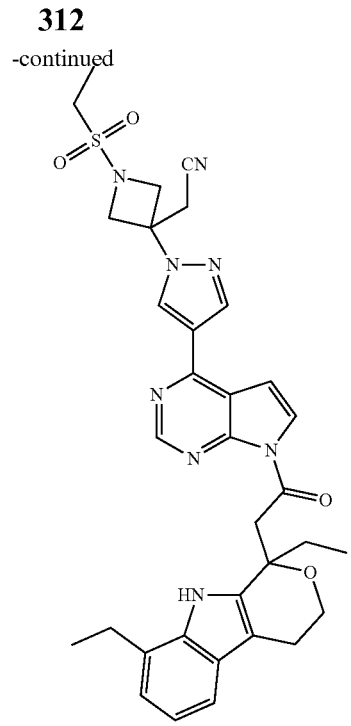

Synthesis of 2-(3-(4-(7-(2-(1, 8-diethyl-1, 3, 4, 9-tetrahydropyrano [3, 4-b] indol-1-yl) acetyl)-7H-pyrrolo [2, 3-d] pyrimidin-4-yl)-1H-pyrazol-1-yl)-1-(ethylsulfonyl) azetidin-3-yl) acetonitrile 1-(Ethylsulfonyl)-3-[4-(7H-pyrrolo [2, 3-d] pyrimidin-4-yl)-1H-pyrazol-1-yl]-3-azetidine acetonitrile (baricitinib, 186 mg, 0.5 mmol), 4-dimethylamino pyridine (DMAP, 61 mg, 0.5 mmol), 1, 8-diethyl-1, 3, 4, 9-tetrahydropyran [3, 4-b] indole-1-acetic acid (etodolac, 158 mg, 0.55 mmol) and 1-(3-dimethylaminopropyl)-3-ethylcarbodiimide hydrochloride (EDCI, 144 mg, 0.75 mmol) were dissolved in dichloromethane (10 mL) and stirred at room temperature for 14 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=5:1 to 1:1) to give the title compound as a white solid, 0.18 g, 56% yield. MS (m/z): [M+H]$^+$ calcd for $C_{33}H_{36}N_8O_4S$, 641.76; found, 641.2. $^1$H NMR (400 MHz, DMSO-$d_6$) δ 10.59 (s, 1H), 9.04 (s, 1H), 8.95 (s, 1H), 8.55 (s, 1H), 8.15 (d, J=4.2 Hz, 1H), 7.44 (d, J=4.2 Hz, 1H), 7.27 (dd, J=7.4, 1.6 Hz, 1H), 7.00-6.88 (m, 2H), 4.71-4.56 (m, 3H), 4.29 (d, J=9.1 Hz, 2H), 4.22 (d, J=14.5 Hz, 1H), 3.91 (ddd, J=11.7, 7.1, 4.9 Hz, 1H), 3.83-3.76 (m, 1H), 3.74 (s, 2H), 3.27 (q, J=7.3 Hz, 2H), 2.89 (q, J=7.5 Hz, 2H), 2.64 (dt, J=6.8, 4.2 Hz, 2H), 2.21 (q, J=7.2 Hz, 2H), 1.29 (td, J=7.4, 4.3 Hz, 6H), 0.76 (t, J=7.3 Hz, 3H).

Example 26

Tert-butyl (S)-(2-(4-(1-(3-(cyanomethyl)-1-(ethylsulfonyl) azetidin-3-yl)-1H-pyrazol-4-yl)-7H-pyrrolo [2, 3-d] pyrimidin-7-yl)-2-oxo-1-phenylethyl) carbamate

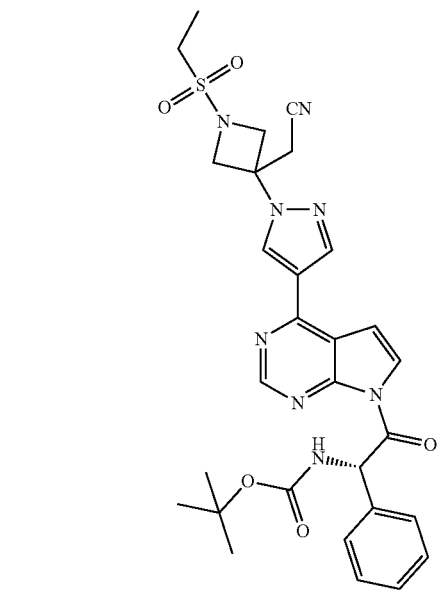

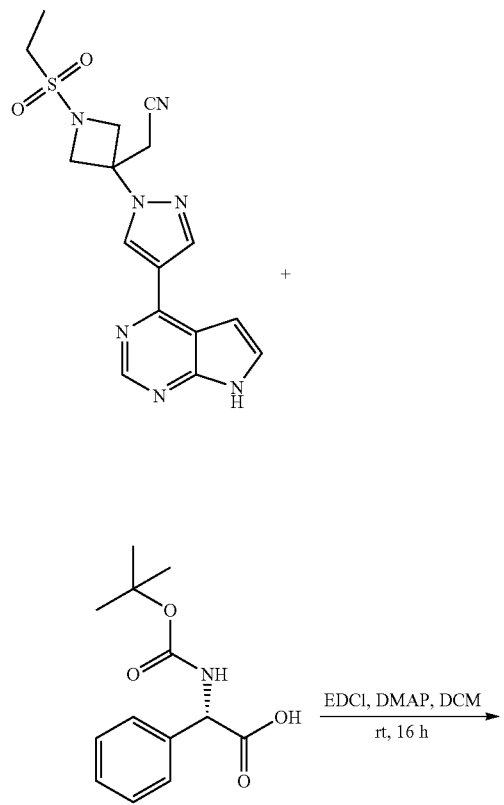

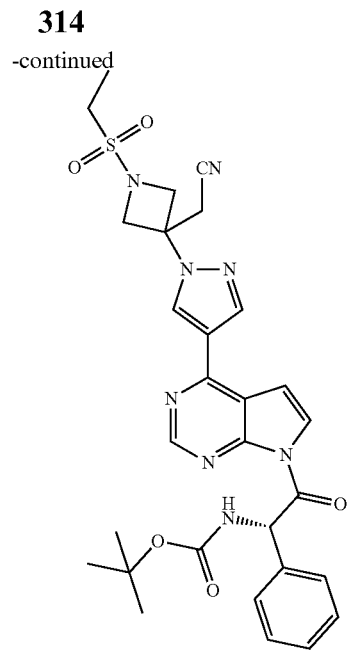

Synthesis of tert-butyl (S)-(2-(4-(1-(3-(cyanomethyl)-1-(ethylsulfonyl) azetidin-3-yl)-1H-pyrazol-4-yl)-7H-pyrrolo [2, 3-d] pyrimidin-7-yl)-2-oxo-1-phenylethyl) carbamate 1-(Ethylsulfonyl)-3-[4-(7H-pyrrolo [2, 3-d] pyrimidin-4-yl)-1H-pyrazol-1-yl]-3-azetidine acetonitrile (baricitinib, 371 mg, 1 mmol), N-Boc-L-phenylglycine (301.5 mg, 1.2 mmol), 4-dimethylamino pyridine (DMAP, 183 mg, 1.5 mmol) and 1-(3-dimethylaminopropyl)-3-ethylcarbodiimide hydrochloride (EDCI, 288 mg, 1.5 mmol) were dissolved in dichloromethane (15 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=2:1 to 1:2) to give the title compound as a white solid, 0.12 g, 19.8% yield. MS (m/z): [M+H]$^+$ calcd for $C_{29}H_{32}N_8O_5S$, 605.69; found, 605.3. $^1$H NMR (400 MHz, DMSO-d$_6$) δ 9.00 (d, J=3.7 Hz, 2H), 8.51 (s, 1H), 8.18 (d, J=4.1 Hz, 1H), 7.99 (d, J=7.5 Hz, 1H), 7.61-7.37 (m, 4H), 7.36-7.23 (m, 3H), 4.60 (d, J=9.1 Hz, 2H), 4.24 (d, J=9.1 Hz, 2H), 3.69 (s, 2H), 3.23 (q, J=7.3 Hz, 2H), 1.40 (s, 9H), 1.24 (t, J=7.4 Hz, 3H).

Example 27

1-((1S, 4R)-4-((7-((S)-2-(4-isobutylphenyl) propanoyl)-7H-pyrrolo [2, 3-d] pyrimidin-4-yl)(methyl) amino) cyclohexyl)-N-methyl methanesulfonamide

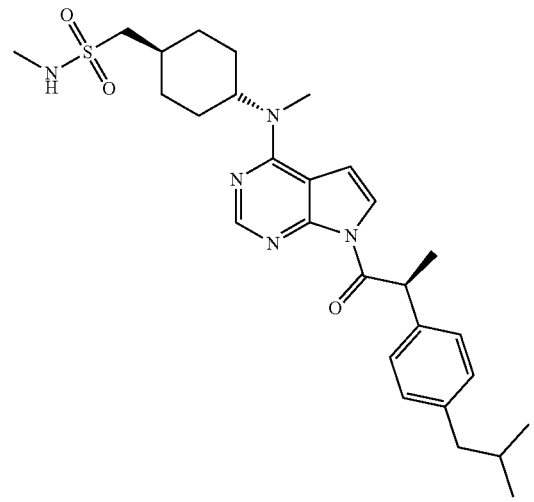

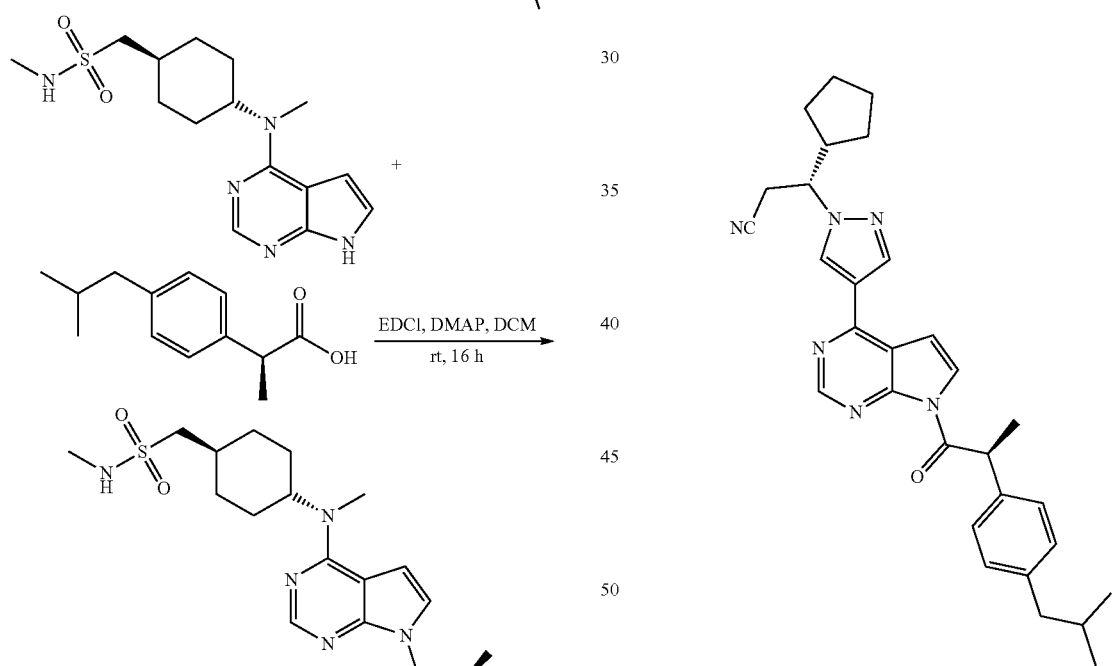

N-methyl-1-((1R, 4R)-4-(methyl (7H-pyrrolo [2, 3-d] pyrimidin-4-yl) amino) cyclohexyl) methanesulfonamide (oclacitinib, 338 mg, 1 mmol), 4-dimethylamino pyridine (DMAP, 122 mg, 1 mmol), (S)-(+)-2-(4-isobutylphenyl) propanoic acid ((S)-(+)-ibuprofen, 247 mg, 1.2 mmol) and 1-(3-dimethylaminopropyl)-3-ethylcarbodiimide hydrochloride (EDCI, 288 mg, 1.5 mmol) were dissolved in dichloromethane (10 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=5:1 to 2:1) to give the title compound as a white solid, 0.14 g, 26.6% yield. MS (m/z): [M+H]$^+$ calcd for $C_{28}H_{39}N_5O_3S$, 526.71; found, 526.2. $^1$H NMR (400 MHz, DMSO-$d_6$) δ 8.36 (s, 1H), 7.66 (d, J=4.2 Hz, 1H), 7.29 (d, J=8.1 Hz, 2H), 7.06 (d, J=7.8 Hz, 2H), 6.93-6.79 (m, 2H), 6.10 (q, J=6.9 Hz, 1H), 4.63 (s, 1H), 3.14 (s, 3H), 2.94 (d, J=6.2 Hz, 2H), 2.59 (d, J=5.0 Hz, 3H), 2.35 (d, J=7.2 Hz, 2H), 2.04 (d, J=13.1 Hz, 2H), 1.88-1.74 (m, 2H), 1.74-1.63 (m, 4H), 1.52 (d, J=7.0 Hz, 3H), 1.27-1.21 (m, 2H), 0.81 (d, J=6.6 Hz, 6H).

Example 28

(R)-3-cyclopentyl-3-(4-(7-(S)-2-(4-isobutylphenyl) propanoyl)-7H-pyrrolo [2, 3-d] pyrimidin-4-yl)-1H-pyrazol-1-yl) propanenitrile

317

-continued

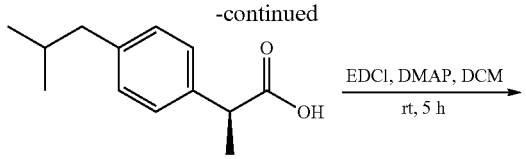

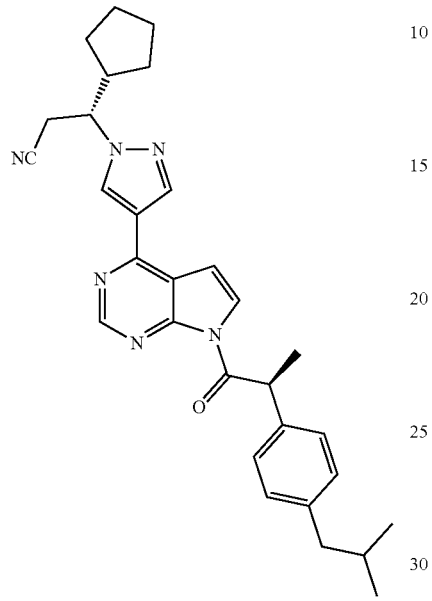

(R)-3-(4-(7h-pyrrolo [2, 3-d] pyridin-4-yl)-1h-pyrazol-1-yl)-3-cyclopentylpropane (ruxolitinib, 306 mg, 1 mmol), 4-dimethylamino pyridine (DMAP, 12 mg, 0.1 mmol), (S)-(+)-2-(4-isobutylphenyl) propanoic acid ((S)-(+)-ibuprofen, 247 mg, 1.2 mmol) and 1-(3-dimethylaminopropyl)-3-ethylcarbodiimide hydrochloride (EDCI, 288 mg, 1.5 mmol) were dissolved in dichloromethane (10 mL) and stirred at room temperature for 5 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=5:1 to 3:1) to give the title compound as a white solid, 0.42 g, 85% yield. MS (m/z): [M+H]$^+$ calcd for $C_{30}H_{34}N_6O_4$, 495.64; found, 495.2. $^1$H NMR (400 MHz, DMSO-d$_6$) δ 8.96 (s, 1H), 8.87 (s, 1H), 8.40 (s, 1H), 8.11 (d, J=4.2 Hz, 1H), 7.36-7.27 (m, 3H), 7.07 (d, J=8.0 Hz, 2H), 6.00 (q, J=6.9 Hz, 1H), 4.53 (td, J=9.6, 4.3 Hz, 1H), 3.23 (qd, J=17.1, 6.9 Hz, 2H), 2.47-2.38 (m, 1H), 2.34 (d, J=7.1 Hz, 2H), 1.77 (ddd, J=27.2, 12.6, 7.2 Hz, 2H), 1.66-1.47 (m, 5H), 1.47-1.11 (m, 5H), 0.88-0.76 (m, 6H).

318

Example 29

3-((3R, 4R)-4-methyl-3-(methyl (7-(2-(4-(1-oxoisoindolin-2-yl) phenyl) butanoyl)-7H-pyrrolo [2, 3-d]pyrimidin-4-yl) amino) piperidin-1-yl)-3-oxopropanenitrile

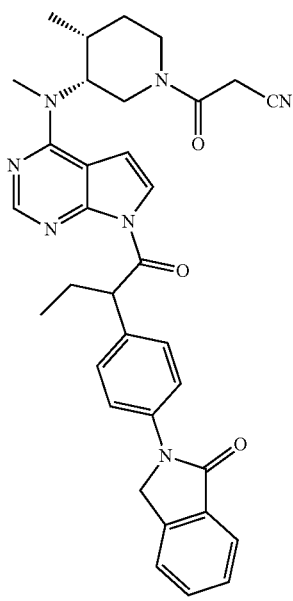

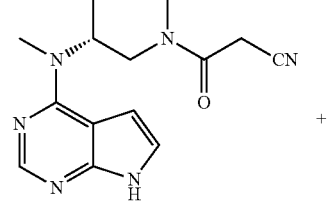

+

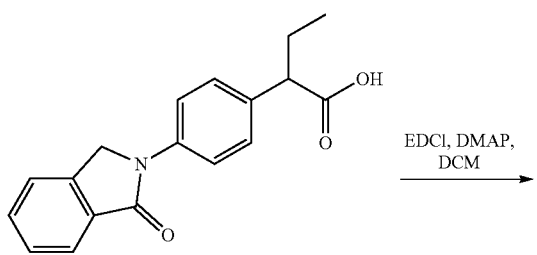

EDCl, DMAP, DCM

319

-continued

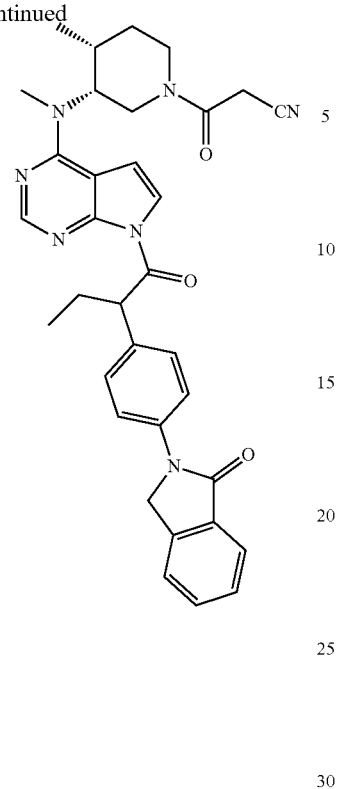

3-{(3R, 4R)-4-methyl-3-[methyl-(7H-pyrrolo [2, 3-d] pyrimidin-4-yl)-piperidin-1-yl]-3-oxo-propionitrile (tofacitinib, 312 mg, 1 mmol), 4-dimethylamino pyridine (DMAP, 12 mg, 0.1 mmol), 2-(4-(1-oxoisoindolin-2-yl) phenyl) butanoic acid (indobufen, 384 mg, 1.3 mmol) and 1-(3-dimethylaminopropyl)-3-ethylcarbodiimide hydrochloride (EDCI, 249 mg, 1.3 mmol) was dissolved in dichloromethane (10 mL) and stirred at room temperature for 20 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=1:1 to 1:5) to give the title compound as a white solid, 0.27 g, 45.8% yield. MS (m/z): [M+H]$^+$ calcd for $C_{34}H_{35}N_7O_3$, 590.70; found, 590.2. $^1$H NMR (400 MHz, DMSO-d$_6$) δ 8.52-8.37 (m, 1H), 7.84 (d, J=8.1 Hz, 2H), 7.74 (dd, J=22.3, 5.9 Hz, 2H), 7.66 (d, J=7.1 Hz, 2H), 7.57-7.50 (m, 1H), 7.50-7.44 (m, 2H), 6.90 (d, J=4.6 Hz, 1H), 6.01-5.91 (m, 1H), 4.97 (s, 2H), 4.84 (s, 1H), 4.18-4.00 (m, 2H), 3.99-3.53 (m, 3H), 3.41 (d, J=6.3 Hz, 1H), 3.24 (s, 3H), 2.43-2.30 (m, 1H), 2.27-2.14 (m, 1H), 1.95-1.50 (m, 3H), 1.00 (d, J=7.1 Hz, 3H), 0.91 (t, J=7.3 Hz, 3H).

320

Example 30

2-2-(1-(Ethylsulfonyl)-3-(4-(7-(2-(4-(1-oxoisoindolin-2-yl) phenyl) butanoyl)-7H-pyrrolo [2, 3-d] pyrimidin-4-yl)-1H-pyrazol-1-yl) azetidin-3-yl) acetonitrile

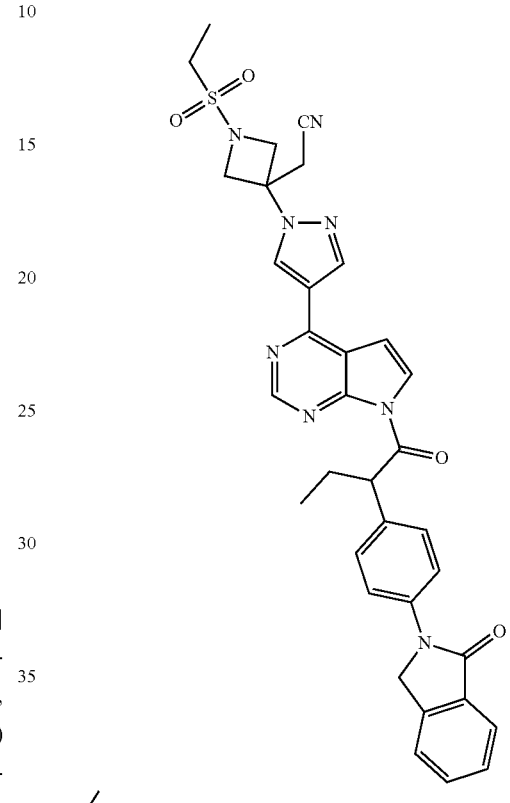

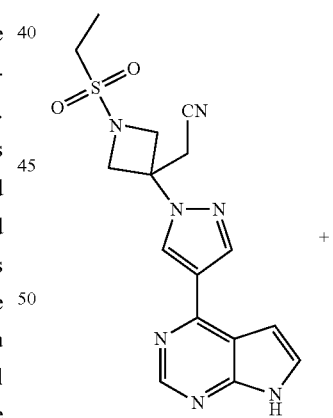

+

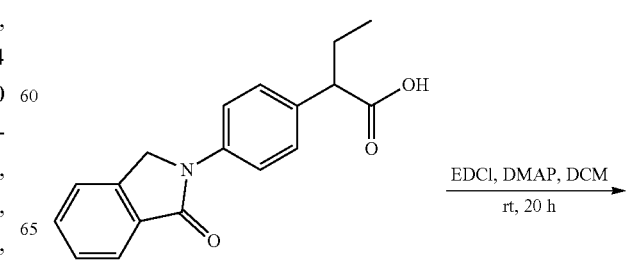

EDCl, DMAP, DCM
rt, 20 h

321
-continued

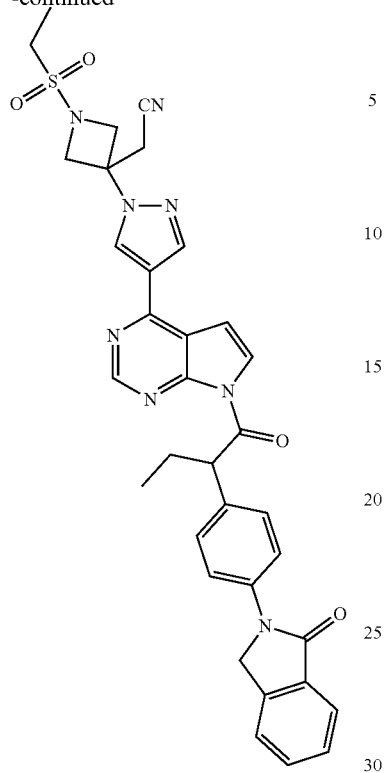

1-(Ethylsulfonyl)-3-[4-(7H-pyrrolo [2, 3-d] pyrimidin-4-yl)-1H-pyrazol-1-yl]-3-azetidine acetonitrile (baricitinib, 371 mg, 1 mmol), 4-dimethylamino pyridine (DMAP, 61 mg, 0.5 mmol), 2-(4-(1-oxoisoindolin-2-yl) phenyl) butanoic acid (indobufen, 354 mg, 1.2 mmol) and 1-(3-dimethylaminopropyl)-3-ethylcarbodiimide hydrochloride (EDCI, 288 mg, 1.5 mmol) was dissolved in dichloromethane (15 mL) and stirred at room temperature for 20 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=5:1 to 1:1) to give the title compound as a white solid, 0.46 g, 70.9% yield. MS (m/z): [M+H]$^+$ calcd for C$_{34}$H$_{32}$N$_8$O$_4$S, 649.74; found, 649.3. $^1$H NMR (400 MHz, DMSO) δ 9.05 (s, 1H), 8.98 (s, 1H), 8.50 (s, 1H), 8.16 (d, J=3.9 Hz, 1H), 7.86 (d, J=8.4 Hz, 2H), 7.73 (t, J=14.0 Hz, 1H), 7.69-7.58 (m, 2H), 7.52 (d, J=8.4 Hz, 3H), 7.40 (d, J=3.9 Hz, 1H), 5.85 (t, J=7.2 Hz, 1H), 4.96 (s, 2H), 4.59 (d, J=9.0 Hz, 2H), 4.24 (d, J=9.0 Hz, 2H), 3.68 (s, 2H), 3.22 (dd, J=14.5, 7.2 Hz, 2H), 2.26 (dt, J=13.8, 7.1 Hz, 1H), 1.94 (dd, J=13.6, 7.2 Hz, 1H), 1.23 (dd, J=14.8, 7.6 Hz, 3H), 0.94 (t, J=7.1 Hz, 3H).

322

Example 31

(R)-3-cyclopentyl-3-(4-(7-((S)-2-(6-methoxynaphthalen-2-yl) propanoyl)-7H-pyrrolo [2, 3-d] pyrimidin-4-yl))-1H-pyrazol-1-yl) propanenitrile

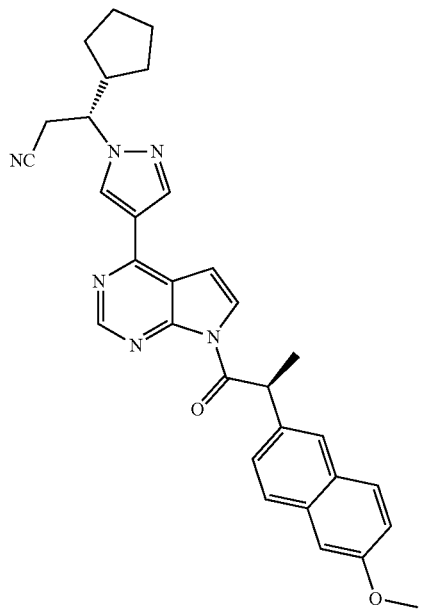

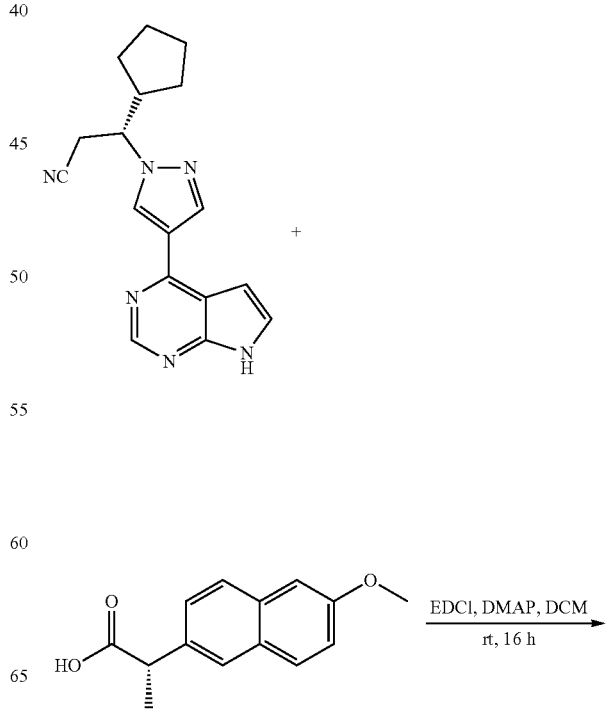

323

-continued

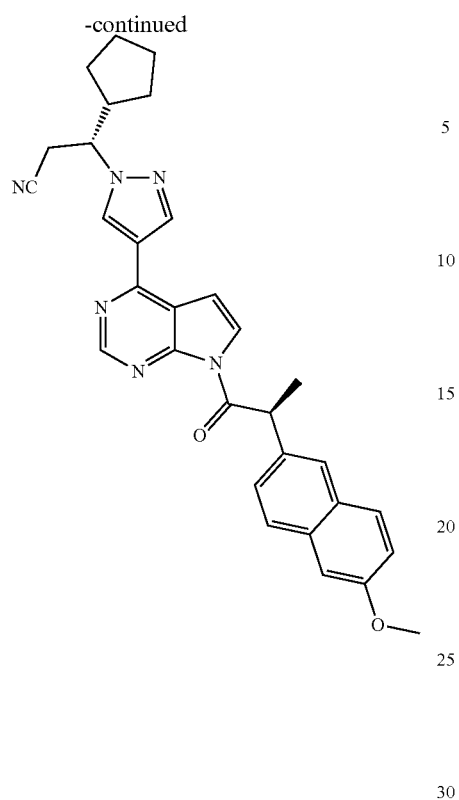

(R)-3-(4-(7h-pyrrolo [2, 3-d] pyridin-4-yl)-1h-pyrazol-1-yl)-3-cyclopentylpropane (Ruxolitinib, 153 mg, 0.5 mmol), 4-dimethylamino pyridine (DMAP, 6 mg, 0.05 mmol), (S)-(+)-2-(6-methoxy-2-naphthyl) propanoic acid (naproxen, 138 mg, 0.6 mmol) and 1-(3-dimethylaminopropyl)-3-ethylcarbodiimide hydrochloride (EDCI, 144 mg, 0.75 mmol) were dissolved in dichloromethane (10 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=1:1 to 1:2) to give the title compound as a white solid, 0.16 g, 61.7% yield. MS (m/z): [M+H]$^+$ calcd for $C_{31}H_{30}N_6O_2$, 519.62; found, 519.3. $^1$H NMR (400 MHz, DMSO) δ 8.99 (s, 1H), 8.85 (s, 1H), 8.39 (s, 1H), 8.14 (d, J=4.2 Hz, 1H), 7.84 (s, 1H), 7.81-7.73 (m, 2H), 7.55 (dd, J=8.6, 1.5 Hz, 1H), 7.30 (d, J=4.2 Hz, 1H), 7.24 (d, J=2.2 Hz, 1H), 7.11 (dd, J=9.0, 2.4 Hz, 1H), 6.13 (q, J=6.8 Hz, 1H), 4.53 (td, J=9.6, 4.2 Hz, 1H), 3.83 (s, 3H), 3.29-3.14 (m, 2H), 2.47-2.34 (m, 1H), 1.81 (td, J=11.7, 7.3 Hz, 1H), 1.68 (d, J=6.9 Hz, 3H), 1.63-1.38 (m, 4H), 1.38-1.21 (m, 3H).

324

Example 32

(3R)-3-(4-(7-(2-(3-benzoylphenyl) propanoyl)-7H-pyrrolo [2, 3-d] pyrimidin-4-yl)-1H-pyrazol-1-yl)-3-cyclopentylpropanenitrile

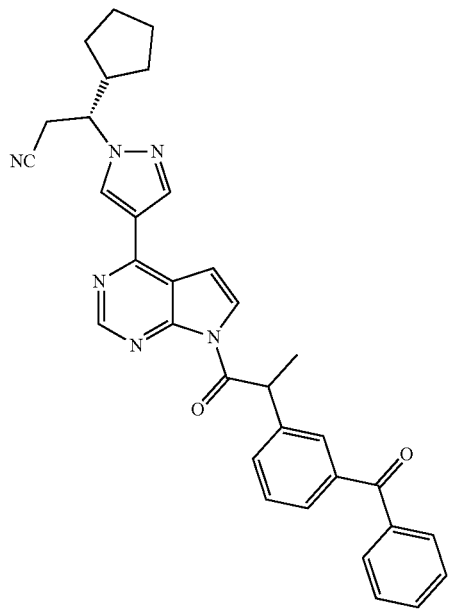

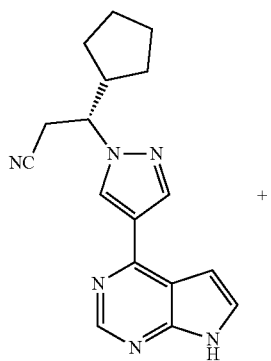

+

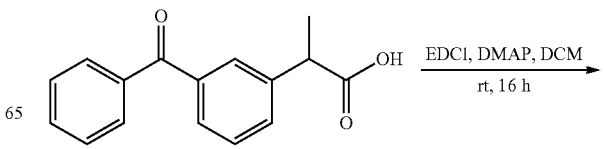

325

-continued

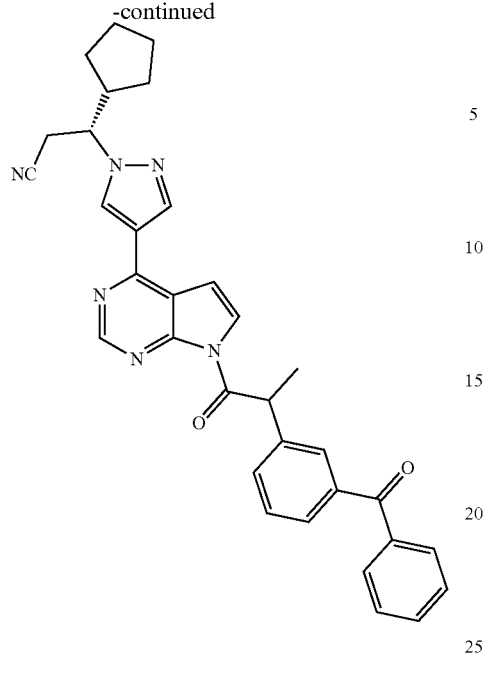

(R)-3-(4-(7h-pyrrolo [2, 3-d] pyridin-4-yl)-1h-pyrazol-1-yl)-3-cyclopentylpropane (Ruxolitinib, 153 mg, 0.5 mmol), 4-dimethylamino pyridine (DMAP, 6 mg, 0.05 mmol), 2-(3-benzoylphenyl) propanoic acid (ketoprofen, 152 mg, 0.6 mmol) and 1-(3-dimethylaminopropyl)-3-ethylcarbodiimide hydrochloride (EDCI, 144 mg, 0.75 mmol) were dissolved in dichloromethane (10 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=10:1 to 1:1) to give the title compound as a white solid, 0.18 g, 66.4% yield. MS (m/z): [M+H]$^+$ calcd for C$_{33}$H$_{30}$N$_6$O$_2$, 543.64; found, 543.2. $^1$H NMR (400 MHz, DMSO) δ 8.89 (d, J=6.4 Hz, 2H), 8.41 (s, 1H), 8.14 (d, J=4.2 Hz, 1H), 7.82 (s, 1H), 7.76 (d, J=7.7 Hz, 1H), 7.70-7.59 (m, 4H), 7.53 (t, J=7.6 Hz, 3H), 7.33 (d, J=4.1 Hz, 1H), 6.08 (q, J=6.8 Hz, 1H), 4.55 (td, J=9.6, 4.2 Hz, 1H), 3.29-3.16 (m, 2H), 2.42 (dt, J=17.0, 8.5 Hz, 1H), 1.82 (td, J=11.6, 7.3 Hz, 1H), 1.70-1.39 (m, 7H), 1.39-1.20 (m, 3H).

326

Example 33

(3R)-3-cyclopentyl-3-(4-(7-(2-(2-fluoro-[1, 1'-biphenyl]-4-yl) propanoyl)-7H-pyrrolo [2, 3-d] pyrimidin-4-yl)-1H-pyrazol-1-yl) propanenitrile

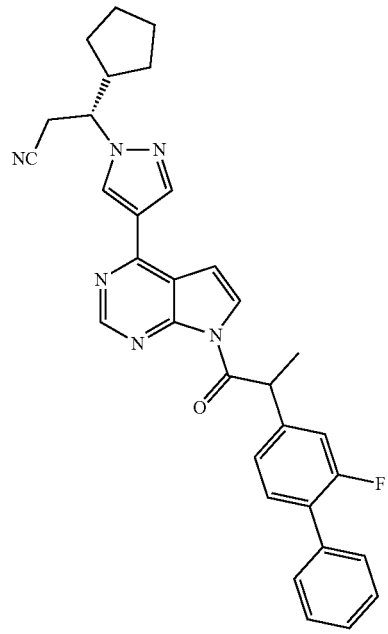

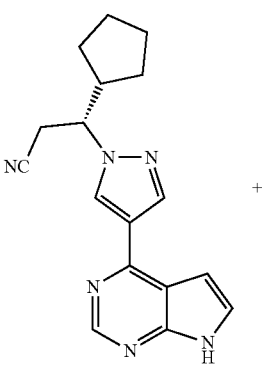

+

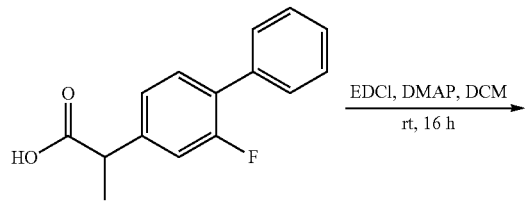

327

-continued

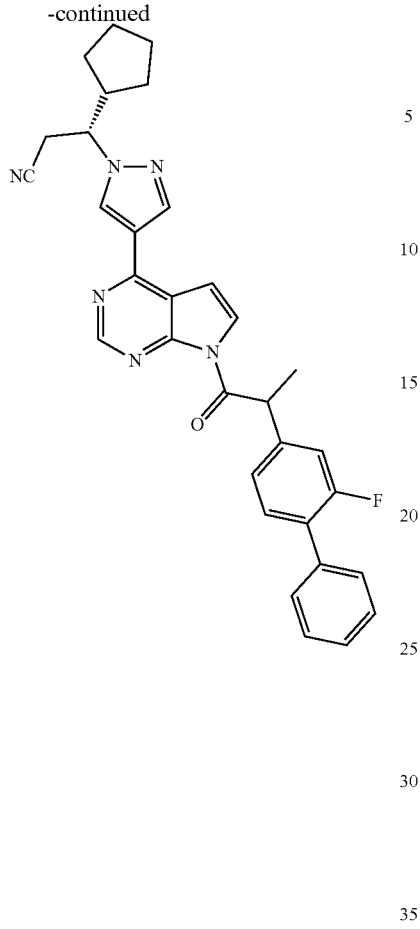

(R)-3-(4-(7h-pyrrolo [2, 3-d] pyridin-4-yl)-1h-pyrazol-1-yl)-3-cyclopentylpropane (Ruxolitinib, 153 mg, 0.5 mmol), 4-dimethylamino pyridine (DMAP, 6 mg, 0.05 mmol), 2-(2-fluoro-4-biphenyl) propanoic acid (flurbiprofen, 146 mg, 0.6 mmol) and 1-(3-dimethylaminopropyl)-3-ethylcarbodiimide hydrochloride (EDCI, 144 mg, 0.75 mmol) were dissolved in dichloromethane (10 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=1:1 to 1:2) to give the title compound as a white solid, 0.17 g, 63.9% yield. MS (m/z): [M+H]+ calcd for $C_{32}H_{29}FN_6O$, 533.62; found, 533.2. $^1$H NMR (400 MHz, DMSO) δ 9.00 (s, 1H), 8.88 (s, 1H), 8.41 (s, 1H), 8.15 (d, J=4.1 Hz, 1H), 7.52-7.29 (m, 9H), 6.08 (q, J=6.7 Hz, 1H), 4.54 (td, J=9.4, 4.0 Hz, 1H), 3.28-3.15 (m, 2H), 2.43 (dd, J=16.9, 8.4 Hz, 1H), 1.87-1.76 (m, 1H), 1.70-1.38 (m, 7H), 1.38-1.20 (m, 3H).

328

Example 34

(3R)-3-cyclopentyl-3-(4-(7-(2-(4-(1-oxoisoindolin-2-yl) phenyl) butanoyl)-7H-pyrrolo [2, 3-d] pyrimidin-4-yl)-1H-pyrazol-1-yl) propanenitrile

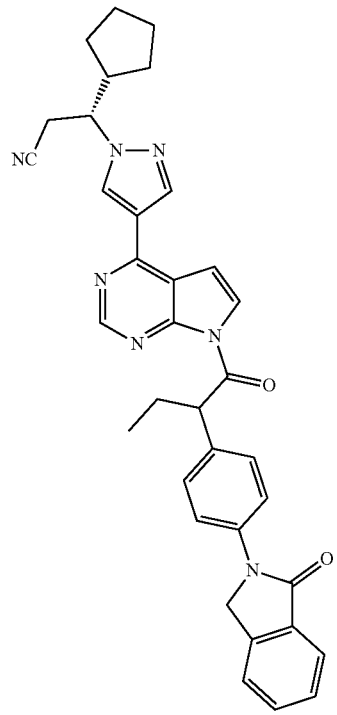

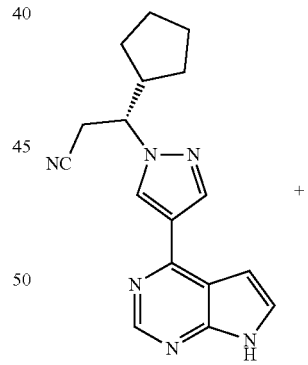

+

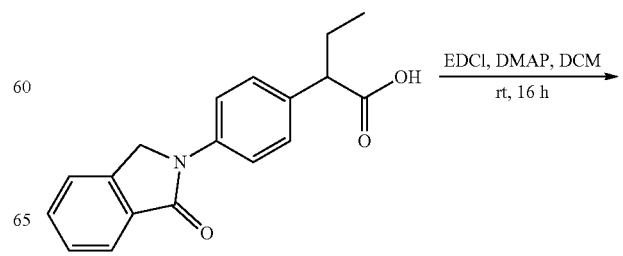

329
-continued

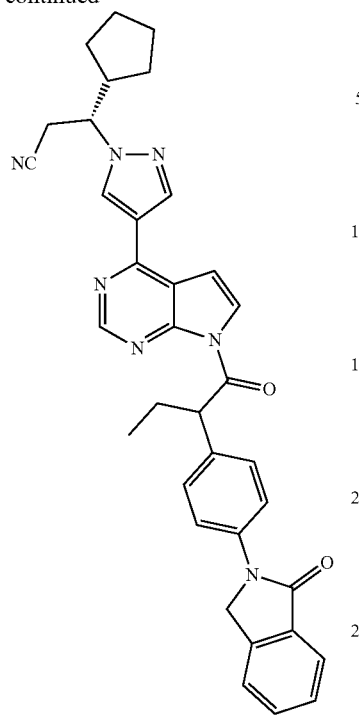

(R)-3-(4-(7h-pyrrolo [2, 3-d] pyridin-4-yl)-1h-pyrazol-1-yl)-3-cyclopentylpropane (ruxolitinib, 153 mg, 0.5 mmol), 4-dimethylamino pyridine (DMAP, 6 mg, 0.05 mmol), 2-(4-(1-oxoisoindolin-2-yl) phenyl) butanoic acid (indobufen, 177 mg, 0.6 mmol) and 1-(3-dimethylaminopropyl)-3-ethylcarbodiimide hydrochloride (EDCI, 144 mg, 0.75 mmol) were dissolved in dichloromethane (10 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=5:1 to 1:1) to give the title compound as a white solid, 0.17 g, 58.3% yield. MS (m/z): [M+H]$^+$ calcd for $C_{35}H_{33}N_7O_2$, 584.70; found, 584.3. $^1$H NMR (400 MHz, DMSO) δ 9.01 (s, 1H), 8.86 (s, 1H), 8.39 (s, 1H), 8.13 (d, J=4.2 Hz, 1H), 7.86 (d, J=8.7 Hz, 2H), 7.75 (d, J=7.6 Hz, 1H), 7.70-7.59 (m, 2H), 7.52 (t, J=7.0 Hz, 3H), 7.30 (d, J=3.9 Hz, 1H), 5.86 (t, J=7.4 Hz, 1H), 4.96 (s, 2H), 4.53 (td, J=9.5, 4.2 Hz, 1H), 3.28-3.14 (m, 2H), 2.41 (dt, J=17.2, 8.5 Hz, 1H), 2.25 (td, J=14.2, 7.2 Hz, 1H), 1.97-1.88 (m, 1H), 1.80 (dt, J=11.9, 5.8 Hz, 1H), 1.65-1.39 (m, 3H), 1.36-1.21 (m, 4H), 0.94 (t, J=7.3 Hz, 3H).

330
Example 35

N-methyl-1-((trans)-4-(methyl (7-(2-(4-(1-oxoisoindolin-2-yl) phenyl) butanoyl)-7H-pyrrolo [2, 3-d] pyrimidin-4-yl) amino) cyclohexyl) methanesulfonamide

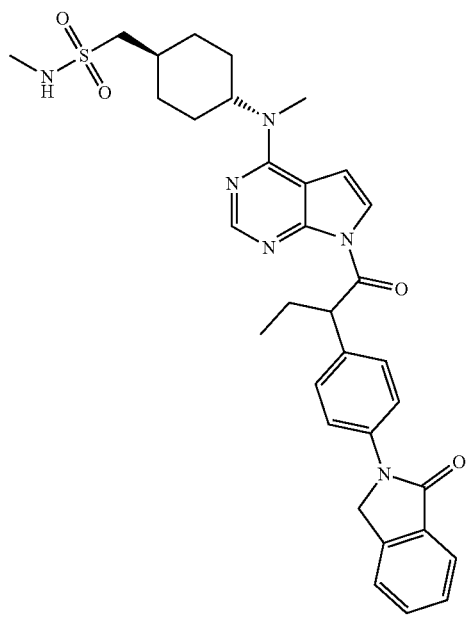

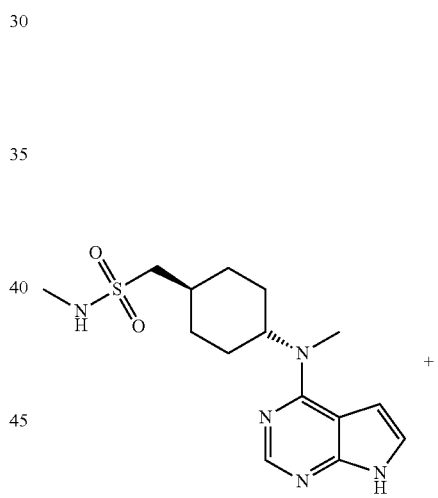

+

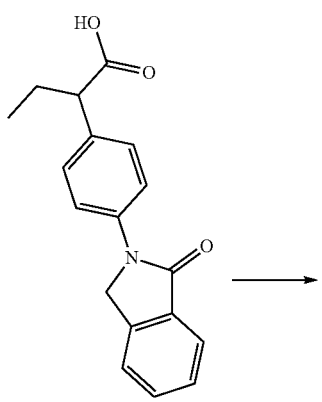

→

331
-continued

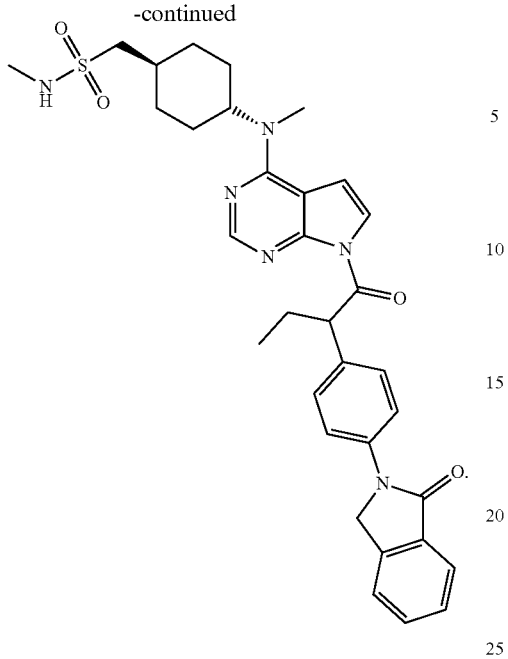

(N-methyl-1-((trans)-4-(methyl (7H-pyrrolo [2, 3-d] pyrimidin-4-yl) amino) cyclohexyl) methanesulfonamide (oclacitinib, 203 mg, 0.6 mmol), 4-dimethylamino pyridine (DMAP, 73 mg, 0.6 mmol), 2-(4-(1-oxoisoindolin-2-yl) phenyl) butanoic acid (indobufen, 230 mg, 0.78 mmol) and 1-(3-dimethylaminopropyl)-3-ethylcarbodiimide hydrochloride (EDCI, 173 mg, 0.9 mmol) were dissolved in dichloromethane (10 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=5:1 to 1:1) to give the title compound as a white solid, 0.22 g, 59.7% yield. MS (m/z): [M+H]$^+$ calcd for $C_{33}H_{38}N_6O_4S$, 615.77; found, 615.3. $^1$H NMR (400 MHz, DMSO) δ 8.41 (s, 1H), 7.83 (d, J=8.3 Hz, 2H), 7.76 (d, J=7.4 Hz, 1H), 7.67 (dd, J=9.6, 5.5 Hz, 3H), 7.59-7.42 (m, 3H), 6.92-6.73 (m, 2H), 5.97 (t, J=7.1 Hz, 1H), 4.96 (s, 2H), 4.64 (s, 1H), 3.14 (s, 3H), 2.94 (d, J=5.8 Hz, 2H), 2.57 (t, J=9.7 Hz, 3H), 2.26-2.13 (m, 1H), 2.03 (d, J=12.0 Hz, 2H), 1.97-1.77 (m, 2H), 1.68 (s, 4H), 1.37-1.13 (m, 2H), 0.90 (dd, J=18.8, 11.8 Hz, 3H).

332
Example 36

1-((Trans)-4-((7-(2-(2-fluoro-[1, 1'-biphenyl]-4-yl) propanoyl)-7H-pyrrolo [2, 3-d] pyrimidin-4-yl) (methyl) amino) cyclohexyl)-N-methyl methanesulfonamide

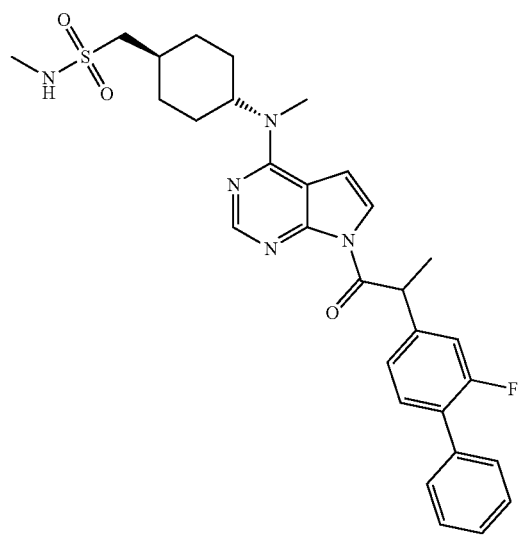

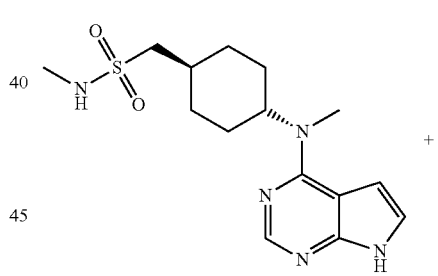

+

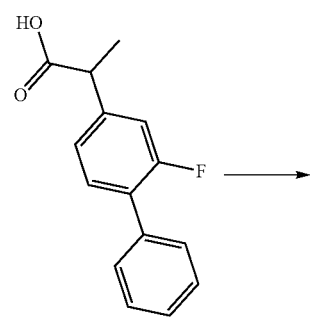

→

333
-continued

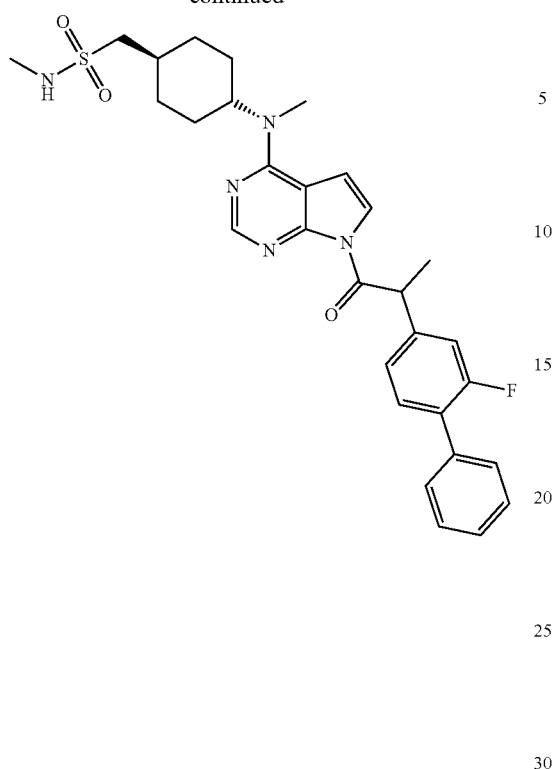

N-methyl-1-((trans)-4-(methyl (7H-pyrrolo [2, 3-d] pyrimidin-4-yl) amino) cyclohexyl) methanesulfonamide (oclacitinib, 203 mg, 0.6 mmol), 4-dimethylamino pyridine (DMAP, 73 mg, 0.6 mmol), 2-(2-fluoro-4-biphenyl) propanoic acid (flurbiprofen, 191 mg, 0.78 mmol) and 1-(3-dimethylaminopropyl)-3-ethylcarbodiimide hydrochloride (EDCI, 173 mg, 0.9 mmol) were dissolved in dichloromethane (10 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=1:1 to 1:2) to give the title compound as a white solid, 0.22 g, 65.1% yield. MS (m/z): [M+H]$^+$ calcd for $C_{30}H_{34}FN_5O_3S$, 564.69; found, 564.3. $^1$H NMR (400 MHz, DMSO) δ 8.39 (s, 1H), 7.70 (d, J=4.2 Hz, 1H), 7.52-7.41 (m, 5H), 7.35 (dt, J=19.2, 7.4 Hz, 3H), 6.92-6.82 (m, 2H), 6.17 (q, J=6.8 Hz, 1H), 4.64 (s, 1H), 3.16 (s, 3H), 2.94 (d, J=6.2 Hz, 2H), 2.59 (d, J=4.9 Hz, 3H), 2.04 (d, J=12.5 Hz, 2H), 1.85 (s, 1H), 1.65 (d, J=26.0 Hz, 4H), 1.59 (d, J=7.0 Hz, 3H), 1.37-1.19 (m, 2H).

334
Example 37

1-((Trans)-4-((7-(2-(1, 8-diethyl-1, 3, 4, 9-tetrahydropyrano [3, 4-b] indol-1-yl) acetyl)-7H-pyrrolo [2, 3-d]pyrimidin-4-yl) (methyl) amino) cyclohexyl)-N-methyl methanesulfonamide

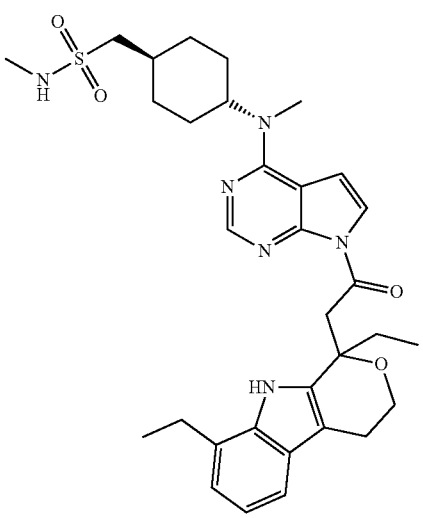

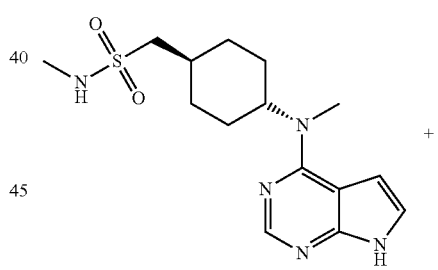
+

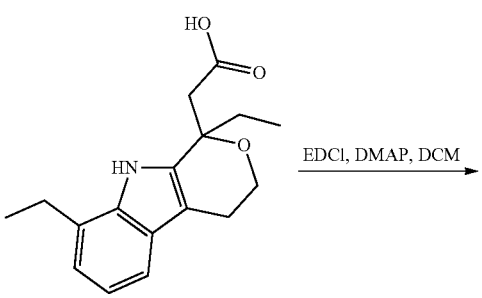
→ EDCl, DMAP, DCM

335
-continued

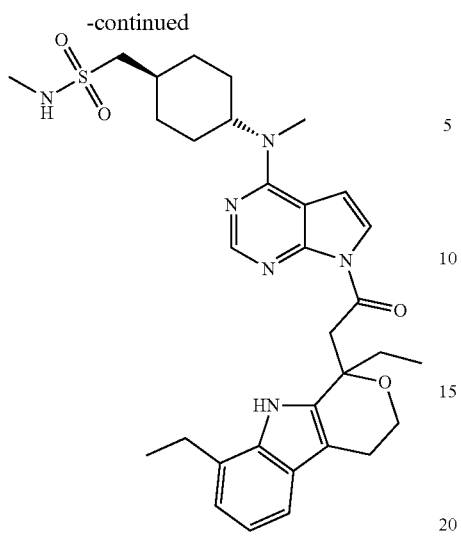

N-methyl-1-((trans)-4-(methyl (7H-pyrrolo [2, 3-d] pyrimidin-4-yl) amino) cyclohexyl) methanesulfonamide (oclacitinib, 203 mg, 0.6 mmol), 4-dimethylamino pyridine (DMAP, 73 mg, 0.6 mmol), 1, 8-diethyl-1, 3, 4, 9-tetrahydropyran [3, 4-b] indole-1-acetic acid (etodolac, 224 mg, 0.78 mmol) and 1-(3-dimethylaminopropyl)-3-ethylcarbodiimide hydrochloride (EDCI, 173 mg, 0.9 mmol) was dissolved in dichloromethane (15 mL) and stirred at room temperature for 3 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=3:1 to 1:1) to give the title compound as a white solid, 0.23 g, 63.2% yield. MS (m/z): [M+H]$^+$ calcd for $C_{32}H_{42}N_6O_4S$, 607.79; found, 607.3. $^1$H NMR (400 MHz, DMSO-$d_6$) δ 10.47 (s, 1H), 8.27 (s, 1H), 7.64 (d, J=4.2 Hz, 1H), 7.22 (dd, J=7.4, 1.6 Hz, 1H), 6.98-6.78 (m, 4H), 4.66 (d, J=14.6 Hz, 2H), 4.03 (d, J=7.5 Hz, 1H), 3.89 (s, 1H), 3.76 (dt, J=10.7, 4.4 Hz, 1H), 3.16 (s, 3H), 2.94 (d, J=6.2 Hz, 2H), 2.84 (q, J=7.5 Hz, 2H), 2.59 (t, J=3.8 Hz, 5H), 2.15 (tt, J=7.2, 4.6 Hz, 2H), 2.09-2.01 (m, 2H), 1.85 (t, J=7.5 Hz, 1H), 1.69 (s, 4H), 1.35-1.21 (m, 5H), 0.68 (t, J=7.3 Hz, 3H).

Example 38

1-((Trans)-4-((7-(2-(3-benzoylphenyl) propanoyl)-7H-pyrrolo [2, 3-d] pyrimidin-4-yl) (methyl) amino) cyclohexyl)-N-methyl methanesulfonamide

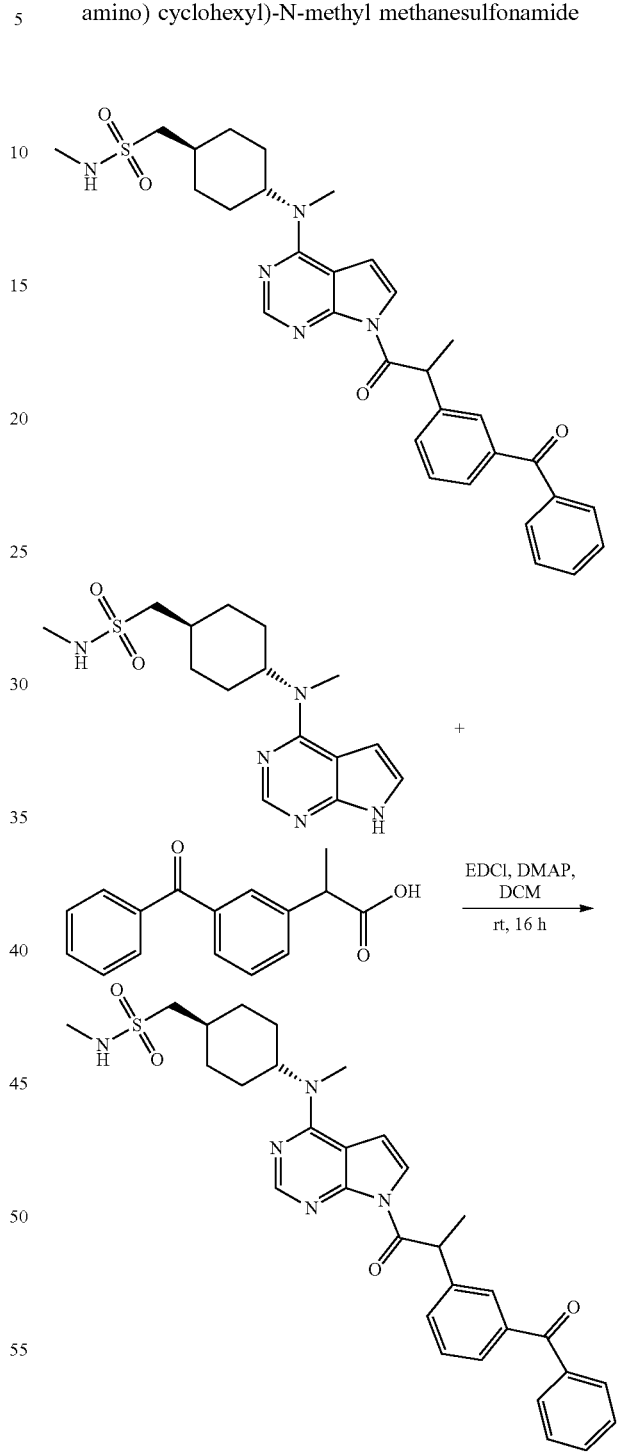

N-methyl-1-((trans)-4-(methyl (7H-pyrrolo [2, 3-d] pyrimidin-4-yl) amino) cyclohexyl) methanesulfonamide (oclacitinib, 203 mg, 0.6 mmol), 4-dimethylamino pyridine (DMAP, 73 mg, 0.6 mmol), 2-(3-benzoylphenyl) propanoic acid (ketoprofen, 198 mg, 0.78 mmol) and 1-(3-dimethyl-aminopropyl)-3-ethylcarbodiimide hydrochloride (EDCI, 173 mg, 0.9 mmol) were dissolved in dichloromethane (15 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=2:1 to 1:1) to give the title compound as a white solid, 0.17 g, 49.4% yield. MS (m/z): [M+H]$^+$ calcd for $C_{31}H_{35}N_5O_4S$, 574.71; found, 574.3. $^1$H NMR (400 MHz, DMSO-d$_6$) δ 8.30 (s, 1H), 7.78 (t, J=1.9 Hz, 1H), 7.74-7.57 (m, 6H), 7.52 (dt, J=11.6, 7.7 Hz, 3H), 6.86 (t, J=4.9 Hz, 2H), 6.16 (q, J=6.9 Hz, 1H), 4.64 (s, 1H), 3.15 (s, 3H), 2.95 (d, J=6.2 Hz, 2H), 2.59 (d, J=5.0 Hz, 3H), 2.04 (d, J=13.0 Hz, 2H), 1.84 (dq, J=13.3, 6.8 Hz, 1H), 1.68 (d, J=8.5 Hz, 4H), 1.58 (d, J=7.0 Hz, 3H), 1.28 (s, 2H).

Example 39

1-((Trans)-4-((7-((S)-2-(6-methoxynaphthalen-2-yl) propanoyl)-7H-pyrrolo [2, 3-d] pyrimidin-4-yl) (methyl) amino) cyclohexyl)-N-methyl methanesulfonamide

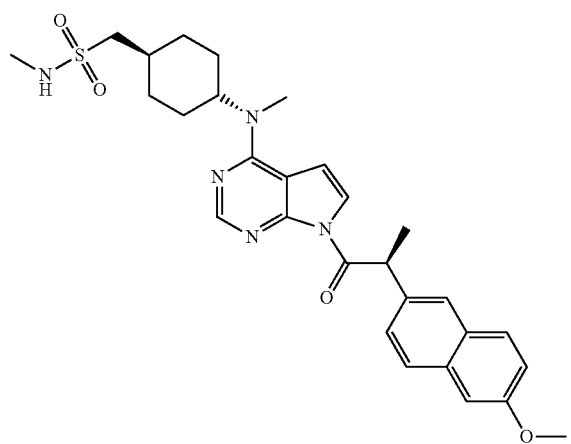

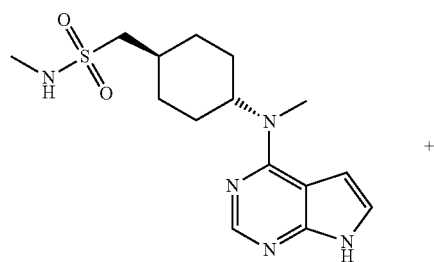

+

-continued

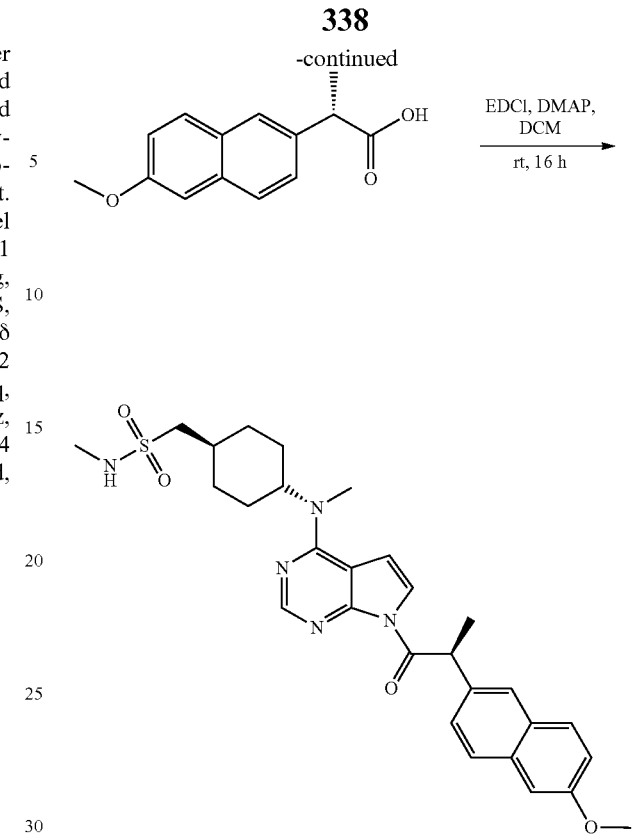

N-Methyl-1-((trans)-4-(methyl (7H-pyrrolo [2, 3-d] pyrimidin-4-yl) amino) cyclohexyl) methanesulfonamide (oclacitinib, 203 mg, 0.6 mmol), 4-dimethylamino pyridine (DMAP, 73 mg, 0.6 mmol), (S)-(+)-2-(6-methoxy-2-naphthyl) propanoic acid (naproxen, 180 mg, 0.78 mmol) and 1-(3-dimethylaminopropyl)-3-ethylcarbodiimide hydrochloride (EDCI, 173 mg, 0.9 mmol) were dissolved in dichloromethane (15 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=2:1 to 1:1) to give the title compound as a white solid, 0.23 g, 69.8% yield. MS (m/z): [M+H]$^+$ calcd for $C_{29}H_{35}N_5O_4S$, 550.69; found, 550.4. $^1$H NMR (400 MHz, DMSO-d$_6$) δ 8.39 (s, 1H), 7.78 (d, J=7.8 Hz, 1H), 7.74 (t, J=8.9 Hz, 2H), 7.68 (d, J=4.1 Hz, 1H), 7.50 (dd, J=8.5, 1.3 Hz, 1H), 7.23 (d, J=2.1 Hz, 1H), 7.11 (dd, J=8.9, 2.4 Hz, 1H), 6.87 (q, J=4.5 Hz, 1H), 6.79 (d, J=3.0 Hz, 1H), 6.21 (q, J=6.8 Hz, 1H), 4.61 (s, 1H), 3.83 (s, 3H), 3.10 (s, 3H), 2.93 (d, J=6.2 Hz, 2H), 2.59 (d, J=4.8 Hz, 3H), 2.06-1.98 (m, 2H), 1.83 (s, 1H), 1.63 (t, J=9.3 Hz, 7H), 1.36-1.15 (m, 2H).

Example 40

2-(3-(4-(7-(2-((3-Chloro-2-methylphenyl) amino) benzoyl)-7H-pyrrolo [2, 3-d] pyrimidin-4-yl)-1H-pyrazol-1-yl)-1-(ethylsulfonyl) azetidin-3-yl) acetonitrile

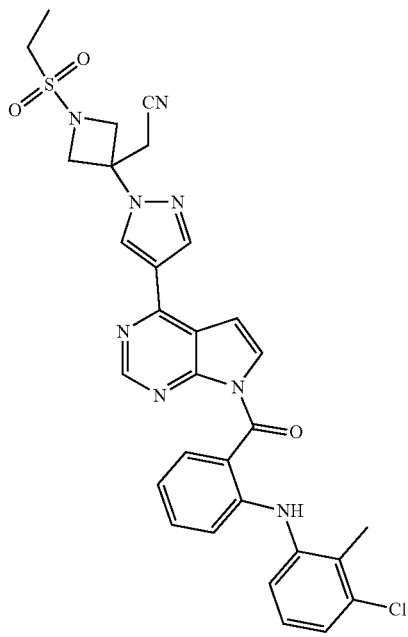

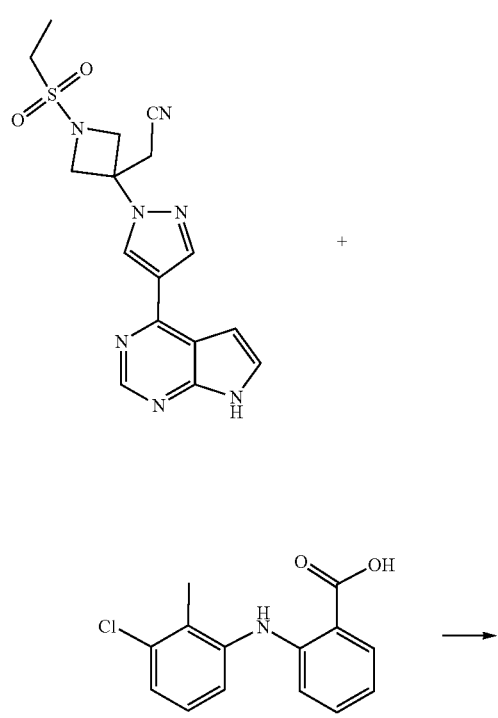

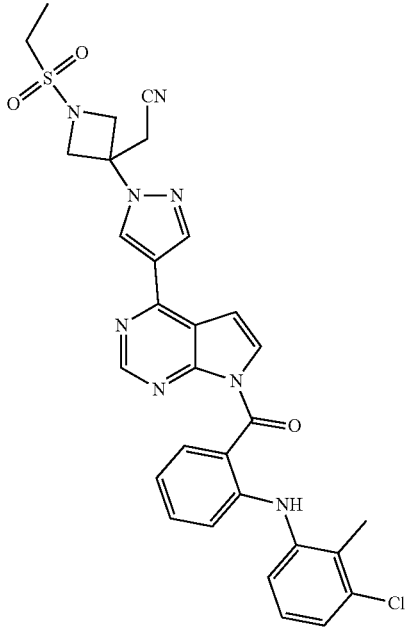

1-(Ethylsulfonyl)-3-[4-(7H-pyrrolo [2, 3-d] pyrimidin-4-yl)-1H-pyrazol-1-yl]-3-azetidine acetonitrile (baricitinib, 371 mg, 1 mmol), 4-dimethylamino pyridine (DMAP, 61 mg, 0.5 mmol), 2-((3-chloro-2-methylphenyl) amino) benzoic acid (tolfenamic acid, 313 mg, 1.2 mmol) and 1-(3-dimethylaminopropyl)-3-ethylcarbodiimide hydrochloride (EDCI, 288 mg, 1.5 mmol) were dissolved in dichloromethane (10 mL) and stirred at room temperature for 24 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=5:1 to 1:1) to give the title compound as a white solid, 0.22 g, 35.7% yield. MS (m/z): [M+H]$^+$ calcd for $C_{30}H_{27}ClN_8O_3S$, 616.11; found, 616.3. $^1$H NMR (400 MHz, DMSO-d$_6$) δ 8.99 (s, 1H), 8.73 (s, 1H), 8.51 (s, 1H), 8.21 (s, 1H), 7.83 (d, J=4.1 Hz, 1H), 7.50 (dd, J=8.3, 6.5 Hz, 2H), 7.37 (d, J=4.1 Hz, 1H), 7.09-7.04 (m, 3H), 7.00-6.90 (m, 2H), 4.61 (d, J=9.1 Hz, 2H), 4.25 (d, J=9.1 Hz, 2H), 3.70 (s, 2H), 3.24 (q, J=7.3 Hz, 2H), 2.01 (s, 3H), 1.25 (t, J=7.4 Hz, 3H).

Example 41

1-((Trans)-4-((7-(2-((3-chloro-2-methylphenyl)amino)benzoyl)-7H-pyrrolo [2, 3-d] pyrimidin-4-yl)(methyl)amino)cyclohexyl)-N-methyl methanesulfonamide

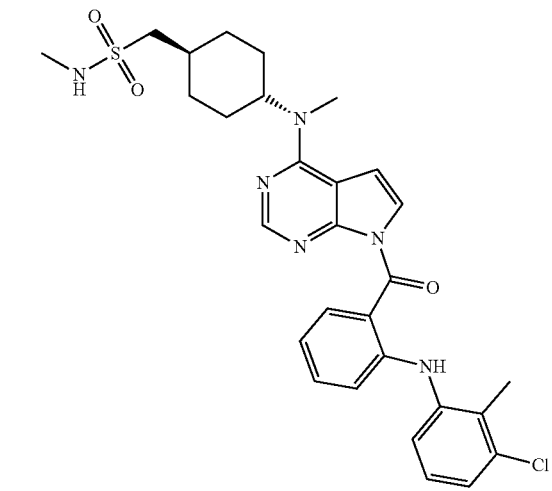

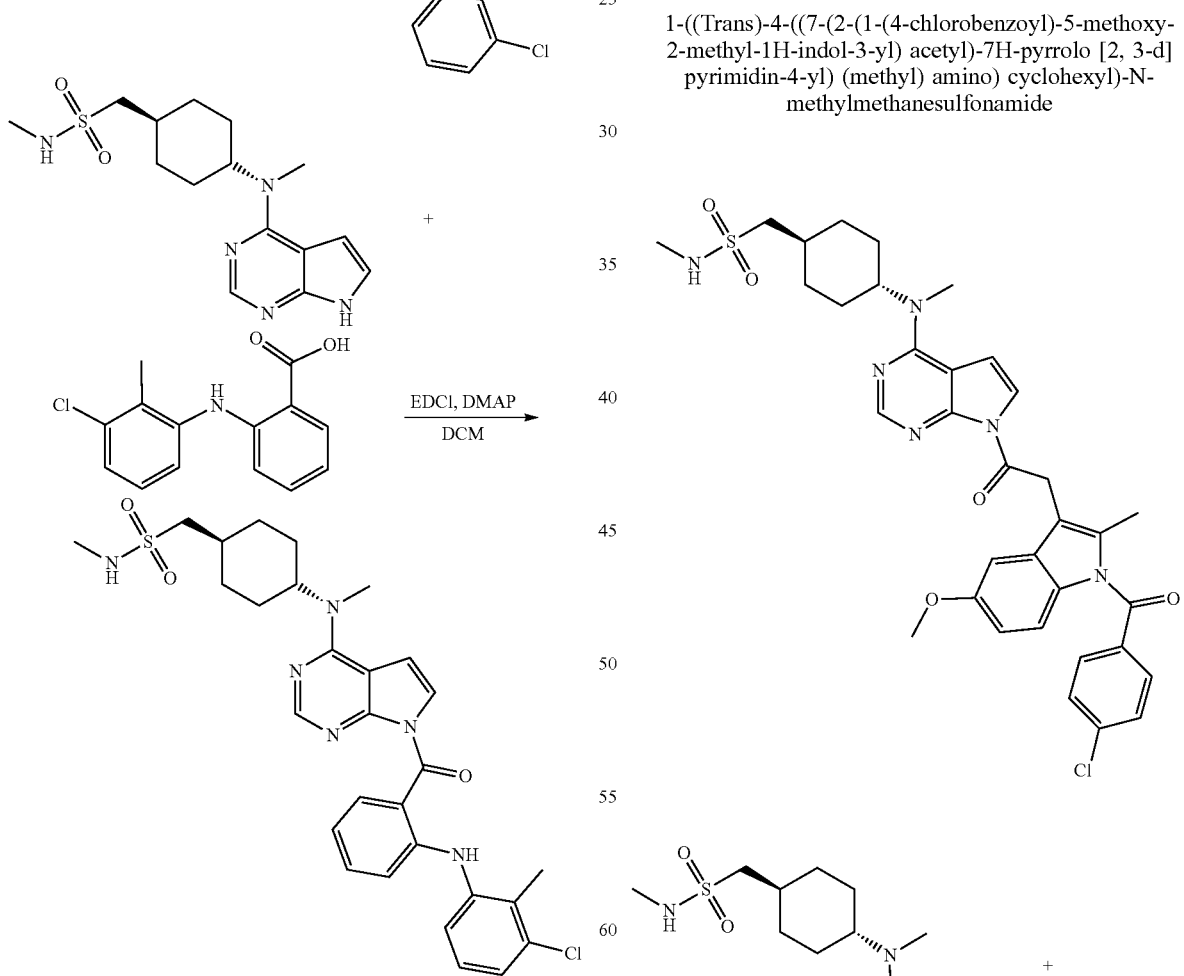

N-methyl-1-((trans)-4-(methyl (7H-pyrrolo [2, 3-d] pyrimidin-4-yl) amino) cyclohexyl) methanesulfonamide (oclacitinib, 203 mg, 0.6 mmol), 4-dimethylamino pyridine (DMAP, 73 mg, 0.6 mmol), 2-((3-chloro-2-methylphenyl) amino) benzoic acid (tolfenamic acid, 204 mg, 0.78 mmol) and 1-(3-dimethylaminopropyl)-3-ethylcarbodiimide hydrochloride (EDCI, 173 mg, 0.9 mmol) were dissolved in dichloromethane (15 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further purified by silica gel column chromatography (petroleum ether/ethyl acetate=2:1 to 1:1) to give the title compound as a yellow solid, 0.2 g, 57.4% yield. MS (m/z): [M+H]$^+$ calcd for $C_{29}H_{33}ClN_6O_3S$, 581.20; found, 581.4. $^1$H NMR (400 MHz, DMSO-$d_6$) δ 8.24 (s, 1H), 8.08 (s, 1H), 7.45 (dd, J=11.4, 4.2 Hz, 1H), 7.41-7.22 (m, 2H), 7.14-7.01 (m, 3H), 6.96 (d, J=8.3 Hz, 1H), 6.93-6.75 (m, 3H), 4.63 (s, 1H), 3.17 (s, 3H), 2.95 (d, J=6.1 Hz, 2H), 2.60 (d, J=4.9 Hz, 3H), 2.13-2.01 (s, 5H), 1.89 (d, J=22.2 Hz, 1H), 1.78-1.62 (m, 4H), 1.36-1.24 (m, 2H).

Example 42

1-((Trans)-4-((7-(2-(1-(4-chlorobenzoyl)-5-methoxy-2-methyl-1H-indol-3-yl) acetyl)-7H-pyrrolo [2, 3-d] pyrimidin-4-yl)(methyl)amino)cyclohexyl)-N-methylmethanesulfonamide

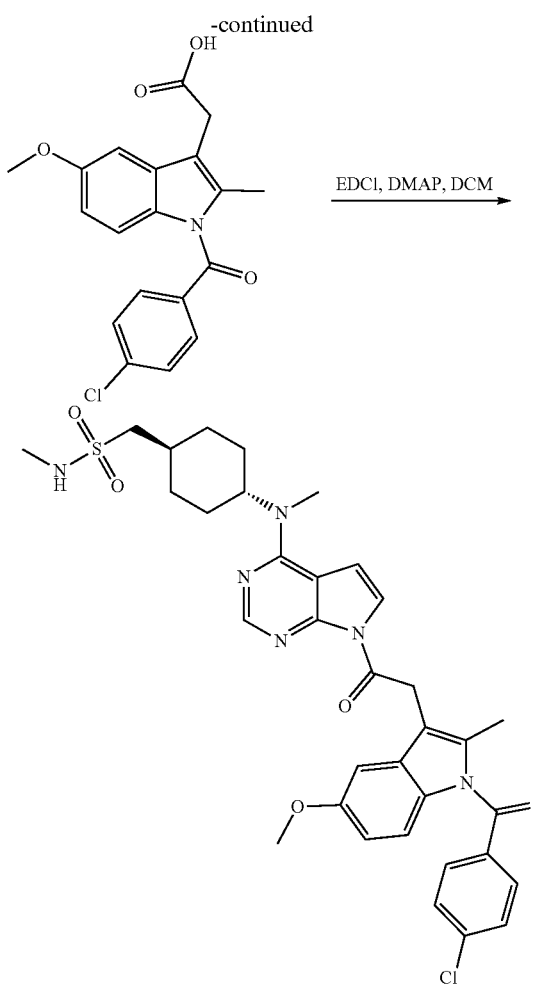

Synthesis of 1-((trans)-4-((7-(2-(1-(4-chlorobenzoyl)-5-methoxy-2-methyl-1H-indol-3-yl) acetyl)-7H-pyrrolo [2, 3-d] pyrimidin-4-yl) (methyl) amino) cyclohexyl)-N-methyl methanesulfonamide N-methyl-1-((trans)-4-(methyl (7H-pyrrolo [2, 3-d] pyrimidin-4-yl) amino) cyclohexyl) methanesulfonamide (oclacitinib, 168 mg, 0.5 mmol), 4-dimethylamino pyridine (DMAP, 61 mg, 0.5 mmol), 1-(4-chlorobenzoyl)-5-methoxy-2-methyl-1H-indole-3-acetic acid (indomethacin, 233 mg, 0.65 mmol) and 1-(3-dimethylaminopropyl)-3-ethylcarbodiimide hydrochloride (EDCI, 144 mg, 0.75 mmol) was dissolved in dichloromethane (15 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further purified by silica gel column chromatography (petroleum ether/ethyl acetate=2:1 to 1:1) to give the title compound as a yellow solid, 0.14 g, 41.4% yield. MS (m/z): [M+H]+ calcd for $C_{34}H_{37}C_1N_6O_5S$, 677.22; found, 677.3 0.1H NMR (400 MHz, DMSO-$d_6$) δ 8.42 (s, 1H), 7.76-7.60 (m, 5H), 7.11 (d, J=2.6 Hz, 1H), 6.98 (d, J=9.0 Hz, 1H), 6.89 (dt, J=9.9, 4.5 Hz, 2H), 6.71 (dd, J=9.0, 2.6 Hz, 1H), 4.99 (s, 2H), 4.69 (s, 1H), 3.69 (s, 3H), 3.20 (s, 3H), 2.96 (d, J=6.2 Hz, 2H), 2.59 (d, J=4.9 Hz, 3H), 2.24 (s, 3H), 2.06 (d, J=12.6 Hz, 2H), 1.87 (dt, J=15.5, 5.8 Hz, 1H), 1.72 (dt, J=8.5, 5.0 Hz, 4H), 1.41-1.27 (m, 2H).

Example 43

1-((trans)-4-((7-(2-((2, 3-dimethylphenyl) amino) benzoyl)-7H-pyrrolo [2, 3-d] pyrimidin-4-yl) (methyl) amino) cyclohexyl)-N-methyl methanesulfonamide

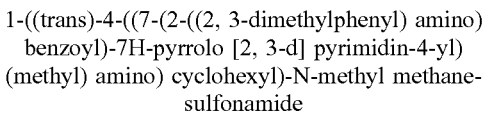

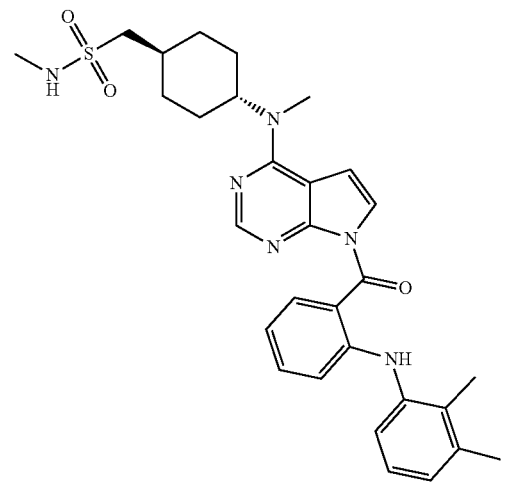

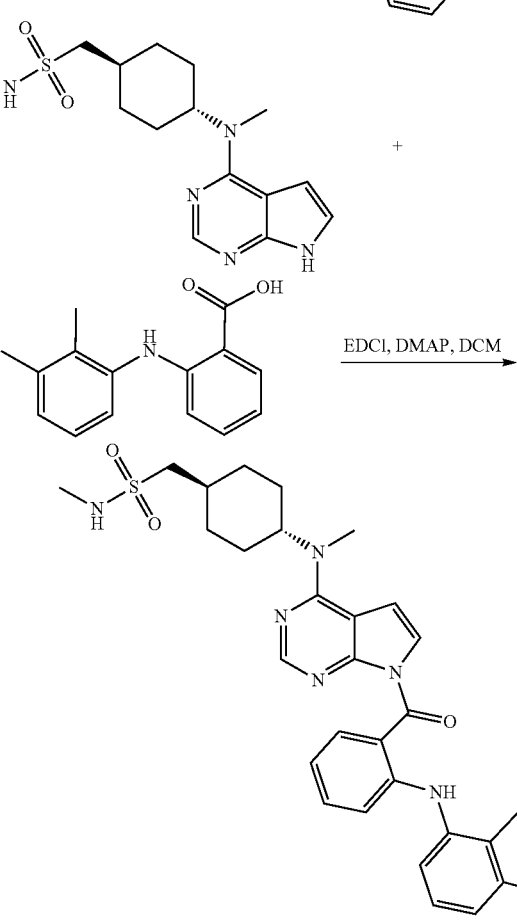

Synthesis of 1-((trans)-4-((7-(2-((2, 3-dimethylphenyl) amino) benzoyl)-7H-pyrrolo [2, 3-d] pyrimidin-4-yl) (methyl) amino) cyclohexyl)-N-methyl methanesulfonamide N-methyl-1-((trans)-4-(methyl (7H-pyrrolo [2, 3-d] pyrimidin-4-yl) amino) cyclohexyl) methanesulfonamide (oclacitinib, 168 mg, 0.5 mmol), 4-dimethylamino pyridine (DMAP, 61 mg, 0.5 mmol), 2-((2, 3-dimethylphenyl) amino) benzoic acid (mefenamic acid, 157 mg, 0.65 mmol), and 1-(3-dimethylaminopropyl)-3-ethylcarbodiimide hydrochloride (EDCI, 144 mg, 0.75 mmol) were dissolved in dichloromethane (15 mL) and stirred at room temperature for 7 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further purified by silica gel column chromatography (petroleum ether/ethyl acetate=2:1 to 1:1) to give the title compound as a yellow solid, 0.17 g, 60.7% yield. MS (m/z): [M+H]$^+$ calcd for $C_{30}H_{36}N_6O_3S$, 561.26; found, 561.3. $^1$H NMR (400 MHz, DMSO-d$_6$) δ 8.59 (s, 1H), 8.12 (s, 1H), 7.48 (d, J=4.0 Hz, 1H), 7.43-7.28 (m, 2H), 7.13-6.96 (m, 3H), 6.92-6.79 (m, 3H), 6.77-6.66 (m, 1H), 4.82-4.49 (m, 1H), 3.19 (s, 3H), 2.95 (d, J=6.2 Hz, 2H), 2.59 (d, J=4.9 Hz, 3H), 2.27 (d, J=9.8 Hz, 3H), 2.07 (d, J=21.6 Hz, 5H), 1.92-1.82 (m, 1H), 1.72 (h, J=3.3 Hz, 4H), 1.37-1.26 (m, 211).

Example 44

N-methyl-1-((trans)-4-(methyl (7-(2-(4-((2-oxocyclopentyl) methyl) phenyl) propanoyl)-7H-pyrrolo [2, 3-d]pyrimidin-4-yl) amino) cyclohexyl) methanesulfonamide

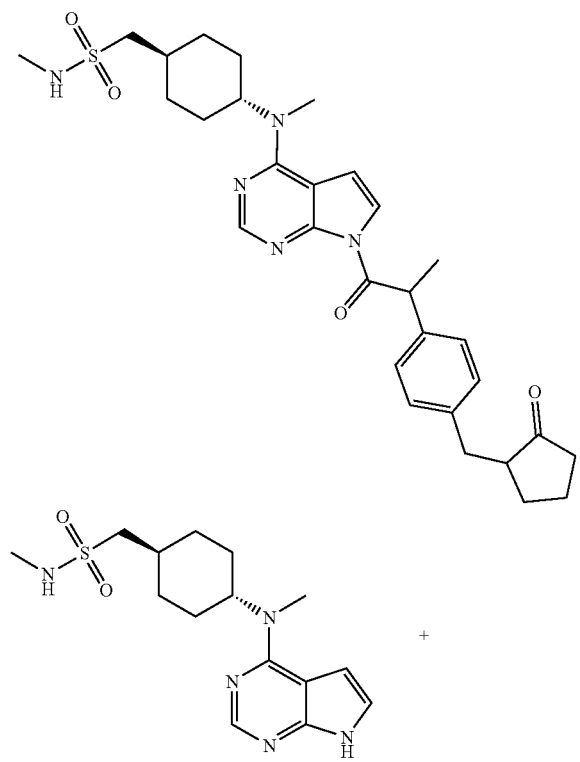

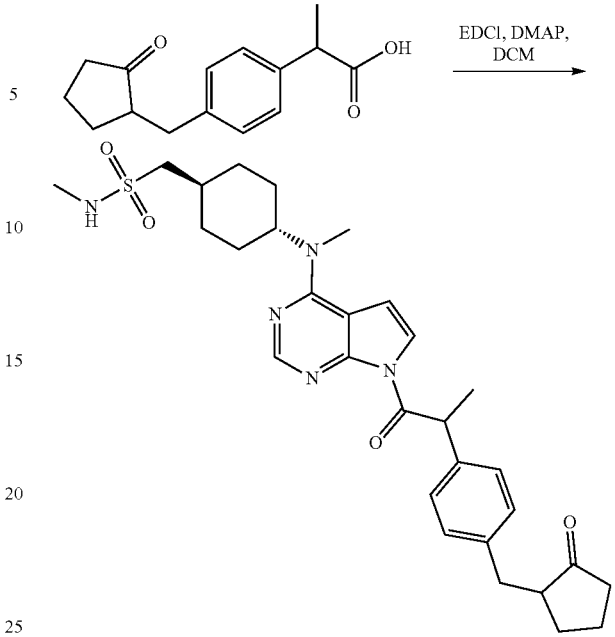

Synthesis of N-methyl-1-((trans)-4-(methyl (7-(2-(4-((2-oxocyclopentyl) methyl) phenyl) propanoyl)-7H-pyrrolo [2, 3-d] pyrimidin-4-yl) amino) cyclohexyl) methanesulfonamide N-methyl-1-((trans)-4-(methyl (7H-pyrrolo [2, 3-d] pyrimidin-4-yl) amino) cyclohexyl) methanesulfonamide (oclacitinib, 168 mg, 0.5 mmol), 4-dimethylamino pyridine (DMAP, 61 mg, 0.5 mmol), 2-[4-(2-oxocyclopentan-1-ylmethyl) phenyl] propanoic acid (loxoprofen, 160 mg, 0.65 mmol), and 1-(3-dimethylaminopropyl)-3-ethylcarbodiimide hydrochloride (EDCI, 144 mg, 0.75 mmol) were dissolved in dichloromethane (15 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=2:1 to 1:1) to give the title compound as a white solid, 0.2 g, 70.7% yield. MS (m/z): [M+H]$^+$ calcd for $C_{30}H_{39}N_5O_4S$, 566.27; found, 566.4. $^1$H NMR (400 MHz, DMSO-d$_6$) δ 8.36 (s, 1H), 7.65 (d, J=4.2 Hz, 1H), 7.29 (d, J=7.8 Hz, 2H), 7.09 (d, J=8.1 Hz, 2H), 6.95-6.79 (m, 2H), 6.09 (q, J=6.9 Hz, 1H), 4.63 (s, 1H), 3.14 (s, 3H), 2.98-2.87 (m, 3H), 2.58 (d, J=2.6 Hz, 3H), 2.41-2.17 (m, 3H), 2.10-2.00 (m, 3H), 1.92-1.77 (m, 3H), 1.75-1.60 (m, 5H), 1.52 (d, J=7.0 Hz, 3H), 1.46-1.38 (m, 1H), 1.35-1.22 (m, 2H).

Example 45

(3R)-3-cyclopentyl-3-(4-(7-(2-(1, 8-diethyl-1, 3, 4, 9-tetrahydropyran [3, 4-b] indol-1-yl) acetyl)-7H-pyrrolo [2, 3-d] pyrimidin-4-yl)-1H-pyrazol-1-yl) propanenitrile

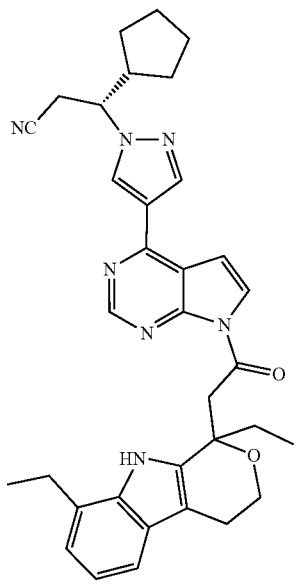

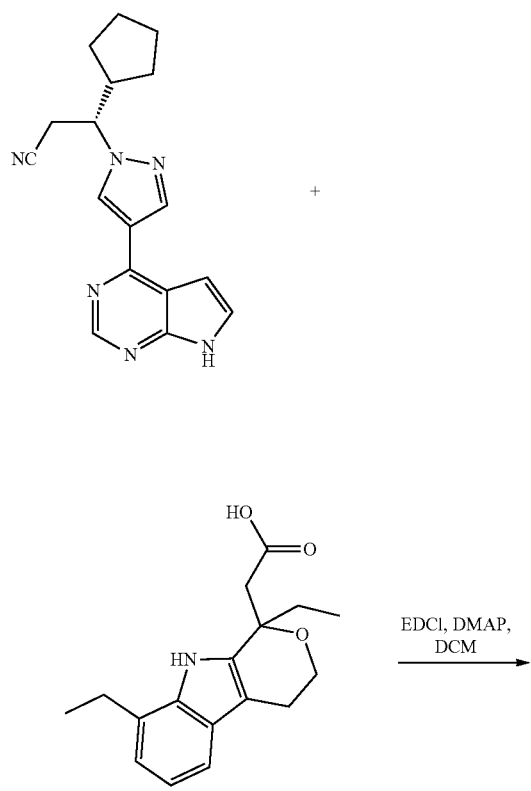

-continued

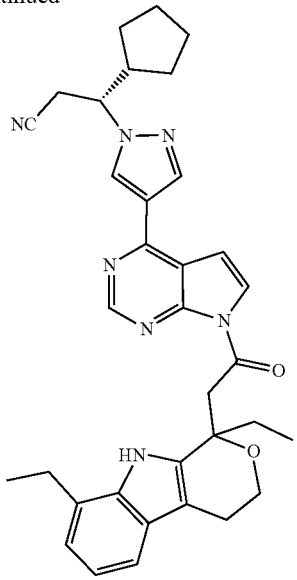

Synthesis of (3R)-3-cyclopentyl-3-(4-(7-(2-(1, 8-diethyl-1, 3, 4, 9-tetrahydropyran [3, 4-b] indol-1-yl) acetyl)-7H-pyrrolo [2, 3-d] pyrimidin-4-yl)-1H-pyrazol-1-yl) propanenitrile (R)-3-(4-(7h-pyrrolo [2, 3-d] pyridin-4-yl)-1h-pyrazol-1-yl)-3-cyclopentylpropane (ruxolitinib, 184 mg, 0.6 mmol), 4-dimethylamino pyridine (DMAP, 7 mg, 0.06 mmol), 1, 8-diethyl-1, 3, 4, 9-tetrahydropyran [3, 4-b]indole-1-acetic acid (etodolac, 224 mg, 0.78 mmol), and 1-(3-dimethylaminopropyl)-3-ethylcarbodiimide hydrochloride (EDCI, 173 mg, 0.9 mmol) were dissolved in dichloromethane (10 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=5:1 to 1:1) to give the title compound as a white solid, 0.28 g, 81.5% yield. MS (m/z): [M+H]$^+$ calcd for $C_{34}H_{37}N_7O_2$, 576.30; found, 576.2. $^1$H NMR (400 MHz, DMSO-$d_6$) δ 10.54 (s, 1H), 8.88 (d, J=3.1 Hz, 2H), 8.42 (s, 1H), 8.09 (d, J=4.2 Hz, 1H), 7.30 (d, J=4.3 Hz, 1H), 7.24 (dd, J=7.4, 1.5 Hz, 1H), 6.96-6.87 (m, 2H), 4.66-4.51 (m, 2H), 4.19 (dd, J=14.5, 1.7 Hz, 1H), 3.88 (ddd, J=11.8, 7.2, 5.0 Hz, 1H), 3.76 (dt, J=11.1, 4.6 Hz, 1H), 3.30-3.15 (m, 2H), 2.86 (q, J=7.5 Hz, 2H), 2.64-2.56 (m, 2H), 2.44 (q, J=8.4 Hz, 1H), 2.18 (q, J=7.2 Hz, 2H), 1.89-1.78 (m, 1H), 1.70-1.41 (m, 4H), 1.41-1.22 (m, 6H), 0.73 (t, J=7.3 Hz, 3H).

Example 46 tert-butyl ((S)-2-(4-(methyl ((trans)-4-((N-methylsulfamoyl) methyl) cyclohexyl) amino)-7H-pyrrolo [2, 3-d]pyrimidin-7-yl)-2-oxo-1-phenylethyl) carbamate

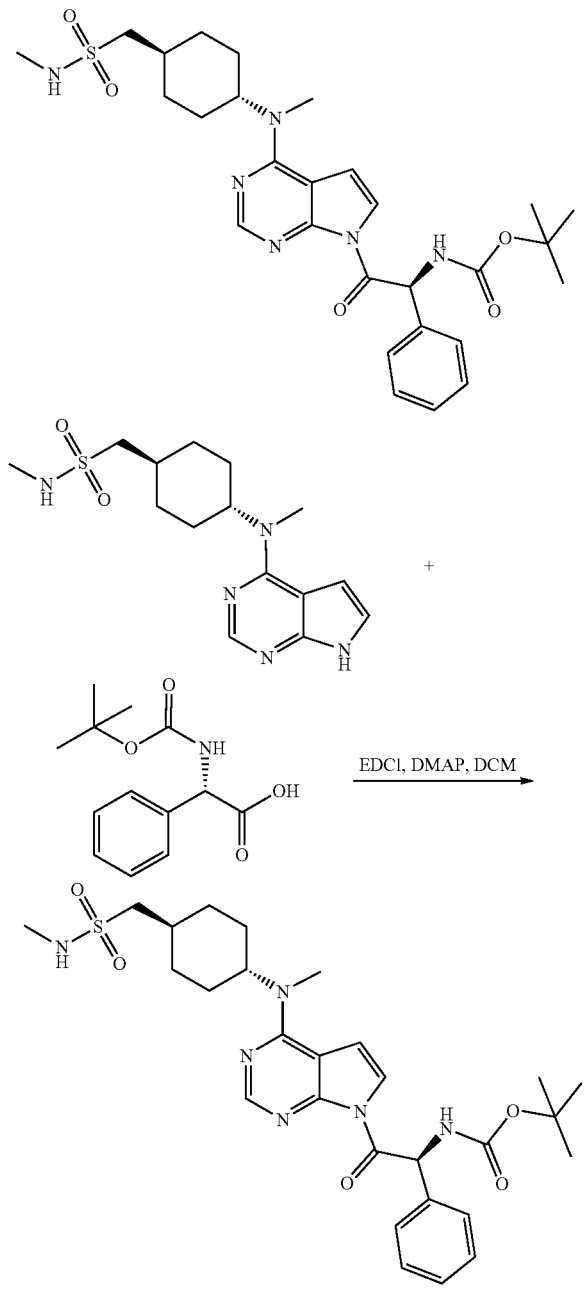

Synthesis of tert-butyl ((S)-2-(4-(methyl ((trans)-4-((N-methylsulfamoyl) methyl) cyclohexyl) amino)-7H-pyrrolo [2, 3-d] pyrimidin-7-yl)-2-oxo-1-phenylethyl) carbamate N-methyl-1-((trans)-4-(methyl (7H-pyrrolo [2, 3-d] pyrimidin-4-yl) amino) cyclohexyl) methanesulfonamide (oclacitinib, 168 mg, 0.5 mmol), 4-dimethylamino pyridine (DMAP, 61 mg, 0.5 mmol), N-Boc-L-phenylglycine (163 mg, 0.65 mmol) and 1-(3-dimethylaminopropyl)-3-ethylcarbodiimide hydrochloride (EDCI, 144 mg, 0.75 mmol) were dissolved in dichloromethane (15 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=2:1 to 1:1) to give the title compound as a white solid, 0.027 g, 9.4% yield. MS (m/z): [M+H]$^+$ calcd for $C_{28}H_{38}N_6O_5S$, 571.26; found, 571.3. $^1$H NMR (400 MHz, DMSO-d6) δ 8.36 (s, 1H), 7.80 (d, J=7.7 Hz, 1H), 7.68 (d, J=4.1 Hz, 1H), 7.56-7.45 (m, 3H), 7.29 (d, J=7.7 Hz, 3H), 6.86 (d, J=4.9 Hz, 2H), 4.63 (s, 1H), 3.14 (s, 3H), 2.94 (d, J=6.2 Hz, 2H), 2.58 (d, J=5.0 Hz, 3H), 2.03 (d, J=12.7 Hz, 2H), 1.90-1.79 (m, 1H), 1.67 (d, J=8.0 Hz, 4H), 1.39 (s, 9H), 1.32-1.21 (m, 2H).

Example 47

2-(3-(4-(7-(2-((2, 3-Dimethylphenyl) amino) benzoyl)-7H-pyrrolo [2, 3-d] pyrimidin-4-yl)-1H-pyrazol-1-yl)-1-(ethylsulfonyl) azetidin-3-yl) acetonitrile

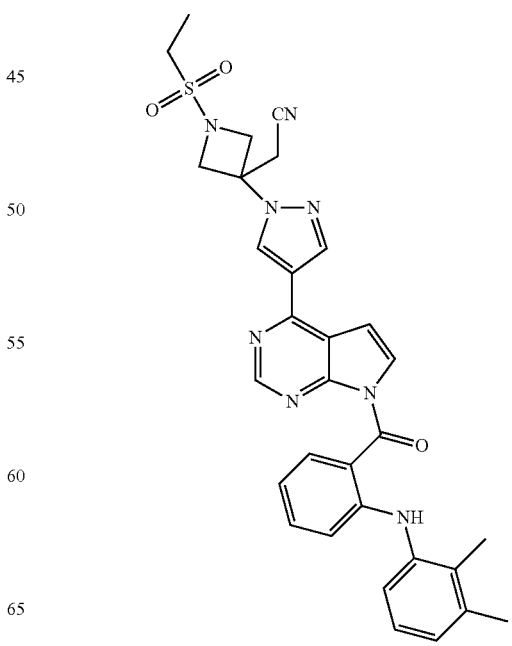

-continued

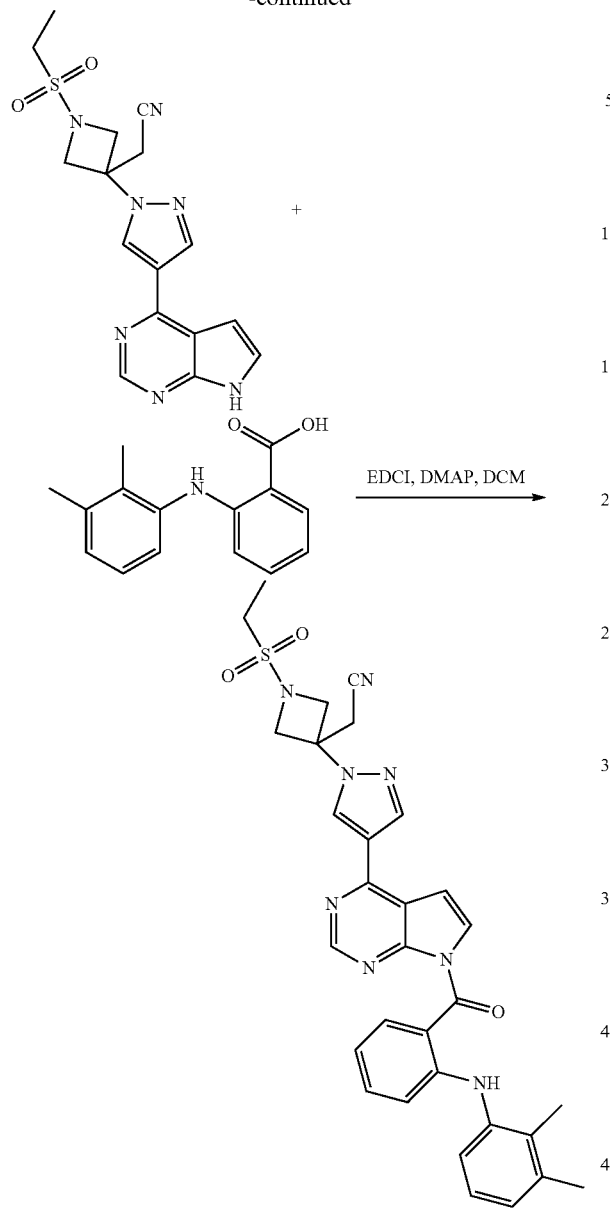

Synthesis of 2-(3-(4-(7-(2-((2, 3-dimethylphenyl) amino) benzoyl)-7H-pyrrolo [2, 3-d] pyrimidin-4-yl)-1H-pyrazol-1-yl)-1-(ethylsulfonyl) azetidin-3-yl) acetonitrile 1-(Ethylsulfonyl)-3-[4-(7H-pyrrolo [2, 3-d] pyrimidin-4-yl)-1H-pyrazol-1-yl]-3-azetidine acetonitrile (baricitinib, 371 mg, 1 mmol), 4-dimethylamino pyridine (DMAP, 12 mg, 0.1 mmol), 2-((2, 3-dimethylphenyl) amino) benzoic acid (mefenamic acid, 289 mg, 1.2 mmol), and 1-(3-dimethylaminopropyl)-3-ethylcarbodiimide hydrochloride (EDCI, 289 mg, 1.5 mmol) were dissolved in dichloromethane (10 mL) and stirred at room temperature for 24 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further purified by silica gel column chromatography (petroleum ether/ethyl acetate=10:1 to 1:1) to give the title compound as a yellow solid, 0.25 g, 42% yield. MS (m/z): [M+H]$^+$ calcd for $C_{31}H_{30}N_8O_3S$, 595.22; found, 595.2. $^1$H NMR (400 MHz, DMSO-d$_6$) δ 9.01 (s, 1H), 8.76 (s, 1H), 8.53 (s, 1H), 8.44 (s, 1H), 7.90 (d, J=4.1 Hz, 1H), 7.42 (ddd, J=12.4, 6.6, 3.0 Hz, 3H), 7.08-6.99 (m, 2H), 6.94 (dd, J=5.6, 3.2 Hz, 1H), 6.91-6.75 (m, 2H), 4.62 (d, J=9.1 Hz, 2H), 4.26 (d, J=9.1 Hz, 2H), 3.71 (s, 2H), 3.24 (q, J=7.3 Hz, 2H), 2.23 (s, 3H), 1.97 (s, 3H), 1.25 (t, J=7.5 Hz, 3H).

Example 48

4-(((3R, 4R)-1-(2-cyanoacetyl)-4-methylpiperidin-3-yl) (methyl) amino)-7H-pyrrolo [2, 3-d] pyrimidin-7-yl) methyl (S)-2-(6-methoxynaphthalen-2-yl) propanoate

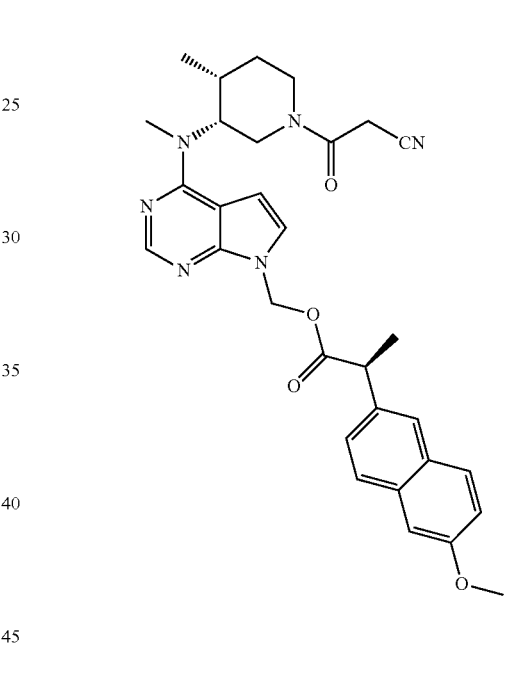

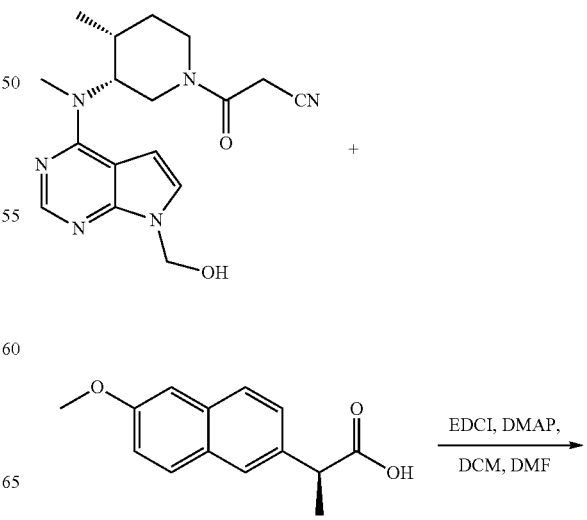

353

-continued

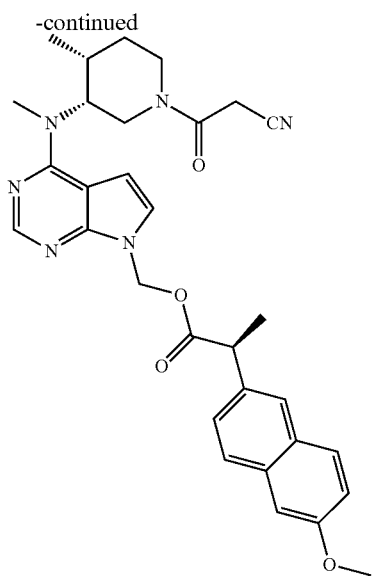

Synthesis of 4-(((3R, 4R)-1-(2-cyanoacetyl)-4-methylpiperidin-3-yl) (methyl) amino)-7H-pyrrolo [2, 3-d]pyrimidin-7-yl) methyl (S)-2-(6-methoxynaphthalen-2-yl) propanoate 3-((3R, 4R)-3-((7-(hydroxymethyl)-7H-pyrrolo [2, 3-d] pyrimidin-4-yl) (methyl) amino)-4-methylpiperidin-1-yl)-3-oxopropanenitrile (170 mg, 0.5 mmol), 4-dimethylaminopyridine (DMAP, 61 mg, 0.5 mmol), (S)-(+)-2-(6-methoxy-2-naphthyl) propanoic acid (naproxen, 170 mg, 0.75 mmol) and 1-(3-dimethylaminopropyl)-3-ethylcarbodiimide hydrochloride (EDCI, 144 mg, 0.75 mmol) were dissolved in a mixed solvent of dichloromethane (8.5 mL) and dimethylformamide (0.3 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=5:1 to 1:1) to give the title compound as a white solid, 0.107 g, 38.6% yield. MS (m/z): [M+H]$^+$ calcd for $C_{31}H_{34}N_6O_4$, 555.26; found, 555.3. $^1$H NMR (400 MHz, Chloroform-d) δ 8.31 (d, J=4.1 Hz, 1H), 7.69-7.49 (m, 3H), 7.32 (dt, J=8.6, 2.5 Hz, 1H), 7.20-7.02 (m, 3H), 6.47 (d, J=3.8 Hz, 1H), 6.22-6.06 (m, 2H), 5.10 (d, J=8.2 Hz, 1H), 4.06 (dd, J=13.4, 4.5 Hz, 1H), 3.91 (s, 3H), 3.88-3.66 (m, 2H), 3.66-3.44 (m, 4H), 3.34 (d, J=11.5 Hz, 3H), 2.49 (dt, J=20.2, 6.2 Hz, 1H), 1.99-1.83 (m, 1H), 1.81-1.65 (m, 1H), 1.54 (d, J=7.1 Hz, 3H), 1.08 (dd, J=9.5, 7.0 Hz, 3H).

354

Example 49

(4-(((3R, 4R)-1-(2-cyanoacetyl)-4-methylpiperidin-3-yl) (methyl) amino)-7H-pyrrolo [2, 3-d] pyrimidin-7-yl) methyl 2-(3-benzoylphenyl) propanoate

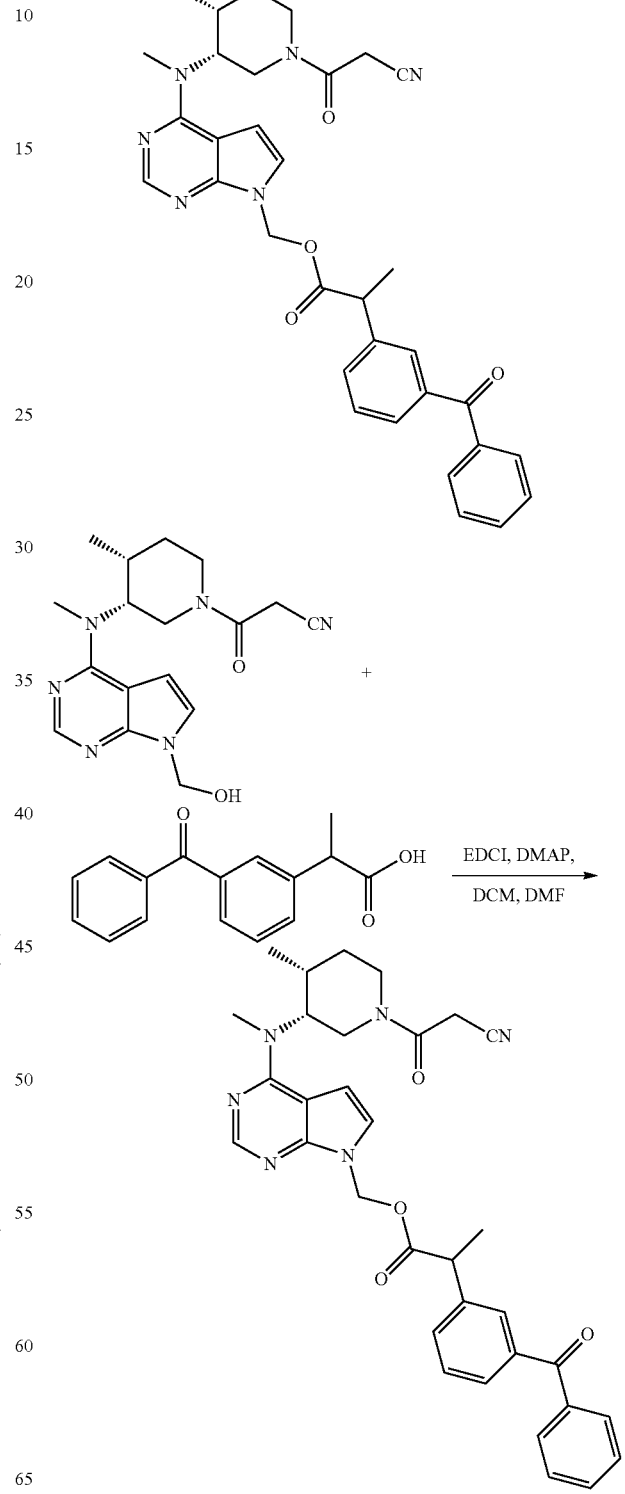

Synthesis of (4-(((3R, 4R)-1-(2-cyanoacetyl)-4-methylpiperidin-3-yl) (methyl) amino)-7H-pyrrolo [2, 3-d]pyrimidin-7-yl) methyl 2-(3-benzoylphenyl) propanoate 3-((3R, 4R)-3-((7-(hydroxymethyl)-7H-pyrrolo [2, 3-d] pyrimidin-4-yl) (methyl) amino)-4-methylpiperidin-1-yl)-3-oxopropanenitrile (170 mg, 0.5 mmol), 4-dimethylamino pyridine (DMAP, 61 mg, 0.5 mmol), 2-(3-benzoylphenyl) propanoic acid (ketoprofen, 191 mg, 1.5 mmol) and 1-(3-dimethylaminopropyl)-3-ethylcarbodiimide hydrochloride (EDCI, 144 mg, 0.75 mmol) was dissolved in a mixed solvent of dichloromethane (8.5 mL) and dimethylformamide (0.3 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=2:1 to 1:1) to give the title compound as a white solid, 0.153 g, 52.9% yield. MS (m/z): [M+H]$^+$ calcd for $C_{33}H_{34}N_6O_4$, 579.26; found, 579.3. $^1$H NMR (400 MHz, Chloroform-d) δ 8.29 (d, J=4.5 Hz, 1H), 7.78-7.69 (m, 2H), 7.68-7.54 (m, 3H), 7.51-7.42 (m, 3H), 7.36 (td, J=7.6, 2.1 Hz, 1H), 7.10-7.01 (m, 1H), 6.52-6.42 (m, 1H), 6.21-6.10 (m, 2H), 5.10 (dt, J=9.0, 4.7 Hz, 1H), 4.09-3.72 (m, 3H), 3.67-3.43 (m, 4H), 3.35 (dd, J=13.1, 4.9 Hz, 3H), 2.56-2.41 (m, 1H), 2.00-1.85 (m, 1H), 1.80-1.71 (m, 1H), 1.50 (d, J=7.2 Hz, 3H), 1.07 (dd, J=10.5, 7.1 Hz, 3H).

Example 50

(4-(((3R, 4R)-1-(2-cyanoacetyl)-4-methylpiperidin-3-yl) (methyl) amino)-7H-pyrrolo [2, 3-d] pyrimidin-7-yl) methyl 2-(2-fluoro-[1, 1'-biphenyl]-4-yl) propanoate

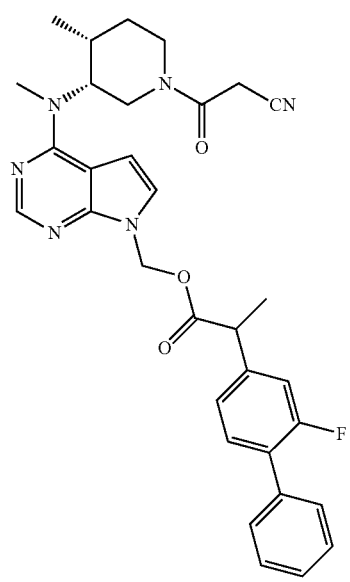 [SMILES: CC(C(=O)OCn1ccc2c(N(C)[C@H]3CN(C(=O)CC#N)CC[C@H]3C)ncnc21)c1ccc(-c2ccccc2)c(F)c1]

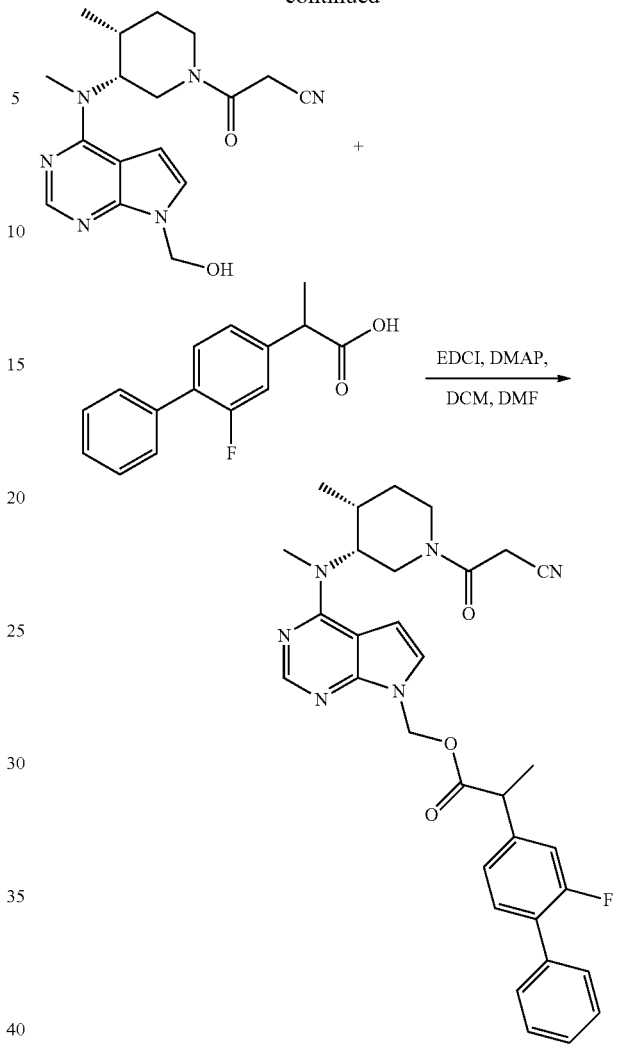

Synthesis of (4-(((3R, 4R)-1-(2-cyanoacetyl)-4-methylpiperidin-3-yl) (methyl) amino)-7H-pyrrolo [2, 3-d]pyrimidin-7-yl) methyl 2-(2-fluoro-[1, 1'-biphenyl]-4-yl) propanoate 3-((3R, 4R)-3-((7-(hydroxymethyl)-7H-pyrrolo [2, 3-d] pyrimidin-4-yl) (methyl) amino)-4-methylpiperidin-1-yl)-3-oxopropanenitrile (170 mg, 0.5 mmol), 4-dimethylamino pyridine (DMAP, 61 mg, 0.5 mmol), 2-(2-fluoro-4-biphenyl) propanoic acid (flurbiprofen, 183 mg, 0.75 mmol) and 1-(3-dimethylaminopropyl)-3-ethylcarbodiimide hydrochloride (EDCI, 144 mg, 0.75 mmol) was dissolved in dichloromethane (8.5 mL) and dimethylformamide (0.3 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=2:1 to 1:1) to give the title compound as a white solid, 0.083 g, 29.2% yield. MS (m/z): [M+H]$^+$ calcd for $C_{32}H_{33}FN_6O_3$, 569.26; found, 569.3. $^1$H NMR (400 MHz, Chloroform-d) δ 8.31 (d, J=2.2 Hz, 1H), 7.53-7.47 (m, 2H), 7.46-7.40 (m, 2H), 7.39-7.28 (m, 2H), 7.16-7.09 (m, 1H), 7.08-6.85 (m, 2H), 6.51 (q, J=3.3 Hz, 1H), 6.23-6.10 (m, 2H), 5.09 (s, 1H), 4.08-3.69 (m, 4H), 3.67-3.33 (m, 6H), 2.55-2.37 (m, 1H), 1.99-1.81 (m, 1H), 1.80-1.71 (m, 1H), 1.49 (dd, J=7.3, 2.6 Hz, 3H), 1.10-1.00 (m, 3H).

Example 51

(4-(((3R, 4R)-1-(2-cyanoacetyl)-4-methylpiperidin-3-yl) (methyl) amino)-7H-pyrrolo [2, 3-d] pyrimidin-7-yl) methyl 2-(2-((2, 6-dichlorophenyl) amino) phenyl) acetate

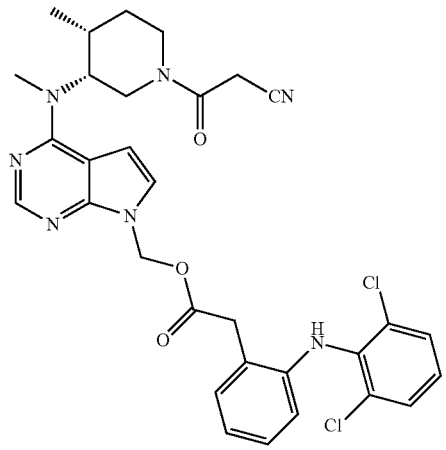 [SMILES: C[C@@H]1CCN(C(=O)CC#N)C[C@@H]1N(C)c1ncnc2c1ccn2COC(=O)Cc1ccccc1Nc1c(Cl)cccc1Cl]

+

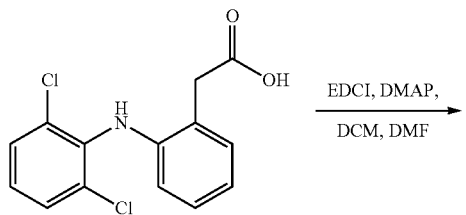

EDCI, DMAP,
DCM, DMF
→

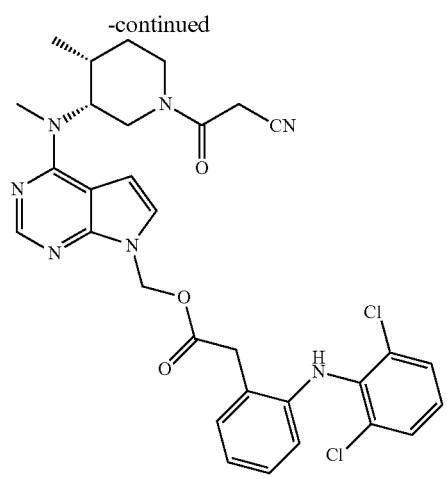

Synthesis of (4-(((3R, 4R)-1-(2-cyanoacetyl)-4-methylpiperidin-3-yl) (methyl) amino)-7H-pyrrolo [2, 3-d]pyrimidin-7-yl) methyl 2-(2-((2, 6-dichlorophenyl) amino) phenyl) acetate 3-((3R, 4R)-3-((7-(hydroxymethyl)-7H-pyrrolo [2, 3-d] pyrimidin-4-yl) (methyl) amino)-4-methylpiperidin-1-yl)-3-oxopropanenitrile (170 mg, 0.5 mmol), 4-dimethylamino pyridine (DMAP, 61 mg, 0.5 mmol), 2-(2, 6-dichloroanilino) phenylacetic acid (diclofenac, 222 mg, 0.75 mmol) and 1-(3-dimethylaminopropyl)-3-ethylcarbodiimide hydrochloride (EDCI, 144 mg, 0.75 mmol) was dissolved in dichloromethane (8.5 mL) and dimethylformamide (0.3 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=2:1 to 1:1) to give the title compound as a white solid, 0.106 g, 34.2% yield. MS (m/z): [M+H]$^+$ calcd for $C_{31}H_{31}Cl_2N_7O_3$, 620.19; found, 620.3. $^1$H NMR (400 MHz, Chloroform-d) δ 8.34 (d, J=8.2 Hz, 1H), 7.32 (dd, J=8.1, 1.8 Hz, 2H), 7.18 (dd, J=7.5, 1.7 Hz, 1H), 7.12 (dd, J=9.3, 5.7 Hz, 2H), 6.96 (dt, J=15.1, 7.8 Hz, 2H), 6.64 (d, J=9.4 Hz, 1H), 6.53 (dq, J=7.6, 3.3 Hz, 2H), 6.23 (d, J=3.9 Hz, 2H), 5.13 (s, 1H), 4.10-3.56 (m, 6H), 3.52 (t, J=7.6 Hz, 2H), 3.39 (s, 1H), 3.34 (s, 2H), 2.50 (ddd, J=19.4, 9.7, 4.0 Hz, 1H), 1.99-1.83 (m, 1H), 1.76 (dq, J=17.7, 3.9, 3.2 Hz, 1H), 1.09 (dd, J=13.9, 7.1 Hz, 3H).

Example 52

(4-(((3R, 4R)-1-(2-cyanoacetyl)-4-methylpiperidin-3-yl) (methyl) amino)-7H-pyrrolo [2, 3-d] pyrimidin-7-yl) methyl 2-(3-phenoxyphenyl) propanoate

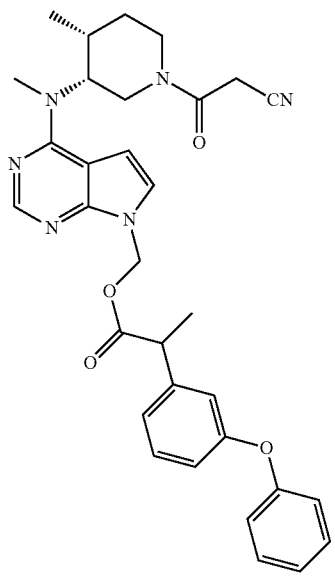 [SMILES: CC(C(=O)OCn1ccc2c(N(C)[C@H]3CN(C(=O)CC#N)CC[C@H]3C)ncnc21)c1cccc(Oc2ccccc2)c1]

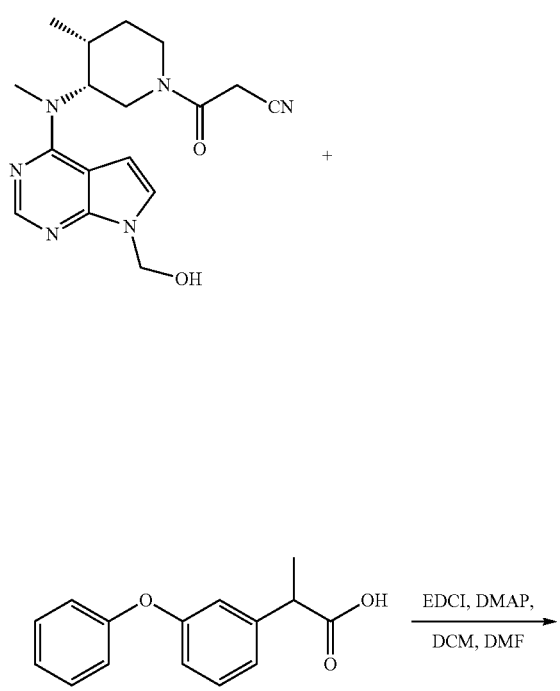

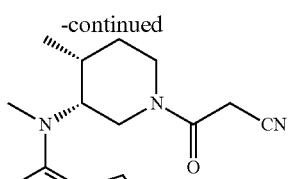

Synthesis of (4-(((3R, 4R)-1-(2-cyanoacetyl)-4-methylpiperidin-3-yl) (methyl) amino)-7H-pyrrolo [2, 3-d]pyrimidin-7-yl) methyl 2-(3-phenoxyphenyl) propanoate 3-((3R, 4R)-3-((7-(hydroxymethyl)-7H-pyrrolo [2, 3-d] pyrimidin-4-yl) (methyl) amino)-4-methylpiperidin-1-yl)-3-oxopropanenitrile (170 mg, 0.5 mmol), 4-dimethylamino pyridine (DMAP, 61 mg, 0.5 mmol), 2-(3-phenoxyphenyl) propanoic acid (fenoprofen, 182 mg, 0.75 mmol) and 1-(3-dimethylaminopropyl)-3-ethylcarbodiimide hydrochloride (EDCI, 144 mg, 0.75 mmol) was dissolved in dichloromethane (8.5 mL) and dimethylformamide (0.3 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=2:1 to 1:1) to give the title compound as a white solid, 0.13 g, 45.9% yield. MS (m/z): [M+H]$^+$ calcd for $C_{32}H_{34}N_6O_4$, 567.26; found, 567.3. $^1$H NMR (400 MHz, Chloroform-d) δ 8.32 (d, J=6.6 Hz, 1H), 7.32 (t, J=7.8 Hz, 2H), 7.20 (td, J=7.9, 2.2 Hz, 1H), 7.13-7.05 (m, 2H), 6.96 (d, J=7.2 Hz, 3H), 6.92-6.87 (m, 1H), 6.83 (d, J=8.2 Hz, 1H), 6.51 (t, J=3.1 Hz, 1H), 6.21-6.07 (m, 2H), 5.11 (dp, J=9.4, 4.8, 4.4 Hz, 1H), 4.10-3.65 (m, 3H), 3.63-3.49 (m, 3H), 3.47-3.41 (m, 1H), 3.40-3.31 (m, 3H), 2.48 (dp, J=25.5, 6.1 Hz, 1H), 1.94 (dt, J=9.4, 4.6 Hz, 1H), 1.80-1.66 (m, 1H), 1.45 (d, J=7.2 Hz, 3H), 1.08 (dd, J=12.3, 7.1 Hz, 3H).

Example 53

(4-(((3R, 4R)-1-(2-cyanoacetyl)-4-methylpiperidin-3-yl) (methyl) amino)-7H-pyrrolo [2, 3-d] pyrimidin-7-yl) methyl 2-(4-((2-oxocyclopentyl) methyl) phenyl) propanoate

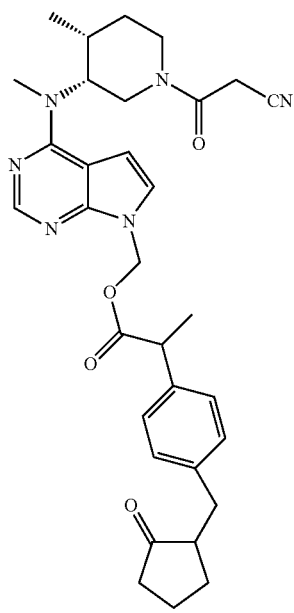 [SMILES: CC(C(=O)OCn1ccc2c(N(C)[C@H]3CN(C(=O)CC#N)CC[C@H]3C)ncnc21)c1ccc(CC2CCCC2=O)cc1]

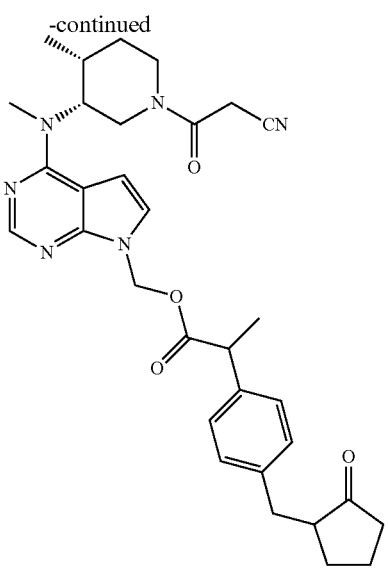

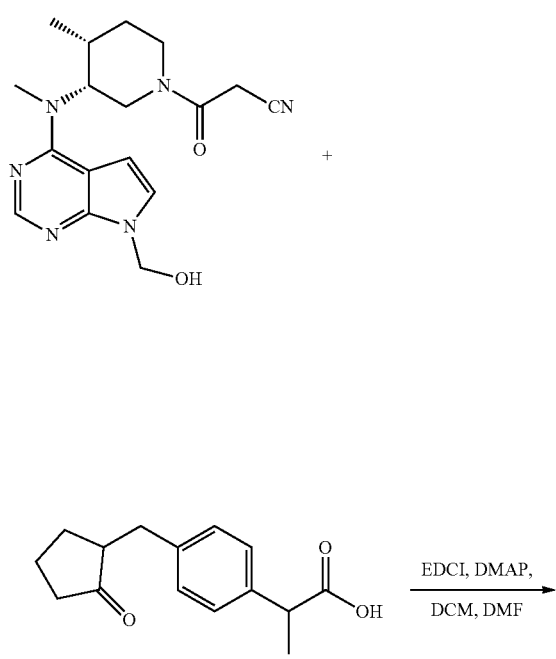

Synthesis of (4-(((3R, 4R)-1-(2-cyanoacetyl)-4-methylpiperidin-3-yl) (methyl) amino)-7H-pyrrolo [2, 3-d]pyrimidin-7-yl) methyl 2-(4-((2-oxocyclopentyl) methyl) phenyl) propanoate 3-((3R, 4R)-3-((7-(hydroxymethyl)-7H-pyrrolo [2, 3-d] pyrimidin-4-yl) (methyl) amino)-4-methylpiperidin-1-yl)-3-oxopropanenitrile (170 mg, 0.5 mmol), 4-dimethylamino pyridine (DMAP, 61 mg, 0.5 mmol), 2-[4-(2-oxocyclopentan-1-ylmethyl) phenyl] propanoic acid (loxoprofen, 185 mg, 0.75 mmol) and 1-(3-dimethylaminopropyl)-3-ethylcarbodiimide hydrochloride (EDCI, 144 mg, 0.75 mmol) were dissolved in dichloromethane (8.5 mL) and dimethylformamide (0.3 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=2:1 to 1:1) to give the title compound as a white solid, 0.08 g, 28% yield. MS (m/z): [M+H]$^+$ calcd for $C_{32}H_{38}N_6O_4$, 571.30; found, 571.3. $^1$H NMR (400 MHz, Chloroform-d) δ 8.34-8.27 (m, 1H), 7.11 (tt, J=9.3, 7.5, 3.4 Hz, 3H), 7.04 (dt, J=8.3, 2.9 Hz, 2H), 6.51 (s, 1H), 6.17 (dd, J=10.5, 4.6 Hz, 1H), 6.10 (dt, J=10.6, 2.8 Hz, 1H), 5.12 (qd, J=8.6, 5.0 Hz, 1H), 4.11-3.57 (m, 5H), 3.50 (q, J=9.1, 7.3 Hz, 3H), 3.40 (d, J=2.2 Hz, 1H), 3.14-3.02 (m, 1H), 2.49 (ddd, J=23.3, 11.0, 4.9 Hz, 2H), 2.33 (dd, J=17.7, 8.4 Hz, 2H), 2.16-2.01 (m, 2H), 1.95 (tdd, J=11.1, 5.8, 2.8 Hz, 2H), 1.83-1.60 (m, 3H), 1.58-1.47 (m, 1H), 1.44 (dd, J=7.2, 1.8 Hz, 3H), 1.08 (t, J=7.2 Hz, 3H).

363

Example 54

(3R)-3-cyclopentyl-3-(4-(7-(2-(3-phenoxyphenyl) propanoyl)-7H-pyrrolo [2, 3-d] pyrimidin-4-yl)-1H-pyrazol-1-yl) propanenitrile

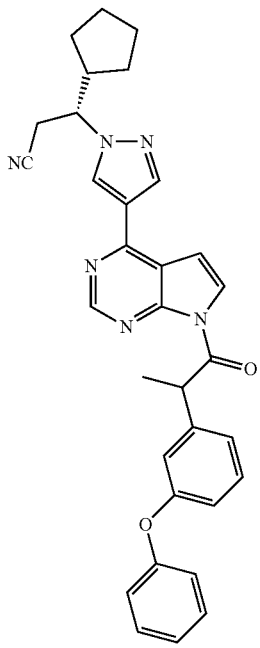 [SMILES: CC(C(=O)n1ccc2c(-c3cnn([C@H](CC#N)C4CCCC4)c3)ncnc21)c1cccc(Oc2ccccc2)c1]

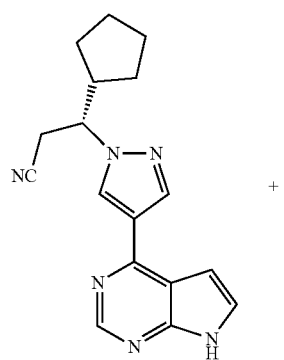 +

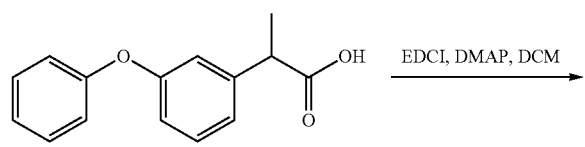

364

-continued

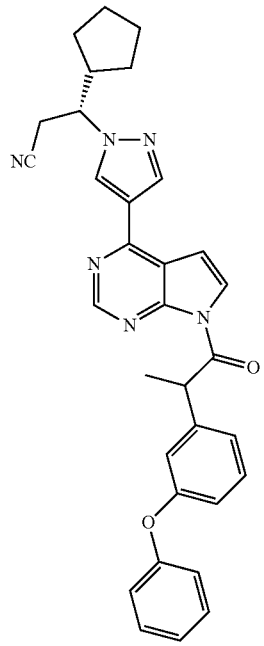

Synthesis of (3R)-3-cyclopentyl-3-(4-(7-(2-(3-phenoxyphenyl) propanoyl)-7H-pyrrolo [2, 3-d] pyrimidin-4-yl)-1H-pyrazol-1-yl) propanenitrile (R)-3-(4-(7h-pyrrolo [2, 3-d] pyridin-4-yl)-1h-pyrazol-1-yl)-3-cyclopentylpropane (Ruxolitinib, 184 mg, 0.6 mmol), 4-dimethylamino pyridine (DMAP, 7 mg, 0.06 mmol), 2-(3-phenoxyphenyl) propanoic acid (fenoprofen, 189 mg, 0.78 mmol) and 1-(3-dimethylaminopropyl)-3-ethylcarbodiimide hydrochloride (EDCI, 173 mg, 0.9 mmol) were dissolved in dichloromethane (10 mL) and stirred at room temperature for 2 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=5:1 to 3:1) to give the title compound as a white solid, 0.2 g, 62.8% yield. MS (m/z): [M+H]$^+$ calcd for $C_{32}H_{30}N_6O_2$, 531.24; found, 531.2. $^1$H NMR (400 MHz, DMSO-d$_6$) δ 8.86 (d, J=13.5 Hz, 2H), 8.41 (s, 1H), 8.09 (d, J=4.2 Hz, 1H), 7.40-7.26 (m, 4H), 7.20-7.09 (m, 2H), 7.07 (t, J=2.1 Hz, 1H), 6.91 (d, J=8.0 Hz, 2H), 6.84 (dd, J=8.1, 2.5 Hz, 1H), 5.96 (q, J=6.9 Hz, 1H), 4.54 (td, J=9.6, 4.2 Hz, 1H), 3.29-3.15 (m, 2H), 2.42 (p, J=8.5 Hz, 1H), 1.82 (dtd, J=12.1, 7.4, 3.8 Hz, 1H), 1.66-1.40 (m, 7H), 1.37-1.18 (m, 3H).

Example 55

(4-(((3R, 4R)-1-(2-cyanoacetyl)-4-methylpiperidin-3-yl) (methyl) amino)-7H-pyrrolo [2, 3-d] pyrimidin-7-yl) methyl 2-(1-(4-chlorobenzoyl)-5-methoxy-2-methyl-1H-indol-3-yl) acetate

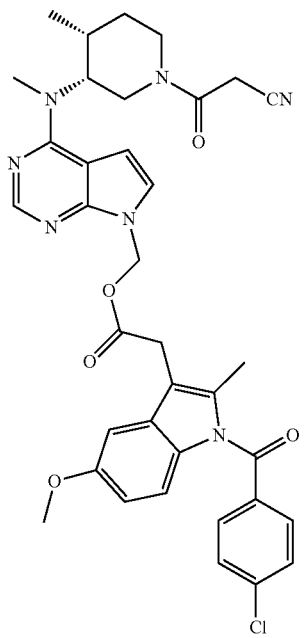

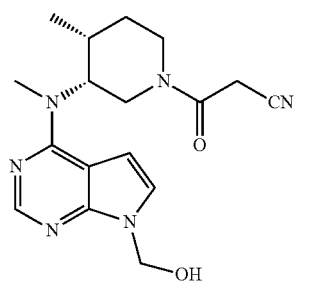

+

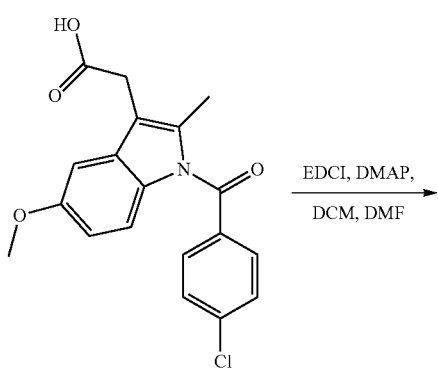

EDCI, DMAP,
DCM, DMF
→

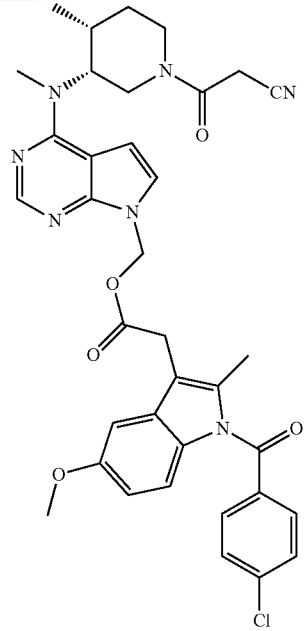 [SMILES: COc1ccc2c(c1)c(CC(=O)OCn1ccc3c(N(C)[C@H]4CN(C(=O)CC#N)CC[C@H]4C)ncnc31)c(C)n2C(=O)c1ccc(Cl)cc1]

Synthesis of (4-(((3R, 4R)-1-(2-cyanoacetyl)-4-methylpiperidin-3-yl) (methyl) amino)-7H-pyrrolo [2, 3-d]pyrimidin-7-yl) methyl 2-(1-(4-chlorobenzoyl)-5-methoxy-2-methyl-1H-indol-3-yl) acetate 3-((3R, 4R)-3-((7-(hydroxymethyl)-7H-pyrrolo [2, 3-d] pyrimidin-4-yl) (methyl) amino)-4-methylpiperidin-1-yl)-3-oxopropanenitrile (170 mg, 0.5 mmol), 4-dimethylamino pyridine (DMAP, 61 mg, 0.5 mmol), 1-(4-chlorobenzoyl)-5-methoxy-2-methyl-1H-indole-3-acetic acid (indomethacin, 277 mg, 0.75 mmol) and 1-(3-dimethylaminopropyl)-3-ethylcarbodiimide hydrochloride (EDCI, 144 mg, 0.75 mmol) were dissolved in dichloromethane (8.5 mL) and dimethylformamide (0.3 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further purified by silica gel column chromatography (petroleum ether/ethyl acetate=2:1 to 1:1) to give the title compound as a light yellow solid, 0.036 g, 10.5% yield. MS (m/z): [M+H]$^+$ calcd for $C_{36}H_{36}C_1N_7O_5$, 682.25; found, 682.3. $^1$H NMR (400 MHz, Chloroform-d) δ 8.32 (s, 1H), 7.68-7.59 (m, 2H), 7.51-7.43 (m, 2H), 7.09 (d, J=3.8 Hz, 1H), 6.91-6.78 (m, 2H), 6.65 (dd, J=9.0, 2.4 Hz, 1H), 6.50 (dd, J=8.2, 3.8 Hz, 1H), 6.19 (s, 2H), 5.19-5.09 (m, 1H), 4.10-3.73 (m, 6H), 3.70-3.56 (m, 4H), 3.55-3.45 (m, 3H), 3.39 (s, 1H), 2.58-2.42 (m, 1H), 2.29 (d, J=10.3 Hz, 3H), 2.03-1.85 (m, 1H), 1.81-1.73 (m, 1H), 1.09 (dd, J=11.4, 7.1 Hz, 3H).

Example 56

(4-(((3R, 4R)-1-(2-cyanoacetyl)-4-methylpiperidin-3-yl) (methyl) amino)-7H-pyrrolo [2, 3-d] pyrimidin-7-yl) methyl 2-acetoxybenzoate

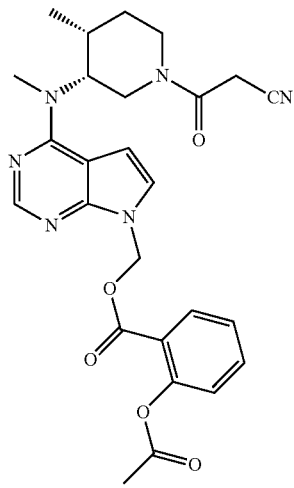 [SMILES: CC(=O)Oc1ccccc1C(=O)OCn1ccc2c(N(C)[C@H]3CN(C(=O)CC#N)CC[C@H]3C)ncnc21]

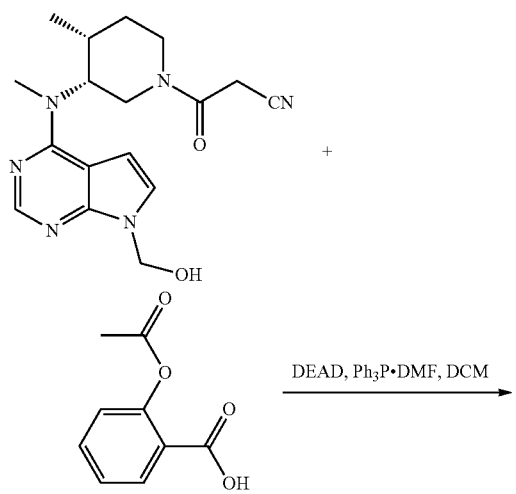

Synthesis of (4-(((3R, 4R)-1-(2-cyanoacetyl)-4-methylpiperidin-3-yl) (methyl) amino)-7H-pyrrolo [2, 3-d]pyrimidin-7-yl) methyl 2-acetoxybenzoate 3-((3R, 4R)-3-((7-(hydroxymethyl)-7H-pyrrolo [2, 3-d] pyrimidin-4-yl) (methyl) amino)-4-methylpiperidin-1-yl)-3-oxopropanenitrile (170 mg, 0.5 mmol), 4-dimethylamino pyridine (DMAP, 61 mg, 0.5 mmol), 2-acetoxybenzoic acid (aspirin, 135 mg, 0.75 mmol) and 1-(3-dimethylaminopropyl)-3-ethylcarbodiimide hydrochloride (EDCI, 144 mg, 0.75 mmol) was dissolved in dichloromethane (8.5 mL) and dimethylformamide (0.3 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further purified by silica gel column chromatography (petroleum ether/ethyl acetate=2:1 to 1:1) to give the title compound as a light yellow solid, 0.178 g, 70.6% yield. MS (m/z): [M+H]$^+$ calcd for $C_{26}H_{28}N_6O_5$, 505.21; found, 505.3. $^1$H NMR (400 MHz, Chloroform-d) δ 8.34 (d, J=6.5 Hz, 1H), 8.01 (d, J=7.9 Hz, 1H), 7.60-7.50 (m, 1H), 7.31-7.18 (m, 2H), 7.07 (d, J=8.1 Hz, 1H), 6.57 (d, J=3.8 Hz, 1H), 6.37 (d, J=2.6 Hz, 2H), 5.12 (tt, J=8.3, 4.6 Hz, 1H), 4.25-3.98 (m, 1H), 3.80 (ddt, J=13.2, 8.8, 4.7 Hz, 1H), 3.62-3.50 (m, 3H), 3.37 (d, J=15.2 Hz, 3H), 2.49 (dp, J=24.6, 6.0 Hz, 1H), 2.25 (d, J=12.7 Hz, 3H), 1.93 (dtt, J=17.8, 9.0, 4.5 Hz, 2H), 1.74 (dtt, J=17.9, 7.6, 3.5 Hz, 1H), 1.08 (dd, J=13.2, 7.0 Hz, 3H).

Example 57

(R)-3-(4-(7-(2-((3-chloro-2-methylphenyl) amino) benzoyl)-7H-pyrrolo [2, 3-d] pyrimidin-4-yl)-1H-pyrazol-1-yl)-3-cyclopentylpropanenitrile

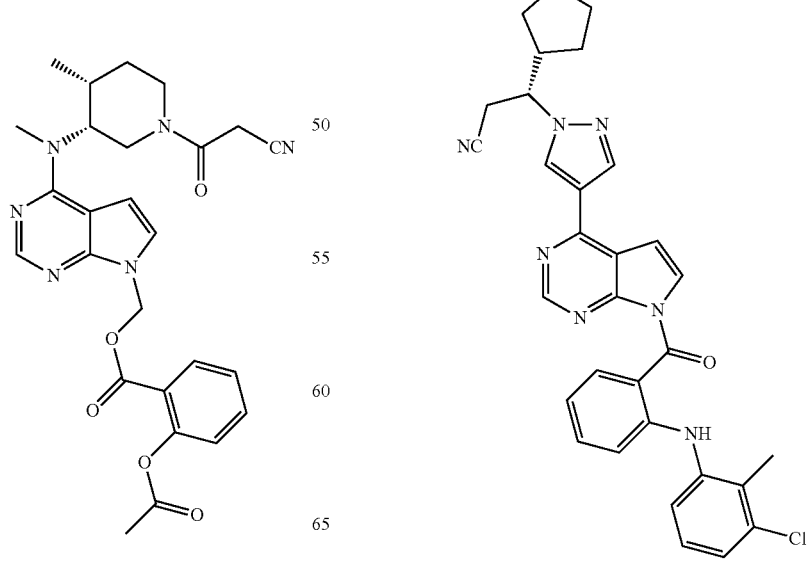

-continued

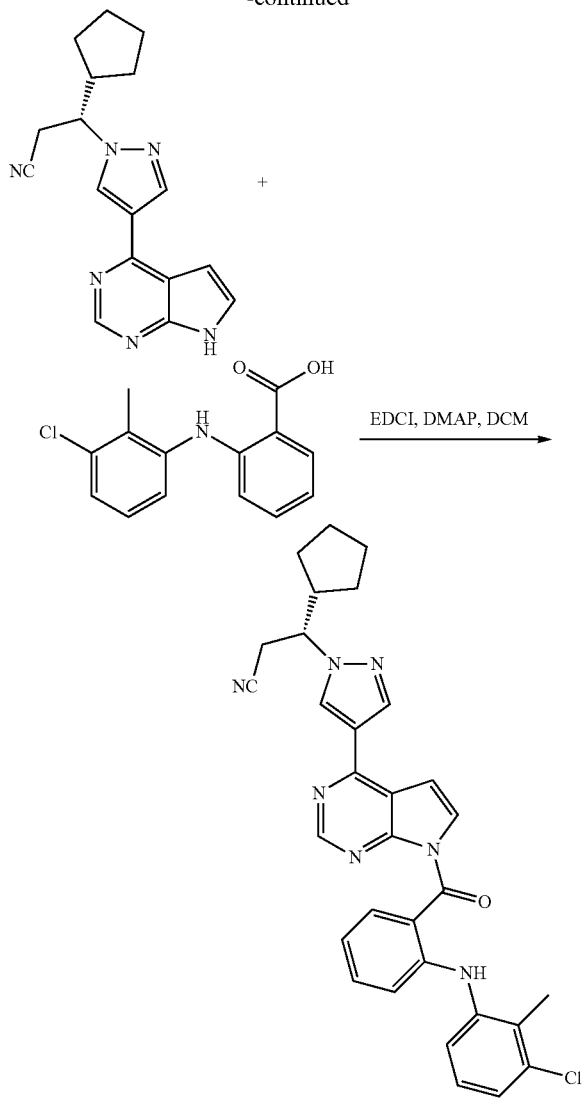

Synthesis of (R)-3-(4-(7-(2-((3-chloro-2-methylphenyl) amino) benzoyl)-7H-pyrrolo [2, 3-d] pyrimidin-4-yl)-1H-pyrazol-1-yl)-3-cyclopentylpropanenitrile (R)-3-(4-(7h-pyrrolo [2, 3-d] pyridin-4-yl)-1h-pyrazol-1-yl)-3-cyclopentylpropane (Ruxolitinib, 306 mg, 1 mmol), 4-dimethylamino pyridine (DMAP, 12 mg, 0.1 mmol), 2-((3-chloro-2-methylphenyl) amino) benzoic acid (tolfenamic acid, 261 mg, 1 mmol) and 1-(3-dimethylaminopropyl)-3-ethylcarbodiimide hydrochloride (EDCI, 289 mg, 1.5 mmol) were dissolved in dichloromethane (10 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further purified by silica gel column chromatography (petroleum ether/ethyl acetate=5:1 to 1:1) to give the title compound as a yellow solid, 0.26 g, 47.3% yield. MS (m/z): [M+H]$^+$ calcd for $C_{31}H_{28}C_1N_7O$, 550.20; found, 550.1. $^1$H NMR (400 MHz, DMSO-d$_6$) δ 8.87 (s, 1H), 8.70 (s, 1H), 8.41 (s, 1H), 8.23 (s, 1H), 7.80 (d, J=4.1 Hz, 1H), 7.49 (t, J=7.7 Hz, 2H), 7.27 (d, J=4.1 Hz, 1H), 7.12-7.00 (m, 3H), 7.00-6.91 (m, 2H), 4.55 (td, J=9.6, 4.2 Hz, 1H), 3.29-3.17 (m, 2H), 2.43 (p, J=8.5 Hz, 1H), 2.02 (s, 3H), 1.83 (dtd, J=11.9, 7.3, 3.9 Hz, 1H), 1.69-1.42 (m, 4H), 1.41-1.27 (m, 2H), 1.23 (td, J=9.4, 8.7, 2.9 Hz, 1H).

Example 58

N-(4-(2-(4-(methyl ((trans)-4-((N-methylsulfamoyl) methyl) cyclohexyl) amino)-7H-pyrrolo [2, 3-d] pyrimidin-7-yl)-2-oxoethyl) phenyl) acetamide

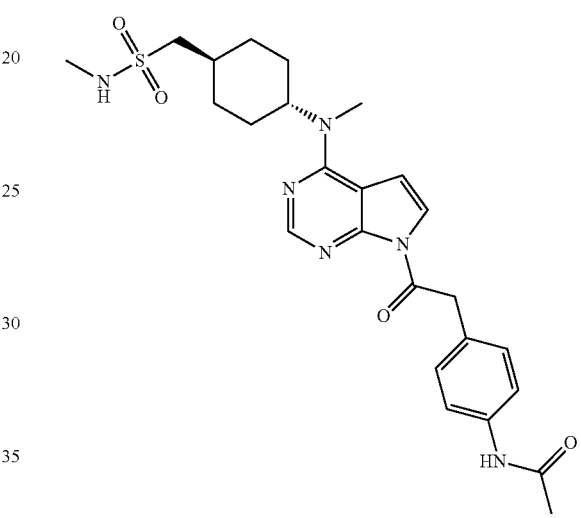

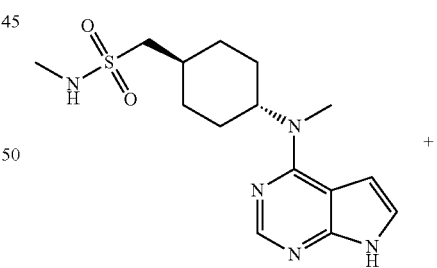

+

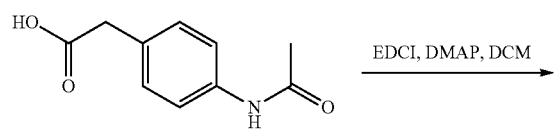

371
-continued

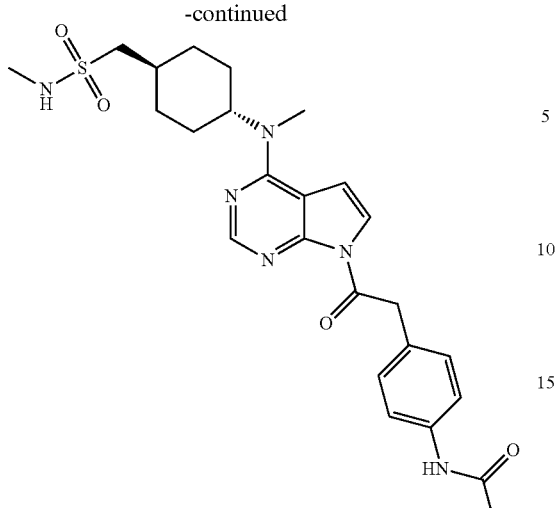

Synthesis of N-(4-(2-(4-(methyl ((trans)-4-((N-methylsulfamoyl) methyl) cyclohexyl) amino)-7H-pyrrolo [2, 3-d] pyrimidin-7-yl)-2-oxoethyl) phenyl) acetamide N-Methyl-1-((trans)-4-(methyl (7H-pyrrolo [2, 3-d] pyrimidin-4-yl) amino) cyclohexyl) methanesulfonamide (oclacitinib, 168 mg, 0.5 mmol), 4-dimethylamino pyridine (DMAP, 61 mg, 0.5 mmol), 2-(4-acetamidophenyl) acetic acid (actarit, 126 mg, 0.65 mmol) and 1-(3-dimethylaminopropyl)-3-ethylcarbodiimide hydrochloride (EDCI, 144 mg, 0.75 mmol) were dissolved in dichloromethane (15 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=2:1 to 0:1) to give the title compound as a white solid, 0.017 g, 6.6% yield. MS (m/z): [M+H]$^+$ calcd for $C_{25}H_{32}N_6O_4S$, 513.22; found, 513.3. $^1$H NMR (400 MHz, DMSO-$d_6$) δ 9.90 (s, 1H), 8.37 (s, 1H), 7.68 (d, J=4.2 Hz, 1H), 7.51 (d, J=8.4 Hz, 2H), 7.25 (d, J=8.4 Hz, 2H), 6.88 (d, J=4.9 Hz, 2H), 4.81 (s, 2H), 4.67 (s, 1H), 3.18 (s, 3H), 2.95 (d, J=6.2 Hz, 2H), 2.59 (d, J=4.9 Hz, 3H), 2.03 (s, 5H), 1.94-1.80 (m, 1H), 1.70 (dd, J=8.6, 3.4 Hz, 4H), 1.37-1.26 (m, 2H).

372
Example 59

(4-(((3R, 4R)-1-(2-cyanoacetyl)-4-methylpiperidin-3-yl) (methyl) amino)-7H-pyrrolo [2, 3-d] pyrimidin-7-yl) methyl 2-(4-acetamidophenyl) acetate

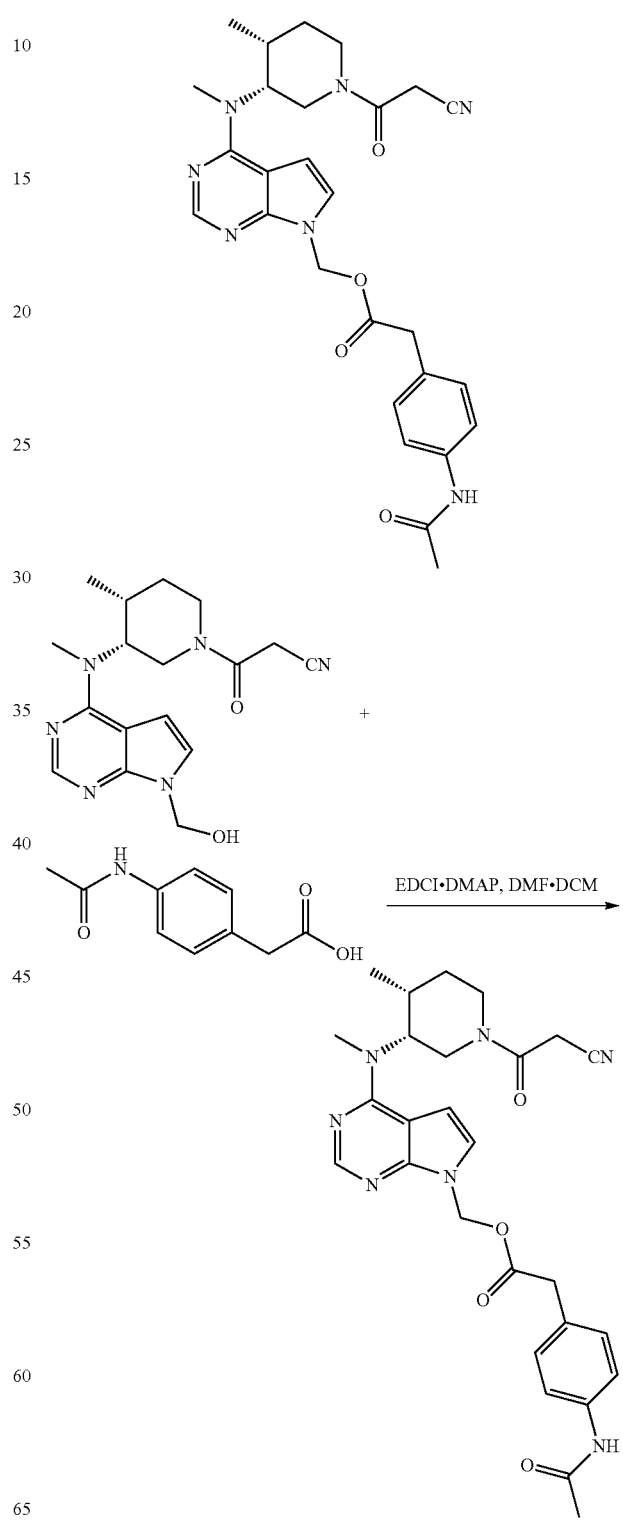

Synthesis of (4-(((3R, 4R)-1-(2-cyanoacetyl)-4-methylpiperidin-3-yl) (methyl) amino)-7H-pyrrolo [2, 3-d]pyrimidin-7-yl) methyl 2-(4-acetamidophenyl) acetate 3-((3R, 4R)-3-((7-(hydroxymethyl)-7H-pyrrolo [2, 3-d] pyrimidin-4-yl) (methyl) amino)-4-methylpiperidin-1-yl)-3-oxopropanenitrile (171 mg, 0.5 mmol), 4-dimethylamino pyridine (DMAP, 61 mg, 0.5 mmol), 2-(4-acetamidophenyl) acetic acid (actarit, 145 mg, 0.75 mmol) and 1-(3-dimethylaminopropyl)-3-ethylcarbodiimide hydrochloride (EDCI, 144 mg, 0.75 mmol) was dissolved in a mixed solvent of dichloromethane (8.5 mL) and N, N-dimethylformamide (0.3 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=150:1 to 50:1) to give the title compound as a white solid, 0.154 g, yield 59.5%. MS (m/z): [M+H]$^+$ calcd for $C_{27}H_{31}N_7O_4$, 518.24; found, 518.3. $^1$H NMR (400 MHz, Chloroform-d) δ 8.33 (d, J=4.2 Hz, 1H), 7.71 (d, J=29.0 Hz, 1H), 7.40 (d, J=8.1 Hz, 2H), 7.10 (dt, J=13.1, 4.8 Hz, 3H), 6.51 (dd, J=8.4, 3.9 Hz, 1H), 6.16 (s, 2H), 5.10 (ft, J=9.2, 4.4 Hz, 1H), 4.10-3.75 (m, 2H), 3.63-3.44 (m, 6H), 3.36 (d, J=18.1 Hz, 3H), 2.55-2.44 (m, 1H), 2.00 (s, 3H), 1.97-1.87 (m, 1H), 1.83-1.67 (m, 1H), 1.09 (t, J=7.5 Hz, 3H).

Example 60

Methyl (4-(1-(3-(cyanomethyl)-1-(ethylsulfonyl) azetidin-3-yl)-1H-pyrazol-4-yl)-7H-pyrrolo [2, 3-d] pyrimidin-7-yl) (S)-2-(4-isobutylphenyl) propanoate

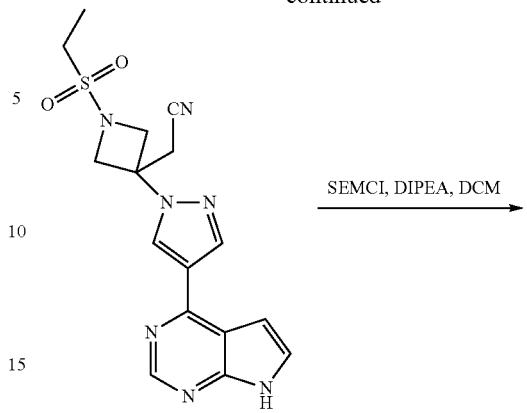

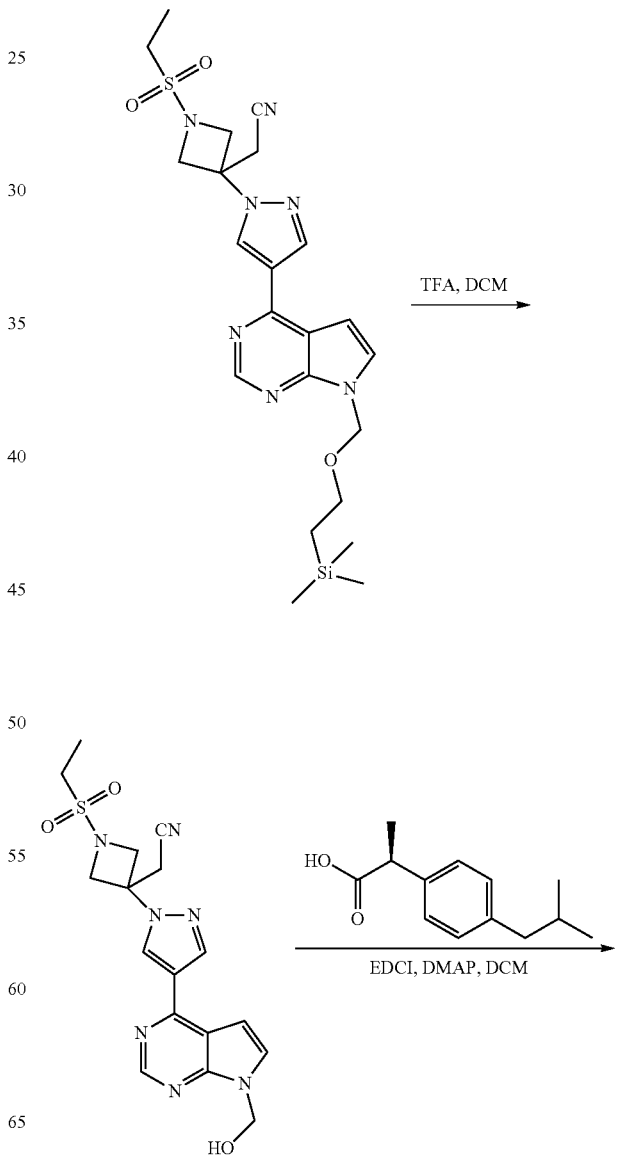

-continued

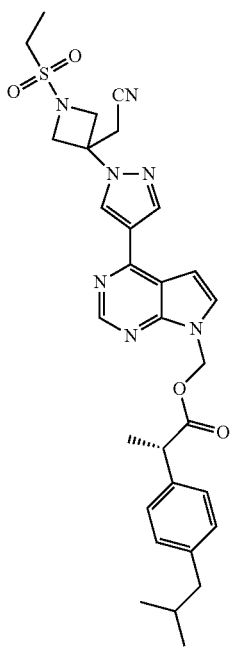

First step: synthesis of 2-(1-(ethylsulfonyl)-3-(4-(7-((2-(trimethylsilyl) ethoxy) methyl)-7H-pyrrolo [2, 3-d]pyrimidin-4-yl)-1H-pyrazol-1-yl) azetidin-3-yl) acetonitrile 1-(Ethylsulfonyl)-3-[4-(7H-pyrrolo [2, 3-d] pyrimidin-4-yl)-1H-pyrazol-1-yl]-3-azetidine acetonitrile (baricitinib, 7420 mg, 20 mmol) and N, N-diisopropylethyl amine (3.12 g, 24 mmol) were dissolved in dichloromethane (200 mL) under nitrogen protection. After stirring at room temperature for half an hour, (2-(chloromethoxy) ethyl) trimethylsilane (4 g, 24 mmol) was added, stirring was continued at room temperature overnight. The solvent was evaporated under reduced pressure to give the crude product. The crude product was further isolated by silica gel column chromatography to give the title compound as a white solid, 5 g, 49% yield. MS (m/z): [M+H]$^+$ calcd for $C_{22}H_{31}N_7O_3SSi$, 502.20; found, 502.3.

Step 2: synthesis of 2-(1-(ethylsulfonyl)-3-(4-(7-(hydroxymethyl)-7H-)) pyrrolo [2, 3-d] pyrimidin-4-yl)-1H-pyrazol-1-yl) azetidin-3-yl) acetonitrile Trifluoroacetic acid (6.44 g, 56.5 mmol) was slowly added dropwise to a solution of 2-(1-(ethylsulfonyl)-3-(4-(7-((2-(trimethylsilyl) ethoxy) methyl)-7H-pyrrolo [2, 3-d] pyrimidin-4-yl)-1H-pyrazol-1-yl) azetidin-3-yl) acetonitrile (5 g, 11.3 mmol) in dichloromethane (100 mL) under nitrogen in an ice-water bath. After half an hour, the ice-water bath was removed and the temperature was raised to room temperature and stirring was continued for 24 hours. Saturated sodium bicarbonate solution was added to the above reaction solution at 0° C. to adjust the pH to 8. Then, the mixture was poured into a separation funnel and separated. The organic layer was washed with a saturated salt water solution, and dried over anhydrous sodium sulfate. After filtration, the solvent was evaporated under reduced pressure to give the title product 3.5 g, 90% yield. MS (m/z): [M+H]$^+$ calcd for $C_{17}H_{19}N_7O_3S$, 402.13; found, 402.3.

Step 3: synthesis of methyl (4-(1-(3-(cyanomethyl)-1-(ethylsulfonyl) azetidin-3-yl)-1H-pyrazol-4-yl)-7H-pyrrolo [2, 3-d] pyrimidin-7-yl) (S)-2-(4-isobutylphenyl) propanoate 2-(1-(Ethylsulfonyl)-3-(4-(7-(hydroxymethyl)-7H-)) pyrrolo [2, 3-d] pyrimidin-4-yl)-1H-pyrazol-1-yl) azetidin-3-yl) acetonitrile (201 mg, 0.5 mmol), 4-dimethylamino pyridine (DMAP, 61 mg, 0.5 mmol), (S)-(+)-2-(4-isobutylphenyl) propanoic acid((S)-(+)-ibuprofen, 123.6 mg, 0.6 mmol) and 1-(3-dimethylaminopropyl)-3-ethylcarbodiimide hydrochloride (EDCI, 144 mg, 0.75 mmol) were dissolved in dichloromethane (10 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=2:1 to 1:1) to give the title compound as a white solid, 0.025 g, 8.4% yield. MS (m/z): [M+H]$^+$ calcd for $C_{30}H_{35}N_7O_4S$, 590.25, found 590.3. $^1$H NMR (400 MHz, DMSO-$d_6$) δ 8.95 (s, 1H), 8.77 (s, 1H), 8.48 (s, 1H), 7.70 (d, J=3.8 Hz, 1H), 7.16 (d, J=3.8 Hz, 1H), 7.06 (d, J=7.8 Hz, 2H), 6.96 (d, J=7.8 Hz, 2H), 6.25 (d, J=3.2 Hz, 2H), 4.60 (d, J=9.1 Hz, 2H), 4.25 (d, J=9.1 Hz, 2H), 3.76 (q, J=7.0 Hz, 1H), 3.69 (s, 2H), 3.24 (q, J=7.3 Hz, 2H), 2.32 (d, J=7.1 Hz, 2H), 1.71 (hept, J=6.7 Hz, 1H), 1.34 (d, J=7.1 Hz, 3H), 1.26 (d, J=7.4 Hz, 3H), 0.77 (d, J=6.5 Hz, 6H).

Example 61

Methyl (4-(1-(3-(cyanomethyl)-1-(ethylsulfonyl) azetidin-3-yl)-1H-pyrazol-4-yl)-7H-pyrrolo [2, 3-d] pyrimidin-7-yl) (S)-2-(6-methoxynaphthalen-2-yl) propanoate

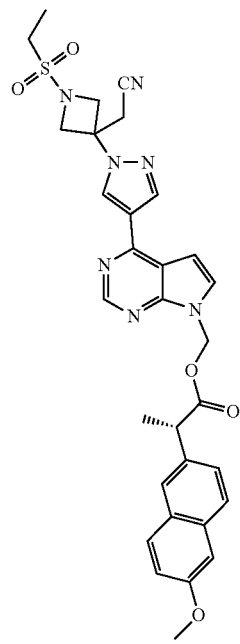 [SMILES: CCS(=O)(=O)N1CC(CC#N)(n2cc(-c3ncnc4c3ccn4COC(=O)[C@@H](C)c3ccc4cc(OC)ccc4c3)cn2)C1]

-continued

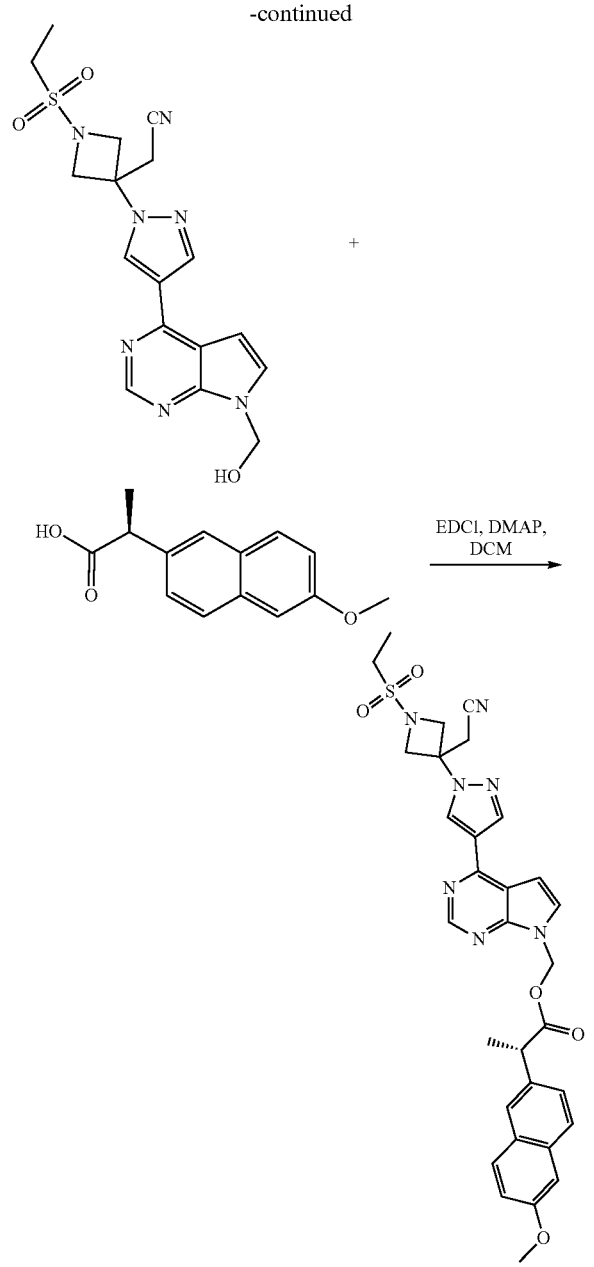

Synthesis of methyl (4-(1-(3-(cyanomethyl)-1-(ethylsulfonyl) azetidin-3-yl)-1H-pyrazol-4-yl)-7H-pyrrolo [2, 3-d] pyrimidin-7-yl) (S)-2-(6-methoxynaphthalen-2-yl) propanoate 2-(1-(Ethylsulfonyl)-3-(4-(7-(hydroxymethyl)-7H-)) pyrrolo [2, 3-d] pyrimidin-4-yl)-1H-pyrazol-1-yl) azetidin-3-yl) acetonitrile (401 mg, 1 mmol), 4-dimethylamino pyridine (DMAP, 61 mg, 0.5 mmol), (S)-(+)-2-(6-methoxy-2-naphthyl) propanoic acid (naproxen, 276 mg, 1.2 mmol) and 1-(3-dimethylaminopropyl)-3-ethylcarbodiimide hydrochloride (EDCI, 288 mg, 1.5 mmol) were dissolved in dichloromethane (10 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=10:1 to 1:1) to give the title compound as a white solid, 0.31 g, 50.5% yield. MS (m/z): [M+H]$^+$ calcd for $C_{31}H_{31}N_7O_5S$, 614.21; found, 614.3. $^1$H NMR (400 MHz, DMSO-d$_6$) δ 8.94 (s, 1H), 8.76 (s, 1H), 8.48 (s, 1H), 7.72 (d, J=3.8 Hz, 1H), 7.65 (dd, J=10.9, 8.8 Hz, 2H), 7.56 (d, J=1.9 Hz, 1H), 7.29 (dd, J=8.5, 1.9 Hz, 1H), 7.22 (d, J=2.6 Hz, 1H), 7.16 (d, J=3.8 Hz, 1H), 7.08 (dd, J=8.9, 2.6 Hz, 1H), 6.28 (s, 2H), 4.61 (d, J=9.1 Hz, 2H), 4.26 (d, J=9.1 Hz, 2H), 3.94 (q, J=7.0 Hz, 1H), 3.83 (s, 3H), 3.70 (s, 2H), 3.24 (q, J=7.3 Hz, 2H), 1.44 (d, J=7.1 Hz, 3H), 1.26 (t, J=7.4 Hz, 3H).

Example 62

4-(1-(3-(cyanomethyl)-1-(ethylsulfonyl) azetidin-3-yl)-1H-pyrazol-4-yl)-7H-pyrrolo [2, 3-d] pyrimidin-7-yl) methyl 2-(3-benzoylphenyl) propanoate

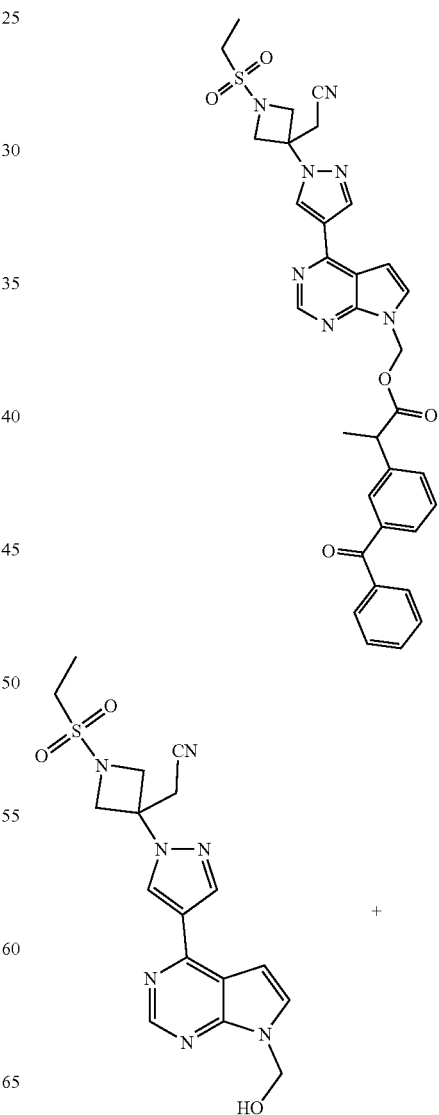

379

-continued

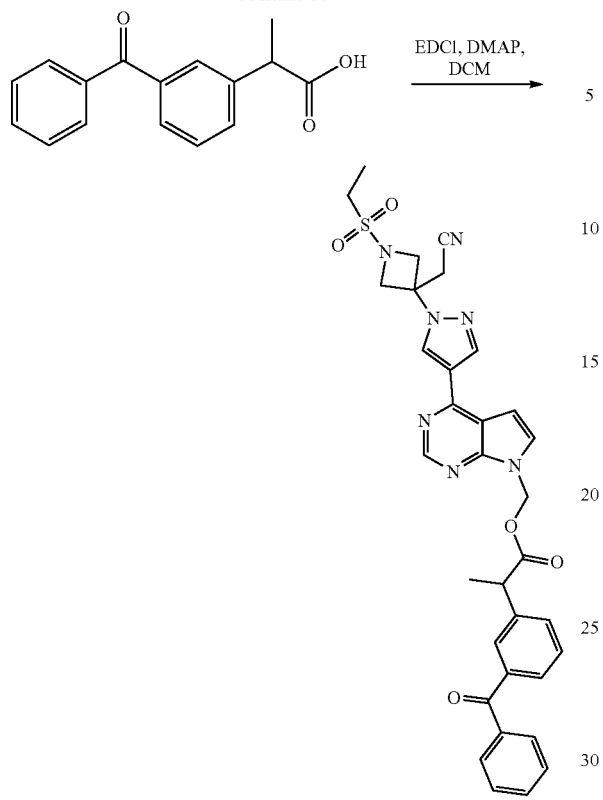

380

Example 63

(4-(((3R, 4R)-1-(2-cyanoacetyl)-4-methylpiperidin-3-yl)(methyl) amino)-7H-pyrrolo [2, 3-d] pyrimidin-7-yl) methyl 2-(1, 8-diethyl-1, 3, 4, 9-tetrahydropyrano [3, 4-b] indol-1-yl) acetate

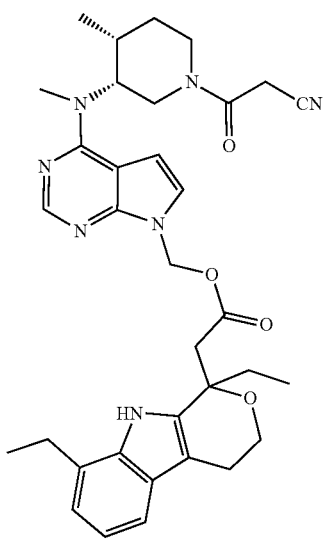

Synthesis of 4-(1-(3-(cyanomethyl)-1-(ethylsulfonyl) azetidin-3-yl)-1H-pyrazol-4-yl)-7H-pyrrolo [2, 3-d]pyrimidin-7-yl) methyl 2-(3-benzoylphenyl) propanoate 2-(1-(Ethylsulfonyl)-3-(4-(7-(hydroxymethyl)-7H-)) pyrrolo [2, 3-d] pyrimidin-4-yl)-1H-pyrazol-1-yl) azetidin-3-yl) acetonitrile (401 mg, 1 mmol), 4-dimethylamino pyridine (DMAP, 61 mg, 0.5 mmol) 2-(3-benzoylphenyl) propanoic acid (ketoprofen, 305 mg, 1.2 mmol) and 1-(3-dimethylaminopropyl)-3-ethylcarbodiimide hydrochloride (EDCI, 288 mg, 1.5 mmol) were dissolved in dichloromethane (10 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=10:1 to 1:1) to give the title compound as a white solid, 0.43 g, 67.5% yield. MS (m/z): [M+H]$^+$ calcd for $C_{33}H_{31}N_7O_5S$, 638.21; found, 638.2. $^1$H NMR (400 MHz, DMSO-d$_6$) δ 8.95 (s, 1H), 8.75 (s, 1H), 8.48 (s, 1H), 7.71 (d, J=3.8 Hz, 1H), 7.69-7.62 (m, 3H), 7.59 (t, J=1.8 Hz, 1H), 7.57-7.49 (m, 4H), 7.43 (t, J=7.6 Hz, 1H), 7.17 (d, J=3.8 Hz, 1H), 6.28 (d, J=4.4 Hz, 2H), 4.62 (d, J=9.1 Hz, 2H), 4.27 (d, J=9.1 Hz, 2H), 3.99 (q, J=7.1 Hz, 1H), 3.71 (s, 2H), 3.25 (q, J=7.3 Hz, 2H), 1.41 (d, J=7.1 Hz, 3H), 1.26 (t, J=7.3 Hz, 3H).

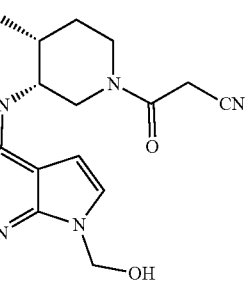

+

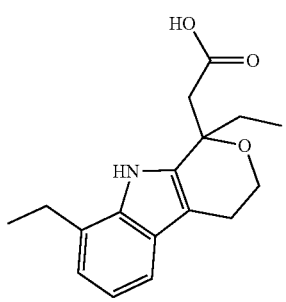

EDCl, DMAP,
DMF, DCM

381

-continued

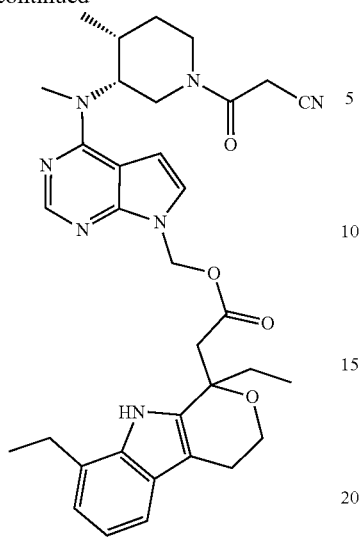

Synthesis of (4-(((3R, 4R)-1-(2-cyanoacetyl)-4-methylpiperidin-3-yl) (methyl) amino)-7H-pyrrolo [2, 3-d]pyrimidin-7-yl) methyl 2-(1, 8-diethyl-1, 3, 4, 9-tetrahydropyrano [3, 4-b] indol-1-yl) acetate 3-((3R, 4R)-3-((7-(hydroxymethyl)-7H-pyrrolo [2, 3-d] pyrimidin-4-yl) (methyl) amino)-4-methylpiperidin-1-yl)-3-oxopropanenitrile (171 mg, 0.5 mmol), 4-dimethylamino pyridine (DMAP, 61 mg, 0.5 mmol), 1, 8-diethyl-1, 3, 4, 9-tetrahydropyran [3, 4-b] indole-1-acetic acid (etodolac, 216 mg, 0.75 mmol) and 1-(3-dimethylaminopropyl)-3-ethylcarbodiimide hydrochloride (EDCI, 144 mg, 0.75 mmol) were dissolved in a mixed solvent of dichloromethane (8.5 mL) and dimethylformamide (0.3 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=150:1 to 50:1) to give the title compound as a white solid, 0.18 g, 58.9% yield. MS (m/z): [M+H]$^+$ calcd for $C_{34}H_{41}N_7O_4$, 612.32; found, 612.3. $^1$H NMR (400 MHz, Chloroform-d) δ 8.97 (d, J=13.6 Hz, 1H), 8.31 (d, J=8.1 Hz, 1H), 7.33 (d, J=7.6 Hz, 1H), 7.10-7.02 (m, 2H), 7.00 (d, J=7.3 Hz, 1H), 6.51 (d, J=4.1 Hz, 1H), 6.17 (dtd, J=15.9, 10.7, 4.1 Hz, 2H), 5.10 (dp, J=14.0, 4.6 Hz, 1H), 4.09-3.70 (m, 5H), 3.60-3.47 (m, 3H), 3.35 (d, J=14.9 Hz, 3H), 3.02 (d, J=16.2 Hz, 1H), 2.87 (ddd, J=16.8, 12.9, 5.8 Hz, 3H), 2.68 (dt, J=15.4, 4.3 Hz, 1H), 2.56-2.41 (m, 1H), 2.07 (dt, J=14.3, 6.8 Hz, 1H), 1.98 (s, 2H), 1.90 (d, J=24.6 Hz, 3H), 1.79-1.65 (m, 1H), 1.37 (ddd, J=10.0, 6.5, 2.4 Hz, 3H), 1.06 (dt, J=13.8, 6.3 Hz, 3H), 0.74 (t, J=7.3 Hz, 3H).

382

Example 64

(4-(((3R, 4R)-1-(2-cyanoacetyl)-4-methylpiperidin-3-yl) (methyl) amino)-7H-pyrrolo [2, 3-d] pyrimidin-7-yl) methyl (S)-2-((tert-butoxycarbonyl) amino)-2-phenylacetate

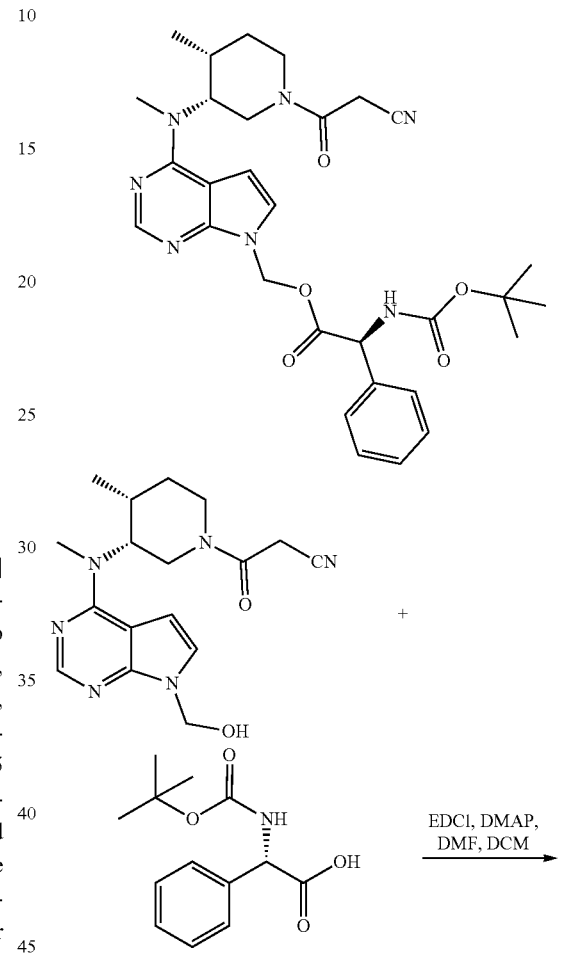

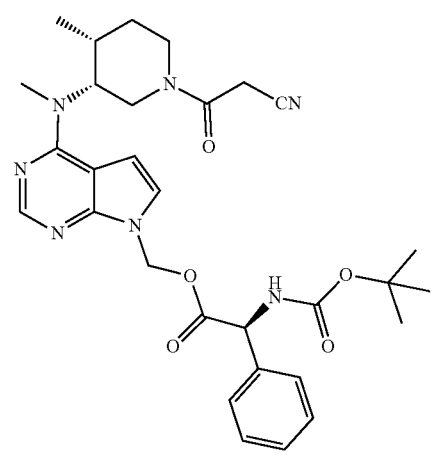

Synthesis of (4-(((3R, 4R)-1-(2-cyanoacetyl)-4-methylpiperidin-3-yl) (methyl) amino)-7H-pyrrolo [2, 3-d]pyrimidin-7-yl) methyl (S)-2-((tert-butoxycarbonyl) amino)-2-phenylacetate 3-((3R, 4R)-3-((7-(hydroxymethyl)-7H-pyrrolo [2, 3-d]pyrimidin-4-yl) (methyl) amino)-4-methylpiperidin-1-yl)-3-oxopropanenitrile (171 mg, 0.5 mmol), 4-dimethylaminopyridine (DMAP, 61 mg, 0.5 mmol), N-Boc-L-phenylglycine (189 mg, 0.75 mmol) and 1-(3-dimethylaminopropyl)-3-ethylcarbodiimide hydrochloride (EDCI, 144 mg, 0.75 mmol) was dissolved in a mixed solvent of dichloromethane (8.5 mL) and N, N-dimethylformamide (0.3 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=150:1 to 50:1) to give the title compound as a white solid, 0.148 g, 51.4% yield. MS (m/z): [M+H]$^+$ calcd for $C_{30}H_{37}N_7O_5$, 576.29; found, 576.3. $^1$H NMR (400 MHz, Chloroform-d) δ 8.28 (d, J=9.3 Hz, 1H), 7.25 (d, J=6.9 Hz, 5H), 7.07 (dd, J=16.0, 3.9 Hz, 1H), 6.51 (dd, J=7.1, 3.7 Hz, 1H), 6.23-6.14 (m, 2H), 5.49 (d, J=7.5 Hz, 1H), 5.29 (d, J=7.5 Hz, 1H), 5.11 (dt, J=9.7, 4.5 Hz, 1H), 4.13-3.76 (m, 2H), 3.63-3.46 (m, 4H), 3.36 (d, J=17.3 Hz, 3H), 2.49 (tt, J=13.9, 6.0 Hz, 1H), 1.87 (dd, J=9.5, 4.6 Hz, 1H), 1.82-1.67 (m, 1H), 1.39 (s, 9H), 1.08 (dd, J=13.5, 7.1 Hz, 3H).

Example 65

(4-(((3R, 4R)-1-(2-cyanoacetyl)-4-methylpiperidin-3-yl) (methyl) amino)-7H-pyrrolo [2, 3-d] pyrimidin-7-yl) methyl 2-(4-(1-oxoisoindol-2-yl)) phenyl) butanoate

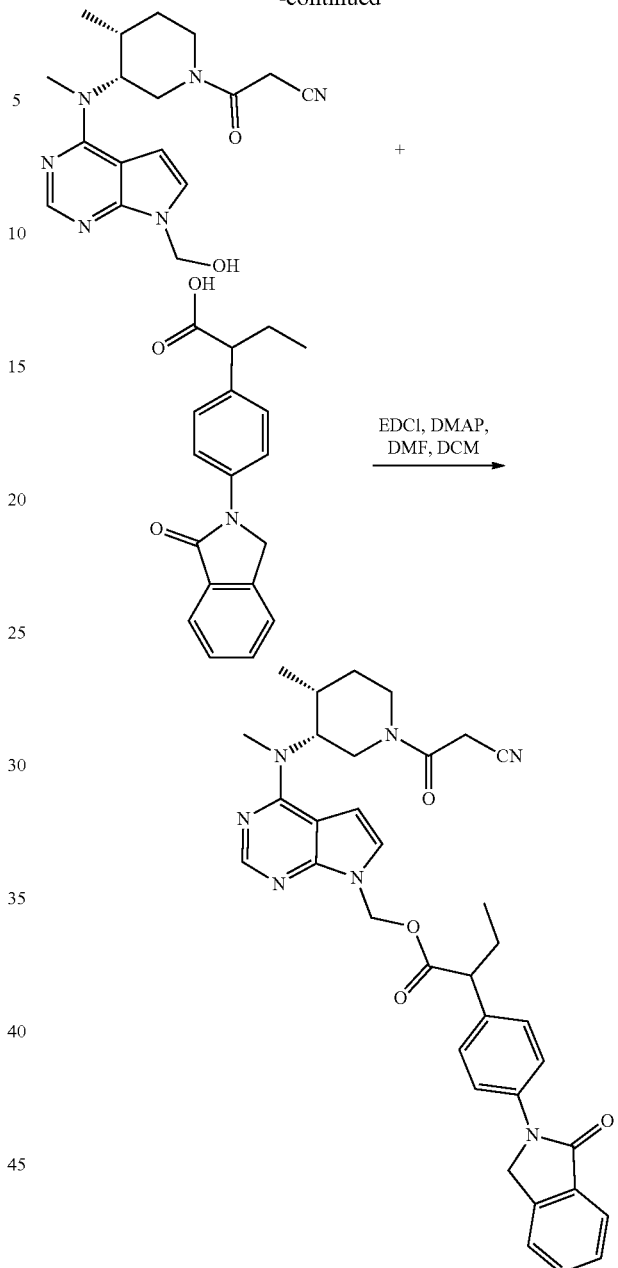

Synthesis of (4-(((3R, 4R)-1-(2-cyanoacetyl)-4-methylpiperidin-3-yl) (methyl) amino)-7H-pyrrolo [2, 3-d]pyrimidin-7-yl) methyl 2-(4-(1-oxoisoindol-2-yl)) phenyl) butanoate 3-((3R, 4R)-3-((7-(hydroxymethyl)-7H-pyrrolo [2, 3-d] pyrimidin-4-yl) (methyl) amino)-4-methylpiperidin-1-yl)-3-oxopropanenitrile (20 mg, 0.058 mmol), 4-dimethylamino pyridine (DMAP, 4 mg, 0.03 mmol), 2-(4-(1-oxoisoindolin-2-yl) phenyl) butanoic acid (indobufen, 26 mg, 0.09 mmol) and 1-(3-dimethylaminopropyl)-3-ethylcarbodiimide hydrochloride (EDCI, 17 mg, 0.09 mmol) were dissolved in a mixed solvent of dichloromethane (0.5 mL) and N, N-dimethylformamide (0.05 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=150:1 to 50:1) to give the title compound as a white solid, 0.012 g, 33.4% yield. MS (m/z): [M+H]$^+$ calcd for $C_{35}H_{37}N_7O_4$, 620.29; found, 620.3. $^1$H NMR (400 MHz, Chloroform-d) δ 8.30 (d, J=8.7 Hz, 1H), 7.90 (d, J=7.5 Hz, 1H), 7.80-7.69 (m, 2H), 7.59 (t, J=7.5 Hz, 1H), 7.51 (d, J=8.4 Hz, 2H), 7.33-7.22 (m, 2H), 7.14-7.06 (m, 1H), 6.53-6.45 (m, 1H), 6.15 (dt, J=18.9, 10.9 Hz, 2H), 5.08 (s, 1H), 4.82 (s, 2H), 4.05 (d, J=13.5 Hz, 1H), 3.92-3.66 (m, 2H), 3.53 (q, J=6.6, 5.1 Hz, 3H), 3.37-3.27 (m, 3H), 2.54-2.40 (m, 1H), 2.07 (dq, J=14.1, 7.3 Hz, 2H), 1.93 (s, 1H), 1.76 (tt, J=19.7, 8.8 Hz, 2H), 1.06 (s, 3H), 0.82 (s, 3H).

Example 66

(4-(((3R, 4R)-1-(2-cyanoacetyl)-4-methylpiperidin-3-yl) (methyl) amino)-7H-pyrrolo [2, 3-d] pyrimidin-7-yl) methyl 2-((3-chloro-2-methylphenyl) amino) benzoate

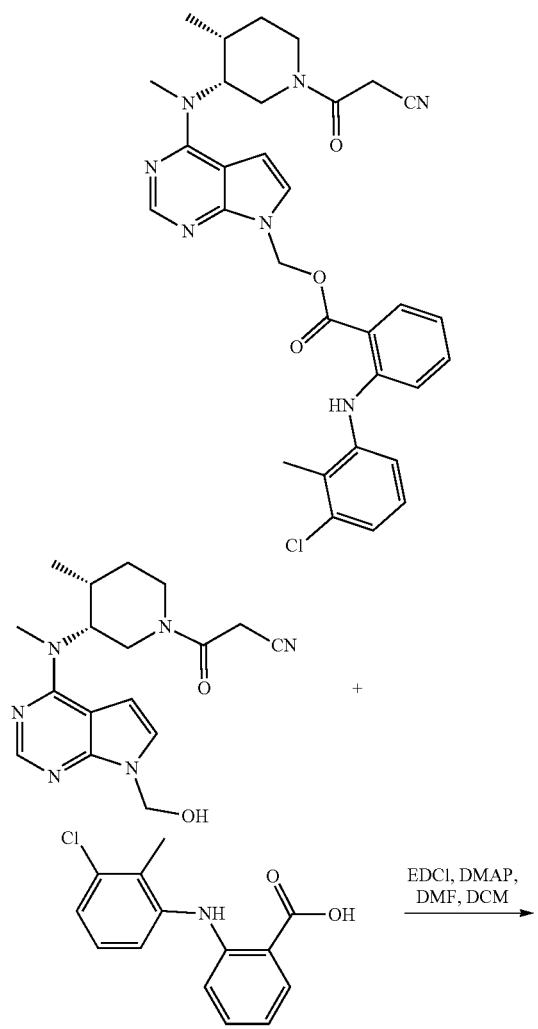

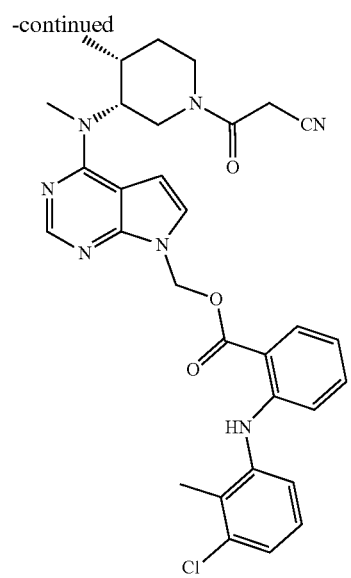

Synthesis of (4-(((3R, 4R)-1-(2-cyanoacetyl)-4-methylpiperidin-3-yl) (methyl) amino)-7H-pyrrolo [2, 3-d]pyrimidin-7-yl) methyl 2-((3-chloro-2-methylphenyl) amino) benzoate 3-((3R, 4R)-3-((7-(hydroxymethyl)-7H-pyrrolo [2, 3-d] pyrimidin-4-yl) (methyl) amino)-4-methylpiperidin-1-yl)-3-oxopropanenitrile (200 mg, 0.58 mmol), 4-dimethylamino pyridine (DMAP, 35 mg, 0.29 mmol), 2-((3-chloro-2-methylphenyl) amino) benzoic acid (tolfenamic acid, 230 mg, 0.88 mmol) and 1-(3-dimethylaminopropyl)-3-ethylcarbodiimide hydrochloride (EDCI, 168 mg, 0.88 mmol) were dissolved in a mixed solvent of dichloromethane (10 mL) and N, N-dimethylformamide (0.2 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further purified by silica gel column chromatography (petroleum ether/ethyl acetate=2:1 to 1:1) to give the title compound as a yellow solid, 0.145 g, 42.7% yield. MS (m/z): [M+H]$^+$ calcd for $C_{31}H_{32}ClN_7O_3$, 586.23; found, 586.3. $^1$H NMR (400 MHz, Chloroform-d) δ 9.20 (s, 1H), 8.37 (d, J=7.1 Hz, 1H), 7.95 (dd, J=8.2, 1.7 Hz, 1H), 7.30-7.17 (m, 4H), 7.12 (t, J=7.9 Hz, 1H), 6.75 (d, J=8.5 Hz, 1H), 6.65 (t, J=7.6 Hz, 1H), 6.60-6.55 (m, 1H), 6.42 (d, J=3.3 Hz, 2H), 5.13 (q, J=6.0, 5.5 Hz, 1H), 4.12-3.75 (m, 2H), 3.64-3.56 (m, 1H), 3.53-3.46 (m, 2H), 3.38 (d, J=16.8 Hz, 3H), 2.58-2.44 (m, 1H), 2.32 (s, 3H), 1.97-1.82 (m, 2H), 1.81-1.68 (m, 1H), 1.08 (dd, J=12.9, 7.0 Hz, 3H).

Example 67

(4-(((3R, 4R)-1-(2-cyanoacetyl)-4-methylpiperidin-3-yl) (methyl) amino)-7H-pyrrolo [2, 3-d] pyrimidin-7-yl) methyl 2-((2, 3-dimethylphenyl) amino) benzoate

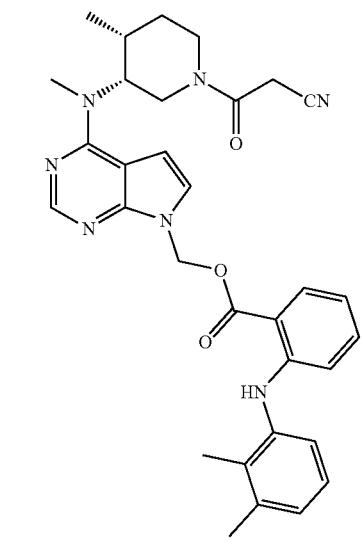

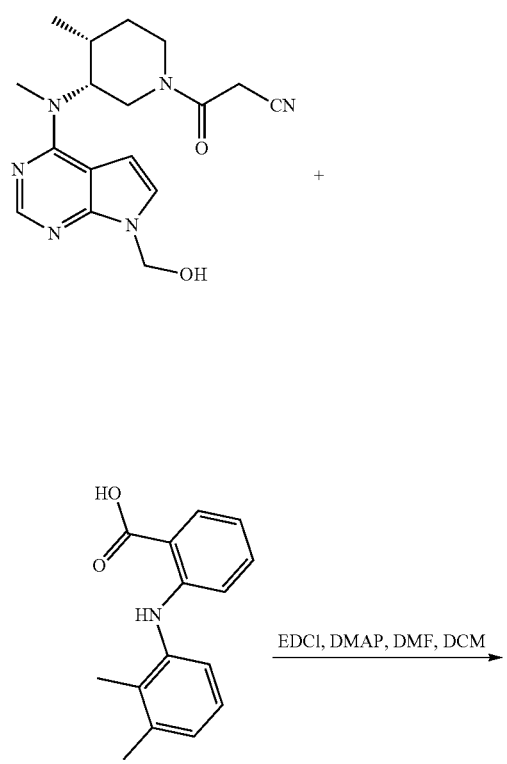

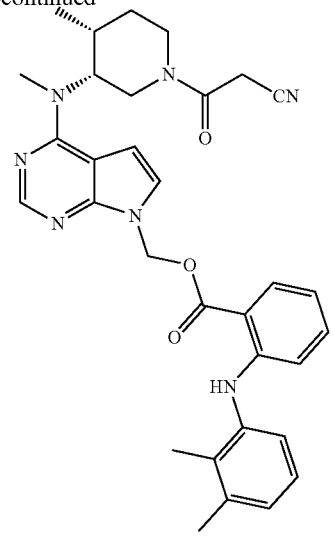

Synthesis of (4-(((3R, 4R)-1-(2-cyanoacetyl)-4-methylpiperidin-3-yl) (methyl) amino)-7H-pyrrolo [2, 3-d]pyrimidin-7-yl) methyl 2-((2, 3-dimethylphenyl) amino) benzoate 3-((3R, 4R)-3-((7-(hydroxymethyl)-7H-pyrrolo [2, 3-d] pyrimidin-4-yl) (methyl) amino)-4-methylpiperidin-1-yl)-3-oxopropanenitrile (171 mg, 0.5 mmol), 4-dimethylaminopyridine (DMAP, 61 mg, 0.5 mmol), 2-((2, 3-dimethylphenyl) amino) benzoic acid (mefenamic acid, 181 mg, 0.75 mmol) and 1-(3-dimethylaminopropyl)-3-ethylcarbodiimide hydrochloride (EDCI, 144 mg, 0.75 mmol) were dissolved in a mixed solvent of dichloromethane (8.5 mL) and N,N-dimethylformamide (0.3 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=150:1 to 50:1) to give the title compound as a yellow solid, 0.012 g, 45.6% yield. MS (m/z): [M+H]$^+$ calcd for $C_{32}H_{35}N_7O_3$, 566.28; found, 566.3. $^1$H NMR (400 MHz, Chloroform-d) δ 9.14 (s, 1H), 8.37 (d, J=7.1 Hz, 1H), 7.93 (dd, J=8.1, 1.7 Hz, 1H), 7.29 (dd, J=15.0, 3.7 Hz, 1H), 7.25-7.16 (m, 1H), 7.16-7.06 (m, 2H), 7.03 (d, J=6.8 Hz, 1H), 6.68 (d, J=8.6 Hz, 1H), 6.63-6.53 (m, 2H), 6.41 (d, J=3.0 Hz, 2H), 5.12 (dt, J=9.7, 4.7 Hz, 1H), 4.05 (dd, J=13.2, 4.4 Hz, 1H), 3.78 (ddd, J=15.8, 13.2, 8.1 Hz, 1H), 3.58 (td, J=11.3, 10.3, 5.0 Hz, 1H), 3.54-3.47 (m, 2H), 3.37 (d, J=15.3 Hz, 3H), 2.57-2.41 (m, 1H), 2.33 (s, 3H), 2.17 (s, 3H), 1.99 (s, 1H), 1.97-1.84 (m, 1H), 1.72 (dtd, J=32.5, 6.4, 3.6 Hz, 1H), 1.07 (dd, J=13.3, 7.0 Hz, 3H).

Example 68

N-methyl-1-((trans)-4-(methyl (7-(2-(3-phenoxyphenyl) propanoyl)-7H-pyrrolo [2, 3-d] pyrimidin-4-yl) amino) cyclohexyl) methanesulfonamide

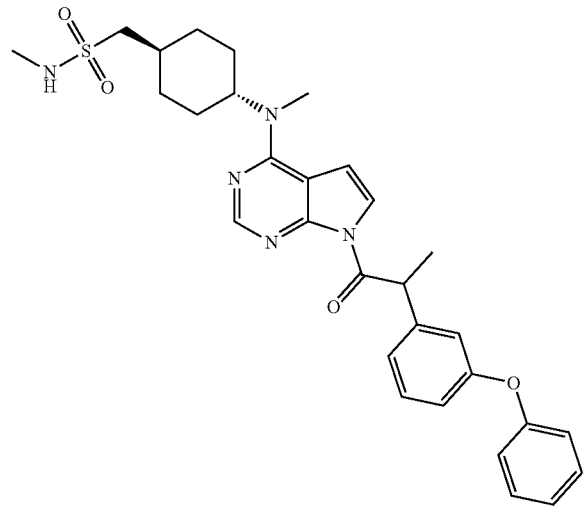

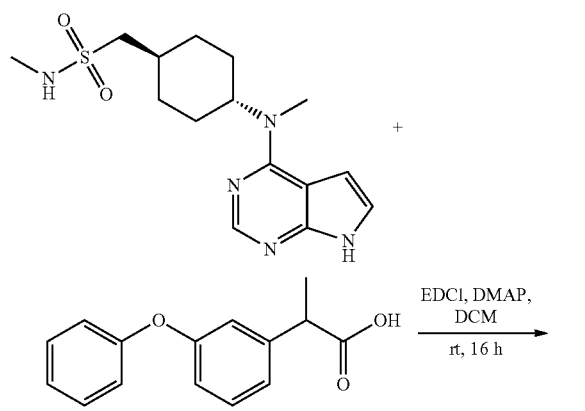

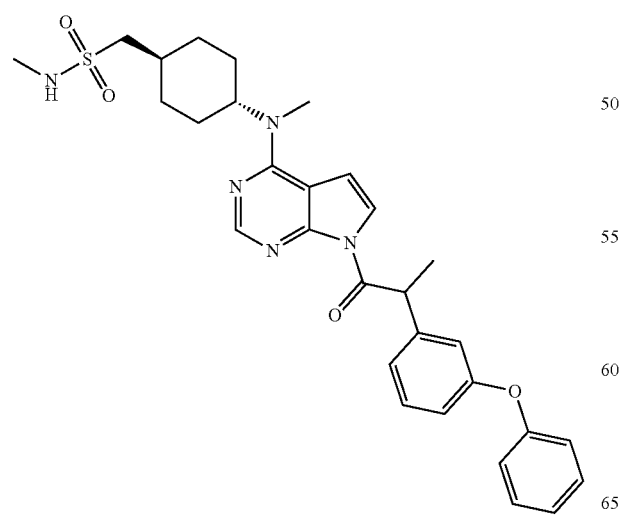

Synthesis of N-methyl-1-((trans)-4-(methyl (7-(2-(3-phenoxyphenyl) propanoyl)-7H-pyrrolo [2, 3-d] pyrimidin-4-yl) amino) cyclohexyl) methanesulfonamide N-methyl-1-((trans)-4-(methyl (7H-pyrrolo [2, 3-d] pyrimidin-4-yl) amino) cyclohexyl) methanesulfonamide (oclacitinib, 168 mg, 0.5 mmol), 4-dimethylamino pyridine (DMAP, 61 mg, 0.5 mmol), 2-(3-phenoxyphenyl) propanoic acid (fenoprofen, 158 mg, 0.65 mmol) and 1-(3-dimethylaminopropyl)-3-ethylcarbodiimide hydrochloride (EDCI, 144 mg, 0.75 mmol) were dissolved in dichloromethane (15 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=2:1 to 5:3) to give the title compound as a white solid, 0.18 g, 64.1% yield. MS (m/z): [M+H]$^+$ calcd for $C_{30}H_{35}N_5O_4S$, 562.24; found, 562.4. $^1$H NMR (400 MHz, DMSO-d$_6$) δ 8.26 (s, 1H), 7.65 (d, J=4.2 Hz, 1H), 7.40-7.33 (m, 2H), 7.29 (t, J=7.9 Hz, 1H), 7.18-7.11 (m, 2H), 7.05 (t, J=2.1 Hz, 1H), 6.98-6.90 (m, 2H), 6.90-6.78 (m, 3H), 6.06 (q, J=6.9 Hz, 1H), 4.64 (s, 1H), 3.15 (s, 3H), 2.95 (d, J=6.2 Hz, 2H), 2.60 (d, J=5.0 Hz, 3H), 2.10-2.02 (m, 2H), 1.92-1.77 (m, 1H), 1.70 (tt, J=8.2, 3.1 Hz, 4H), 1.53 (d, J=7.0 Hz, 3H), 1.29 (d, J=12.9 Hz, 2H).

Example 69

Methyl (4-(1-(3-(cyanomethyl)-1-(ethylsulfonyl) azetidin-3-yl)-1H-pyrazol-4-yl)-7H-pyrrolo [2, 3-d] pyrimidin-7-yl) 2-(2-fluoro-[1, 1'-biphenyl]-4-yl) propanoate

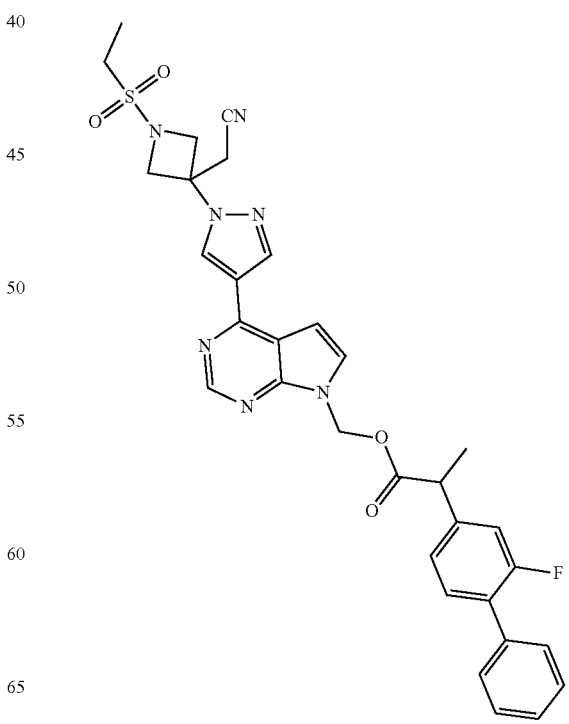

-continued

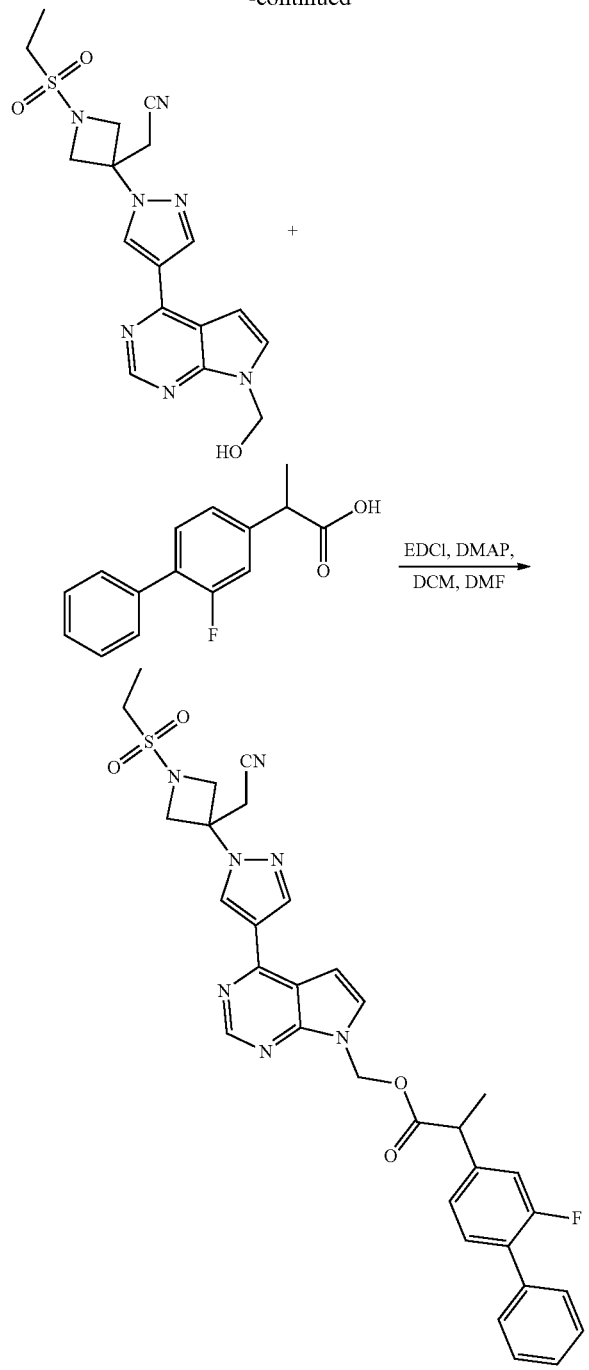

Synthesis of methyl (4-(1-(3-(cyanomethyl)-1-(ethylsulfonyl) azetidin-3-yl)-1H-pyrazol-4-yl)-7H-pyrrolo [2, 3-d] pyrimidin-7-yl) 2-(2-fluoro-[1, 1'-biphenyl]-4-yl) propanoate 2-(1-(Ethylsulfonyl)-3-(4-(7-(hydroxymethyl)-7H-)) pyrrolo [2, 3-d] pyrimidin-4-yl)-1H-pyrazol-1-yl) azetidin-3-yl) acetonitrile (201 mg, 0.5 mmol), 4-dimethylamino pyridine (DMAP, 31 mg, 0.25 mmol), 2-(2-fluoro-4-biphenyl) propanoic acid (flurbiprofen, 146 mg, 0.6 mmol) and 1-(3-dimethylaminopropyl)-3-ethylcarbodiimide hydrochloride (EDCI, 144 mg, 0.75 mmol) were dissolved in dichloromethane (10 mL) and N, N-dimethylformamide (1 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=5:1 to 1:2) to give the title compound as a white solid, 0.27 g, 86.1% yield. MS (m/z): [M+H]$^+$ calcd for $C_{32}H_{30}FN_7O_4S$, 628.21; found, 628.3. $^1$H NMR (400 MHz, DMSO-d$_6$) δ 8.95 (s, 1H), 8.78 (s, 1H), 8.48 (s, 1H), 7.75 (d, J=3.8 Hz, 1H), 7.50-7.41 (m, 4H), 7.40-7.32 (m, 2H), 7.19 (d, J=3.8 Hz, 1H), 7.17-7.08 (m, 2H), 6.37-6.24 (m, 2H), 4.60 (d, J=9.1 Hz, 2H), 4.25 (d, J=9.1 Hz, 2H), 3.93 (q, J=7.0 Hz, 1H), 3.69 (s, 2H), 3.23 (q, J=7.3 Hz, 2H), 1.40 (d, J=7.1 Hz, 3H), 1.25 (t, J=7.2 Hz, 3H).

Example 70

Methyl (4-(1-(3-(cyanomethyl)-1-(ethylsulfonyl) azetidin-3-yl)-1H-pyrazol-4-yl)-7H-pyrrolo [2, 3-d] pyrimidin-7-yl) 2-(2-((2, 6-dichlorophenyl) amino) phenyl) acetate

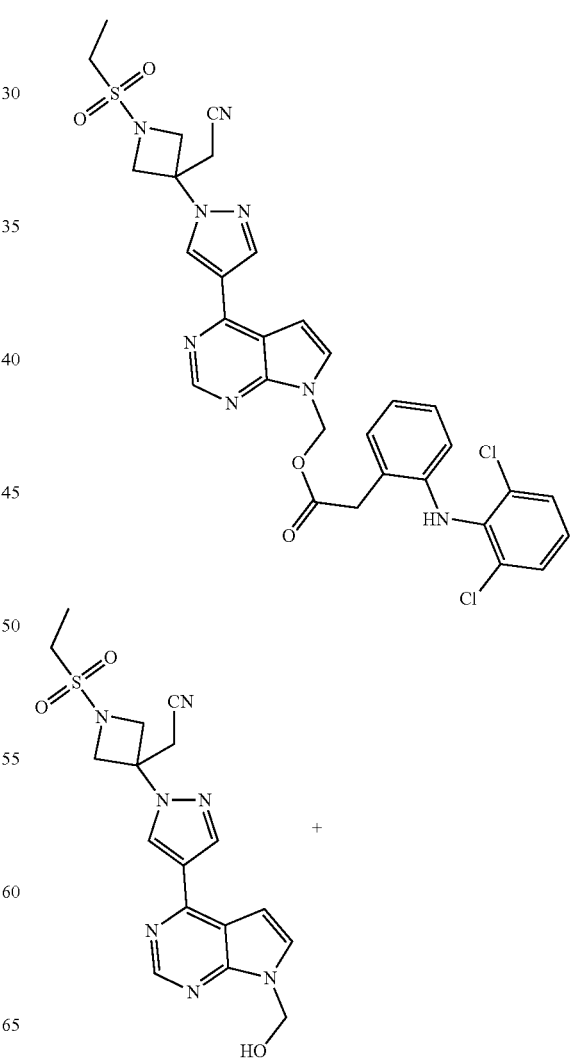

393

-continued

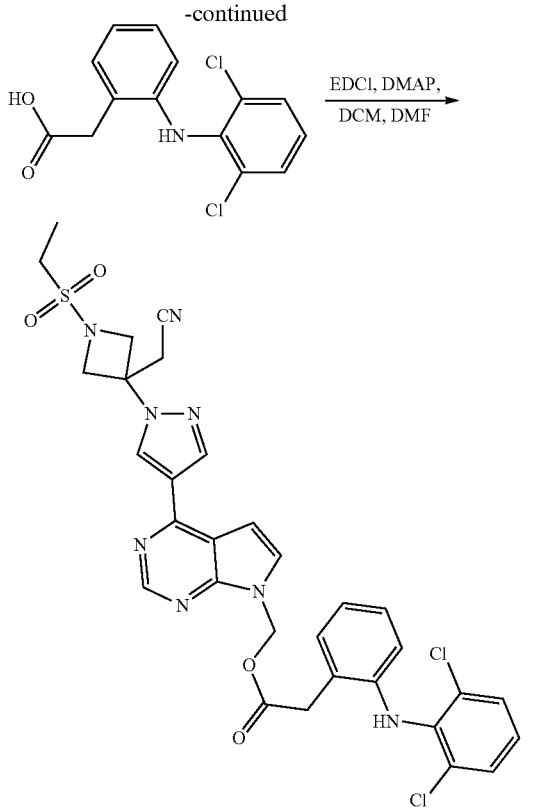

Synthesis of methyl (4-(1-(3-(cyanomethyl)-1-(ethylsulfonyl) azetidin-3-yl)-1H-pyrazol-4-yl)-7H-pyrrolo [2, 3-d] pyrimidin-7-yl) 2-(2-((2, 6-dichlorophenyl) amino) phenyl) acetate 2-(1-(Ethylsulfonyl)-3-(4-(7-(hydroxymethyl)-7H-)) pyrrolo [2, 3-d] pyrimidin-4-yl)-1H-pyrazol-1-yl) azetidin-3-yl) acetonitrile (201 mg, 0.5 mmol), 4-dimethylamino pyridine (DMAP, 31 mg, 0.25 mmol), 2-(2, 6-dichloroanilino) phenylacetic acid (diclofenac, 148 mg, 0.5 mmol) and 1-(3-dimethylaminopropyl)-3-ethylcarbodiimide hydrochloride (EDCI, 144 mg, 0.75 mmol) were dissolved in dichloromethane (10 mL) and N, N-dimethylformamide (2 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=10:1 to 1:2) to give the title compound as a white solid, 0.07 g, 20.6% yield. MS (m/z): [M+H]$^+$ calcd for $C_{31}H_{28}C_2N_8O_4S$, 679.13; found, 679.1. $^1$H NMR (400 MHz, DMSO-d$_6$) δ 8.96 (s, 1H), 8.80 (s, 1H), 8.50 (s, 1H), 7.76 (d, J=3.8 Hz, 1H), 7.49 (d, J=8.1 Hz, 2H), 7.24-7.12 (m, 3H), 7.04 (td, J=7.7, 1.6 Hz, 1H), 6.92 (s, 1H), 6.81 (td, J=7.4, 1.2 Hz, 1H), 6.32 (s, 2H), 6.22 (d, J=8.0 Hz, 1H), 4.61 (d, J=9.1 Hz, 2H), 4.26 (d, J=9.1 Hz, 2H), 3.86 (s, 2H), 3.70 (s, 2H), 3.24 (q, J=7.4 Hz, 2H), 1.26 (t, J=7.4 Hz, 3H).

394

Example 71

Methyl (4-(1-(3-(cyanomethyl)-1-(ethylsulfonyl) azetidin-3-yl)-1H-pyrazol-4-yl)-7H-pyrrolo [2, 3-d] pyrimidin-7-yl) 2-(3-phenoxyphenyl) propanoate

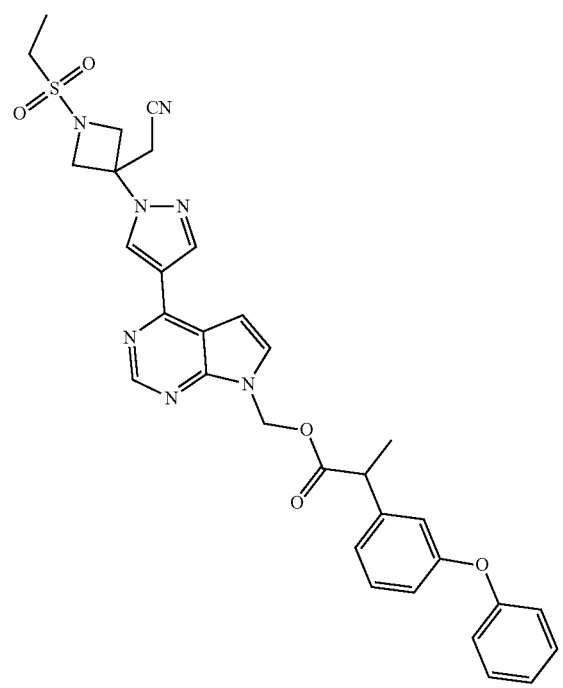 [SMILES: CCS(=O)(=O)N1CC(CC#N)(n2cc(-c3ncnc4c3ccn4COC(=O)C(C)c3cccc(Oc4ccccc4)c3)cn2)C1]

+

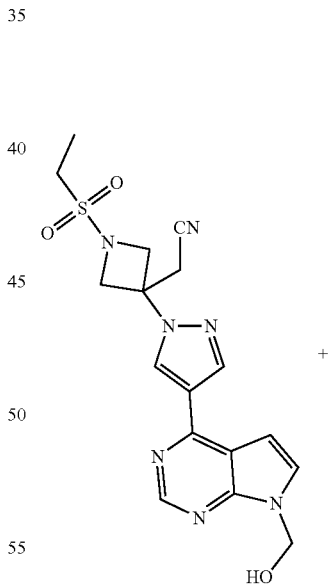

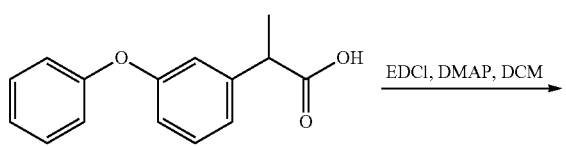

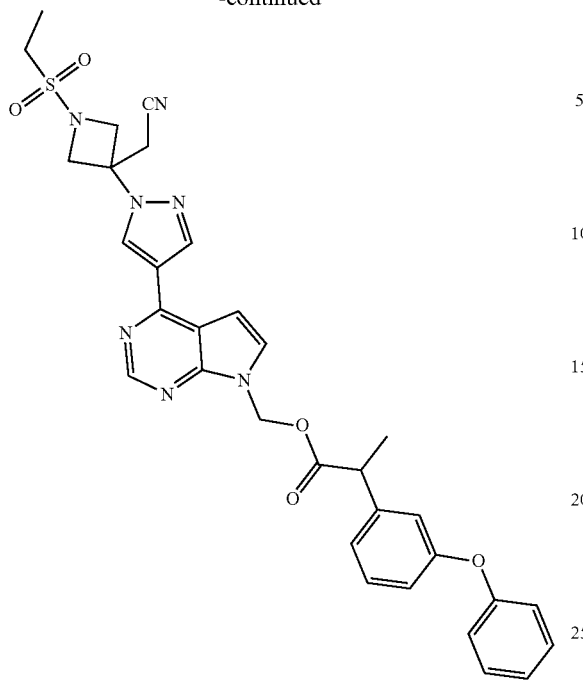

Synthesis of methyl (4-(1-(3-(cyanomethyl)-1-(ethylsulfonyl) azetidin-3-yl)-1H-pyrazol-4-yl)-7H-pyrrolo [2, 3-d] pyrimidin-7-yl) 2-(3-phenoxyphenyl) propanoate 2-(1-(Ethylsulfonyl)-3-(4-(7-(hydroxymethyl)-7H-)) pyrrolo [2, 3-d] pyrimidin-4-yl)-1H-pyrazol-1-yl) azetidin-3-yl) acetonitrile (201 mg, 0.5 mmol), 4-dimethylamino pyridine (DMAP, 31 mg, 0.25 mmol), 2-(3-phenoxyphenyl) propanoic acid (fenoprofen, 1345 mg, 0.6 mmol) and 1-(3-dimethylaminopropyl)-3-ethylcarbodiimiide hydrochloride (EDCI, 144 mg, 0.75 mmol) were dissolved in dichloromethane (10 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=5:1 to 1:2) to give the title compound as a white solid, 0.22 g, 70.4% yield. MS (m/z): [M+H]$^+$ calcd for $C_{32}H_{31}N_7O_5S$, 626.21; found, 626.1. $^1$H NMR (400 MHz, DMSO-$d_6$) δ 8.96 (s, 1H), 8.78 (s, 1H), 8.50 (s, 1H), 7.71 (d, J=3.8 Hz, 1H), 7.39-7.30 (m, 2H), 7.24 (t, J=7.9 Hz, 1H), 7.19 (d, J=3.8 Hz, 1H), 7.11 (t, J=7.4 Hz, 1H), 6.97 (d, J=7.7 Hz, 1H), 6.90 (d, J=8.0 Hz, 2H), 6.85 (t, J=2.1 Hz, 1H), 6.79 (dd, J=8.1, 2.5 Hz, 1H), 6.27 (d, J=4.3 Hz, 2H), 4.61 (d, J=9.1 Hz, 2H), 4.26 (d, J=9.1 Hz, 2H), 3.84 (q, J=7.1 Hz, 1H), 3.70 (s, 2H), 3.24 (q, J=7.3 Hz, 2H), 1.35 (d, J=7.1 Hz, 3H), 1.25 (t, J=7.2 Hz, 3H).

Example 72

Methyl (4-(1-(3-(cyanomethyl)-1-(ethylsulfonyl) azetidin-3-yl)-1H-pyrazol-4-yl)-7H$_1$-pyrrolo [2, 3-d] pyrimidin-7-yl) 2-(4-((2-oxocyclopentyl) methyl) phenyl) propanoate

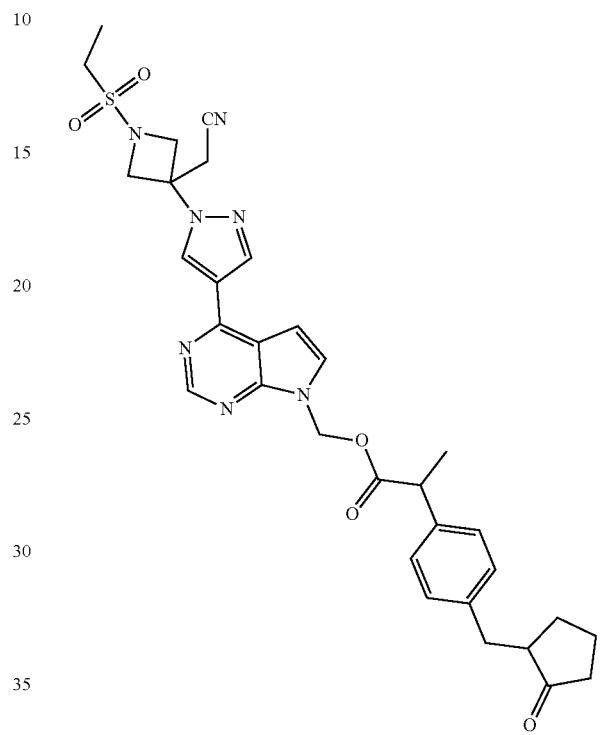

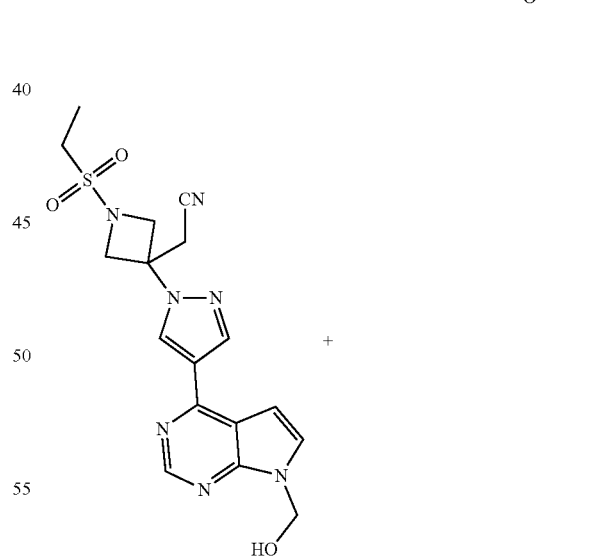

+

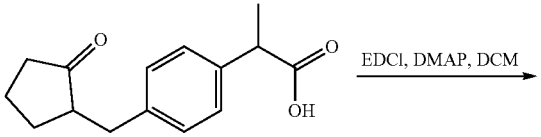

EDCl, DMAP, DCM →

397

-continued

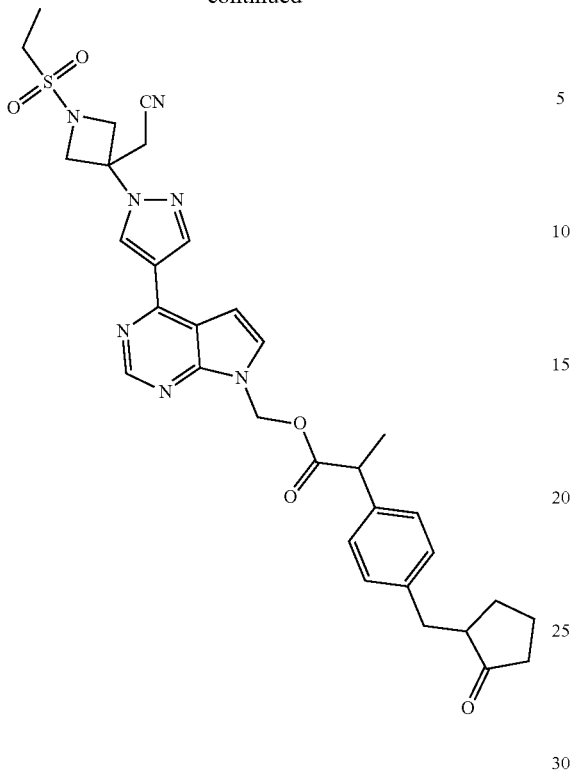

Synthesis of methyl (4-(1-(3-(cyanomethyl)-1-(ethylsulfonyl) azetidin-3-yl)-1H-pyrazol-4-yl)-7H-pyrrolo [2, 3-d] pyrimidin-7-yl) 2-(4-((2-oxocyclopentyl) methyl) phenyl) propanoate 2-(1-(Ethylsulfonyl)-3-(4-(7-(hydroxymethyl)-7H-)) pyrrolo [2, 3-d] pyrimidin-4-yl)-1H-pyrazol-1-yl) azetidin-3-yl) acetonitrile (201 mg, 0.5 mmol), 4-dimethylamino pyridine (DMAP, 31 mg, 0.25 mmol), 2-[4-(2-oxocyclopentan-1-ylmethyl) phenyl] propanoic acid (loxoprofen, 148 mg, 06 mmol) and 1-(3-dimethylaminopropyl)-3-ethylcarbodiimide hydrochloride (EDCI, 144 mg, 0.75 mmol) were dissolved in dichloromethane (10 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=5:1 to 1:2) to give the title compound as a white solid, 0.26 g, 82.6% yield. MS (m/z): [M+H]$^+$ calcd for $C_{32}H_{35}N_7O_5S$, 630.24; found, 630.1. $^1$H NMR (400 MHz, DMSO-d$_6$) δ 8.96 (s, 1H), 8.78 (d, J=1.6 Hz, 1H), 8.49 (s, 1H), 7.71 (d, J=3.8 Hz, 1H), 7.17 (d, J=3.8 Hz, 1H), 7.04 (ddd, J=25.3, 8.1, 2.3 Hz, 4H), 6.26 (d, J=4.2 Hz, 2H), 4.60 (d, J=9.1 Hz, 2H), 4.25 (d, J=9.1 Hz, 2H), 3.77 (q, J=7.1 Hz, 1H), 3.69 (s, 2H), 3.24 (q, J=7.3 Hz, 2H), 2.87 (dd, J=13.3, 3.7 Hz, 1H), 2.40-2.15 (m, 3H), 2.04 (dd, J=10.2, 8.5 Hz, 1H), 1.80 (d, J=12.9 Hz, 2H), 1.70-156 (m, 1H), 1.44-1.31 (m, 4H), 1.28-1.23 (m, 3H).

398

Example 73

Methyl (4-(1-(3-(cyanomethyl)-1-(ethylsulfonyl) azetidin-3-yl)-1H-pyrazol-4-yl)-7H-pyrrolo [2, 3-d] pyrimidin-7-yl) 2-(1-(4-chlorobenzoyl)-5-methoxy-2-methyl-1H-indol-3-yl) acetate

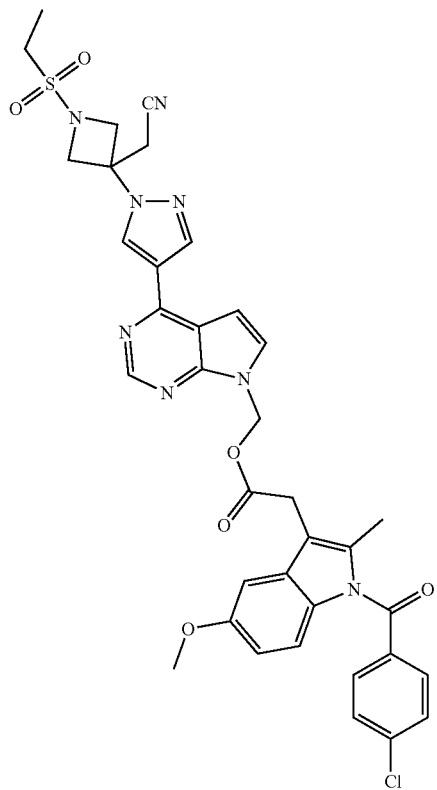 [SMILES: CCS(=O)(=O)N1CC(CC#N)(n2cc(-c3ncnc4c3ccn4COC(=O)Cc3c(C)n(C(=O)c4ccc(Cl)cc4)c4ccc(OC)cc34)cn2)C1]

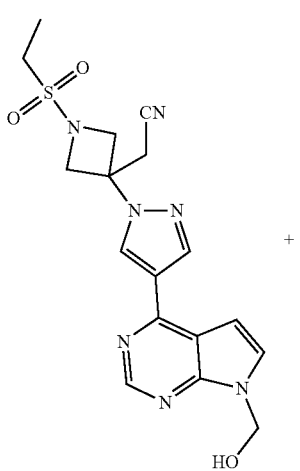

+

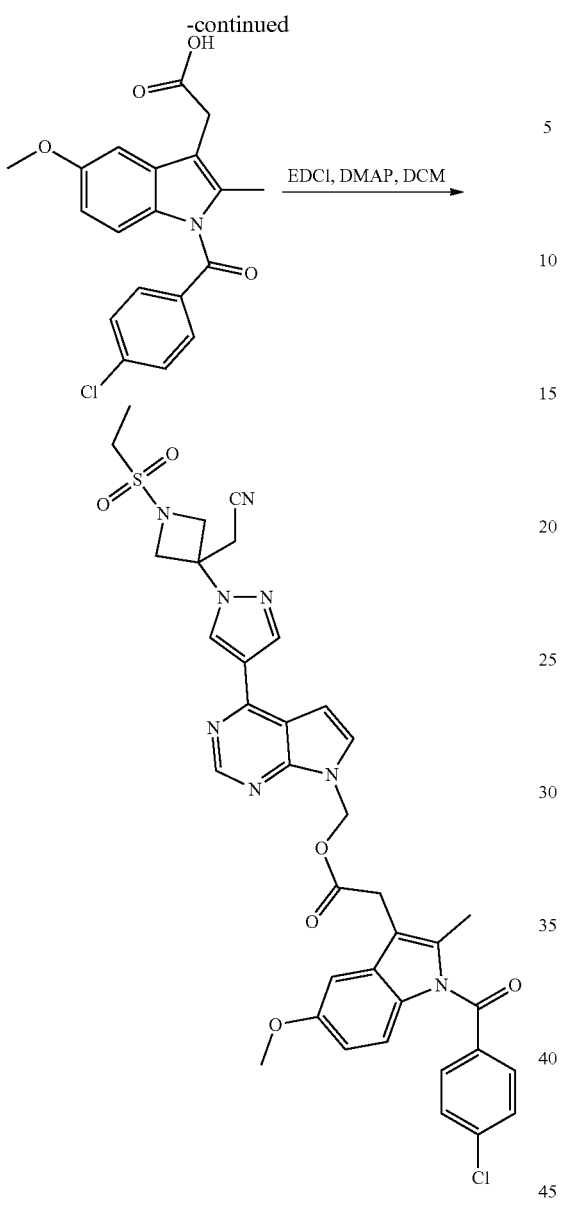

Synthesis of methyl (4-(1-(3-(cyanomethyl)-1-(ethylsulfonyl) azetidin-3-yl)-1H-pyrazol-4-yl)-7H-pyrrolo [2, 3-d] pyrimidin-7-yl) 2-(1-(4-chlorobenzoyl)-5-methoxy-2-methyl-1H-indol-3-yl) acetate 2-(1-(Ethylsulfonyl)-3-(4-(7-(hydroxymethyl)-7H-)) pyrrolo [2, 3-d] pyrimidin-4-yl)-1H-pyrazol-1-yl) azetidin-3-yl) acetonitrile (201 mg, 0.5 mmol), 4-dimethylamino pyridine (DMAP, 31 mg, 0.25 mmol), 1-(4-chlorobenzoyl)-5-methoxy-2-methyl-1H-indole-3-acetic acid (indomethacin, 214 mg, 0.6 mmol) and 1-(3-dimethylaminopropyl)-3-ethylcarbodiimide hydrochloride (EDCI, 144 mg, 0.75 mmol) were dissolved in dichloromethane (10 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=5:1 to 1:2) to give the title compound as a yellow solid, 0.26 g, 75.6% yield. MS (m/z): [M+H]$^+$ calcd for $C_{36}H_{33}Cl_1N_8O_6S$, 741.19; found, 741.1. $^1$H NMR (400 MHz, DMSO-$d_6$) δ 8.98 (s, 1H), 8.79 (s, 1H), 8.52 (s, 1H), 7.76 (d, J=3.8 Hz, 1H), 7.63 (s, 4H), 7.21 (d, J=3.8 Hz, 1H), 6.96-6.87 (m, 2H), 6.68 (dd, J=9.0, 2.5 Hz, 1H), 6.31 (s, 2H), 4.63 (d, J=9.2 Hz, 2H), 4.27 (d, J=9.1 Hz, 2H), 3.83 (s, 2H), 3.72 (s, 2H), 3.67 (s, 3H), 3.25 (q, J=7.4 Hz, 2H), 2.14 (s, 3H), 1.27 (t, J=7.3 Hz, 3H).

Example 74

Methyl (4-(1-(3-(cyanomethyl)-1-(ethylsulfonyl) azetidin-3-yl)-1H-pyrazol-4-yl)-7H-pyrrolo [2, 3-d] pyrimidin-7-yl) (S)-2-((tert-butoxycarbonyl) amino)-2-phenylacetate

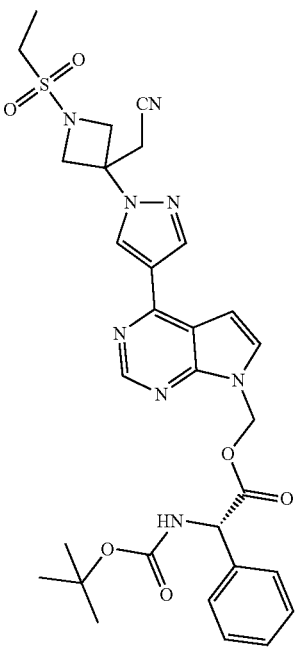 [SMILES: CCS(=O)(=O)N1CC(CC#N)(n2cc(-c3ncnc4c3ccn4COC(=O)[C@@H](NC(=O)OC(C)(C)C)c3ccccc3)cn2)C1]

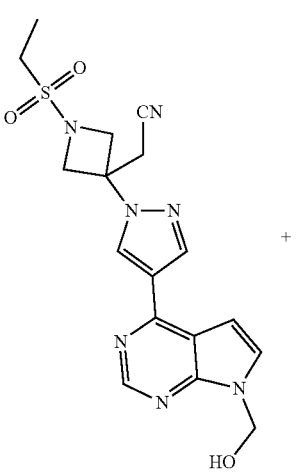

+

401

-continued

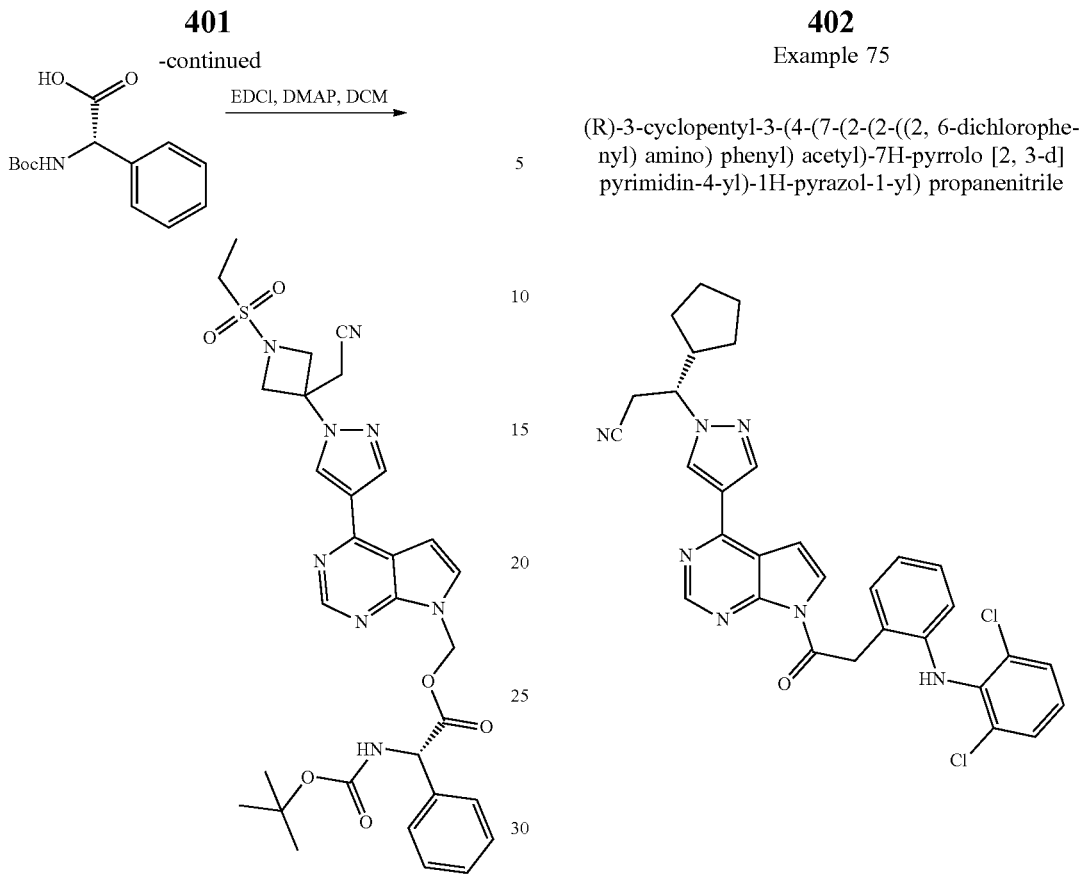

EDCl, DMAP, DCM

Synthesis of methyl (4-(1-(3-(cyanomethyl)-1-(ethylsulfonyl) azetidin-3-yl)-1H-pyrazol-4-yl)-7H-pyrrolo [2, 3-d] pyrimidin-7-yl) (S)-2-((tert-butoxycarbonyl) amino)-2-phenylacetate 2-(1-(Ethylsulfonyl)-3-(4-(7-(hydroxymethyl)-7H-)) pyrrolo [2, 3-d] pyrimidin-4-yl)-1H-pyrazol-1-yl) azetidin-3-yl) acetonitrile (201 mg, 0.5 mmol), 4-dimethylamino pyridine (DMAP, 31 mg, 0.25 mmol), N-Boc-L-phenylglycine (151 mg, 0.6 mmol) and 1-(3-dimethylaminopropyl)-3-ethylcarbodiimide hydrochloride (EDCI, 144 mg, 0.75 mmol) were dissolved in dichloromethane (10 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=5:1 to 1:2) to give the title compound as a white solid, 0.23 g, 72.5% yield. MS (m/z): [M+H]+ calcd for $C_{30}H_{34}N_8O_6S$, 635.23; found, 635.2. $^1$H NMR (400 MHz, DMSO-$d_6$) δ 8.97 (s, 1H), 8.79 (s, 1H), 8.51 (s, 1H), 7.79 (d, J=7.8 Hz, 1H), 7.70 (s, 1H), 7.41-7.16 (m, 6H), 6.42-6.24 (m, 2H), 5.20 (d, J=7.8 Hz, 1H), 4.63 (d, J=9.1 Hz, 2H), 4.27 (d, J=9.2 Hz, 2H), 3.71 (s, 2H), 3.25 (q, J=7.3 Hz, 2H), 1.38-1.21 (m, 12H).

402

Example 75

(R)-3-cyclopentyl-3-(4-(7-(2-(2-((2, 6-dichlorophenyl) amino) phenyl) acetyl)-7H-pyrrolo [2, 3-d] pyrimidin-4-yl)-1H-pyrazol-1-yl) propanenitrile

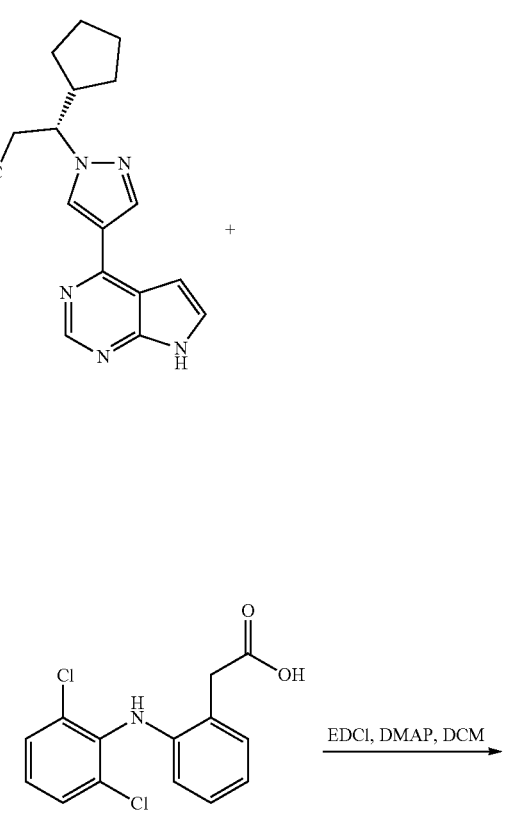

EDCl, DMAP, DCM

403
-continued

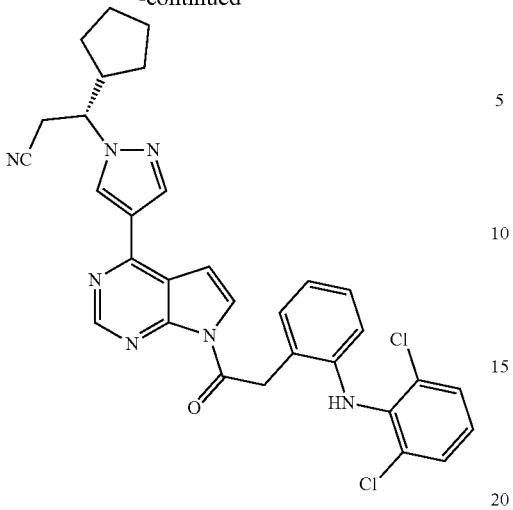

Synthesis of (R)-3-cyclopentyl-3-(4-(7-(2-(2-((2, 6-dichlorophenyl) amino) phenyl) acetyl)-7H-pyrrolo [2, 3-d]pyrimidin-4-yl)-1H-pyrazol-1-yl) propanenitrile (R)-3-(4-(7h-pyrrolo [2, 3-d] pyridin-4-yl)-1h-pyrazol-1-yl)-3-cyclopentylpropane (Ruxolitinib, 184 mg, 0.6 mmol), 4-dimethylamino pyridine (DMAP, 7 mg, 0.06 mmol), 2-(2, 6-dichloroanilino) phenylacetic acid (diclofenac, 231 mg, 0.78 mmol) and 1-(3-dimethylaminopropyl)-3-ethylcarbodiimide hydrochloride (EDCI, 173 mg, 0.9 mmol) were dissolved in dichloromethane (10 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=10:1 to 5:1) to give the title compound as a white solid, 0.11 g, 31.4% yield. MS (m/z): [M+H]$^+$ calcd for $C_{31}H_{27}Cl_2N_7O$, 584.17; found, 584.1. $^1$H NMR (400 MHz, DMSO-d$_6$) δ 8.99 (s, 1H), 8.91 (s, 1H), 8.45 (s, 1H), 8.17 (d, J=4.1 Hz, 1H), 7.51 (d, J=8.1 Hz, 2H), 7.41-7.29 (m, 2H), 7.21 (dd, J=17.2, 9.1 Hz, 2H), 7.15-7.02 (m, 1H), 6.84 (t, J=7.4 Hz, 1H), 6.25 (d, J=8.1 Hz, 1H), 5.01 (s, 2H), 4.56 (td, J=9.7, 4.2 Hz, 1H), 3.31-3.17 (m, 2H), 2.45 (q, J=8.5 Hz, 1H), 1.83 (dtd, J=12.2, 7.5, 3.9 Hz, 1H), 1.68-1.41 (m, 4H), 1.39-1.21 (m, 3H).

Example 76

Methyl (4-(1-(3-(cyanomethyl)-1-(ethylsulfonyl) azetidin-3-yl)-1H-pyrazol-4-yl)-7H-pyrrolo [2, 3-d] pyrimidin-7-yl) 2-(4-(1-oxoisoindolin-2-yl) phenyl) butanoate

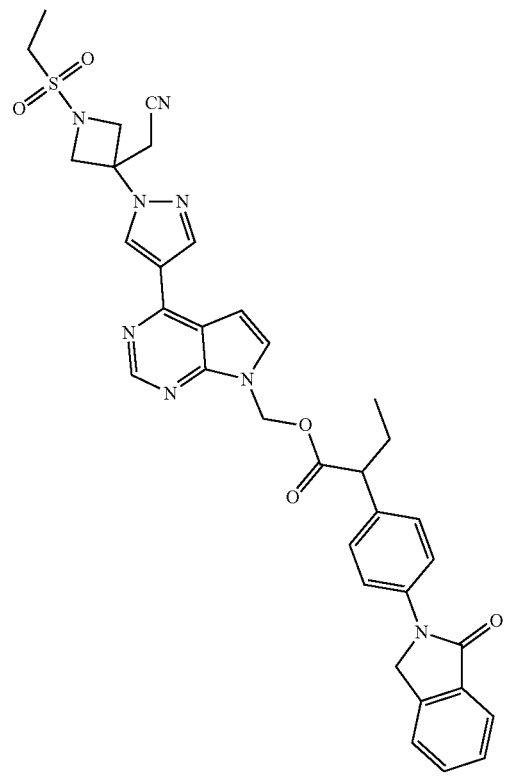 [SMILES: CCC(C(=O)OCn1ccc2c(-c3cnn(C4(CC#N)CN(S(=O)(=O)CC)C4)c3)ncnc21)c1ccc(N2Cc3ccccc3C2=O)cc1]

+

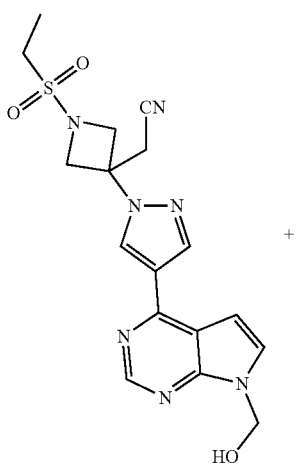

405

-continued

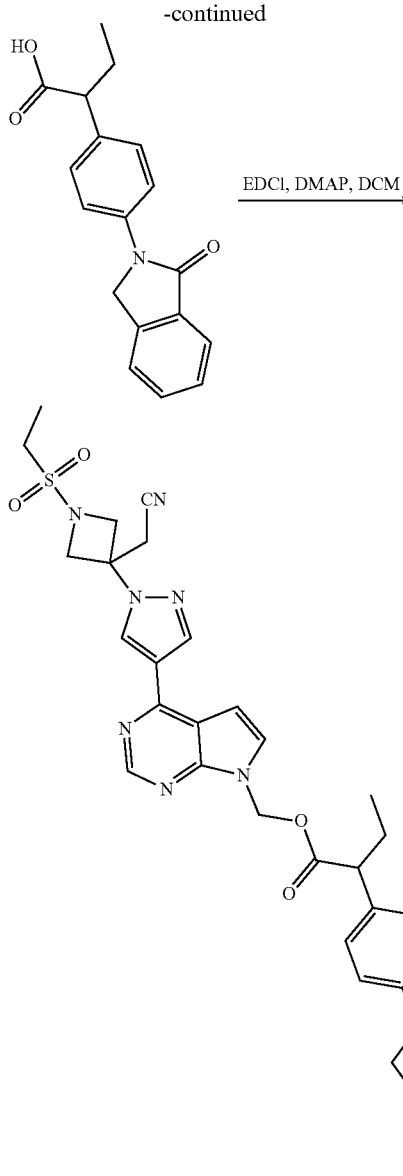

Synthesis of methyl (4-(1-(3-(cyanomethyl)-1-(ethylsulfonyl) azetidin-3-yl)-1H-pyrazol-4-yl)-7H-pyrrolo [2, 3-d] pyrimidin-7-yl) 2-(4-(1-oxoisoindolin-2-yl) phenyl) butanoate 2-(1-(Ethylsulfonyl)-3-(4-(7-(hydroxymethyl)-7H-)) pyrrolo [2, 3-d] pyrimidin-4-yl)-1H-pyrazol-1-yl) azetidin-3-yl) acetonitrile (201 mg, 0.5 mmol), 4-dimethylamino pyridine (DMAP, 31 mg, 0.25 mmol), 2-(4-(1-oxoisoindolin-2-yl) phenyl) butanoic acid (indobufen, 177 mg, 0.6 mmol) and 1-(3-dimethylaminopropyl)-3-ethylcarbodiimide hydrochloride (EDCI, 144 mg, 0.75 mmol) were dissolved in dichloromethane (10 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to give the title compound as a white solid, 0.28 g, 82.5% yield. MS (m/z): [M+H]+ calcd for $C_{35}H_{34}N_8O_5S$, 679.24; found,

406

679.2. $^1$H NMR (400 MHz, DMSO-$d_6$) δ 8.98 (s, 1H), 8.83 (s, 1H), 8.49 (s, 1H), 7.87-7.77 (m, 4H), 7.77-7.66 (m, 2H), 7.62-7.53 (m, 1H), 7.36-7.27 (m, 2H), 7.23 (d, J=3.8 Hz, 1H), 6.32 (q, J=10.8 Hz, 2H), 5.00 (s, 2H), 4.63 (d, J=9.1 Hz, 2H), 4.28 (d, J=9.1 Hz, 2H), 3.72 (s, 2H), 3.63 (t, J=7.6 Hz, 1H), 3.28 (q, J=7.3 Hz, 2H), 2.04-1.97 (m, 1H), 1.76 (dt, J=13.6, 7.0 Hz, 1H), 1.32-1.28 (m, 3H), 0.82 (t, J=7.3 Hz, 3H).

Example 77

(3R)-3-cyclopentyl-3-(4-(7-(2-(4-((2-oxocyclopentyl) methyl) phenyl) propanoyl)-7H-pyrrolo [2, 3-d] pyrimidin-4-yl)-1H-pyrazol-1-yl) propanenitrile

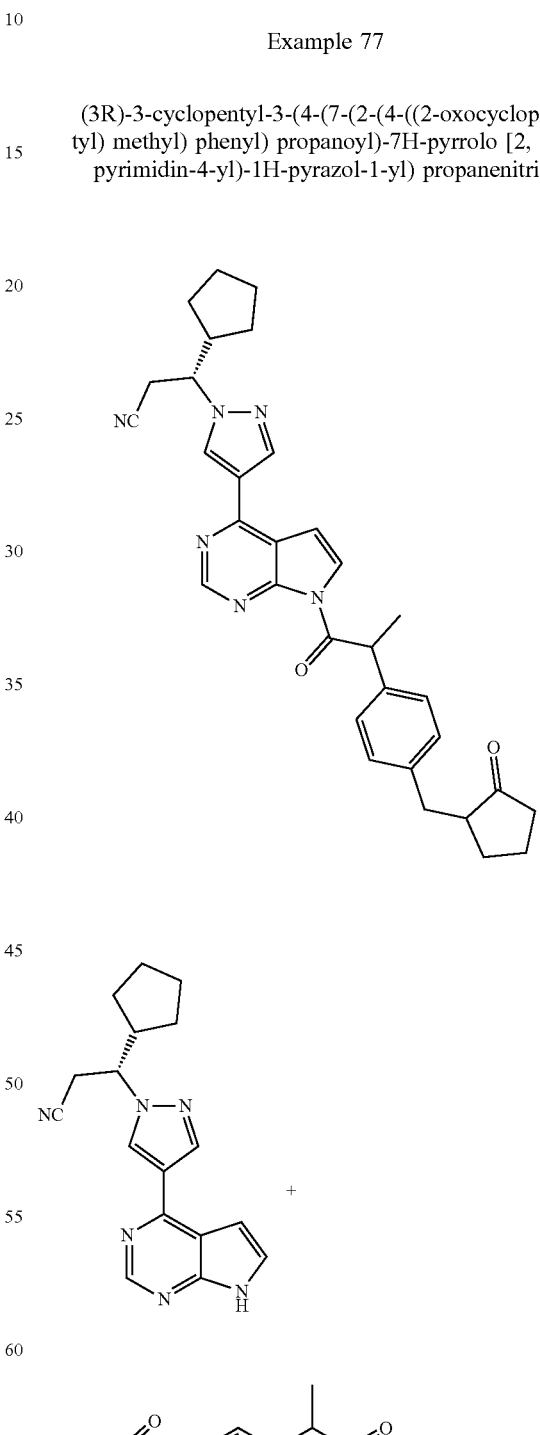

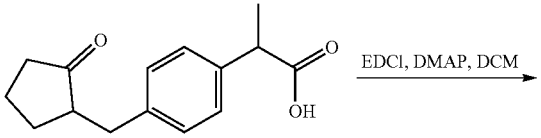

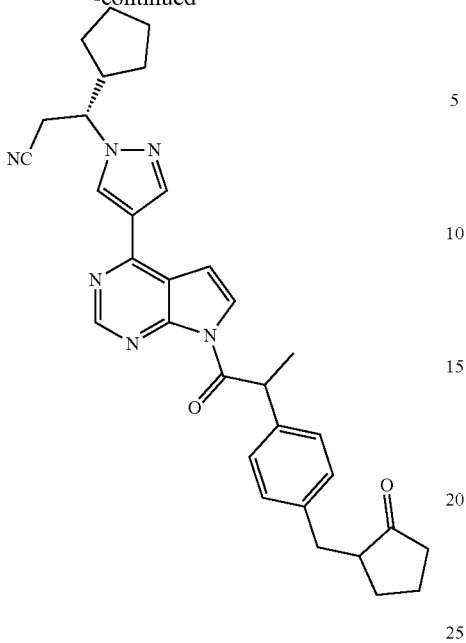

Synthesis of (3R)-3-cyclopentyl-3-(4-(7-(2-(4-((2-oxocyclopentyl) methyl) phenyl) propanoyl)-7H-pyrrolo [2, 3-d] pyrimidin-4-yl)-1H-pyrazol-1-yl) propanenitrile (R)-3-(4-(7h-pyrrolo [2, 3-d] pyridin-4-yl)-1h-pyrazol-1-yl)-3-cyclopentylpropane (Ruxolitinib, 184 mg, 0.6 mmol), 4-dimethylamino pyridine (DMAP, 7 mg, 0.06 mmol), 2-[4-(2-oxocyclopentan-1-ylmethyl) phenyl]propanoic acid (loxoprofen, 192 mg, 0.78 mmol) and 1-(3-dimethylaminopropyl)-3-ethylcarbodiimide hydrochloride (EDCI, 173 mg, 0.9 mmol) were dissolved in dichloromethane (10 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=5:1 to 2:1) to give the title compound as a light yellow solid, 0.26 g, 81.1% yield. MS (m/z): [M+H]$^+$ calcd for $C_{32}H_{34}N_6O_2$, 535.27; found, 535.4. $^1$H NMR (400 MHz, DMSO-$d_6$) δ 8.97 (s, 1H), 8.87 (d, J=1.6 Hz, 1H), 8.40 (s, 1H), 8.11 (d, J=4.2 Hz, 1H), 7.34 (d, J=7.8 Hz, 2H), 7.30 (d, J=4.2 Hz, 1H), 7.11 (d, J=7.8 Hz, 2H), 6.00 (q, J=6.8 Hz, 1H), 4.55 (td, J=9.6, 4.2 Hz, 1H), 3.31-3.15 (m, 2H), 2.90 (dd, J=13.2, 3.4 Hz, 1H), 2.38 (tdd, J=20.0, 14.0, 5.9 Hz, 3H), 2.20 (ddd, J=18.1, 8.2, 2.8 Hz, 1H), 2.05 (dd, J=10.1, 8.6 Hz, 1H), 1.92-1.75 (m, 3H), 1.68-1.50 (m, 7H), 1.48-1.22 (m, 5H)

Example 78

(R)—N-(4-(2-(4-(1-(2-cyano-1-cyclopentylethyl)-1H-pyrazol-4-yl)-7H-pyrrolo [2, 3-d] pyrimidin-7-yl)-2-oxoethyl) phenyl) acetamide

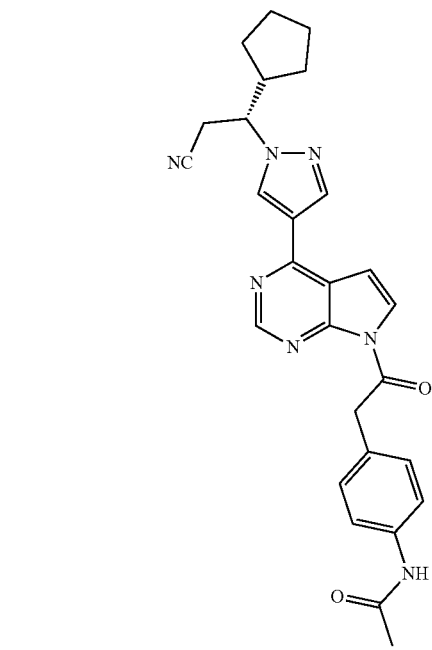

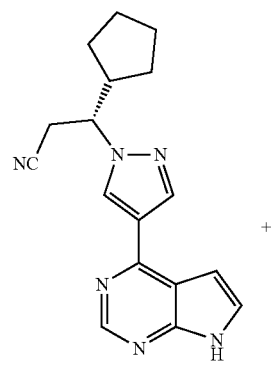

+

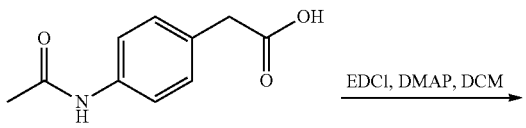

EDCl, DMAP, DCM

409

-continued

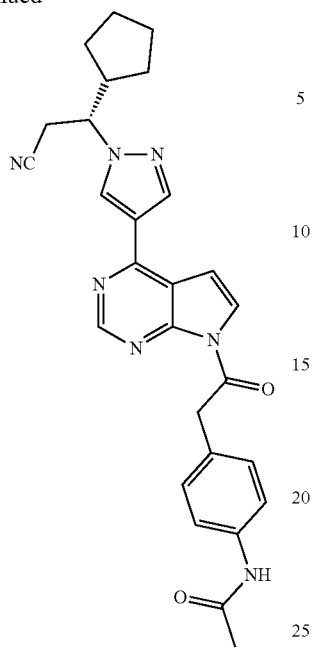

Synthesis of (R)—N-(4-(2-(4-(1-(2-cyano-1-cyclo-pentylethyl)-1H-pyrazol-4-yl)-7H-pyrrolo [2, 3-d] pyrimidin-7-yl)-2-oxoethyl) phenyl) acetamide (R)-3-(4-(7h-pyrrolo [2, 3-d] pyridin-4-yl)-1h-pyrazol-1-yl)-3-cyclopentylpropane (Ruxolitinib, 184 mg, 0.6 mmol), 4-dimethylamino pyridine (DMAP, 7 mg, 0.06 mmol), 2-(4-acetamidophenyl) acetic acid (actarit, 151 mg, 0.78 mmol) and 1-(3-dimethylaminopropyl)-3-ethylcarbodiimide hydrochloride (EDCI, 173 mg, 0.9 mmol) were dissolved in dichloromethane (10 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=2:1 to 2:3) to give the title compound as a light yellow solid, 0.18 g, 62.3% yield. MS (m/z): [M+H]+ calcd for $C_{27}H_{27}N_7O_2$, 482.22; found, 482.3. $^1$H NMR (400 MHz, DMSO-$d_6$) δ 9.90 (s, 1H), 8.97 (s, 1H), 8.90 (s, 1H), 8.43 (s, 1H), 8.12 (d, J=4.2 Hz, 1H), 7.54 (d, J=8.1 Hz, 2H), 7.32 (dd, J=16.1, 6.1 Hz, 3H), 4.87 (s, 2H), 4.55 (td, J=9.6, 4.1 Hz, 1H), 3.30-3.17 (m, 2H), 2.43 (p, J=8.5 Hz, 1H), 2.04 (s, 3H), 1.83 (dhept, J=12.4, 4.1, 3.7 Hz, 1H), 1.67-1.41 (m, 4H), 1.39-1.16 (m, 3H).

410

Example 79

(R)-3-(4-(7-(2-(1-(4-chlorobenzoyl)-5-methoxy-2-methyl-1H-indol-3-yl) acetyl)-7H-pyrrolo [2, 3-d] pyrimidin-4-yl)-1H-pyrazol-1-yl)-3-cyclopentylpropanenitrile

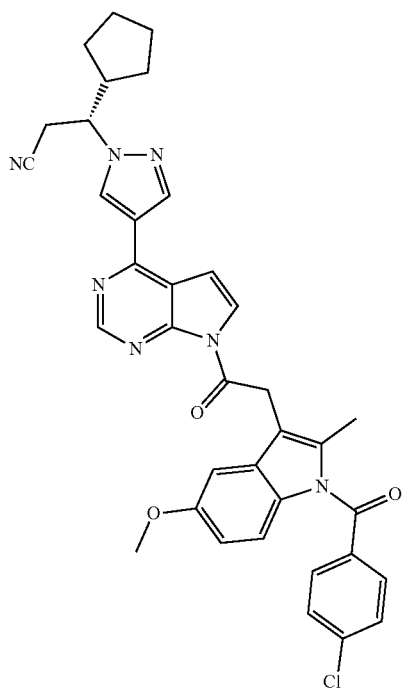 [SMILES: COc1ccc2c(c1)c(CC(=O)n1ccc3c(-c4cnn([C@H](CC#N)C5CCCC5)c4)ncnc31)c(C)n2C(=O)c1ccc(Cl)cc1]

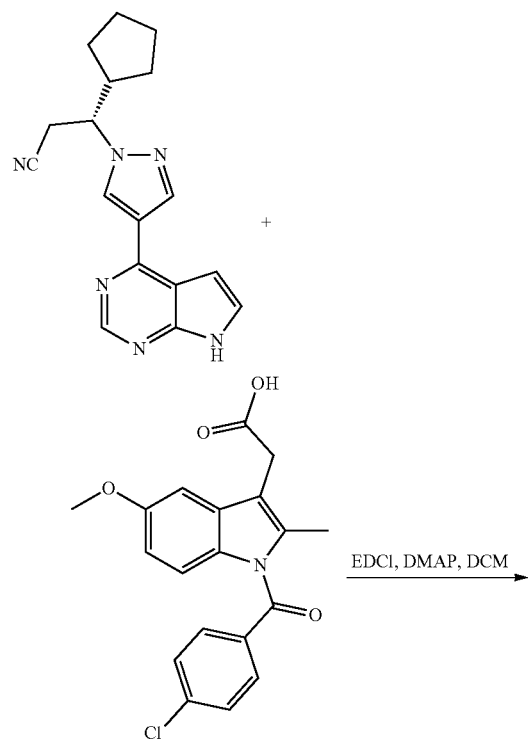

EDCl, DMAP, DCM →

411

-continued

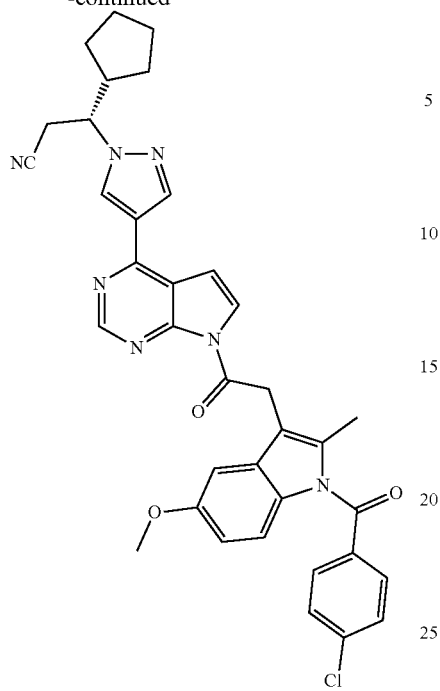

Synthesis of (R)-3-(4-(7-(2-(1-(4-chlorobenzoyl)-5-methoxy-2-methyl-1H-indol-3-yl) acetyl)-7H-pyrrolo [2, 3-d] pyrimidin-4-yl)-1H-pyrazol-1-yl)-3-cyclopentylpropanenitrile (R)-3-(4-(7h-pyrrolo [2, 3-d] pyridin-4-yl)-1H-pyrazol-1-yl)-3-cyclopentylpropane (Ruxolitinib, 184 mg, 0.6 mmol), 4-dimethylamino pyridine (DMAP, 7 mg, 0.06 mmol), 1-(4-chlorobenzoyl)-5-methoxy-2-methyl-1H-indole-3-acetic acid (indomethacin, 279 mg, 0.78 mmol), and 1-(3-dimethylaminopropyl)-3-ethylcarbodiimide hydrochloride (EDCI, 173 mg, 0.9 mmol) was dissolved in dichloromethane (10 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=5:1 to 2:1) to give the title compound as a light yellow solid, 0.3 g, 77.5% yield. MS (m/z): [M+H]+ calcd for $C_{36}H_{32}C_1N_7O_3$, 646.23; found, 646.1. $^1$H NMR (400 MHz, DMSO-$d_6$) δ 9.03 (s, 1H), 8.93 (s, 1H), 8.47 (s, 1H), 8.16 (d, J=4.2 Hz, 1H), 7.76-7.63 (m, 4H), 7.38 (d, J=4.2 Hz, 1H), 7.18 (d, J=2.5 Hz, 1H), 7.00 (d, J=9.0 Hz, 1H), 6.73 (dd, J=9.1, 2.6 Hz, 1H), 5.05 (s, 2H), 4.58 (td, J=9.6, 4.3 Hz, 1H), 3.71 (s, 3H), 3.31-3.19 (m, 2H), 2.46 (q, J=8.2 Hz, 1H), 2.28 (s, 3H), 1.90-1.80 (m, 1H), 1.68-1.31 (m, 7H).

412

Example 80

Tert-butyl ((S)-2-(4-(1-((R)-2-cyano-1-cyclopentylethyl)-1H-pyrazol-4-yl)-7H-pyrrolo [2, 3-d] pyrimidin-7-yl)-2-oxo-1-phenylethyl) carbamate

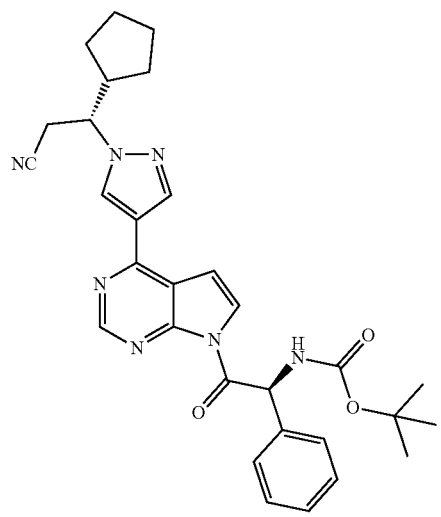

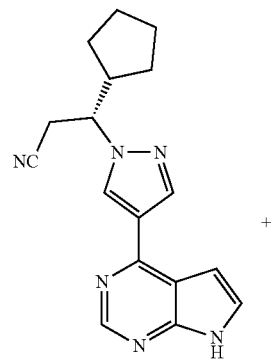

+

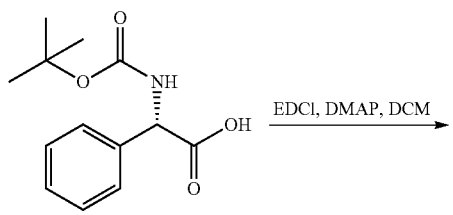

EDCl, DMAP, DCM →

413
-continued

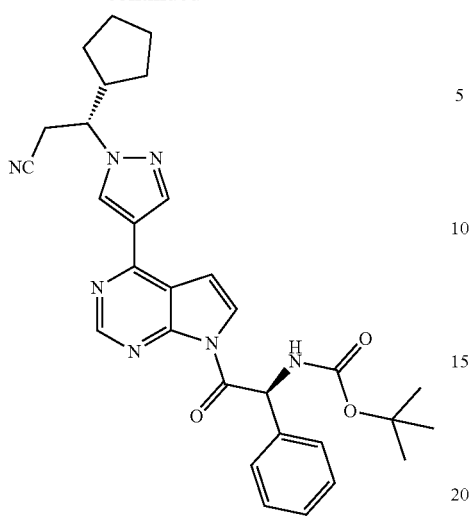

Synthesis of tert-butyl ((S)-2-(4-(1-((R)-2-cyano-1-cyclopentylethyl)-1H-pyrazol-4-yl)-7H-pyrrolo [2,3-d]pyrimidin-7-yl)-2-oxo-1-phenylethyl) carbamate (R)-3-(4-(7h-pyrrolo [2, 3-d] pyridin-4-yl)-1h-pyrazol-1-yl)-3-cyclopentylpropane (Ruxolitinib, 184 mg, 0.6 mmol), 4-dimethylamino pyridine (DMAP, 7 mg, 0.06 mmol), N-Boc-L-phenylglycine (196 mg, 0.78 mmol) and 1-(3-dimethylaminopropyl)-3-ethylcarbodiimide hydrochloride (EDCI, 173 mg, 0.9 mmol) were dissolved in dichloromethane (10 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=5:1 to 2:1) to give the title compound as a yellow solid, 0.26 g, 55.6% yield. MS (m/z): [M+H]$^+$ calcd for C$_{30}$H$_{33}$N$_7$O$_3$, 540.26; found, 540.3. $^1$H NMR (400 MHz, DMSO-d$_6$) δ 8.97 (s, 1H), 8.87 (s, 1H), 8.41 (s, 1H), 8.14 (d, J=4.2 Hz, 1H), 7.95 (d, J=7.6 Hz, 1H), 7.52 (d, J=7.3 Hz, 2H), 7.42 (d, J=7.7 Hz, 1H), 7.31 (td, J=11.8, 10.6, 5.4 Hz, 4H), 4.54 (td, J=9.6, 4.3 Hz, 1H), 3.29-3.12 (m, 2H), 2.43 (h, J=8.5 Hz, 1H), 1.82 (dtd, J=11.9, 7.4, 4.2 Hz, 1H), 1.65-1.50 (m, 3H), 1.46-1.23 (m, 13H).

414
Example 81

Methyl (4-(1-(3-(cyanomethyl)-1-(ethylsulfonyl)azetidin-3-yl)-1H-pyrazol-4-yl)-7H-pyrrolo [2, 3-d]pyrimidin-7-yl) 2-((3-chloro-2-methylphenyl)amino) benzoate

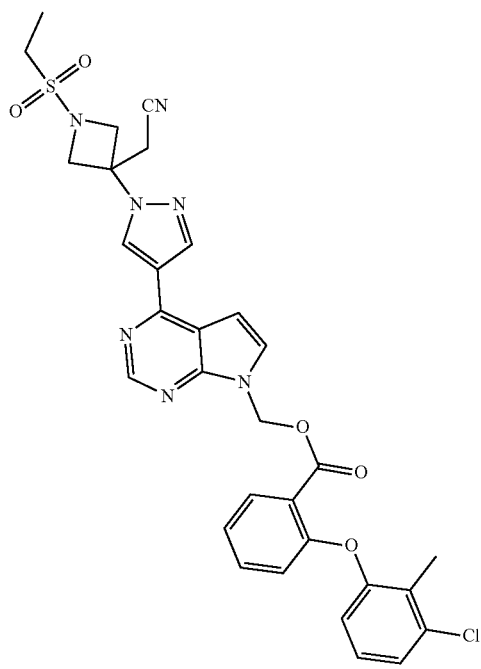 [SMILES: CCS(=O)(=O)N1CC(CC#N)(n2cc(-c3ncnc4c3ccn4COC(=O)c3ccccc3Oc3cccc(Cl)c3C)cn2)C1]

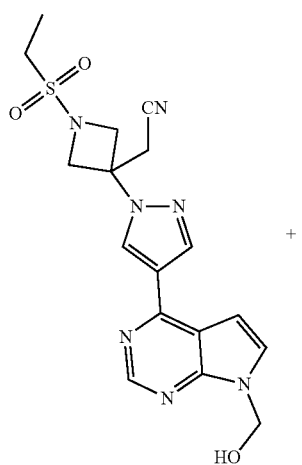

+

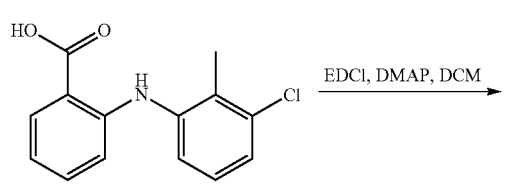

415
-continued

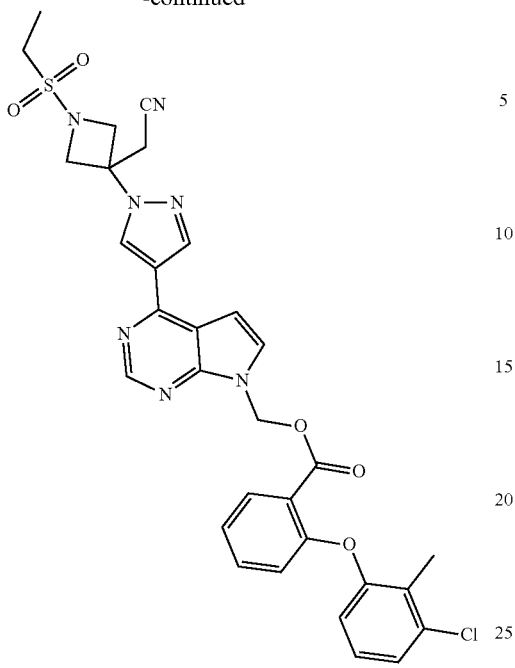

Synthesis of methyl (4-(1-(3-(cyanomethyl)-1-(ethylsulfonyl) azetidin-3-yl)-1H-pyrazol-4-yl)-7H-pyrrolo [2, 3-d] pyrimidin-7-yl) 2-((3-chloro-2-methylphenyl) amino) benzoate 2-(1-(Ethylsulfonyl)-3-(4-(7-(hydroxymethyl)-7H-)) pyrrolo [2, 3-d] pyrimidin-4-yl)-1H-pyrazol-1-yl) azetidin-3-yl) acetonitrile (201 mg, 0.5 mmol), 4-dimethylamino pyridine (DMAP, 31 mg, 0.25 mmol), 2-((3-chloro-2-methylphenyl) amino) benzoic acid (tolfenamic acid, 137 mg, 0.53 mmol) and 1-(3-dimethylaminopropyl)-3-ethylcarbodiimide hydrochloride (EDCI, 144 mg, 0.75 mmol) were dissolved in dichloromethane (10 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=5:1 to 1:2) to give the title compound as a yellow solid, 0.26 g, 80.7% yield. MS (m/z): [M+H]$^+$ calcd for $C_{31}H_{29}C_1N_8O_4S$, 645.17; found, 645.1. $^1$H NMR (400 MHz, DMSO-d$_6$) δ 9.12 (s, 1H), 8.98 (s, 1H), 8.84 (s, 1H), 8.52 (s, 1H), 7.93 (d, J=3.8 Hz, 1H), 7.79 (dd, J=8.4, 1.7 Hz, 1H), 7.37 (td, J=7.6, 7.1, 1.7 Hz, 1H), 7.33-7.21 (m, 4H), 6.78-6.70 (m, 2H), 6.55 (s, 2H), 4.62 (d, J=9.1 Hz, 2H), 4.26 (d, J=9.1 Hz, 2H), 3.71 (s, 2H), 3.24 (q, J=7.3 Hz, 2H), 2.24 (s, 3H), 1.26 (t, J=7.3 Hz, 3H).

416

Example 82

(R)-3-cyclopentyl-3-(4-(7-(2-((2, 3-dimethylphenyl) amino) benzoyl)-7H-pyrrolo [2, 3-d] pyrimidin-4-yl)-1H-pyrazol-1-yl) propanenitrile

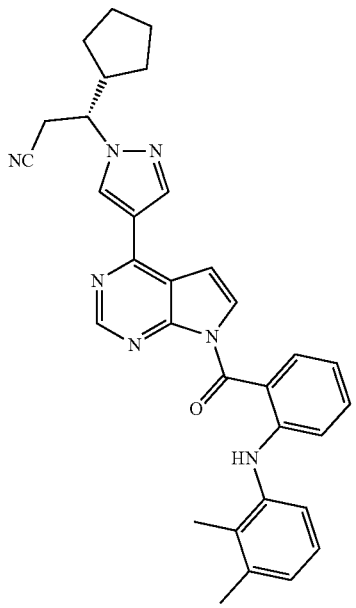

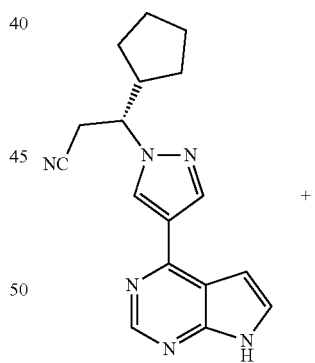
+

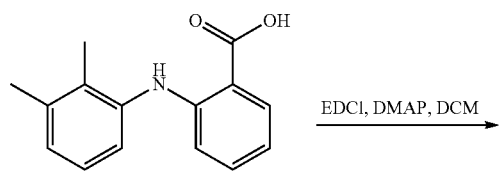
→ EDCI, DMAP, DCM

417
-continued

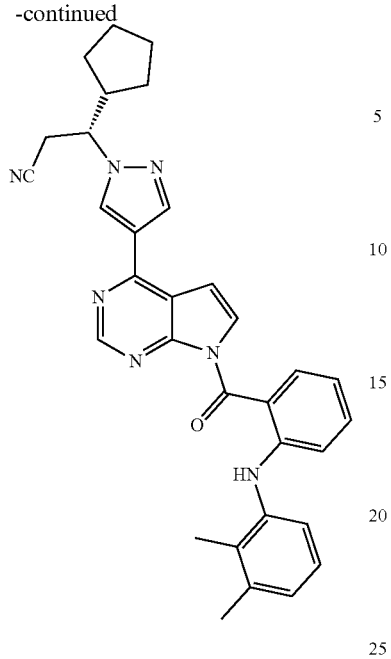

Synthesis of (R)-3-cyclopentyl-3-(4-(7-(2-((2, 3-dimethylphenyl) amino) benzoyl)-7H-pyrrolo [2, 3-d] pyrimidin-4-yl)-1H-pyrazol-1-yl) propanenitrile (R)-3-(4-(7h-pyrrolo [2, 3-d] pyridin-4-yl)-1h-pyrazol-1-yl)-3-cyclopentylpropane (Ruxolitinib, 184 mg, 0.6 mmol), 4-dimethylamino pyridine (DMAP, 7 mg, 0.06 mmol), 2-((2, 3-dimethylphenyl) amino) benzoic acid (mefenamic acid, 188 mg, 0.78 mmol) and 1-(3-dimethylaminopropyl)-3-ethylcarbodiimide hydrochloride (EDCI, 173 mg, 0.9 mmol) were dissolved in dichloromethane (10 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=4:1 to 3:1) to give the title compound as a yellow solid, 0.08 g, 25.2% yield. MS (m/z): [M+H]$^+$ calcd for $C_{32}H_{31}N_7O$, 530.26; found, 530.3. $^1$H NMR (400 MHz, DMSO-$d_6$) δ 8.88 (s, 1H), 8.73 (s, 1H), 8.44 (d, J=13.9 Hz, 2H), 7.87 (d, J=4.0 Hz, 1H), 7.42 (ddd, J=7.7, 4.5, 2.8 Hz, 2H), 7.29 (d, J=4.1 Hz, 1H), 7.08-7.01 (m, 2H), 6.94 (dd, J=6.2, 2.6 Hz, 1H), 6.87-6.75 (m, 2H), 4.56 (td, J=9.7, 4.2 Hz, 1H), 3.29-3.15 (m, 2H), 2.45 (q, J=8.4 Hz, 1H), 2.22 (s, 3H), 1.98 (s, 3H), 1.83 (dtd, J=12.3, 7.4, 3.8 Hz, 1H), 1.55 (tdt, J=32.5, 29.7, 18.3, 6.6 Hz, 4H), 1.39-1.22 (m, 3H).

418
Example 83

Methyl (4-(1-(3-(cyanomethyl)-1-(ethylsulfonyl) azetidin-3-yl)-1H-pyrazol-4-yl)-7H-pyrrolo [2, 3-d] pyrimidin-7-yl) 2-((2, 3-dimethylphenyl) amino) benzoate

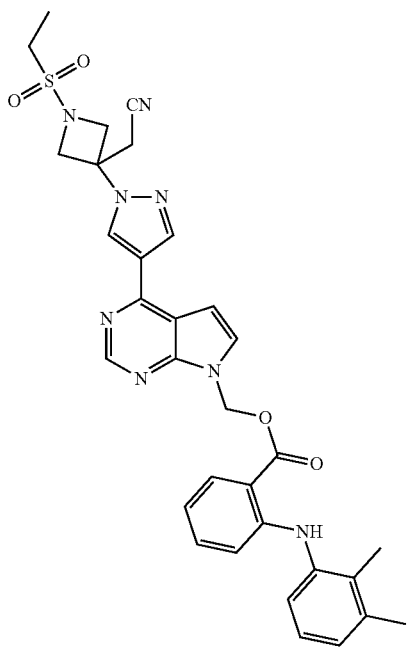 [SMILES: CCS(=O)(=O)N1CC(CC#N)(n2cc(-c3ncnc4c3ccn4COC(=O)c3ccccc3Nc3cccc(C)c3C)cn2)C1]

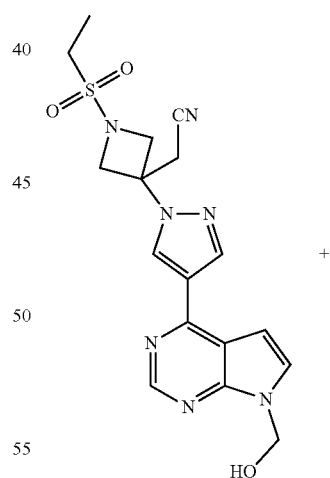

+

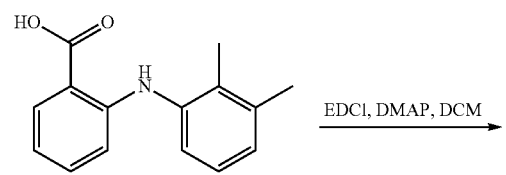

EDCI, DMAP, DCM

419

-continued

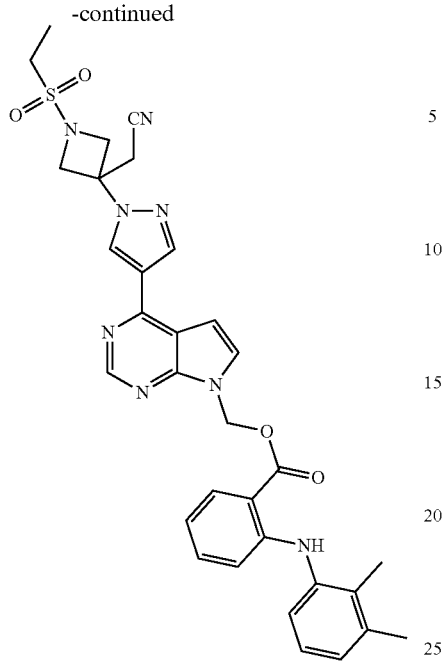

Synthesis of methyl (4-(1-(3-(cyanomethyl)-1-(ethylsulfonyl) azetidin-3-yl)-1H-pyrazol-4-yl)-7H-pyrrolo [2, 3-d] pyrimidin-7-yl) 2-((2, 3-dimethylphenyl) amino) benzoate 2-(1-(ethylsulfonyl)-3-(4-(7-(hydroxymethyl)-7H-)) pyr-rolo [2, 3-d] pyrimidin-4-yl)-1H-pyrazol-1-yl) azetidin-3-yl) acetonitrile (201 mg, 0.5 mmol), 4-dimethylamino pyridine (DMAP, 31 mg, 0.25 mmol), 22-((2, 3-dimethylphenyl) amino) benzoic acid (mefenamic acid, 127 mg, 0.53 mmol) and 1-(3-dimethylaminopropyl)-3-ethylcarbodiimide hydrochloride (EDCI, 144 mg, 0.75 mmol) were dissolved in dichloromethane (10 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=5:1 to 1:2) to give the title compound as a yellow solid, 0.27 g, 86.5% yield. MS (m/z): [M+H]$^+$ calcd for $C_{32}H_{32}N_8O_4S$, 625.23; found, 625.2. $^1$H NMR (400 MHz, DMSO-$d_6$) δ 9.06 (s, 1H), 8.98 (s, 1H), 8.85 (s, 1H), 8.52 (s, 1H), 7.94 (d, J=3.8 Hz, 1H), 7.76 (dd, J=8.1, 1.7 Hz, 1H), 7.32 (ddd, J=8.6, 7.0, 1.7 Hz, 1H), 7.27 (d, J=3.8 Hz, 1H), 7.18-7.05 (m, 3H), 6.70-6.59 (m, 2H), 6.55 (s, 2H), 4.61 (d, J=9.1 Hz, 2H), 4.25 (d, J=9.1 Hz, 2H), 3.70 (s, 2H), 3.24 (q, J=7.3 Hz, 2H), 2.30 (s, 3H), 2.09 (s, 3H), 1.25 (t, J=7.3 Hz, 3H).

420

Example 84

Methyl (4-(1-(3-(cyanomethyl)-1-(ethylsulfonyl) azetidin-3-yl)-1H-pyrazol-4-yl)-7H-pyrrolo [2, 3-d] pyrimidin-7-yl) 2-(4-acetamidophenyl) acetate

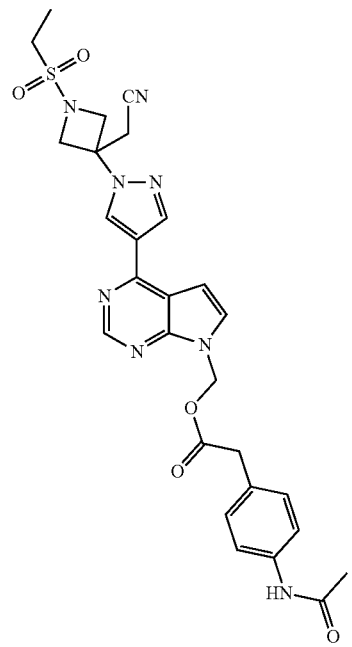 [SMILES: CCS(=O)(=O)N1CC(CC#N)(n2cc(-c3ncnc4c3ccn4COC(=O)Cc3ccc(NC(C)=O)cc3)cn2)C1]

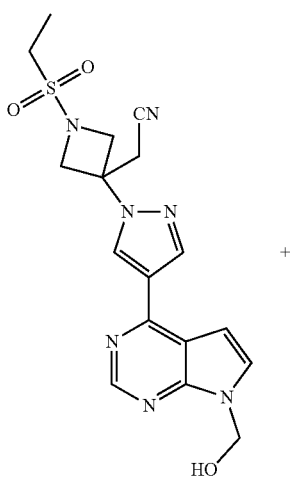

+

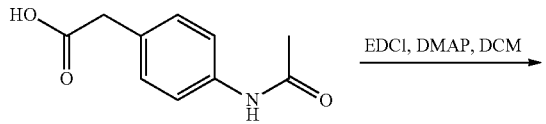

-continued

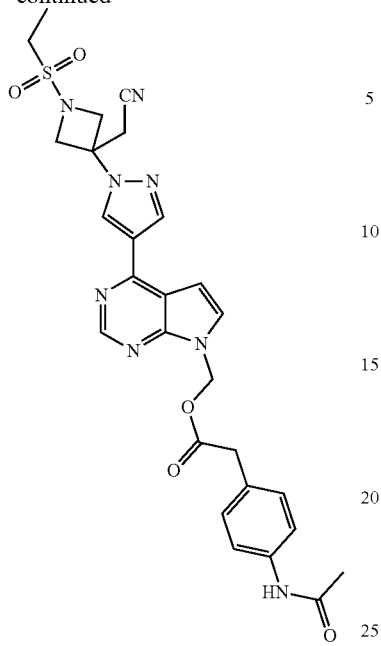

Synthesis of methyl (4-(1-(3-(cyanomethyl)-1-(ethylsulfonyl) azetidin-3-yl)-1H-pyrazol-4-yl)-7H-pyrrolo [2, 3-d] pyrimidin-7-yl) 2-(4-acetamidophenyl) acetate 2-(1-(Ethylsulfonyl)-3-(4-(7-(hydroxymethyl)-7H-)) pyrrolo [2, 3-d] pyrimidin-4-yl)-1H-pyrazol-1-yl) azetidin-3-yl) acetonitrile (201 mg, 0.5 mmol), 4-dimethylamino pyridine (DMAP, 31 mg, 0.25 mmol), 2-(4-acetamidophenyl) acetic acid (actarit, 116 mg, 0.6 mmol), and 1-(3-dimethylaminopropyl)-3-ethylcarbodiimide hydrochloride (EDCI, 144 mg, 0.75 mmol) were dissolved in dichloromethane (10 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to give the title compound as a white solid, 0.22 g, 76.3% yield. MS (m/z): [M+H]+ calcd for $C_{27}H_{28}N_8O_5S$, 577.19; found, 577.2. $^1$H NMR (400 MHz, DMSO-$d_6$) δ 9.89 (s, 1H), 8.98 (s, 1H), 8.84 (s, 1H), 8.52 (s, 1H), 7.78 (d, J=3.8 Hz, 1H), 7.49 (d, J=8.0 Hz, 2H), 7.19 (dd, J=31.5, 5.9 Hz, 3H), 6.29 (s, 2H), 4.63 (d, J=9.1 Hz, 2H), 4.27 (d, J=9.1 Hz, 2H), 3.69 (d, J=20.8 Hz, 4H), 3.26 (q, J=7.3 Hz, 2H), 2.04 (s, 3H), 1.27 (t, J=7.4 Hz, 3H).

Example 85

Methyl (4-(1-(3-(cyanomethyl)-1-(ethylsulfonyl) azetidin-3-yl)-1H-pyrazol-4-yl)-7H-pyrrolo [2, 3-d] pyrimidin-7-yl) 2-(1, 8-diethyl-1, 3, 4, 9-tetrahydropyrano [3, 4-b] indol-1-yl) acetate

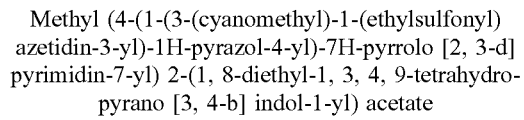

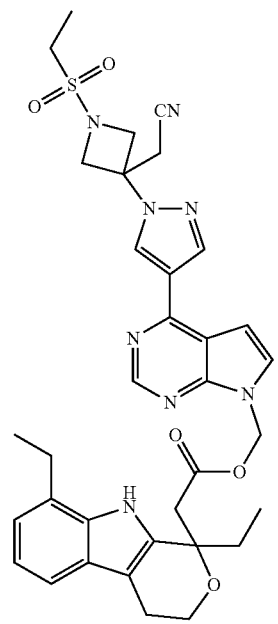 [SMILES: CCc1cccc2c3c([nH]c12)C(CC)(CC(=O)OCn1ccc2c(-c4cnn(C5(CC#N)CN(S(=O)(=O)CC)C5)c4)ncnc21)OCC3]

+

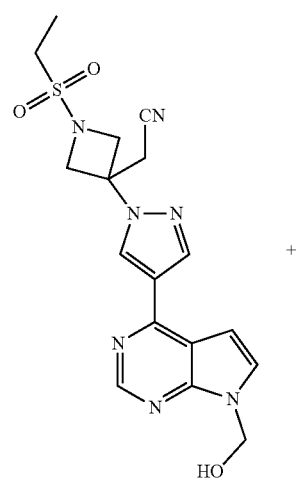

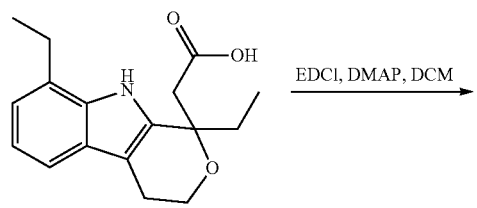

EDCl, DMAP, DCM →

423
-continued

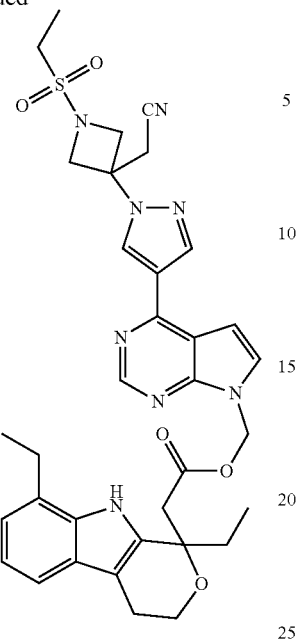

Synthesis of methyl (4-(1-(3-(cyanomethyl)-1-(ethylsulfonyl) azetidin-3-yl)-1H-pyrazol-4-yl)-7H-pyrrolo [2, 3-d] pyrimidin-7-yl) 2-(1, 8-diethyl-1, 3, 4, 9-tetrahydropyrano [3, 4-b] indol-1-yl) acetate 2-(1-(Ethylsulfonyl)-3-(4-(7-(hydroxymethyl)-7H-)) pyrrolo [2, 3-d] pyrimidin-4-yl)-1H-pyrazol-1-yl) azetidin-3-yl) acetonitrile (201 mg, 0.5 mmol), 4-dimethylamino pyridine (DMAP, 31 mg, 0.25 mmol), 1, 8-diethyl-1, 3, 4, 9-tetrahydropyran [3, 4-b] indole-1-acetic acid (etodolac, 172 mg, 0.6 mmol), and 1-(3-dimethylaminopropyl)-3-ethylcarbodiimide hydrochloride (EDCI, 144 mg, 0.75 mmol) were dissolved in dichloromethane (10 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=5:1 to 1:2) to give the title compound as a white solid, 0.17 g, 50.7% yield. MS (m/z): [M+H]+ calcd for $C_{34}H_{38}N_8O_5S$, 671.27; found, 671.2. $^1$H NMR (400 MHz, DMSO-$d_6$) δ 10.42 (s, 1H), 8.97 (s, 1H), 8.80 (s, 1H), 8.51 (s, 1H), 7.61 (d, J=3.8 Hz, 1H), 7.20-7.10 (m, 2H), 6.93-6.81 (m, 2H), 6.27-6.12 (m, 2H), 4.63 (d, J=9.1 Hz, 2H), 4.27 (d, J=9.1 Hz, 2H), 3.88-3.76 (m, 2H), 3.72 (s, 2H), 3.25 (q, J=7.3 Hz, 2H), 3.06 (d, J=13.6 Hz, 1H), 2.86 (d, J=13.6 Hz, 1H), 2.81-2.75 (m, 2H), 2.61-2.48 (m, 2H), 2.01-1.80 (m, 2H), 1.30-1.21 (m, 6H), 0.58 (t, J=7.3 Hz, 3H).

Example 86

(4-(1-((R)-2-cyano-1-cyclopentylethyl)-1H-pyrazol-4-yl)-7H-pyrrolo [2, 3-d] pyrimidin-7-yl) methyl (S)-2-(4-isobutylphenyl) propanoate

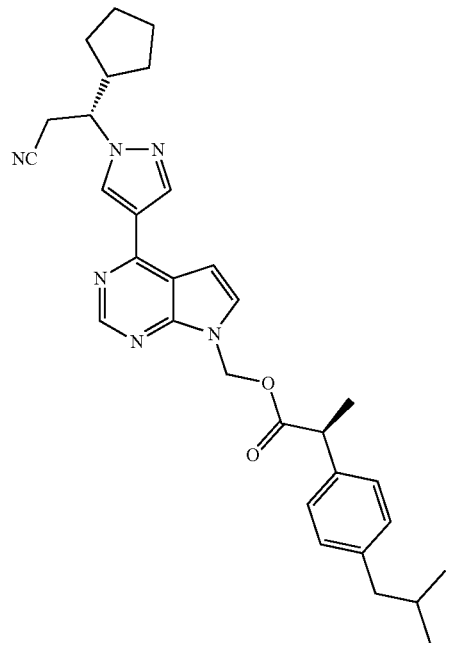

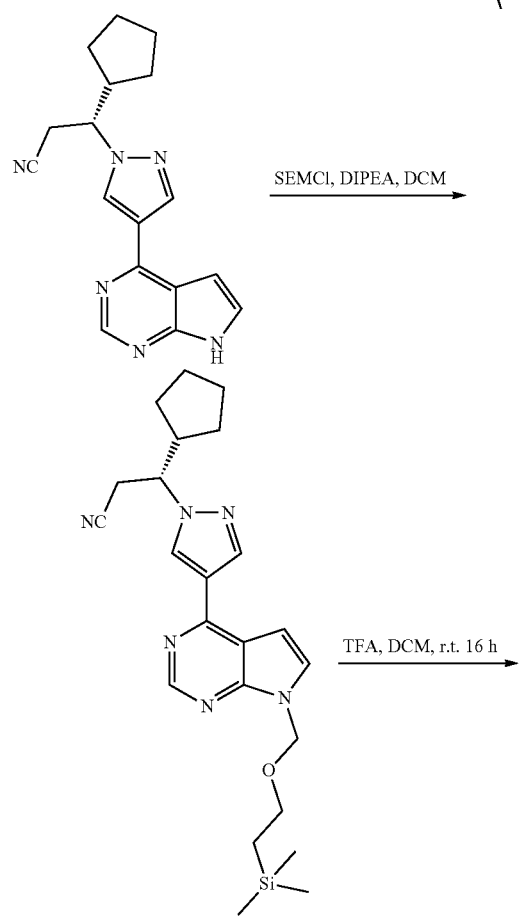

-continued

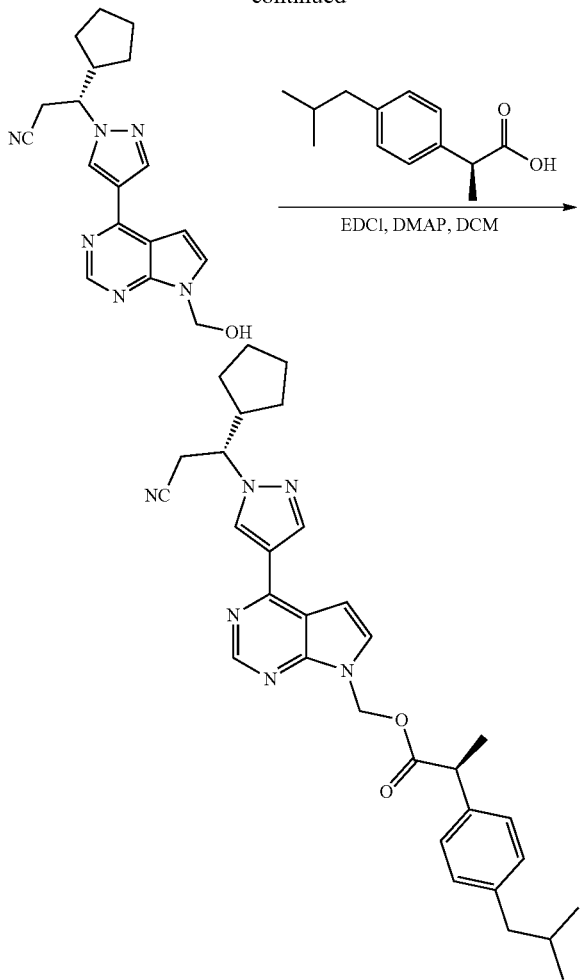

First step: Synthesis of (R)-3-cyclopentyl-3-(4-(7-((2-(trimethylsilyl) ethoxy) methyl)-7H-pyrrolo [2,3-d]pyrimidin-4-yl)-1H-pyrazol-1-yl) propanenitrile (R)-3-(4-(7h-pyrrolo [2, 3-d] pyridin-4-yl)-1h-pyrazol-1-yl)-3-cyclopentylpropane (Ruxolitinib, 1000 mg, 3.26 mmol) and N, N-diisopropylethyl amine (0.7 mL, 4.9 mmoL) were added in dichloromethane (8 mL) under nitrogen. After stirring at room temperature for half an hour, (2-(chloromethoxy) ethyl) trimethylsilane (0.65 g, 3.92 mmol) was added in an ice-water bath, and stirring was continued at room temperature for 3 hours. The reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=150:1 to 50:1) to give the title compound 1.4 g, 98.5% yield. MS (m/z): [M+H]$^+$ calcd for $C_{23}H_{32}N_6OSi$, 437.24; found, 437.3.

Step 2: Synthesis of (R)-3-cyclopentyl-3-(4-(7-(hydroxymethyl)-7H-pyrrolo [2, 3-d] pyrimidin-4-yl)-1H-pyrazol-1-yl) propanenitrile Trifluoroacetic acid (9 mL, 13.8 mg, 121 mmol) was slowly added dropwise to a solution of (R)-3-cyclopentyl-3-(4-(7-((2-(trimethylsilyl) ethoxy) methyl)-7H-pyrrolo [2, 3-d] pyrimidin-4-yl)-1H-pyrazol-1-yl) propanenitrile (1.4 g, 3.2 mmol) in dichloromethane (90 mL) under nitrogen in an ice-water bath. After half an hour, the ice-water bath was removed. The temperature was raised to room temperature and stirring was continued for an additional 2 hours. Saturated sodium bicarbonate solution was added to the above reaction solution at 0° C. to adjust the pH to 8. Then the mixture was poured into a separating funnel for separation. The organic layer was washed with a saturated salt water solution and dried over anhydrous sodium sulfate. After the filtration, the solvent was evaporated under reduced pressure to obtain the crude product. The crude product was further separated by silica gel column chromatography (dichloromethane/methanol=100:1 to 30:1) to give the title product 0.36 g, 33.4% yield. MS (m/z): [M+H]$^+$ calcd for $C_{18}H_{20}N_6$, 337.17; found, 337.3. $^1$H NMR (400 MHz, DMSO-d6) δ 8.95-8.80 (m, 2H), 8.49 (s, 1H), 7.81 (d, J=3.7 Hz, 1H), 7.15 (d, J=3.7 Hz, 1H), 6.75 (t, J=7.3 Hz, 1H), 5.72 (d, J=7.3 Hz, 2H), 4.64 (td, J=9.6, 4.2 Hz, 1H), 3.42-3.26 (m, 2H), 2.53 (q, J=8.5 Hz, 1H), 1.92 (dtd, J=11.8, 7.5, 4.2 Hz, 1H), 1.76-1.50 (m, 4H), 1.50-1.23 (m, 3H).

Step 3: synthesis of (4-(1-((R)-2-cyano-1-cyclopentylethyl)-1H-pyrazol-4-yl)-7H-pyrrolo [2, 3-d] pyrimidin-7-yl) methyl (S)-2-(4-isobutylphenyl) propanoate (R)-3-cyclopentyl-3-(4-(7-(hydroxymethyl)-7H-pyrrolo [2, 3-d] pyrimidin-4-yl)-1H-pyrazol-1-yl) propanenitrile (120 mg, 0.36 mmol), 4-dimethylamino pyridine (DMAP, 44 mg, 0.36 mmol), (S)-(+)-2-(4-isobutylphenyl) propanoic acid ((S)-(+)-ibuprofen, 110 mg, 0.54 mmol) and 1-(3-dimethylaminopropyl)-3-ethylcarbodiimide hydrochloride (EDCI, 103 mg, 0.54 mmol) were dissolved in a mixed solvent of dichloromethane (2.5 mL) and dimethylformamide (0.25 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=150:1 to 50:1) to give the title compound as a white solid, 0.106 g, 56.1% yield. MS (m/z): [M+H]$^+$ calcd for $C_{31}H_{36}N_6O_2$, 525.29; found, 525.3. $^1$H NMR (400 MHz, Chloroform-d) δ 8.85 (s, 1H), 8.31 (d, J=10.9 Hz, 2H), 7.41 (d, J=3.8 Hz, 1H), 7.10 (d, J=8.1 Hz, 2H), 7.00 (d, J=7.9 Hz, 2H), 6.72 (d, J=3.8 Hz, 1H), 6.30-6.18 (m, 2H), 4.28 (ddd, J=10.1, 8.6, 4.0 Hz, 1H), 3.71 (q, J=7.1 Hz, 1H), 3.14 (dd, J=17.0, 8.6 Hz, 1H), 2.97 (dd, J=17.0, 4.0 Hz, 1H), 2.61 (ddd, J=16.8, 8.2, 4.6 Hz, 1H), 2.40 (d, J=7.1 Hz, 2H), 2.00-1.93 (m, 1H), 1.85-1.53 (m, 6H), 1.47 (d, J=7.2 Hz, 3H), 1.37-1.23 (m, 2H), 0.86 (d, J=6.6 Hz, 6H).

Example 87

(4-(1-((R)-2-cyano-1-cyclopentylethyl)-1H-pyrazol-4-yl)-7H-pyrrolo [2, 3-d] pyrimidin-7-yl) methyl (S)-2-(6-methoxynaphthalen-2-yl) propanoate

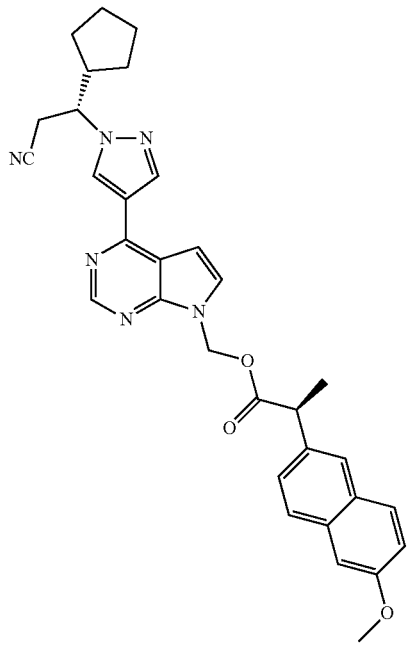 [SMILES: COc1ccc2cc([C@H](C)C(=O)OCn3ccc4c(-c5cnn([C@H](CC#N)C6CCCC6)c5)ncnc43)ccc2c1]

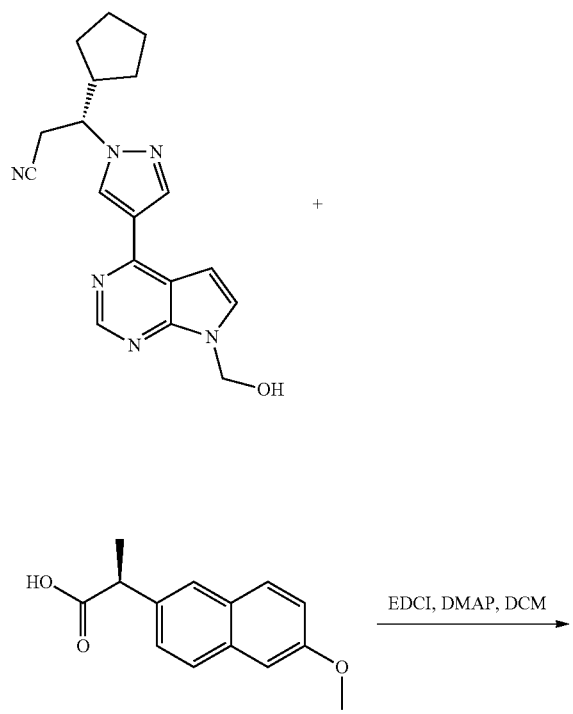

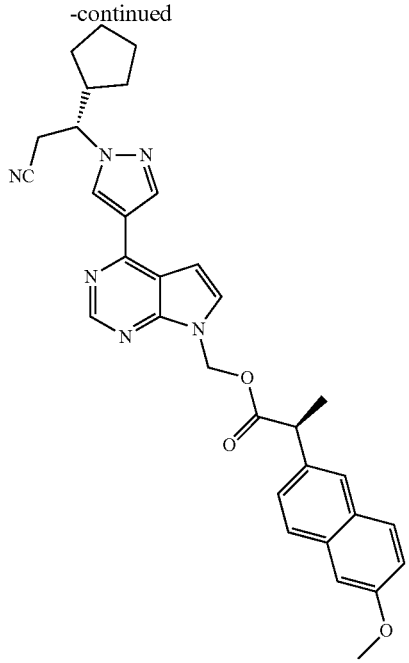

Synthesis of (4-(1-((R)-2-cyano-1-cyclopentylethyl)-1H-pyrazol-4-yl)-7H-pyrrolo [2, 3-d] pyrimidin-7-yl) methyl (S)-2-(6-methoxynaphthalen-2-yl) propanoate (R)-3-cyclopentyl-3-(4-(7-(hydroxymethyl)-7H-pyrrolo [2, 3-d] pyrimidin-4-yl)-1H-pyrazol-1-yl) propanenitrile (140 mg, 0.42 mmol), 4-dimethylamino pyridine (DMAP, 51 mg, 0.42 mmol), (S)-(+)-2-(6-methoxy-2-naphthyl) propanoic acid (naproxen, 144 mg, 0.63 mmol) and 1-(3-dimethylaminopropyl)-3-ethylcarbodiimide hydrochloride (EDCI, 120 mg, 0.63 mmol) were dissolved in dichloromethane (3 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=150:1 to 50:1) to give the title compound as a white solid, 0.146 g, 63.4% yield. MS (m/z): [M+H]$^+$ calcd for $C_{32}H_{32}N_6O_3$, 549.25; found, 549.3. $^1$H NMR (400 MHz, Chloroform-d) δ 8.83 (s, 1H), 8.29 (d, J=7.0 Hz, 2H), 7.60 (t, J=8.6 Hz, 2H), 7.54 (d, J=1.8 Hz, 1H), 7.39 (d, J=3.8 Hz, 1H), 7.29 (dd, J=6.6, 1.9 Hz, 1H), 7.14-7.03 (m, 2H), 6.68 (d, J=3.8 Hz, 1H), 6.24 (d, J=2.4 Hz, 2H), 4.27 (ddd, J=10.1, 8.6, 4.0 Hz, 1H), 3.89 (s, 3H), 3.14 (dd, J=17.0, 8.6 Hz, 1H), 2.96 (dd, J=17.0, 4.0 Hz, 1H), 2.66-2.53 (m, 1H), 2.05-1.92 (m, 1H), 1.79-1.50 (m, 9H), 1.29 (td, J=12.8, 6.5 Hz, 2H).

Example 88

(4-(Methyl ((trans)-4-((N-methylsulfamoyl) methyl) cyclohexyl) amino)-7H-pyrrolo [2, 3-d] pyrimidin-7-yl) methyl (S)-2-(4-isobutylphenyl) propanoate

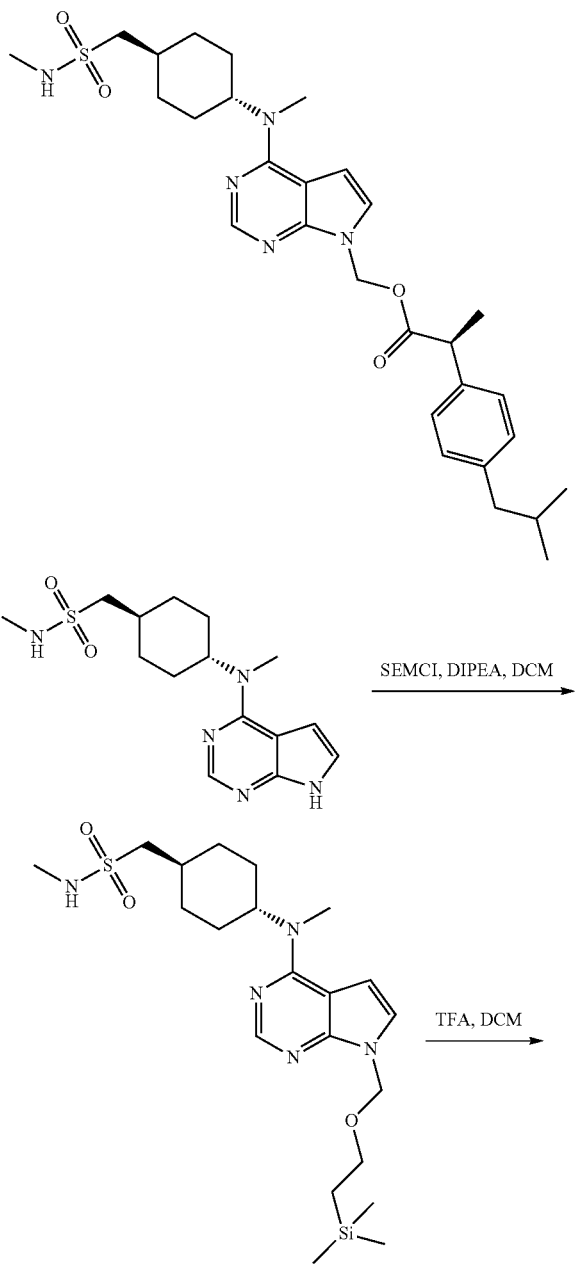

First step: synthesis of N-methyl-1-((trans)-4-(methyl (7-((2-(trimethylsilyl) ethoxy) methyl)-7H-pyrrolo [2, 3-d] pyrimidin-4-yl) amino) cyclohexyl) methanesulfonamide N-Methyl-1-((trans)-4-(methyl (7H-pyrrolo [2, 3-d] pyrimidin-4-yl) amino) cyclohexyl) methanesulfonamide (oclacitinib, 1687 mg, 5 mmol) and N, N-diisopropylethyl amine (780 mg, 6 mmol) were added in dichloromethane (50 mL) under nitrogen. After stirring at room temperature for half an hour, (2-(chloromethoxy) ethyl) trimethylsilane (1 g, 6 mmol) was added in an ice-water bath. Stirring was continued at room temperature overnight. After completion of the reaction, the reaction mixture was diluted with dichloromethane and washed with water and saturated salt water solution. The organic layer was dried over anhydrous sodium sulfate, and filtered. The solvent was evaporated under reduced pressure to give the title compound as an oily solid, 2 g, 85.6% yield. MS (m/z): [M+H]$^+$ calcd for $C_{21}H_{37}N_5O_3SSi$, 468.24; found, 468.2.

Step 2: synthesis of 1-((trans)-4-((7-(hydroxymethyl)-7H-pyrrolo [2, 3-d] pyrimidin-4-yl) (methyl) amino) cyclohexyl)-N-methyl methanesulfonamide Trifluoroacetic acid (6 mL, 9.2 g, 80.8 mmol) was slowly added dropwise to a solution of N-methyl-1-((trans)-4-(methyl (7-((2-(trimethylsilyl) ethoxy) methyl)-7H-pyrrolo [2, 3-d] pyrimidin-4-yl) amino) cyclohexyl) methanesulfonamide (2 g, 4.29 mmol) in dichloromethane (60 mL) under nitrogen in an ice-water bath. After half an hour, the ice-water bath was removed and the temperature was raised to room temperature and stirring was continued for 24 hours. Saturated sodium bicarbonate solution was added to the above reaction solution at 0° C. to adjust the pH to 8. Then the mixture was poured into a separating funnel for separation. The organic layer was washed with a saturated salt water solution and dried over anhydrous sodium sulfate. After the filtration, the solvent was evaporated under reduced pressure to obtain the crude product. The crude product was further separated by silica gel column chromatography (petroleum ether/ethyl acetate=1:1 to 0:1) to give

431 the title product, 0.9 g, 98.5% yield. MS (m/z): [M+H]+ calcd for $C_{16}H_{25}N_5O_3S$, 368.17; found, 368.2.

Step 3: synthesis of (4-(methyl ((trans)-4-((N-methylsulfamoyl) methyl) cyclohexyl) amino)-7H-pyrrolo [2, 3-d] pyrimidin-7-yl) methyl (S)-2-(4-isobutylphenyl) propanoate 1-((Trans)-4-((7-(hydroxymethyl)-7H-pyrrolo [2, 3-d] pyrimidin-4-yl) (methyl) amino) cyclohexyl)-N-methyl methanesulfonamide (150 mg, 0.41 mmol), 4-dimethylaminopyridine (DMAP, 50 mg, 0.41 mmol), (S)-(+)-2-(4-isobutylphenyl) propanoic acid ((S)-(+)-ibuprofen, 126 mg, 0.61 mmol), and 1-(3-dimethylaminopropyl)-3-ethylcarbodiimide hydrochloride (EDCI, 117 mg, 0.61 mmol) were dissolved in dichloromethane (3 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=10:1 to 1:2) to give the title compound as a white solid, 0.086 g, 37.7% yield. MS (m/z): [M+H]+ calcd for $C_{29}H_{41}N_5O_4S$, 556.29; found, 556.3. $^1$H NMR (400 MHz, Chloroform-d) δ 8.32 (s, 1H), 7.11 (d, J=7.7 Hz, 2H), 7.08-6.94 (m, 3H), 6.48 (d, J=3.8 Hz, 1H), 6.22-6.04 (m, 2H), 4.75 (s, 1H), 4.31 (q, J=5.3 Hz, 1H), 3.68 (q, J=7.2 Hz, 1H), 3.20 (s, 3H), 2.96 (d, J=6.2 Hz, 2H), 2.82 (d, J=5.1 Hz, 3H), 2.41 (d, J=7.1 Hz, 2H), 2.24-2.13 (m, 2H), 2.06-1.95 (m, 1H), 1.84 (ddd, J=22.7, 13.2, 5.3 Hz, 3H), 1.76-1.62 (m, 2H), 1.44 (d, J=7.3 Hz, 3H), 1.36 (dd, J=12.4, 9.1 Hz, 2H), 0.87 (d, J=6.6 Hz, 6H).

Example 89

(4-(Methyl ((trans)-4-((N-methylsulfamoyl) methyl) cyclohexyl) amino)-7H-pyrrolo [2, 3-d] pyrimidin-7-yl) methyl (S)-2-(6-methoxynaphthalen-2-yl) propanoate

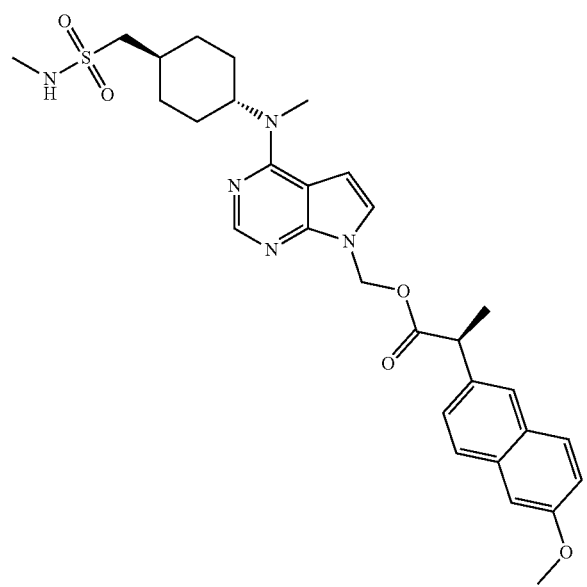

432

-continued

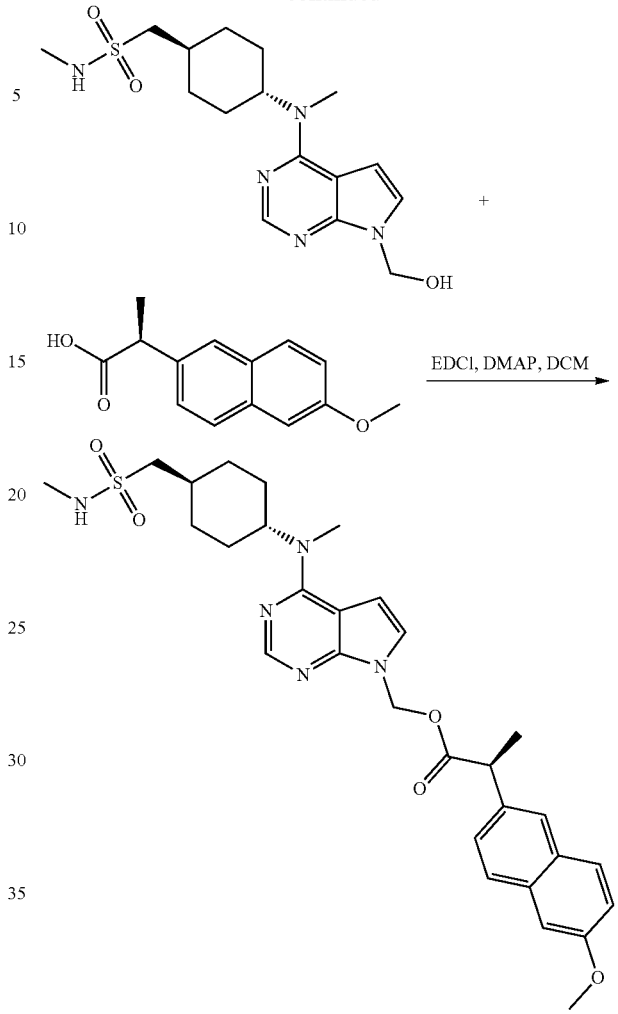

Synthesis of (4-(methyl ((trans)-4-((N-methylsulfamoyl) methyl) cyclohexyl) amino)-7H-pyrrolo [2, 3-d]pyrimidin-7-yl) methyl (S)-2-(6-methoxynaphthalen-2-yl) propanoate 1-((Trans)-4-((7-(hydroxymethyl)-7H-pyrrolo [2, 3-d] pyrimidin-4-yl) (methyl) amino) cyclohexyl)-N-methyl methanesulfonamide (150 mg, 0.41 mmol), 4-dimethyl-amino pyridine (DMAP, 50 mg, 0.41 mmol), (S)-(+)-2-(6-methoxy-2-naphthyl) propanoic acid (naproxen, 141 mg, 0.61 mmol) and 1-(3-dimethylaminopropyl)-3-ethylcarbodiimide hydrochloride (EDCI, 117 mg, 0.61 mmol) were dissolved in dichloromethane (3 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=10:1 to 1:2) to give the title compound as a white solid, 0.056 g, 23.5% yield. MS (m/z): [M+H]+ calcd for $C_{30}H_{37}N_5O_5S$, 580.25; found, 580.3. $^1$H NMR (400 MHz, Chloroform-d) δ 8.31 (s, 1H), 7.69-7.44 (m, 3H), 7.40-7.22 (m, 1H), 7.17-6.99 (m, 3H), 6.43 (d, J=3.8 Hz, 1H), 6.14 (q, J=10.6 Hz, 2H), 4.72 (s, 1H), 4.24 (q, J=5.4 Hz, 1H), 3.97-3.78 (m, 4H), 3.17 (s, 3H), 2.95 (d, J=6.2 Hz, 2H), 2.82 (d, J=5.3 Hz, 3H), 2.16 (d, J=13.1 Hz, 2H), 1.99 (s, 1H), 1.85 (d, J=11.1 Hz, 2H), 1.74-1.60 (m, 2H), 1.53 (d, J=7.2 Hz, 3H), 1.36 (td, J=13.7, 5.9 Hz, 2H).

Example 90

(4-(Methyl ((trans)-4-((N-methylsulfamoyl) methyl) cyclohexyl) amino)-7H-pyrrolo [2, 3-d] pyrimidin-7-yl) methyl 2-(3-benzoylphenyl) propanoate

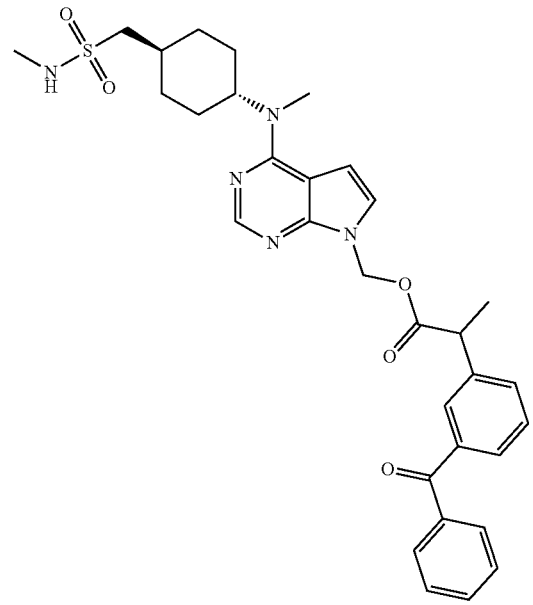

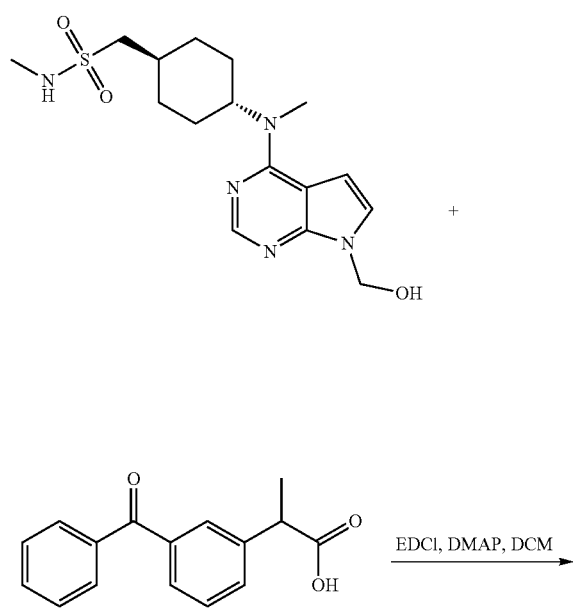

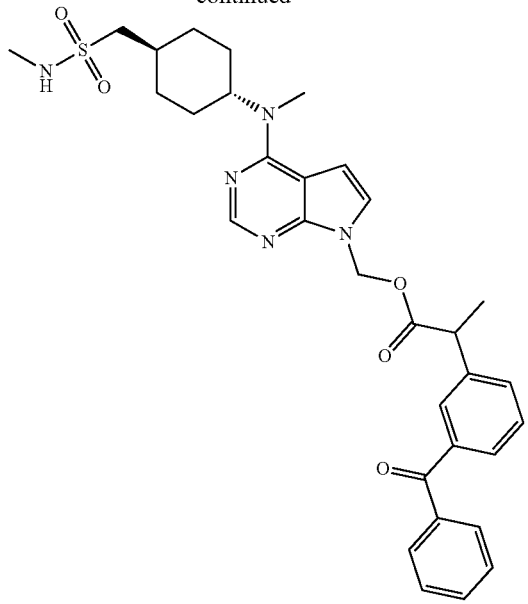

Synthesis of (4-(methyl ((trans)-4-((N-methylsulfamoyl) methyl) cyclohexyl) amino)-7H-pyrrolo [2, 3-d]pyrimidin-7-yl) methyl 2-(3-benzoylphenyl) propanoate 1-((Trans)-4-((7-(hydroxymethyl)-7H-pyrrolo [2, 3-d] pyrimidin-4-yl) (methyl) amino) cyclohexyl)-N-methyl methanesulfonamide (220 mg, 0.6 mmol), 4-dimethylamino pyridine (DMAP, 7 mg, 0.06 mmol), 2-(3-benzoylphenyl) propanoic acid (ketoprofen, 198 mg, 0.78 mmol) and 1-(3-dimethylaminopropyl)-3-ethylcarbodiimide hydrochloride (EDCI, 173 mg, 0.9 mmol) were dissolved in dichloromethane (10 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=2:1 to 1:2) to give the title compound as a white solid, 0.16 g, 44.2% yield. MS (m/z): [M+H]$^+$ calcd for $C_{32}H_{37}N_5O_5S$, 604.25; found, 604.4. $^1$H NMR (400 MHz, DMSO-d$_6$) δ 8.12 (s, 1H), 7.71-7.65 (m, 3H), 7.61-7.51 (m, 5H), 7.46 (t, J=8.0 Hz, 1H), 7.23 (d, J=3.8 Hz, 1H), 6.88 (q, J=4.9 Hz, 1H), 6.60 (d, J=3.7 Hz, 1H), 6.14 (s, 2H), 4.63 (s, 1H), 3.95 (q, J=7.1 Hz, 1H), 3.13 (s, 3H), 2.95 (d, J=6.2 Hz, 2H), 2.59 (d, J=5.0 Hz, 3H), 2.09-2.01 (m, 2H), 1.81 (s, 1H), 1.72-1.62 (m, 4H), 1.39 (d, J=7.1 Hz, 3H), 1.35-1.26 (m, 2H).

Example 91

(4-(Methyl ((trans)-4-((N-methylsulfamoyl) methyl) cyclohexyl) amino)-7H-pyrrolo [2, 3-d] pyrimidin-7-yl) methyl (S)-2-((tert-butoxycarbonyl) amino)-2-phenylacetate

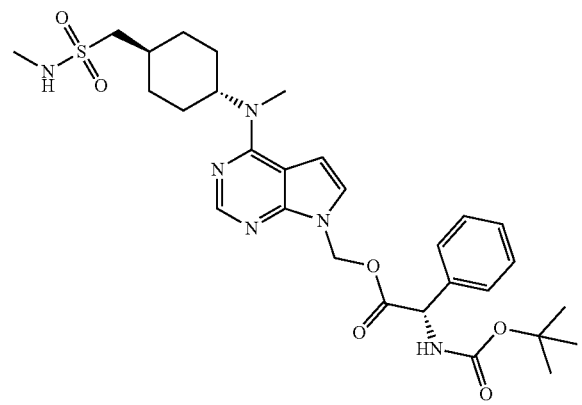

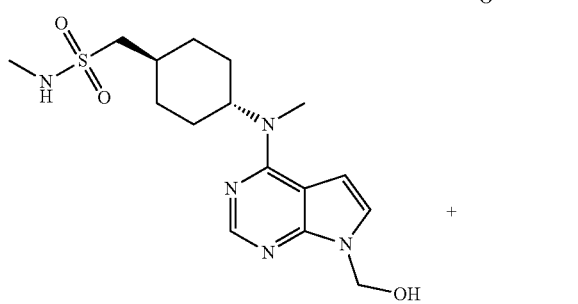

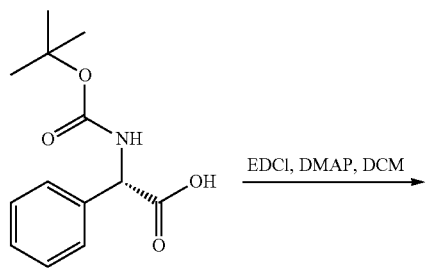

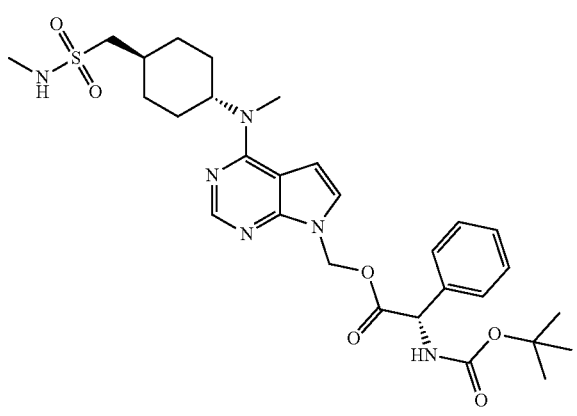

Synthesis of (4-(methyl ((trans)-4-((N-methylsulfamoyl) methyl) cyclohexyl) amino)-7H-pyrrolo [2, 3-d]pyrimidin-7-yl) methyl (S)-2-((tert-butoxycarbonyl) amino)-2-phenylacetate 1-((Trans)-4-((7-(hydroxymethyl)-7H-pyrrolo [2, 3-d] pyrimidin-4-yl) (methyl) amino) cyclohexyl)-N-methyl methanesulfonamide (220 mg, 0.6 mmol), 4-dimethylaminopyridine (DMAP, 7 mg, 0.06 mmol), N-Boc-L-phenylglycine (196 mg, 0.78 mmol) and 1-(3-dimethylaminopropyl)-3-ethylcarbodiimide hydrochloride (EDCI, 173 mg, 0.9 mmol) were dissolved in dichloromethane (10 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=2:1 to 1:2) to give the title compound as a white solid, 0.14 g, 38.8% yield. MS (m/z): [M+H]$^+$ calcd for $C_{29}H_{40}N_6O_6S$, 601.27; found, 601.4. $^1$H NMR (400 MHz, DMSO-$d_6$) δ 8.21 (s, 1H), 7.85 (d, J=8.0 Hz, 1H), 7.39-7.25 (m, 6H), 6.94 (q, J=5.0 Hz, 1H), 6.67 (d, J=3.8 Hz, 1H), 6.27-6.16 (m, 2H), 5.22 (d, J=7.9 Hz, 1H), 4.71 (s, 1H), 3.21 (s, 3H), 3.01 (d, J=6.2 Hz, 2H), 2.64 (d, J=5.0 Hz, 3H), 2.10 (d, J=12.7 Hz, 2H), 1.95-1.85 (m, 1H), 1.73 (d, J=7.5 Hz, 4H), 1.41 (s, 11H).

Example 92

(4-(Methyl ((trans)-4-((N-methylsulfamoyl) methyl) cyclohexyl) amino)-7H-pyrrolo [2, 3-d] pyrimidin-7-yl) methyl 2-(2-((2, 6-dichlorophenyl) amino) phenyl) acetate

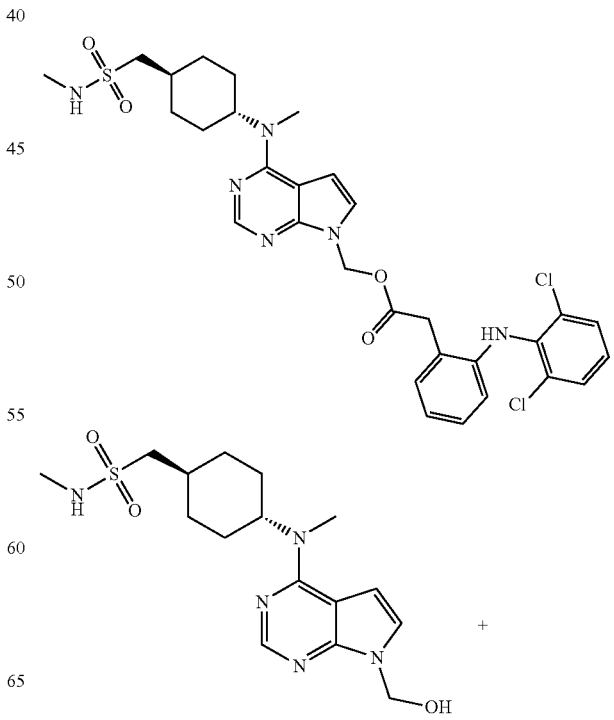

437

-continued

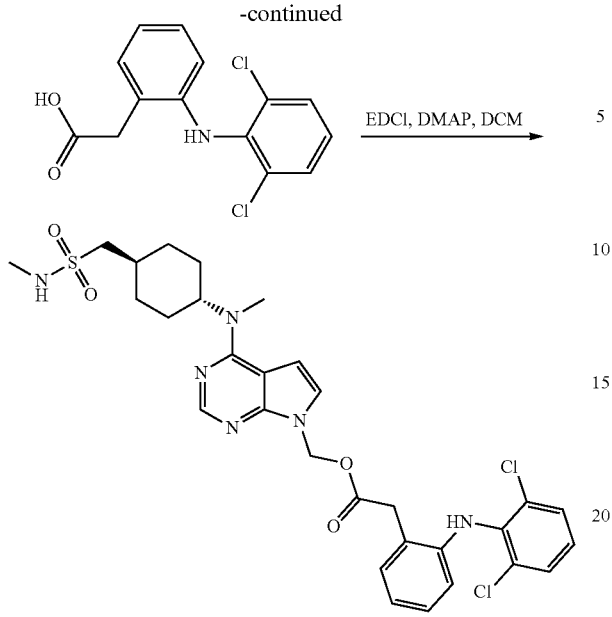

Synthesis of (4-(methyl ((trans)-4-((N-methylsulfa-moyl) methyl) cyclohexyl) amino)-7H-pyrrolo [2, 3-d]pyrimidin-7-yl) methyl 2-(2-((2, 6-dichlorophe-nyl) amino) phenyl) acetate 1-((Trans)-4-((7-(hydroxymethyl)-7H-pyrrolo [2, 3-d] pyrimidin-4-yl) (methyl) amino) cyclohexyl)-N-methyl methanesulfonamide (220 mg, 0.6 mmol), 4-dimethylamino pyridine (DMAP, 7 mg, 0.06 mmol), 2-(2, 6-dichloroanilino) phenylacetic acid (diclofenac, 444 mg, 1.5 mmol) and 1-(3-dimethylaminopropyl)-3-ethylcarbodiimide hydrochloride (EDCI, 173 mg, 0.9 mmol) were dissolved in dichloromethane (10 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=2:1 to 1:1) to give the title compound as a white solid, 0.14 g, 36.2% yield. MS (m/z): [M+H]$^+$ calcd for $C_{30}H_{34}Cl_2N_6O_4S$, 645.17; found, 645.3. $^1$H NMR (400 MHz, DMSO-d$_6$) δ 8.17 (s, 1H), 7.52 (d, J=8.1 Hz, 2H), 7.30 (d, J=3.8 Hz, 1H), 7.24-7.12 (m, 2H), 7.05 (td, J=7.7, 1.6 Hz, 1H), 6.95 (s, 1H), 6.87 (q, J=4.9 Hz, 1H), 6.82 (td, J=7.4, 1.2 Hz, 1H), 6.64 (d, J=3.8 Hz, 1H), 6.23 (dd, J=8.0, 1.2 Hz, 1H), 6.19 (s, 2H), 4.66 (s, 1H), 3.82 (s, 2H), 3.16 (s, 3H), 2.95 (d, J=6.2 Hz, 2H), 2.59 (d, J=5.0 Hz, 3H), 2.05 (d, J=12.1 Hz, 2H), 1.82 (s, 1H), 1.75-1.65 (m, 4H), 1.30 (q, J=7.9, 7.2 Hz, 2H).

438

Example 93

(4-(Methyl ((trans)-4-((N-methylsulfamoyl) methyl) cyclohexyl) amino)-7H-pyrrolo [2, 3-d] pyrimidin-7-yl) methyl 2-(4-acetamidophenyl) acetate

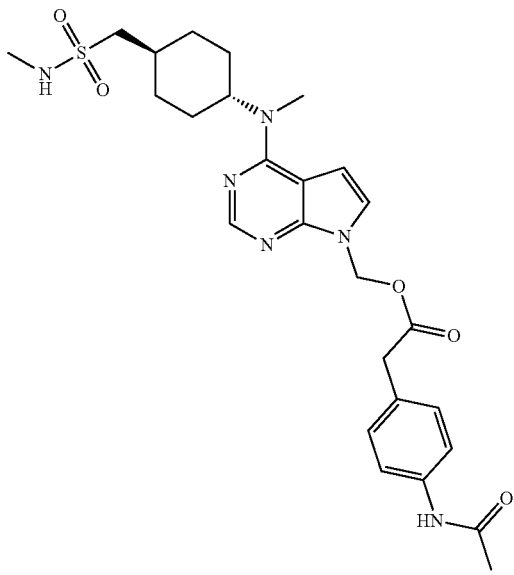

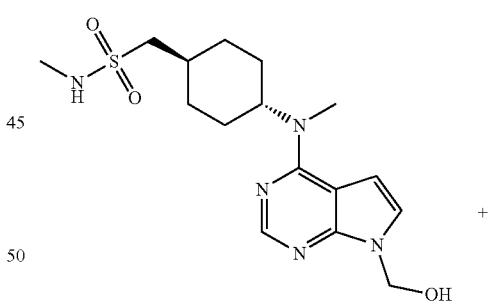

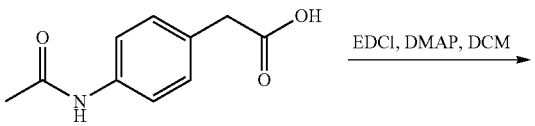

-continued

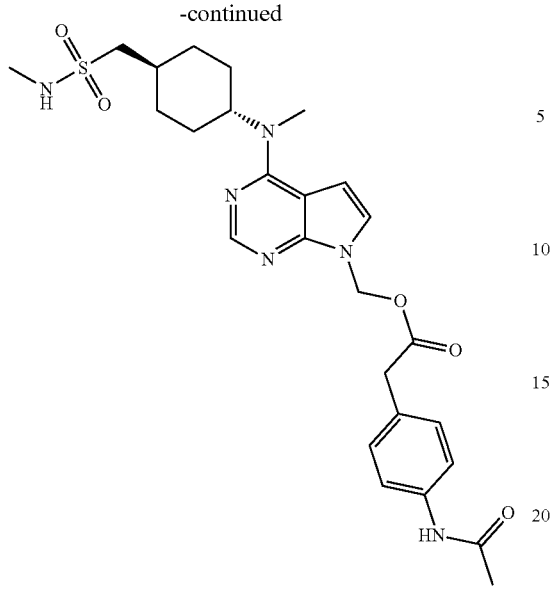

Synthesis of (4-(methyl ((trans)-4-((N-methylsulfamoyl) methyl) cyclohexyl) amino)-7H-pyrrolo [2, 3-d]pyrimidin-7-yl) methyl 2-(4-acetamidophenyl) acetate 1-((Trans)-4-((7-(hydroxymethyl)-7H-pyrrolo [2, 3-d] pyrimidin-4-yl) (methyl) amino) cyclohexyl)-N-methyl methanesulfonamide (220 mg, 0.6 mmol), 4-dimethylaminopyridine (DMAP, 7 mg, 0.06 mmol), 2-(4-acetamidophenyl) acetic acid (actarit, 151 mg, 0.78 mmol), and 1-(3-dimethylaminopropyl)-3-ethylcarbodiimide hydrochloride (EDCI, 173 mg, 0.9 mmol) were dissolved in dichloromethane (10 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=2:1 to 0:1) to give the title compound as a white solid, 0.016 g, 49.2% yield. MS (m/z): [M+H]+ calcd for $C_{26}H_{34}N_6O_5S$, 543.23; found, 543.3. $^1$H NMR (400 MHz, DMSO-$d_6$) δ 9.89 (s, 1H), 8.19 (s, 1H), 7.54-7.39 (m, 2H), 7.29 (d, J=3.8 Hz, 1H), 7.19-7.09 (m, 2H), 6.87 (q, J=4.9 Hz, 1H), 6.65 (d, J=3.7 Hz, 1H), 6.14 (s, 2H), 4.67 (s, 1H), 3.61 (s, 2H), 3.17 (s, 3H), 2.95 (d, J=6.2 Hz, 2H), 2.59 (d, J=5.0 Hz, 3H), 2.03 (s, 5H), 1.84 (s, 1H), 1.70 (q, J=6.7 Hz, 4H), 1.37-1.27 (m, 2H).

Example 94

(4-(Methyl ((trans)-4-((N-methylsulfamoyl) methyl) cyclohexyl) amino)-7H-pyrrolo [2, 3-d] pyrimidin-7-yl) methyl 2-(1, 8-diethyl-1, 3, 4, 9-tetrahydropyran [3, 4-b] indol-1-yl) acetate

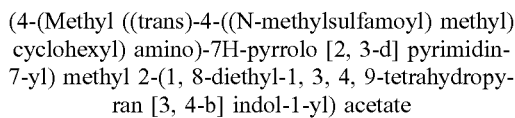

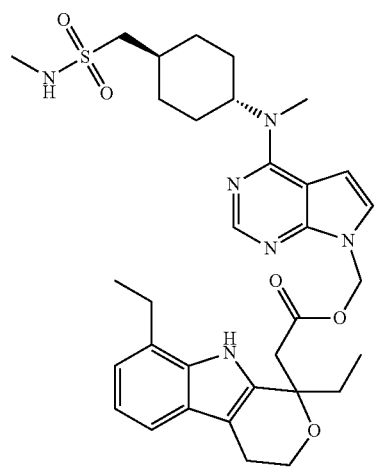

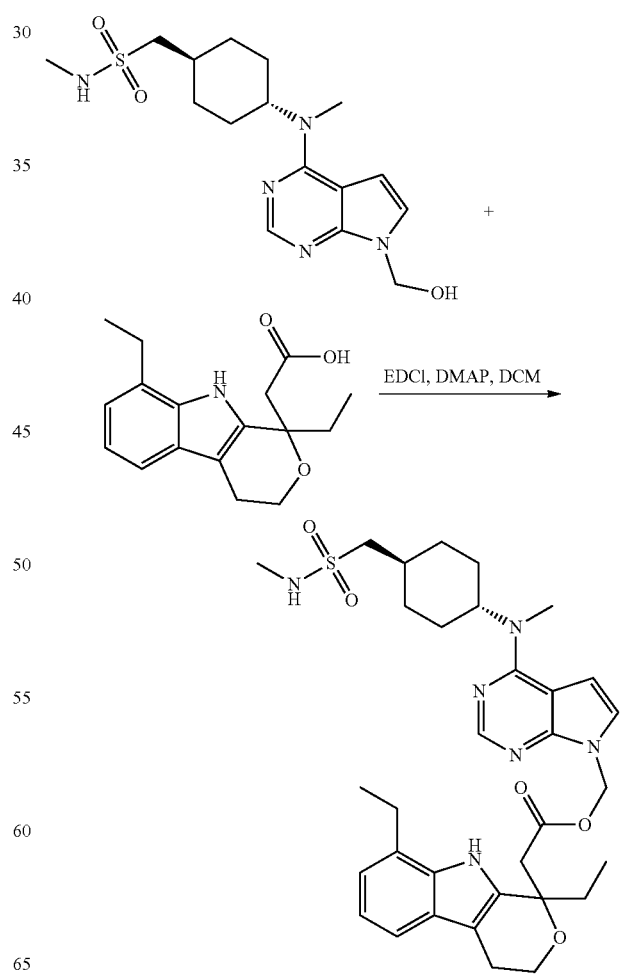

Synthesis of (4-(methyl ((trans)-4-((N-methylsulfa-moyl) methyl) cyclohexyl) amino)-7H-pyrrolo [2, 3-d]pyrimidin-7-yl) methyl 2-(1, 8-diethyl-1, 3, 4, 9-tetrahydropyran [3, 4-b] indol-1-yl) acetate 1-((Trans)-4-((7-(hydroxymethyl)-7H-pyrrolo [2, 3-d] pyrimidin-4-yl) (methyl) amino) cyclohexyl)-N-methyl methanesulfonamide (220 mg, 0.6 mmol), 4-dimethylamino pyridine (DMAP, 7 mg, 0.06 mmol), 21, 8-diethyl-1, 3, 4, 9-tetrahydropyran [3, 4-b] indole-1-acetic acid (etodolac, 224 mg, 0.78 mmol), and 1-(3-dimethylaminopropyl)-3-ethylcarbodiimide hydrochloride (EDCI, 173 mg, 0.9 mmol) were dissolved in dichloromethane (10 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=2:1 to 0:1) to give the title compound as a white solid, 0.14 g, 36.6% yield. MS (m/z): [M+H]+ calcd for $C_{33}H_{44}N_6O_5S$, 637.31; found, 637.3. $^1$H NMR (400 MHz, DMSO-$d_6$) δ 10.42 (s, 1H), 8.18 (s, 1H), 7.20 (dd, J=7.6, 1.4 Hz, 1H), 7.13 (d, J=3.8 Hz, 1H), 6.94-6.84 (m, 3H), 6.56 (d, J=3.8 Hz, 1H), 6.13-6.02 (m, 2H), 4.66 (s, 1H), 3.92-3.77 (m, 2H), 3.17 (s, 3H), 3.06-2.92 (m, 3H), 2.88-2.76 (m, 3H), 2.69-2.56 (m, 5H), 2.10-2.00 (m, 3H), 1.93-1.81 (m, 2H), 1.76-1.64 (m, 4H), 1.39-1.27 (m, 2H), 1.26-1.18 (m, 3H), 0.59 (t, J=7.3 Hz, 3H).

Example 95

2-(1-(ethylsulfonyl)-3-(4-(7-(2-(4-isobutylphenyl) propanoyl)-7H-pyrrolo [2, 3-d] pyrimidin-4-yl)-1H-pyrazol-1-yl) azetidin-3-yl) acetonitrile

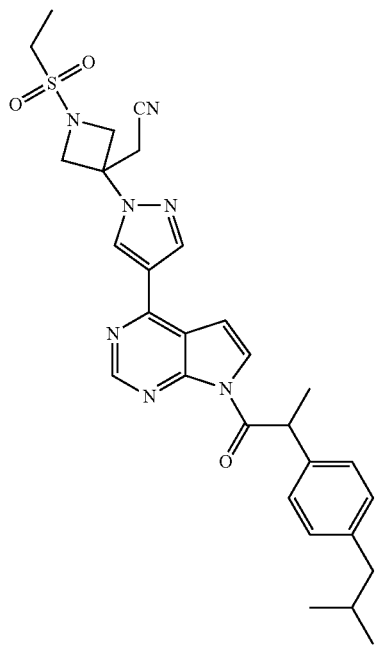 [SMILES: CCS(=O)(=O)N1CC(CC#N)(n2cc(-c3ncnc4c3ccn4C(=O)C(C)c3ccc(CC(C)C)cc3)cn2)C1]

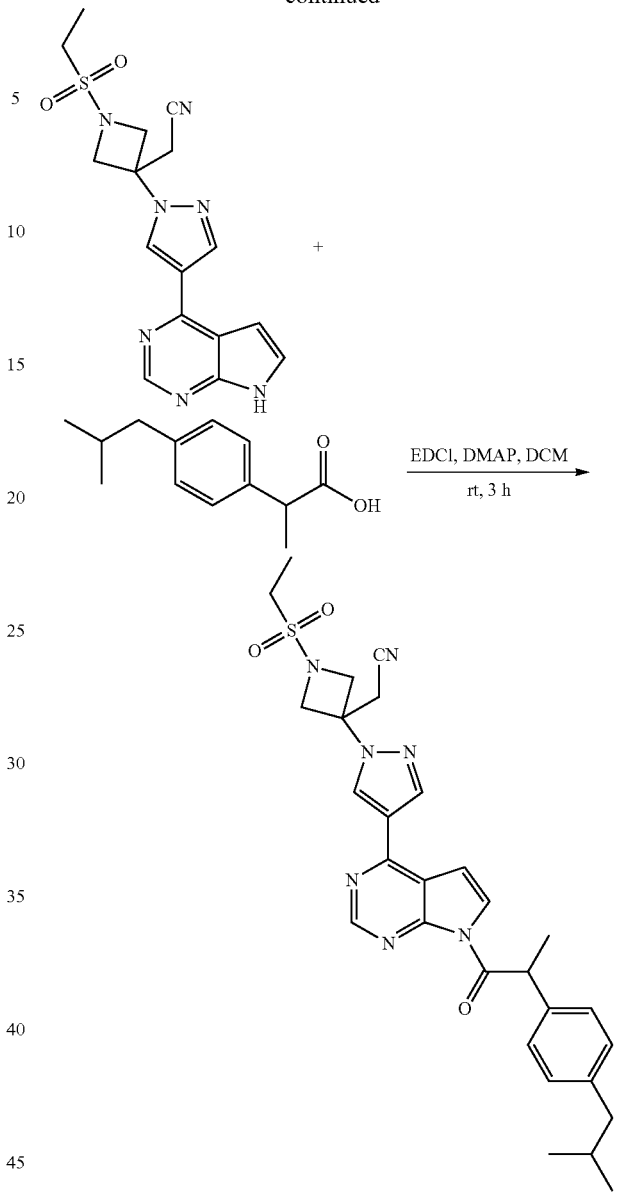

Synthesis of 2-(1-(ethylsulfonyl)-3-(4-(7-(2-(4-isobutylphenyl) propanoyl)-7H-pyrrolo [2, 3-d] pyrimidin-4-yl)-1H-pyrazol-1-yl) azetidin-3-yl) acetonitrile 1-(Ethylsulfonyl)-3-[4-(7H-pyrrolo [2, 3-d] pyrimidin-4-yl)-1H-pyrazol-1-yl]-3-azetidine acetonitrile (baricitinib, 1113 mg, 3 mmol), 4-dimethylamino pyridine (DMAP, 36.6 mg, 0.3 mmol), 2-(4-isobutylphenyl) propanoic acid (ibuprofen, 742 mg, 3.6 mmol) and 1-(3-dimethylaminopropyl)-3-ethylcarbodiimide hydrochloride (EDCI, 864 mg, 4.5 mmol) were dissolved in dichloromethane (30 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=2:1 to 1:2) to give the title compound as a white solid, 0.12 g, 71.5% yield. MS (m/z): [M+H]$^+$ calcd for $C_{29}H_{33}N_7O_3S$, 560.69; found, 560.3. $^1$H NMR (400 MHz, DMSO-d$_6$) δ 8.99 (d, J=4.2 Hz, 2H), 8.50 (s, 1H), 8.14 (d, J=4.2 Hz, 1H), 7.40 (d, J=4.2 Hz, 1H), 7.37-7.29 (m, 2H), 7.08 (d, J=7.9 Hz, 2H), 5.99 (q, J=6.9 Hz, 1H), 4.59 (d, J=9.1 Hz, 2H), 4.24 (d, J=9.1 Hz, 2H), 3.68 (s, 2H), 3.23 (q, J=7.3 Hz, 2H), 2.35 (d, J=7.2 Hz, 2H), 1.76 (hept, J=6.7 Hz, 1H), 1.58 (d, J=6.9 Hz, 3H), 1.24 (t, J=7.3 Hz, 3H), 0.80 (d, J=6.6 Hz, 6H).

Example 96

1-((Trans)-4-((7-(2-(4-isobutylphenyl) propanoyl)-7H-pyrrolo [2, 3-d] pyrimidin-4-yl) (methyl) amino) cyclohexyl)-N-methyl methanesulfonamide

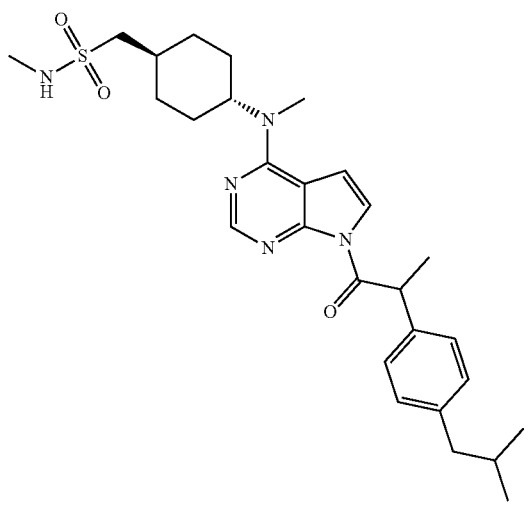

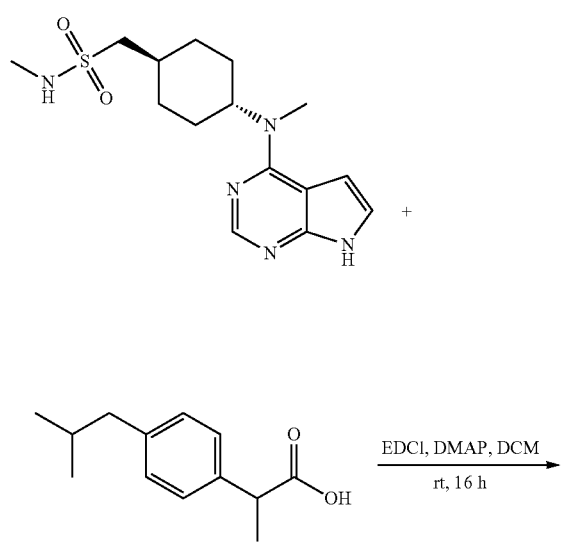

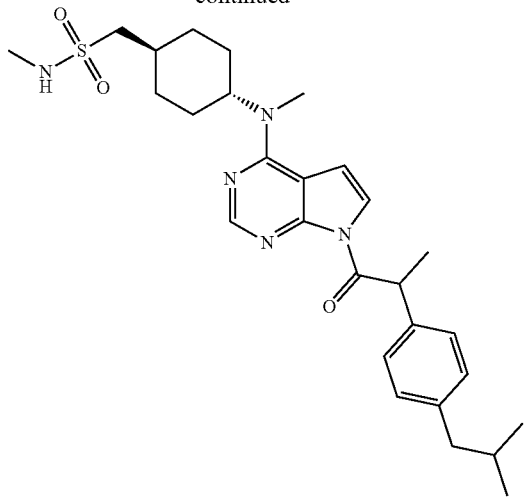

Synthesis of 1-((trans)-4-((7-(2-(4-isobutylphenyl) propanoyl)-7H-pyrrolo [2, 3-d] pyrimidin-4-yl) (methyl) amino) cyclohexyl)-N-methyl methanesulfonamide N-methyl-1-((trans)-4-(methyl (7H-pyrrolo [2, 3-d] pyrimidin-4-yl) amino) cyclohexyl) methanesulfonamide (oclacitinib, 150 mg, 0.44 mmol), 4-dimethylamino pyridine (DMAP, 6 mg, 0.044 mmol), 2-(4-isobutylphenyl) propanoic acid (ibuprofen, 96 mg, 0.468 mmol) and 1-(3-dimethylaminopropyl)-3-ethylcarbodiimide hydrochloride (EDCI, 128 mg, 0.666 mmol) were dissolved in dichloromethane (6 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=4:1 to 2:1) to give the title compound as a white solid, 0.07 g, 30% yield. MS (m/z): [M+H]$^+$ calcd for $C_{28}H_{39}N_5O_3S$, 526.28; found, 526.1. $^1$H NMR (400 MHz, DMSO-d$_6$) δ 8.36 (s, 1H), 7.66 (d, J=4.2 Hz, 1H), 7.33-7.26 (m, 2H), 7.07 (d, J=8.0 Hz, 2H), 6.95-6.81 (m, 2H), 6.10 (q, J=6.9 Hz, 1H), 4.66 (s, 1H), 3.15 (s, 3H), 2.94 (d, J=6.2 Hz, 2H), 2.58 (d, J=5.0 Hz, 3H), 2.36 (d, J=7.1 Hz, 2H), 2.10-1.96 (m, 2H), 1.91-1.60 (m, 6H), 1.52 (d, J=7.0 Hz, 3H), 1.35-1.22 (m, 2H), 0.82 (d, J=6.7 Hz, 6H).

Example 97

4-((4-(((3R, 4R)-1-(2-cyanoacetyl)-4-methylpiperidin-3-yl) (methyl) amino)-7H-pyrrolo [2, 3-d] pyrimidin-7-yl) methoxy)-2-methyl-N-(pyridin-2-yl)-2H-benzo [e] [1, 2] thiazine-3-carboxamide 1, 1-dioxide

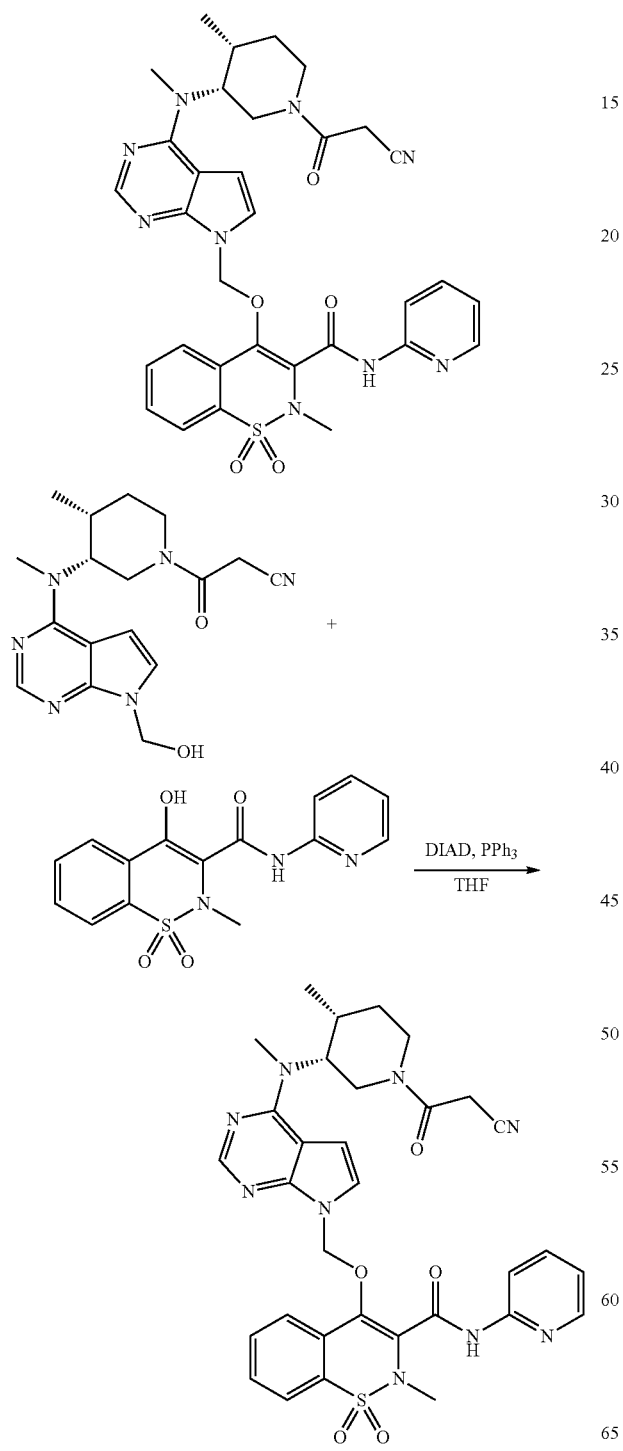

Synthesis of 4-((4-(((3R, 4R)-1-(2-cyanoacetyl)-4-methylpiperidin-3-yl) (methyl) amino)-7H-pyrrolo [2, 3-d]pyrimidin-7-yl) methoxy)-2-methyl-N-(pyridin-2-yl)-2H-benzo [e] [1, 2] thiazine-3-carboxamide 1, 1-dioxide 4-Hydroxy-2-methyl-N-(pyridin-2-yl)-2H-benzo [e] [1, 2] thiazine-3-carboxamide 1, 1-dioxide (piroxicam, 66 mg, 0.2 mmol) and triphenylphosphine (PPh$_3$, 79 mg, 0.3 mmol) were added to tetrahydrofuran (0.4 mL) and stirred under nitrogen. After cooling to −10° C., diisopropyl azodicarboxylate (DIAD, 53 mg, 0.26 mmol) was added dropwise to the mixture with stirring. After stirring at −10° C. for 20 minutes, the mixture was allowed to warm to room temperature naturally. 3-((3R, 4R)-3-((7-(hydroxymethyl)-7H-pyrrolo [2, 3-d] pyrimidin-4-yl) (methyl) amino)-4-methylpiperidin-1-yl)-3-oxopropanenitrile (68 mg, 0.2 mmol) was added and stirring was continued. The reaction was monitored by TLC. After complete exhaust of the starting material (1 h), the solvent was evaporated under reduced pressure to give the crude product. The crude product was further separated by silica gel column chromatography (dichloromethane/acetonitrile=20:1 to 9:1) to give the title compound as a yellow solid, 0.005 g, 3.8% yield. MS (m/z): [M+H]$^+$ calcd for C$_{32}$H$_{33}$N$_9$O$_5$S, 656.23, found 656.2. $^1$H NMR (400 MHz, Chloroform-d) δ 15.22 (d, J=17.7 Hz, 1H), 8.52 (t, J=8.4 Hz, 1H), 8.32 (d, J=9.2 Hz, 1H), 8.23 (d, J=3.1 Hz, 1H), 8.07-7.91 (m, 2H), 7.83 (d, J=7.5 Hz, 1H), 7.71-7.55 (m, 3H), 6.70-6.58 (m, 2H), 6.51 (dd, J=9.8, 3.8 Hz, 1H), 4.95 (s, 1H), 4.06 (dd, J=13.0, 4.4 Hz, 1H), 3.85-3.67 (m, 1H), 3.66-3.55 (m, 1H), 3.54-3.36 (m, 4H), 3.27 (d, J=18.4 Hz, 3H), 3.03 (s, 3H), 2.53-2.39 (m, 1H), 1.95-1.85 (m, 1H), 1.73-1.61 (m, 1H), 1.01 (t, J=7.7 Hz, 3H).

Example 98

(R)-3-cyclopentyl-3-(4-(7-2-(4-isobutylphenyl) propanoyl)-7H-pyrrolo [2, 3-d] pyrimidin-4-yl)-1H-pyrazol-1-yl) propanenitrile

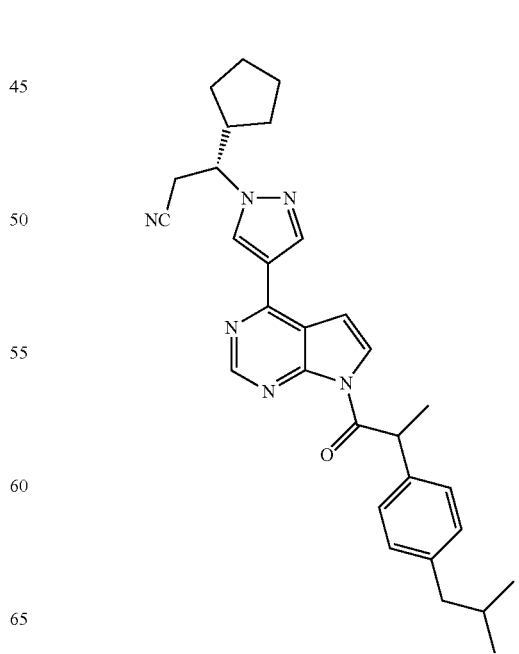

J=11.3 Hz, 1H), 8.12 (d, J=4.2 Hz, 1H), 7.40-7.28 (m, 3H), 7.09 (dd, J=7.9, 5.8 Hz, 2H), 6.00 (q, J=6.9 Hz, 1H), 4.54 (td, J=9.6, 4.6 Hz, 1H), 3.28-3.15 (m, 2H), 2.47-2.31 (m, 3H), 1.88-1.71 (m, 2H), 1.65-1.40 (m, 5H), 1.40-1.16 (m, 5H), 0.99-0.76 (m, 6H).

Example 99

(4-(1-((R)-2-cyano-1-cyclopentylethyl)-1H-pyrazol-4-yl)-7H-pyrrolo [2, 3-d] pyrimidin-7-yl) methyl 2-(3-benzoylphenyl) propanoate

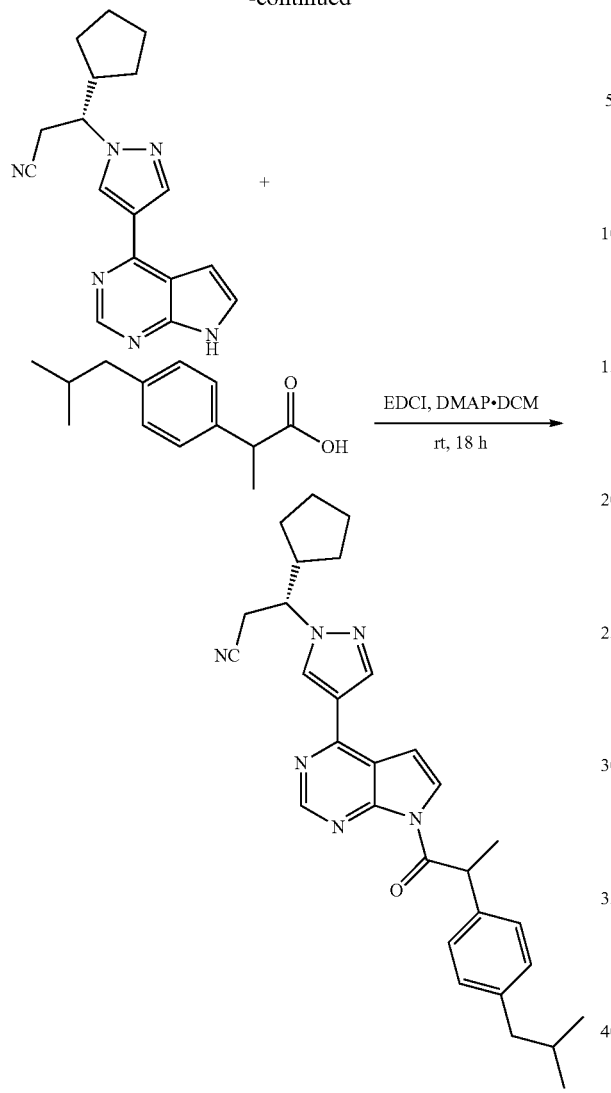

Synthesis of (R)-3-cyclopentyl-3-(4-(7-2-(4-isobutylphenyl) propanoyl)-7H-pyrrolo [2, 3-d] pyrimidin-4-yl)-1H-pyrazol-1-yl) propanenitrile (R)-3-(4-(7h-pyrrolo [2, 3-d] pyridin-4-yl)-1h-pyrazol-1-yl)-3-cyclopentylpropane (Ruxolitinib, 50 mg, 0.163 mmol), 4-dimethylamino pyridine (DMAP, 2 mg, 0.016 mmol), 2-(4-isobutylphenyl) propanoic acid (ibuprofen, 35.5 mg, 0.172 mmol), and 1-(3-dimethylaminopropyl)-3-ethylcarbodiimide hydrochloride (EDCI, 47 mg, 0.245 mmol) were dissolved in dichloromethane (2 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (petroleum ether/ethyl acetate=4:1 to 3:1) to give the title compound as a white solid, 0.05 g, 61% yield. MS (m/z): [M+H]$^+$ calcd for $C_{30}H_{34}N_6O_4$, 495.64; found, 495.2. $^1$H NMR (400 MHz, DMSO-d$_6$) δ 8.97 (s, 1H), 8.88 (d, J=1.6 Hz, 1H), 8.39 (d,

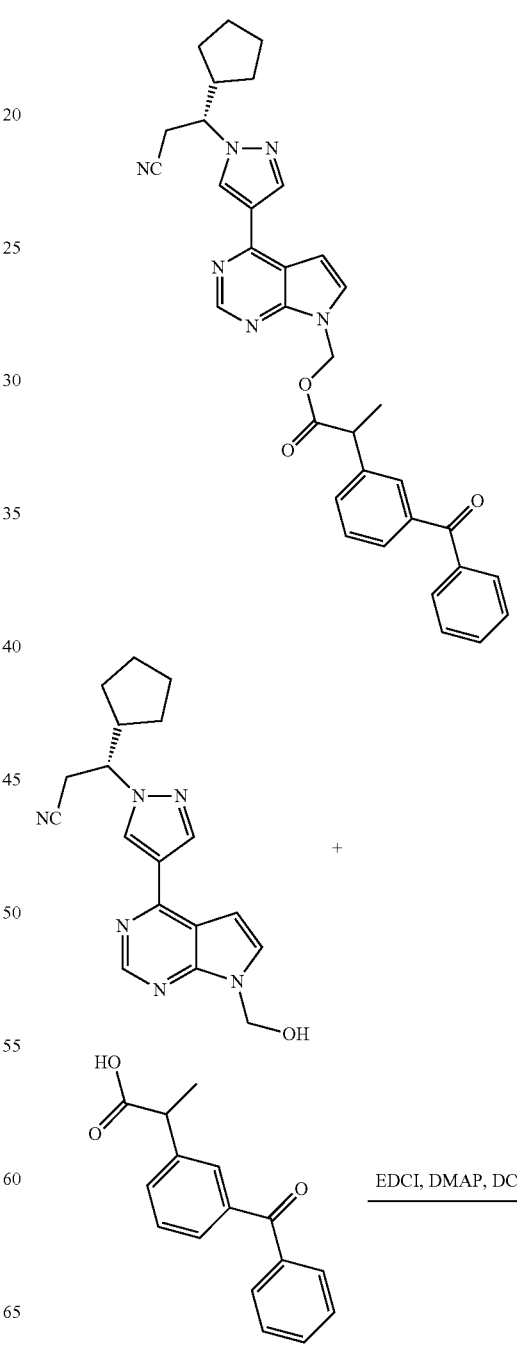

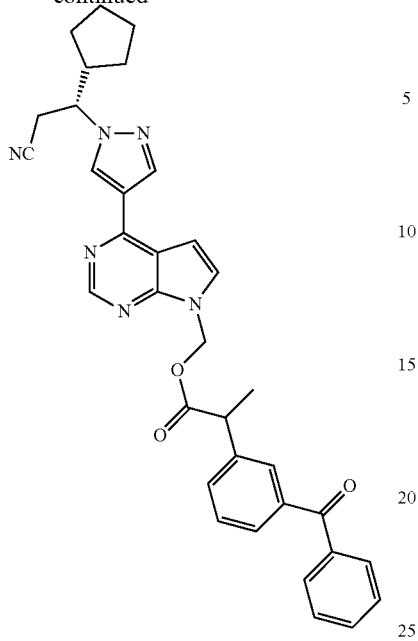

Synthesis of (4-(1-((R)-2-cyano-1-cyclopentyl-ethyl)-1H-pyrazol-4-yl)-7H-pyrrolo [2, 3-d] pyrimidin-7-yl) methyl 2-(3-benzoylphenyl) propanoate (R)-3-cyclopentyl-3-(4-(7-(hydroxymethyl)-7H-pyrrolo [2, 3-d] pyrimidin-4-yl)-1H-pyrazol-1-yl) propanenitrile (170 mg, 0.5 mmol), 4-dimethylamino pyridine (DMAP, 61 mg, 0.5 mmol), 2-(3-benzoylphenyl) propanoic acid (ketoprofen, 191 mg, 1.5 mmol) and 1-(3-dimethylaminopropyl)-3-ethylcarbodiimide hydrochloride (EDCI, 144 mg, 0.75 mmol) was dissolved in a mixed solvent of dichloromethane (8.5 mL) and dimethylformamide (0.3 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=150:1 to 50:1) to give the title compound as a white solid, 0.143 g, 50% yield. MS (m/z): [M+H]$^+$ calcd for $C_{34}H_{32}N_6O_3$, 573.25; found, 573.3. $^1$H NMR (400 MHz, DMSO-d$_6$) δ 8.83 (d, J=0.7 Hz, 1H), 8.72 (s, 1H), 8.38 (s, 1H), 7.69 (d, J=3.8 Hz, 1H), 7.68-7.62 (m, 3H), 7.58 (d, J=1.8 Hz, 1H), 7.57-7.49 (m, 4H), 7.44 (t, J=7.6 Hz, 1H), 7.08 (d, J=3.8 Hz, 1H), 6.33-6.22 (m, 2H), 4.55 (td, J=9.7, 4.2 Hz, 1H), 3.99 (q, J=7.0 Hz, 1H), 3.32-3.15 (m, 2H), 2.48-2.35 (m, 1H), 1.87-1.76 (m, 1H), 1.67-1.44 (m, 3H), 1.42-1.37 (m, 3H), 1.36-1.13 (m, 4H).

Example 100

(4-(1-((R)-2-cyano-1-cyclopentylethyl)-1H-pyrazol-4-yl)-7H-pyrrolo [2, 3-d] pyrimidin-7-yl) methyl 2-(2-fluoro-[1, 1'-biphenyl]-4-yl) propanoate

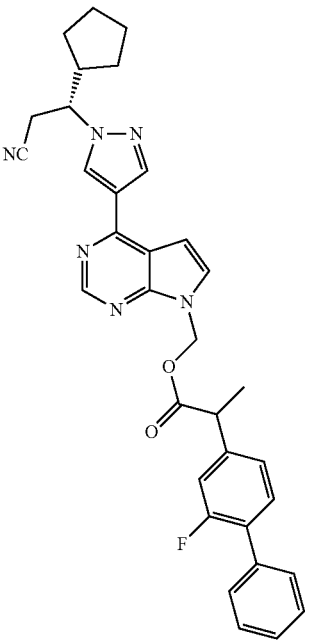 [SMILES: CC(C(=O)OCn1ccc2c(-c3cnn([C@H](CC#N)C4CCCC4)c3)ncnc21)c1ccc(-c2ccccc2)c(F)c1]

+

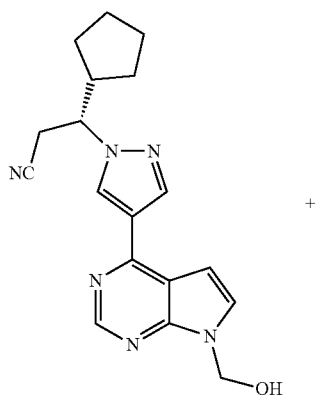

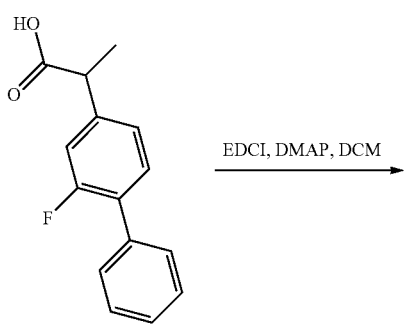

EDCI, DMAP, DCM →

451

-continued

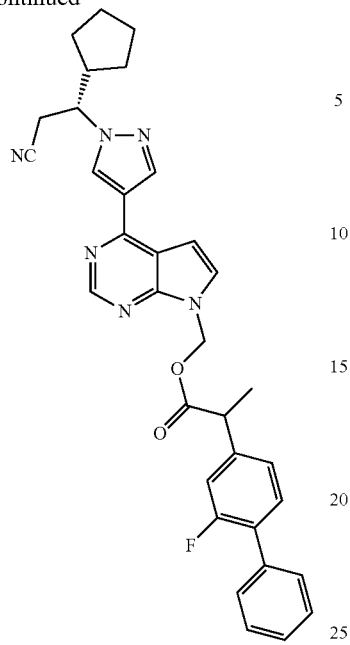

Synthesis of (4-(1-((R)-2-cyano-1-cyclopentyl-ethyl)-1H-pyrazol-4-yl)-7H-pyrrolo [2, 3-d] pyrimidin-7-yl) methyl 2-(2-fluoro-[1, 1'-biphenyl]-4-yl) propanoate (R)-3-cyclopentyl-3-(4-(7-(hydroxymethyl)-7H-pyrrolo [2, 3-d] pyrimidin-4-yl)-1H-pyrazol-1-yl) propanenitrile (170 mg, 0.5 mmol), 4-dimethylamino pyridine (DMAP, 61 mg, 0.5 mmol), 2-(2-fluoro-4-biphenyl) propanoic acid (flurbiprofen, 183 mg, 0.75 mmol), and 1-(3-dimethylaminopropyl)-3-ethylcarbodiimide hydrochloride (EDCI, 144 mg, 0.75 mmol) were dissolved in dichloromethane (8.5 mL) and dimethylformamide (0.3 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=150:1 to 50:1) to give the title compound as a white solid, 0.15 g, 53.3% yield. MS (m/z): [M+H]$^+$ calcd for $C_{33}H_{31}FN_6O_2$, 563.25; found, 563.3. $^1$H NMR (400 MHz, DMSO-d$_6$) δ 8.83 (s, 1H), 8.75 (s, 1H), 8.39 (s, 1H), 7.73 (d, J=3.7 Hz, 1H), 7.50-7.31 (m, 6H), 7.17-7.07 (m, 3H), 6.35-6.24 (m, 2H), 4.54 (td, J=9.7, 4.2 Hz, 1H), 3.92 (q, J=7.1 Hz, 1H), 3.33-3.14 (m, 2H), 2.42 (h, J=8.5 Hz, 1H), 1.82 (dtd, J=12.0, 7.6, 4.5 Hz, 1H), 1.64-1.48 (m, 3H), 1.48-1.11 (m, 7H).

452

Example 101

(R)-(4-(1-(2-cyano-1-cyclopentylethyl)-1H-pyrazol-4-yl)-7H-pyrrolo [2, 3-d] pyrimidin-7-yl) methyl 2-(2-((2, 6-dichlorophenyl) amino) phenyl) acetate

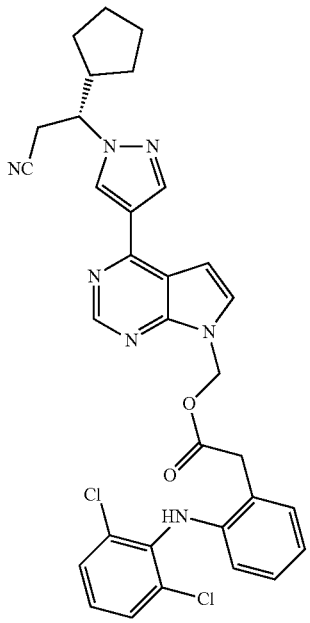 [SMILES: N#CC[C@H](C1CCCC1)n1cc(-c2ncnc3c2ccn3COC(=O)Cc2ccccc2Nc2c(Cl)cccc2Cl)cn1]

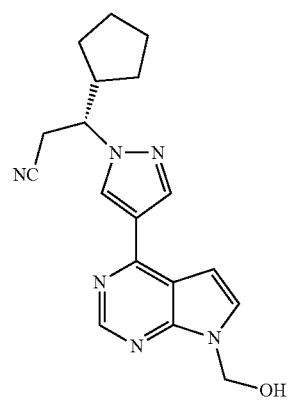

+

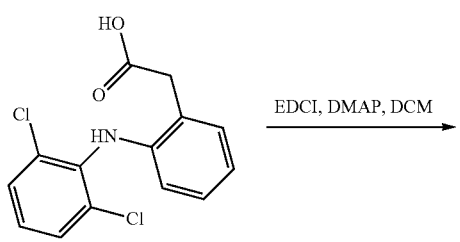

EDCI, DMAP, DCM

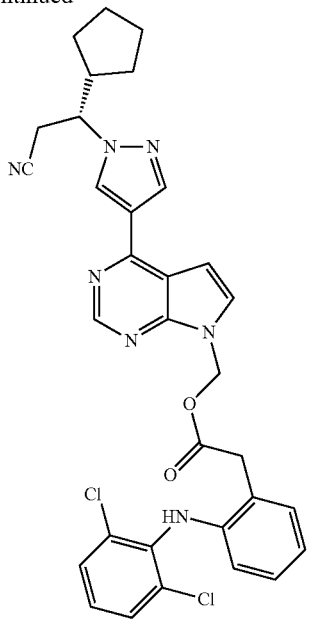

Synthesis of (R)-(4-(1-(2-cyano-1-cyclopentyl-ethyl)-1H-pyrazol-4-yl)-7H-pyrrolo [2, 3-d] pyrimidin-7-yl) methyl 2-(2-((2, 6-dichlorophenyl) amino) phenyl) acetate (R)-3-cyclopentyl-3-(4-(7-(hydroxymethyl)-7H-pyrrolo [2, 3-d] pyrimidin-4-yl)-1H-pyrazol-1-yl) propanenitrile (170 mg, 0.5 mmol), 4-dimethylamino pyridine (DMAP, 61 mg, 0.5 mmol), 2-(2, 6-dichloroanilino) phenylacetic acid (diclofenac, 222 mg, 0.75 mmol), and 1-(3-dimethylamino-propyl)-3-ethylcarbodiimide hydrochloride (EDCI, 144 mg, 0.75 mmol) was dissolved in dichloromethane (8.5 mL) and dimethylformamide (0.3 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=150:1 to 50:1) to give the title compound as a white solid, 0.12 g, 39.1% yield. MS (m/z): [M+H]+ calcd for $C_{32}H_{29}Cl_2N_7O_2$, 614.18; found, 614.2. $^1$H NMR (400 MHz, DMSO-$d_6$) δ 8.86-8.73 (m, 2H), 8.40 (s, 1H), 7.81-7.68 (m, 2H), 7.49 (d, J=8.1 Hz, 2H), 7.26-6.94 (m, 4H), 6.81 (td, J=7.4, 1.1 Hz, 1H), 6.31 (s, 2H), 6.21 (d, J=8.1 Hz, 1H), 4.55 (td, J=9.7, 4.2 Hz, 1H), 3.87 (d, J=14.3 Hz, 2H), 3.24 (qd, J=17.2, 6.9 Hz, 2H), 2.43 (h, J=8.3 Hz, 1H), 1.82 (qt, J=7.5, 5.4, 4.1 Hz, 1H), 1.67-1.40 (m, 4H), 1.40-1.13 (m, 3H).

Example 102

(4-(1-((R)-2-cyano-1-cyclopentylethyl)-1H-pyrazol-4-yl)-7H-pyrrolo [2, 3-d] pyrimidin-7-yl) methyl 2-(3-phenoxyphenyl) propanoate

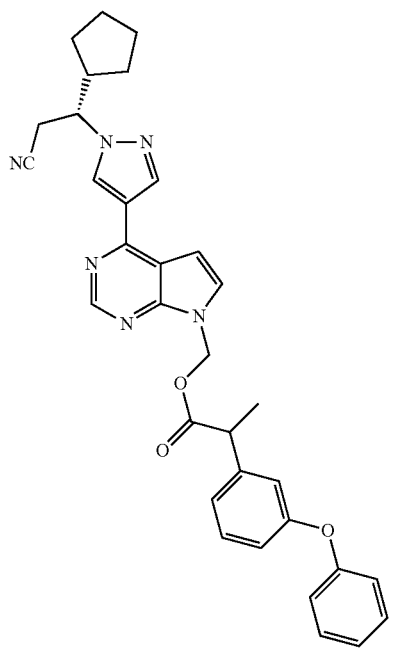 [SMILES: CC(C(=O)OCn1ccc2c(-c3cnn([C@H](CC#N)C4CCCC4)c3)ncnc21)c1cccc(Oc2ccccc2)c1]

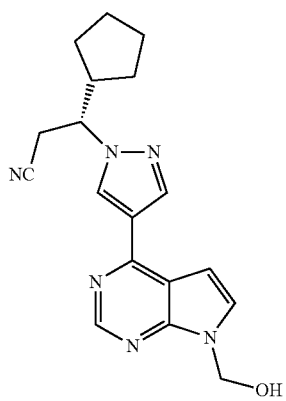

+

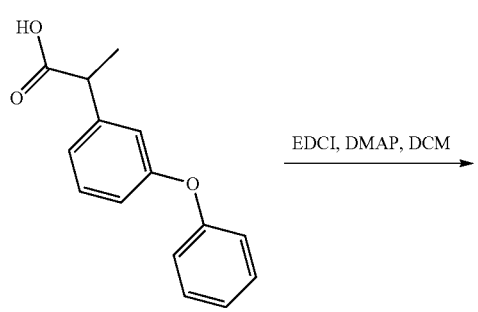

EDCI, DMAP, DCM

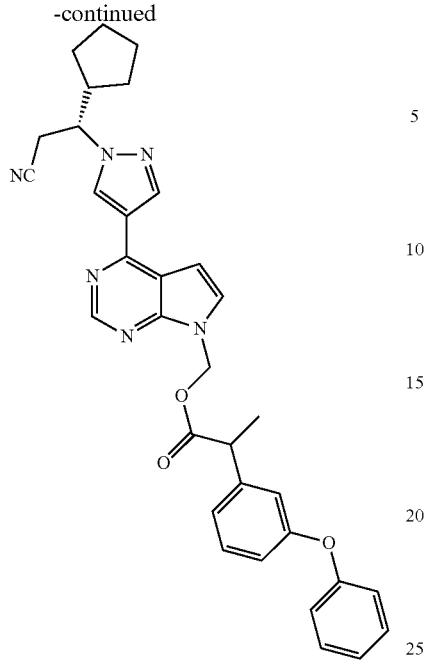

Synthesis of (4-(1-((R)-2-cyano-1-cyclopentyl-ethyl)-1H-pyrazol-4-yl)-7H-pyrrolo [2, 3-d] pyrimidin-7-yl) methyl 2-(3-phenoxyphenyl) propanoate (R)-3-cyclopentyl-3-(4-(7-(hydroxymethyl)-7H-pyrrolo [2, 3-d] pyrimidin-4-yl)-1H-pyrazol-1-yl) propanenitrile (170 mg, 0.5 mmol), 4-dimethylamino pyridine (DMAP, 61 mg, 0.5 mmol), 2-(3-phenoxyphenyl) propanoic acid (fenoprofen, 182 mg, 0.75 mmol), and 1-(3-dimethylaminopropyl)-3-ethylcarbodiimide hydrochloride (EDCI, 144 mg, 0.75 mmol) were dissolved in dichloromethane (8.5 mL) and dimethylformamide (0.3 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=150:1 to 50:1) to give the title compound as a white solid, 0.133 g, 457.5% yield. MS (m/z): [M+H]$^+$ calcd for $C_{33}H_{32}N_6O_3$, 561.25; found, 561.4. $^1$H NMR (400 MHz, DMSO-d$_6$) δ 8.83 (s, 1H), 8.74 (s, 1H), 8.40 (s, 1H), 7.67 (d, J=3.8 Hz, 1H), 7.33 (dd, J=8.5, 7.3 Hz, 2H), 7.24 (t, J=7.9 Hz, 1H), 7.14-7.05 (m, 2H), 6.97 (dt, J=7.7, 1.2 Hz, 1H), 6.93-6.86 (m, 2H), 6.86-6.75 (m, 2H), 6.32-6.20 (m, 2H), 4.55 (td, J=9.7, 4.2 Hz, 1H), 3.83 (q, J=7.0 Hz, 1H), 3.28 (dd, J=17.2, 9.6 Hz, 1H), 3.19 (dd, J=17.2, 4.2 Hz, 1H), 2.42 (h, J=8.6 Hz, 1H), 1.82 (dtd, J=11.9, 7.5, 4.4 Hz, 1H), 1.66-1.43 (m, 4H), 1.43-1.12 (m, 6H).

Example 103

(4-(1-((R)-2-cyano-1-cyclopentylethyl)-1H-pyrazol-4-yl)-7H-pyrrolo [2, 3-d] pyrimidin-7-yl) methyl 2-(4-((2-oxocyclopentyl) methyl) phenyl) propanoate

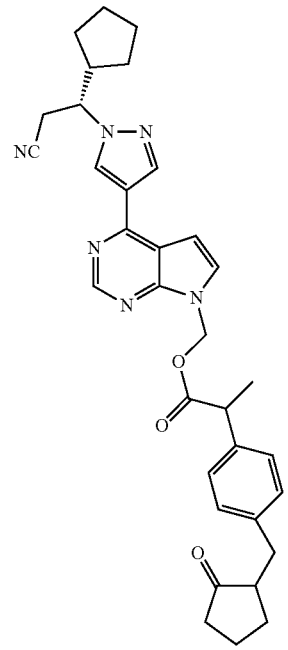 [SMILES: CC(C(=O)OCn1ccc2c(-c3cnn([C@H](CC#N)C4CCCC4)c3)ncnc21)c1ccc(CC2CCCC2=O)cc1]

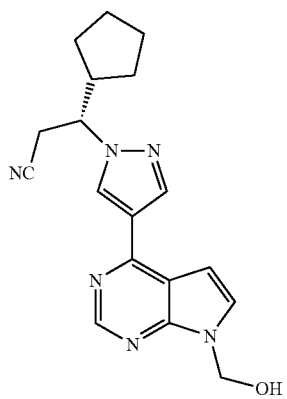

+

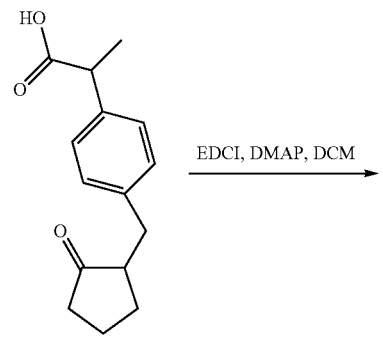

EDCI, DMAP, DCM →

457

-continued

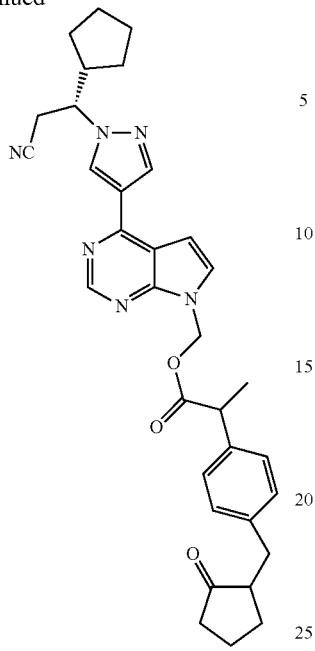

Synthesis of (4-(1-((R)-2-cyano-1-cyclopentyl-ethyl)-1H-pyrazol-4-yl)-7H-pyrrolo [2, 3-d] pyrimidin-7-yl) methyl 2-(4-((2-oxocyclopentyl) methyl) phenyl) propanoate (R)-3-cyclopentyl-3-(4-(7-(hydroxymethyl)-7H-pyrrolo [2, 3-d] pyrimidin-4-yl)-1H-pyrazol-1-yl) propanenitrile (170 mg, 0.5 mmol), 4-dimethylamino pyridine (DMAP, 61 mg, 0.5 mmol), 2-[4-(2-oxocyclopentan-1-ylmethyl) phenyl] propanoic acid (loxoprofen, 185 mg, 0.75 mmol), and 1-(3-dimethylaminopropyl)-3-ethylcarbodiimide hydrochloride (EDCI, 144 mg, 0.75 mmol) were dissolved in dichloromethane (8.5 mL) and dimethylformamide (0.3 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=150:1 to 50:1) to give the title compound as a white solid, 0.125 g, 44.3% yield. MS (m/z): [M+H]$^+$ calcd for $C_{33}H_{36}N_6O_3$, 565.28; found, 565.3. $^1$H NMR (400 MHz, DMSO-d$_6$) δ 8.82 (s, 1H), 8.74 (d, J=1.7 Hz, 1H), 8.39 (s, 1H), 7.68 (d, J=3.8 Hz, 1H), 7.11-6.96 (m, 5H), 6.28-6.19 (m, 2H), 4.54 (td, J=9.6, 4.2 Hz, 1H), 3.76 (q, J=7.0 Hz, 1H), 3.23 (qd, J=17.1, 6.9 Hz, 2H), 2.92-2.82 (m, 1H), 2.50-2.14 (m, 5H), 2.08-1.89 (m, 1H), 1.86-1.74 (m, 3H), 1.69-1.47 (m, 4H), 1.40-1.12 (m, 7H).

458

Example 104

(R)-2-(4-(1-(2-cyano-1-cyclopentylethyl)-1H-pyrazol-4-yl)-7H-pyrrolo [2, 3-d] pyrimidin-7-yl) methyl 2-(1-(4-chlorobenzoyl)-5-methoxy-2-methyl-1H-indol-3-yl) acetate

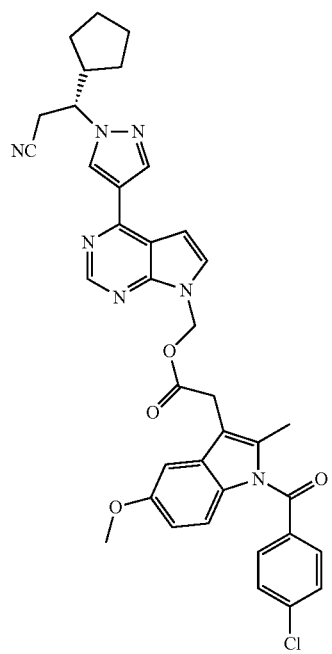 [SMILES: COc1ccc2c(c1)c(CC(=O)OCn1ccc3c(-c4cnn([C@H](CC#N)C5CCCC5)c4)ncnc31)c(C)n2C(=O)c1ccc(Cl)cc1]

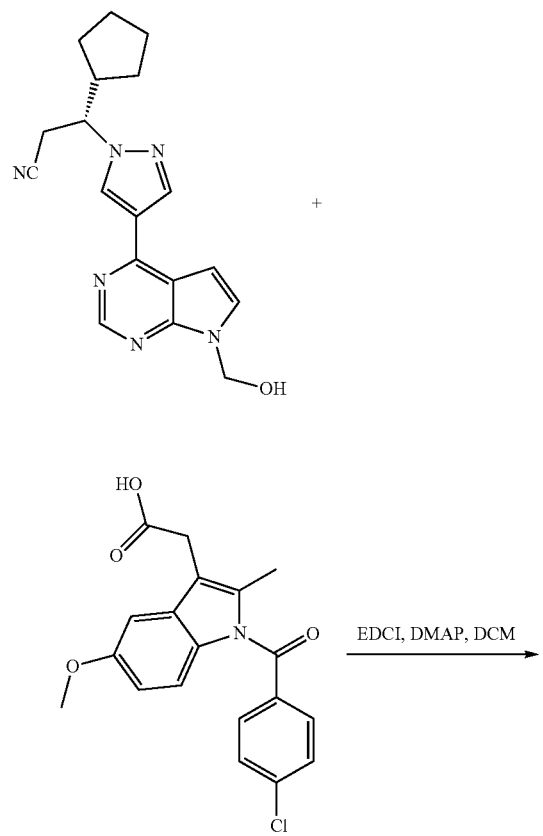

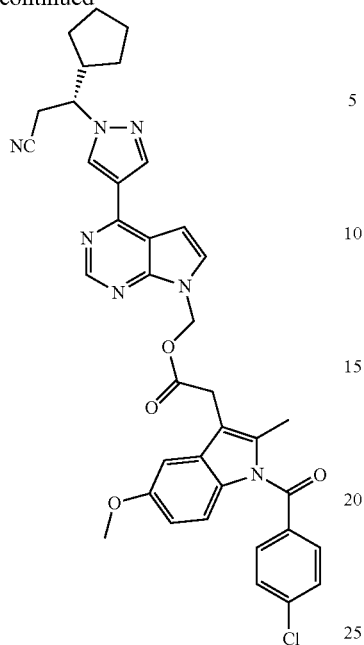

Synthesis of (R)-2-(4-(1-(2-cyano-1-cyclopentyl-ethyl)-1H-pyrazol-4-yl)-7H-pyrrolo [2, 3-d] pyrimidin-7-yl) methyl 2-(1-(4-chlorobenzoyl)-5-methoxy-2-methyl-1H-indol-3-yl) acetate (R)-3-cyclopentyl-3-(4-(7-(hydroxymethyl)-7H-pyrrolo [2, 3-d] pyrimidin-4-yl)-1H-pyrazol-1-yl) propanenitrile (170 mg, 0.5 mmol), 4-dimethylamino pyridine (DMAP, 61 mg, 0.5 mmol), 1-(4-chlorobenzoyl)-5-methoxy-2-methyl-1H-indole-3-acetic acid (indomethacin, 277 mg, 0.75 mmol) and 1-(3-dimethylaminopropyl)-3-ethylcarbodiimide hydrochloride (EDCI, 144 mg, 0.75 mmol) were dissolved in dichloromethane (8.5 mL) and dimethylformamide (0.3 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=150:1 to 50:1) to give the title compound as a light yellow solid, 0.176 g, 52.1% yield. MS (m/z): [M+H]$^+$ calcd for $C_{37}H_{34}C_1N_7O_4$, 676.24; found, 676.3. $^1$H NMR (400 MHz, DMSO-d$_6$) δ 8.84 (s, 1H), 8.75 (s, 1H), 8.40 (s, 1H), 7.71 (d, J=3.8 Hz, 1H), 7.62 (s, 4H), 7.10 (d, J=3.8 Hz, 1H), 6.95-6.85 (m, 2H), 6.66 (dd, J=9.0, 2.5 Hz, 1H), 6.29 (s, 2H), 4.55 (td, J=9.7, 4.2 Hz, 1H), 3.82 (s, 2H), 3.65 (s, 3H), 3.32-3.15 (m, 2H), 2.42 (p, J=8.5 Hz, 1H), 2.13 (s, 3H), 1.89-1.76 (m, 1H), 1.59 (dddd, J=26.4, 12.6, 7.1, 4.5 Hz, 3H), 1.41-1.12 (m, 4H).

Example 105

(4-(1-((R)-2-cyano-1-cyclopentylethyl)-1H-pyrazol-4-yl)-7H-pyrrolo [2, 3-d] pyrimidin-7-yl) methyl 2-(4-(1-oxoisoindolin-2-yl) phenyl) butanoate

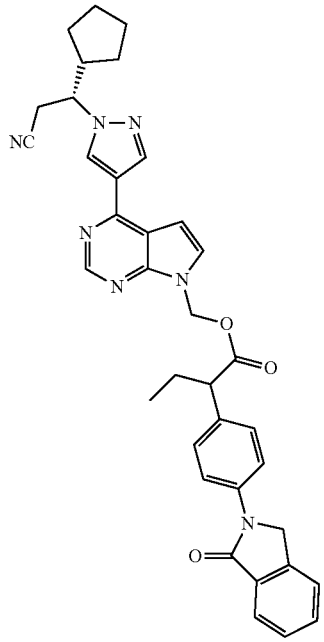 [SMILES: CCC(C(=O)OCn1ccc2c(-c3cnn([C@H](CC#N)C4CCCC4)c3)ncnc21)c1ccc(N2Cc3ccccc3C2=O)cc1]

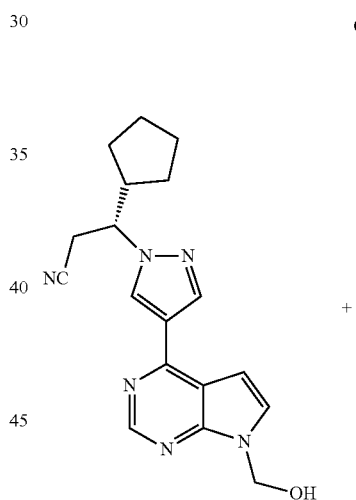

+

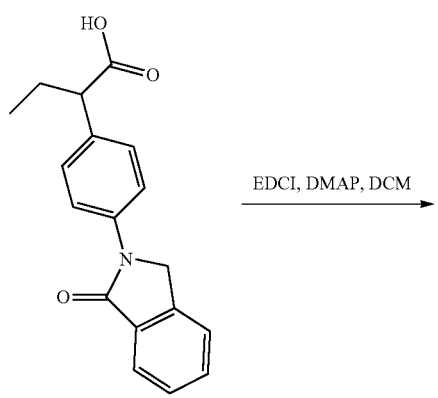

EDCI, DMAP, DCM →

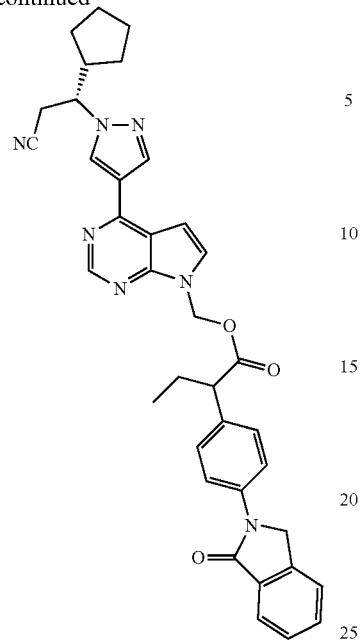

Synthesis of (4-(1-((R)-2-cyano-1-cyclopentyl-ethyl)-1H-pyrazol-4-yl)-7H-pyrrolo [2, 3-d] pyrimidin-7-yl) methyl 2-(4-(1-oxoisoindolin-2-yl) phenyl) butanoate (R)-3-cyclopentyl-3-(4-(7-(hydroxymethyl)-7H-pyrrolo [2, 3-d] pyrimidin-4-yl)-1H-pyrazol-1-yl) propanenitrile (20 mg, 0.058 mmol), 4-dimethylamino pyridine (DMAP, 4 mg, 0.03 mmol), 2-(4-(1-oxoisoindolin-2-yl) phenyl) butanoic acid (indobufen, 26 mg, 0.09 mmol) and 1-(3-dimethylaminopropyl)-3-ethylcarbodiimide hydrochloride (EDCI, 17 mg, 0.09 mmol) were dissolved in a mixed solvent of dichloromethane (0.5 mL) and N, N-dimethylformamide (0.05 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=150:1 to 50:1) to give the title compound as a white solid, 0.152 g, 49.6% yield. MS (m/z): [M+H]$^+$ calcd for $C_{36}H_{35}N_7O_3$, 614.28; found, 614.4. $^1$H NMR (400 MHz, DMSO-d$_6$) δ 8.83 (s, 1H), 8.38 (s, 1H), 7.79 (t, J=8.5 Hz, 3H), 7.74-7.67 (m, 2H), 7.67-7.62 (m, 1H), 7.54 (td, J=7.2, 1.5 Hz, 1H), 7.29 (d, J=8.4 Hz, 2H), 7.10 (d, J=3.7 Hz, 1H), 6.35-6.21 (m, 2H), 4.96 (s, 2H), 4.53 (td, J=9.6, 4.2 Hz, 1H), 3.58 (t, J=7.6 Hz, 1H), 3.23 (qd, J=17.2, 6.9 Hz, 2H), 2.42 (h, J=8.4 Hz, 1H), 2.07-1.88 (m, 1H), 1.81 (dtd, J=12.1, 7.6, 4.4 Hz, 1H), 1.76-1.40 (m, 5H), 1.40-1.11 (m, 4H), 0.77 (t, J=7.3 Hz, 3H).

Example 106

(R)-(4-(1-(2-cyano-1-cyclopentylethyl)-1H-pyrazol-4-yl)-7H-pyrrolo [2, 3-d] pyrimidin-7-yl) methyl 2-((2, 3-dimethylphenyl) amino) benzoate

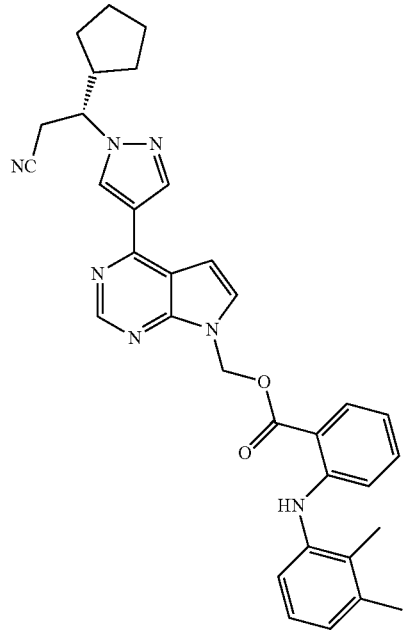 [SMILES: Cc1cccc(Nc2ccccc2C(=O)OCn2ccc3c(-c4cnn([C@H](CC#N)C5CCCC5)c4)ncnc32)c1C]

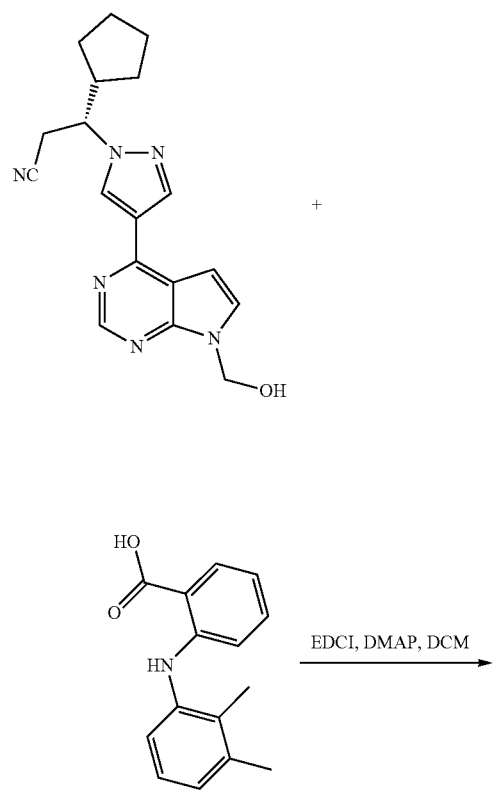

-continued

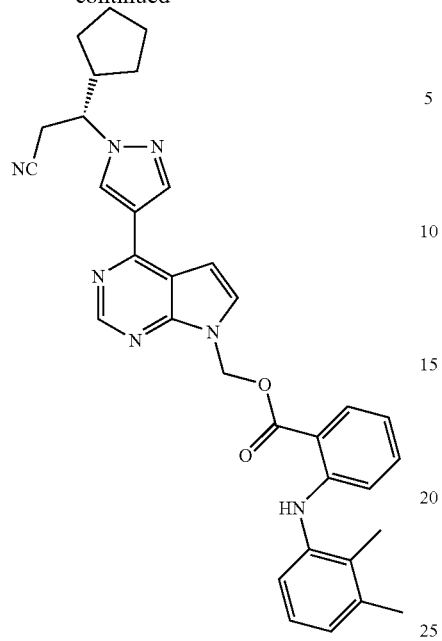

Synthesis of (R)-(4-(1-(2-cyano-1-cyclopentyl-ethyl)-1H-pyrazol-4-yl)-7H-pyrrolo [2, 3-d] pyrimidin-7-yl) methyl 2-((2, 3-dimethylphenyl) amino) benzoate (R)-3-cyclopentyl-3-(4-(7-(hydroxymethyl)-7H-pyrrolo [2, 3-d] pyrimidin-4-yl)-1H-pyrazol-1-yl) propanenitrile (171 mg, 0.5 mmol), 4-dimethylaminopyridine (DMAP, 61 mg, 0.5 mmol), 2-((2, 3-dimethylphenyl) amino) benzoic acid (mefenamic acid, 181 mg, 0.75 mmol) and 1-(3-dimethylaminopropyl)-3-ethylcarbodiimide hydrochloride (EDCI, 144 mg, 0.75 mmol) were dissolved in a mixed solvent of dichloromethane (8.5 mL) and N, N-dimethylformamide (0.3 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=150:1 to 50:1) to give the title compound as a yellow solid, 0.147 g, 52.6% yield. MS (m/z): [M+H]$^+$ calcd for $C_{33}H_{33}N_7O_2$, 560.27; found, 560.3. $^1$H NMR (400 MHz, DMSO-$d_6$) δ 9.08 (s, 1H), 8.84 (d, J=18.4 Hz, 2H), 8.42 (s, 1H), 7.91 (d, J=3.8 Hz, 1H), 7.75 (dd, J=8.1, 1.6 Hz, 1H), 7.32 (ddd, J=8.8, 7.2, 1.7 Hz, 1H), 7.20-7.00 (m, 4H), 6.69-6.59 (m, 2H), 6.54 (s, 2H), 4.55 (td, J=9.7, 4.2 Hz, 1H), 3.24 (qd, J=17.2, 6.9 Hz, 2H), 2.43 (q, J=8.4 Hz, 1H), 2.29 (s, 3H), 2.08 (s, 3H), 1.82 (dtd, J=12.0, 7.4, 3.9 Hz, 1H), 1.65-1.50 (m, 3H), 1.49-1.12 (m, 4H).

Example 107

(R)-(4-(1-(2-cyano-1-cyclopentylethyl)-1H-pyrazol-4-yl)-7H-pyrrolo [2, 3-d] pyrimidin-7-yl) methyl 2-((3-chloro-2-methylphenyl) amino) benzoate

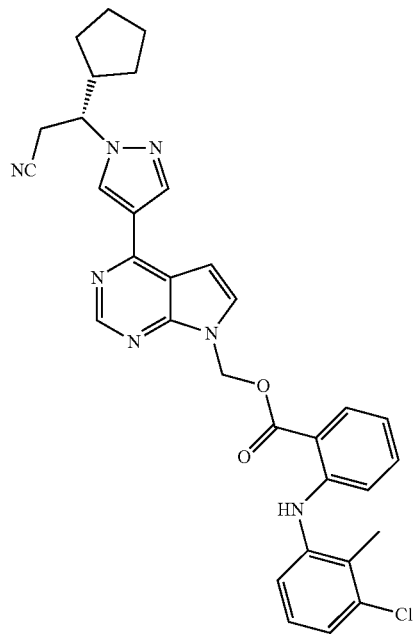 [SMILES: Cc1c(Cl)cccc1Nc1ccccc1C(=O)OCn1ccc2c(-c3cnn([C@H](CC#N)C4CCCC4)c3)ncnc21]

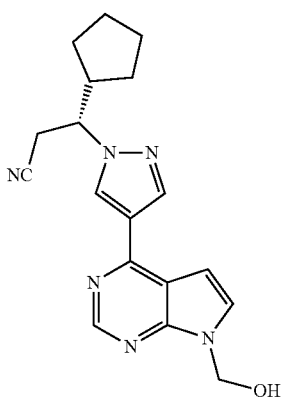

+

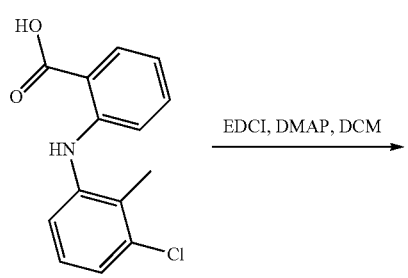

EDCI, DMAP, DCM →

465
-continued

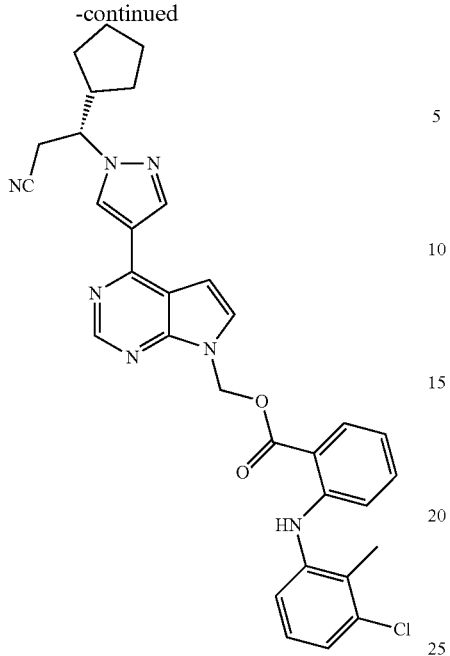

Synthesis of (R)-(4-(1-(2-cyano-1-cyclopentyl-ethyl)-1H-pyrazol-4-yl)-7H-pyrrolo [2, 3-d] pyrimidin-7-yl) methyl 2-((3-chloro-2-methylphenyl) amino) benzoate (R)-3-cyclopentyl-3-(4-(7-(hydroxymethyl)-7H-pyrrolo [2, 3-d] pyrimidin-4-yl)-1H-pyrazol-1-yl) propanenitrile (200 mg, 0.58 mmol), 4-dimethylamino pyridine (DMAP, 35 mg, 0.29 mmol), 2-((3-chloro-2-methylphenyl) amino) benzoic acid (tolfenamic acid, 230 mg, 0.88 mmol) and 1-(3-dimethylaminopropyl)-3-ethylcarbodiimide hydrochloride (EDCI, 168 mg, 0.88 mmol) were dissolved in a mixed solvent of dichloromethane (10 mL) and N, N-dimethylformamide (0.20 mL) and stirred at room temperature for 16 hours. After completion of the reaction, the reaction solution was diluted with dichloromethane and washed with water and saturated salt water solution.

The organic layer was dried over anhydrous sodium sulfate and filtered. The solvent was evaporated under reduced pressure to obtain the crude product. The crude product was further separated by silica gel column chromatography (dichloromethane/methanol=150:1 to 50:1) to give the title compound as a yellow solid, 0.161 g, 55.6% yield. MS (m/z): [M+H]$^+$ calcd for $C_{32}H_{30}ClN_7O_2$, 580.21; found, 580.3. $^1$H NMR (400 MHz, DMSO-d$_6$) δ 9.13 (s, 1H), 8.83 (d, J=18.6 Hz, 2H), 8.42 (s, 1H), 7.90 (d, J=3.8 Hz, 1H), 7.78 (dd, J=8.0, 1.6 Hz, 1H), 7.37 (ddd, J=8.8, 7.1, 1.7 Hz, 1H), 7.32-7.21 (m, 3H), 7.17 (d, J=3.8 Hz, 1H), 6.78-6.68 (m, 2H), 6.54 (s, 2H), 4.55 (td, J=9.6, 4.2 Hz, 1H), 3.33-3.15 (m, 2H), 2.43 (q, J=8.4 Hz, 1H), 2.24 (s, 3H), 1.82 (dtd, J=11.9, 7.4, 4.2 Hz, 1H), 1.59 (ddd, J=23.3, 7.9, 5.7 Hz, 2H), 1.47-1.12 (m, 5H).

466

Example 108

(4-(1-((R)-2-cyano-1-cyclopentylethyl)-1H-pyrazol-4-yl)-7H-pyrrolo [2, 3-d] pyrimidin-7-yl) methyl 2-(4-isobutylphenyl) propanoate

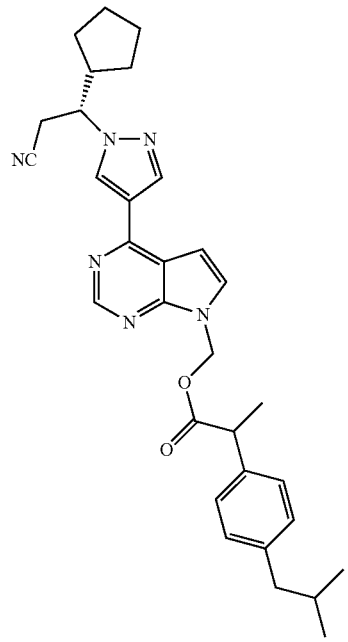 [SMILES: CC(C)Cc1ccc(C(C)C(=O)OCn2ccc3c(-c4cnn([C@H](CC#N)C5CCCC5)c4)ncnc32)cc1]

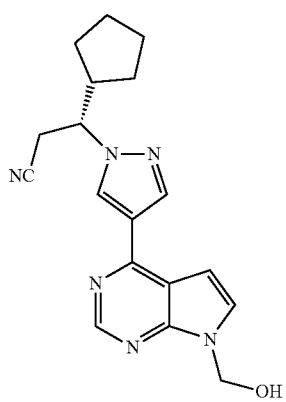

+

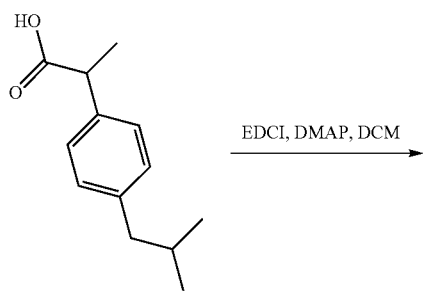

EDCI, DMAP, DCM →

467

-continued

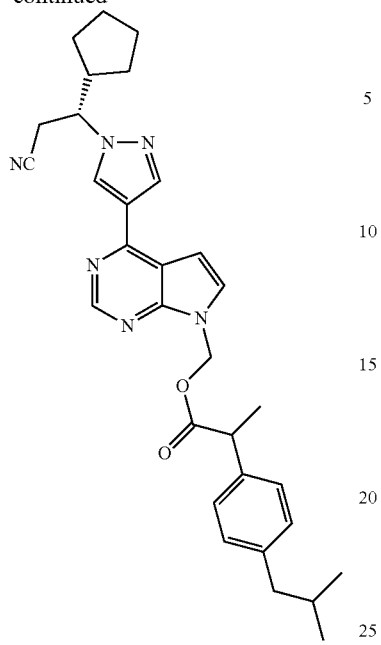

Synthesis of (4-(1-((R)-2-cyano-1-cyclopentyl-ethyl)-1H-pyrazol-4-yl)-7H-pyrrolo [2, 3-d] pyrimidin-7-yl) methyl 2-(4-isobutylphenyl) propanoate (R)-3-cyclopentyl-3-(4-(7-(hydroxymethyl)-7H-pyrrolo [2, 3-d] pyrimidin-4-yl)-1H-pyrazol-1-yl) propanenitrile (201 mg, 0.5 mmol), 4-dimethylamino pyridine (DMAP, 61 mg, 0.5 mmol), 2-(4-isobutylphenyl) propanoic acid (ibuprofen, 123.6 mg, 0.6 mmol) and 1-(3-dimethylaminopropyl)-3-ethylcarbodiimide hydrochloride (EDCI, 144 mg, 0.75 mmol) were dissolved in dichloromethane (10 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=150:1 to 50:1) to give the title compound as a white solid, 0.145 g, 55.3% yield. MS (m/z): [M+H]$^+$ calcd for $C_{31}H_{36}N_6O_2$, 525.29, found 525.3. $^1$H NMR (400 MHz, DMSO-d$_6$) δ 8.83 (s, 1H), 8.74 (s, 1H), 8.39 (s, 1H), 7.68 (d, J=3.8 Hz, 1H), 7.12-7.02 (m, 3H), 6.95 (d, J=7.9 Hz, 2H), 6.25 (q, J=10.7 Hz, 2H), 4.55 (td, J=9.7, 4.2 Hz, 1H), 3.76 (q, J=7.0 Hz, 1H), 3.30-3.15 (m, 2H), 2.43 (q, J=8.5 Hz, 1H), 2.32 (d, J=7.1 Hz, 2H), 1.89-1.77 (m, 1H), 1.70 (hept, J=6.8 Hz, 1H), 1.64-1.48 (m, 3H), 1.41-1.13 (m, 7H), 0.76 (dd, J=6.6, 1.0 Hz, 6H).

468

Example 109

(4-(1-((R)-2-cyano-1-cyclopentylethyl)-1H-pyrazol-4-yl)-7H-pyrrolo [2, 3-d] pyrimidin-7-yl) methyl 2-(1, 8-diethyl-1, 3, 4, 9-tetrahydropyran [3, 4-b] indol-1-yl) acetate

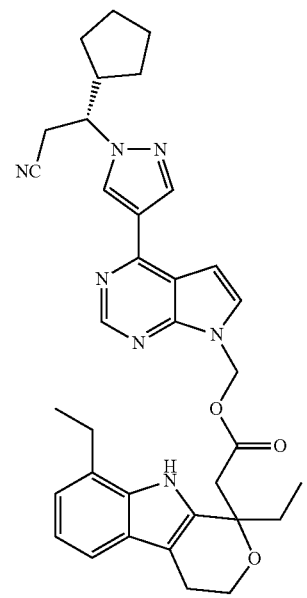 [SMILES: CCc1cccc2c3c([nH]c12)C(CC)(CC(=O)OCn1ccc2c(-c4cnn([C@H](CC#N)C5CCCC5)c4)ncnc21)OCC3]

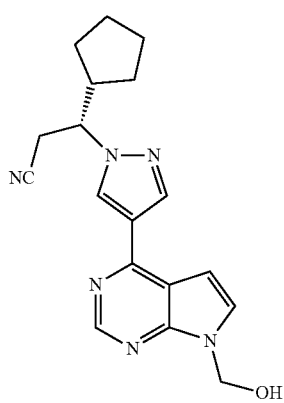

+

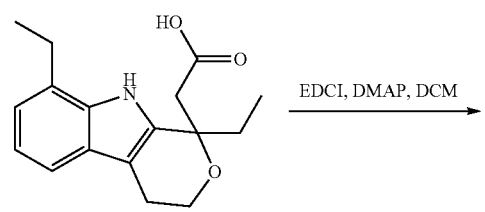

EDCI, DMAP, DCM

469

-continued

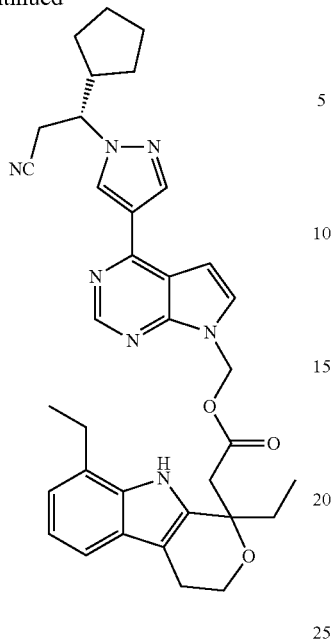

Synthesis of (4-(1-((R)-2-cyano-1-cyclopentyl-ethyl)-1H-pyrazol-4-yl)-7H-pyrrolo [2, 3-d] pyrimidin-7-yl) methyl 2-(1, 8-diethyl-1, 3, 4, 9-tetrahydropyran [3, 4-b] indol-1-yl) acetate (R)-3-cyclopentyl-3-(4-(7-(hydroxymethyl)-7H-pyrrolo [2, 3-d] pyrimidin-4-yl)-1H-pyrazol-1-yl) propanenitrile (171 mg, 0.5 mmol), 4-dimethylamino pyridine (DMAP, 61 mg, 0.5 mmol), 1, 8-diethyl-1, 3, 4, 9-tetrahydropyran [3, 4-b] indol-1-acetic acid (etodolac, 216 mg, 0.75 mmol) and 1-(3-dimethylaminopropyl)-3-ethylcarbodiimide hydrochloride (EDCI, 144 mg, 0.75 mmol) were dissolved in a mixed solvent of dichloromethane (8.5 mL) and dimethylformamide (0.3 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=150:1 to 50:1) to give the title compound as a white solid, 0.153 g, 50.5% yield. MS (m/z): [M+H]$^+$ calcd for $C_{35}H_{39}N_7O_3$, 606.31; found, 606.3. $^1$H NMR (400 MHz, DMSO-d$_6$) δ 10.42 (s, 1H), 8.83 (s, 1H), 8.76 (s, 1H), 8.40 (s, 1H), 7.56 (dd, J=3.8, 1.5 Hz, 1H), 7.15 (dd, J=7.3, 1.5 Hz, 1H), 7.01 (d, J=3.7 Hz, 1H), 6.90-6.79 (m, 2H), 6.19 (d, J=1.4 Hz, 2H), 4.56 (td, J=9.7, 4.2 Hz, 1H), 3.82 (td, J=11.1, 5.4 Hz, 2H), 3.31-3.15 (m, 2H), 3.05 (d, J=13.6 Hz, 1H), 2.88-2.69 (m, 3H), 2.60 (ddd, J=15.0, 8.1, 5.3 Hz, 1H), 2.44 (q, J=8.4 Hz, 1H), 2.07-1.76 (m, 3H), 1.68-1.41 (m, 4H), 1.41-1.14 (m, 7H), 0.57 (t, J=7.2 Hz, 3H).

470

Example 110

(R)-(4-(1-(2-cyano-1-cyclopentylethyl)-1H-pyrazol-4-yl)-7H-pyrrolo [2, 3-d] pyrimidin-7-yl) methyl 2-(4-acetamidophenyl) acetate

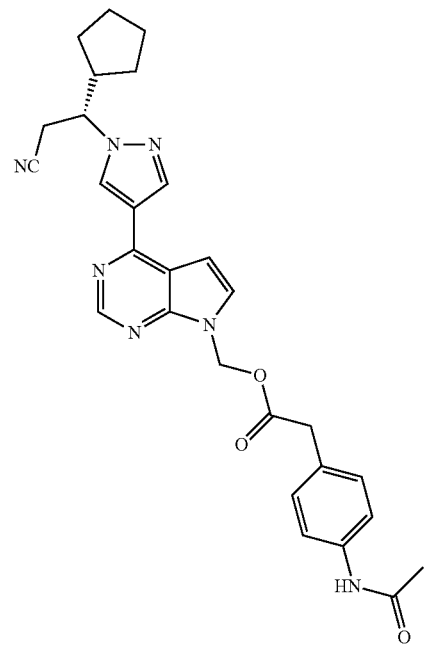 [SMILES: CC(=O)Nc1ccc(CC(=O)OCn2ccc3c(-c4cnn([C@H](CC#N)C5CCCC5)c4)ncnc32)cc1]

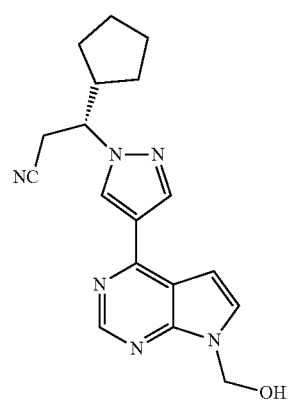

+

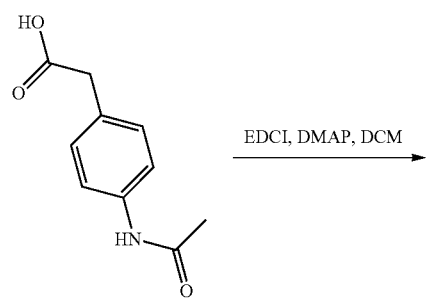

EDCI, DMAP, DCM

-continued

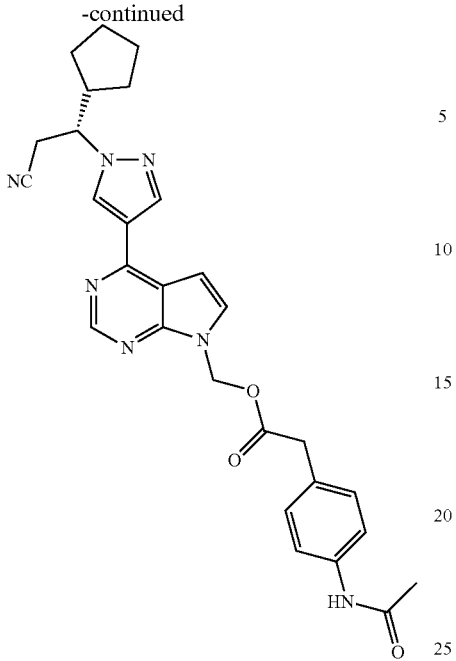

Synthesis of (R)-(4-(1-(2-cyano-1-cyclopentyl-ethyl)-1H-pyrazol-4-yl)-7H-pyrrolo [2, 3-d] pyrimidin-7-yl) methyl 2-(4-acetamidophenyl) acetate (R)-3-cyclopentyl-3-(4-(7-(hydroxymethyl)-7H-pyrrolo [2, 3-d] pyrimidin-4-yl)-1H-pyrazol-1-yl) propanenitrile (171 mg, 0.5 mmol), 4-dimethylamino pyridine (DMAP, 61 mg, 0.5 mmol), 2-(4-acetamidophenyl) acetic acid (actarit, 145 mg, 0.75 mmol) and 1-(3-dimethylaminopropyl)-3-ethylcarbodiimide hydrochloride (EDCI, 144 mg, 0.75 mmol) were dissolved in a mixed solvent of dichloromethane (8.5 mL) and N, N-dimethylformamide (0.3 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=150:1 to 50:1) to give the title compound as a white solid, 0.133 g, 52% yield. MS (m/z): [M+H]$^+$ calcd for $C_{28}H_{29}N_7O_3$, 512.23; found, 512.3. $^1$H NMR (400 MHz, DMSO-$d_6$) δ 9.91 (s, 1H), 8.83 (d, J=20.0 Hz, 2H), 8.41 (s, 1H), 7.75 (d, J=3.7 Hz, 1H), 7.49 (d, J=8.3 Hz, 2H), 7.18-7.10 (m, 3H), 6.27 (s, 2H), 4.55 (td, J=9.6, 4.2 Hz, 1H), 3.65 (s, 2H), 3.30-3.15 (m, 2H), 2.48-2.37 (m, 1H), 2.03 (s, 3H), 1.87-1.76 (m, 1H), 1.66-1.42 (m, 4H), 1.41-1.15 (m, 3H).

Example 111

(4-(1-((R)-2-cyano-1-cyclopentylethyl)-1H-pyrazol-4-yl)-7H-pyrrolo [2, 3-d] pyrimidin-7-yl) methyl (S)-2-((tert-butoxycarbonyl) amino)-2-phenylacetate

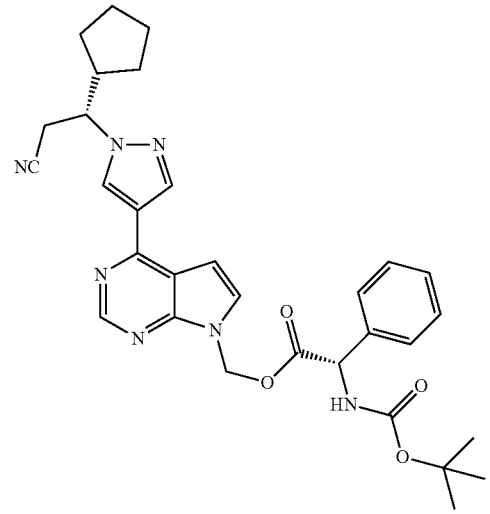 [SMILES: CC(C)(C)OC(=O)N[C@H](C(=O)OCn1ccc2c(-c3cnn([C@H](CC#N)C4CCCC4)c3)ncnc21)c1ccccc1]

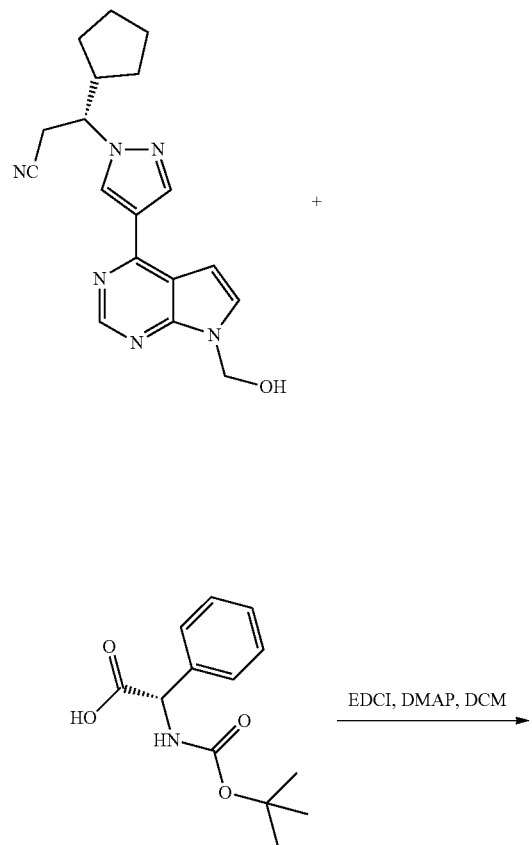

EDCI, DMAP, DCM

473
-continued

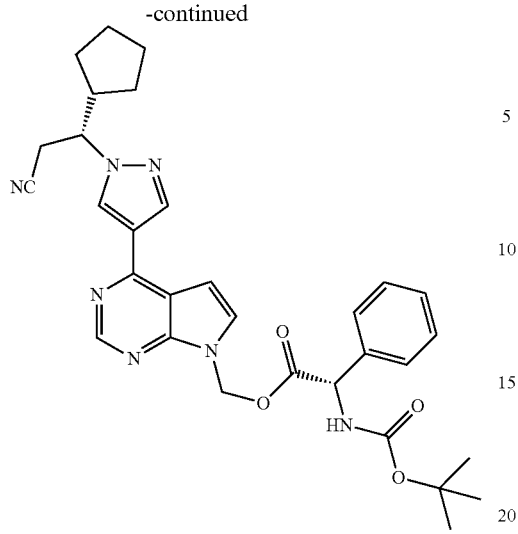

Synthesis of (4-(1-((R)-2-cyano-1-cyclopentyl-ethyl)-1H-pyrazol-4-yl)-7H-pyrrolo [2, 3-d] pyrimidin-7-yl) methyl (S)-2-((tert-butoxycarbonyl) amino)-2-phenylacetate (R)-3-cyclopentyl-3-(4-(7-(hydroxymethyl)-7H-pyrrolo [2, 3-d] pyrimidin-4-yl)-1H-pyrazol-1-yl) propanenitrile (171 mg, 0.5 mmol), 4-dimethylaminopyridine (DMAP, 61 mg, 0.5 mmol), N-Boc-L-phenylglycine (189 mg, 0.75 mmol) and 1-(3-dimethylaminopropyl)-3-ethylcarbodiimide hydrochloride (EDCI, 144 mg, 0.75 mmol) were dissolved in a mixed solvent of dichloromethane (8.5 mL) and N, N-dimethylformamide (0.3 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=150:1 to 50:1) to give the title compound as a white solid, 0.153 g, 53.7% yield. MS (m/z): [M+H]$^+$ calcd for $C_{31}H_{35}N_7O_4$, 570.28; found, 570.2. $^1$H NMR (400 MHz, DMSO-d$_6$) δ 8.84 (s, 1H), 8.75 (s, 1H), 8.40 (s, 1H), 7.82 (d, J=7.8 Hz, 1H), 7.66 (d, J=3.7 Hz, 1H), 7.40-7.19 (m, 5H), 7.09 (d, J=3.8 Hz, 1H), 6.37-6.22 (m, 2H), 5.19 (d, J=7.8 Hz, 1H), 4.55 (td, J=9.7, 4.2 Hz, 1H), 3.29-3.15 (m, 2H), 2.45-2.34 (m, 1H), 1.88-1.77 (m, 1H), 1.67-1.40 (m, 4H), 1.39-1.11 (m, 12H).

474

Example 112

Methyl (4-(1-(3-(cyanomethyl)-1-(ethylsulfonyl) azetidin-3-yl)-1H-pyrazol-4-yl)-7H-pyrrolo [2, 3-d] pyrimidin-7-yl) 2-(4-isobutylphenyl) propanoate

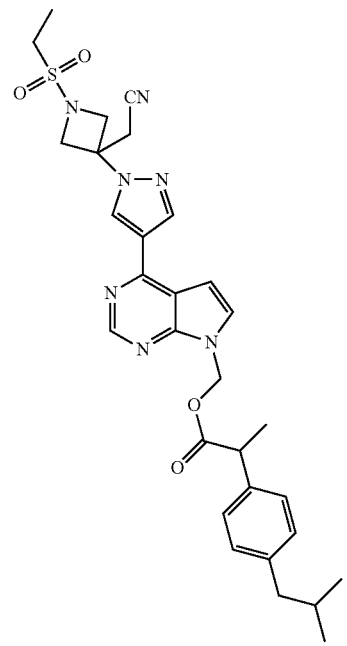 [SMILES: CCS(=O)(=O)N1CC(CC#N)(n2cc(-c3ncnc4c3ccn4COC(=O)C(C)c3ccc(CC(C)C)cc3)cn2)C1]

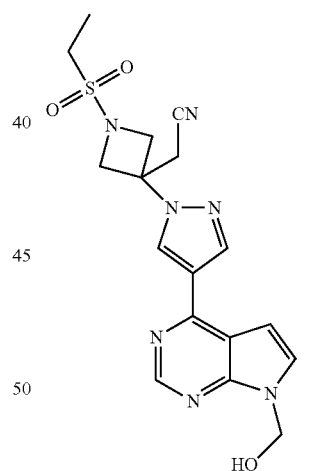

+

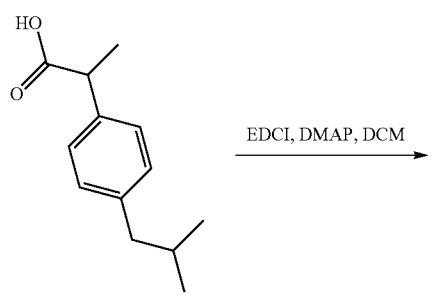

EDCI, DMAP, DCM
→

475

-continued

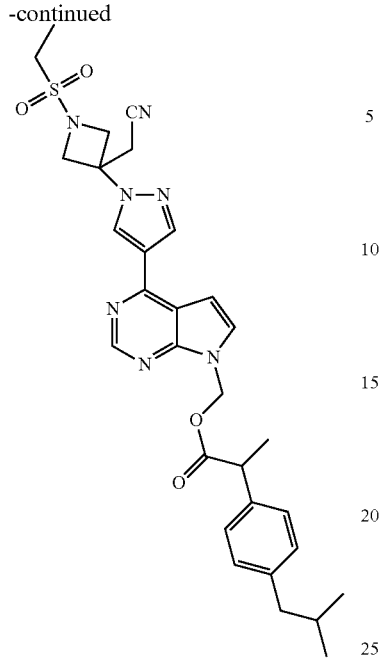

Synthesis of methyl (4-(1-(3-(cyanomethyl)-1-(ethylsulfonyl) azetidin-3-yl)-1H-pyrazol-4-yl)-7H-pyrrolo [2, 3-d] pyrimidin-7-yl) 2-(4-isobutylphenyl) propanoate 2-(1-(Ethylsulfonyl)-3-(4-(7-(hydroxymethyl)-7H-)) pyrrolo [2, 3-d] pyrimidin-4-yl)-1H-pyrazol-1-yl) azetidin-3-yl) acetonitrile (143 mg, 0.356 mmol), 4-dimethylamino pyridine (DMAP, 44 mg, 0.356 mmol), 2-(4-isobutylphenyl) propanoic acid (ibuprofen, 110 mg, 0.534 mmol) and 1-(3-dimethylaminopropyl)-3-ethylcarbodiimide hydrochloride (EDCI, 103 mg, 0.534 mmol) were dissolved in dichloromethane (3 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=150:1 to 50:1) to give the title compound as a white solid, 0.191 g, 91% yield. MS (m/z): [M+H]$^+$ calcd for $C_{30}H_{35}N_7O_4S$, 590.25, found 590.3. $^1$H NMR (400 MHz, Chloroform-d) δ 8.85 (s, 1H), 8.49 (s, 1H), 8.31 (s, 1H), 7.44 (d, J=3.8 Hz, 1H), 7.09 (d, J=8.1 Hz, 2H), 7.00 (d, J=8.1 Hz, 2H), 6.71 (d, J=3.8 Hz, 1H), 6.27-6.17 (m, 2H), 4.63 (d, J=9.2 Hz, 2H), 4.29-4.22 (m, 2H), 3.70 (q, J=7.1 Hz, 1H), 3.40 (s, 2H), 3.08 (q, J=7.4 Hz, 2H), 2.38 (d, J=7.2 Hz, 2H), 1.79 (dh, J=13.5, 6.7 Hz, 1H), 1.48-1.38 (m, 6H), 0.85 (d, J=6.6 Hz, 6H).

476

Example 113

(4-(Methyl ((trans)-4-((N-methylsulfamoyl) methyl) cyclohexyl) amino)-7H-pyrrolo [2, 3-d] pyrimidin-7-yl) methyl 2-(2-fluoro-[1, 1'-biphenyl]-4-yl) propanoate

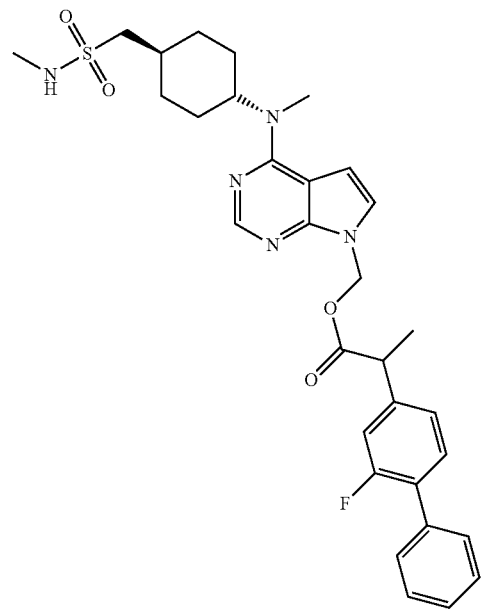

477
-continued

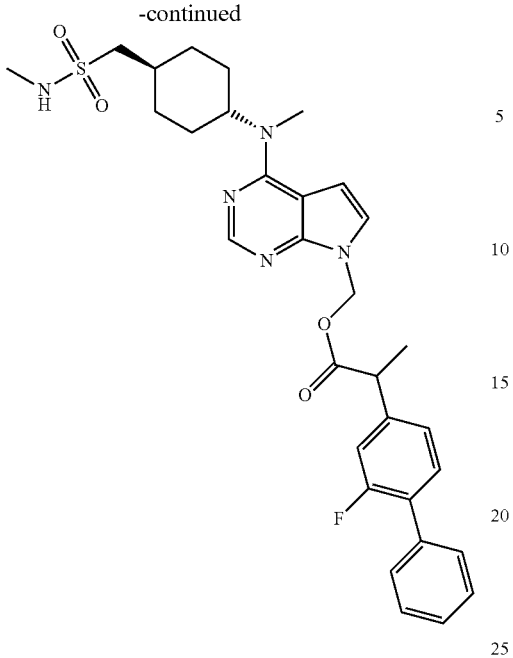

Synthesis of (4-(methyl ((trans)-4-((N-methylsulfa-moyl) methyl) cyclohexyl) amino)-7H-pyrrolo [2, 3-d]pyrimidin-7-yl) methyl 2-(2-fluoro-[1, 1'-biphe-nyl]-4-yl) propanoate 1-((Trans)-4-((7-(hydroxymethyl)-7H-pyrrolo [2, 3-d] pyrimidin-4-yl) (methyl) amino) cyclohexyl)-N-methyl methanesulfonamide (170 mg, 0.5 mmol), 4-dimethylamino pyridine (DMAP, 61 mg, 0.5 mmol), 2-(2-fluoro-4-biphenyl) propanoic acid (flurbiprofen, 183 mg, 0.75 mmol) and 1-(3-dimethylaminopropyl)-3-ethylcarbodiimide hydrochloride (EDCI, 144 mg, 0.75 mmol) were dissolved in dichloromethane (8.5 mL) and dimethylformamide (0.3 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=150:1 to 50:1) to give the title compound as a white solid, 0.072 g, 24.2% yield. MS (m/z): [M+H]$^+$ calcd for $C_{31}H_{36}FN_5O_4S$, 594.25; found, 594.1. $^1$H NMR (400 MHz, DMSO-d$_6$) δ 8.16 (s, 1H), 7.54-7.44 (m, 4H), 7.42-7.35 (m, 2H), 7.29 (d, J=3.7 Hz, 1H), 7.12 (d, J=9.9 Hz, 2H), 6.90 (q, J=5.0 Hz, 1H), 6.63 (d, J=3.7 Hz, 1H), 6.17 (d, J=2.1 Hz, 2H), 4.64 (s, 1H), 3.89 (q, J=7.1 Hz, 1H), 3.15 (s, 3H), 2.95 (d, J=6.2 Hz, 2H), 2.59 (d, J=5.0 Hz, 3H), 2.07-1.99 (m, 2H), 1.84 (dt, J=11.8, 6.9 Hz, 1H), 1.75-1.61 (m, 4H), 1.39 (d, J=7.1 Hz, 3H), 1.36-1.21 (m, 2H).

478
Example 114

(4-(Methyl ((trans)-4-((N-methylsulfamoyl) methyl) cyclohexyl) amino)-7H-pyrrolo [2, 3-d] pyrimidin-7-yl) methyl 2-(3-phenoxyphenyl) propanoate

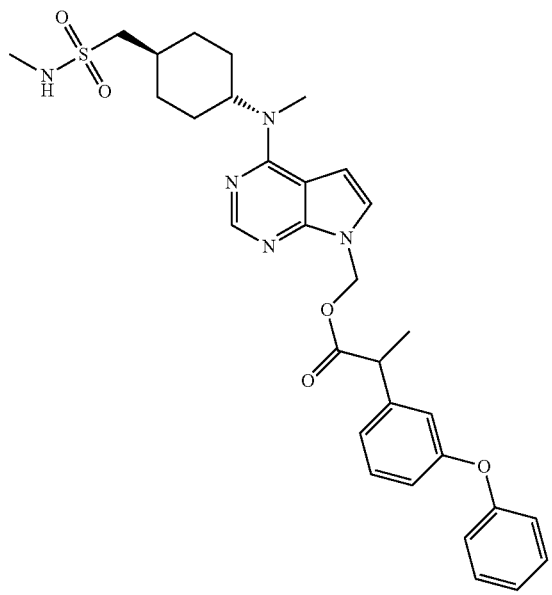

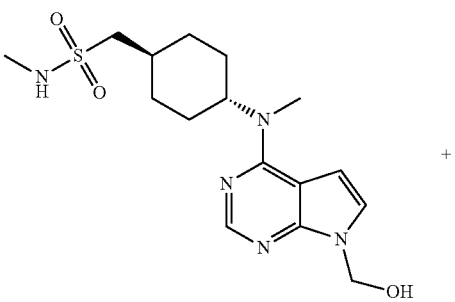

+

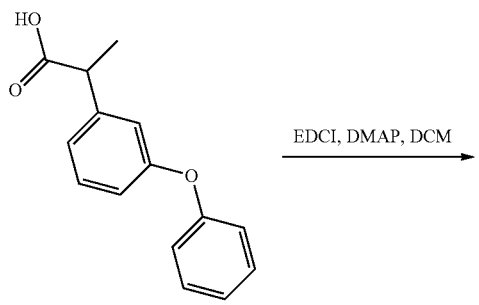

EDCI, DMAP, DCM
→

-continued

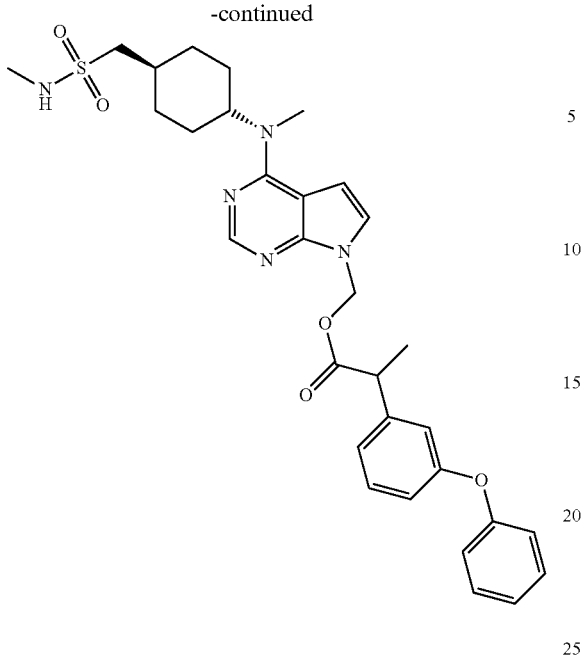

Synthesis of (4-(methyl ((trans)-4-((N-methylsulfamoyl) methyl) cyclohexyl) amino)-7H-pyrrolo [2, 3-d]pyrimidin-7-yl) methyl 2-(3-phenoxyphenyl) propanoate 1-((Trans)-4-((7-(hydroxymethyl)-7H-pyrrolo [2, 3-d]pyrimidin-4-yl) (methyl) amino) cyclohexyl)-N-methyl methanesulfonamide (170 mg, 0.5 mmol), 4-dimethylaminopyridine (DMAP, 61 mg, 0.5 mmol), 2-(3-phenoxyphenyl) propanoic acid (fenoprofen, 182 mg, 0.75 mmol) and 1-(3-dimethylaminopropyl)-3-ethylcarbodiimide hydrochloride (EDCI, 144 mg, 0.75 mmol) were dissolved in dichloromethane (8.5 mL) and dimethylformamide (0.3 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=150:1 to 50:1) to give the title compound as a white solid, 0.118 g, 39.9% yield. MS (m/z): [M+H]$^+$ calcd for $C_{31}H_{37}N_5O_5S$, 592.25; found, 592.2. $^1$H NMR (400 MHz, DMSO-$d_6$) δ 8.22 (s, 1H), 7.42 (dd, J=8.5, 7.3 Hz, 2H), 7.35-7.28 (m, 2H), 7.19 (t, J=7.4 Hz, 1H), 7.07-6.85 (m, 6H), 6.68 (d, J=3.7 Hz, 1H), 6.19 (s, 2H), 4.71 (s, 1H), 3.86 (q, J=7.1 Hz, 1H), 3.21 (s, 3H), 3.01 (d, J=6.2 Hz, 2H), 2.64 (d, J=5.0 Hz, 3H), 2.10 (d, J=12.9 Hz, 2H), 1.97-1.82 (m, 1H), 1.73 (t, J=5.3 Hz, 4H), 1.42-1.27 (m, 5H).

Example 115

(4-(Methyl ((trans)-4-((N-methylsulfamoyl) methyl) cyclohexyl) amino)-7H-pyrrolo [2, 3-d] pyrimidin-7-yl) methyl 2-(4-((2-oxocyclopentyl) methyl) phenyl) propanoate

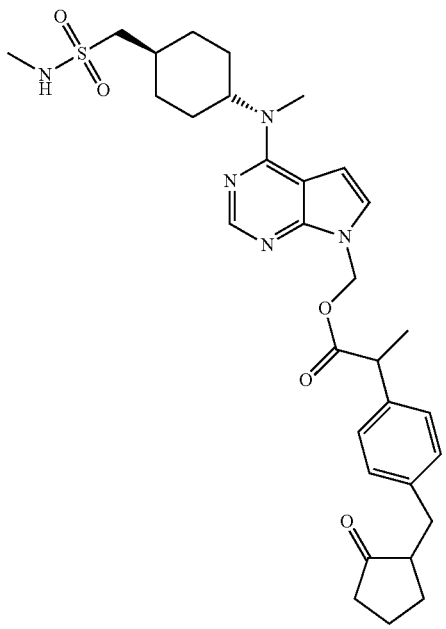

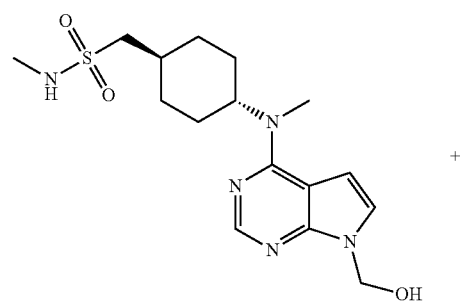

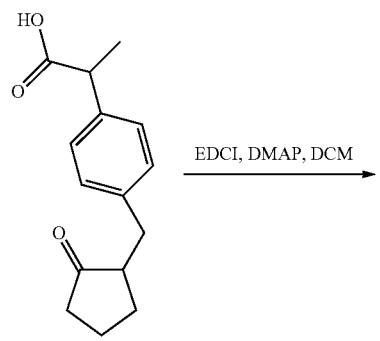

EDCI, DMAP, DCM

481
-continued

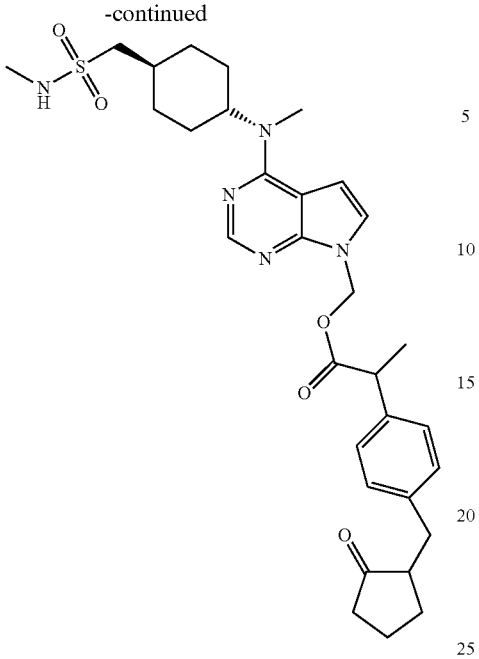

Synthesis of (4-(methyl ((trans)-4-((N-methylsulfa-moyl) methyl) cyclohexyl) amino)-7H-pyrrolo [2, 3-d]pyrimidin-7-yl) methyl 2-(4-((2-oxocyclopentyl) methyl) phenyl) propanoate 1-((Trans)-4-((7-(hydroxymethyl)-7H-pyrrolo [2, 3-d] pyrimidin-4-yl) (methyl) amino) cyclohexyl)-N-methyl methanesulfonamide (170 mg, 0.5 mmol), 4-dimethylamino pyridine (DMAP, 61 mg, 0.5 mmol), 2-[4-(2-oxocyclopen-tan-1-ylmethyl) phenyl] propanoic acid (loxoprofen, 185 mg, 0.75 mmol) and 1-(3-dimethylaminopropyl)-3-ethylcar-bodiimide hydrochloride (EDCI, 144 mg, 0.75 mmol) were dissolved in dichloromethane (8.5 mL) and dimethylforma-mide (0.3 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/metha-nol=150:1 to 50:1) to give the title compound as a white solid, 0.073 g, 24.5% yield. MS (m/z): [M+H]$^+$ calcd for $C_{31}H_{41}N_5O_5S$, 596.28; found, 596.2. $^1$H NMR (400 MHz, DMSO-d$_6$) δ 8.15 (d, J=1.9 Hz, 1H), 7.25 (d, J=3.7 Hz, 1H), 7.07 (qd, J=8.3, 2.9 Hz, 4H), 6.89 (q, J=4.9 Hz, 1H), 6.62 (d, J=3.8 Hz, 1H), 6.12 (d, J=1.6 Hz, 2H), 4.65 (s, 1H), 3.74 (q, J=7.0 Hz, 1H), 3.16 (s, 3H), 3.00-2.80 (m, 3H), 2.59 (d, J=5.0 Hz, 3H), 2.45-2.16 (m, 3H), 2.05 (dddd, J=14.5, 10.1, 8.5, 1.7 Hz, 3H), 1.93-1.78 (m, 3H), 1.74-1.60 (m, 5H), 1.48-1.41 (m, 1H), 1.36-1.21 (m, 5H).

482

Example 116

(4-(Methyl ((trans)-4-((N-methylsulfamoyl) methyl) cyclohexyl) amino)-7H-pyrrolo [2, 3-d] pyrimidin-7-yl) methyl 2-(1-(4-chlorobenzoyl)-5-methoxy-2-methyl-1H-indol-3-yl) acetate

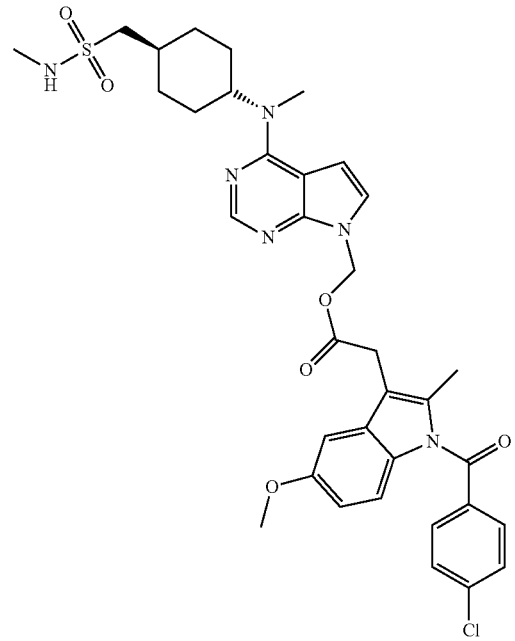

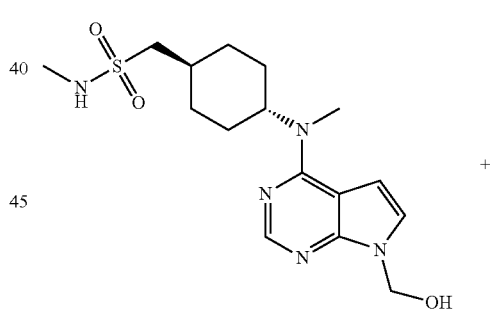

+

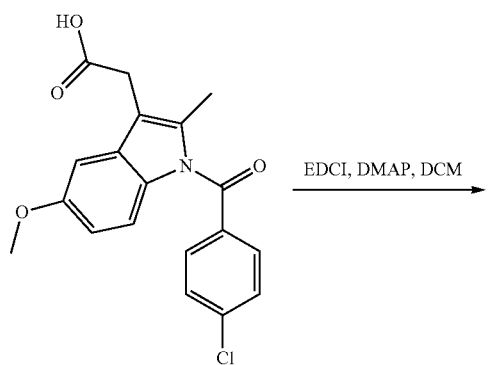

EDCI, DMAP, DCM
→

483

-continued

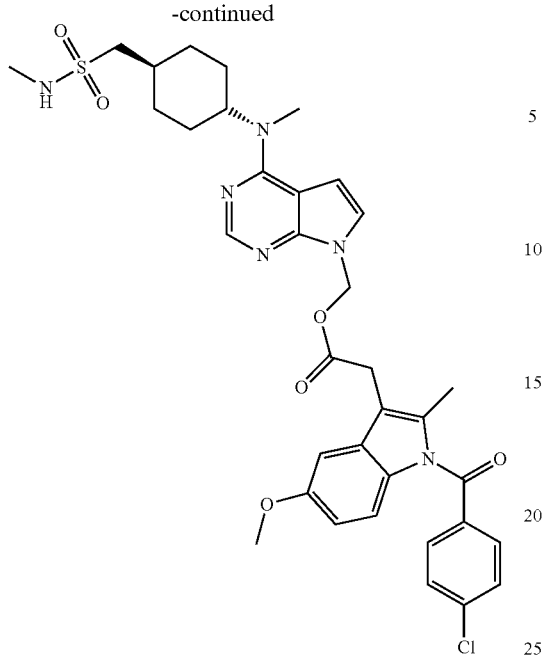

Synthesis of (4-(Methyl ((trans)-4-((N-methylsulfa-moyl) methyl) cyclohexyl) amino)-7H-pyrrolo [2, 3-d]pyrimidin-7-yl) methyl 2-(1-(4-chlorobenzoyl)-5-methoxy-2-methyl-1H-indol-3-yl) acetate 1-((Trans)-4-((7-(hydroxymethyl)-7H-pyrrolo [2, 3-d] pyrimidin-4-yl) (methyl) amino) cyclohexyl)-N-methyl methanesulfonamide (170 mg, 0.5 mmol), 4-dimethylamino pyridine (DMAP, 61 mg, 0.5 mmol), 1-(4-chlorobenzoyl)-5-methoxy-2-methyl-1H-indole-3-acetic acid (indomethacin, 277 mg, 0.75 mmol) and 1-(3-dimethylaminopropyl)-3-ethylcarbodiimide hydrochloride (EDCI, 144 mg, 0.75 mmol) were dissolved in dichloromethane (8.5 mL) and dimethylformamide (0.3 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=150:1 to 50:1) to give the title compound as a light yellow solid, 0.136 g, 38.5% yield. MS (m/z): [M+H]$^+$ calcd for $C_{35}H_{39}C_1N_6O_6S$, 707.23; found, 707.0. $^1$H NMR (400 MHz, DMSO-$d_6$) δ 8.17 (s, 1H), 7.64 (s, 4H), 7.28 (d, J=3.7 Hz, 1H), 7.01-6.83 (m, 3H), 6.70 (dd, J=9.0, 2.6 Hz, 1H), 6.64 (d, J=3.8 Hz, 1H), 6.17 (s, 2H), 4.67 (s, 1H), 3.80 (s, 2H), 3.70 (s, 3H), 3.17 (s, 3H), 2.96 (d, J=6.2 Hz, 2H), 2.60 (d, J=4.9 Hz, 3H), 2.14 (s, 3H), 2.06 (d, J=12.8 Hz, 2H), 1.96-1.80 (m, 1H), 1.77-1.63 (m, 4H), 1.31 (p, J=4.9, 4.3 Hz, 2H).

484

Example 117

(4-(Methyl ((trans)-4-((N-methylsulfamoyl) methyl) cyclohexyl) amino)-7H-pyrrolo [2, 3-d] pyrimidin-7-yl) methyl 2-(4-(1-) oxoisoindolin-2-yl) phenyl) butanoate

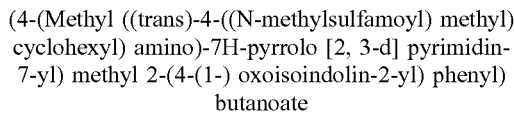

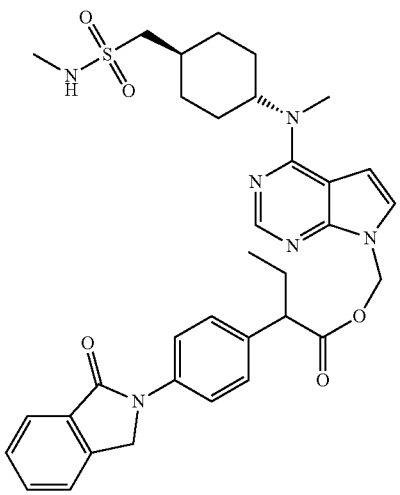

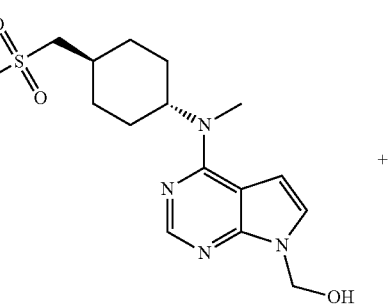

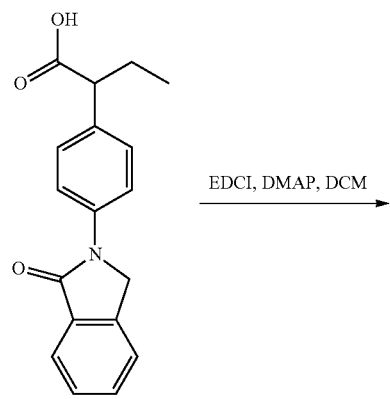

EDCI, DMAP, DCM

485

-continued

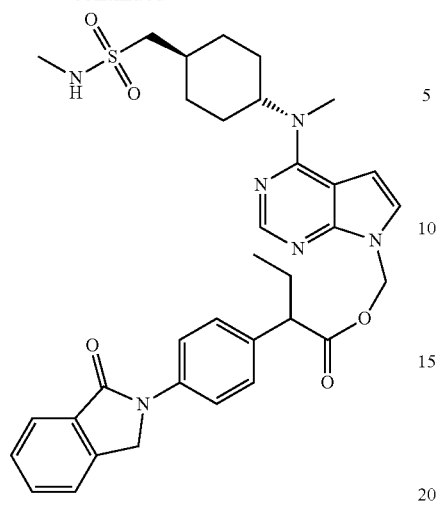

Synthesis of (4-(methyl ((trans)-4-((N-methylsulfa-moyl) methyl) cyclohexyl) amino)-7H-pyrrolo [2, 3-d]pyrimidin-7-yl) methyl 2-(4-(1-) oxoisoindolin-2-yl) phenyl) butanoate 1-((Trans)-4-((7-(hydroxymethyl)-7H-pyrrolo [2, 3-d] pyrimidin-4-yl) (methyl) amino) cyclohexyl)-N-methyl methanesulfonamide (20 mg, 0.058 mmol), 4-dimethyl-amino pyridine (DMAP, 4 mg, 0.03 mmol), 2-(4-(1-oxoisoindolin-2-yl) phenyl) butanoic acid (indobufen, 26 mg, 0.09 mmol) and 1-(3-dimethylaminopropyl)-3-ethylcarbodiimide hydrochloride (EDCI, 17 mg, 0.09 mmol) were dissolved in a mixed solvent of dichloromethane (0.5 mL) and N, N-dimethylformamide (0.05 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=150:1 to 50:1) to give the title compound as a white solid, 0.156 g, 48.4% yield. MS (m/z): [M+H]$^+$ calcd for $C_{34}H_{40}N_6O_5S$, 645.28; found, 645.1. $^1$H NMR (400 MHz, DMSO-d$_6$) δ 8.17 (s, 1H), 7.86-7.75 (m, 3H), 7.68 (dd, J=6.3, 1.2 Hz, 2H), 7.55 (ddd, J=8.1, 6.3, 2.0 Hz, 1H), 7.34-7.24 (m, 3H), 6.88 (q, J=5.0 Hz, 1H), 6.62 (d, J=3.8 Hz, 1H), 6.22-6.08 (m, 2H), 4.99 (s, 2H), 4.64 (s, 1H), 3.55 (t, J=7.6 Hz, 1H), 3.14 (s, 3H), 2.94 (d, J=6.2 Hz, 2H), 2.59 (d, J=5.0 Hz, 3H), 2.06-1.91 (m, 3H), 1.89-1.78 (m, 1H), 1.77-1.61 (m, 5H), 1.33-1.21 (m, 2H), 0.79 (t, J=7.3 Hz, 3H).

486

Example 118

(4-(Methyl ((trans)-4-((N-methylsulfamoyl) methyl) cyclohexyl) amino)-7H-pyrrolo [2, 3-d] pyrimidin-7-yl) methyl 2-((2, 3-dimethylphenyl) amino) benzoate

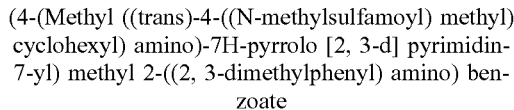

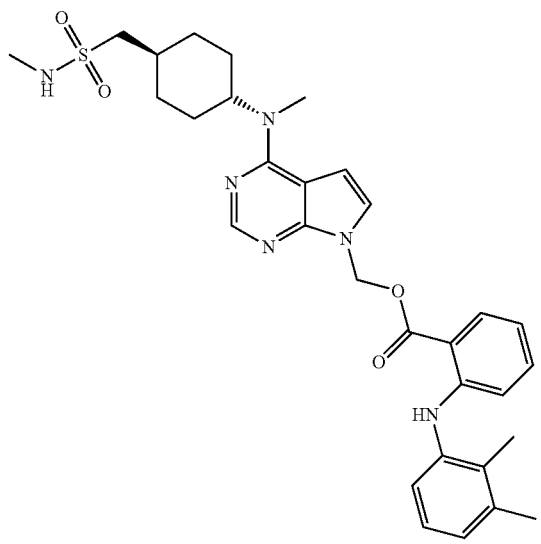

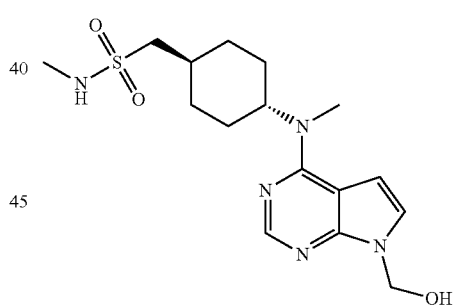

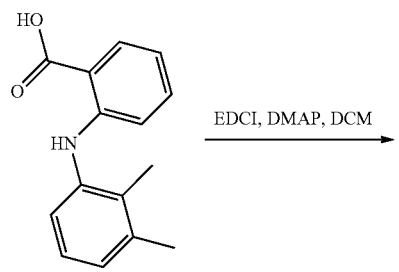

487

-continued

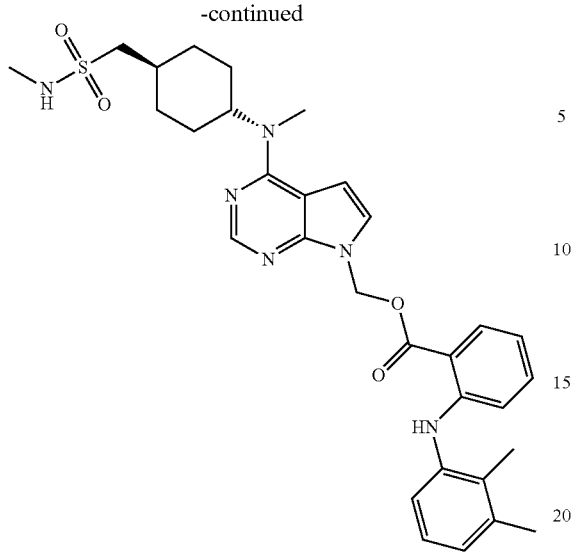

Synthesis of (4-(methyl ((trans)-4-((N-methylsulfa-moyl) methyl) cyclohexyl) amino)-7H-pyrrolo [2, 3-d]pyrimidin-7-yl) methyl 2-((2, 3-dimethylphenyl) amino) benzoate 1-((Trans)-4-((7-(hydroxymethyl)-7H-pyrrolo [2, 3-d] pyrimidin-4-yl) (methyl) amino) cyclohexyl)-N-methyl methanesulfonamide (171 mg, 0.5 mmol), 4-dimethylaminopyridine (DMAP, 61 mg, 0.5 mmol), 2-((2, 3-dimethylphenyl) amino) benzoic acid (mefenamic acid, 181 mg, 0.75 mmol) and 1-(3-dimethylaminopropyl)-3-ethylcarbodiimide hydrochloride (EDCI, 144 mg, 0.75 mmol) were dissolved in a mixed solvent of dichloromethane (8.5 mL) and N, N-dimethylformamide (0.3 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=150:1 to 50:1) to give the title compound as a yellow solid, 0.096 g, 32.5% yield. MS (m/z): [M+H]$^+$ calcd for $C_{31}H_{38}N_6O_4S$, 591.27; found, 591.2. $^1$H NMR (400 MHz, DMSO-d$_6$) δ 9.07 (s, 1H), 8.21 (s, 1H), 7.73 (dd, J=8.1, 1.6 Hz, 1H), 7.47 (dd, J=8.8, 3.9 Hz, 1H), 7.32 (ddd, J=8.6, 7.0, 1.7 Hz, 1H), 7.19-7.03 (m, 3H), 6.90 (q, J=4.9 Hz, 1H), 6.66 (ddd, J=20.2, 9.1, 4.5 Hz, 3H), 6.41 (s, 2H), 4.68 (s, 1H), 3.22-3.13 (m, 3H), 2.95 (d, J=6.2 Hz, 2H), 2.59 (d, J=4.9 Hz, 3H), 2.29 (s, 3H), 2.06 (d, J=14.3 Hz, 5H), 1.92-1.79 (m, 1H), 1.70 (h, J=3.4 Hz, 4H), 1.38-1.19 (m, 2H).

488

Example 119

(4-(Methyl ((trans)-4-((N-methylsulfamoyl) methyl) cyclohexyl) amino)-7H-pyrrolo [2, 3-d] pyrimidin-7-yl) methyl 2-(4-isobutylphenyl) propanoate

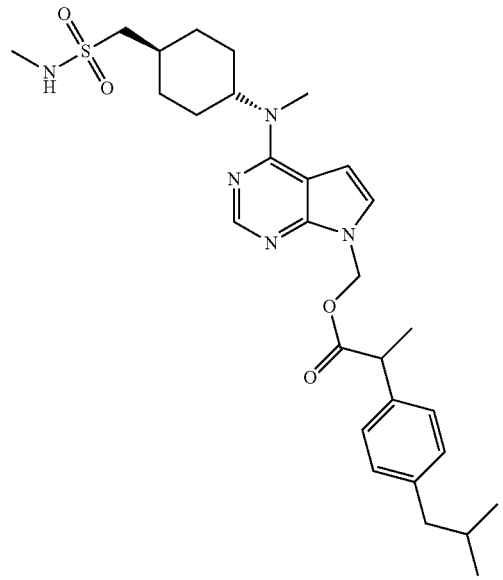

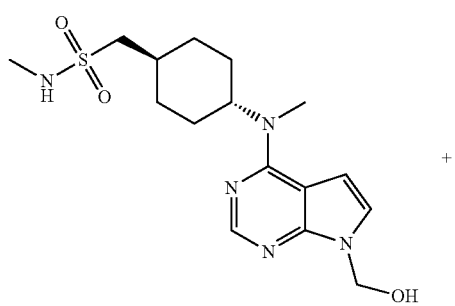

+

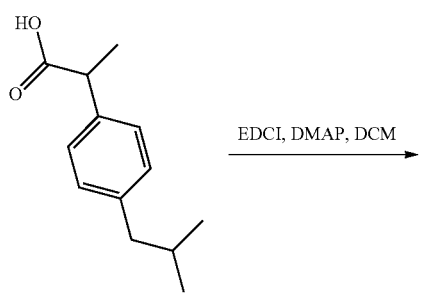

EDCI, DMAP, DCM
⟶

489

-continued

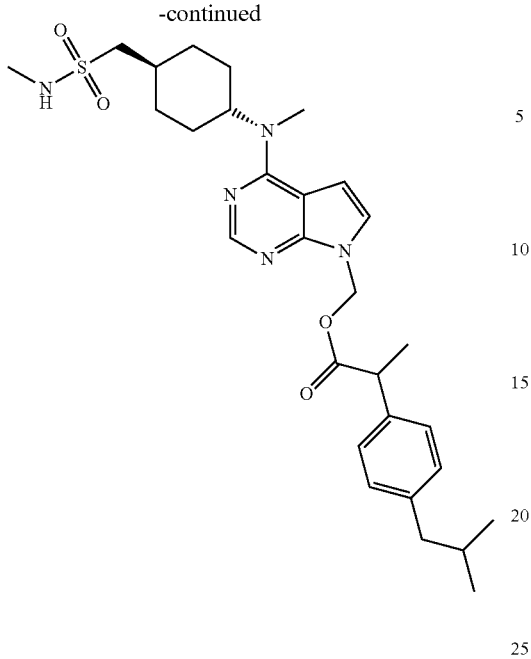

Synthesis of (4-(methyl ((trans)-4-((N-methylsulfamoyl) methyl) cyclohexyl) amino)-7H-pyrrolo [2, 3-d]pyrimidin-7-yl) methyl 2-(4-isobutylphenyl) propanoate 1-((Trans)-4-((7-(hydroxymethyl)-7H-pyrrolo [2, 3-d] pyrimidin-4-yl) (methyl) amino) cyclohexyl)-N-methyl methanesulfonamide (201 mg, 0.5 mmol), 4-dimethylamino pyridine (DMAP, 61 mg, 0.5 mmol), 2-(4-isobutylphenyl) propanoic acid (ibuprofen, 123.6 mg, 0.6 mmol) and 1-(3-dimethylaminopropyl)-3-ethylcarbodiimide hydrochloride (EDCI, 144 mg, 0.75 mmol) were dissolved in dichloromethane (10 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=150:1 to 50:1) to give the title compound as a white solid, 0.142 g, 51.1% yield. MS (m/z): [M+H]$^+$ calcd for $C_{29}H_{41}N_5O_4S$, 556.29, found 556.2 $^1$H NMR (400 MHz, DMSO-$d_6$) δ 8.15 (s, 1H), 7.24 (d, J=3.8 Hz, 1H), 7.08 (d, J=8.1 Hz, 2H), 7.01 (d, J=8.0 Hz, 2H), 6.89 (q, J=5.0 Hz, 1H), 6.61 (d, J=3.7 Hz, 1H), 6.12 (s, 2H), 4.66 (s, 1H), 3.73 (q, J=7.0 Hz, 1H), 3.15 (s, 3H), 2.95 (d, J=6.2 Hz, 2H), 2.59 (d, J=5.0 Hz, 3H), 2.37 (d, J=7.1 Hz, 2H), 2.05 (d, J=12.9 Hz, 2H), 1.91-1.80 (m, 1H), 1.79-1.64 (m, 5H), 1.37-1.25 (m, 5H), 0.82 (d, J=6.6 Hz, 6H).

490

Example 120

(4-(Methyl ((trans)-4-((N-methylsulfamoyl) methyl) cyclohexyl) amino)-7H-pyrrolo [2, 3-d] pyrimidin-7-yl) methyl 2-((3-chloro-2-methylphenyl) amino) benzoate

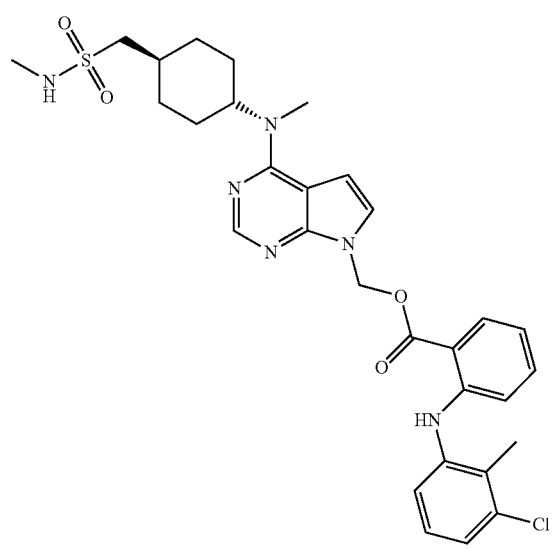

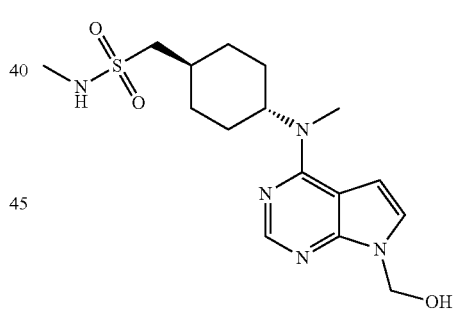

+

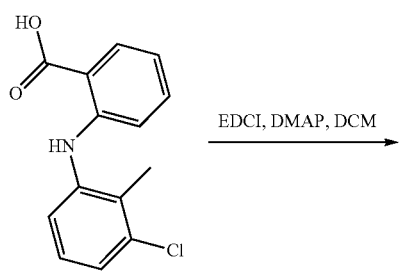

EDCI, DMAP, DCM →

491
-continued

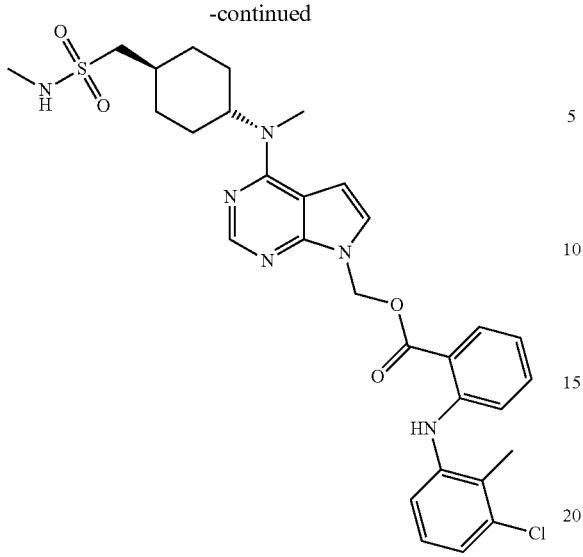

Synthesis of (4-(methyl ((trans)-4-((N-methylsulfa-moyl) methyl) cyclohexyl) amino)-7H-pyrrolo [2, 3-d]pyrimidin-7-yl) methyl 2-((3-chloro-2-methylphenyl) amino) benzoate 1-((Trans)-4-((7-(hydroxymethyl)-7H-pyrrolo [2, 3-d] pyrimidin-4-yl) (methyl) amino) cyclohexyl)-N-methyl methanesulfonamide (200 mg, 0.58 mmol), 4-dimethylamino pyridine (DMAP, 35 mg, 0.29 mmol), 2-((3-chloro-2-methylphenyl) amino) benzoic acid (tolfenamic acid, 230 mg, 0.88 mmol) and 1-(3-dimethylaminopropyl)-3-ethylcarbodiimide hydrochloride (EDCI, 168 mg, 0.88 mmol) were dissolved in a mixed solvent of dichloromethane (10 mL) and N, N-dimethylformamide (0.2 mL), and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=150:1 to 50:1) to give the title compound as a yellow solid, 0.137 g, 44.9% yield. MS (m/z): [M+H]$^+$ calcd for C$_{30}$H$_{35}$ClN$_6$O$_4$S, 611.21; found, 611.2. $^1$H NMR (400 MHz, DMSO-d$_6$) δ 9.18 (s, 1H), 8.26 (s, 1H), 7.81 (dd, J=8.2, 1.5 Hz, 1H), 7.51 (d, J=3.7 Hz, 1H), 7.43 (td, J=7.7, 7.1, 1.7 Hz, 1H), 7.40-7.20 (m, 3H), 6.95 (q, J=5.0 Hz, 1H), 6.84-6.73 (m, 3H), 6.47 (s, 2H), 4.74 (s, 1H), 3.24 (s, 3H), 3.01 (d, J=6.2 Hz, 2H), 2.65 (d, J=4.9 Hz, 3H), 2.29 (s, 3H), 2.11 (dd, J=10.1, 5.0 Hz, 2H), 2.00-1.86 (m, 1H), 1.74 (d, J=9.5 Hz, 4H), 1.36 (q, J=10.0, 7.2 Hz, 2H).

492

Example 121

4-((4-(1-(3-(Cyanomethyl)-1-(ethylsulfonyl) azetidin-3-yl)-1H-pyrazol-4-yl)-7H-pyrrolo [2, 3-d] pyrimidin-7-yl) methoxy)-2-methyl-N-(pyridin-2-yl)-2H-benzo [e] [1, 2] thiazine-3-carboxamide 1, 1-dioxide

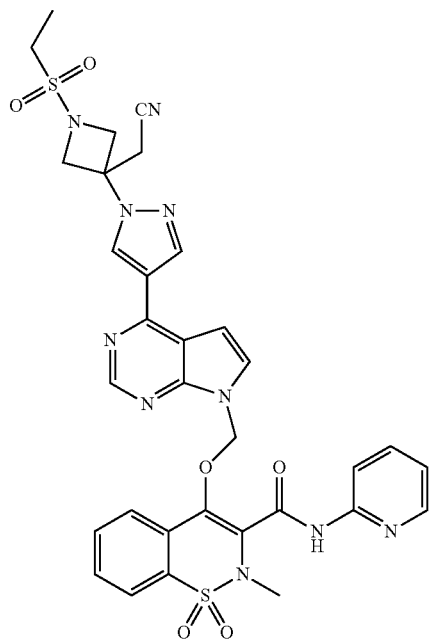 [SMILES: CCS(=O)(=O)N1CC(CC#N)(n2cc(-c3ncnc4c3ccn4COC3=C(C(=O)Nc4ccccn4)N(C)S(=O)(=O)c4ccccc43)cn2)C1]

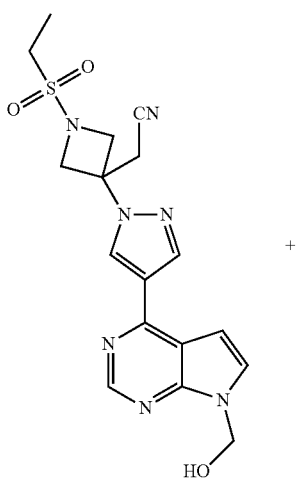 +

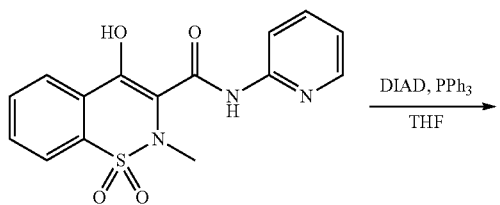

493
-continued

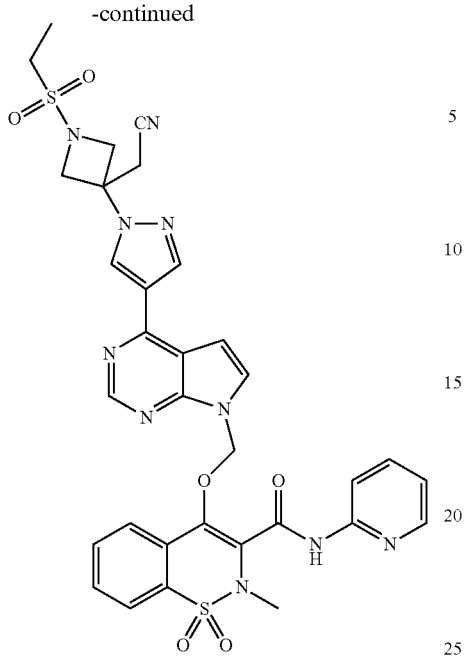

Synthesis of 4-((4-(1-(3-(Cyanomethyl)-1-(ethyl-sulfonyl) azetidin-3-yl)-1H-pyrazol-4-yl)-7H-pyrrolo [2, 3-d]pyrimidin-7-yl) methoxy)-2-methyl-N-(pyridin-2-yl)-2H-benzo [e] [1, 2] thiazine-3-carboxamide 1, 1-dioxide 4-Hydroxy-2-methyl-N-(pyridin-2-yl)-2H-benzo [e] [1, 2] thiazine-3-carboxamide 1, 1-dioxide (piroxicam, 103 mg, 0.312 mmol) and triphenylphosphine (PPh$_3$, 164 mg, 0.624 mmol) were added to tetrahydrofuran (3 mL) under nitrogen. After cooling to −10° C., diisopropyl azodicarboxylate (DIAD, 95 mg, 0.468 mmol) was added dropwise to the mixture with stirring. After stirring at −10° C. for 20 minutes, the mixture was allowed to warm to room temperature naturally, 2-(1-(Ethylsulfonyl)-3-(4-(7-(hydroxymethyl)-7H-)) pyrrolo [2, 3-d] pyrimidin-4-yl)-1H-pyrazol-1-yl) azetidin-3-yl) acetonitrile (150 mg, 0.374 mmol) was added and the stirring was continued. The reaction was monitored by TLC. After complete exhaust of the starting material (1 h), the solvent was evaporated under reduced pressure to give the crude product. The crude product was further separated by silica gel column chromatography (dichloromethane/acetonitrile=20:1 to 9:1) to give the title compound as a yellow solid, 0.012 g, 5.3% yield. MS (m/z): [M+H]$^+$ calcd for $C_{32}H_{30}N_{10}O_6S_2$, 715.18, found 715.2. $^1$H NMR (400 MHz, Chloroform-d) δ 8.79 (s, 1H), 8.48 (s, 1H), 8.24 (s, 1H), 8.12 (s, 1H), 7.94-7.85 (m, 2H), 7.76-7.68 (m, 2H), 7.51 (d, J=8.3 Hz, 1H), 7.38-7.32 (m, 1H), 7.24 (d, J=3.8 Hz, 1H), 6.92-6.86 (m, 1H), 6.60 (d, J=3.8 Hz, 1H), 6.05 (s, 2H), 4.56 (d, J=9.3 Hz, 2H), 4.18 (d, J=9.3 Hz, 2H), 3.35 (s, 2H), 3.08-2.96 (m, 5H), 1.36 (t, J=7.4 Hz, 3H).

494

Example 122

4-((4-(1-(3-(Cyanomethyl)-1-(ethylsulfonyl) azetidin-3-yl)-1H-pyrazol-4-yl)-7H-pyrrolo [2, 3-d]pyrimidin-7-yl) methoxy)-2-methyl-N-(5-methylthiazol-2-yl)-2H-benzo [e] [1, 2] thiazine-3-carboxamide 1, 1-dioxide

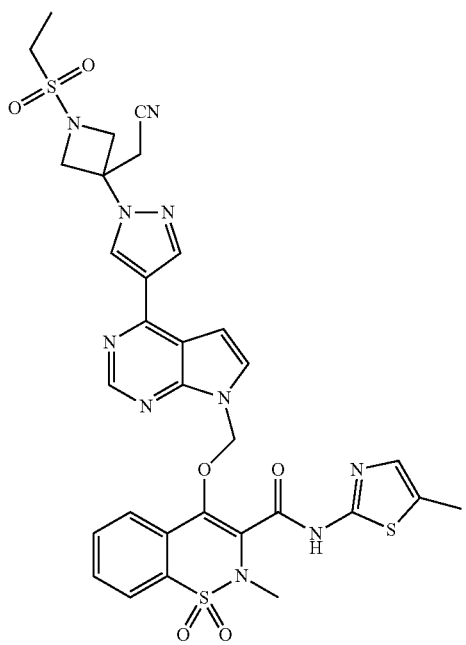 [SMILES: CCS(=O)(=O)N1CC(CC#N)(n2cc(-c3ncnc4c3ccn4COC3=C(C(=O)Nc4ncc(C)s4)N(C)S(=O)(=O)c4ccccc43)cn2)C1]

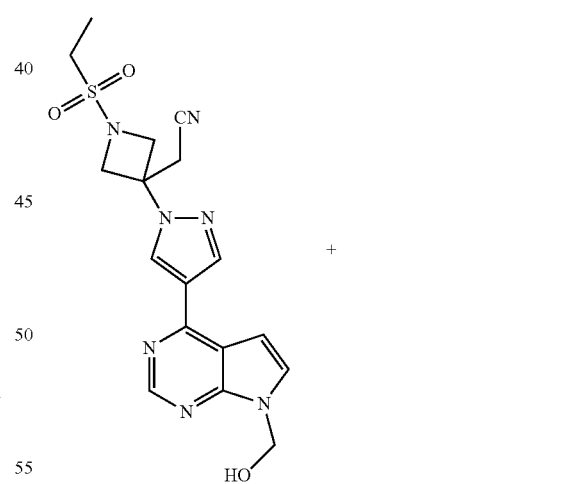

+

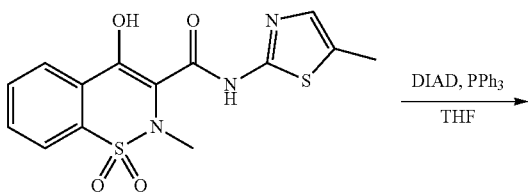

495
-continued

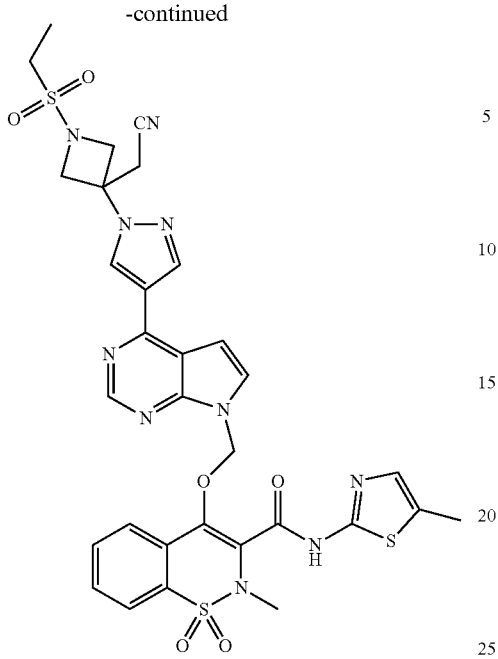

Synthesis of 4-((4-(1-(3-(Cyanomethyl)-1-(ethylsulfonyl) azetidin-3-yl)-1H-pyrazol-4-yl)-7H-pyrrolo [2, 3-d]pyrimidin-7-yl) methoxy)-2-methyl-N-(5-methylthiazol-2-yl)-2H-benzo [e] [1, 2] thiazine-3-carboxamide 1, 1-dioxide 4-Hydroxy-2-methyl-N-(5-methylthiazol-2-yl)-2H-benzo [e] [1, 2] thiazine-3-carboxamide 1, 1-dioxide (meloxicam, 147 mg, 0.42 mmol) and triphenylphosphine (PPh$_3$, 137 mg, 0.52 mmol) were added to tetrahydrofuran (2.8 mL) under nitrogen. Diisopropyl azodicarboxylate (DIAD, 92 mg, 0.45 mmol) was added dropwise to the mixture with stirring. After stirring at −10° C. for 20 minutes, the mixture was allowed to warm to room temperature naturally. 2-(1-(Ethylsulfonyl)-3-(4-(7-(hydroxymethyl)-7H-)) pyrrolo [2, 3-d] pyrimidin-4-yl)-1H-pyrazol-1-yl) azetidin-3-yl) acetonitrile (140 mg, 0.35 mmol) was added and the stirring was continued. The reaction was monitored by TLC. After complete exhaust of the starting material (1 h), the solvent was evaporated under reduced pressure to give the crude product. The crude product was further separated by silica gel column chromatography (dichloromethane/acetonitrile=20:1 to 9:1) to give the title compound as a yellow solid, 0.005 g, 1.9% yield. MS (m/z): [M+H]$^+$ calcd for C$_{31}$H$_{30}$N$_{10}$O$_6$S$_3$, 735.15, found 735.1. $^1$H NMR (400 MHz, DMSO-d$_6$) δ 14.61 (s, 1H), 8.94 (s, 1H), 8.77 (s, 1H), 8.49 (s, 1H), 8.02 (d, J=7.7 Hz, 1H), 7.88-7.78 (m, 3H), 7.73 (d, J=3.7 Hz, 1H), 7.28 (s, 1H), 7.15 (d, J=3.7 Hz, 1H), 5.62 (s, 2H), 4.60 (d, J=9.1 Hz, 2H), 4.24 (dd, J=9.1, 2.4 Hz, 2H), 3.69 (d, J=2.7 Hz, 2H), 3.27-3.20 (m, 2H), 2.85 (s, 3H), 2.32 (s, 3H), 1.27-1.20 (m, 3H).

496

Example 123

(3S, 4R)-3-ethyl-4-(3-((S)-2-(4-isobutylphenyl) propanoyl)-3H-imidazo [1, 2-a] pyrrolo [2, 3-e] pyrazin-8-yl)-N-(2, 2, 2-trifluoroethyl) pyrrolidine-1-carboxamide

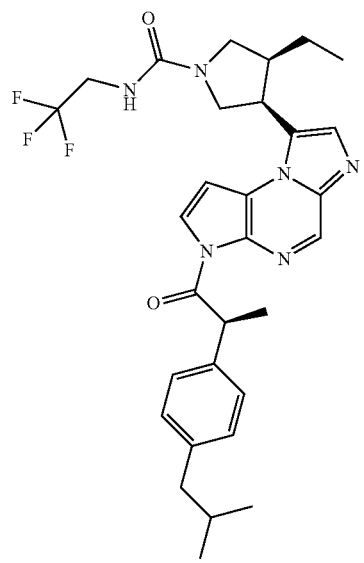 [SMILES: CC[C@@H]1CN(C(=O)NCC(F)(F)F)C[C@@H]1c1cnc2cnc3c(ccn3C(=O)[C@@H](C)c3ccc(CC(C)C)cc3)n12]

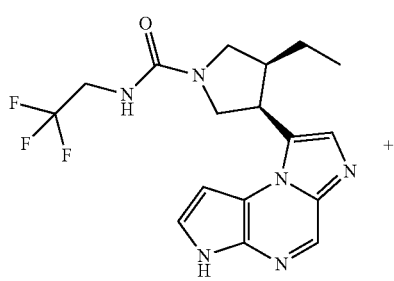
+

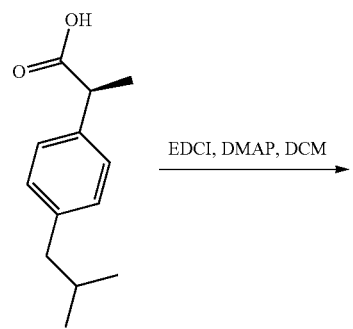

EDCI, DMAP, DCM

497

-continued

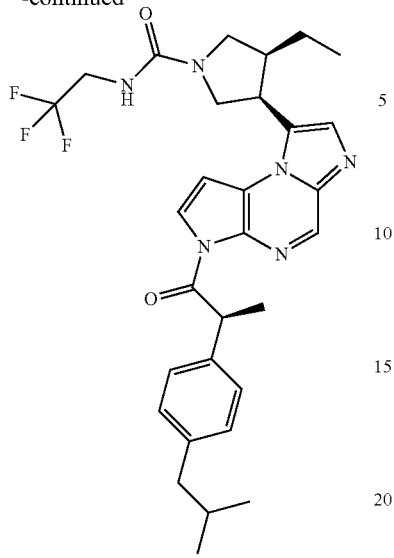

Synthesis of (3S, 4R)-3-ethyl-4-(3-((S)-2-(4-isobutylphenyl) propanoyl)-3H-imidazo [1, 2-a] pyrrolo [2, 3-e]pyrazin-8-yl)-N-(2, 2, 2-trifluoroethyl) pyrrolidine-1-carboxamide (3S, 4R)-3-ethyl-4-(3H-imidazo [1, 2-a] pyrrolo [2, 3-e] pyrazin-8-yl)-N-(2, 2, 2-trifluoroethyl) pyrrolidine-1-carboxamide (Upadacitinib, 338 mg, 1 mmol), 4-dimethyl-amino pyridine (DMAP, 122 mg, 1 mmol), (S)-(+)-2-(4-isobutylphenyl) propanoic acid ((S)-(+)-ibuprofen, 247 mg, 1.2 mmol) and 1-(3-dimethylaminopropyl)-3-ethylcarbodiimide hydrochloride (EDCI, 288 mg, 1.5 mmol) were dissolved in dichloromethane (10 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=50:1 to 25:1) to give the title compound as a white solid, 0.05 g, 17.6% yield. MS (m/z): [M+H]+ calcd for $C_{30}H_{35}F_3N_6O_2$, 569.28; found, 569.3. $^1$H NMR (400 MHz, DMSO-$d_6$) δ 8.88 (s, 1H), 8.04 (d, J=4.2 Hz, 1H), 7.63 (s, 1H), 7.37-7.29 (m, 2H), 7.19-7.04 (m, 3H), 6.97 (t, J=6.3 Hz, 1H), 5.99 (q, J=6.9 Hz, 1H), 4.34 (q, J=6.5 Hz, 1H), 3.91-3.71 (m, 4H), 3.71-3.61 (m, 1H), 3.25 (dd, J=10.2, 5.7 Hz, 1H), 2.38 (dd, J=23.9, 7.1 Hz, 3H), 1.83-1.72 (m, 1H), 1.59 (d, J=6.9 Hz, 3H), 1.07-0.93 (m, 1H), 0.92-0.80 (m, 7H), 0.60 (t, J=7.3 Hz, 3H).

498

Example 124

(3S, 4R)-3-ethyl-4-(3-(2-(4-isobutylphenyl) propanoyl)-3H-imidazo [1, 2-a] pyrrolo [2, 3-e] pyrazin-8-yl)-N-(2, 2, 2-trifluoroethyl) pyrrolidine-1-carboxamide

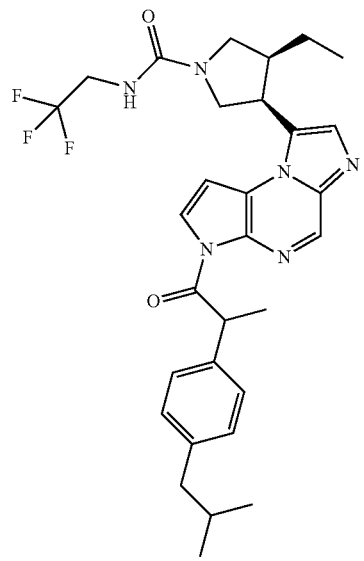 [SMILES: CC[C@@H]1CN(C(=O)NCC(F)(F)F)C[C@@H]1c1cnc2cnc3c(ccn3C(=O)C(C)c3ccc(CC(C)C)cc3)n12]

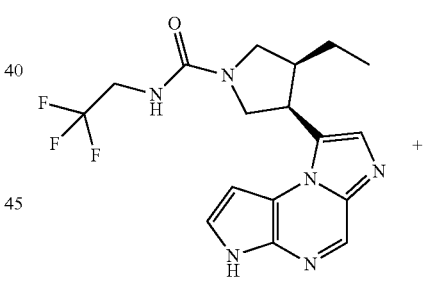

+

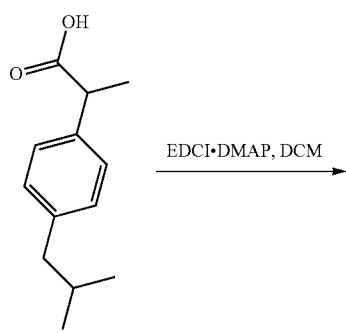

EDCI·DMAP, DCM

499

-continued

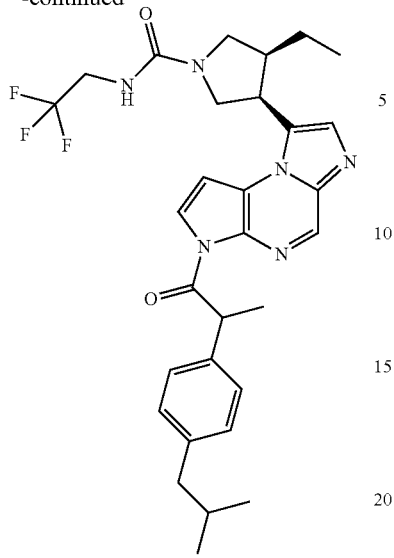

Synthesis of (3S, 4R)-3-ethyl-4-(3-(2-(4-isobutylphenyl) propanoyl)-3H-imidazo [1, 2-a] pyrrolo [2, 3-e]pyrazin-8-yl)-N-(2, 2, 2-trifluoroethyl) pyrrolidine-1-carboxamide (3S, 4R)-3-ethyl-4-(3H-imidazo [1, 2-a] pyrrolo [2, 3-e] pyrazin-8-yl)-N-(2, 2, 2-trifluoroethyl) pyrrolidine-1-carboxamide (upadacitinib, 100 mg, 0.25 mmol), 4-dimethylamino pyridine (DMAP, 3 mg, 0.025 mmol), 2-(4-isobutylphenyl) propanoic acid (ibuprofen, 54 mg, 0.264 mmol) and 1-(3-dimethylaminopropyl)-3-ethylcarbodiimide hydrochloride (EDCI, 73 mg, 0.377 mmol) were dissolved in dichloromethane (4 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=50:1 to 25:1) to give the title compound as a white solid, 0.097 g, 34.1% yield. MS (m/z): [M+H]+ calcd for $C_{30}H_{35}F_3N_6O_2$, 569.28; found, 569.3. $^1$H NMR (400 MHz, Chloroform-d) δ 8.79 (s, 1H), 7.93 (t, J=3.7 Hz, 1H), 7.52 (d, J=4.3 Hz, 1H), 7.36-7.26 (m, 2H), 7.06-6.94 (m, 3H), 6.78 (dd, J=4.2, 1.5 Hz, 1H), 5.98 (qd, J=6.9, 3.4 Hz, 1H), 4.70 (t, J=6.5 Hz, 1H), 4.08 (dt, J=12.2, 6.2 Hz, 1H), 3.98-3.61 (m, 4H), 3.29 (d, J=8.3 Hz, 1H), 2.62-2.46 (m, 1H), 2.31 (dd, J=9.0, 7.2 Hz, 2H), 1.82-1.67 (m, 1H), 1.61 (dd, J=6.9, 1.2 Hz, 3H), 1.27-1.09 (m, 1H), 0.87-0.73 (m, 7H), 0.66 (dt, J=10.3, 7.3 Hz, 3H).

500

Example 125

(3S, 4R)-3-ethyl-4-(3-(2-(2-fluoro-[1, 1'-biphenyl]-4-yl) propanoyl)-3H-imidazo [1, 2-a] pyrrolo [2, 3-e]pyrazin-8-yl)-N-(2, 2, 2-trifluoroethyl) pyrrolidine-1-carboxamide

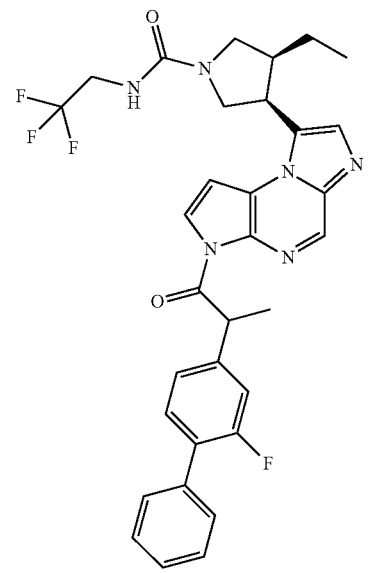 [SMILES: CC[C@@H]1CN(C(=O)NCC(F)(F)F)C[C@@H]1c1cnc2cnc3c(ccn3C(=O)C(C)c3ccc(-c4ccccc4)c(F)c3)n12]

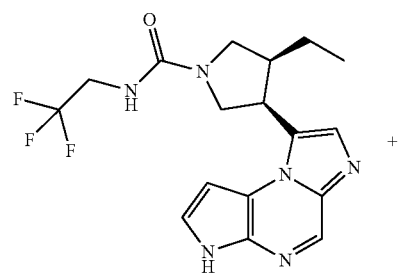

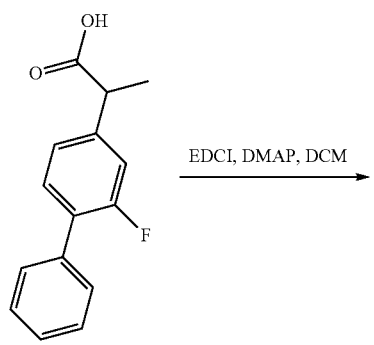

501

-continued

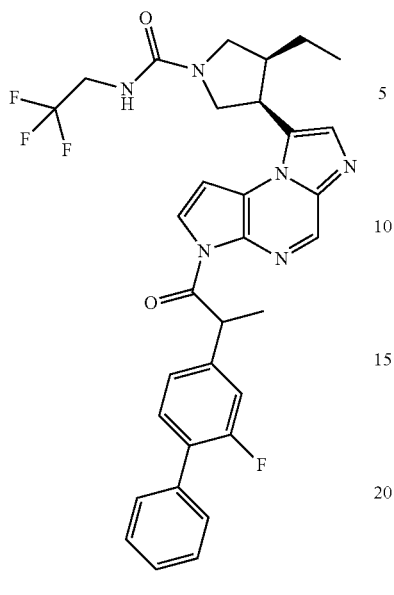

Synthesis of (3S, 4R)-3-ethyl-4-(3-(2-(2-fluoro-[1, 1'-biphenyl]-4-yl) propanoyl)-3H-imidazo [1, 2-a] pyrrolo [2, 3-e] pyrazin-8-yl)-N-(2, 2, 2-trifluoro-ethyl) pyrrolidine-1-carboxamide (3S, 4R)-3-ethyl-4-(3H-imidazo [1, 2-a] pyrrolo [2, 3-e] pyrazin-8-yl)-N-(2, 2, 2-trifluoroethyl) pyrrolidine-1-carboxamide (Upadacitinib, 100 mg, 0.25 mmol), 4-dimethyl-amino pyridine (DMAP, 3 mg, 0.025 mmol), 2-(2-fluoro-4-biphenyl) propanoic acid (flurbiprofen, 64 mg, 0.264 mmol) and 1-(3-dimethylaminopropyl)-3-ethylcarbodiimide hydrochloride (EDCI, 73 mg, 0.377 mmol) were dissolved in dichloromethane (4 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=50:1 to 25:1) to give the title compound as a white solid, 0.03 g, 9.9% yield. MS (m/z): [M+H]$^+$ calcd for $C_{32}H_{30}F_4N_6O_2$, 607.24; found, 607.3. $^1$H NMR (400 MHz, DMSO-d$_6$) δ 8.93 (d, J=2.0 Hz, 1H), 8.10 (dd, J=4.2, 2.5 Hz, 1H), 7.65 (d, J=6.9 Hz, 1H), 7.58-7.32 (m, 9H), 6.98 (t, J=5.8 Hz, 1H), 6.09 (p, J=6.9 Hz, 1H), 4.36 (s, 1H), 3.95-3.74 (m, 4H), 3.69 (dt, J=10.7, 6.1 Hz, 1H), 3.26 (dd, J=10.2, 5.3 Hz, 1H), 3.09 (td, J=7.3, 4.7 Hz, 1H), 1.66 (d, J=6.9 Hz, 3H), 1.12-0.96 (m, 1H), 0.93-0.75 (m, 1H), 0.63 (dt, J=10.2, 7.3 Hz, 3H).

502

Example 126

(3R, 4S)-3-(3-(2-(3-benzoylphenyl) propanoyl)-3H-imidazo [1, 2-a] pyrrolo [2, 3-e] pyrazin-8-yl)-4-ethyl-N-(2, 2, 2-trifluoroethyl) pyrrolidine-1-carboxamide

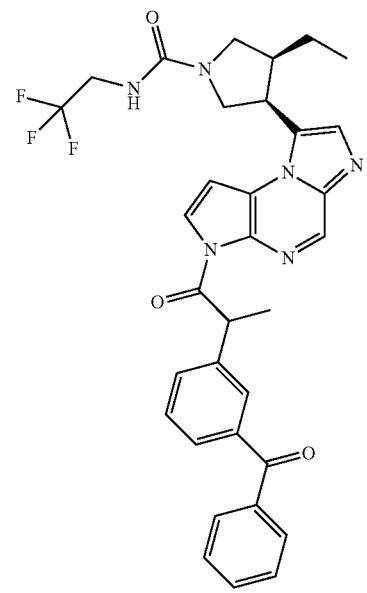 [SMILES: CC[C@@H]1CN(C(=O)NCC(F)(F)F)C[C@@H]1c1cnc2cnc3c(ccn3C(=O)C(C)c3cccc(C(=O)c4ccccc4)c3)n12]

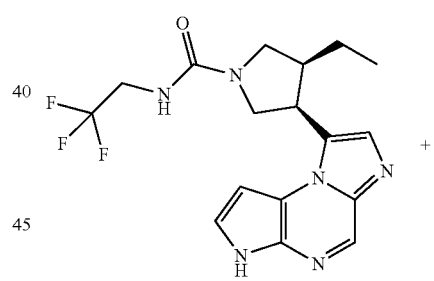
+

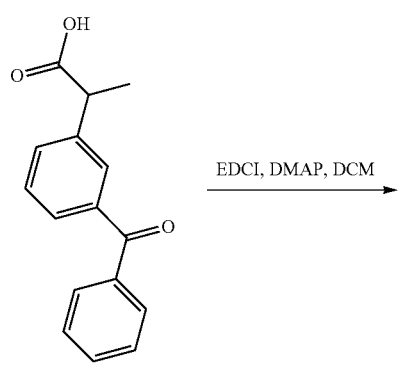

EDCI, DMAP, DCM →

-continued

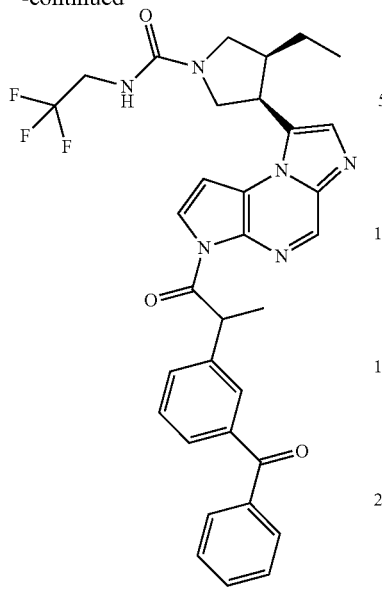

Synthesis of (3R, 4S)-3-(3-(2-(3-benzoylphenyl) propanoyl)-3H-imidazo [1, 2-a] pyrrolo [2, 3-e] pyrazin-8-yl)-4-ethyl-N-(2, 2, 2-trifluoroethyl) pyrrolidine-1-carboxamide (3S, 4R)-3-ethyl-4-(3H-imidazo [1, 2-a] pyrrolo [2, 3-e] pyrazin-8-yl)-N-(2, 2, 2-trifluoroethyl) pyrrolidine-1-carboxamide (Upadacitinib, 100 mg, 0.25 mmol), 4-dimethylamino pyridine (DMAP, 3 mg, 0.025 mmol), 2-(3-benzoylphenyl) propanoic acid (ketoprofen, 67 mg, 0.264 mmol) and 1-(3-dimethylaminopropyl)-3-ethylcarbodiimide hydrochloride (EDCI, 73 mg, 0.377 mmol) were dissolved in dichloromethane (4 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=50:1 to 25:1) to give the title compound as a white solid, 0.13 g, 84.4% yield. MS (m/z): [M+H]⁺ calcd for $C_{33}H_{31}F_3N_6O_3$, 617.24; found, 617.2. ¹H NMR (400 MHz, DMSO-d₆) δ 8.80 (d, J=5.8 Hz, 1H), 8.07 (dd, J=4.3, 1.8 Hz, 1H), 7.85-7.71 (m, 2H), 7.71-7.57 (m, 5H), 7.57-7.47 (m, 3H), 7.45 (d, J=4.3 Hz, 1H), 6.97 (t, J=6.3 Hz, 1H), 6.09 (p, J=7.0 Hz, 1H), 4.35 (q, J=6.5 Hz, 1H), 3.90-3.63 (m, 5H), 3.26 (dt, J=10.1, 5.1 Hz, 1H), 2.58-2.49 (m, 1H), 1.64 (dd, J=7.0, 2.1 Hz, 3H), 1.03 (dp, J=20.6, 7.0 Hz, 1H), 0.81 (s, 1H), 0.61 (dt, J=14.6, 7.3 Hz, 3H).

Example 127

(3R, 4S)-3-(3-(2-(2-((2, 6-dichlorophenyl) amino) phenyl) acetyl)-3H-imidazo [1, 2-a] pyrrolo [2, 3-e] pyrazin-8-yl)-4-ethyl-N-(2, 2, 2-trifluoroethyl) pyrrolidine-1-carboxamide

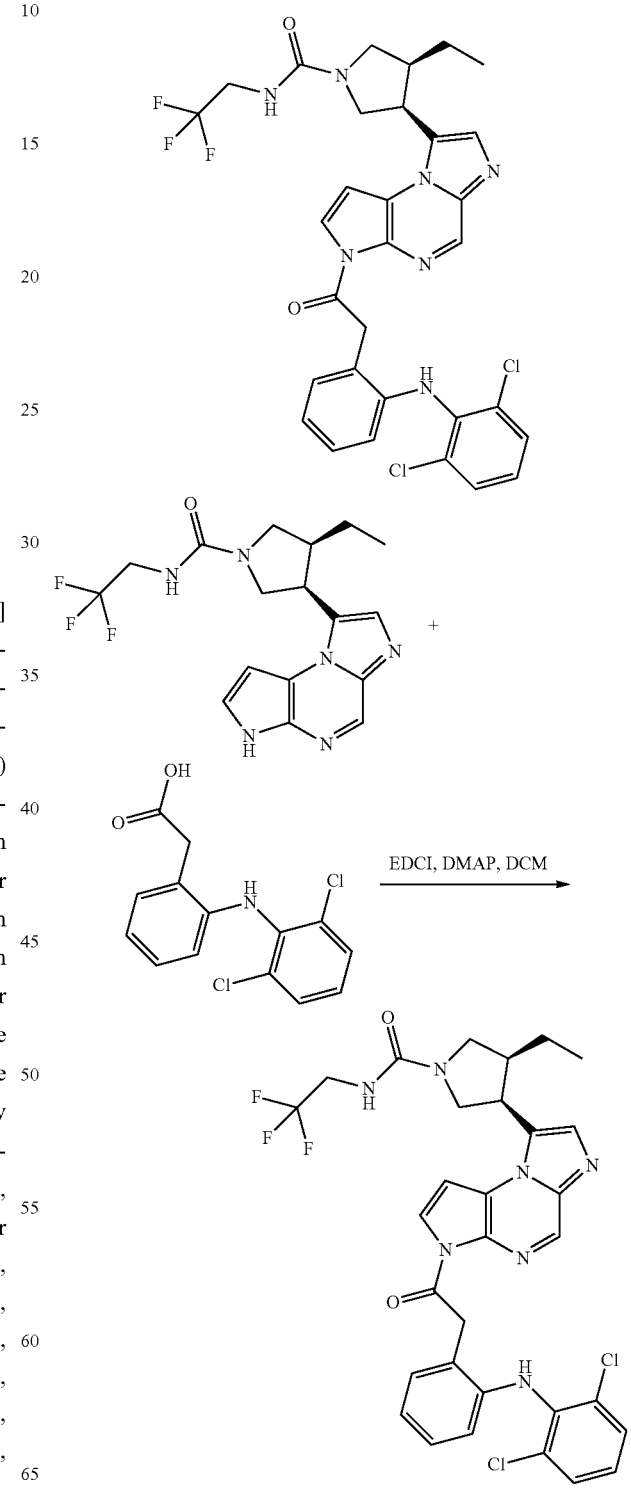

Synthesis of (3R, 4S)-3-(3-(2-(2-((2, 6-dichlorophenyl) amino) phenyl) acetyl)-3H-imidazo [1, 2-a] pyrrolo [2, 3-e] pyrazin-8-yl)-4-ethyl-N-(2, 2, 2-trifluoroethyl) pyrrolidine-1-carboxamide (3S, 4R)-3-ethyl-4-(3H-imidazo [1, 2-a] pyrrolo [2, 3-e] pyrazin-8-yl)-N-(2, 2, 2-trifluoroethyl) pyrrolidine-8-yl)-N-(2, 2, 2-trifluoroethyl) pyrrolidine-1-carboxamide (Upadacitinib, 100 mg, 0.25 mmol), 4-dimethylamino pyridine (DMAP, 3 mg, 0.025 mmol), 2-(2, 6-dichloroanilino) phenylacetic acid (diclofenac, 78 mg, 0.264 mmol) and 1-(3-dimethylaminopropyl)-3-ethylcarbodiimide hydrochloride (EDCI, 73 mg, 0.377 mmol) were dissolved in dichloromethane (4 mL) and stirred at room temperature for 24 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=50:1 to 25:1) to give the title compound as a white solid, 0.011 g, 6.6% yield. MS (m/z): [M+H]$^+$ calcd for $C_{31}H_{28}Cl_2F_3N_7O_2$, 658.16; found, 658.1. $^1$H NMR (400 MHz, Chloroform-d) δ 8.85 (s, 1H), 8.00 (d, J=4.1 Hz, 1H), 7.58 (s, 1H), 7.38 (dd, J=7.5, 1.5 Hz, 1H), 7.26 (d, J=8.1 Hz, 2H), 7.08 (td, J=7.8, 1.6 Hz, 1H), 6.93-6.85 (m, 4H), 6.52 (d, J=8.0 Hz, 1H), 5.11 (s, 2H), 4.69 (t, J=6.3 Hz, 1H), 4.15 (q, J=6.1 Hz, 1H), 3.89 (tt, J=15.6, 8.6 Hz, 4H), 3.72-3.66 (m, 1H), 3.30 (t, J=8.2 Hz, 1H), 2.57 (dd, J=11.0, 6.3 Hz, 1H), 1.27-1.14 (m, 1H), 0.84-0.77 (m, 1H), 0.69 (t, J=7.3 Hz, 3H).

Example 128

(3S, 4R)-3-ethyl-4-(3-(2-(3-phenoxyphenyl) propanoyl)-3H-imidazo [1, 2-a] pyrrolo [2, 3-e] pyrazin-8-yl)-N-(2, 2, 2-trifluoroethyl) pyrrolidine-1-carboxamide

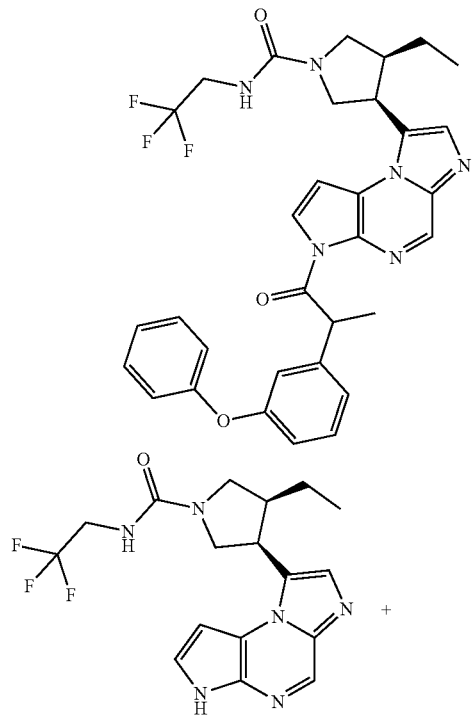

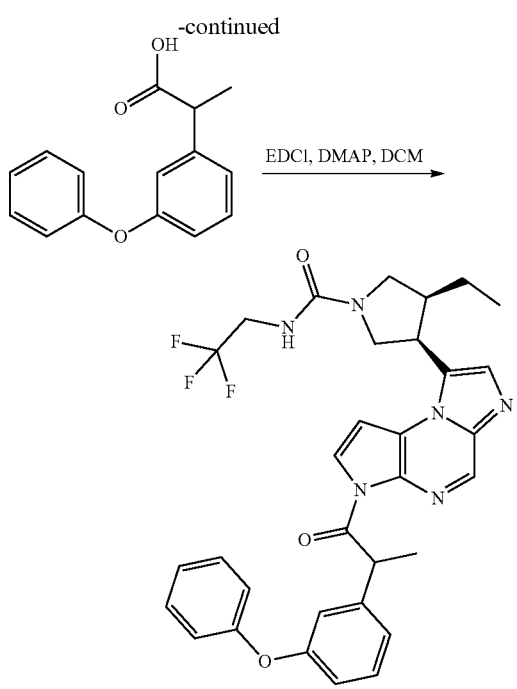

Synthesis of (3S, 4R)-3-ethyl-4-(3-(2-(3-phenoxyphenyl) propanoyl)-3H-imidazo [1, 2-a] pyrrolo [2, 3-e]pyrazin-8-yl)-N-(2, 2, 2-trifluoroethyl) pyrrolidine-1-carboxamide (3S, 4R)-3-ethyl-4-(3H-imidazo [1, 2-a] pyrrolo [2, 3-e] pyrazin-8-yl)-N-(2, 2, 2-trifluoroethyl) pyrrolidine-1-carboxamide (EDCI, 100 mg, 0.25 mmol), 4-dimethylamino pyridine (DMAP, 3 mg, 0.025 mmol), 2-(3-phenoxyphenyl) propanoic acid (fenoprofen, 64 mg, 0.264 mmol) and 1-(3-dimethylaminopropyl)-3-ethylcarbodiimide hydrochloride (Upadacitinib, 73 mg, 0.377 mmol) were dissolved in dichloromethane (4 mL) and stirred at room temperature for 20 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=50:1 to 25:1) to give the title compound as a white solid, 0.101 g, 66.8% yield. MS (m/z): [M+H]$^+$ calcd for $C_{32}H_{31}F_3N_6O_3$, 605.24; found, 605.2. $^1$H NMR (400 MHz, DMSO-d$_6$) δ 8.74 (d, J=6.8 Hz, 1H), 8.04 (t, J=3.9 Hz, 1H), 7.65 (d, J=6.7 Hz, 1H), 7.49-7.26 (m, 4H), 7.23-6.80 (m, 7H), 5.97 (p, J=6.8 Hz, 1H), 4.38-4.30 (m, 1H), 3.92-3.75 (m, 3H), 3.69 (dd, J=8.4, 6.0 Hz, 2H), 3.26 (dt, J=10.3, 6.7 Hz, 1H), 2.52-2.48 (m, 1H), 1.62-1.55 (m, 3H), 1.07-0.98 (m, 1H), 0.90-0.78 (m, 1H), 0.63 (td, J=7.4, 3.7 Hz, 3H).

Example 129

(3R, 4S)-3-(3-(2-((2, 3-dimethylphenyl) amino) benzoyl)-3H-imidazo [1, 2-a] pyrrolo [2, 3-e] pyrazin-8-yl)-4-ethyl-N-(2, 2, 2-trifluoroethyl) pyrrolidine-1-carboxamide

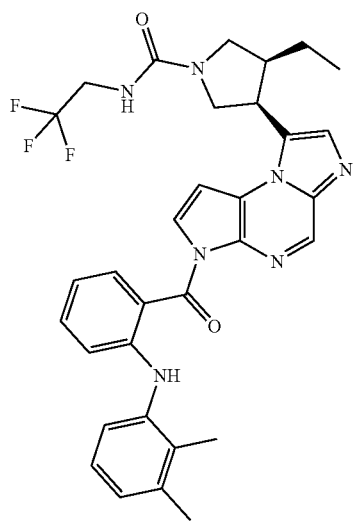

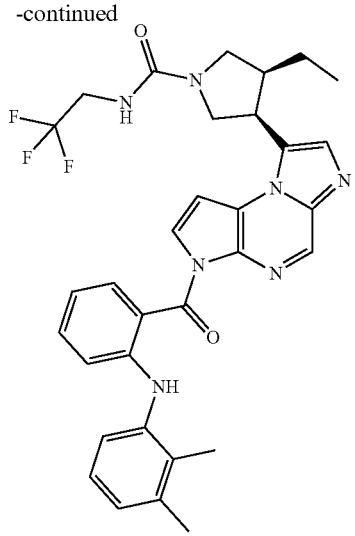

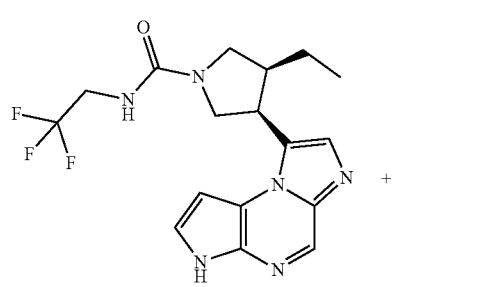

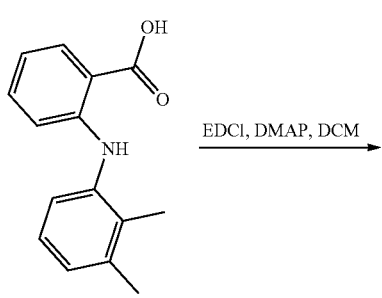

EDCI, DMAP, DCM

Synthesis of (3R, 4S)-3-(3-(2-((2, 3-dimethylphenyl) amino) benzoyl)-3H-imidazo [1, 2-a] pyrrolo [2, 3-e]pyrazin-8-yl)-4-ethyl-N-(2, 2, 2-trifluoroethyl) pyrrolidine-1-carboxamide (3S, 4R)-3-ethyl-4-(3H-imidazo [1, 2-a] pyrrolo [2, 3-e] pyrazin-8-yl)-N-(2, 2, 2-trifluoroethyl) pyrrolidine-1-carboxamide (Upadacitinib, 100 mg, 0.25 mmol), 4-dimethylamino pyridine (DMAP, 3 mg, 0.025 mmol), 2-((2, 3-dimethylphenyl) amino) benzoic acid (mefenamic acid, 64 mg, 0.264 mmol) and 1-(3-dimethylaminopropyl)-3-ethylcarbodiimide hydrochloride (EDCI, 73 mg, 0.377 mmol) were dissolved in dichloromethane (4 mL) and stirred at room temperature for 20 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=50:1 to 25:1) to give the title compound as a yellow solid, 0.012 g, 85.5% yield. MS (m/z): [M+H]$^+$ calcd for $C_{32}H_{32}F_3N_7O_2$, 604.264; found, 604.2. $^1$H NMR (400 MHz, DMSO-d$_6$) δ 8.65 (s, 1H), 8.57 (s, 1H), 7.77 (d, J=3.9 Hz, 1H), 7.61 (s, 1H), 7.48-7.36 (m, 3H), 7.09-6.95 (m, 4H), 6.88-6.74 (m, 2H), 4.38 (t, J=6.5 Hz, 1H), 3.92-3.70 (m, 5H), 3.31-3.25 (m, 1H), 2.63-2.52 (m, 1H), 2.23 (s, 3H), 2.00 (s, 3H), 1.19-1.04 (m, 1H), 0.90-0.82 (m, 1H), 0.68 (t, J=7.3 Hz, 3H).

Example 130

(3R, 4S)-3-(3-(2-((3-chloro-2-methylphenyl) amino) benzoyl)-3H-imidazo [1, 2-a] pyrrolo [2, 3-e] pyrazin-8-yl)-4-ethyl-N-(2, 2, 2-trifluoroethyl) pyrrolidine-1-carboxamide

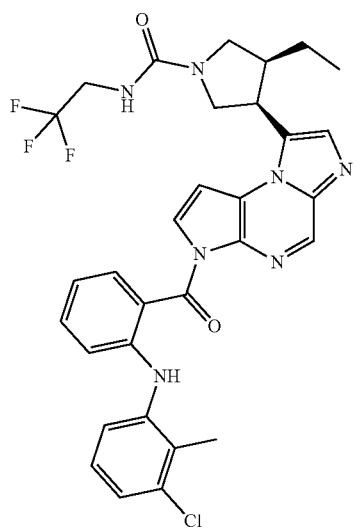

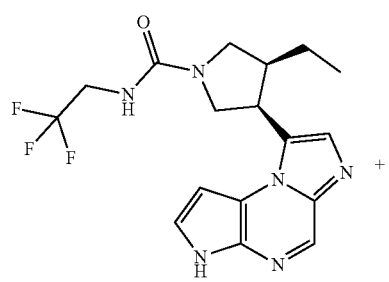

EDCI, DMAP, DCM

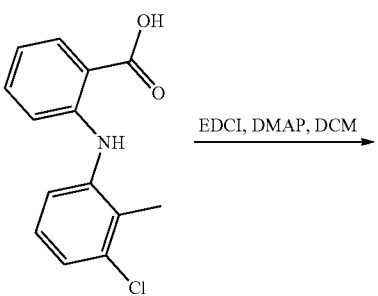

-continued

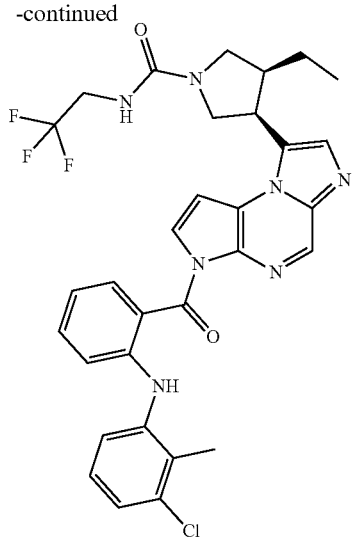

Synthesis of (3R, 4S)-3-(3-(2-((3-chloro-2-methylphenyl) amino) benzoyl)-3H-imidazo [1, 2-a] pyrrolo [2, 3-e]pyrazin-8-yl)-4-ethyl-N-(2, 2, 2-trifluoroethyl) pyrrolidine-1-carboxamide (3S, 4R)-3-ethyl-4-(3H-imidazo [1, 2-a] pyrrolo [2, 3-e] pyrazin-8-yl)-N-(2, 2, 2-trifluoroethyl) pyrrolidine-1-carboxamide (Upadacitinib, 100 mg, 0.25 mmol), 4-dimethylamino pyridine (DMAP, 3 mg, 0.025 mmol), 2-((3-chloro-2-methylphenyl) amino) benzoic acid (tolfenamic acid, 68 mg, 0.264 mmol) and 1-(3-dimethylaminopropyl)-3-ethylcarbodiimide hydrochloride (EDCI, 73 mg, 0.377 mmol) were dissolved in dichloromethane (4 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=50:1 to 25:1) to give the title compound as a yellow solid, 0.09 g, 29.7% yield. MS (m/z): [M+H]$^+$ calcd for $C_{31}H_{29}CF_3N_7O_2$, 624.20; found, 624.2. $^1$H NMR (400 MHz, DMSO-d$_6$) δ 8.61 (s, 1H), 8.25 (s, 1H), 7.67-7.58 (m, 1H), 7.56-7.44 (m, 2H), 7.36 (d, J=4.2 Hz, 1H), 7.22 (d, J=4.9 Hz, 1H), 7.10-6.85 (m, 5H), 6.81-6.75 (m, 1H), 4.36 (d, J=6.6 Hz, 1H), 3.96-3.65 (m, 5H), 3.34-3.21 (m, 1H), 2.62-2.53 (m, 1H), 1.96 (s, 3H), 1.16-1.01 (m, 1H), 0.93-0.76 (m, 1H), 0.72-0.66 (m, 3H).

Example 131

(3S, 4R)-3-ethyl-4-(3-((S)-2-(6-) methoxynaphthalen-2-yl) propanoyl)-3H-imidazo [1, 2-a] pyrrolo [2, 3-e]pyrazin-8-yl)-N-(2, 2, 2-trifluoroethyl) pyrrolidine-1-carboxamide

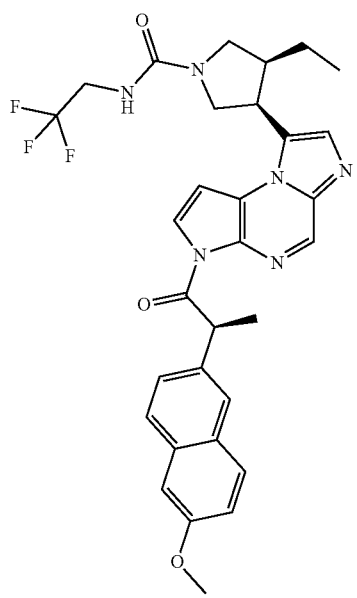

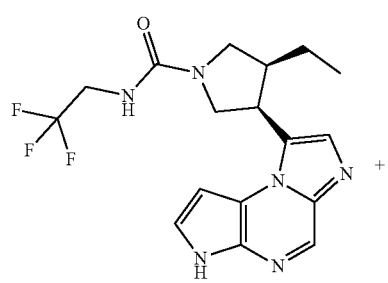

+

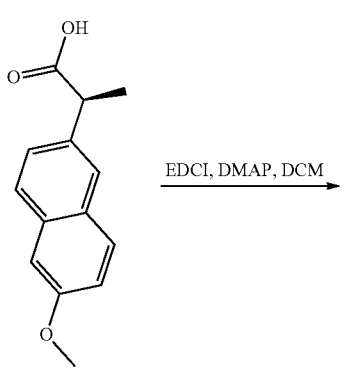

EDCI, DMAP, DCM →

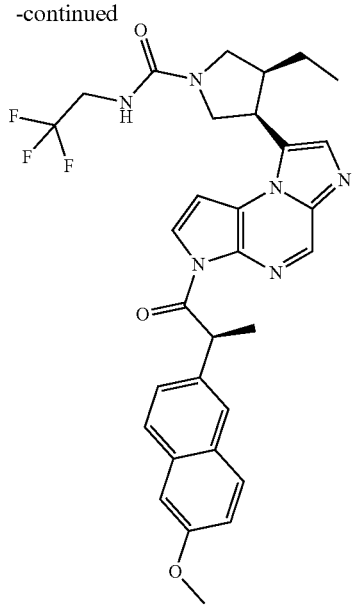

Synthesis of (3S, 4R)-3-ethyl-4-(3-((S)-2-(6-)methoxynaphthalen-2-yl) propanoyl)-3H-imidazo [1, 2-a]pyrrolo [2, 3-e] pyrazin-8-yl)-N-(2, 2, 2-trifluoroethyl) pyrrolidine-1-carboxamide (3S, 4R)-3-ethyl-4-(3H-imidazo [1, 2-a] pyrrolo [2, 3-e] pyrazin-8-yl)-N-(2, 2, 2-trifluoroethyl) pyrrolidine-1-carboxamide (Upadacitinib, 100 mg, 0.25 mmol), 4-dimethylamino pyridine (DMAP, 3 mg, 0.025 mmol), (S)-(+)-2-(6-methoxy-2-naphthyl) propanoic acid (Naproxen, 60 mg, 0.264 mmol) and 1-(3-dimethylaminopropyl)-3-ethylcarbodiimide hydrochloride (EDCI, 73 mg, 0.377 mmol) were dissolved in dichloromethane (4 mL) and stirred at room temperature for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=50:1 to 25:1) to give the title compound as a white solid, 0.028 g, 18.9% yield. MS (m/z): [M+H]$^+$ calcd for $C_{31}H_{31}F_3N_6O_3$, 593.24; found, 593.2. $^1$H NMR (400 MHz, DMSO-d$_6$) δ 8.92 (s, 1H), 8.08 (d, J=4.2 Hz, 1H), 7.91-7.68 (m, 3H), 7.63 (s, 1H), 7.57 (dd, J=8.5, 1.8 Hz, 1H), 7.43-7.39 (m, 1H), 7.25 (d, J=2.6 Hz, 1H), 7.12 (dd, J=9.0, 2.6 Hz, 1H), 6.96 (t, J=6.2 Hz, 1H), 6.13 (q, J=6.9 Hz, 1H), 4.33 (d, J=6.7 Hz, 1H), 3.97-3.72 (m, 7H), 3.65 (dd, J=10.3, 6.7 Hz, 1H), 3.24 (dd, J=10.3, 5.7 Hz, 1H), 2.53-2.42 (m, 1H), 1.68 (d, J=6.9 Hz, 3H), 1.03-0.92 (m, 1H), 0.89-0.71 (m, 1H), 0.57 (t, J=7.3 Hz, 3H).

Example 132

(3S, 4R)-3-ethyl-4-(3-(2-(4-((2-oxocyclopentyl) methyl) phenyl) propanoyl)-3H-imidazo [1, 2-a] pyrrolo [2, 3-e] pyrazin-8-yl)-N-(2, 2, 2-trifluoroethyl) pyrrolidine-1-carboxamide

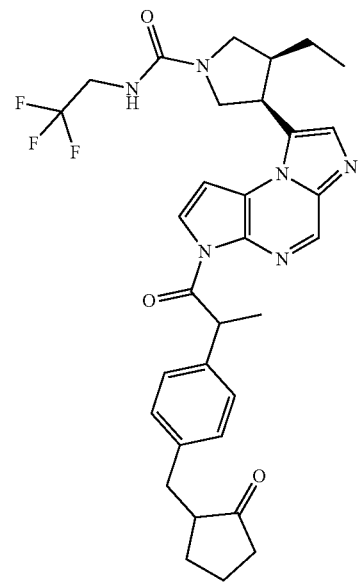

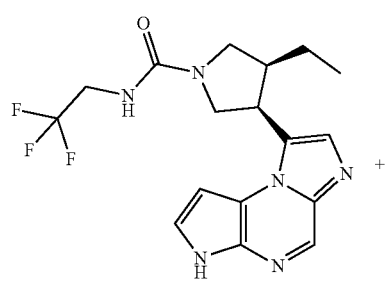

+

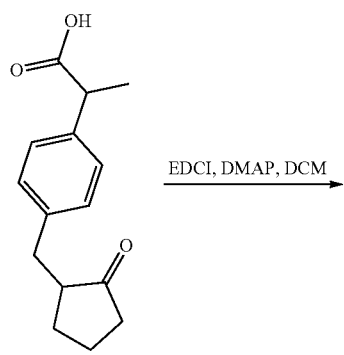

→ EDCI, DMAP, DCM

-continued

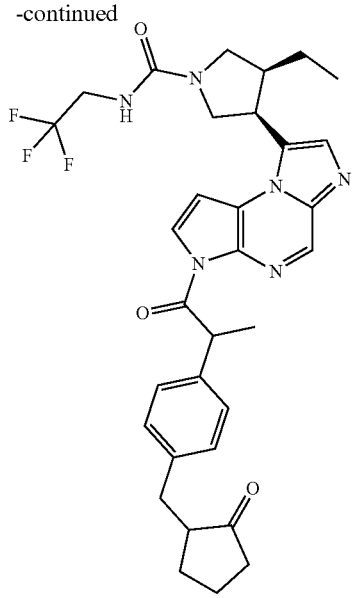

Synthesis of (3S, 4R)-3-ethyl-4-(3-(2-(4-((2-oxocyclopentyl) methyl) phenyl) propanoyl)-3H-imidazo [1, 2-a]pyrrolo [2, 3-e] pyrazin-8-yl)-N-(2, 2, 2-trifluoroethyl) pyrrolidine-1-carboxamide (3S, 4R)-3-ethyl-4-(3H-imidazo [1, 2-a] pyrrolo [2, 3-e] pyrazin-8-yl)-N-(2, 2, 2-trifluoroethyl) pyrrolidine-1-carboxamide (Upadacitinib, 100 mg, 0.25 mmol), 4-dimethylamino pyridine (DMAP, 3 mg, 0.025 mmol), 2-[4-(2-oxocyclopentan-1-ylmethyl) phenyl] propanoic acid (loxoprofen, 65 mg, 0.264 mmol) and 1-(3-dimethylaminopropyl)-3-ethylcarbodiimide hydrochloride (EDCI, 73 mg, 0.377 mmol) were dissolved in dichloromethane (4 mL) and stirred at room temperature for 20 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=50:1 to 25:1) to give the title compound as a white solid, 0.066 g, 43.4% yield. MS (m/z): [M+H]$^+$ calcd for $C_{32}H_{35}F_3N_6O_3$, 609.27, found 609.3. $^1$H NMR (400 MHz, DMSO-$d_6$) δ 8.88 (d, J=0.9 Hz, 1H), 8.04 (t, J=3.9 Hz, 1H), 7.63 (d, J=7.0 Hz, 1H), 7.44-7.30 (m, 3H), 7.22-7.07 (m, 2H), 6.97 (t, J=6.3 Hz, 1H), 6.00 (p, J=7.0 Hz, 1H), 4.34 (d, J=6.2 Hz, 1H), 3.96-3.72 (m, 4H), 3.67 (ddd, J=10.9, 6.7, 4.6 Hz, 1H), 3.25 (dt, J=10.3, 5.1 Hz, 1H), 2.93-2.84 (m, 1H), 2.56-2.51 (m, 1H), 2.43-2.26 (m, 2H), 2.20 (dd, J=18.6, 8.4 Hz, 1H), 2.12-1.96 (m, 1H), 1.91-1.73 (m, 2H), 1.72-1.50 (m, 4H), 1.48-1.36 (m, 1H), 1.02 (ddq, J=19.7, 12.8, 7.1, 6.6 Hz, 1H), 0.80 (ddt, J=16.9, 13.8, 6.5 Hz, 1H), 0.62 (dt, J=10.3, 7.3 Hz, 3H).

Example 133

(3R, 4S)-3-(3-(2-(1-(4-Chlorobenzoyl)-5-methoxy-2-methyl-1H-indol-3-yl) acetyl)-3H-imidazo [1, 2-a]pyrrolo [2, 3-e] pyrazin-8-yl)-4-ethyl-N-(2, 2, 2-trifluoroethyl) pyrrolidine-1-carboxamide

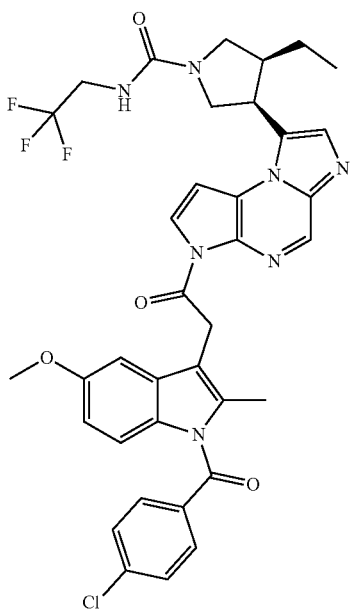

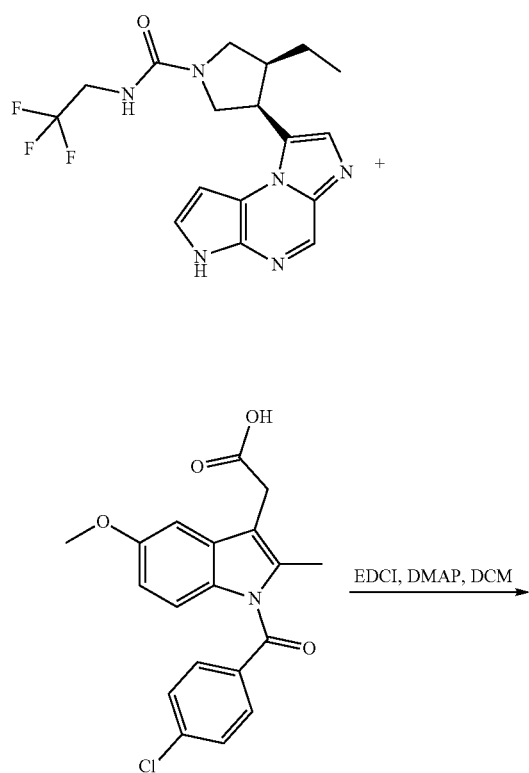

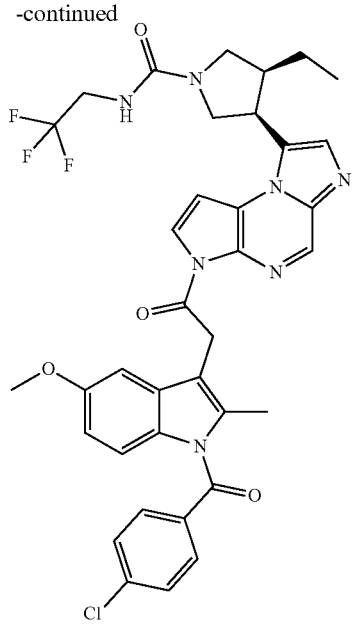

Synthesis of (3R, 4S)-3-(3-(2-(1-(4-Chlorobenzoyl)-5-methoxy-2-methyl-1H-indol-3-yl) acetyl)-3H-imidazo [1, 2-a] pyrrolo [2, 3-e] pyrazin-8-yl)-4-ethyl-N-(2, 2, 2-trifluoroethyl) pyrrolidine-1-carboxamide (3S, 4R)-3-ethyl-4-(3H-imidazo [1, 2-a] pyrrolo [2, 3-e] pyrazin-8-yl)-N-(2, 2, 2-trifluoroethyl) pyrrolidine-1-carboxamide (Upadacitinib, 100 mg, 0.25 mmol), 4-dimethylamino pyridine (DMAP, 3 mg, 0.025 mmol), 1-(4-chlorobenzoyl)-5-methoxy-2-methyl-1H-indole-3-acetic acid (indomethacin, 95 mg, 0.264 mmol) and 1-(3-dimethylaminopropyl)-3-ethylcarbodiimide hydrochloride (EDCI, 73 mg, 0.377 mmol) were dissolved in dichloromethane (4 mL) and stirred at room temperature for 20 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=50:1 to 25:1) to give the title compound as a light yellow solid, 0.139 g, 77.3% yield. MS (m/z): [M+H]+ calcd for $C_{36}H_{33}C_1F_3N_7O_4$, 720.22, found 720.1. $^1$H NMR (400 MHz, DMSO-$d_6$) δ 8.95 (s, 1H), 8.10 (d, J=4.1 Hz, 1H), 7.75-7.63 (m, 5H), 7.50 (d, J=4.2 Hz, 1H), 7.18 (d, J=2.6 Hz, 1H), 7.00 (dd, J=7.7, 5.0 Hz, 2H), 6.73 (dd, J=9.0, 2.5 Hz, 1H), 5.06 (d, J=4.3 Hz, 2H), 4.41 (q, J=6.4 Hz, 1H), 3.93-3.83 (m, 3H), 3.83-3.67 (m, 5H), 3.27 (dd, J=10.2, 5.9 Hz, 1H), 2.58 (s, 1H), 2.27 (s, 3H), 1.07 (ddd, J=12.8, 7.4, 4.9 Hz, 1H), 0.82 (ddd, J=13.3, 10.0, 7.0 Hz, 1H), 0.65 (t, J=7.3 Hz, 3H).

Example 134

(3R, 4S)-3-(3-(2-(4-acetamidophenyl) acetyl)-3H-imidazo [1, 2-a] pyrrolo [2, 3-e] pyrazin-8-yl)-4-ethyl-N-(2, 2, 2-trifluoroethyl) pyrrolidine-1-carboxamide

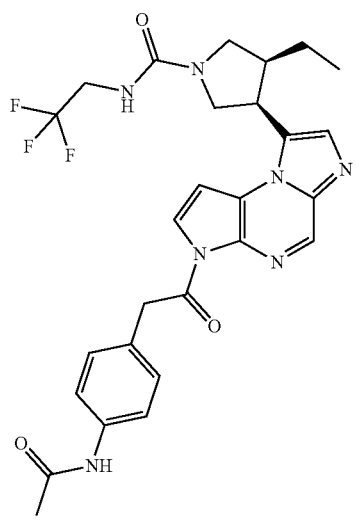

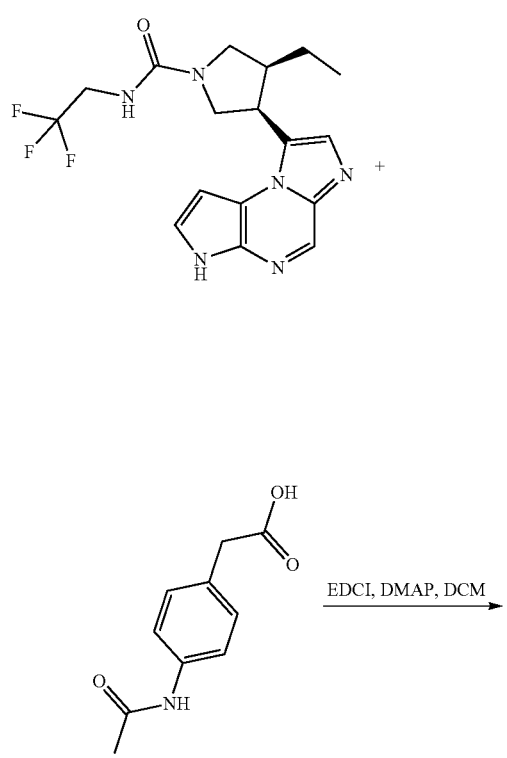

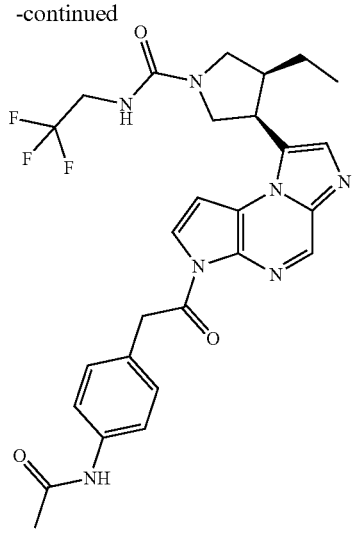

Synthesis of (3R, 4S)-3-(3-(2-(4-acetamidophenyl) acetyl)-3H-imidazo [1, 2-a] pyrrolo [2, 3-e] pyrazin-8-yl)-4-ethyl-N-(2, 2, 2-trifluoroethyl) pyrrolidine-1-carboxamide (3S, 4R)-3-ethyl-4-(3H-imidazo [1, 2-a] pyrrolo [2, 3-e] pyrazin-8-yl)-N-(2, 2, 2-trifluoroethyl) pyrrolidine-1-carboxamide (Upadacitinib, 100 mg, 0.25 mmol), 4-dimethylamino pyridine (DMAP, 3 mg, 0.025 mmol), 2-(4-acetamidophenyl) acetic acid (actarit, 51 mg, 0.264 mmol) and 1-(3-dimethylaminopropyl)-3-ethylcarbodiimide hydrochloride (EDCI, 73 mg, 0.377 mmol) were dissolved in dichloromethane (4 mL) and stirred at room temperature for 20 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=50:1 to 25:1) to give the title compound as a white solid, 0.082 g, 59% yield. MS (m/z): [M+H]$^+$ calcd for $C_{27}H_{28}F_3N_7O_3$, 556.22, found 556.1. $^1$H NMR (400 MHz, DMSO-$d_6$) δ 9.93 (s, 1H), 8.89 (s, 1H), 8.06 (d, J=4.2 Hz, 1H), 7.65 (s, 1H), 7.57-7.48 (m, 2H), 7.46 (d, J=4.1 Hz, 1H), 7.35-7.27 (m, 2H), 6.99 (t, J=6.4 Hz, 1H), 4.88 (d, J=3.6 Hz, 2H), 4.39 (q, J=6.7 Hz, 1H), 3.92-3.74 (m, 4H), 3.70 (dd, J=10.2, 6.7 Hz, 1H), 3.26 (dd, J=10.2, 5.9 Hz, 1H), 2.56 (s, 1H), 2.03 (s, 3H), 1.06 (ddd, J=12.9, 7.7, 5.2 Hz, 1H), 0.89-0.73 (m, 1H), 0.64 (t, J=7.3 Hz, 3H).

Example 135

(3R, 4S)-3-(3-(2-(1, 8-diethyl-1, 3, 4, 9-tetrahydropyrano [3, 4-b] indol-1-yl) acetyl)-3H-imidazo [1, 2-a]pyrrolo [2, 3-e] pyrazin-8-yl)-4-ethyl-N-(2, 2, 2-trifluoroethyl) pyrrolidine-1-carboxamide

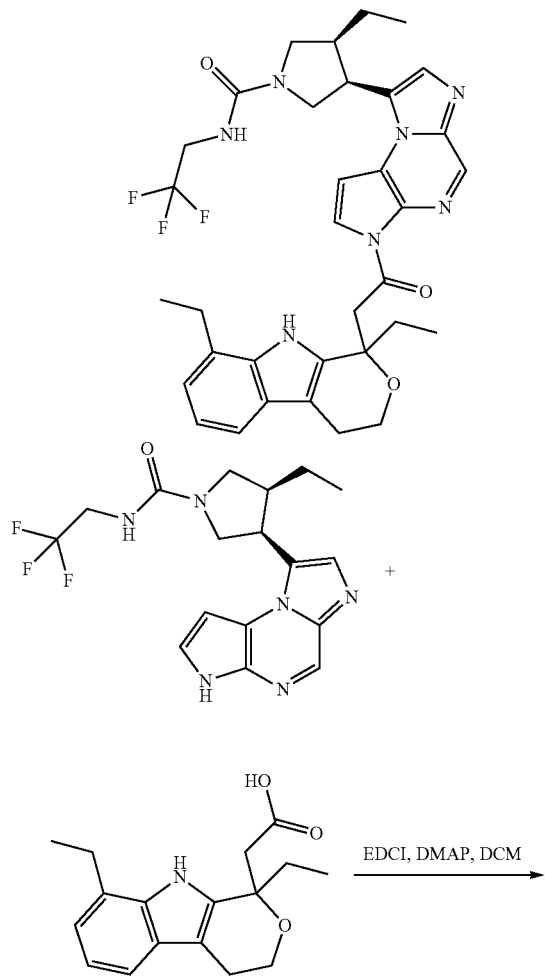

Synthesis of (3R, 4S)-3-(3-(2-(1, 8-diethyl-1, 3, 4, 9-tetrahydropyrano [3, 4-b] indol-1-yl) acetyl)-3H-imidazo [1, 2-a] pyrrolo [2, 3-e] pyrazin-8-yl)-4-ethyl-N-(2, 2, 2-trifluoroethyl) pyrrolidine-1-carboxamide (3S, 4R)-3-ethyl-4-(3H-imidazo [1, 2-a] pyrrolo [2, 3-e] pyrazin-8-yl)-N-(2, 2, 2-trifluoroethyl) pyrrolidine-1-carboxamide (Upadacitinib, 100 mg, 0.25 mmol), 4-dimethylamino pyridine (DMAP, 3 mg, 0.025 mmol), 1, 8-diethyl-1, 3, 4, 9-tetrahydropyran [3, 4-b] indole-1-acetic acid (etodolac, 76 mg, 0.264 mmol) and 1-(3-dimethylaminopropyl)-3-ethylcarbodiimide hydrochloride (EDCI, 73 mg, 0.377 mmol) were dissolved in dichloromethane (4 mL) and stirred at room temperature for 20 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=50:1 to 25:1) to give the title compound as a white solid, 0.108 g, 66.5% yield. MS (m/z): [M+H]$^+$ calcd for $C_{34}H_{38}F_3N_7O_3$, 650.30, found 650.3. $^1$H NMR (400 MHz, DMSO-d$_6$) δ 10.55 (d, J=10.5 Hz, 1H), 8.79 (s, 1H), 8.01 (t, J=4.1 Hz, 1H), 7.62 (d, J=2.5 Hz, 1H), 7.40 (d, J=4.2 Hz, 1H), 7.22 (td, J=7.5, 1.6 Hz, 1H), 6.99 (t, J=6.3 Hz, 1H), 6.89 (td, J=7.4, 5.1 Hz, 2H), 4.61 (dd, J=47.7, 14.4 Hz, 1H), 4.36 (d, J=6.7 Hz, 1H), 4.13 (dd, J=41.9, 14.4 Hz, 1H), 3.95-3.74 (m, 6H), 3.69 (dd, J=10.3, 6.9 Hz, 1H), 3.26 (dd, J=10.3, 5.8 Hz, 1H), 2.90-2.81 (m, 2H), 2.60 (q, J=4.7 Hz, 2H), 2.24-2.14 (m, 2H), 1.25 (td, J=7.4, 2.7 Hz, 4H), 1.10-1.00 (m, 1H), 0.82 (dtd, J=13.7, 7.0, 3.4 Hz, 1H), 0.71 (q, J=7.1 Hz, 3H), 0.64 (td, J=7.3, 2.8 Hz, 3H).

Example 136

2-(8-((3R, 4S)-4-ethyl-1-((2, 2, 2-trifluoroethyl) carbamoyl) pyrrolidin-3-yl)-3H-imidazo [1, 2-a] pyrrolo [2, 3-e] pyrazine-3-carbonyl) phenylacetate

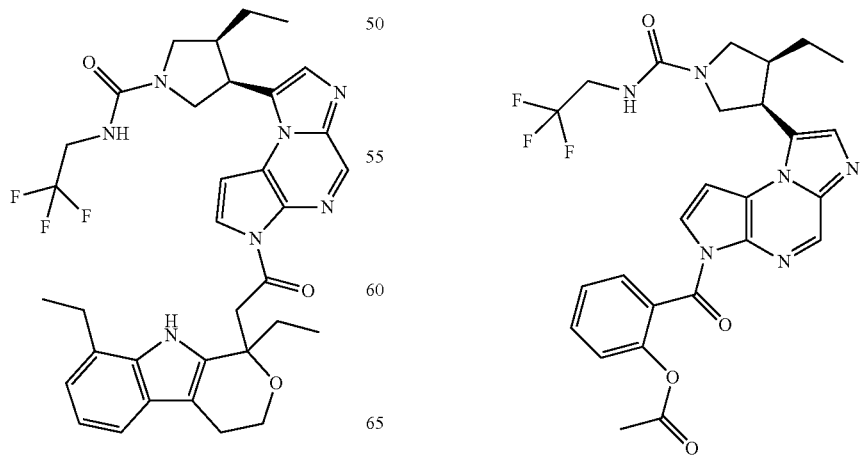

521

-continued

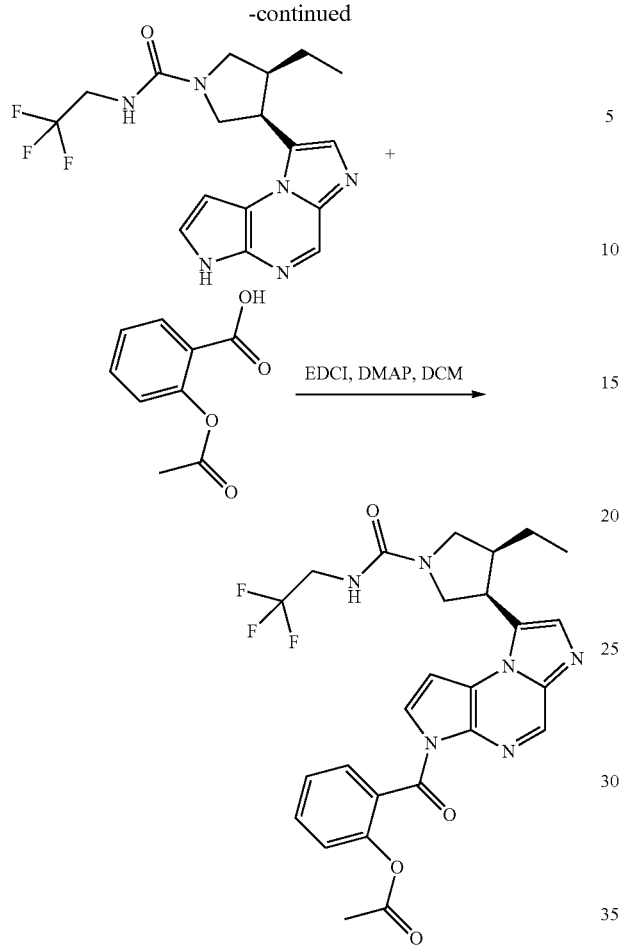

Synthesis of 2-(8-((3R, 4S)-4-ethyl-1-((2, 2, 2-trifluoroethyl) carbamoyl) pyrrolidin-3-yl)-3H-imidazo [1, 2-a]pyrrolo [2, 3-e] pyrazine-3-carbonyl) phenylacetate (3S, 4R)-3-ethyl-4-(3H-imidazo [1, 2-a] pyrrolo [2, 3-e] pyrazin-8-yl)-N-(2, 2, 2-trifluoroethyl) pyrrolidine-1-carboxamide (EDCI, 100 mg, 0.25 mmol), 4-dimethylamino pyridine (DMAP, 3 mg, 0.025 mmol), 2-acetoxy benzoic acid (aspirin, 47.5 mg, 0.264 mmol) and 1-(3-dimethylaminopropyl)-3-ethylcarbodiimide hydrochloride (Upadacitinib, 73 mg, 0.377 mmol) was dissolved in dichloromethane (4 mL) and stirred at room temperature for 20 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=50:1 to 25:1) to give the title compound as a white solid, 0.025 g, 18.4% yield. MS (m/z): [M+H]$^+$ calcd for $C_{26}H_{25}F_3N_6O_4$, 543.19, found 543.1. $^1$H NMR (400 MHz, DMSO-$d_6$) δ 8.56 (s, 1H), 7.85 (d, J=4.2 Hz, 1H), 7.78-7.71 (m, 2H), 7.60 (s, 1H), 7.51-7.44 (m, 2H), 7.34 (dd, J=8.1, 1.0 Hz, 1H), 6.99 (t, J=6.3 Hz, 1H), 4.43-4.35 (m, 1H), 3.92-3.75 (m, 4H), 3.70 (dd, J=10.2, 6.9 Hz, 1H), 3.27-3.20 (m, 1H), 2.62-2.49 (m, 1H), 1.89 (s, 3H), 1.08 (ddd, J=12.9, 7.4, 4.9 Hz, 1H), 0.83-0.75 (m, 1H), 0.64 (t, J=7.3 Hz, 3H).

522

Example 137

Tert-butyl ((S)-2-(8-((3R, 4S)-4-ethyl-1-((2, 2, 2-trifluoroethyl) carbamoyl) pyrrolidin-3-yl)-3H-imidazo [1, 2-a] pyrrolo [2, 3-e] pyrazin-3-yl)-2-oxo-1-phenethyl) carbamate

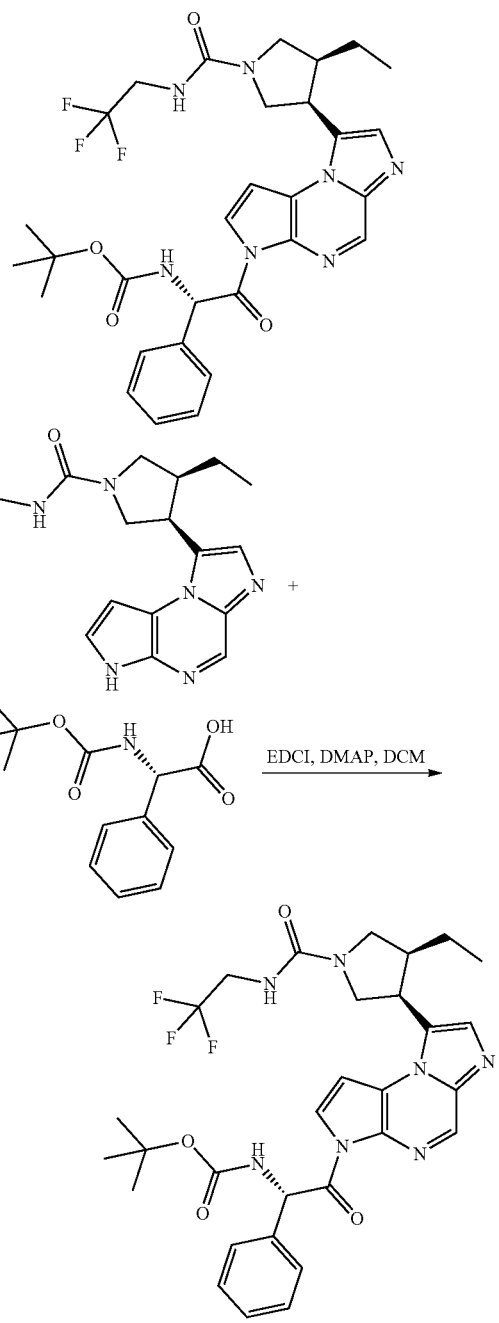

Synthesis of tert-butyl ((S)-2-(8-((3R, 4S)-4-ethyl-1-((2, 2, 2-trifluoroethyl) carbamoyl) pyrrolidin-3-yl)-3H-imidazo [1, 2-a] pyrrolo [2, 3-e] pyrazin-3-yl)-2-oxo-1-phenethyl) carbamate (3S, 4R)-3-ethyl-4-(3H-imidazo [1, 2-a] pyrrolo [2, 3-e] pyrazin-8-yl)-N-(2, 2, 2-trifluoroethyl) pyrrolidine-1-carboxamide (Upadacitinib, 100 mg, 0.25 mmol), 4-dimethyl-amino pyridine (DMAP, 3 mg, 0.025 mmol), N-Boc-L-phenylglycine (66 mg, 0.264 mmol) and 1-(3-dimethylaminopropyl)-3-ethylcarbodiimide hydrochloride (EDCI, 73 mg, 0.377 mmol) were dissolved in dichloromethane (4 mL) and stirred at room temperature for 20 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=50:1 to 25:1) to give the title compound as a white solid, 0.088 g, 57.4% yield. MS (m/z): [M+H]$^+$ calcd for $C_{30}H_{34}F_3N_7O_4$, 614.26, found 614.2. $^1$H NMR (400 MHz, DMSO-$d_6$) δ 8.89 (s, 1H), 8.07 (t, J=4.2 Hz, 1H), 7.99 (dd, J=7.5, 4.5 Hz, 1H), 7.67-7.24 (m, 8H), 6.97 (td, J=6.3, 2.3 Hz, 1H), 4.37-4.29 (m, 1H), 3.91-3.72 (m, 4H), 3.67 (dt, J=10.3, 6.4 Hz, 1H), 3.28-3.18 (m, 1H), 2.52-2.43 (m, 1H), 1.40 (d, J=2.5 Hz, 9H), 1.05-0.92 (m, 1H), 0.88-0.68 (m, 1H), 0.62 (dt, J=14.5, 7.3 Hz, 3H).

Example 138

(3S, 4R)-3-ethyl-4-(3-(2-(4-(1-) oxoisoindolin-2-yl) phenyl) butanoyl)-3H-imidazo [1, 2-a] pyrrolo [2, 3-e]pyrazin-8-yl)-N-(2, 2, 2-trifluoroethyl) pyrrolidine-1-carboxamide

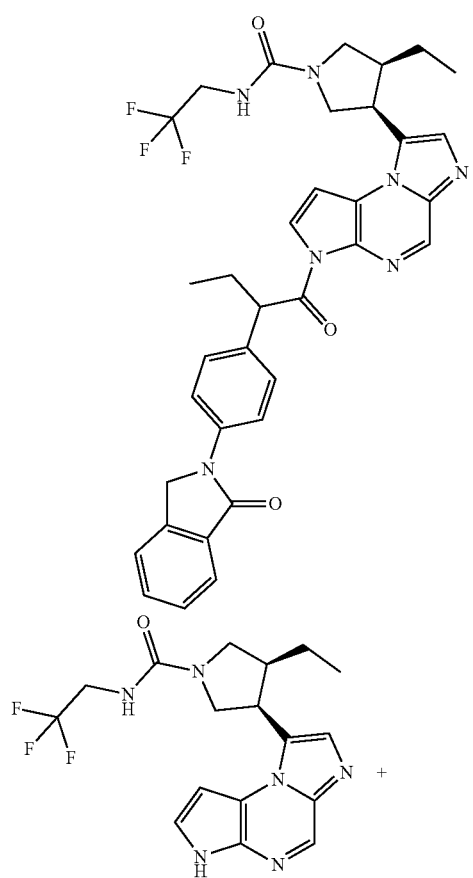

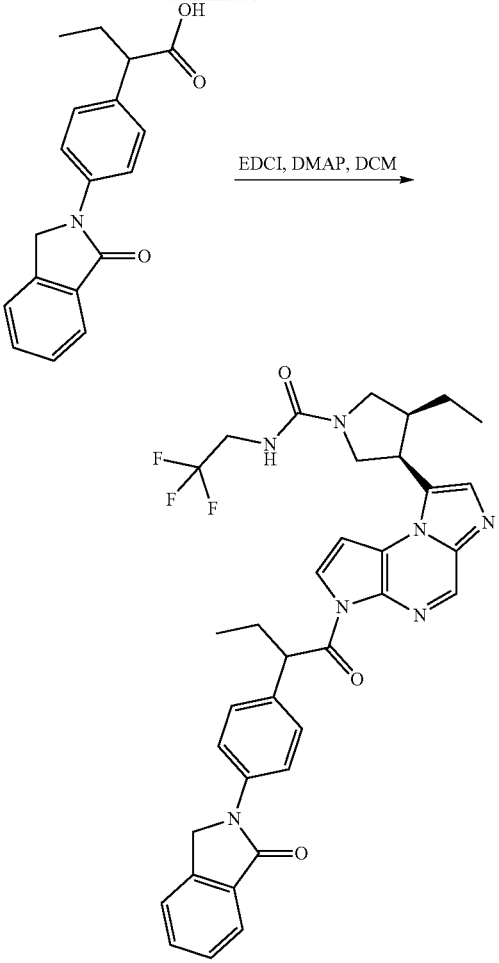

Synthesis of (3S, 4R)-3-ethyl-4-(3-(2-(4-(1-) oxoisoindolin-2-yl) phenyl) butanoyl)-3H-imidazo [1, 2-a]pyrrolo [2, 3-e] pyrazin-8-yl)-N-(2, 2, 2-trifluoroethyl) pyrrolidine-1-carboxamide (3S, 4R)-3-ethyl-4-(3H-imidazo [1, 2-a] pyrrolo [2, 3-e] pyrazin-8-yl)-N-(2, 2, 2-trifluoroethyl) pyrrolidine-1-carboxamide (Upadacitinib, 100 mg, 0.25 mmol), 4-dimethyl-amino pyridine (DMAP, 3 mg, 0.025 mmol), 2-(4-(1-oxoisoindolin-2-yl) phenyl) butanoic acid (indobufen, 78 mg, 0.264 mmol) and 1-(3-dimethylaminopropyl)-3-ethylcarbodiimide hydrochloride (EDCI, 73 mg, 0.377 mmol) were dissolved in dichloromethane (4 mL) and stirred at room temperature for 20 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=50:1 to 25:1) to give the title compound as a white solid, 0.145 g, 88.2% yield. MS (m/z): [M+H]$^+$ calcd for $C_{35}H_{34}F_3N_7O_3$, 658.27, found 658.2. $^1$H NMR (400 MHz, DMSO-$d_6$) δ 8.93 (d, J=1.8 Hz, 1H), 8.07 (dd, J=7.3, 4.1 Hz, 1H), 7.91-7.80 (m, 2H), 7.75 (dd, J=7.6, 3.0 Hz, 1H), 7.71-7.59 (m, 3H), 7.58-7.46 (m, 3H), 7.41 (t, J=4.7 Hz, 1H), 6.96 (td, J=6.3, 2.1 Hz, 1H), 5.86 (t, J=7.4

Hz, 1H), 4.96 (d, J=6.1 Hz, 2H), 4.37-4.29 (m, 1H), 3.91-3.73 (m, 4H), 3.67 (dt, J=10.2, 6.4 Hz, 1H), 3.25 (dd, J=10.3, 5.8 Hz, 1H), 2.56-2.49 (m, 1H), 2.34-2.19 (m, 1H), 1.94 (dtd, J=12.8, 7.5, 4.7 Hz, 1H), 1.12-0.99 (m, 1H), 0.95 (td, J=7.3, 5.7 Hz, 3H), 0.80 (ddd, J=16.9, 14.2, 7.4 Hz, 1H), 0.62 (dt, J=17.9, 7.3 Hz, 3H).

Example 139

3-((3S, 4R)-6-(7-(2-(4-isobutylphenyl) propanoyl)-7H-pyrrolo [2, 3-d] pyrimidin-4-yl)-3-methyl-1, 6-diazaspiro [3.4] oct-1-yl)-3-oxopropanenitrile

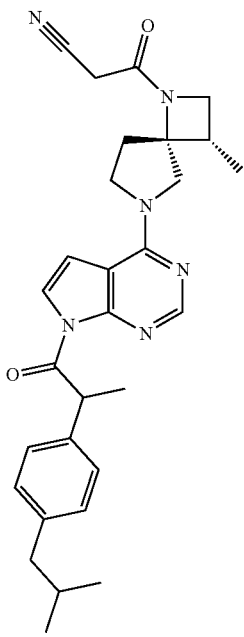

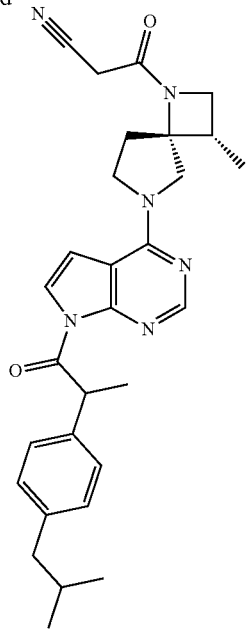

Synthesis of 3-((3S, 4R)-6-(7-(2-(4-isobutylphenyl) propanoyl)-7H-pyrrolo [2, 3-d] pyrimidin-4-yl)-3-methyl-1, 6-diazaspiro [3.4] oct-1-yl)-3-oxopropanenitrile 3-((3S, 4R)-3-methyl-6-(7H-pyrrolo [2, 3-d] pyrimidin-4-yl)-1, 6-diazaspiro [3.4] oct-1-yl)-3-oxopropanenitrile (Delgocitinib, 75 mg, 0.24 mmol), 4-dimethylamino pyridine (DMAP, 30 mg, 0.24 mmol), 2-(4-isobutylphenyl) propanoic acid (ibuprofen, 65 mg, 0.31 mmol) and 1-(3-dimethylaminopropyl)-3-ethylcarbodiimide hydrochloride (EDCI, 70 mg, 0.36 mmol) were dissolved in dichloromethane (1 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=30:1 to 10:1) to give the title compound as a white solid, 0.081 g, 67.7% yield. MS (m/z): [M+H]$^+$ calcd for $C_{29}H_{34}N_6O_2$, 499.27, found 499.2. $^1$H NMR (400 MHz, DMSO-d$_6$) δ 8.37 (s, 1H), 7.67 (d, J=4.1 Hz, 1H), 7.31 (d, J=8.1 Hz, 2H), 7.07 (d, J=8.0 Hz, 2H), 6.90 (d, J=4.1 Hz, 1H), 6.10 (q, J=6.8 Hz, 1H), 4.20-4.06 (m, 2H), 4.04-3.24 (m, 3H), 3.68 (d, J=3.3 Hz, 2H), 3.65-3.53 (m, 1H), 2.72-2.55 (m, 2H), 2.36 (d, J=7.1 Hz, 2H), 2.20 (s, 1H), 1.82-1.75 (m, 1H), 1.54 (d, J=6.9 Hz, 3H), 1.13 (d, J=7.0 Hz, 3H), 0.82 (d, J=6.6 Hz, 6H).

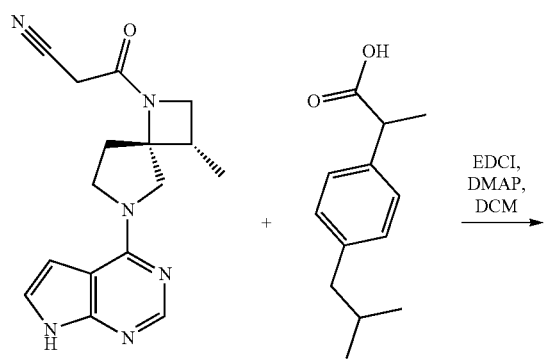

Example 140

3-((3S, 4R)-6-(7-((S)-2-(4-isobutylphenyl) propanoyl)-7H-pyrrolo [2, 3-d] pyrimidin-4-yl)-3-methyl-1, 6-diazaspiro [3.4] oct-1-yl)-3-oxopropanenitrile

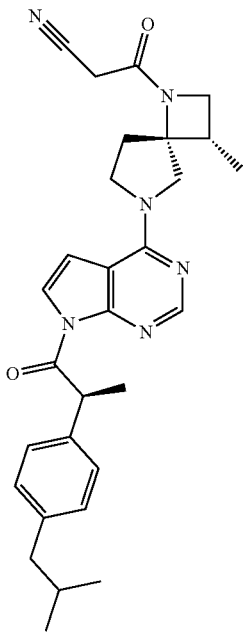

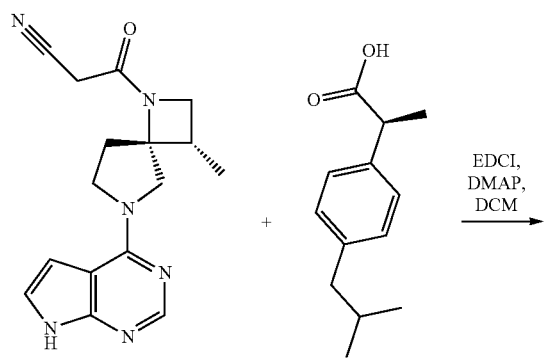

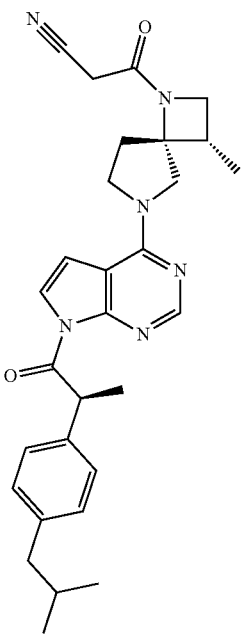

Synthesis of 3-((3S, 4R)-6-(7-((S)-2-(4-isobutylphenyl) propanoyl)-7H-pyrrolo [2, 3-d] pyrimidin-4-yl)-3-methyl-1, 6-diazaspiro [3.4] oct-1-yl)-3-oxo-propanenitrile 3-((3S, 4R)-3-methyl-6-(7H-pyrrolo [2, 3-d] pyrimidin-4-yl)-1, 6-diazaspiro [3.4] oct-1-yl)-3-oxopropanenitrile (Delgocitinib, 75 mg, 0.24 mmol), 4-dimethylamino pyridine (DMAP, 30 mg, 0.24 mmol), (S)-(+)-2-(4-isobutylphenyl) propanoic acid((S)-(+)-ibuprofen, 65 mg, 0.31 mmol) and 1-(3-dimethylaminopropyl)-3-ethylcarbodiimide hydrochloride (EDCI, 70 mg, 0.36 mmol) were dissolved in dichloromethane (1 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=30:1 to 10:1) to give the title compound as a white solid, 0.071 g, 59.4% yield. MS (m/z): [M+H]$^+$ calcd for $C_{29}H_{34}N_6O_2$, 499.27, found 499.3. $^1$H NMR (400 MHz, DMSO-$d_6$) δ 8.37 (s, 1H), 7.67 (d, J=4.1 Hz, 1H), 7.31 (d, J=8.1 Hz, 2H), 7.07 (d, J=8.0 Hz, 2H), 6.90 (d, J=4.1 Hz, 1H), 6.10 (q, J=6.8 Hz, 1H), 4.20-4.05 (m, 2H), 4.04-3.24 (m, 3H), 3.68 (d, J=3.3 Hz, 2H), 3.65-3.53 (m, 1H), 2.73-2.55 (m, 2H), 2.36 (d, J=7.1 Hz, 2H), 2.20 (s, 1H), 1.77 (hept, J=6.8 Hz, 1H), 1.54 (d, J=6.9 Hz, 3H), 1.13 (d, J=7.0 Hz, 3H), 0.82 (d, J=6.6 Hz, 6H).

Example 141

3-((3S, 4R)-6-(7-((S)-2-(6-methoxynaphthalen-2-yl)propanoyl)-7H-pyrrolo [2, 3-d] pyrimidin-4-yl)-3-methyl-1, 6-diazaspiro [3.4] octan-1-yl)-3-oxopropanenitrile

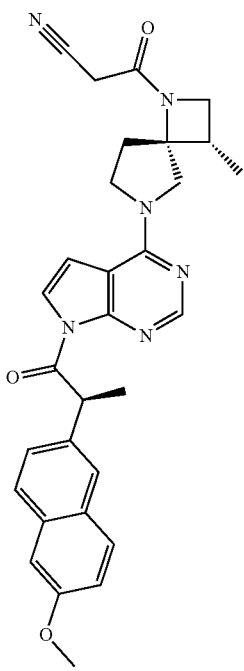

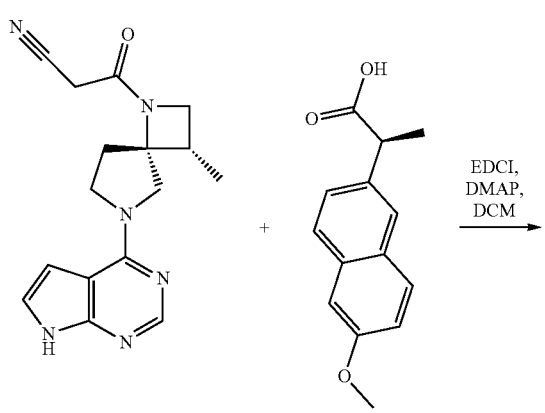

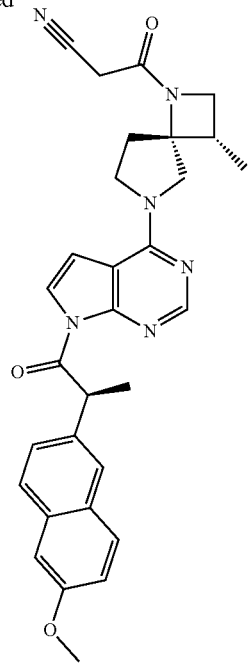

Synthesis of 3-((3S, 4R)-6-(7-((S)-2-(6-methoxynaphthalen-2-yl) propanoyl)-7H-pyrrolo [2, 3-d] pyrimidin-4-yl)-3-methyl-1, 6-diazaspiro [3.4] octan-1-yl)-3-oxopropanenitrile 3-((3S, 4R)-3-methyl-6-(7H-pyrrolo [2, 3-d] pyrimidin-4-yl)-1, 6-diazaspiro [3.4] oct-1-yl)-3-oxopropanenitrile (Delgocitinib, 75 mg, 0.24 mmol), 4-dimethylamino pyridine (DMAP, 30 mg, 0.24 mmol), (S)-(+)-2-(6-methoxy-2-naphthyl) propanoic acid (Naproxen, 70 mg, 0.31 mmol) and 1-(3-dimethylaminopropyl)-3-ethylcarbodiimide hydrochloride (EDCI, 70 mg, 0.36 mmol) were dissolved in dichloromethane (1 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=30:1 to 10:1) to give the title compound as a white solid, 0.013 g, 10.3% yield. MS (m/z): [M+H]+ calcd for $C_{30}H_{30}N_6O_3$, 523.24, found 523.2. $^1$H NMR (400 MHz, Chloroform-d) δ 8.38 (s, 1H), 7.76 (d, J=1.7 Hz, 1H), 7.67-7.56 (m, 2H), 7.51 (dd, J=8.6, 1.8 Hz, 1H), 7.40-7.35 (m, 1H), 7.08-6.98 (m, 2H), 6.53 (d, J=4.2 Hz, 1H), 6.19 (q, J=6.9 Hz, 1H), 4.30-3.91 (m, 2H), 3.82 (d, J=13.5 Hz, 5H), 3.69 (s, 1H), 3.63-3.57 (m, 2H), 3.20-3.05 (m, 1H), 2.84-2.74 (m, 1H), 2.63 (p, J=7.6, 7.2 Hz, 1H), 2.10-1.99 (m, 1H), 1.21-1.08 (m, 3H), 0.85-0.75 (m, 3H).

Example 142

4-((4-(((3R, 4R)-1-(2-cyanoacetyl)-4-methylpiperidin-3-yl) (methyl) amino)-7H-pyrrolo [2, 3-d] pyrimidin-7-yl) methoxy)-2-methyl-N-(5-methylthiazol-2-yl)-2H-benzo [e] [1, 2] thiazine-3-carboxamide 1, 1-dioxide

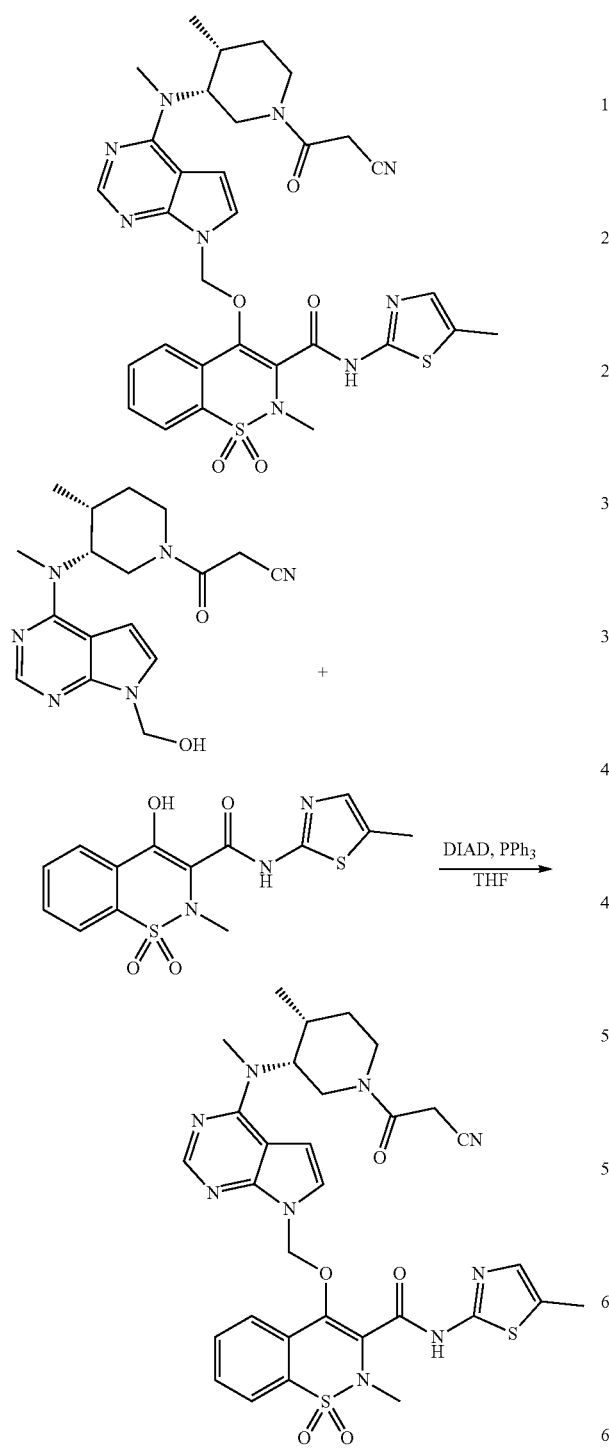

Synthesis of 4-((4-(((3R, 4R)-1-(2-cyanoacetyl)-4-methylpiperidin-3-yl) (methyl) amino)-7H-pyrrolo [2, 3-d]pyrimidin-7-yl) methoxy)-2-methyl-N-(5-methylthiazol-2-yl)-2H-benzo [e] [1, 2] thiazine-3-carboxamide 1, 1-dioxide 4-Hydroxy-2-methyl-N-(5-methylthiazol-2-yl)-2H-benzo [e] [1, 2] thiazine-3-carboxamide 1, 1-dioxide (meloxicam, 246 mg, 0.7 mmol) and triphenylphosphine (PPh$_3$, 190 mg, 0.73 mmol) were added to tetrahydrofuran (3.4 mL) under nitrogen. After cooling to −10° C., diisopropyl azodicarboxylate (DIAD, 148 mg, 0.73 mmol) was added dropwise to the mixture with stirring. After stirring at −10° C. for 20 min, the mixture was allowed to warm to room temperature. 3-((3R, 4R)-3-((7-(hydroxymethyl)-7H-pyrrolo [2, 3-d] pyrimidin-4-yl) (methyl) amino)-4-methylpiperidin-1-yl)-3-oxopropanenitrile (170 mg, 0.5 mmol) was added and the stirring continued. The reaction was monitored by TLC. After complete exhaust of the starting material (1 h), the solvent was evaporated under reduced pressure to give the crude product. The crude product was further separated by silica gel column chromatography (dichloromethane/acetonitrile=20:1 to 9:1) to give the title compound as a yellow solid, 0.009 g, 2.6% yield. MS (m/z): [M+H]$^+$ calcd for C$_{31}$H$_{33}$N$_9$O$_5$S$_2$, 676.20, found 676.2. $^1$H NMR (400 MHz, Chloroform-d) δ 14.01 (s, 1H), 8.28 (s, 1H), 8.03 (dd, J=7.6, 1.4 Hz, 1H), 7.84 (dd, J=7.4, 1.5 Hz, 1H), 7.73-7.52 (m, 3H), 7.30 (d, J=4.5 Hz, 1H), 6.51 (dd, J=11.0, 3.8 Hz, 1H), 6.42 (s, 2H), 5.01 (d, J=26.1 Hz, 1H), 4.04 (dd, J=13.2, 4.2 Hz, 1H), 3.86-3.68 (m, 1H), 3.64 (dd, J=13.2, 8.7 Hz, 1H), 3.56-3.39 (m, 3H), 3.29 (d, J=18.7 Hz, 3H), 3.09 (s, 3H), 2.53-2.39 (m, 1H), 2.21 (d, J=1.4 Hz, 3H), 2.00-1.80 (m, 1H), 1.73-1.63 (m, 1H), 1.02 (dd, J=9.5, 7.1 Hz, 3H).

Example 143

3-((3S, 4R)-3-methyl-6-(7-(2-(4-(1-oxoisoindolin-2-yl) phenyl) butanoyl)-7H-pyrrolo [2, 3-d] pyrimidin-4-yl)-1, 6-diazaspiro [3.4] octan-1-yl)-3-oxopropanenitrile

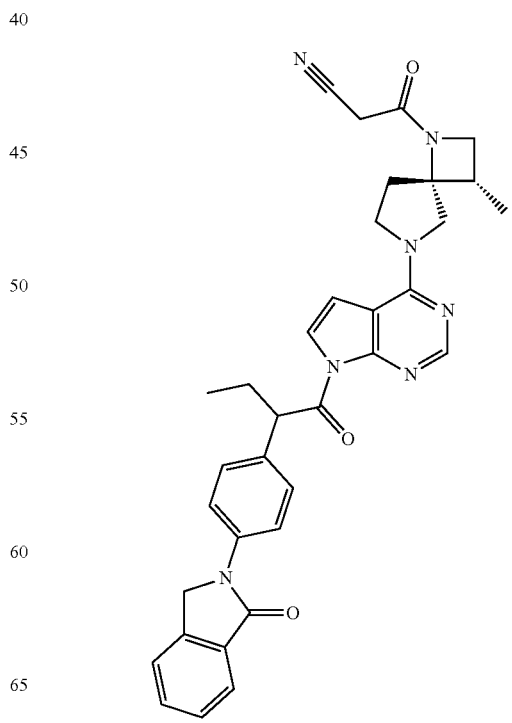

533

-continued

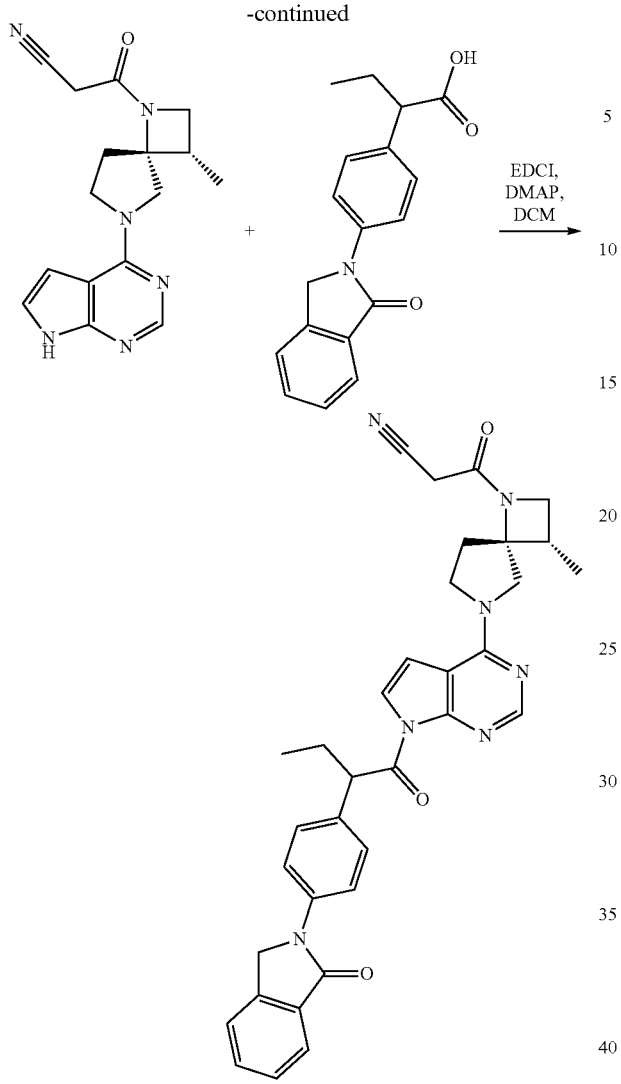

Synthesis of 3-((3S, 4R)-3-methyl-6-(7-(2-(4-(1-oxoisoindolin-2-yl) phenyl) butanoyl)-7H-pyrrolo [2, 3-d]pyrimidin-4-yl)-1, 6-diazaspiro [3.4] octan-1-yl)-3-oxopropanenitrile 3-((3S, 4R)-3-methyl-6-(7H-pyrrolo [2, 3-d] pyrimidin-4-yl)-1, 6-diazaspiro [3.4] oct-1-yl)-3-oxopropanenitrile (delgocitinib, 75 mg, 0.24 mmol), 4-dimethylamino pyridine (DMAP, 30 mg, 0.24 mmol), 2-(4-(1-oxoisoindolin-2-yl) phenyl) butanoic acid (indobufen, 92 mg, 0.31 mmol) and 1-(3-dimethylaminopropyl)-3-ethylcarbodiimide hydrochloride (EDCI, 70 mg, 0.36 mmol) were dissolved in dichloromethane (1 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=30:1 to 10:1) to give the title compound as a white solid, 0.018 g, 12.7% yield. MS (m/z): [M+H]+ calcd for $C_{34}H_{33}N_7O_3$, 588.26, found 588.0. $^1$H NMR (400 MHz,

534

Chloroform-d) δ 8.37 (s, 1H), 7.86-7.79 (m, 1H), 7.70 (dd, J=8.7, 1.1 Hz, 2H), 7.60 (dd, J=4.2, 1.5 Hz, 1H), 7.56-7.46 (m, 3H), 7.46-7.39 (m, 2H), 6.55 (t, J=4.1 Hz, 1H), 5.93 (t, J=7.5 Hz, 1H), 4.74 (s, 2H), 4.26 (t, J=8.4 Hz, 1H), 4.16 (dd, J=12.0, 8.2 Hz, 1H), 4.12-3.94 (m, 2H), 3.73 (s, 1H), 3.62 (ddd, J=8.4, 6.0, 2.4 Hz, 1H), 3.14 (d, J=3.0 Hz, 2H), 2.81 (t, J=13.0, 5.9 Hz, 1H), 2.67 (s, 1H), 2.22 (dt, J=14.2, 7.3 Hz, 1H), 2.09 (s, 1H), 1.96-1.86 (m, 1H), 1.16 (dd, J=7.1, 4.4 Hz, 3H), 0.92 (td, J=7.3, 1.2 Hz, 3H).

Example 144

(4-((3S, 4R)-1-(2-cyanoacetyl)-3-methyl-1, 6-diazaspiro [3.4] octan-6-yl)-7H-pyrrolo [2, 3-d] pyrimidin-7-yl) methyl (S)-2-(4-isobutylphenyl) propanoate

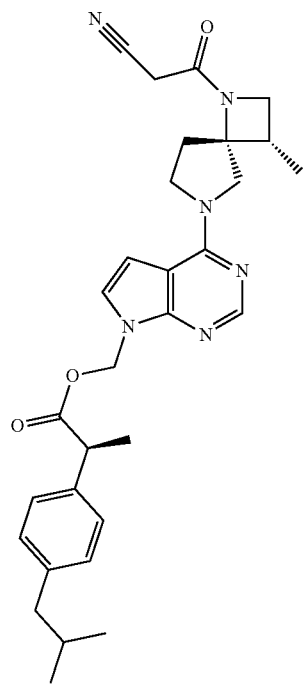

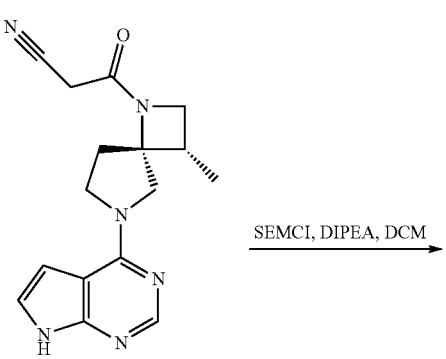

SEMCl, DIPEA, DCM

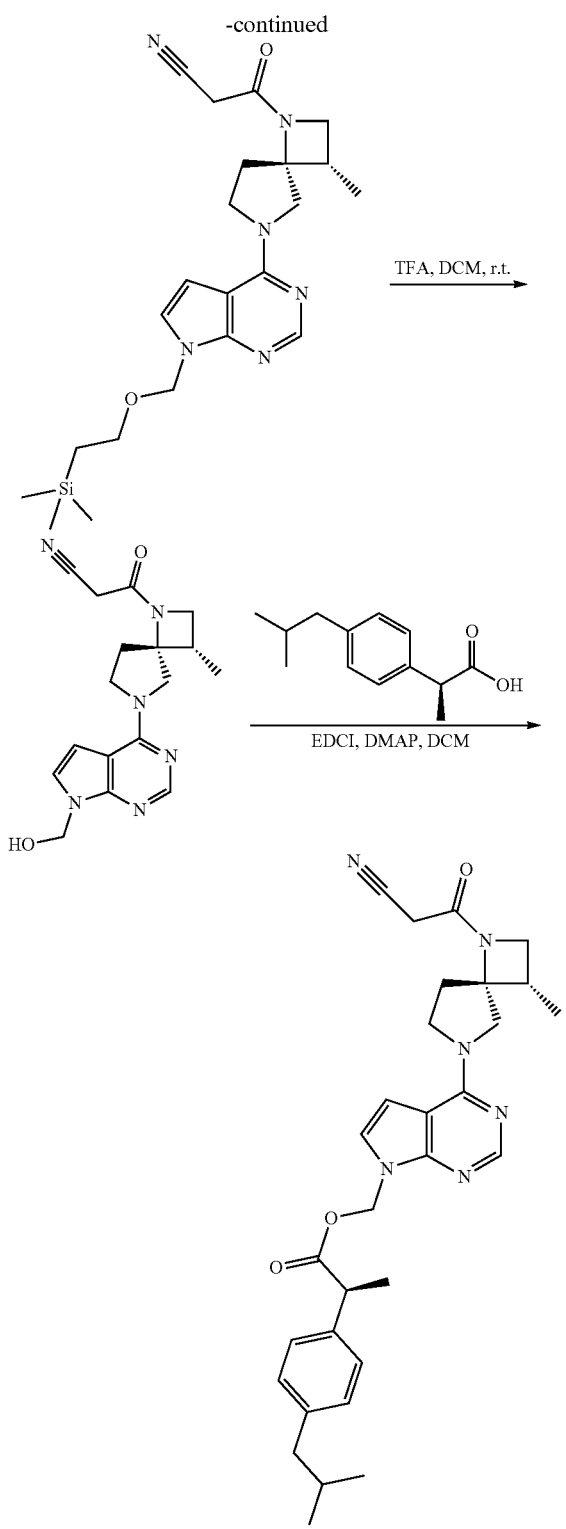

First step: synthesis of 3-((3S, 4R)-3-methyl-6-(7-((2-(trimethylsilyl) ethoxy) methyl)-7H-pyrrolo [2, 3-d]pyrimidin-4-yl)-1, 6-diazaspiro [3.4] oct-1-yl)-3-oxopropanenitrile Under nitrogen protection, 3-((3S, 4R)-3-methyl-6-(7H-pyrrolo [2, 3-d] pyrimidin-4-yl)-1, 6-diazaspiro [3.4]oct-1-yl)-3-oxopropanenitrile (Delgocitinib, 200 mg, 0.644 mmol) and N, N-diisopropylethyl amine (0.17 mL, 0.966 mmoL) were added in dichloromethane (2 mL). After stirring at room temperature for half an hour, (2-(chloromethoxy) ethyl) trimethylsilane (140 mg, 0.838 mmol) was added in an ice water, and stirring was continued at room temperature for 3 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=200:1 to 20:1) to give the title compound, 0.234 g, 82.5% yield. MS (m/z): [M+H]$^+$ calcd for $C_{22}H_{32}N_6O_2Si$, 441.24; found, 441.2.

Step 2: synthesis of 3-((3S, 4R)-6-(7-(hydroxymethyl)-7H-pyrrolo [2, 3-d] pyrimidin-4-yl)-3-methyl-1, 6-diazaspiro [3.4] octan-1-yl)-3-oxopropanenitrile Trifluoroacetic acid (1 mL) was slowly added dropwise to a solution of 3-((3S, 4R)-3-methyl-6-(7-((2-(trimethylsilyl) ethoxy) methyl)-7H-pyrrolo [2, 3-d] pyrimidin-4-yl)-1, 6-diazaspiro [3.4]oct-1-yl)-3-oxopropanenitrile (0.234 g, 0.53 mmol) in dichloromethane (15 mL) under nitrogen in an ice-water bath. After half an hour, the ice-water bath was removed and the temperature was raised to room temperature and stirring was continued for 2 hours. Saturated sodium bicarbonate solution was added to the above reaction solution at 0° C. to adjust the pH to 8. Then the mixture was poured into a separating funnel for separation. The organic layer was washed with a saturated salt water solution and dried over anhydrous sodium sulfate. After the filtration, the solvent was evaporated under reduced pressure to obtain the crude product. The crude product was further separated by silica gel column chromatography (dichloromethane/methanol=50:1 to 9:1) to give the title compound, 0.055 g, 30.4% yield. MS (m/z): [M+H]$^+$ calcd for $C_{17}H_{20}N_6O_2$, 341.16; found, 341.1.

Step 3: synthesis of (4-(1-((R)-2-cyano-1-cyclopentylethyl)-1H-pyrazol-4-yl)-7H-pyrrolo [2, 3-d] pyrimidin-7-yl) methyl (S)-2-(4-isobutylphenyl) propanoate 3-((3S, 4R)-6-(7-(hydroxymethyl)-7H-pyrrolo [2, 3-d] pyrimidin-4-yl)-3-methyl-1, 6-diazaspiro [3.4] octan-1-yl)-3-oxopropanenitrile (55 mg, 0.16 mmol), 4-dimethylamino pyridine (DMAP, 19 mg, 0.16 mmol), (S)-(+)-2-(4-isobutylphenyl) propanoic acid((S)-(+)-ibuprofen, 32 mg, 0.17 mmol) and 1-(3-dimethylaminopropyl)-3-ethylcarbodiimide hydrochloride (EDCI, 50 mg, 0.26 mmol) were dissolved in a mixed solvent of dichloromethane (1 mL) and dimethylformamide (0.25 mL) and stirring was continued for 16 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=30:1 to 10:1) to give the title compound as a white solid, 0.02 g, 23.6% yield. MS (m/z): [M+H]$^+$ calcd for $C_{30}H_{36}N_6O_3$, 529.28, found 529.2. $^1$H NMR (400 MHz, Chloroform-d) δ 8.28 (s, 1H), 7.09-6.92 (m, 5H), 6.45 (d, J=3.7 Hz, 1H), 6.10 (d, J=10.6 Hz, 1H), 6.01 (d, J=10.6 Hz, 1H), 4.31-4.14 (m, 2H), 4.03 (d, J=11.9 Hz, 2H), 3.77 (s, 1H), 3.67-3.59 (m, 2H), 3.16 (s, 2H), 2.83 (dt, J=13.0, 7.5 Hz, 1H), 2.67 (h, J=7.0 Hz, 1H), 2.35 (d, J=7.2 Hz, 2H), 2.10 (s, 1H), 1.75 (dt, J=13.5, 6.7 Hz, 1H), 1.38 (d, J=7.2 Hz, 3H), 1.18 (d, J=2.8 Hz, 3H), 0.81 (d, J=6.7 Hz, 6H).

Example 145

3-((3S, 4R)-6-(7-(2-(3-benzoylphenyl) propanoyl)-7H-pyrrolo [2, 3-d] pyrimidin-4-yl)-3-methyl-1, 6-diazaspiro [3.4] oct-1-yl)-3-oxopropanenitrile

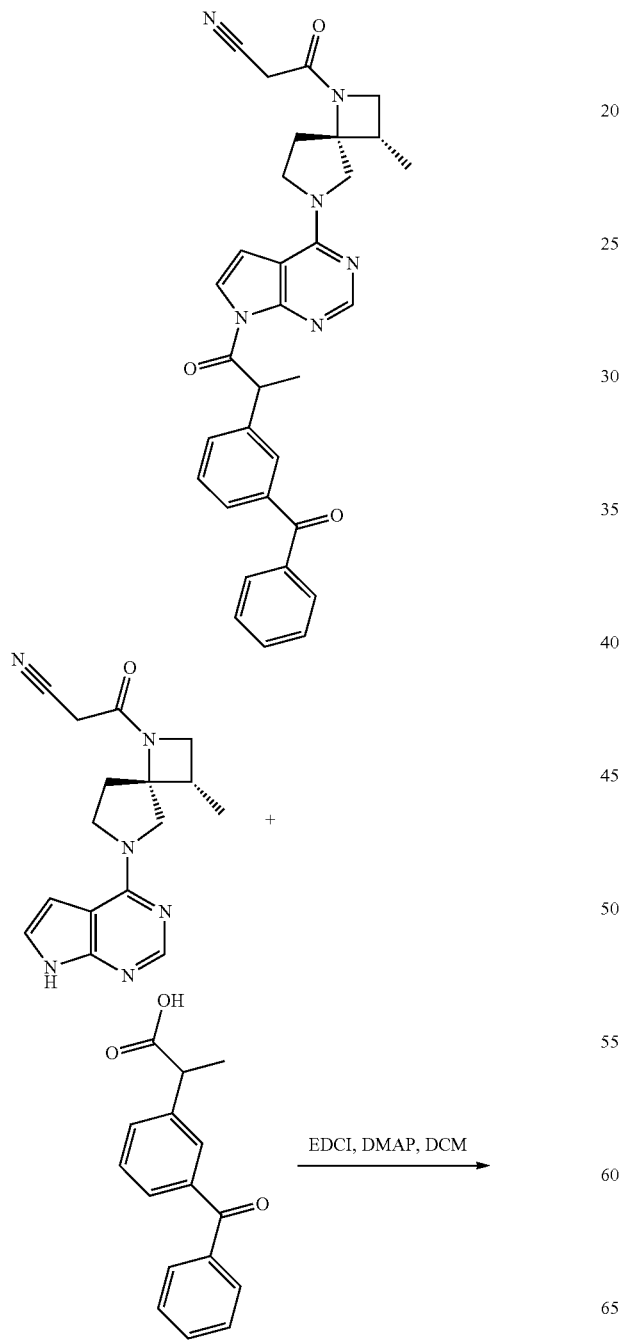

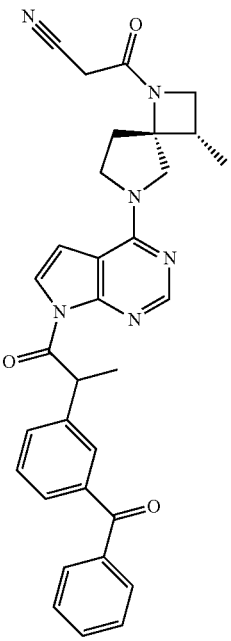 [SMILES: CC(C(=O)n1ccc2c(N3CC[C@]4(C3)[C@@H](C)CN4C(=O)CC#N)ncnc21)c1cccc(C(=O)c2ccccc2)c1]

Synthesis of 3-((3S, 4R)-6-(7-(2-(3-benzoylphenyl) propanoyl)-7H-pyrrolo [2, 3-d] pyrimidin-4-yl)-3-methyl-1, 6-diazaspiro [3.4] oct-1-yl)-3-oxopropanenitrile 3-((3S, 4R)-3-methyl-6-(7H-pyrrolo [2, 3-d] pyrimidin-4-yl)-1, 6-diazaspiro [3.4] oct-1-yl)-3-oxopropanenitrile (Delgocitinib, 75 mg, 0.24 mmol), 4-dimethylamino pyridine (DMAP, 30 mg, 0.24 mmol), 2-(3-benzoylphenyl) propanoic acid (ketoprofen, 79 mg, 0.31 mmol) and 1-(3-dimethylaminopropyl)-3-ethylcarbodiimide hydrochloride (EDCI, 70 mg, 0.36 mmol) were dissolved in dichloromethane (1 mL) and stirred at room temperature for 18 hours. After completion of the reaction, the reaction solution was diluted with dichloromethane and washed with water and saturated salt water solution. The organic layer was dried over anhydrous sodium sulfate and filtered. The solvent was evaporated under reduced pressure to obtain the crude product. The crude product was further separated by silica gel column chromatography (dichloromethane/methanol=30:1 to 10:1) to give the title compound as a white solid, 0.038 g, 29% yield. MS (m/z): [M+H]$^+$ calcd for $C_{32}H_{30}N_6O_3$, 547.24, found 547.1. $^1$H NMR (400 MHz, Chloroform-d) δ 8.35 (s, 1H), 7.94 (s, 1H), 7.81-7.63 (m, 5H), 7.61-7.55 (m, 1H), 7.50-7.43 (m, 2H), 7.40 (t, J=7.7 Hz, 1H), 6.65 (dd, J=4.3, 1.5 Hz, 1H), 6.19 (q, J=7.0 Hz, 1H), 4.32 (t, J=8.4 Hz, 1H), 4.24 (dd, J=12.1, 7.2 Hz, 1H), 4.14 (s, 1H), 4.04 (dd, J=12.1, 8.4 Hz, 1H), 3.85-3.77 (m, 1H), 3.69 (dd, J=8.3, 5.9 Hz, 1H), 3.21 (d, J=2.7 Hz, 2H), 2.93-2.80 (m, 1H), 2.78-2.68 (m, 1H), 2.17 (dq, J=13.2, 7.3 Hz, 1H), 1.65 (d, J=7.0 Hz, 3H), 1.26-1.19 (m, 3H).

Example 146

4-((4-(((3R, 4R)-1-(2-cyanoacetyl)-4-methylpiperidin-3-yl) (methyl) amino)-7H-pyrrolo [2, 3-d] pyrimidin-7-yl) methoxy)-2-methyl-N-(pyridin-2-yl)-2H-thieno [3, 2-e] [1, 2] thiazine-3-carboxamide 1, 1-dioxide

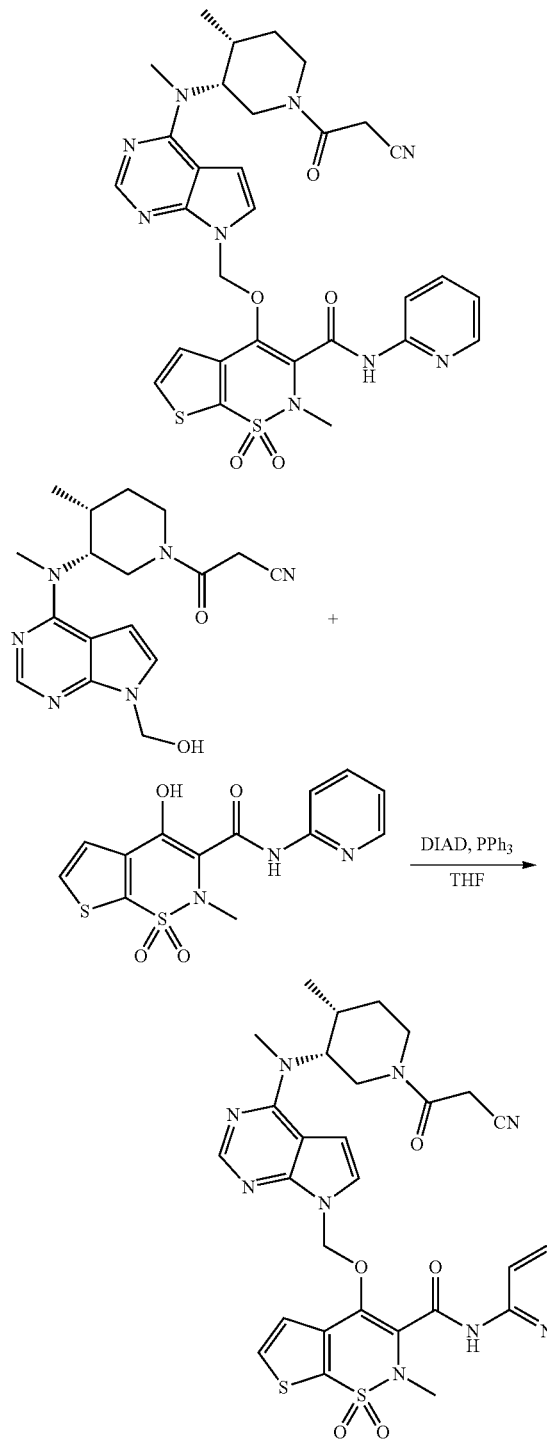

Synthesis of 4-((4-(((3R, 4R)-1-(2-cyanoacetyl)-4-methylpiperidin-3-yl) (methyl) amino)-7H-pyrrolo [2, 3-d]pyrimidin-7-yl) methoxy)-2-methyl-N-(pyridin-2-yl)-2H-thieno [3, 2-e] [1, 2] thiazine-3-carboxamide 1, 1-dioxide 4-Hydroxy-2-methyl-N-(pyridin-2-yl)-2H-thieno [3, 2-e] [1, 2] thiazine-3-carboxamide 1, 1-dioxide (tenoxicam, 98 mg, 0.292 mmol) and triphenylphosphine (PPh$_3$, 230 mg, 0.876 mmol) were added to tetrahydrofuran (2 mL) under nitrogen. Diisopropyl azodicarboxylate (DIAD, 88 mg, 0.438 mmol) was added dropwise to the mixture with stirring. After stirring at −10° C. for 20 minutes, the mixture was allowed to warm to room temperature. 3-((3R, 4R)-3-((7-(hydroxymethyl)-7H-pyrrolo [2, 3-d] pyrimidin-4-yl) (methyl) amino)-4-methylpiperidin-1-yl)-3-oxopropanenitrile (100 mg, 0.292 mmol) was added and stirring was continued. The reaction was monitored by TLC. After complete exhaust of the starting material (1 h), the solvent was evaporated under reduced pressure to give the crude product. The crude product was further separated by silica gel column chromatography (dichloromethane/acetonitrile=20:1 to 9:1) to give the title compound as a yellow solid, 0.011 g, 5.6% yield. MS (m/z): [M+H]$^+$ calcd for C$_{30}$H$_{31}$N$_9$O$_5$S$_2$, 662.19, found 662.2. $^1$H NMR (400 MHz, DMSO-d6) δ 16.02 (s, 1H), 8.63 (t, J=10.2 Hz, 1H), 8.38-8.23 (m, 2H), 8.19-8.10 (m, 1H), 8.06 (dd, J=5.2, 2.2 Hz, 1H), 7.75 (dd, J=6.7, 3.8 Hz, 1H), 7.49 (dd, J=5.2, 1.8 Hz, 1H), 7.25-7.17 (m, 1H), 6.81-6.63 (m, 3H), 4.85 (s, 1H), 4.19-3.88 (m, 3H), 3.81-3.59 (m, 3H), 3.27 (d, J=3.8 Hz, 3H), 2.99 (d, J=2.0 Hz, 3H), 2.41-2.33 (m, 1H), 1.90-1.69 (m, 1H), 1.63-1.56 (m, 1H), 1.00 (d, J=7.1 Hz, 3H).

Example 147

2-Methyl-4-((4-(methyl ((trans)-4-((N-methylsulfamoyl) methyl) cyclohexyl) amino)-7H-pyrrolo [2, 3-d]pyrimidin-7-yl) methoxy)-N-(pyridin-2-yl)-2H-benzo [e] [1, 2] thiazine-3-carboxamide 1, 1-dioxide

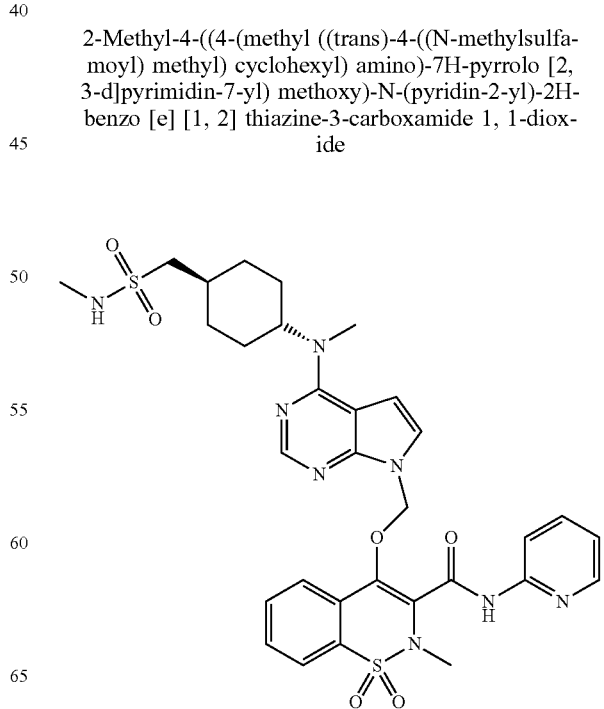

541

-continued

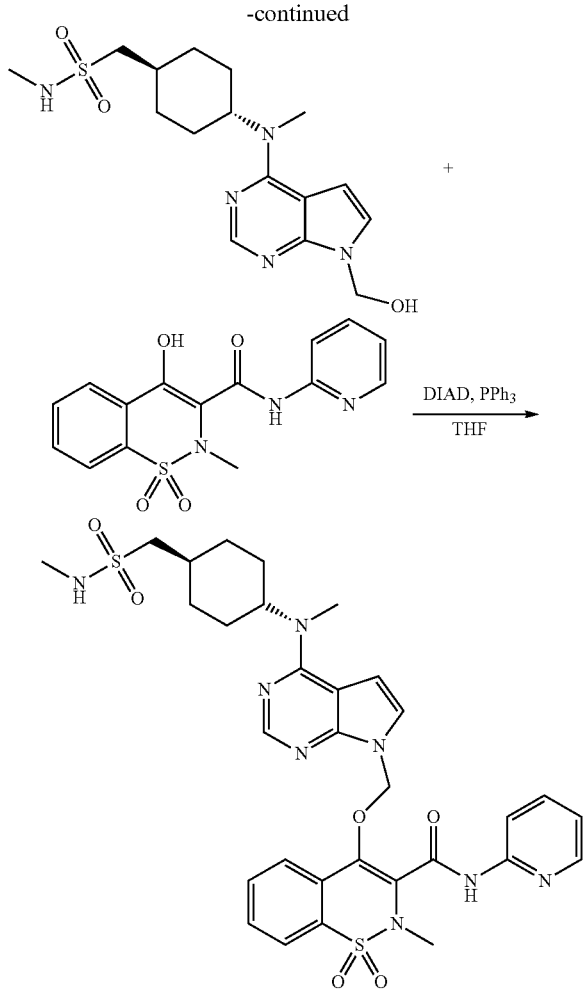

Synthesis of 2-methyl-4-((4-(methyl ((trans)-4-((N-methylsulfamoyl) methyl) cyclohexyl) amino)-7H-pyrrolo [2, 3-d] pyrimidin-7-yl) methoxy)-N-(pyridin-2-yl)-2H-benzo [e] [1, 2] thiazine-3-carboxamide 1, 1-dioxide 4-Hydroxy-2-methyl-N-(pyridin-2-yl)-2H-benzo [e] [1, 2] thiazine-3-carboxamide 1, 1-dioxide (piroxicam, 122 mg, 0.368 mmol) and triphenylphosphine ($PPh_3$, 214 mg, 0.817 mmol) were added to tetrahydrofuran (3 mL) under nitrogen. After cooling to −10° C., diisopropyl azodicarboxylate (DIAD, 124 mg, 0.613 mmol) was added dropwise to the mixture with stirring. After stirring at −10° C. for 20 minutes, the mixture was allowed to warm to room temperature. 1-((Trans)-4-((7-(hydroxymethyl)-7H-pyrrolo [2, 3-d] pyrimidin-4-yl) (methyl) amino) cyclohexyl)-N-methylmethane sulfonamide (150 mg, 0.409 mmol) was added and the stirring was continued. The reaction was monitored by TLC. After complete exhaust of the starting material, the solvent was evaporated under reduced pressure to give the crude product. The crude product was further separated by silica gel column chromatography (dichloromethane/acetonitrile=20:1 to 9:1) to give the title compound as a yellow solid, 0.012 g, 4.8% yield. MS (m/z): [M+H]$^+$ calcd for $C_{31}H_{36}N_8O_6S_2$, 681.22, found 681.2. $^1$H NMR (400 MHz, Chloroform-d) δ 15.31 (s, 1H), 8.59 (d, J=6.6 Hz, 1H), 8.39 (d, J=9.1 Hz, 1H), 8.32 (s, 1H), 8.10 (dd, J=7.7, 1.4 Hz, 1H),

542

8.02 (s, 1H), 7.90 (dd, J=7.6, 1.4 Hz, 1H), 7.77-7.61 (m, 3H), 6.85-6.65 (m, 2H), 6.55 (d, J=3.8 Hz, 1H), 5.40-5.31 (m, 2H), 4.69 (s, 1H), 3.19 (s, 3H), 3.10 (s, 3H), 2.95 (d, J=6.2 Hz, 2H), 2.82 (d, J=5.3 Hz, 3H), 2.19-2.11 (m, 2H), 2.02-1.94 (m, 1H), 1.90-1.65 (m, 4H), 1.37-1.27 (m, 211).

Example 148

4-((4-(1-(3-(Cyanomethyl)-1-(ethylsulfonyl) azetidin-3-yl)-1H-pyrazol-4-yl)-7H-pyrrolo [2, 3-d] pyrimidin-7-yl) methoxy)-2-methyl-N-(pyridin-2-yl)-2H-thieno [3, 2-e] [1, 2] thiazine-3-carboxamide 1, 1-dioxide

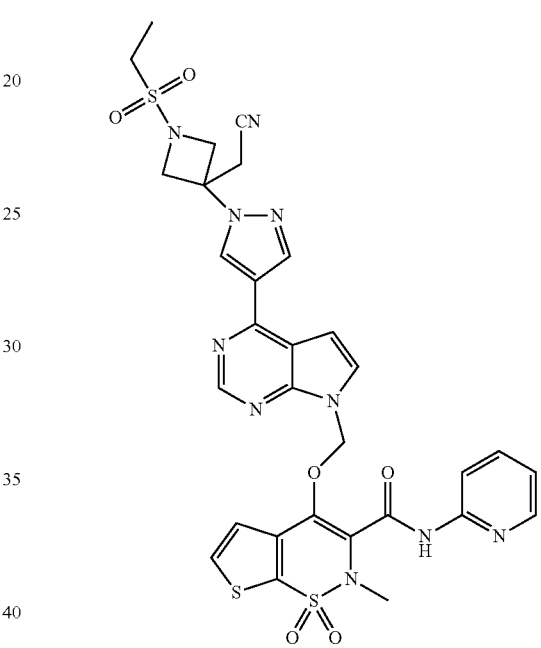

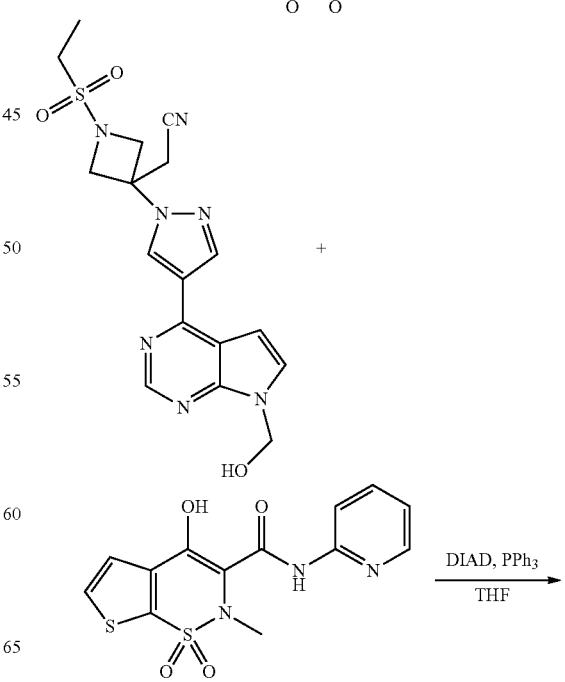

543
-continued

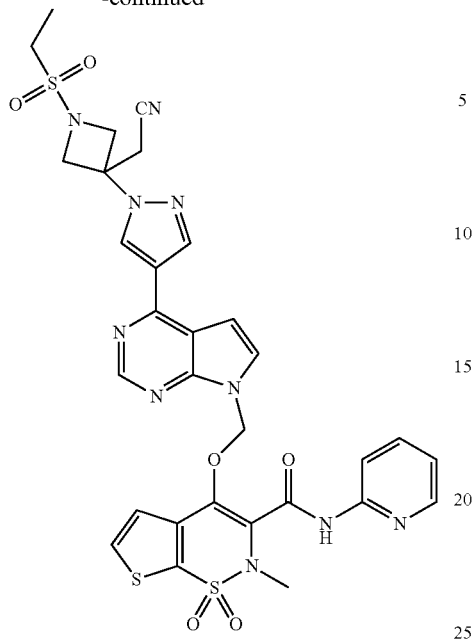

Synthesis of 4-((4-(1-(3-(Cyanomethyl)-1-(ethylsulfonyl) azetidin-3-yl)-1H-pyrazol-4-yl)-7H-pyrrolo [2, 3-d]pyrimidin-7-yl) methoxy)-2-methyl-N-(pyridin-2-yl)-2H-thieno [3, 2-e] [1, 2] thiazine-3-carboxamide 1, 1-dioxide 4-Hydroxy-2-methyl-N-(pyridin-2-yl)-2H-thieno [3, 2-e] [1, 2] thiazine-3-carboxamide 1, 1-dioxide (tenoxicam, 75 mg, 0.224 mmol) and triphenylphosphine (PPh$_3$, 196 mg, 0.748 mmol) were added to tetrahydrofuran (2 mL) under nitrogen. After cooling to −10° C., diisopropyl azodicarboxylate (DIAD, 75 mg, 0.374 mmol) was added dropwise to the mixture with stirring. After stirring at −10° C. for 20 minutes, the mixture was allowed to warm to room temperature naturally. 2-(1-(Ethylsulfonyl)-3-(4-(7-(hydroxymethyl)-7H-)) pyrrolo [2, 3-d] pyrimidin-4-yl)-1H-pyrazol-1-yl) azetidin-3-yl) acetonitrile (100 mg, 0.249 mmol) was added and the stirring was continued. The reaction was monitored by TLC. After complete exhaust of the starting material, the solvent was evaporated under reduced pressure to give the crude product. The crude product was further separated by silica gel column chromatography (dichloromethane/acetonitrile=20:1 to 9:1) to give the title compound as a yellow solid, 0.008 g, 4.9% yield. MS (m/z): [M+H]$^+$ calcd for C$_{30}$H$_{28}$N$_{10}$O$_6$S$_3$, 721.14, found 721.2. $^1$H NMR (400 MHz, Chloroform-d) δ 13.45 (s, 1H), 8.65 (s, 1H), 8.46 (s, 1H), 8.25 (s, 1H), 8.18-8.08 (m, 2H), 7.65-7.56 (m, 2H), 7.44-7.31 (m, 2H), 6.90 (ddd, J=7.3, 4.9, 1.0 Hz, 1H), 6.60 (d, J=3.7 Hz, 1H), 6.17 (s, 2H), 4.56 (d, J=9.2 Hz, 2H), 4.18 (d, J=9.2 Hz, 2H), 3.35 (s, 2H), 3.12-2.99 (m, 5H), 1.35 (td, J=7.5, 3.8 Hz, 3H).

544

Example 149

2-Methyl-4-((4-(methyl ((trans)-4-((N-methylsulfamoyl) methyl) cyclohexyl) amino)-7H-pyrrolo [2, 3-d]pyrimidin-7-yl) methoxy)-N-(pyridin-2-yl)-2H-thieno [3, 2-e] [1, 2] thiazine-3-carboxamide 1, 1-dioxide

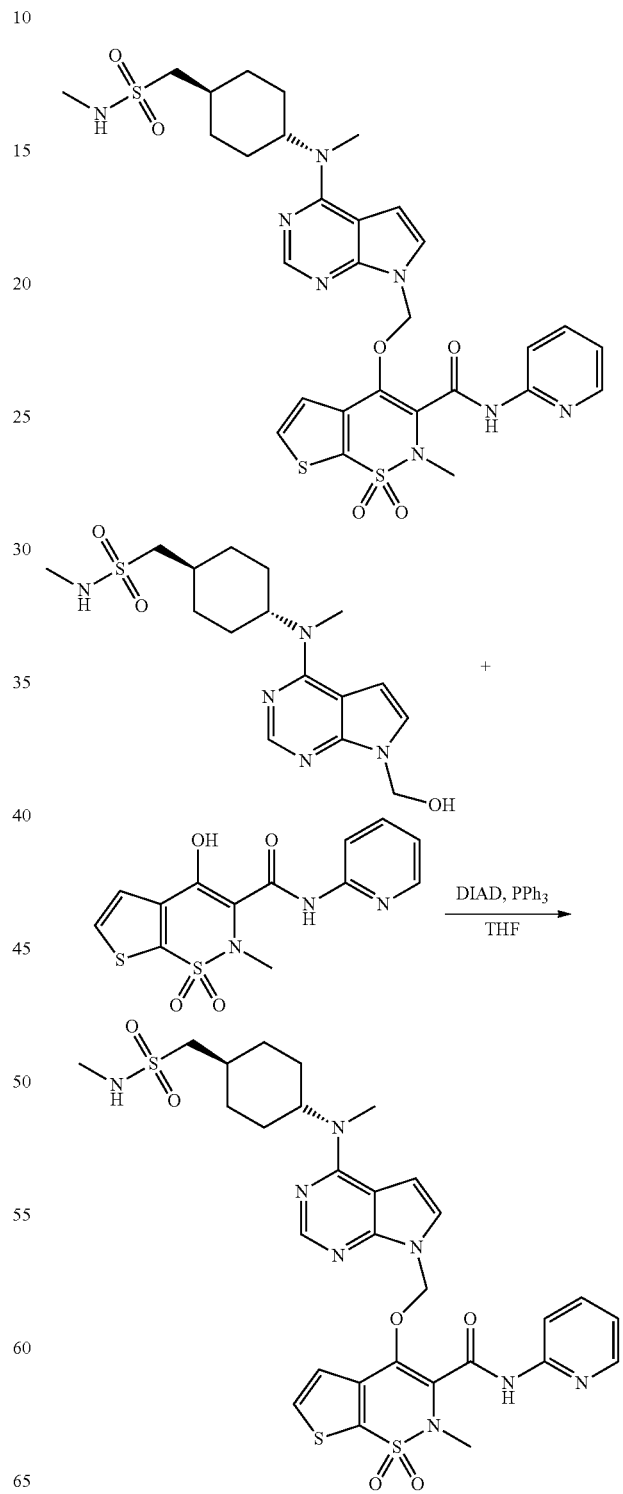

Synthesis of 2-methyl-4-((4-(methyl ((trans)-4-((N-methylsulfamoyl) methyl) cyclohexyl) amino)-7H-pyrrolo [2, 3-d] pyrimidin-7-yl) methoxy)-N-(pyridin-2-yl)-2-thieno [3, 2-e] [1, 2] thiazine-3-carboxamide 1, 1-dioxide 4-Hydroxy-2-methyl-N-(pyridin-2-yl)-2H-thieno [3, 2-e] [1, 2] thiazine-3-carboxamide 1, 1-dioxide (tenoxicam, 75 mg, 0.224 mmol) and triphenylphosphine (PPh$_3$, 196 mg, 0.748 mmol) were added to tetrahydrofuran (2 mL) under nitrogen. After cooling to −10° C., diisopropyl azodicarboxylate (DIAD, 75 mg, 0.374 mmol) was added dropwise to the mixture with stirring. After stirring at −10° C. for 20 minutes, the mixture was allowed to warm to room temperature naturally. 1-((Trans)-4-((7-(hydroxymethyl)-7H-pyrrolo [2, 3-d] pyrimidin-4-yl) (methyl) amino) cyclohexyl)-N-methylmethane sulfonamide (100 mg, 0.272 mmol) was added and the stirring was continued. The reaction was monitored by TLC. After complete exhaust of the starting material, the solvent was evaporated under reduced pressure to give the crude product. The crude product was further separated by silica gel column chromatography (dichloromethane/acetonitrile=20:1 to 9:1) to give the title compound as a yellow solid, 0.006 g, 3.9% yield. MS (m/z): [M+H]$^+$ calcd for $C_{29}H_{34}N_8O_6S_3$, 687.18, found 687.2. $^1$H NMR (400 MHz, Chloroform-d) δ 8.89 (s, 1H), 8.29-8.16 (m, 1H), 8.03 (s, 1H), 7.82 (dt, J=8.4, 1.0 Hz, 1H), 7.54 (ddd, J=8.5, 7.4, 1.9 Hz, 1H), 7.00 (ddd, J=7.3, 4.9, 1.0 Hz, 1H), 6.90 (d, J=3.8 Hz, 1H), 6.42 (d, J=3.8 Hz, 1H), 6.16 (s, 2H), 4.59-4.39 (m, 1H), 3.24 (d, J=5.0 Hz, 1H), 3.16 (s, 3H), 3.04 (d, J=14.0 Hz, 3H), 2.98 (d, J=6.3 Hz, 2H), 2.85 (dd, J=5.3, 3.6 Hz, 3H), 2.19 (d, J=12.8 Hz, 3H), 2.03 (q, J=6.2 Hz, 1H), 1.92-1.59 (m, 4H), 1.43-1.33 (m, 2H).

Analysis Method for Hydrolysis Rate of Compounds of the Present Invention

1. Preparation of Standard Working Curve Solution

About 10 mg of JAK inhibitors (tofacitinib and baricitinib) reference substances were weighed into a 25 mL volumetric flask, acetonitrile/water=7/3 (v/v) was added to dissolve and dilute to the marked volume, serving as a stock solution. The stock solution was diluted with a suitable dilution factor to obtain linear solutions of each concentration: 0.0002 mg/mL, 0.0004 mg/mL, 0.004 mg/mL, 0.04 mg/mL, and 0.08 mg/mL.

About 10 mg of JAK inhibitors (Oclacitinib, Ruxolitinib, Delgocitinib, and Upadacitinib) reference substances were weighed into a 25 mL volumetric flask, acetonitrile/water=7/3 (v/v) was added to dissolve and dilute to the marked volume, serving as a stock solution. The stock solution was diluted with a suitable dilution factor to obtain linear solutions of each concentration: 0.0002 mg/mL, 0.0004 mg/mL, 0.004 mg/mL, 0.04 mg/mL, and 0.08 mg/mL.

2. Preparation of Sample Solution

About 5 mg of the sample (the compound prepared in the present invention) was weighed into a 20 mL volumetric flask, acetonitrile/water=7/3 (v/v) was added to dissolve and dilute to the marked volume, serving as a stock solution. An appropriate amount of HPLC was loaded as the 0-day sample. The test solution was sealed with a sealing film and placed in a 37° C. constant temperature shaker. The test samples were taken at the same time on days 1, 2, 3, and 4 respectively. the release amount of JAK inhibitor in the sample was calculated according to the sample weight and JAK inhibitor standard curve.

3. Calculation Formula

% Release of JAK Inhibitor $r=100\% \times ((A_{JAK\ Inhibitor}-b)/a)/((W/20 \times M2/M1)$ wherein $A_{JAK\ inhibitor}$ is the peak area of JAK inhibitor in the sample chromatogram b is the intercept of the standard curve M1 is the molecular weight of the sample a is the slope of the standard curve W is the sample weight (mg) M2 is the molecular weight of the JAK inhibitor 4. Chromatographic Conditions The chromatographic conditions of the test are shown in Table 2.

TABLE 2

| Chromatographic conditions | | | | | |
|---|---|---|---|---|---|
| Chromatographic column | WatersXbridge Shield RP18, 150 × 4.6 mm, 3.5 μm | | | | |
| Flow rate (LPM) | 0.8 mL/min | | Column temperature | | 30° C. |
| Detection wavelength | 220 nm | | Loading volume | | 5 μL |
| Mobile phase | 10 mM KH$_2$PO$_4$(Adjust pH6.5 with KOH)/ACN = 9/1(v/v); B: ACN | | | | |
| | Time | 0 | 10 | 16 | 17 | 22 |
| Elution gradient | A % | 85 | 20 | 20 | 85 | 85 |
| | B % | 15 | 80 | 80 | 15 | 15 |

Table 3 Shows the Drug Release Rate Results of the Compound Drugs Prepared in the Above Examples of the Present Disclosure.

TABLE 3

| Drug Release Rate Table | |
|---|---|
| Ex. No. | Release Rate (%/day) |
| Ex. 1 | 8.26 |
| Ex. 2 | 8.5 |
| Ex. 3 | 0.05 |
| Ex. 4 | 3.32 |
| Ex. 5 | 4.7 |
| Ex. 6 | 9.82 |
| Ex. 7 | 15.65 |
| Ex. 8 | 14.77 |
| Ex. 9 | 13.49 |
| Ex. 10 | 11.25 |
| Ex. 11 | 9.17 |
| Ex. 12 | 18.94 |
| Ex. 13 | 12.18 |
| Ex. 14 | 0.98 |
| Ex. 15 | 1.86 |
| Ex. 16 | 39.31 |
| Ex. 17 | 2.44 |
| Ex. 18 | 2.97 |
| Ex. 19 | 6.25 |

TABLE 3-continued

Drug Release Rate Table

| Ex. No. | Release Rate (%/day) |
|---|---|
| Ex. 20 | 5.06 |
| Ex. 21 | 4.6 |
| Ex. 22 | 2.75 |
| Ex. 23 | 7.63 |
| Ex. 24 | 5.96 |
| Ex. 25 | 0.68 |
| Ex. 26 | 36.19 |
| Ex. 27 | 7.48 |
| Ex. 28 | 2.98 |
| Ex. 29 | 7.08 |
| Ex. 30 | 1.63 |
| Ex. 31 | 3.08 |
| Ex. 32 | 7.12 |
| Ex. 33 | 5.01 |
| Ex. 34 | 1.57 |
| Ex. 35 | 4.57 |
| Ex. 36 | 14.98 |
| Ex. 37 | 1.05 |
| Ex. 38 | 18.42 |
| Ex. 39 | 10.11 |
| Ex. 40 | 0.62 |
| Ex. 41 | 4.27 |
| Ex. 42 | 22.18 |
| Ex. 43 | 2.99 |
| Ex. 44 | 10.18 |
| Ex. 45 | 1.93 |
| Ex. 46 | 25.52 |
| Ex. 47 | 0.36 |
| Ex. 48 | 0.03 |
| Ex. 49 | 0.11 |
| Ex. 50 | 0.05 |
| Ex. 51 | 0.35 |
| Ex. 52 | 0.1 |
| Ex. 53 | 0.06 |
| Ex. 54 | 4.93 |
| Ex. 55 | 0.16 |
| Ex. 56 | 0.07 |
| Ex. 57 | 0.57 |
| Ex. 58 | 12.46 |
| Ex. 59 | 0.15 |
| Ex. 60 | <0.01 |
| Ex. 61 | <0.01 |
| Ex. 62 | 0.01 |
| Ex. 63 | 0.02 |
| Ex. 64 | 0.88 |
| Ex. 65 | 0.01 |
| Ex. 66 | 0.06 |
| Ex. 67 | 0.02 |
| Ex. 68 | 10.6 |
| Ex. 69 | 0.03 |
| Ex. 70 | 0.42 |
| Ex. 71 | 0.01 |
| Ex. 72 | <0.01 |
| Ex. 73 | 0.2 |
| Ex. 74 | 0.44 |
| Ex. 75 | 10.38 |
| Ex. 76 | 0.05 |
| Ex. 77 | 3.69 |
| Ex. 78 | 6.27 |
| Ex. 79 | 7.38 |
| Ex. 80 | 27.29 |
| Ex. 81 | 0.013 |
| Ex. 82 | 0.43 |
| Ex. 83 | 0.003 |
| Ex. 84 | 0.06 |
| Ex. 85 | 0.61 |
| Ex. 86 | <0.01 |
| Ex. 87 | 0.01 |
| Ex. 88 | 0.17 |
| Ex. 89 | 0.16 |
| Ex. 90 | 0.35 |
| Ex. 91 | 1.65 |
| Ex. 92 | 0.82 |
| Ex. 93 | 0.83 |
| Ex. 94 | 0.72 |
| Ex. 99 | 0.21 |
| Ex. 100 | 0.24 |
| Ex. 104 | 0.45 |
| Ex. 105 | 0.17 |
| Ex. 107 | 0.22 |
| Ex. 110 | 0.08 |
| Ex. 113 | 0.42 |
| Ex. 116 | 0.42 |
| Ex. 117 | 0.08 |
| Ex. 120 | 0.42 |
| Ex. 122 | 15.32 |
| Ex. 123 | 3.02 |
| Ex. 124 | 2.75 |
| Ex. 125 | 6.17 |
| Ex. 126 | 7.80 |
| Ex. 130 | 11.67 |
| Ex. 131 | 3.56 |
| Ex. 133 | 10.13 |
| Ex. 138 | 2.15 |
| Ex. 140 | 8.10 |
| Ex. 142 | 0.05 |
| Ex. 143 | 4.29 |
| Ex. 144 | 0.05 |

As can be seen from the results in Table 3 above, the coupling of an anti-inflammatory drug compound containing a carboxylic acid or hydroxyl group with a JAK inhibitor compound to form a coupling compound having an acyloxy group and or methoxy group according to the present invention has a high therapeutic effect and a special effect of controlled-release drug activity.

Pharmacodynamic Evaluation Studies of Compounds of the Invention

Efficacy Evaluation Study of Ointment Transdermal Patch Formulated by Compounds Using IMQ-Induced Psoriasis Mouse Model Experimental Design BALB/c mice (male) aged 6-8 weeks were selected to have depilated back skin with an area of 2×3 cm. 5% IMQ cream 62.5 mg was applied once a day for 9 consecutive days for model induction. Mice were housed in an SPF-grade animal room in IVC cages at a temperature of 20-26° C. and a humidity of 40-70% under a 12-hour light-dark cycle. Diet ad libitum, except where fasting is required.

Mice were randomly divided into groups, a number of 8 mice, administration concentration 20 mg/g, administration amount 50 mg, administration route, and frequency: skin smear, BID. The positive control was compound dexamethasone acetate (Dex) cream which is a commercially available product with a Dex content of 0.75 mg/g (999 Piyanping, Sanjiu Pharmaceutical). Dosing started from day 1 (the first day) (the day of model induction) to day 9.

2. Preparation of Test Ointment

Topical preparations are mostly semi-solid dosage forms. The base and solvent of a semi-solid dosage form are generally widely used in medicine and daily chemical products. The excipients which can be added are also the common excipients in the manual of excipients. Therefore, the patent compounds are prepared into corresponding test ointments. The ointment compound was dissolved with diisopropyl adipate to prepare a vaseline-based ointment. In order to improve the stability of the ointment, microcrystalline cellulose was added as an excipient in the formulation. The white vaseline has a melting point of 45-60° C. The solution, white vaseline, and microcrystalline cellulose are thoroughly mixed while the vaseline is in a molten state.

After cooling to solidification, it was divided into an aluminum ointment, and the specific weight ratios of base, solvent, and excipients are shown in Table 4.

TABLE 4

Composition of ointment formulations for efficacy experiments

| Cmpd No. | CPD-002 | CPD-017 | CPD-027 | CPD-028 | CPD-029 |
|---|---|---|---|---|---|
| Compound percentage | 2 | 2 | 2 | 2 | 2 |
| Solvent percentage | 15 | 15 | 15 | 15 | 15 |
| Matrix percentage | 80 | 80 | 80 | 80 | 80 |
| Excipient Percentage | 3 | 3 | 3 | 3 | 3 |
| Total (w/w) | 100 | 100 | 100 | 100 | 100 |

3. Model Evaluation

Dorsal modeling site skin PASI was performed on the experimental animals. The scoring criteria are shown in Table 5 below:

TABLE 5

Scoring criteria

| Score | Erythema | Dandruff | Skin thickening |
|---|---|---|---|
| 0 | Normal | Normal | Normal |
| 1 | Mild | Mild: small amount of shavings | Mild |
| 2 | Moderate | Moderate: a large amount of scurf | Moderate |
| 3 | Severe | Severe: skin scab | Severe |
| 4 | Extremely severe | Extremely severe: heavy scab | Extremely severe |

Statistical analysis of PASI scores was performed using Two-way ANOVA. All data were analyzed using GraphPad Prism 8.0 software with a $p<0.05$ significant difference (*, $p<0.05$; **, $p<0.01$).

4. Efficacy

PASI Score Curve

Figure 2:
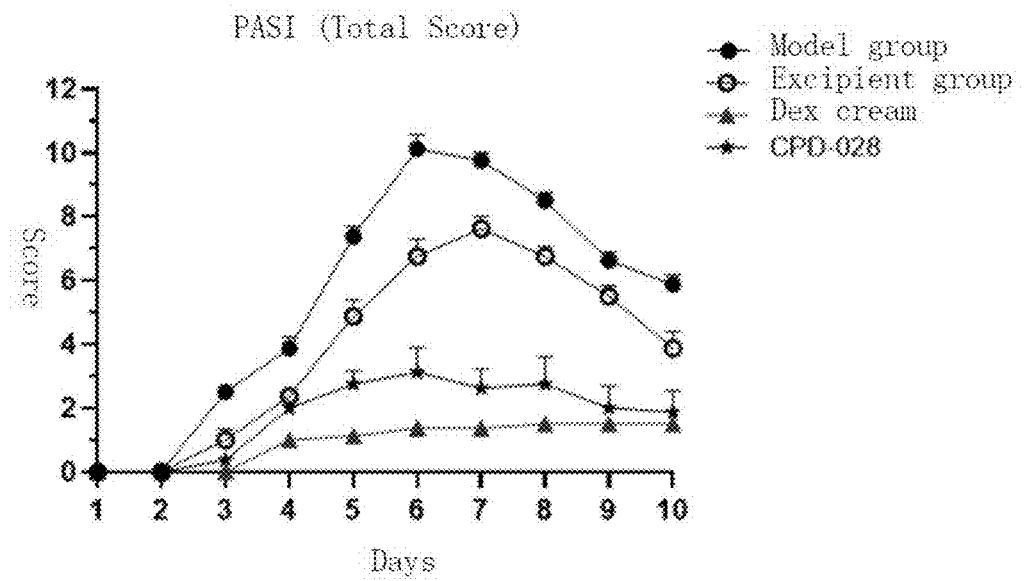
FIG. 2 is a graph of the PASI score of an ointment prepared from CPD-028 of the present invention through skin application to treat psoriasis in a mouse model test.
Figure 3:
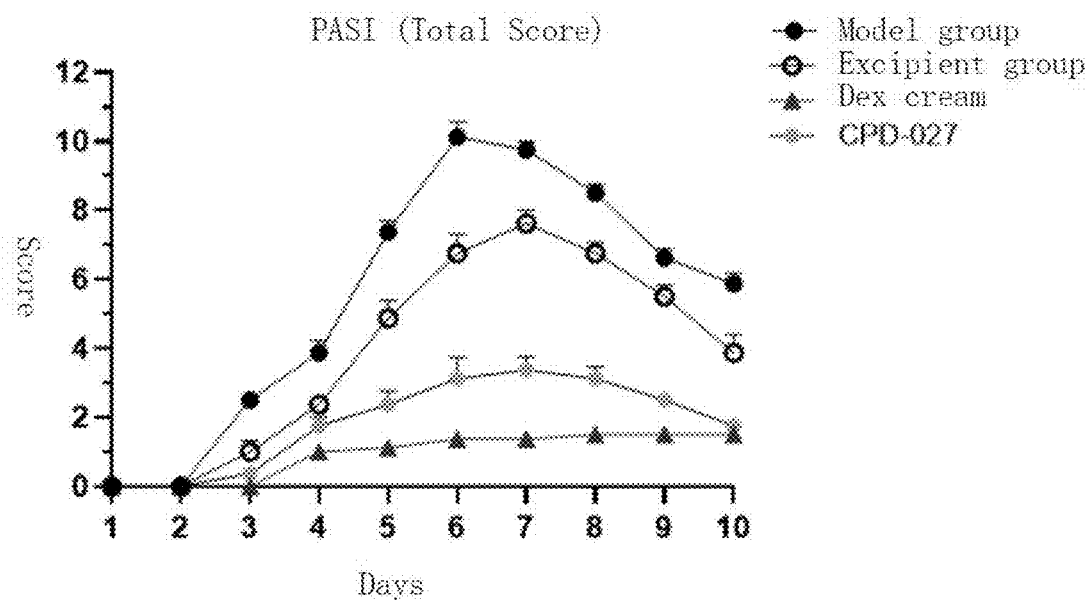
FIG. 3 is a graph of the PASI score of an ointment prepared from CPD-027 of the present invention through skin application to treat psoriasis in a mouse model test.
Figure 4:
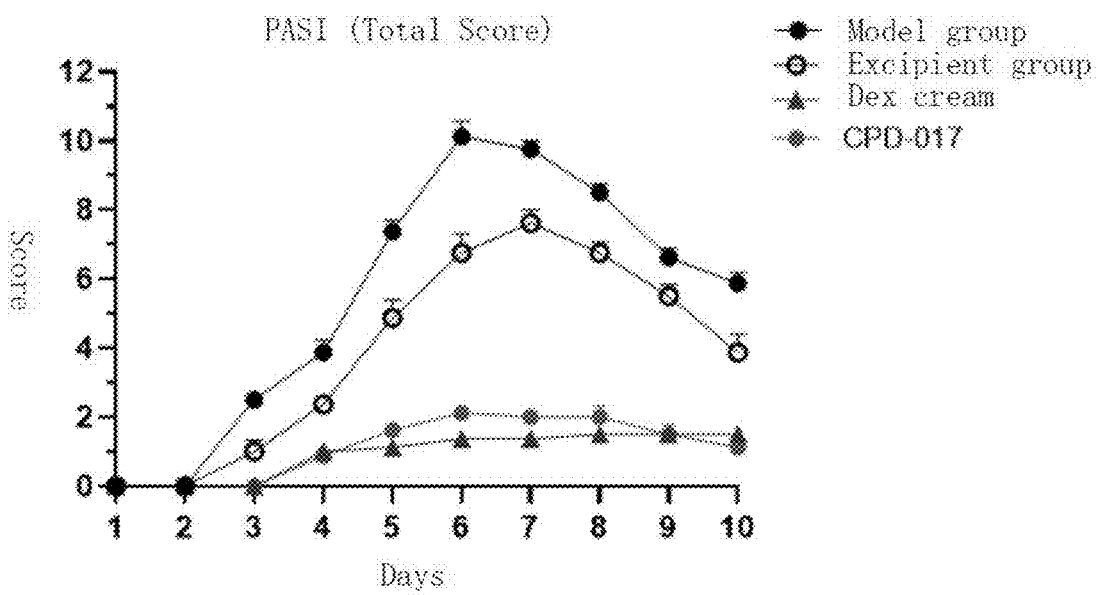
FIG. 4 is a graph of the PASI score of an ointment prepared from CPD-017 of the present invention through skin application to treat psoriasis in a mouse model test.
Figure 5:
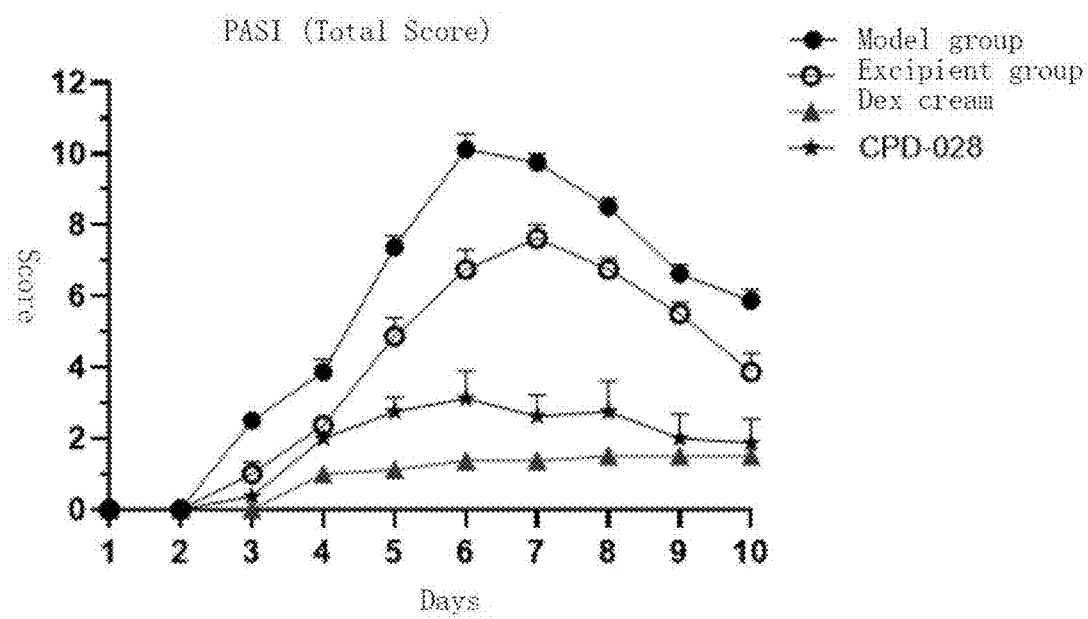
FIG. 5 is a graph of the PASI score of an ointment prepared from CPD-002 of the present invention through skin application to treat psoriasis in a mouse model test.

The PASI score curves of CPD-029, CPD-028, CPD-027, CPD-017, and CPD-002 compared with the model group, excipient group, and Dex cream group are shown in FIGS. 1, 2, 3, 4, and 5, respectively. Among them, the model group was treated with 62.5 mg of 5% IMQ cream applied to the back skin of mice once daily to induce psoriasis, and the excipient group was treated with 15% (w/w) diisopropyl adipate, 80% vaseline, and 3% microcrystalline cellulose.

As can be seen from FIGS. 1-5, the Dex cream group (0.75 mg/g) had a significant therapeutic effect on day 4-day 10 (days 4-10) compared with the excipient group; CPD-017, CPD-027, CPD-028, and CPD-029 had a significant therapeutic effect in day 5-day 10 (days 5-10); CPD-002 had a significant therapeutic effect in day 4 day 8 (days 4-8).

What is claimed is:

1. An anti-inflammatory compound, or a stereoisomer, tautomer, nitrogen oxide, prodrug, pharmaceutically acceptable salt, or solvate thereof, wherein the compound is any one of the following specific compounds:

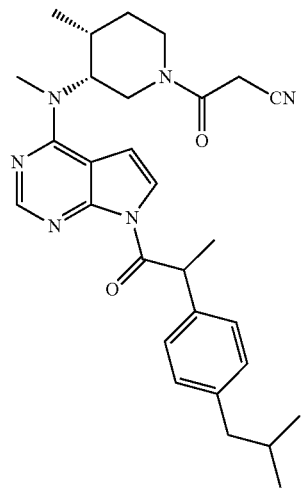

CPD-001

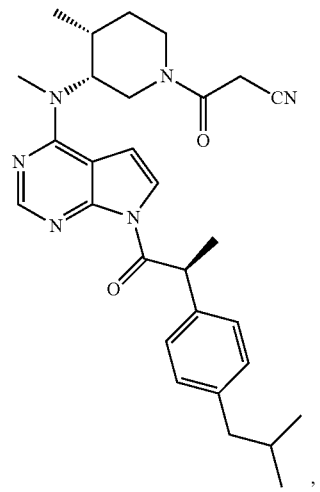

CPD-002

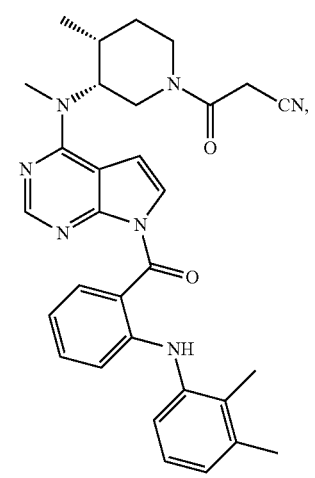

CPD-004

CPD-005
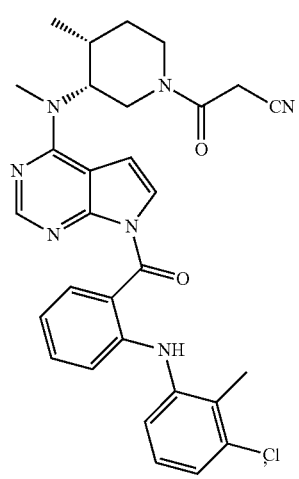
CPD-006
CPD-007
CPD-008
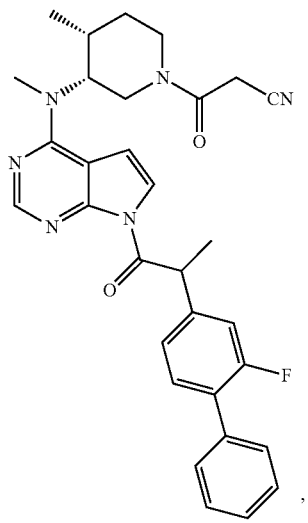
CPD-009
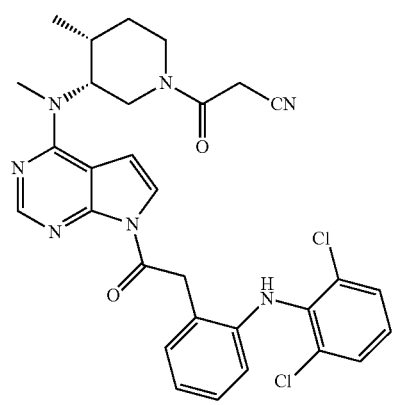
CPD-010
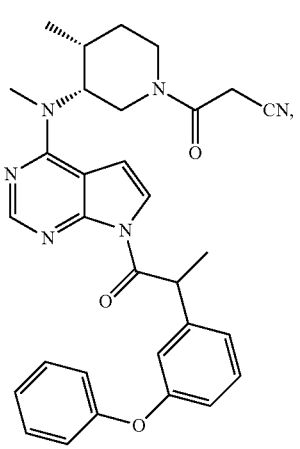

553
-continued
CPD-011
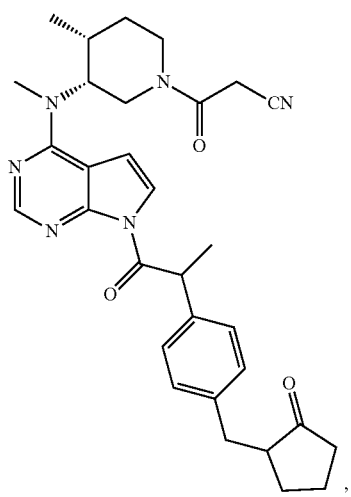
CPD-012
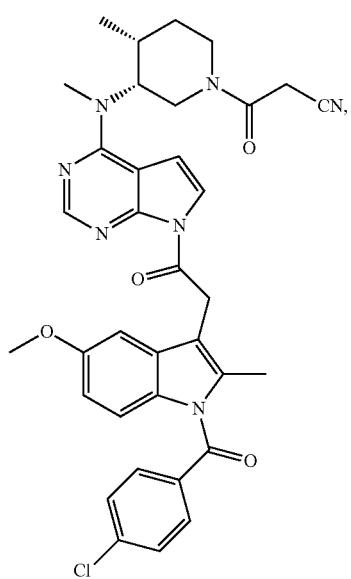
CPD-013
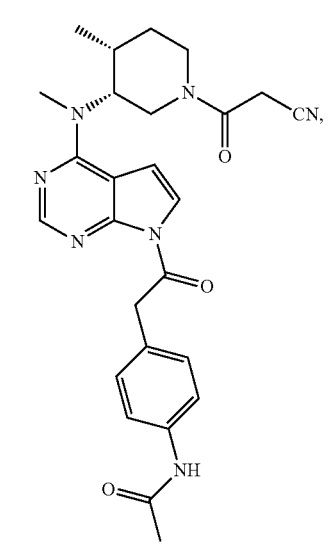
554
-continued
CPD-014
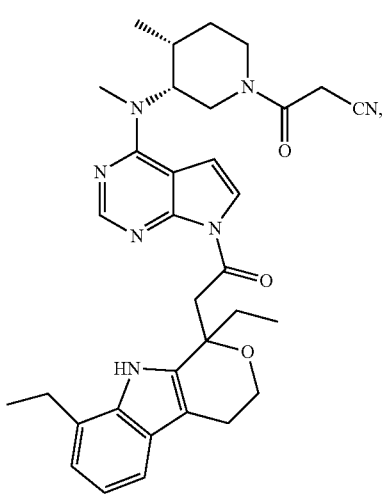
CPD-015
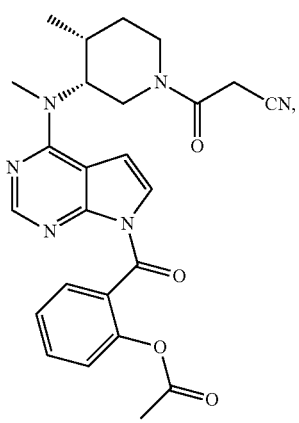
CPD-016
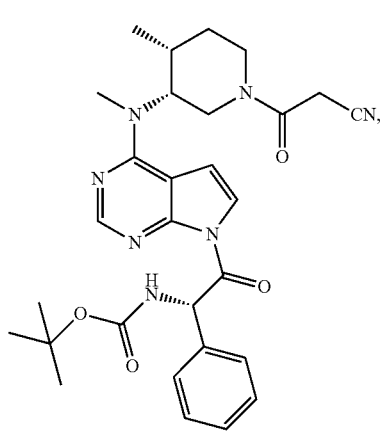

CPD-029
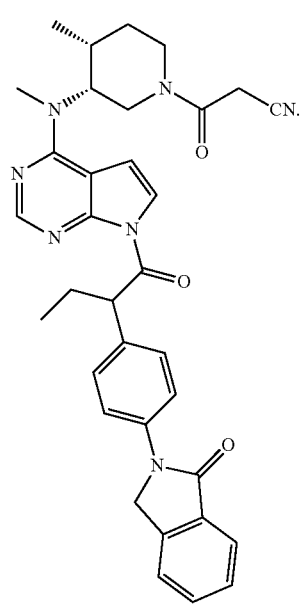
2. An anti-inflammatory compound, or a stereoisomer, tautomer, nitrogen oxide, prodrug, pharmaceutically acceptable salt, or solvate thereof, wherein the compound is any one of the following specific compounds:
CPD-017
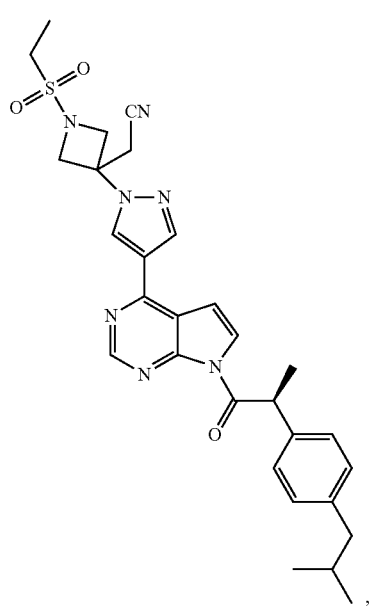
CPD-018
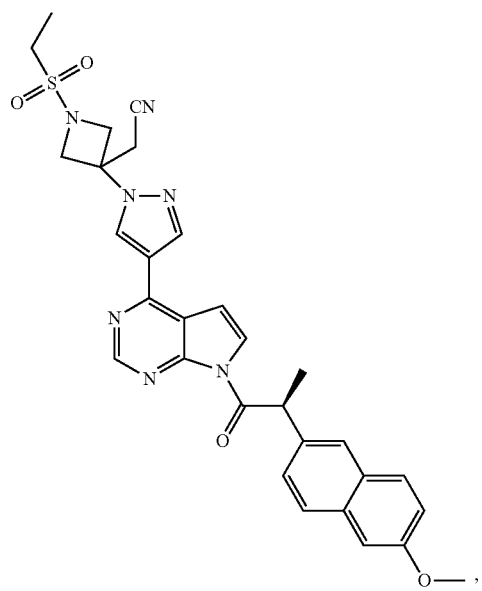
CPD-019
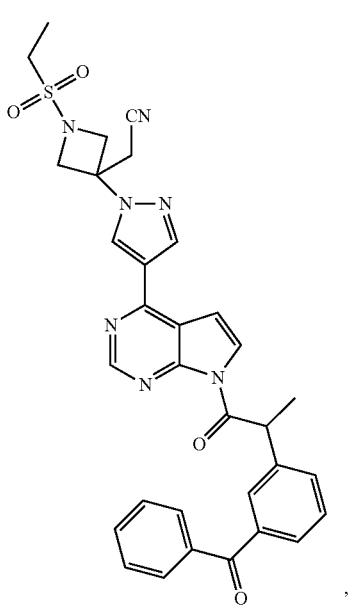

CPD-020
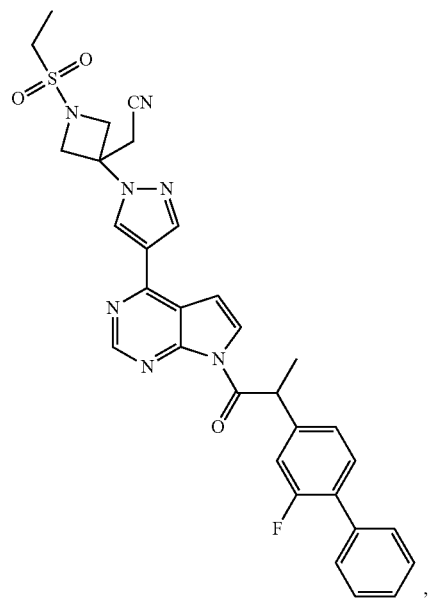
CPD-021
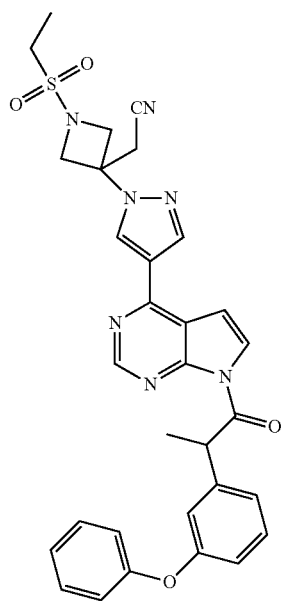
CPD-022
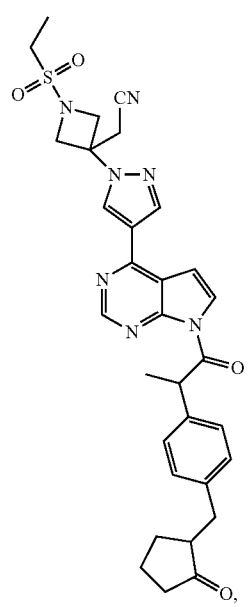
CPD-023
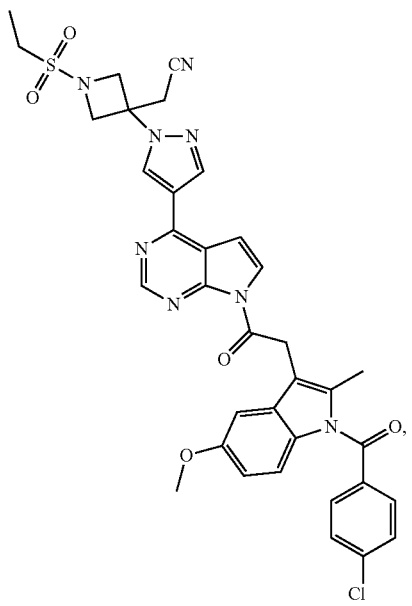

CPD-024
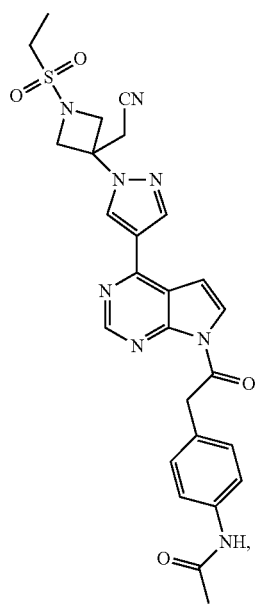
CPD-026
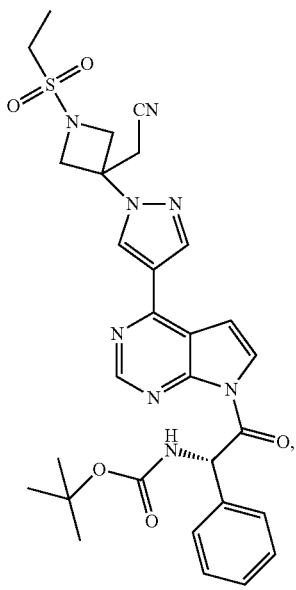
CPD-025
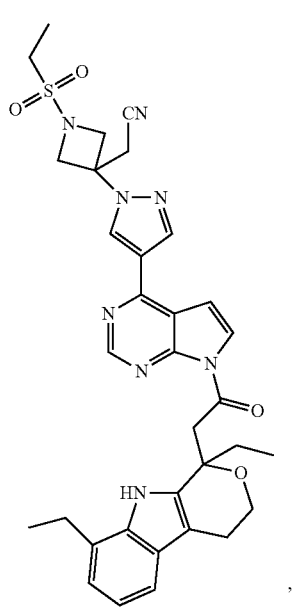
CPD-027
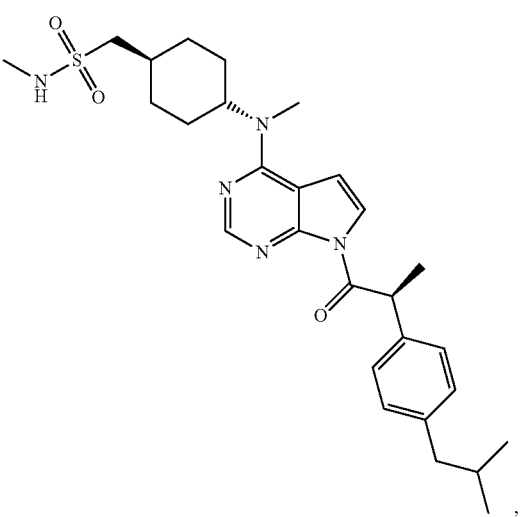

CPD-028
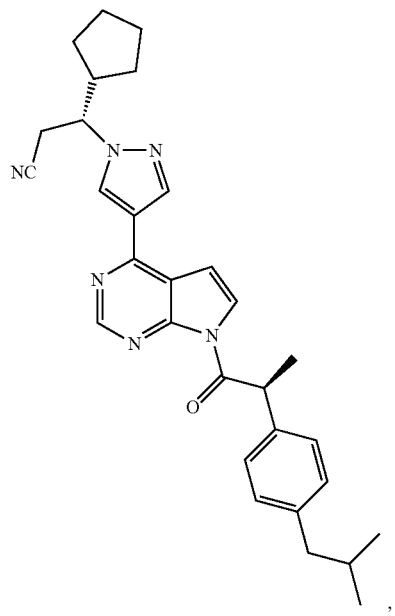
CPD-039
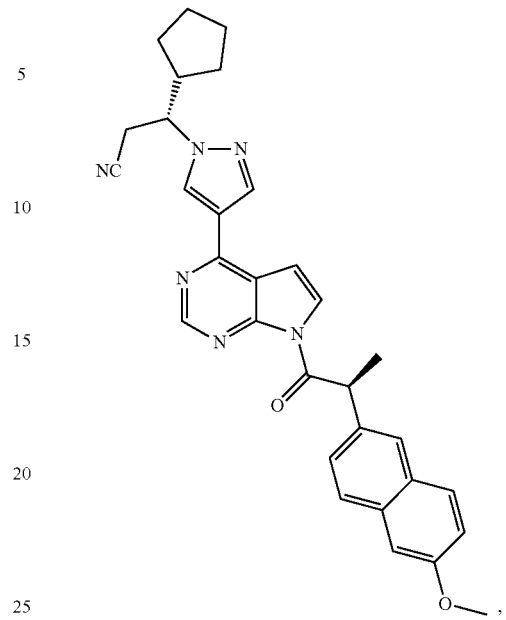
CPD-030
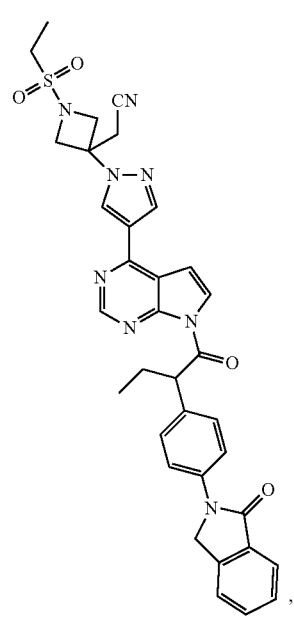
CPD-040
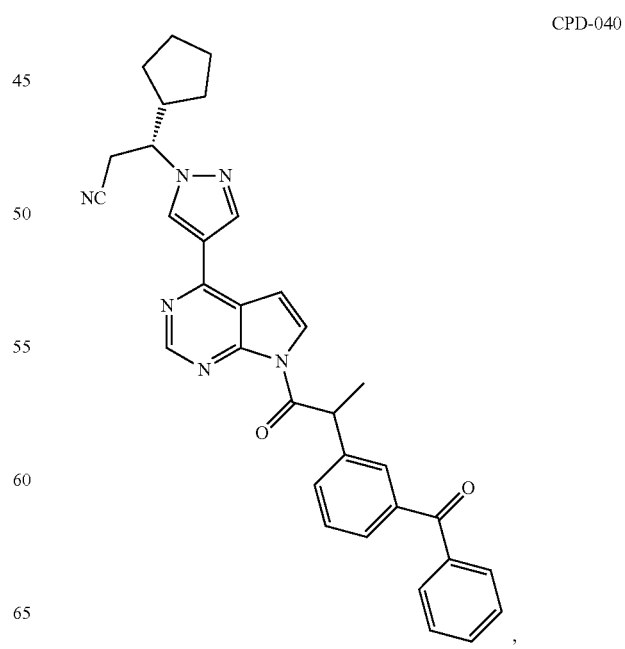

563
-continued
CPD-041
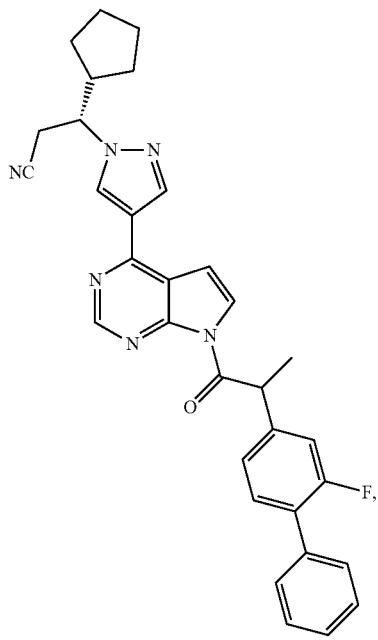
CPD-050
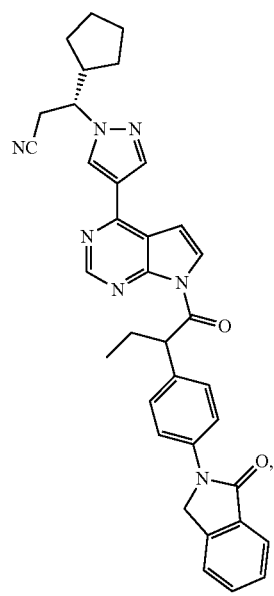
564
-continued
CPD-065
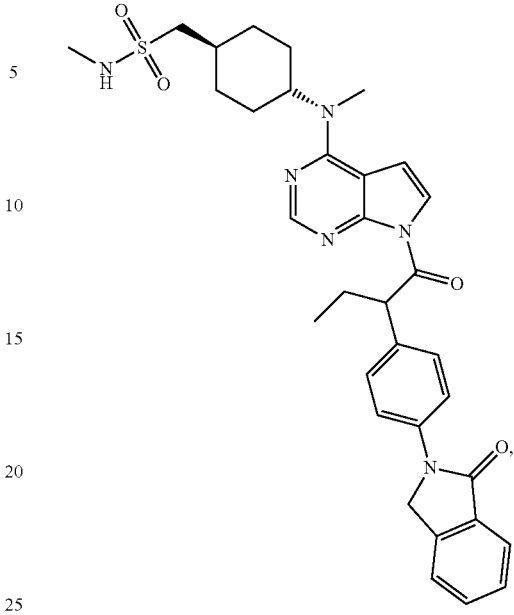
CPD-056
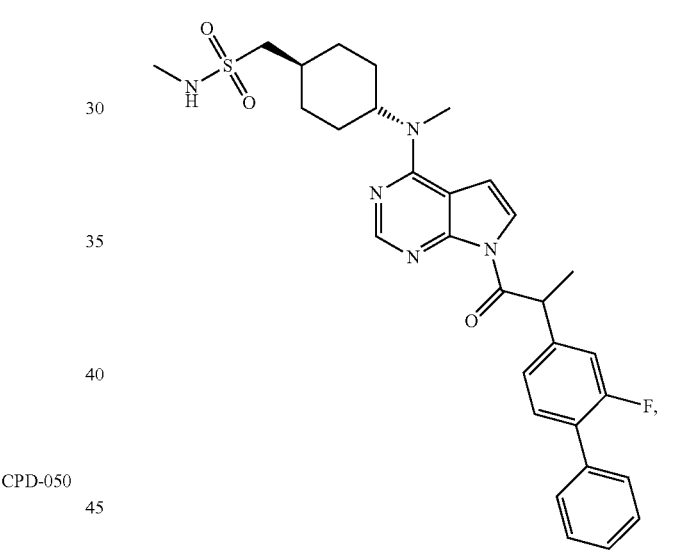
CPD-062
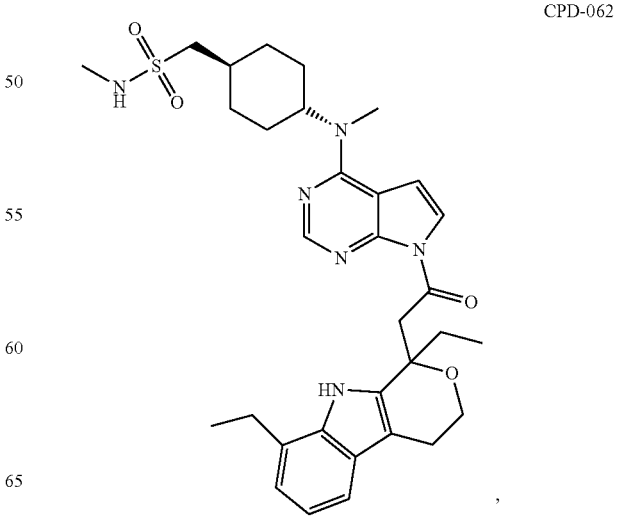

565
-continued

CPD-055

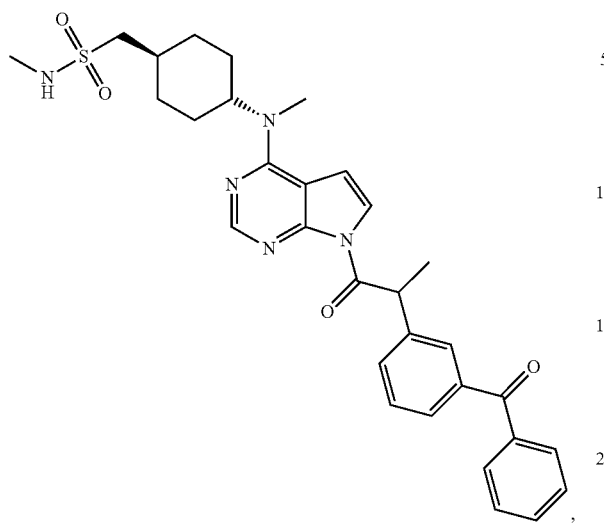

CPD-054

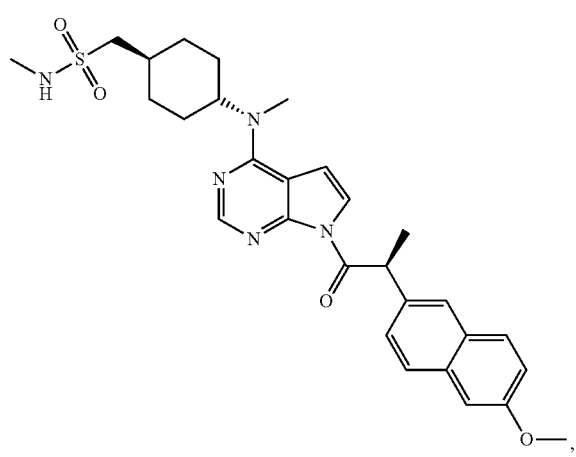

566
-continued

CPD-032

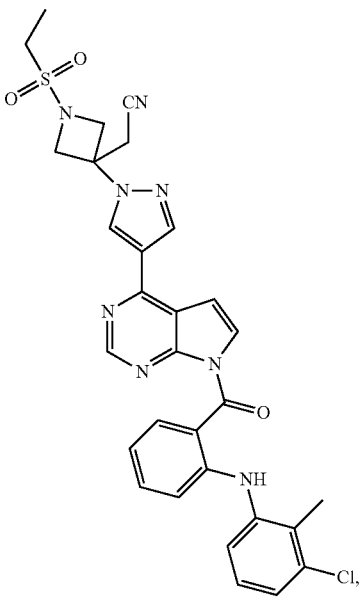

CPD-053

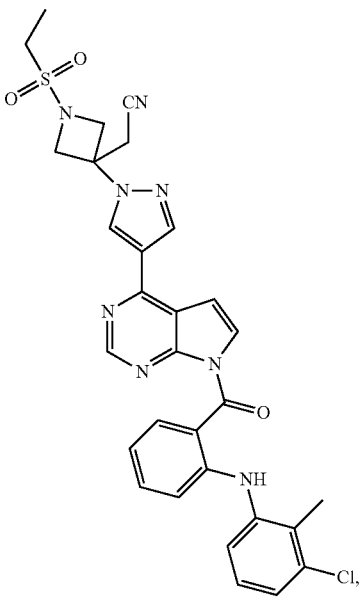

3. A method of treating an inflammatory symptom, comprising administering the anti-inflammatory compound, or the stereoisomer, tautomer, nitrogen oxide, prodrug, pharmaceutically acceptable salt, or solvate thereof of claim 1.

4. A method of treating an inflammatory symptom, comprising administering the anti-inflammatory compound, or the stereoisomer, tautomer, nitrogen oxide, prodrug, pharmaceutically acceptable salt, or solvate thereof of claim 2.

* * * * *